US010501444B2

(12) United States Patent
Ren et al.

(10) Patent No.: US 10,501,444 B2
(45) Date of Patent: Dec. 10, 2019

(54) INHIBITORS OF INFLUENZA VIRUS REPLICATION, APPLICATION METHODS AND USES THEREOF

(71) Applicants: SUNSHINE LAKE PHARMA CO., LTD., Dongguan, Guangdong (CN); NORTH & SOUTH BROTHER PHARMACY INVESTMENT COMPANY LIMITED, Wanchai (HK)

(72) Inventors: Qingyun Ren, Dongguan (CN); Changhua Tang, Dongguan (CN); Junjun Yin, Dongguan (CN); Kai Yi, Dongguan (CN); Yingjun Zhang, Dongguan (CN)

(73) Assignees: SUNSHINE LAKE PHARMA CO., LTD., Dongguan, Guangdong (CN); NORTH & SOUTH BROTHER PHARMACY INVESTMENT COMPANY LIMITED, Wanchai (HK)

( * ) Notice: Subject to any disclaimer, the term of this patent is extended or adjusted under 35 U.S.C. 154(b) by 0 days.

(21) Appl. No.: 16/326,189

(22) PCT Filed: Aug. 15, 2017

(86) PCT No.: PCT/CN2017/097564
§ 371 (c)(1),
(2) Date: Feb. 16, 2019

(87) PCT Pub. No.: WO2018/033082
PCT Pub. Date: Feb. 22, 2018

(65) Prior Publication Data
US 2019/0185456 A1   Jun. 20, 2019

(30) Foreign Application Priority Data

Aug. 16, 2016  (CN) .......................... 2016 1 0675356

(51) Int. Cl.
| | | |
|---|---|---|
| *C07D 403/14* | (2006.01) | |
| *C07D 403/04* | (2006.01) | |
| *C07D 401/14* | (2006.01) | |
| *A61K 31/506* | (2006.01) | |
| *A61P 31/16* | (2006.01) | |
| *C07D 405/14* | (2006.01) | |
| *C07D 409/14* | (2006.01) | |
| *C07D 417/14* | (2006.01) | |
| *C07D 487/04* | (2006.01) | |
| *C07D 513/04* | (2006.01) | |
| *A61K 31/519* | (2006.01) | |
| *A61K 31/5377* | (2006.01) | |
| *A61K 45/06* | (2006.01) | |

(52) U.S. Cl.
CPC .......... *C07D 403/04* (2013.01); *A61K 31/506* (2013.01); *A61K 31/519* (2013.01); *A61K 31/5377* (2013.01); *A61K 45/06* (2013.01); *A61P 31/16* (2018.01); *C07D 401/14* (2013.01); *C07D 403/14* (2013.01); *C07D 405/14* (2013.01); *C07D 409/14* (2013.01); *C07D 417/14* (2013.01); *C07D 487/04* (2013.01); *C07D 513/04* (2013.01)

(58) Field of Classification Search
CPC .. C07D 401/14; C07D 403/04; C07D 403/14; C07D 405/14; C07D 409/14; C07D 411/14; C07D 413/14; C07D 417/14; C07D 471/04; C07D 473/34; C07D 487/04; C07D 513/04; A61K 31/506; A61K 31/517; A61K 31/519; A61K 31/52; A61K 31/5377; A61K 31/553; A61K 45/06; A61K 31/16
See application file for complete search history.

(56) References Cited

U.S. PATENT DOCUMENTS

| | | |
|---|---|---|
| 8,829,007 B2 | 9/2014 | Charifson et al. |
| 8,871,774 B2 | 10/2014 | Charifson et al. |
| 9,051,319 B2 | 6/2015 | Charifson et al. |
| 9,345,708 B2 | 5/2016 | Charifson et al. |
| 9,394,302 B2 | 7/2016 | Charifson et al. |
| 9,518,056 B2 | 12/2016 | Charifson et al. |
| 9,908,878 B2 | 3/2018 | Charifson et al. |
| 9,932,346 B2 | 4/2018 | Jonckers et al. |
| 10,023,569 B2 | 7/2018 | Tanoury et al. |
| 2012/0171245 A1 | 7/2012 | Charifson et al. |
| 2013/0345218 A1 | 12/2013 | Charifson et al. |
| 2014/0005197 A1 | 1/2014 | Charifson et al. |
| 2017/0226102 A1 | 8/2017 | Jonckers et al. |
| 2018/0065962 A1 | 3/2018 | Farmer et al. |
| 2018/0134730 A1 | 5/2018 | Caruso et al. |

(Continued)

FOREIGN PATENT DOCUMENTS

| | | |
|---|---|---|
| WO | 2013184985 A1 | 12/2013 |
| WO | 2017118680 A1 | 7/2017 |

(Continued)

OTHER PUBLICATIONS

B. Muller et al., Antiviral Strategies in, Antiviral Strategies 1-24, 7 (H.-G. Krausslich et al., eds., 2009).*

(Continued)

*Primary Examiner* — Deepak R Rao
(74) *Attorney, Agent, or Firm* — Kam Wah Law

(57) ABSTRACT

The invention provides a novel class of compounds as inhibitors of influenza virus replication, preparation methods thereof, pharmaceutical compositions containing these compounds, and uses of these compounds and pharmaceutical compositions thereof in the treatment of influenza.

21 Claims, No Drawings

(56) References Cited

U.S. PATENT DOCUMENTS

| | | |
|---|---|---|
| 2018/0155342 A1 | 6/2018 | Charifson et al. |
| 2018/0258074 A1 | 9/2018 | Jonckers et al. |
| 2018/0318301 A1 | 11/2018 | Simone et al. |
| 2018/0346463 A1 | 12/2018 | Zhang et al. |

FOREIGN PATENT DOCUMENTS

| | | |
|---|---|---|
| WO | 2017125506 A1 | 7/2017 |
| WO | 2017133657 A1 | 8/2017 |
| WO | 2017133658 A1 | 8/2017 |
| WO | 2017133664 A1 | 8/2017 |
| WO | 2017133665 A1 | 8/2017 |
| WO | 2017133667 A1 | 8/2017 |
| WO | 2017133669 A1 | 8/2017 |
| WO | 2017133670 A1 | 8/2017 |
| WO | 2017198122 A1 | 11/2017 |
| WO | 2018041263 A1 | 3/2018 |

OTHER PUBLICATIONS

N.E. Sharpless et al., Nature Reviews Drug Discovery 1-14, 2 (2006).*

J.H. Poupaert, Drug Design: Basic Principles and Applications, in 2 Encyclopedia of Pharmaceutical Technology 1362-1369, 1367 (James Swarbrick ed., 3rd ed., 2007).*

L.I. Zon et al., Nature Reviews Drug Discovery 4, 35 (2005).*

P.D. Griffiths, Cytomegalovirus in, Principles and Practice of Clinical Virology 85-122 (A.J. Zuckerman et al., eds, 5th ed., 2001).*

Bundgaard, Design of Prodrugs, p. 1, 1985.*

Silverman, Prodrugs and Drug Delivery Systems, The Organic Chemistry of Drug Design and Drug Action, pp. 352-399, 1992.*

Sun et al., Synthesis and evaluation of a new series of substituted acyl(thio)urea and thiadiazolo[2,3-a]pyrimidine derivatives as potent inhibitors of influenza virus neuraminidase, Bioorganic & Medicinal Chemistry, vol. 14, No. 24, pp. 8574-8581 (2006).*

ChemBridge Corporation (9 pages) CHEMCATS, Mar. 7, 2012.*

ISR of PCT/CN2017/097564.

Written Opinion of the ISA of PCT/CN2017/097564.

Bioorganic & Medicinal Chemistry Letters 25 (2015) 1990-1994.

Journal of Medicinal Chemistry(2014),57(15),6668-6678.

Arch. Pharm.Chem.Life Sci. 2016, 349, 202-210.

ACS Medicinal Chemistry Letters (2017), 8(2), 256-260.

ACS Medicinal Chemistry Letters (2017), 8(2), 261-265.

Organic Process Research & Development (2016), 20(5), 965-969.

* cited by examiner

INHIBITORS OF INFLUENZA VIRUS REPLICATION, APPLICATION METHODS AND USES THEREOF

CROSS-REFERENCE TO RELATED APPLICATIONS

This is a U.S. national stage application of the International Patent Application No. PCT/CN2017/097564, filed Aug. 15, 2017, which claims priority to Chinese Patent Application No. 201610675356.4, filed Aug. 16, 2016, both of which are incorporated herein by reference in their entirety.

FIELD

The invention belongs to the pharmaceutical field, specifically, it relates to novel compounds used as inhibitors of influenza virus replication, preparation methods thereof, pharmaceutical compositions containing these compounds, and uses of these compounds and pharmaceutical compositions thereof in the treatment of influenza. More specifically, the compounds of the invention can be used as inhibitors of influenza virus RNA polymerase.

BACKGROUND

Influenza (flu for short hereinafter) is an acute respiratory infectious disease and harmful to human health, which is caused by the influenza virus and characterized by high prevalence, widespread, rapid propagation. Influenza virus can cause serious symptoms in the elderly and children with weaker immune systems, and immunocompromised patients, such as pneumonia or cardiopulmonary failure. Influenza virus was first discovered by Wilson Smith, a British, who called influenza virus as H1N1. The H denotes hemagglutinin; the N denotes neuraminidase, and the numbers represent different types. Influenza virus has caused the global pandemic for many times since the discovery, and the outbreak of influenza virus happens every decade or so, which causes enormous losses in worldwide. Influenza spreads around the world in a yearly outbreak, resulting in about 250,000 to 500,000 deaths, and about three to five million cases of severe illness, and a total of about 5% to 15% of people in worldwide are infected. Every time a pandemic was due to the emergence of new strains in humans. Usually, these new strains are caused by the spread of existing influenza virus from other animal species to humans.

Influenza viruses are RNA viruses belong to the family of orthomyxoviridae, which belong to the genus of influenza virus. According to the differences of the virion nucleoprotein (NP) and matrix protein (M) antigenic characteristics and genetic characteristics, influenza viruses are divided into three types: A, B and C. The three types of influenza viruses have similar biochemical and biological characteristics. The virus particle is 80-120 nanometers in diameter and usually roughly spherical, although filamentous forms can occur. Virus is constituted with three layers, and the inner layer is the viral nucleocapsid containing nucleoprotein (NP), P protein and RNA. NP is a soluble antigen (S antigen) with type specificity and antigenic stability. P protein (P1, P2, P3) may be polymerase required for RNA transcription and replication. Middle viral envelope consists of a lipid layer and a layer of membrane protein (MP), MP has antigenic stability and type specificity. Outer layer is a radial tuber consisting of two different glycoprotein projections, i.e., hemagglutinin (H) and neuraminidase (N). H is a tool for viral absorption on sensitive cell surface which can cause agglutination of erythrocyte, N is a tool for breaking away from cell surface after the completing of virus replication, which is capable of hydrolyzing mucus protein and N-acetylneuraminic acid that locates at the end of cell surface specific glycoprotein receptor. H and N both have variation characteristics, and only have the strain specific antigen, the antibody of which has a protective effect.

Influenzavirus A has one species, influenza A virus. Wild aquatic birds are the natural hosts for a large variety of influenza A. Occasionally, viruses are transmitted to other species and may then cause devastating outbreaks in domestic poultry or give rise to human influenza pandemics. The type A virus is the most virulent human pathogen among the three influenza types and cause the severest disease, and can be transmitted to other species and may then cause human influenza pandemic. The influenza A virus can be subdivided into different serotypes based on the antibody response to these viruses. The serotypes that have been confirmed in humans, ordered by the number of known human pandemic deaths, are: H1N1, which caused Spanish Flu in 1918; H2N2, which caused Asian Flu in 1957; H3N2, which caused Hong Kong Flu in 1968; H5N1, which caused pandemic threats in the influenza season of 2007-2008; H7N7, which has unusual zoonotic potential; H1N2, endemic in humans and pigs; H9N2; H7N2; H7N3; and H10N7.

Influenzavirus B has one species, influenza B virus, which causes local epidemic influenza and can not cause the global influenza pandemic. The only animals known to be susceptible to influenza B infection are humans and the seal. This type of influenza mutates at a rate 2-3 times slower than type A and consequently is less genetically diverse, with only one influenza B serotype. As a result of this lack of antigenic diversity, a degree of immunity to influenza B is usually acquired at an early age. However, influenza B mutates enough that lasting immunity is not possible. This reduced rate of antigenic change, combined with its limited host range (inhibiting cross species antigenic shift), ensures that pandemics of influenza B do not occur.

Influenzavirus C has one species, influenza C virus, which exists in sporadic form, and usually only causes mild disease in children. Influenzavirus C usually can not cause influenza pandemic, and infect humans and pigs.

Unusually for a virus, its genome is not a single piece of nucleic acid; instead, it contains seven or eight pieces of segmented negative-sense RNA. The genome of influenza A viruses encodes 11 proteins: hemagglutinin (H), neuraminidase (N), nucleoprotein (N), M1, M2, NS1, NS2 (NEP), PA, PB1 (polymerase basic 1), PB1-F2 and PB2. Hemagglutinin (H) and neuraminidase (N) are the two large glycoproteins on the outside of the viral particles. HA is a lectin that mediates binding of the virus to target cells and entry of the viral genome into the target cell, while NA is involved in the release of progeny virus from infected cells, by cleaving sugars that bind the mature viral particles. Thus, these proteins are targets for antiviral drugs. Furthermore, they are antigens to which antibodies can be raised. Influenza A viruses are classified into subtypes based on antibody responses to H and N. These different types of HA and NA form the basis of the H and N distinctions in, for example, H5N1.

Vaccination and usage of antiviral drugs are important tools for responding to influenza pandemic. Due to the high mutation rate of the flu virus antigen, the vaccine can't be produced in large scale before influenza pandemic. The two classes of antiviral drugs used against influenza are M2 protein inhibitors (amantadine and rimantadine) and neuraminidase inhibitors (oseltamivir, zanamivir, peramivir and Laninamivir). However, the influenza viruses have developed drug resistance to all these drugs. Therefore, continuing demand for new anti-influenza treatment agent is existing.

Favipiravir, a new antiviral agent, having a new mechanism, has been launched, which plays antiviral action by inhibiting influenza virus RNA polymerase to target the inhibition of viral gene replication, but the therapeutic effect and the drug resistance of influenza viruses still need to be proved. Therefore, other compounds as anti-influenza agents of this mechanism still needed to be researched.

SUMMARY

The invention discloses a novel class of compounds used as inhibitors of influenza virus RNA polymerase. These compounds and compositions thereof can be used in the manufacture of a medicament for preventing, managing, treating or lessening virus infection in patients.

In one aspect, provided herein is a compound having Formula (I) or a stereoisomer, a tautomer, an N-oxide, a solvate, a metabolite, a pharmaceutically acceptable salt or a prodrug thereof,

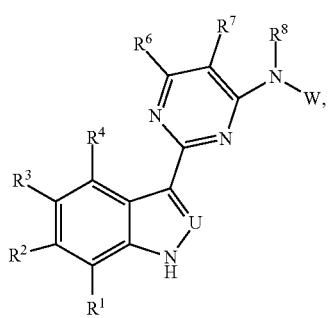

(I)

wherein $R^1$, $R^2$, $R^3$, $R^4$, $R^6$, $R^7$, $R^8$, U and W are as defined herein.

In some embodiments,

U is N or $CR^5$;

each of $R^1$, $R^2$, $R^3$, $R^4$ and $R^5$ is independently H, D, F, Cl, Br, CN, $NO_2$, —C(=O)$R^a$, —C(=O)$OR^b$, —C(=O)$NR^cR^d$, $OR^b$, —$NR^cR^d$, $R^bO$—$C_{1-4}$ alkylene, $R^dR^cN$—$C_{1-4}$ alkylene, $C_{1-6}$ alkyl, $C_{2-6}$ alkenyl or $C_{2-6}$ alkynyl, and wherein each of the $C_{1-6}$ alkyl, $C_{2-6}$ alkenyl and $C_{2-6}$ alkynyl is independently unsubstituted or substituted with 1, 2, 3 or 4 substituents independently selected from D, F, Cl, Br, CN, $OR^b$, —$NR^cR^d$, $C_{1-6}$ alkyl, $C_{1-6}$ haloalkyl, $R^bO$—$C_{1-4}$ alkylene or $R^dR^cN$—$C_{1-4}$ alkylene;

$R^6$ is $OR^b$, $C_{2-6}$ alkyl, $C_{2-6}$ alkenyl, $C_{2-6}$ alkynyl, $C_{3-12}$ carbocyclyl, $C_{3-12}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 16-membered heteroaryl or (5- to 16-membered heteroaryl)-$C_{1-4}$ alkylene, and wherein each of the $C_{2-6}$ alkyl, $C_{2-6}$ alkenyl, $C_{2-6}$ alkynyl, $C_{3-12}$ carbocyclyl, $C_{3-12}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 16-membered heteroaryl and (5- to 16-membered heteroaryl)-$C_{1-4}$ alkylene is independently unsubstituted or substituted with 1, 2, 3, 4 or 5 R';

$R^7$ is H, D, F, Cl, Br, CN, $NO_2$, —C(=O)$R^a$, —C(=O)$OR^b$, —C(=O)$NR^cR^d$, $OR^b$, —$NR^cR^d$, $R^bO$—$C_{1-4}$ alkylene, $R^dR^cN$—$C_{1-4}$ alkylene, $C_{1-6}$ alkyl, $C_{2-6}$ alkenyl, $C_{2-6}$ alkynyl, $C_{3-12}$ cycloalkyl, $C_{3-12}$ cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene, and wherein each of the $C_{1-6}$ alkyl, $C_{2-6}$ alkenyl, $C_{2-6}$ alkynyl, $C_{3-12}$ cycloalkyl, $C_{3-12}$ cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene is independently unsubstituted or substituted with 1, 2, 3, 4 or 5 R';

or, $R^6$ and $R^7$, together with the carbon atoms to which they are attached, form a $C_{3-12}$ carbocyclic ring, 3- to 12-membered heterocyclic ring, $C_{6-10}$ aromatic ring or 5- to 10-membered heteroaromatic ring, and wherein each of the $C_{3-12}$ carbocyclic ring, 3- to 12-membered heterocyclic ring, $C_{6-10}$ aromatic ring and 5- to 10-membered heteroaromatic ring is independently unsubstituted or substituted with 1, 2, 3, 4 or 5 R';

each R' is independently D, F, Cl, Br, CN, $NO_2$, $OR^b$, —$NR^cR^d$, $R^bO$—$C_{1-4}$ alkylene, $R^dR^cN$—$C_{1-4}$ alkylene, —C(=O)$R^a$, —C(=O)$OR^b$, —C(=O)$NR^cR^d$, $C_{1-12}$ alkyl, $C_{1-6}$ haloalkyl, $C_{3-6}$ cycloalkyl, $C_{3-6}$ cycloalkyl-$C_{1-4}$ alkylene, 3- to 8-membered heterocyclyl, (3- to 8-membered heterocyclyl)-$C_{1-4}$ alkylene, $C_{6-10}$ aryl, $C_{6-10}$ aryl-$C_{1-4}$ alkylene, 5- to 8-membered heteroaryl or (5- to 8-membered heteroaryl)-$C_{1-4}$ alkylene, and wherein each of the $C_{1-12}$ alkyl, $C_{1-6}$ haloalkyl, $C_{3-6}$ cycloalkyl, $C_{3-6}$ cycloalkyl-$C_{1-4}$ alkylene, 3- to 8-membered heterocyclyl, (3- to 8-membered heterocyclyl)-$C_{1-4}$ alkylene, $C_{6-10}$ aryl, $C_{6-10}$ aryl-$C_{1-4}$ alkylene, 5- to 8-membered heteroaryl and (5- to 8-membered heteroaryl)-$C_{1-4}$ alkylene is independently unsubstituted or substituted with 1, 2, 3 or 4 substituents independently selected from D, F, Cl, Br, CN, $NO_2$, $OR^b$, —$NR^cR^d$, $C_{1-6}$ alkyl, $C_{1-6}$ haloalkyl, $R^bO$—$C_{1-4}$ alkylene or $R^dR^cN$—$C_{1-4}$ alkylene;

$R^8$ is H, D or $C_{1-6}$ alkyl, and wherein $C_{1-6}$ alkyl is optionally substituted with 1, 2, 3 or 4 substituents independently selected from D, F, Cl, Br, CN, $NO_2$ or $OR^b$;

W is $C_{1-8}$ alkyl, $C_{3-12}$ carbocyclyl or 3- to 12-membered heterocyclyl, and wherein $C_{1-8}$ alkyl, $C_{3-12}$ carbocyclyl and 3- to 12-membered heterocyclyl is independently unsubstituted or substituted with 1, 2, 3 or 4 $R^w$;

each $R^w$ is independently D, F, Cl, Br, CN, $NO_2$, oxo (=O), —C(=O)$R^a$, —C(=O)$OR^b$, —$NR^eC(=O)R^a$, —$NR^eC(=O)NR^cR^d$, —S(=O)$_2R^f$, —S(=O)$_2NR^eC(=O)$$R^a$, —S(=O)$_2NR^cR^d$, $(R^bO)_2P(=O)$—$C_{0-2}$ alkylene, $OR^b$, $R^bO$—$C_{1-2}$ alkylene, $C_{1-6}$ alkyl or 5- to 6-membered heteroaryl, and wherein each of the $C_{1-6}$ alkyl and 5- to 6-membered heteroaryl is independently unsubstituted or substituted with 1, 2, 3 or 4 substituents independently selected from D, F, Cl, Br, CN, $N_3$, oxo (=O), $NO_2$, $OR^b$, $C_{1-6}$ alkyl or $C_{1-6}$ haloalkyl;

each $R^a$, $R^b$, $R^c$, $R^d$, $R^e$ and $R^f$ is independently H, D, $C_{1-6}$ haloalkyl, $C_{1-6}$ alkyl, $C_{2-6}$ alkenyl, $C_{2-6}$ alkynyl, $C_{3-6}$ carbocyclyl, $C_{3-6}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl, (5- to 10-membered heteroaryl)-$C_{1-4}$ alkylene;

or, $R^c$ and $R^d$, together with the nitrogen atom to which they are attached, form 3- to 8-membered heterocyclyl or 5- to 8-membered heteroaryl, and wherein each of the $C_{1-6}$ alkyl, $C_{2-6}$ alkenyl, $C_{2-6}$ alkynyl, $C_{3-6}$ carbocyclyl, $C_{3-6}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl, (5- to 10-membered heteroaryl)-$C_{1-4}$ alkylene, 3- to 8-membered heterocyclyl and 5- to 8-membered heteroaryl is independently unsubstituted or substituted with 1, 2, 3 or 4 substituents independently selected from D, F, Cl, CN, OH, $NH_2$, $C_{1-6}$ alkyl, $C_{1-6}$ haloalkyl, $C_{1-6}$ alkoxy or $C_{1-6}$ alkylamino.

In other embodiments, the compound having Formula (II) or a stereoisomer, a tautomer, an N-oxide, a solvate, a metabolite, a pharmaceutically acceptable salt or a prodrug thereof,

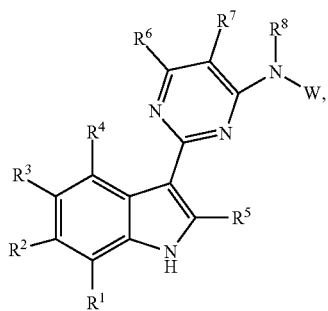

(II)

wherein $R^1$, $R^2$, $R^3$, $R^4$, $R^5$, $R^6$, $R^7$, $R^8$ and W are as defined herein.

In other embodiments, the compound having Formula (III) or a stereoisomer, a tautomer, an N-oxide, a solvate, a metabolite, a pharmaceutically acceptable salt or a prodrug thereof,

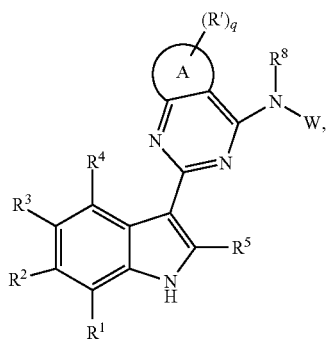

(III)

wherein A is a $C_{3-12}$ carbocyclic ring, 3- to 12-membered heterocyclic ring, $C_{6-10}$ aromatic ring or 5- to 10-membered heteroaromatic ring;

q is 0, 1, 2, 3, 4 or 5; and $R^1$, $R^2$, $R^3$, $R^4$, $R^5$, $R^1$, $R^8$ and W are as defined herein.

In other embodiments, each of $R^1$, $R^2$, $R^3$, $R^4$ and $R^5$ is independently H, D, F, Cl, Br, CN, $NO_2$, —C(=O)$R^a$, —C(=O)$OR^b$, —C(=O)$NR^cR^d$, $OR^b$, —$NR^cR^d$, methyl, ethyl, n-propyl or i-propyl, and wherein each of methyl, ethyl, n-propyl and i-propyl is independently unsubstituted or substituted with 1, 2, 3 or 4 substituents independently selected from D, F, Cl, Br, CN, $OR^b$, —$NR^cR^d$ or $C_{1-3}$ haloalkyl.

In other embodiments, $R^6$ is $OR^b$, $C_{2-3}$ alkyl, $C_{2-4}$ alkenyl, $C_{2-4}$ alkynyl, $C_{3-6}$ carbocyclyl, $C_{3-6}$ carbocyclyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 14-membered heteroaryl or (5- to 14-membered heteroaryl)-$C_{1-4}$ alkylene, and wherein each of the $C_{2-3}$ alkyl, $C_{2-4}$ alkenyl, $C_{2-4}$ alkynyl, $C_{3-6}$ carbocyclyl, $C_{3-6}$ carbocyclyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 14-membered heteroaryl and (5- to 14-membered heteroaryl)-$C_{1-4}$ alkylene is independently unsubstituted or substituted with 1, 2, 3, 4 or 5 R';

$R^7$ is H, D, F, Cl, Br, CN, $NO_2$, —C(=O)$R^a$, —C(=O)$OR^b$, —C(=O)$NR^cR^d$, $OR^b$, —$NR^cR^d$, $C_{1-3}$ alkyl, $C_{2-4}$ alkenyl, $C_{2-4}$ alkynyl, $C_{3-6}$ cycloalkyl, $C_{3-6}$ cycloalkyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 6-membered heteroaryl or (5- to 6-membered heteroaryl)-$C_{1-4}$ alkylene, and wherein each of the $C_{1-3}$ alkyl, $C_{2-4}$ alkenyl, $C_{2-4}$ alkynyl, $C_{3-6}$ cycloalkyl, $C_{3-6}$ cycloalkyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 6-membered heteroaryl and (5- to 6-membered heteroaryl)-$C_{1-4}$ alkylene is independently unsubstituted or substituted with 1, 2, 3, 4 or 5 R';

or, $R^6$ and $R^7$, together with the carbon atoms to which they are attached, form a $C_{3-6}$ carbocyclic ring, 3- to 6-membered heterocyclic ring, $C_{6-10}$ aromatic ring or 5- to 10-membered heteroaromatic ring, and wherein each of the $C_{3-6}$ carbocyclic ring, 3- to 6-membered heterocyclic ring, $C_{6-10}$ aromatic ring and 5- to 10-membered heteroaromatic ring is independently unsubstituted or substituted with 1, 2, 3, 4 or 5 R'.

In other embodiments, each R' is independently D, F, Cl, Br, CN, $NO_2$, $OR^b$, —$NR^cR^d$, —C(=O)$R^a$, —C(=O)$NR^cR^d$, $C_{1-9}$ alkyl, $C_{1-3}$ haloalkyl, $C_{3-6}$ cycloalkyl, 5- to 6-membered heterocyclyl, phenyl, phenyl-$C_{1-2}$ alkylene or 5- to 6-membered heteroaryl, and wherein each of the $C_{1-9}$ alkyl, $C_{1-3}$ haloalkyl, $C_{3-6}$ cycloalkyl, 5- to 6-membered heterocyclyl, phenyl, phenyl-$C_{1-2}$ alkylene and 5- to 6-membered heteroaryl is independently unsubstituted or substituted with 1, 2, 3 or 4 substituents independently selected from D, F, Cl, Br, CN, $NO_2$, $OR^b$, —$NR^cR^d$, methyl, ethyl, n-propyl or i-propyl.

In other embodiments, $R^8$ is H, D, $CF_3$, methyl, ethyl, n-propyl or i-propyl.

In other embodiments, W is $C_{1-6}$ alkyl, $C_{5-8}$ carbocyclyl or 5- to 8-membered heterocyclyl, and wherein each of the $C_{1-6}$ alkyl, $C_{5-8}$ carbocyclyl and 5- to 8-membered heterocyclyl is independently unsubstituted or substituted with 1, 2, 3 or 4 $R^w$.

In other embodiments, each $R^w$ is independently D, F, Cl, Br, CN, $NO_2$, oxo (=O), —C(=O)$OCH_3$, —C(=O)$OCH_2CH_3$, —C(=O)OH, —NHC(=O)$R^a$, —NHC(=O)$NR^cR^d$, —S(=O)$_2R^f$, —S(=O)$_2$NHC(=O)$R^a$, —S(=O)$_2$$NR^cR^d$, $(R^bO)_2P(=O)$—$C_{0-2}$ alkylene, $OR^b$, methyl, ethyl, n-propyl, i-propyl, furyl, pyrrolyl, pyridyl, pyrazolyl, imdazolyl, triazolyl, tetrazolyl, oxazolyl, oxadiazolyl, 1,3,5-triazinyl, thiazolyl, thienyl, pyrazinyl, pyridazinyl or primidinyl, and wherein each of methyl, ethyl, n-propyl, i-propyl, furyl, pyrrolyl, pyridyl, pyrazolyl, imdazolyl, triazolyl, tetrazolyl, oxazolyl, oxadiazolyl, 1,3,5-triazinyl, thiazolyl, thienyl, pyrazinyl, pyridazinyl and primidinyl independently unsubstituted or substituted with 1, 2, 3 or 4 substituents independently selected from D, F, Cl, Br, CN, $N_3$, oxo (=O), $NO_2$, —$OCH_3$, $C_{1-3}$ alkyl or $C_{1-3}$ haloalkyl.

In other embodiments, each $R^a$, $R^b$, $R^c$, $R^d$, $R^e$ and $R^f$ is independently H, D, trifluoromethyl, methyl, ethyl, i-propyl, n-propyl, n-butyl, t-butyl, $C_{3-6}$ carbocyclyl, 5- to 6-membered heterocyclyl, phenyl, 5- to 6-membered heteroaryl, (5- to 6-membered heteroaryl)-$C_{1-4}$ alkylene; or, $R^c$ and $R^d$, together with the nitrogen atom to which they are attached, form a 5- to 6-membered heterocyclyl or 5- to 6-membered heteroaryl, and wherein each of methyl, ethyl, i-propyl, n-propyl, n-butyl, t-butyl, $C_{3-6}$ carbocyclyl, 5- to 6-membered heterocyclyl, phenyl, 5- to 6-membered heteroaryl and (5- to 6-membered heteroaryl)-$C_{1-4}$ alkylene is independently unsubstituted or substituted with 1, 2, 3 or 4 substituents independently selected from D, F, Cl, CN, OH, $NH_2$, $C_{1-3}$ alkyl, $C_{1-3}$ haloalkyl or methoxy.

In other embodiments, A is a $C_{3-6}$ carbocyclic ring, 3- to 6-membered heterocyclic ring, $C_{6-10}$ aromatic ring or 5- to 10-membered heteroaromatic ring.

In other embodiments, $R^6$ is $OR^b$, $C_{2-4}$ alkynyl, $C_{3-6}$ carbocyclyl, 5- to 6-membered heterocyclyl, phenyl, naphthyl, furyl, benzofuryl, pyrrolyl, pyridyl, pyrazolyl, imdazolyl, benzimdazolyl, triazolyl, tetrazolyl, oxazolyl, oxadiazolyl, 1,3,5-triazinyl, thiazolyl, thienyl, benzothienyl, pyrazinyl, pyridazinyl, pyrimidinyl, indolyl, purinyl, quinolyl, isoquinolyl, phenoxathiinyl,

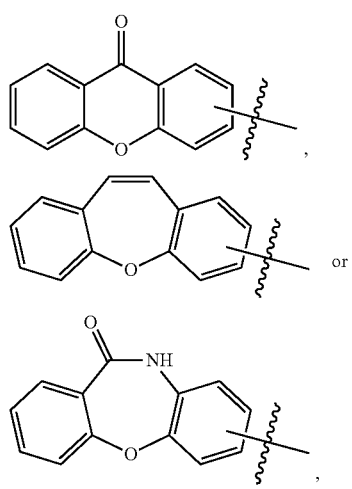

or and wherein each of $C_{2-4}$ alkynyl, $C_{3-6}$ carbocyclyl, 5- to 6-membered heterocyclyl, phenyl, naphthyl, furyl, benzofuryl, pyrrolyl, pyridyl, pyrazolyl, imdazolyl, benzimdazolyl, triazolyl, tetrazolyl, oxazolyl, oxadiazolyl, 1,3,5-triazinyl, thiazolyl, thienyl, benzothienyl, pyrazinyl, pyridazinyl, pyrimidinyl, indolyl, purinyl, quinolyl, isoquinolyl, phenoxathiinyl,

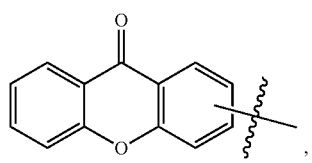

and

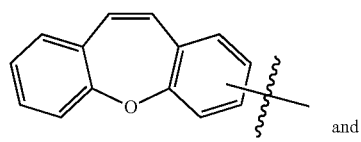

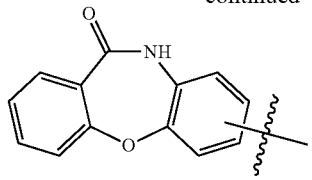

is independently unsubstituted or substituted with 1, 2, 3, 4 or 5 R'.

In other embodiments, A is a $C_{3-6}$ carbocyclic ring, 3- to 6-membered heterocyclic ring, benzene, naphthalene, furan, benzofuran, pyrrole, pyridine, pyrazole, imidazole, benzoimidazole, triazole, tetrazole, oxazole, oxadiazole, 1,3,5-triazine, thiazole, thiophene, benzothiphene, pyrazine, pyridazine, pyrimidine, indole, purine, quinoline or isoquinoline.

In other embodiments, W is one of the following sub-formulae:

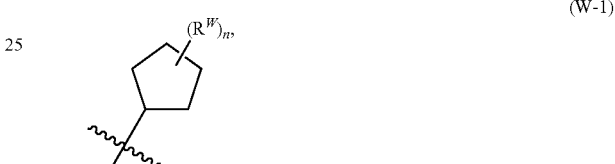
(W-1)

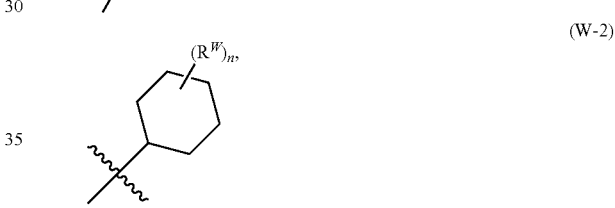
(W-2)

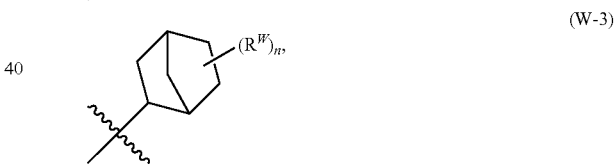
(W-3)

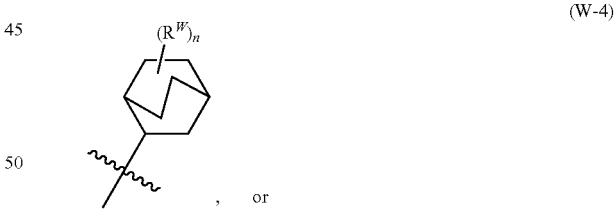
(W-4)

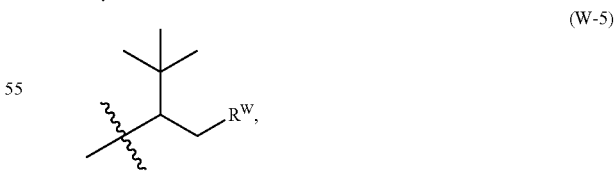
(W-5)

wherein n is 0, 1, 2, 3, or 4; and
each $R^W$ is as defined herein.

In other embodiments, the compound having Formula (IV), (V), (VI), (VII), (VIII), (IX), (X), (XI), (XII), (XIII), (XIV) or (XV), or a stereoisomer, a tautomer, an N-oxide, a solvate, a metabolite, a pharmaceutically acceptable salt or a prodrug thereof,

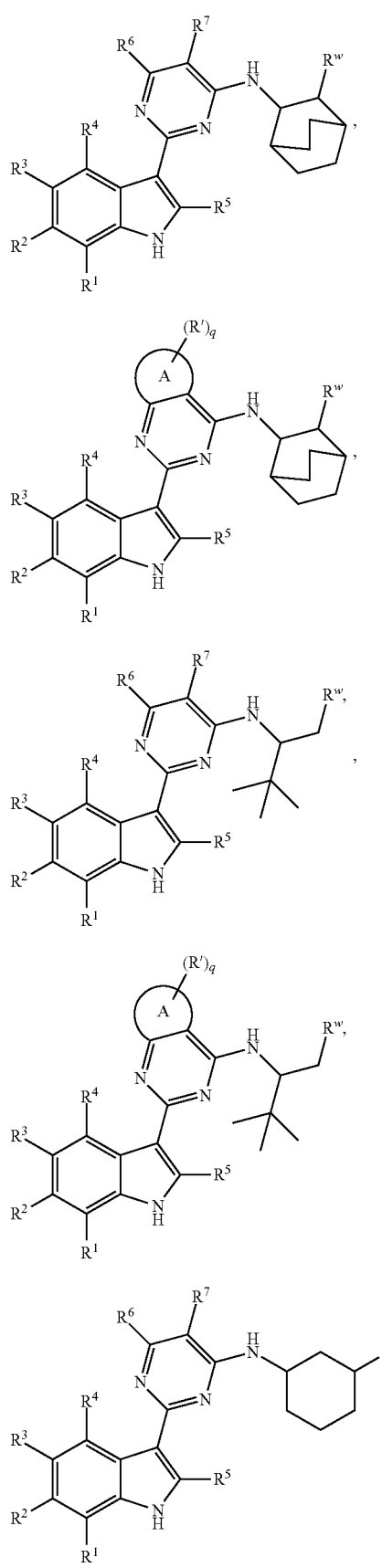
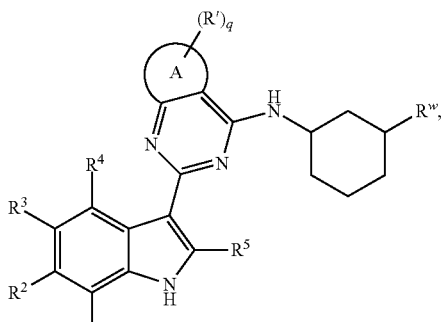
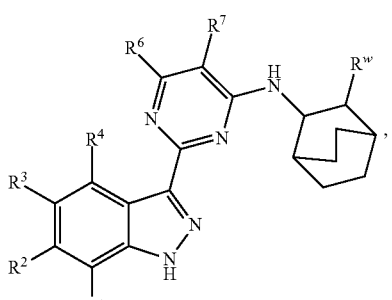
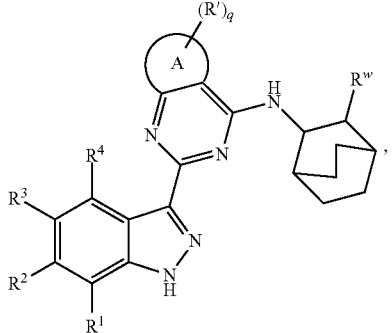
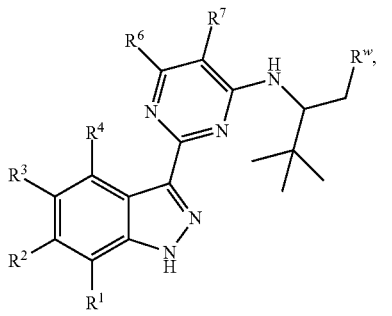

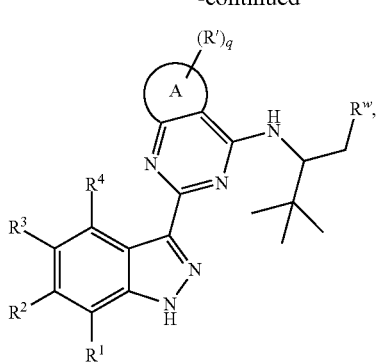
(XIII)

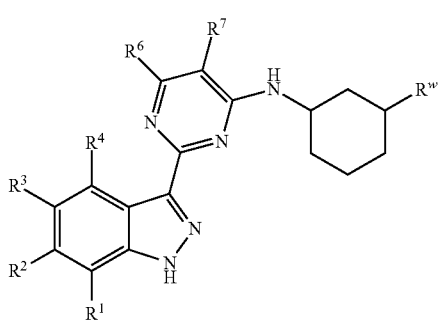
(XIV)

or

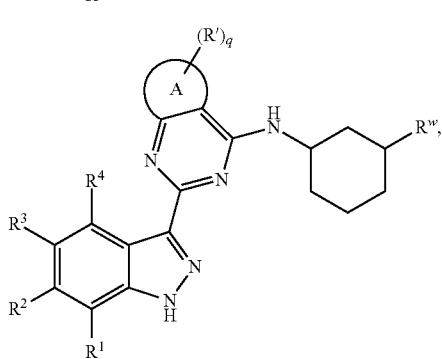
(XV)

wherein A, q, $R^1$, $R^2$, $R^3$, $R^4$, $R^5$, $R^6$, $R^7$, R' and $R^w$ are as defined herein.

In another aspect, provided herein is a pharmaceutical composition comprising the compound of the invention.

In some embodiments, the pharmaceutical composition provided herein further comprises a pharmaceutically acceptable carrier, adjuvant, vehicle or a combination thereof.

In some embodiments, the pharmaceutical composition provided herein further comprises one or more other therapeutic agents.

In other embodiments, the other therapeutic agent disclosed herein is an anti-influenza virus agent or anti-influenza virus vaccine.

In other embodiments, the pharmaceutical composition may be in the form of a liquid, solid, semi-solid, gel or spray.

In other embodiments, the pharmaceutical composition disclosed herein, wherein the other therapeutic agent is amantadine, rimantadine, oseltamivir, zanamivir, peramivir, laninamivir, laninamivir octanoate hydrate, favipiravir, arbidol, ribavirin, stachyflin, ingavirin, fludase, CAS no. 1422050-75-6, JNJ-872, an influenza vaccine (FluMist Quadrivalent®, Fluarix® Quadrivalent, Fluzone® Quadrivalent, Flucelvax® or FluBlok®) or a combination thereof.

In another aspect, provided herein is use of the compound or the pharmaceutical composition disclosed herein in the manufacture of a medicament for preventing, managing, treating or lessening a disorder or disease caused by a virus infection in a patient.

In some embodiments, the virus infection disclosed herein is an influenza virus infection.

In another aspect, provided herein is use of the compound or the pharmaceutical composition disclosed herein in the manufacture of a medicament for inhibiting an influenza virus RNA polymerase.

In another aspect, provided herein is the compound or the pharmaceutical composition disclosed herein for use in preventing, managing, treating or lessening a disorder or disease caused by a virus infection in a patient.

In some embodiments, the virus infection disclosed herein is an influenza virus infection.

In another aspect, provided herein is the compound or the pharmaceutical composition for use in inhibiting an influenza virus RNA polymerase.

In another aspect, provided herein is a method of preventing, managing, treating or lessening a disorder or disease caused by a virus infection in a patient, comprising administering to the patient in need thereof a therapeutically effective amount of the compound or the pharmaceutical composition disclosed herein.

In some embodiments, the virus infection disclosed herein is an influenza virus infection.

In another aspect, provided herein is a method of inhibiting an influenza virus RNA polymerase in a patient, comprising administering to the patient in need thereof a therapeutically effective amount of the compound or the pharmaceutical composition disclosed herein.

Unless otherwise stated, all stereoisomers, geometric isomers, tautomers, solvates, hydrates, metabolites, salts and pharmaceutically acceptable prodrugs of the compounds disclosed herein are within the scope of the invention.

In one embodiment, the salt is a pharmaceutically acceptable salt. The phrase "pharmaceutically acceptable" refers to that the substance or composition must be chemically and/or toxicologically compatible with the other ingredients comprising a formulation, and/or the mammal being treated therewith.

The compound of the invention also embraces the salts thereof, and the salts are not necessarily pharmaceutically acceptable salts, and which may be useful as intermediates for preparing and/or purifying compounds of the invention and/or for separating enantiomers of compounds of the invention.

In another embodiment, the compound disclosed herein may contain several asymmetric centers and therefore exist in the form of racemic mixture generally described. Furthermore, it is intended that all racemic mixture, parts of the racemic mixture, and enantiomer and diastereomers purified by separation form part of the present invention.

The compounds disclosed herein may exists in the form of possible isomers, including rotamers, atropisomers, tautomer or a mixture thereof. It is intended that mixtures of isomers, including rotamers, atropisomers, tautomers, parts of the mixtures of isomers, rotamers, atropisomers, tautomers, and the isomers, including rotamers, atropisomers, tautomer purified by separation form part of the present invention.

In another aspect, the compounds of the invention include isotopically enriched compounds as defined herein, for example those into which radioactive isotopes, such as $^3$H, $^{14}$C and $^{18}$F, or those into which non-radioactive isotopes, such as $^{2}$H and $^{13}$C are present.

In other aspect, provided herein is a method of preparing, separating or purifying the compound of Formula (I).

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless otherwise defined, all technical and scientific terms used herein have the same meaning as is commonly understood by one skilled in the art to which this invention belongs. All patents and publications referred to herein are incorporated by reference in their entirety.

As used herein, the following definitions shall be applied unless otherwise indicated. For purposes disclosed herein, the chemical elements are identified in accordance with the *Periodic Table of the Elements, CAS version, and the Handbook of Chemistry and Physics,* 75 th Ed. 1994. Additionally, general principles of organic chemistry are described in Sorrell et al., "*Organic Chemistry*", University Science Books, Sausalito: 1999, and "*March's Advanced Organic Chemistry*", by Michael B. Smith and Jerry March, John Wiley & Sons, New York: 2007, all of which are incorporated herein by reference in their entireties.

As used herein, the term "subject" refers to an animal. Typically the animal is a mammal. The subject also refers to for example, primates (e.g., humans), cows, sheep, goats, horses, dogs, cats, rabbits, rats, mice, fish, birds and the like. In certain embodiments, the subject is a primate. In other embodiments, the subject is a human.

The term "subject" can be used interchangeably with "patient" in the invention. The term "subject" and "patient" refer to animals (eg., birds such as chicken, quail or turkey, or mammals), specially mammals including non-primates (eg., cattle, pigs, horses, sheep, rabbits, guinea pigs, rats, dogs, cats and mice) and primates (eg., monkeys, chimpanzees and humans), more specially humans. In some embodiments, the subject is a non-human animal, such as livestock (eg., horses, cattle, pigs or sheep) or pet (eg., dogs, cats, guinea pigs or rabbits). In other some embodiments, the "patient" refers to a human. In one embodiment, "patient" refers to a human.

The compounds disclosed herein containing isotopes described above or other atom isotopes and pharmaceutical salts thereof are included within the scope of the present invention. Certain isotopically-labeled compounds of the present invention, for example those into which radioactive isotopes such as $^{3}$H or $^{14}$C are incorporated, are useful in drug and/or substrate tissue distribution assays. Because of easy preparation and detection, isotopes such as tritiated, i.e., $^{3}$H, and carbon-14, i.e., $^{14}$C are preferred. Further, substitution with heavier isotopes, particularly deuterium (i.e., $^{2}$H or D) may afford certain therapeutic advantages resulting from greater metabolic stability, for example increased in vivo half-life or reduced dosage requirements or an improvement in therapeutic index. Therefore, the heavier isotopes may be preferred in somewhere.

Stereochemical definitions and conventions used herein generally follow S. P Parker, Ed., *McGraw-Hill Dictionary of Chemical Terms* (1984) McGraw-Hill Book Company, New York; and Eliel, E. and Wilen, S., "*Stereochemistry of Organic Compounds*", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, different optically active compounds are called stereoisomers and are identical except that they are mirror images of one another. A specific stereoisomer may be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

The compounds disclosed herein may contain asymmetric or chiral centers, and therefore exist in different stereoisomeric forms. It is intended that all stereoisomeric forms of the compounds disclosed herein, including but not limited to, diastereomers, enantiomers, atropisomers and geometric (conformational) isomers as well as mixtures thereof such as racemic mixtures, form part of the present invention.

Unless otherwise specified, the Formula described herein also contain all the isomers thereof (such as, enantiomers, diastereomers, atropisomers and geometric (conformational) isomers; such as all (R)- and (S)-isomers, (Z) and (E) isomers around the double bond, (Z) and (E) conformational isomers. Therefore, single stereochemical isomers as well as enantiomeric, diastereomeric, or geometric mixtures of the present compounds are within the scope disclosed herein.

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. The specific example of phenol-keto tautomerisms is pyridin-4-ol and pyridin-4(1H)-one tautomerism. Unless otherwise stated, all tautomeric forms of the compounds disclosed herein are within the scope of the invention.

An "N-oxide" refers to one or more than one nitrogen atoms oxidised to form an N-oxide or N-oxides, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g. a peroxycarboxylic acid) (See, *Advanced Organic Chemistry*, by Jerry March, 4th Edition, Wiley Interscience, pages). More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and ethanolamine. The term "hydrate" refers to the complex where the solvent molecule is water.

A "metabolite" is a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

A "pharmaceutically acceptable salts" refers to organic or inorganic salts of a compound disclosed herein. Pharmaceutically acceptable salts are well known in the art. For example, S. M. Berge et al., describe pharmaceutically acceptable salts in detail in *J. Pharmaceutical Sciences*, 1977, 66: 1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, alginate, ascorbate, aspartate, benzenesulfonate, benzoate, bisulfate, borate, butyrate, camphanic acid salt, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}\text{alkyl})_4$ salts. This invention also envisions the quaternization of any basic nitrogen-containing groups of the compounds disclosed herein. Water or oil soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic ($C_1$-$C_{24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, J. Rautio et al., Prodrugs: Design and Clinical Applications, *Nature Review Drug Discovery*, 2008, 7, 255-270, and S. J. Hecker et al., Prodrugs of Phosphates and Phosphonates, *Journal of Medicinal Chemistry*, 2008, 51, 2328-2345, all of which are incorporated herein by reference in their entireties.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. If the compound contains a double bond, the substituent may be cis-(Z) or trans-(E) configuration.

Therefore, as the invention described, the compound disclosed herein may exist in the form of any possible isomer, such as rotational isomer, atropisomer, tautomer, or a mixture thereof, i.e., substantially pure geometric (cis- or trans-) isomer, diastereoisomer, optical isomer (enantiomer), racemate or a mixture thereof.

Any resulting mixtures of stereoisomers can be separated on the basis of the physicochemical differences of the constituents, into the pure or substantially pure geometric isomers, optical isomers, diastereoisomers, racemate, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, *Racemates and Resolutions* (Wiley Interscience, New York, 1981); *Principles of Asymmetric Synthesis* (2nd Ed. Robert E. Gawley, Jeffrey Aubé, Elsevier, Oxford, U K, 2012); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

As described herein, compounds disclosed herein may optionally be substituted with one or more substituents, such as are illustrated generally below, or as exemplified by particular classes, subclasses, and species of the invention. It will be appreciated that the phrase "optionally substituted" is used interchangeably with the phrase "substituted or unsubstituted". The term "optional" or "optionally" refers to that a subsequently described event or circumstance may but need not occur, and that the description includes instances where the event or circumstance occurs and instances in which it does not. In general, whenever the term "optionally" is or is not before the term "substituted", the term "substituted" refers to the unreplacement or replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituents may be either the same or different at each position. Substituents described herein may be, but are not limited to, D, F, Cl, Br, CN, $N_3$, OH, $NH_2$, $NO_2$, oxo (=O), —C(=O)$R^a$, —C(=O)O$R^b$, —C(=O)N$R^cR^d$, —N$R^e$C(=O)$R^a$, —N$R^e$C(=O)N$R^cR^d$, —S(=O)$_2R^f$, —S(=O)$_2$N$R^e$C(=O)$R^a$, —S(=O)$_2$N$R^cR^d$, $(R^bO)_2$P(=O)—$C_{0-2}$ alkylene, O$R^b$, —N$R^cR^d$, $R^bO$—$C_{1-4}$ alkylene, $R^dR^cN$—$C_{1-4}$ alkylene, $C_{1-12}$ alkyl, $C_{1-6}$ haloalkyl, $C_{1-6}$ alkoxy, $C_{1-6}$ alkylamino, $C_{2-6}$ alkenyl, $C_{2-6}$ alkynyl, $C_{3-12}$ cycloalkyl, $C_{3-12}$ cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 16-membered heteroaryl or (5- to 16-membered heteroaryl)-$C_{1-4}$ alkylene, and wherein $R^a$, $R^b$, $R^c$, $R^d$, $R^e$ and $R^f$ are as defined herein.

Furthermore, what need to be explained is that the phrase "each . . . is independently" and "each of . . . and . . . is independently", unless otherwise stated, should be broadly understood. The specific options expressed by the same symbol are independent of each other in different groups; or the specific options expressed by the same symbol are independent of each other in same groups.

At various places in the present specification, substituents of compounds disclosed herein are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" refers to a saturated linear or branched-chain monovalent hydrocarbon radical of 1 to 20 carbon atoms. Unless otherwise specified, the alkyl group contains 1-20 carbon atoms. In some embodiments, the alkyl group contains 1-12 carbon atoms. In other embodiments, the alkyl group contains 1-10 carbon atoms. In other embodiments, the alkyl group contains 1-9 carbon atoms. In other embodiments, the alkyl group contains 1-8 carbon atoms. In other embodiments, the alkyl group contains 1-6 carbon atoms. In still other embodiments, the alkyl group contains 1-4 carbon atoms. In yet other embodiments, the alkyl group contains 1-3 carbon atoms.

Some non-limiting examples of the alkyl group include, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), n-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, n-heptyl and n-octyl, etc. Wherein the alkyl group can be independently unsubstituted or substituted with one or more substitutents described herein.

The term "alkyl" or the prefix "alk-" is inclusive of both straight chain and branched saturated carbon chain.

The term "alkylene" refers to a saturated divalent hydrocarbon group derived from a straight or branched chain saturated hydrocarbon by the removal of two hydrogen atoms. Unless otherwise stated, the alkylene group contains 1-10 carbon atoms. In other embodiments, the alkylene group contains 1-6 carbon atoms. In still other embodiments, the alkylene group contains 1-4 carbon atoms. In yet other embodiments, the alkylene group contains 1-2 carbon atoms. Such alkylene group is exemplified by methylene (—$CH_2$—), ethylene (—$CH_2CH_2$—), isopropylene (—$CH(CH_3)CH_2$—), and the like. Wherein the alkylene group may be independently unsubstituted or substituted with one or more substitutents described herein.

The term "alkenyl" refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e., a carbon-carbon, $sp^2$ double bond, wherein the alkenyl radical may be independently unsubstituted or substituted with one or more substituents described herein, and includes radicals having "cis" and "trans" orientations, or alternatively, "E" and "Z"

orientations. Examples of the alkenyl group include, but are not limited to, vinyl (—CH=CH$_2$), allyl (—CH$_2$CH=CH$_2$), and the like.

The term "alkynyl" refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e., a carbon-carbon, sp triple bond, wherein the alkynyl radical is independently unsubstituted or substituted with one or more substituents described herein. Examples of alkynyl group include, but are not limited to, acetenyl (—C≡CH), propargyl (—CH$_2$C≡CH), 1-propynyl (—C≡C—CH$_3$), and the like.

The term "alkoxy" refers to an alkyl group, as previously defined, attached to the parent molecular moiety via an oxygen atom. Unless otherwise specified, the alkyl group contains 1-20 carbon atoms. In other embodiments, the alkyl group contains 1-10 carbon atoms. In other embodiments, the alkyl group contains 1-8 carbon atoms. In still other embodiments, the alkyl group contains 1-6 carbon atoms. In yet other embodiments, the alkyl group contains 1-4 carbon atoms and in still yet other embodiments, the alkyl group contains 1-3 carbon atoms.

Some non-limiting examples of alkoxy group include, methoxy (MeO, —OCH$_3$), ethoxy (EtO, —OCH$_2$CH$_3$), 1-propoxy (n-PrO, n-propoxy, —OCH$_2$CH$_2$CH$_3$), 2-propoxy (i-PrO, i-propoxy, —OCH(CH$_3$)$_2$), 1-butoxy (n-BuO, n-butoxy, —OCH$_2$CH$_2$CH$_2$CH$_3$), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (t-BuO, t-butoxy, —OC(CH$_3$)$_3$), 1-pentoxy (n-pentoxy, —OCH$_2$CH$_2$CH$_2$CH$_2$CH$_3$), 2-pentoxy (—OCH(CH$_3$)CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$), and the like. Wherein the alkoxy group is independently unsubstituted or substituted with one or more substitutents disclosed herein.

The terms "haloalkyl", "haloalkenyl" or "haloalkoxy" refer to alkyl, alkenyl or alkoxy, as the case may be, substituted with one or more halogen atoms. In some embodiments, the haloalkyl group contains 1-10 carbon atoms. In other embodiments, the haloalkyl group contains 1-8 carbon atoms. In other embodiments, the haloalkyl group contains 1-6 carbon atoms. In still other embodiments, the haloalkyl group contains 1-4 carbon atoms. In yet other embodiments, the haloalkyl group contains 1-3 carbon atoms. Some non-limiting examples of the haloalkyl group and haloalkoxy group include trifluoromethyl, trifluoromethoxy, and the like.

The term "carbocycle", "carbocyclyl", "carbocyclic" or "carbocyclic ring" used interchangeably herein refers to a non-aromatic ring system having 3 to 14 ring carbon atoms, which is saturated or contains one or more units of unsaturation. In some embodiments, the number of carbon atom is 3 to 12; in other embodiments, the number of carbon atom is 3 to 10; in other embodiments, the number of carbon atom is 3 to 8; in other embodiments, the number of carbon atom is 3 to 6; in other embodiments, the number of carbon atom is 5 to 6; in other embodiments, the number of carbon atom is 5 to 8; in other embodiments, the number of carbon atom is 6 to 8. The "carbocyclyl" includes a monocyclic, bicyclic, or polycyclic fused ring, spiro ring or bridged ring system, and a polycyclic ring system containing one carbocyclic ring fused with one or more non-aromatic carbocyclic ring or heterocyclic ring, or one or more aromatic ring, or a combination thereof, wherein the linked group or point exists on carbocyclic ring. The bicyclic carbocyclyl groups includes bridged bicyclic carbocyclyl, fused bicyclic carbocyclyl and spiro bicyclic carbocyclyl group, and fused bicyclic system contains two rings which share two adjacent ring atoms. Bridged bicyclic group contains two rings which share three or four adjacent ring atoms. Spiro bicyclic system contains two rings which share one ring atom. Some non-limiting examples of the cycloaliphatic group include cycloalkyl, cycloalkenyl and cycloalkynyl. Further examples of carbocyclyl groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Bridged bicyclic carbocyclyl group includes, but are not limited to, bicyclo[2.2.2]octyl, bicyclo[2.2.1]heptyl, bicyclo[3.3.1]nonyl, bicyclo[3.2.3]nonyl, and the like.

The term "cycloalkyl" refers to a saturated ring having 3 to 12 ring carbon atoms as a monocyclic, bicyclic, or tricyclic ring system, which has one or more attachments attaching to the rest of the molecule. In some embodiments, the cycloalkyl group contains 3 to 10 ring carbon atoms. In other embodiments, the cycloalkyl group contains 3 to 8 ring carbon atoms. In other embodiments, the cycloalkyl group contains 5 to 8 ring carbon atoms. In still other embodiments, the cycloalkyl group contains 3 to 6 ring carbon atoms. In yet other embodiments, the cycloalkyl group contains 5 to 6 ring carbon atoms. Examples of cycloalkyl group include, but are not limited to, cyclopropyl, cyclobutyl, cyclopentyl, and the like. The cycloalkyl radical is independently unsubstituted or substituted with one or more substituents described herein.

The term "heterocycle", "heterocyclyl", or "heterocyclic ring" as used interchangeably herein refers to a saturated or partially unsaturated non-aromatic monocyclic, bicyclic or tricyclic ring containing 3-12 ring atoms of which at least one ring atom is selected from nitrogen, sulfur and oxygen, and the heterocyclyl group is non-aromatic and there is no any aromatic ring existing in it, which may has one ore more attachments attached to the rest of the molecule. The term "heterocyclyl" includes a monocyclic, bicyclic, or polycyclic fused, spiro, bridged heterocyclic ring system. Biheterocyclyl radical includes bridged biheterocyclyl, fused biheterocyclyl and spiro biheterocyclyl. Unless otherwise specified, the heterocyclyl group may be carbon or nitrogen linked, and a —CH$_2$— group can be optionally replaced by a —C(=O)— group. In which, the sulfur can be optionally oxygenized to S-oxide. The nitrogen can be optionally oxygenized to N-oxide. In some embodiments, the heterocyclyl group is a 3- to 8-membered heterocyclyl group; in other embodiments, the heterocyclyl group is a 3- to 6-membered heterocyclyl group; in other embodiments, the heterocyclyl group is a 5- to 7-membered heterocyclyl group; in other embodiments, the heterocyclyl group is a 5- to 8-membered heterocyclyl group; in other embodiments, the heterocyclyl group is a 6- to 8-membered heterocyclyl group; in other embodiments, the heterocyclyl group is a 5- to 6-membered heterocyclyl group; in other embodiments, the heterocyclyl group is a 4-membered heterocyclyl group; in other embodiments, the heterocyclyl group is a 5-membered heterocyclyl group; in other embodiments, the heterocyclyl group is a 6-membered heterocyclyl group; in other embodiments, the heterocyclyl group is a 7-membered heterocyclyl group; in other embodiments, the heterocyclyl group is a 8-membered heterocyclyl group.

Some non-limiting examples of the heterocyclyl group include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, and the like. Some non-limiting examples of heterocyclyl wherein —$CH_2$— group is replaced by —C(=O)— moiety include 2-oxopyrrolidinyl, oxo-1,3-thiazolidinyl, 2-piperidinonyl, 3,5-dioxopiperidinyl, pyrimidinedione-yl, and the like. Some non-limiting examples of heterocyclyl wherein the ring sulfur atom is oxidized is sulfolanyl and 1,1-dioxo-thiomorpholinyl. Some non-limiting examples of the bridged heterocyclyl group include, 2-oxabicyclo[2.2.2]octyl, 1-azabicyclo[2.2.2]octyl, 3-azabicyclo[3.2.1]octyl, and the like. The heterocyclyl group may be optionally substituted with one or more substituents disclosed herein.

The term "bridged" refers to a bond, an atom or an unbranched atoms chain connecting two different parts of a molecule. The two atoms (usually but not always two tertiary carbon atoms) linked by the bridge denotes "bridgeheads".

The term "m-membered", where m is an integer typically describes the number of ring-forming atoms in a moiety where the number of ring-forming atoms is m. For example, piperidinyl is an example of a 6-membered heterocyclyl and 1,2,3,4-tetrahydro-naphthalene is an example of a 10-membered carbocyclyl group.

The term "heteroatom" refers to oxygen (O), sulfur (S), nitrogen (N), phosphorus (P) and silicon (Si), including any oxidized form of nitrogen (N), sulfur (S), or phosphorus (P); the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "halogen" refers to fluorine (F), chlorine (Cl), bromine (Br) or iodine (I).

The term "azido" or "$N_3$" refers to an azide moiety. This radical may be attached to other groups, for example, to a methyl group to form azidomethane (methyl azide, $MeN_3$); or attached to a phenyl group to form phenyl azide ($PhN_3$).

The term "aromaticity" usually refers to a cyclic closed conjugate system, π electrons of which are highly delocalized to produce delocalization energy, and the system has low energy and is stable.

The term "aryl" used alone or as a great part of "arylalkyl", "arylalkoxy" or "aryloxyalkyl", refers to monocyclic, bicyclic and tricyclic carbocyclic ring systems having a total of 6 to 14 ring members, or 6 to 12 ring members, or 6 to 10 ring members, wherein at least one ring in the system is aromatic, wherein each ring in the system contains 3 to 7 ring members and that has a single point or multipoint of attachment to the rest of the molecule. The term "aryl" may be used interchangeably with the term "aryl ring" or "aromatic ring". Some non-limiting examples of the aryl group include phenyl, 2,3-dihydro-1H-indenyl, naphthyl and anthracene. The aryl group may be optionally unsubstituted or substituted with one or more substituents disclosed herein.

The term "heteroaryl" used alone or as a great part of "heteroarylalkyl" or "heteroarylalkoxy", refers to monocyclic, bicyclic and tricyclic ring systems having a total of five to sixteen ring members, and in which at least one ring member is selected from heteroatom, and that has a single point or multipoint of attachment to the rest of the molecule. When a —$CH_2$— group exists in the heteroaryl group, the —$CH_2$— group can be optionally replaced by a —C(=O)— group. The term "heteroaryl" and "heteroaromatic ring" or "heteroaromatic compound" can be used interchangeably herein. In one embodiment, the heteroaryl group is a 5- to 14-membered heteroaryl comprising 1, 2, 3 or 4 heteroatoms independently selected from O, S and N. In another embodiment, the heteroaryl group is a 5- to 12-membered heteroaryl comprising 1, 2, 3 or 4 heteroatoms independently selected from O, S and N. In another embodiment, the heteroaryl group is a 5- to 10-membered heteroaryl comprising 1, 2, 3 or 4 heteroatoms independently selected from O, S and N. In another embodiment, the heteroaryl group is a 5- to 8-membered heteroaryl comprising 1, 2, 3 or 4 heteroatoms independently selected from O, S and N. In another embodiment, the heteroaryl group is a 5- to 7-membered heteroaryl comprising 1, 2, 3 or 4 heteroatoms independently selected from O, S and N. In another embodiment, the heteroaryl group is a 5- to 6-membered heteroaryl comprising 1, 2, 3 or 4 heteroatoms independently selected from O, S and N. In another embodiment, the heteroaryl group is a 5-membered heteroaryl comprising 1, 2, 3 or 4 heteroatoms independently selected from O, S and N. In another embodiment, the heteroaryl group is a 6-membered heteroaryl comprising 1, 2, 3 or 4 heteroatoms independently selected from O, S and N.

Some non-limiting examples of the heteroaryl group include the following monocyclic ring: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5H-tetrazolyl, 2H-tetrazolyl), triazolyl (e.g., 2-triazolyl, 5-triazolyl, 4H-1,2,4-triazolyl, 1H-1,2,4-triazolyl and 1,2,3-triazolyl), 2-thienyl, 3-thienyl, pyrazolyl (e.g., 2-pyrazolyl and 3-pyrazolyl), isothiazolyl, 1,2,3-oxadiazolyl, 1,2,5-oxadiazolyl, 1,2,4-oxadiazolyl, 1,3,4-oxadiazolyl, 1,2,3-thiadiazolyl, 1,3,4-thiadiazolyl, 1,2,5-thiadiazolyl, pyrazinyl, 1,3,5-triazinyl, and the following bicycles, but are not limited to: indolinyl, 1,2,3,4-tetrahydroisoquinolinyl, benzimidazolyl, benzofuryl, benzothiophenyl, indolyl (e.g., 2-indolyl), purinyl, quinolinyl (e.g., 2-quinolinyl, 3-quinolinyl, 4-quinolinyl), isoquinolinyl (e.g., 1-isoquinolinyl, 3-isoquinolinyl or 4-isoquinolinyl), phenoxathianyl,

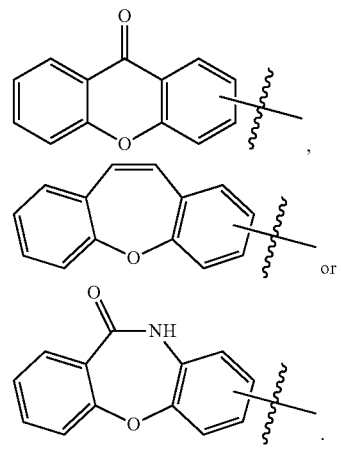

The heteroaryl group is optionally substituted with one or more substituents disclosed herein.

The terms "carboxy" or "carboxyl", whether used alone or with other terms, such as "carboxyalkyl", refer to —CO$_2$H.

The term "carbonyl", whether used alone or with other terms, such as "aminocarbonyl", "acyloxy", denotes —(C=O)—.

The term "alkylamino" refers to "N-alkylamino" and "N,N-dialkylamino" wherein amino groups are independently substituted with one alkyl radical or two alkyl radicals, respectively. In some embodiments, the alkylamino group is lower alkylamino group having one or two alkyl groups of 1 to 6 carbon atoms attached to nitrogen atom. In other embodiments, the alkylamino group is lower alkylamino group having 1 to 3 carbon atoms. Suitable alkylamino radical may be monoalkylamino or dialkylamino. Examples of the alkylamino radical include, but are not limited to, N-methylamino, N-ethylamino, N,N-dimethylamino, N,N-diethylamino, and the like.

The term "arylamino" refers to an amino group substituted with one or two aryl groups. Some non-limiting examples of such group included N-phenylamino. In some embodiments, the aryl group of the arylamino may be further substituted.

The term "aminoalkyl" refers to a C$_{1-10}$ linear or branched-chain alkyl group substituted with one or more amino groups. In some embodiments, the aminoalkyl is a C$_{1-6}$ lower aminoalkyl group generated from a C$_{1-6}$ alkyl which is substituted with one or more amino groups. Some non-limiting examples of the aminoalkyl group include aminomethyl, aminoethyl, aminopropyl, aminobutyl and aminohexyl.

As described herein, a bond drawn from a substituent to the center of one ring within a ring system represents substitution of substituents at any substitutable position on the rings, and wherein the ring system includes mono-, bi- or polycyclic ring system. For example, formula a represents substitution of substituents at any substitutable position on the cyclic system, i.e., formula b-1 to formula b-8:

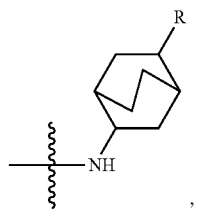

formula a

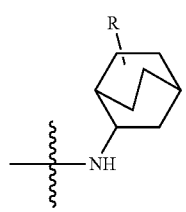

formula b-1

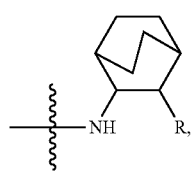

formula b-2

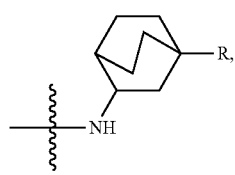

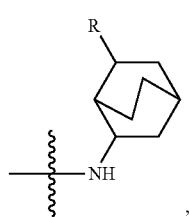

Formula b-3

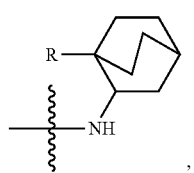

Formula b-4

Formula b-5

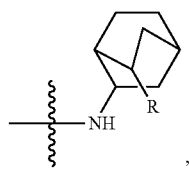

Formula b-6

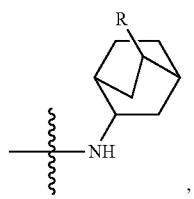

Formula b-7

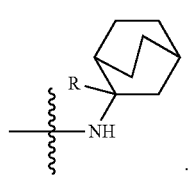

Formula b-8

As described herein, a bond drawn from a substituent to the center of one ring within a ring system represents the bond can attach to the rest of the molecule at any attachable position on the rings. For example, formula c represents substitution of substituents at any substitutable position on the rings, i.e., formula d-1 and formula d-2.

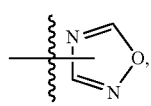

formula c

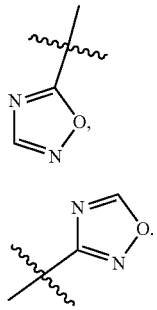

formula d-1

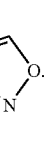

formula d-2

The term "unsaturated" refers to a moiety having one or more units of unsaturation.

The term "include" or "comprise" is meant to be open ended, including the indicated component but not excluding other elements.

As described herein, the term "pharmaceutically acceptable carrier" includes any solvents, dispersion media, coating agents, surfactants, antioxidants, preservatives (e.g., antibacterial agents, antifungal agents), isotonic agents, salt, drug stabilizers, binders, excipients, dispersants, lubricants, sweetening agents, flavoring agents, coloring agents, or a combination thereof, all of which are well known to the skilled in the art. (e.g., *Remington's Pharmaceutical Sciences*, 18th Ed. Mack Printing Company, 1990, pp. 1289-1329, all of which are incorporated herein by reference). Except any conventional carrier is incompatible with the active ingredient, the pharmaceutically acceptable carriers are effectively used in the treatment or pharmaceutical compositions.

As used herein, the term "inhibition of the replication of influenza viruses" includes both the reduction in the amount of virus replication (e.g., the reduction by at least 10%) and the complete arrest of virus replication (i.e., 100% reduction in the amount of virus replication). In some embodiments, the replication of influenza viruses are inhibited by at least 50%, at least 65%, at least 75%, at least 85%, at least 90%, or at least 95%.

As used herein, an "effective amount" refers to an amount sufficient to elicit the desired biological response. In the present invention, the desired biological response is to inhibit the replication of influenza virus, to reduce the amount of influenza viruses or to reduce or ameliorate the severity, duration, progression, or onset of a influenza virus infection, prevent the advancement of an influenza virus infection, prevent the recurrence, development, onset or progression of a symptom associated with an influenza virus infection, or enhance or improve the prophylactic or therapeutic effect(s) of another therapy used against influenza infections. The precise amount of compound administered to a subject will depend on the mode of administration, the type and severity of the infection and on the characteristics of the subject, such as general health, age, sex, body weight and tolerance to drugs. The skilled artisan will be able to determine appropriate dosages depending on these and other factors. When co-administered with other anti viral agents, e.g., when co-administered with an anti-influenza medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between approximately 0.01 to 100 mg/kg body weight/day for therapeutic or prophylactic treatment.

As used herein, the terms "treat", "treatment" and "treating" refer to both therapeutic and prophylactic treatments. For example, therapeutic treatments includes the reduction or amelioration of the progression, severity and/or duration of influenza viruses mediated conditions, or the amelioration of one or more symptoms (specifically, one or more discernible symptoms) of influenza viruses mediated conditions, resulting from the administration of one or more therapies (e.g., one or more therapeutic agents such as a compound or composition of the invention). In specific embodiments, the therapeutic treatment includes the amelioration of at least one measurable physical parameter of an influenza virus mediated condition. In other embodiments the therapeutic treatment includes the inhibition of the progression of an influenza virus mediated condition, either physically by, e.g., stabilization of a discernible symptom, physiologically by, e.g., stabilization of a physical parameter, or both. In other embodiments the therapeutic treatment includes the reduction or stabilization of influenza viruses mediated infections. Antiviral drugs can be used in the community setting to treat people who already have influenza to reduce the severity of symptoms and reduce the number of days that they are sick.

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, p-toluenesulfonyl (Ts), t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl) ethoxymethyl, 2-(p-toluenesulfonyl) ethyl, 2-(p-nitrophenylsulfenyl)ethyl, 2-(diphenylphosphino)ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

DESCRIPTION OF COMPOUNDS OF THE INVENTION

The invention discloses a novel class of compounds used as inhibitors of influenza virus RNA polymerase. These compounds and compositions thereof can be used for preventing, managing, treating or lessening virus infection in patients.

In one aspect, provided herein is a compound having Formula (I) or a stereoisomer, a tautomer, an N-oxide, a solvate, a metabolite, a pharmaceutically acceptable salt or a prodrug thereof,

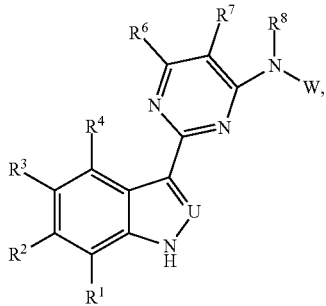

(I)

wherein $R^1$, $R^2$, $R^3$, $R^4$, $R^6$, $R^7$, $R^8$, U and W are as defined herein.

In some embodiments,

U is N or $CR^5$;

each of $R^1$, $R^2$, $R^3$, $R^4$ and $R^5$ is independently H, D, F, Cl, Br, CN, $NO_2$, —C(=O)$R^a$, —C(=O)$OR^b$, —C(=O)$NR^cR^d$, $OR^b$, —$NR^cR^d$, $R^bO$—$C_{1-4}$ alkylene, $R^dR^cN$—$C_{1-4}$ alkylene, $C_{1-6}$ alkyl, $C_{2-6}$ alkenyl or $C_{2-6}$ alkynyl, and wherein each of the $C_{1-6}$ alkyl, $C_{2-6}$ alkenyl and $C_{2-6}$ alkynyl is independently unsubstituted or substituted with 1, 2, 3 or 4 substituents independently selected from D, F, Cl, Br, CN, $OR^b$, —$NR^cR^d$, $C_{1-6}$ alkyl, $C_{1-6}$ haloalkyl, $R^bO$—$C_{1-4}$ alkylene or $R^dR^cN$—$C_{1-4}$ alkylene;

$R^6$ is $OR^b$, $C_{2-6}$ alkyl, $C_{2-6}$ alkenyl, $C_{2-6}$ alkynyl, $C_{3-12}$ carbocyclyl, $C_{3-12}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 16-membered heteroaryl or (5- to 16-membered heteroaryl)-$C_{1-4}$ alkylene, and wherein each of the $C_{2-6}$ alkyl, $C_{2-6}$ alkenyl, $C_{2-6}$ alkynyl, $C_{3-12}$ carbocyclyl, $C_{3-12}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 16-membered heteroaryl and (5- to 16-membered heteroaryl)-$C_{1-4}$ alkylene is independently unsubstituted or substituted with 1, 2, 3, 4 or 5 R';

$R^7$ is H, D, F, Cl, Br, CN, $NO_2$, —C(=O)$R^a$, —C(=O)$OR^b$, —C(=O)$NR^cR^d$, $OR^b$, —$NR^cR^d$, $R^bO$—$C_{1-4}$ alkylene, $R^dR^cN$—$C_{1-4}$ alkylene, $C_{1-6}$ alkyl, $C_{2-6}$ alkenyl, $C_{2-6}$ alkynyl, $C_{3-12}$ cycloalkyl, $C_{3-12}$ cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene, and wherein each of the $C_{1-6}$ alkyl, $C_{2-6}$ alkenyl, $C_{2-6}$ alkynyl, $C_{3-12}$ cycloalkyl, $C_{3-12}$ cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene is independently unsubstituted or substituted with 1, 2, 3, 4 or 5 R';

or, $R^6$ and $R^7$, together with the carbon atoms to which they are attached, form a $C_{3-12}$ carbocyclic ring, 3- to 12-membered heterocyclic ring, $C_{6-10}$ aromatic ring or 5- to 10-membered heteroaromatic ring, and wherein each of the $C_{3-12}$ carbocyclic ring, 3- to 12-membered heterocyclic ring, $C_{6-10}$ aromatic ring and 5- to 10-membered heteroaromatic ring is independently unsubstituted or substituted with 1, 2, 3, 4 or 5 R';

each R' is independently D, F, Cl, Br, CN, $NO_2$, $OR^b$, —$NR^cR^d$, $R^bO$—$C_{1-4}$ alkylene, $R^dR^cN$—$C_{1-4}$ alkylene, —C(=O)$R^a$, —C(=O)$OR^b$, —C(=O)$NR^cR^d$, $C_{1-12}$ alkyl, $C_{1-6}$ haloalkyl, $C_{3-6}$ cycloalkyl, $C_{3-6}$ cycloalkyl-$C_{1-4}$ alkylene, 3- to 8-membered heterocyclyl, (3- to 8-membered heterocyclyl)-$C_{1-4}$ alkylene, $C_{6-10}$ aryl, $C_{6-10}$ aryl-$C_{1-4}$ alkylene, 5- to 8-membered heteroaryl or (5- to 8-membered heteroaryl)-$C_{1-4}$ alkylene, and wherein each of the $C_{1-12}$ alkyl, $C_{1-6}$ haloalkyl, $C_{3-6}$ cycloalkyl, $C_{3-6}$ cycloalkyl-$C_{1-4}$ alkylene, 3- to 8-membered heterocyclyl, (3- to 8-membered heterocyclyl)-$C_{1-4}$ alkylene, $C_{6-10}$ aryl, $C_{6-10}$ aryl-$C_{1-4}$ alkylene, 5- to 8-membered heteroaryl and (5- to 8-membered heteroaryl)-$C_{1-4}$ alkylene is independently unsubstituted or substituted with 1, 2, 3 or 4 substituents independently selected from D, F, Cl, Br, CN, $NO_2$, $OR^b$, —$NR^cR^d$, $C_{1-6}$ alkyl, $C_{1-6}$ haloalkyl, $R^bO$—$C_{1-4}$ alkylene or $R^dR^cN$—$C_{1-4}$ alkylene;

$R^8$ is H, D or $C_{1-6}$ alkyl, and wherein $C_{1-6}$ alkyl is optionally substituted with 1, 2, 3 or 4 substituents independently selected from D, F, Cl, Br, CN, $NO_2$ or $OR^b$;

W is $C_{1-8}$ alkyl, $C_{3-12}$ carbocyclyl or 3- to 12-membered heterocyclyl, and wherein $C_{1-8}$ alkyl, $C_{3-12}$ carbocyclyl and 3- to 12-membered heterocyclyl is independently unsubstituted or substituted with 1, 2, 3 or 4 $R^w$;

each $R^w$ is independently D, F, Cl, Br, CN, $NO_2$, oxo (=O), —C(=O)$R^a$, —C(=O)$OR^b$, —$NR^eC$(=O)$R^a$, —$NR^eC$(=O)$NR^cR^d$, —S(=O)$_2R^f$, —S(=O)$_2NR^eC$(=O)$R^a$, —S(=O)$_2NR^cR^d$, $(R^bO)_2P$(=O)—$C_{0-2}$ alkylene, $OR^b$, $R^bO$—$C_{1-2}$ alkylene, $C_{1-6}$ alkyl or 5- to 6-membered heteroaryl, and wherein each of the $C_{1-6}$ alkyl and 5- to 6-membered heteroaryl is independently unsubstituted or substituted with 1, 2, 3 or 4 substituents independently selected from D, F, Cl, Br, CN, $N_3$, oxo (=O), $NO_2$, $OR^b$, $C_{1-6}$ alkyl or $C_{1-6}$ haloalkyl;

each $R^a$, $R^b$, $R^c$, $R^d$, $R^e$ and $R^f$ is independently H, D, $C_{1-6}$ haloalkyl, $C_{1-6}$ alkyl, $C_{2-6}$ alkenyl, $C_{2-6}$ alkynyl, $C_{3-6}$ carbocyclyl, $C_{3-6}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl, (5- to 10-membered heteroaryl)-$C_{1-4}$ alkylene;

or, $R^c$ and $R^d$, together with the nitrogen atom to which they are attached, form 3- to 8-membered heterocyclyl or 5- to 8-membered heteroaryl, and wherein each of the $C_{1-6}$ alkyl, $C_{2-6}$ alkenyl, $C_{2-6}$ alkynyl, $C_{3-6}$ carbocyclyl, $C_{3-6}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl, (5- to 10-membered heteroaryl)-$C_{1-4}$ alkylene, 3- to 8-membered heterocyclyl and 5- to 8-membered heteroaryl is independently unsubstituted or substituted with 1, 2, 3 or 4 substituents independently selected from D, F, Cl, CN, OH, $NH_2$, $C_{1-6}$ alkyl, $C_{1-6}$ haloalkyl, $C_{1-6}$ alkoxy or $C_{1-6}$ alkylamino.

In other embodiments, the compound having Formula (II) or a stereoisomer, a tautomer, an N-oxide, a solvate, a metabolite, a pharmaceutically acceptable salt or a prodrug thereof,

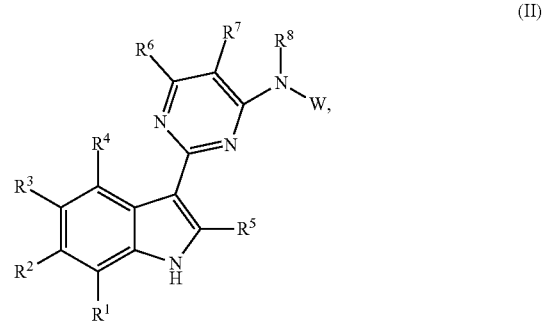

(II)

wherein $R^1$, $R^2$, $R^3$, $R^4$, $R^5$, $R^6$, $R^7$, $R^8$ and W are as defined herein.

In other embodiments, the compound having Formula (III) or a stereoisomer, a tautomer, an N-oxide, a solvate, a metabolite, a pharmaceutically acceptable salt or a prodrug thereof,

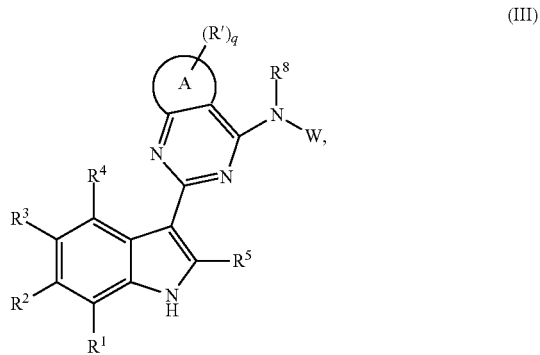

wherein, A is a $C_{3-12}$ carbocyclic ring, 3- to 12-membered heterocyclic ring, $C_{6-10}$ aromatic ring or 5- to 10-membered heteroaromatic ring;

q is 0, 1, 2, 3, 4 or 5; and $R^1$, $R^2$, $R^3$, $R^4$, $R^5$, $R^7$, $R^8$ and W are as defined herein.

In other embodiments, each of $R^1$, $R^2$, $R^3$, $R^4$ and $R^5$ is independently H, D, F, Cl, Br, CN, $NO_2$, —C(=O)$R^a$, —C(=O)$OR^b$, —C(=O)$NR^cR^d$, $OR^b$, —$NR^cR^d$, methyl, ethyl, n-propyl or i-propyl, and wherein each of methyl, ethyl, n-propyl and i-propyl is independently unsubstituted or substituted with 1, 2, 3 or 4 substituents independently selected from D, F, Cl, Br, CN, $OR^b$, —$NR^cR^d$ or $C_{1-3}$ haloalkyl.

In other embodiments, $R^6$ is $OR^b$, $C_{2-3}$ alkyl, $C_{2-4}$ alkenyl, $C_{2-4}$ alkynyl, $C_{3-6}$ carbocyclyl, $C_{3-6}$ carbocyclyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 14-membered heteroaryl or (5- to 14-membered heteroaryl)-$C_{1-4}$ alkylene, and wherein each of the $C_{2-3}$ alkyl, $C_{2-4}$ alkenyl, $C_{2-4}$ alkynyl, $C_{3-6}$ carbocyclyl, $C_{3-6}$ carbocyclyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 14-membered heteroaryl and (5- to 14-membered heteroaryl)-$C_{1-4}$ alkylene is independently unsubstituted or substituted with 1, 2, 3, 4 or 5 R';

$R^7$ is H, D, F, Cl, Br, CN, $NO_2$, —C(=O)$R^a$, —C(=O)$OR^b$, —C(=O)$NR^cR^d$, $OR^b$, —$NR^cR^d$, $C_{1-3}$ alkyl, $C_{2-4}$ alkenyl, $C_{2-4}$ alkynyl, $C_{3-6}$ cycloalkyl, $C_{3-6}$ cycloalkyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 6-membered heteroaryl or (5- to 6-membered heteroaryl)-$C_{1-4}$ alkylene, and wherein each of the $C_{1-3}$ alkyl, $C_{2-4}$ alkenyl, $C_{2-4}$ alkynyl, $C_{3-6}$ cycloalkyl, $C_{3-6}$ cycloalkyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 6-membered heteroaryl and (5- to 6-membered heteroaryl)-$C_{1-4}$ alkylene is independently unsubstituted or substituted with 1, 2, 3, 4 or 5 R';

or, $R^6$ and $R^7$, together with the carbon atoms to which they are attached, form a $C_{3-6}$ carbocyclic ring, 3- to 6-membered heterocyclic ring, $C_{6-10}$ aromatic ring or 5- to 10-membered heteroaromatic ring, and wherein each of the $C_{3-6}$ carbocyclic ring, 3- to 6-membered heterocyclic ring, $C_{6-10}$ aromatic ring and 5- to 10-membered heteroaromatic ring is independently unsubstituted or substituted with 1, 2, 3, 4 or 5 R'.

In other embodiments, each R' is independently D, F, Cl, Br, CN, $NO_2$, $OR^b$, —$NR^cR^d$, —C(=O)$R^a$, —C(=O)$NR^cR^d$, $C_{1-9}$ alkyl, $C_{1-3}$ haloalkyl, $C_{3-6}$ cycloalkyl, 5- to 6-membered heterocyclyl, phenyl, phenyl-$C_{1-2}$ alkylene or 5- to 6-membered heteroaryl, and wherein each of the $C_{1-9}$ alkyl, $C_{1-3}$ haloalkyl, $C_{3-6}$ cycloalkyl, 5- to 6-membered heterocyclyl, phenyl, phenyl-$C_{1-2}$ alkylene and 5- to 6-membered heteroaryl is independently unsubstituted or substituted with 1, 2, 3 or 4 substituents independently selected from D, F, Cl, Br, CN, $NO_2$, $OR^b$, —$NR^cR^d$, methyl, ethyl, n-propyl or i-propyl.

In other embodiments, $R^8$ is H, D, $CF_3$, methyl, ethyl, n-propyl or i-propyl.

In other embodiments, W is $C_{1-6}$ alkyl, $C_{5-8}$ carbocyclyl or 5- to 8-membered heterocyclyl, and wherein each of the $C_{1-6}$ alkyl, $C_{5-8}$ carbocyclyl and 5- to 8-membered heterocyclyl is independently unsubstituted or substituted with 1, 2, 3 or 4 $R^w$.

In other embodiments, each $R^w$ is independently D, F, Cl, Br, CN, $NO_2$, oxo (=O), —C(=O)$OCH_3$, —C(=O)$OCH_2CH_3$, —C(=O)OH, —NHC(=O)$R^a$, —NHC(=O)$NR^cR^d$, —S(=O)$_2R^f$, —S(=O)$_2$NHC(=O)$R^a$, —S(=O)$_2$$NR^cR^d$, $(R^bO)_2$P(=O)—$C_{0-2}$ alkylene, $OR^b$, methyl, ethyl, n-propyl, i-propyl, furyl, pyrrolyl, pyridyl, pyrazolyl, imdazolyl, triazolyl, tetrazolyl, oxazolyl, oxadiazolyl, 1,3,5-triazinyl, thiazolyl, thienyl, pyrazinyl, pyridazinyl or primidinyl, and wherein each of methyl, ethyl, n-propyl, i-propyl, furyl, pyrrolyl, pyridyl, pyrazolyl, imdazolyl, triazolyl, tetrazolyl, oxazolyl, oxadiazolyl, 1,3,5-triazinyl, thiazolyl, thienyl, pyrazinyl, pyridazinyl and primidinyl independently unsubstituted or substituted with 1, 2, 3 or 4 substituents independently selected from D, F, Cl, Br, CN, $N_3$, oxo (=O), $NO_2$, —$OCH_3$, $C_{1-3}$ alkyl or $C_{1-3}$ haloalkyl.

In other embodiments, each $R^a$, $R^b$, $R^c$, $R^d$, $R^e$ and $R^f$ is independently H, D, trifluoromethyl, methyl, ethyl, i-propyl, n-propyl, n-butyl, t-butyl, $C_{3-6}$ carbocyclyl, 5- to 6-membered heterocyclyl, phenyl, 5- to 6-membered heteroaryl, (5- to 6-membered heteroaryl)-$C_{1-4}$ alkylene; or, $R^c$ and $R^d$, together with the nitrogen atom to which they are attached, form a 5- to 6-membered heterocyclyl or 5- to 6-membered heteroaryl, and wherein each of methyl, ethyl, i-propyl, n-propyl, n-butyl, t-butyl, $C_{3-6}$ carbocyclyl, 5- to 6-membered heterocyclyl, phenyl, 5- to 6-membered heteroaryl and (5- to 6-membered heteroaryl)-$C_{1-4}$ alkylene is independently unsubstituted or substituted with 1, 2, 3 or 4 substituents independently selected from D, F, Cl, CN, OH, $NH_2$, $C_{1-3}$ alkyl, $C_{1-3}$ haloalkyl or methoxy.

In other embodiments, A is a $C_{3-6}$ carbocyclic ring, 3- to 6-membered heterocyclic ring, $C_{6-10}$ aromatic ring or 5- to 10-membered heteroaryl.

In other embodiments, $R^6$ is $OR^b$, $C_{2-4}$ alkynyl, $C_{3-6}$ carbocyclyl, 5- to 6-membered heterocyclyl, phenyl, naphthyl, furyl, benzofuryl, pyrrolyl, pyridyl, pyrazolyl, imdazolyl, benzimdazolyl, triazolyl, tetrazolyl, oxazolyl, oxadiazolyl, 1,3,5-triazinyl, thiazolyl, thienyl, benzothienyl, pyrazinyl, pyridazinyl, pyrimidinyl, indolyl, purinyl, quinolyl, isoquinolyl, phenoxathiinyl,

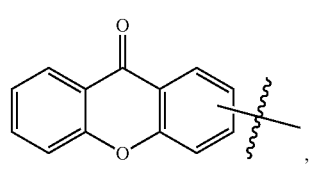

-continued

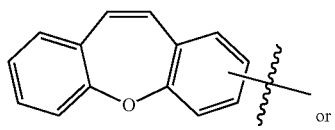
or

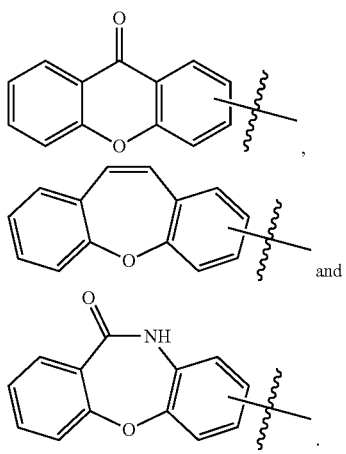
, and wherein each of C$_{2-4}$ alkynyl, C$_{3-6}$ carbocyclyl, 5- to 6-membered heterocyclyl, phenyl, naphthyl, furyl, benzofuryl, pyrrolyl, pyridyl, pyrazolyl, imdazolyl, benzimdazolyl, triazolyl, tetrazolyl, oxazolyl, oxadiazolyl, 1,3,5-triazinyl, thiazolyl, thienyl, benzothienyl, pyrazinyl, pyridazinyl, pyrimidinyl, indolyl, purinyl, quinolyl, isoquinolyl, phenoxathiinyl, is independently unsubstituted or substituted with 1, 2, 3, 4 or 5 R'.

In other embodiments, A is a C$_{3-6}$ carbocyclic ring, 3- to 6-membered heterocyclic ring, benzene, naphthalene, furan, benzofuran, pyrrole, pyridine, pyrazole, imidazole, benzoimidazole, triazole, tetrazole, oxazole, oxadiazole, 1,3,5-triazine, thiazole, thiophene, benzothiphene, pyrazine, pyridazine, pyrimidine, indole, purine, quinoline or isoquinoline.

In other embodiments, W is one of the following sub-formulae:

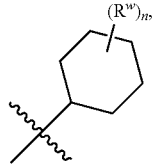 (W-1)

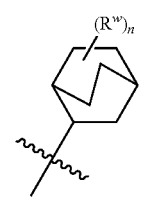 (W-2)

(W-3)

(W-4)

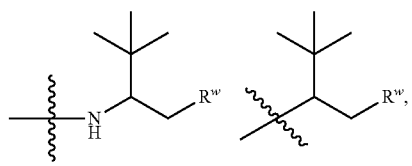
or (W-5)

wherein n is 0, 1, 2, 3, or 4; and
each R$^W$ is as defined herein.

In other embodiments, the compound having Formula (IV) or a stereoisomer, a tautomer, an N-oxide, a solvate, a metabolite, a pharmaceutically acceptable salt or a prodrug thereof,

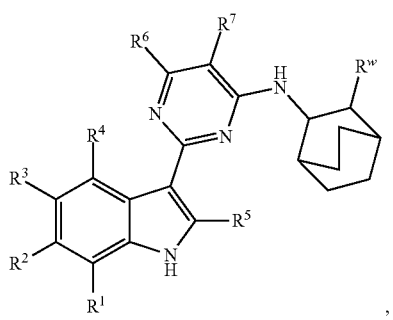
,
(IV)

wherein R$^1$, R$^2$, R$^3$, R$^4$, R$^5$, R$^6$, R$^7$ and R$^w$ are as defined herein.

In other embodiments, the compound having Formula (V) or a stereoisomer, a tautomer, an N-oxide, a solvate, a metabolite, a pharmaceutically acceptable salt or a prodrug thereof, (V)

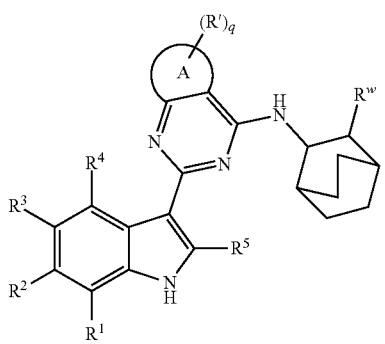

, wherein A, q, $R^1$, $R^2$, $R^3$, $R^4$, $R^5$, R' and $R^w$ are as defined herein.

In other embodiments, the compound having Formula (VI) or a stereoisomer, a tautomer, an N-oxide, a solvate, a metabolite, a pharmaceutically acceptable salt or a prodrug thereof, (VI)

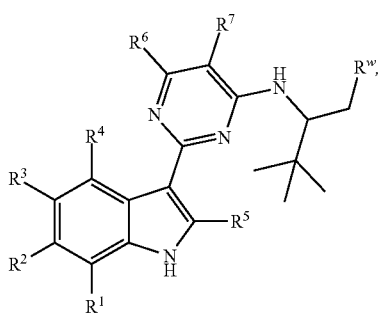

wherein $R^1$, $R^2$, $R^3$, $R^4$, $R^5$, $R^6$, $R^7$ and $R^w$ are as defined herein.

In other embodiments, the compound having Formula (VII) or a stereoisomer, a tautomer, an N-oxide, a solvate, a metabolite, a pharmaceutically acceptable salt or a prodrug thereof, (VII)

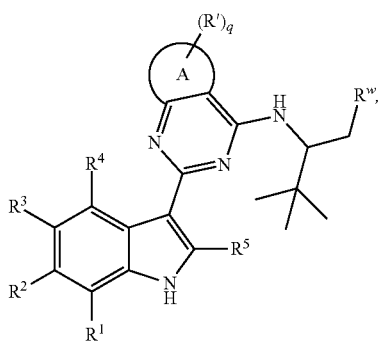

wherein A, q, $R^1$, $R^2$, $R^3$, $R^4$, $R^5$, R' and $R^w$ are as defined herein.

In other embodiments, the compound having Formula (VIII) or a stereoisomer, a tautomer, an N-oxide, a solvate, a metabolite, a pharmaceutically acceptable salt or a prodrug thereof, (VIII)

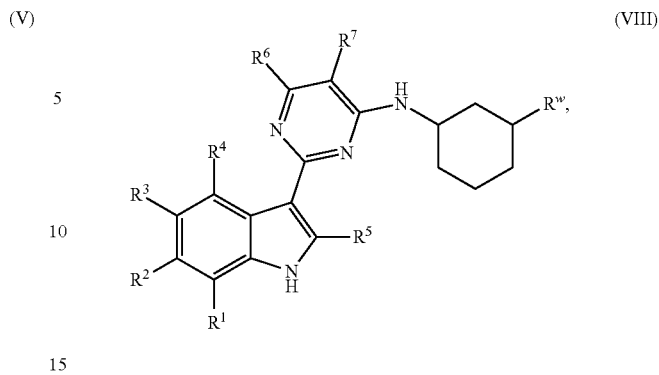

wherein $R^1$, $R^2$, $R^3$, $R^4$, $R^5$, $R^6$, $R^7$ and $R^w$ are as defined herein.

In other embodiments, the compound having Formula (IX) or a stereoisomer, a tautomer, an N-oxide, a solvate, a metabolite, a pharmaceutically acceptable salt or a prodrug thereof, (IX)

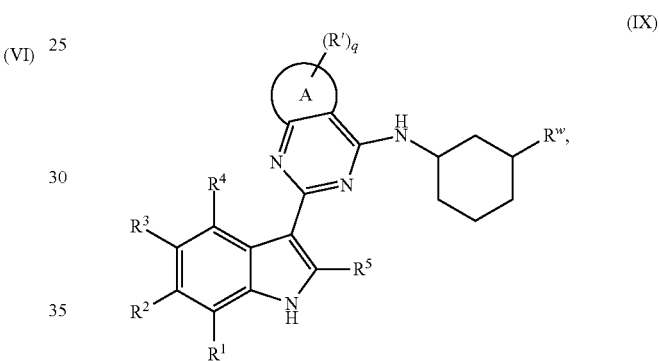

wherein A, q, $R^1$, $R^2$, $R^3$, $R^4$, $R^5$, R' and $R^w$ are as defined herein.

In other embodiments, the compound having Formula (X) or a stereoisomer, a tautomer, an N-oxide, a solvate, a metabolite, a pharmaceutically acceptable salt or a prodrug thereof, (X)


wherein $R^1$, $R^2$, $R^3$, $R^4$, $R^6$, $R^7$ and $R^w$ are as defined herein.

In other embodiments, the compound having Formula (XI) or a stereoisomer, a tautomer, an N-oxide, a solvate, a metabolite, a pharmaceutically acceptable salt or a prodrug thereof,

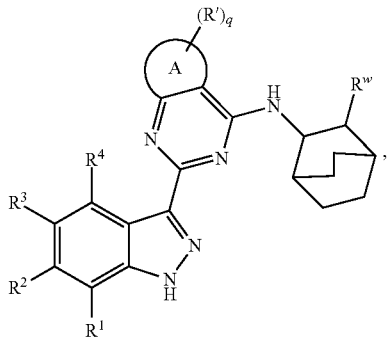

(XI)

wherein A, q, $R^1$, $R^2$, $R^3$, $R^4$, R' and $R^w$ are as defined herein.

In other embodiments, the compound having Formula (XII) or a stereoisomer, a tautomer, an N-oxide, a solvate, a metabolite, a pharmaceutically acceptable salt or a prodrug thereof,

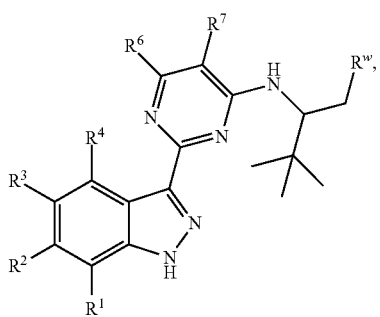

(XII)

wherein $R^1$, $R^2$, $R^3$, $R^4$, $R^6$, $R^7$ and $R^w$ are as defined herein.

In other embodiments, the compound having Formula (XIII) or a stereoisomer, a tautomer, an N-oxide, a solvate, a metabolite, a pharmaceutically acceptable salt or a prodrug thereof,

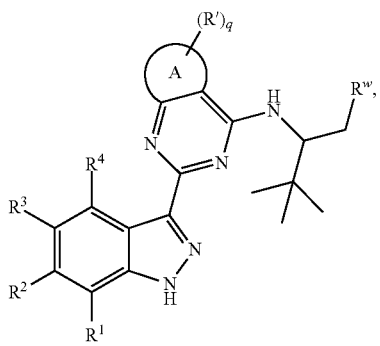

(XIII)

wherein A, q, $R^1$, $R^2$, $R^3$, $R^4$, R' and $R^w$ are as defined herein.

In other embodiments, the compound having Formula (XIV) or a stereoisomer, a tautomer, an N-oxide, a solvate, a metabolite, a pharmaceutically acceptable salt or a prodrug thereof,

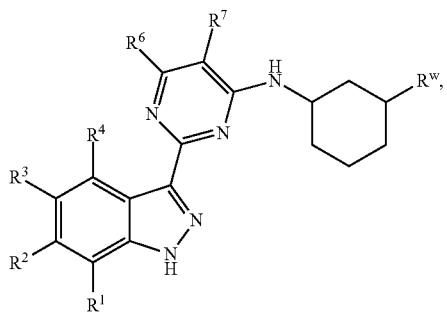

(XIV)

wherein $R^1$, $R^2$, $R^3$, $R^4$, $R^6$, $R^7$ and $R^w$ are as defined herein.

In other embodiments, the compound having Formula (XV) or a stereoisomer, a tautomer, an N-oxide, a solvate, a metabolite, a pharmaceutically acceptable salt or a prodrug thereof,

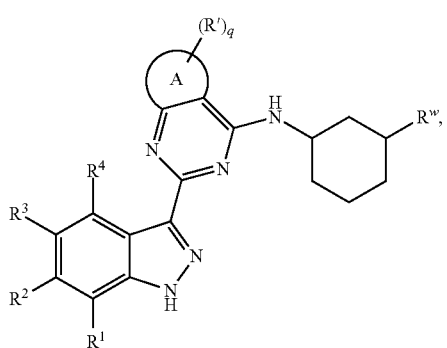

(XV)

Wherein A, q, $R^1$, $R^2$, $R^3$, $R^4$, R' and $R^w$ are as defined herein.

In another aspect, provided herein is one of the following compounds or a stereoisomer, a tautomer, an N-oxide, a solvate, a metabolite, a pharmaceutically acceptable salt or a prodrug thereof, but is not limited to the following compounds:

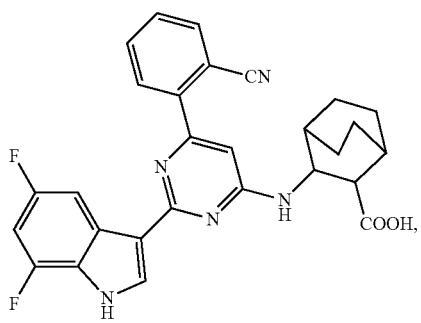

(1)

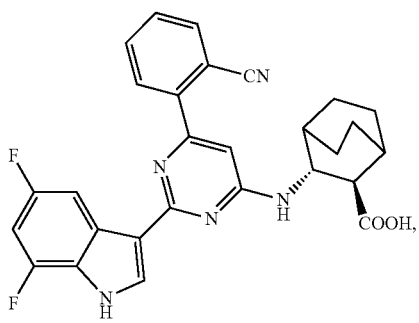
(2)
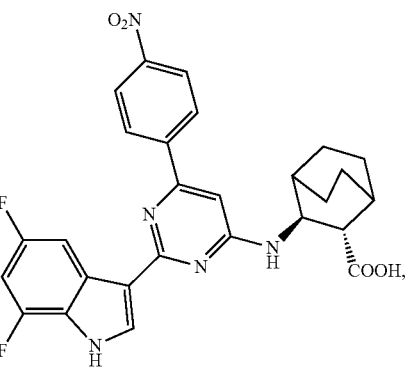
(6)
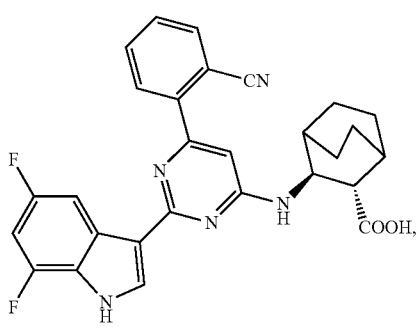
(3)
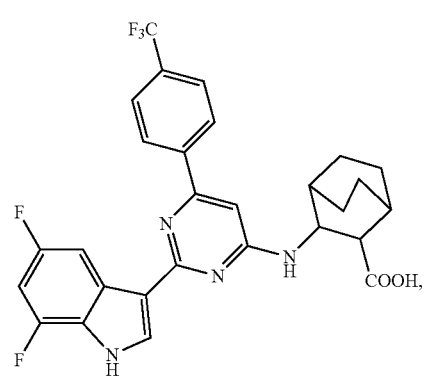
(7)
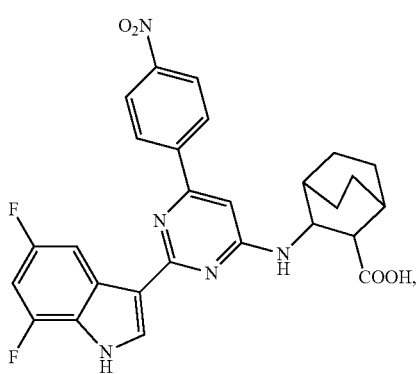
(4)
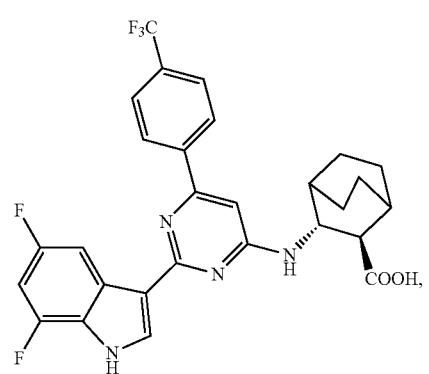
(8)
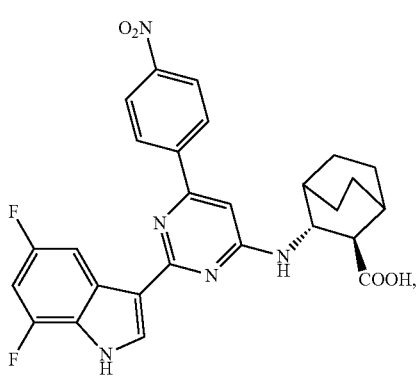
(5)
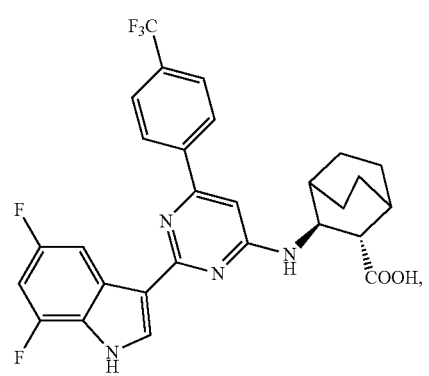
(9)

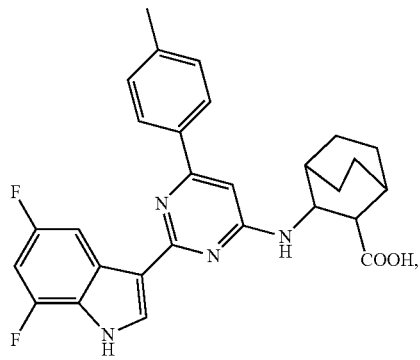
(10)
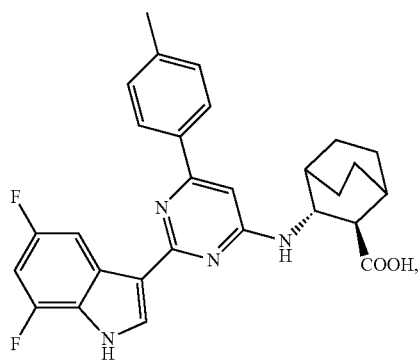
(11)
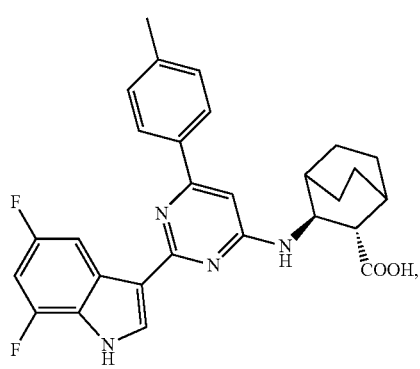
(12)
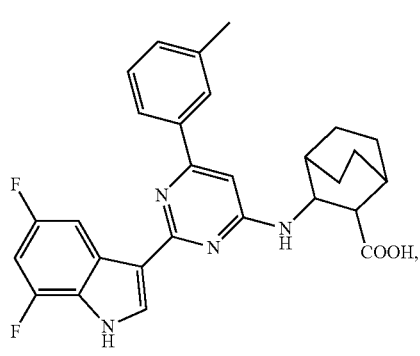
(13)
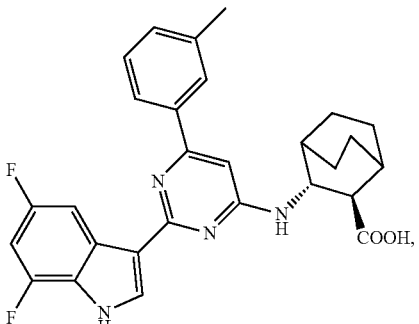
(14)
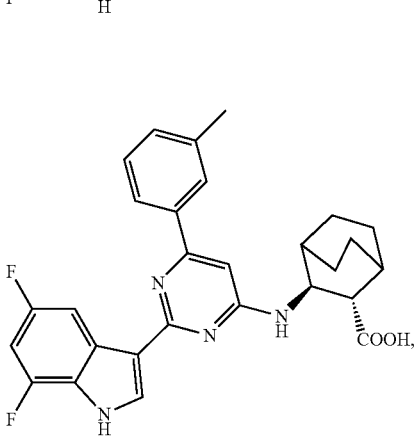
(15)
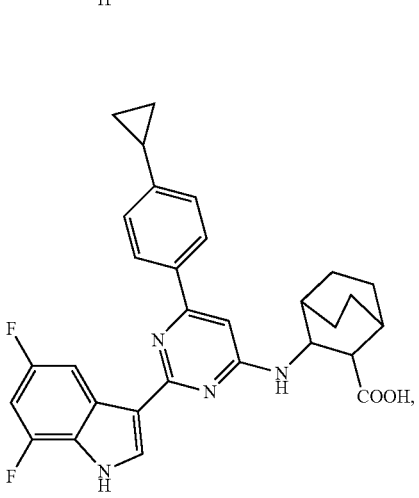
(16)
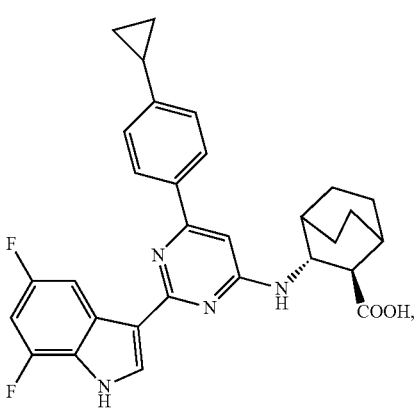
(17)

-continued
(18)
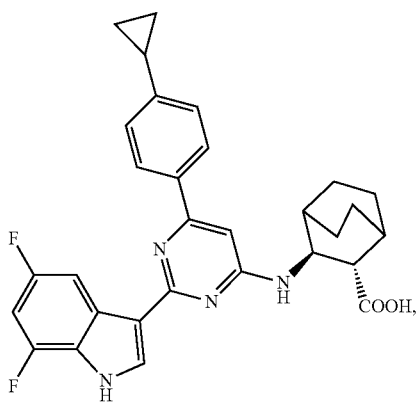
(19)
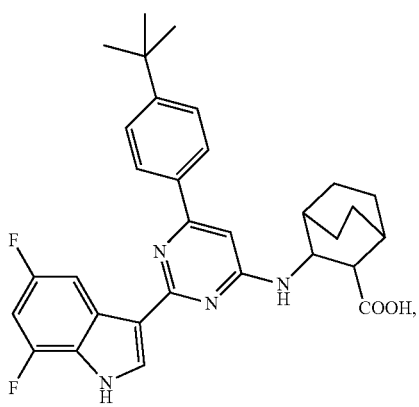
(20)
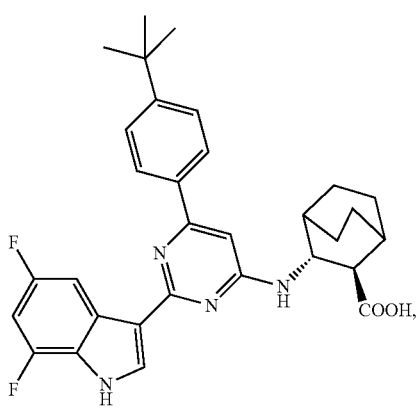
(21)
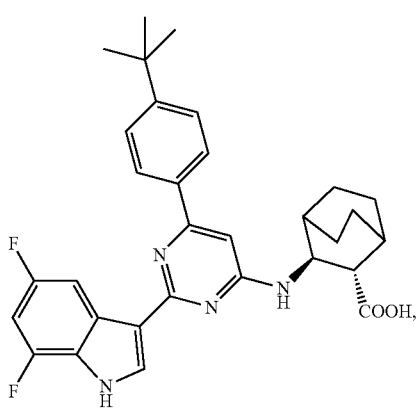
-continued
(22)
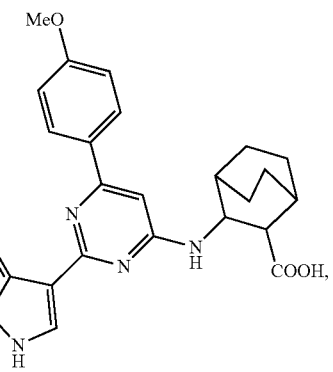
(23)
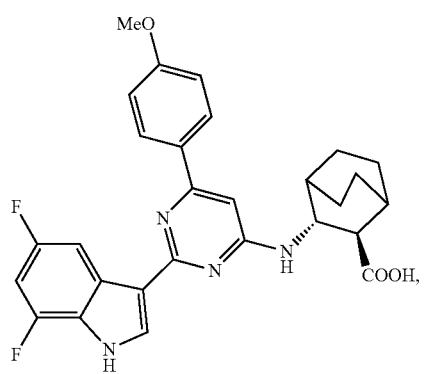
(24)
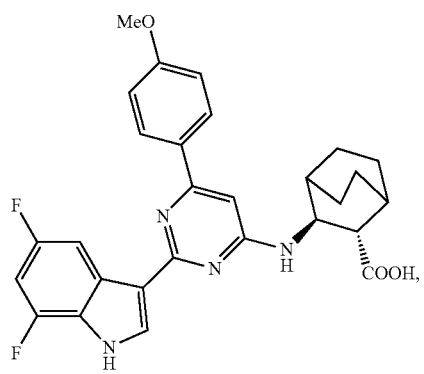
(25)
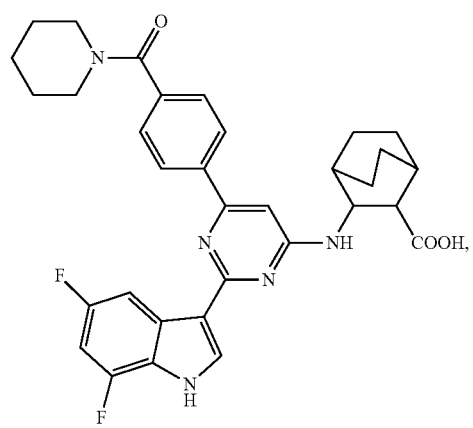

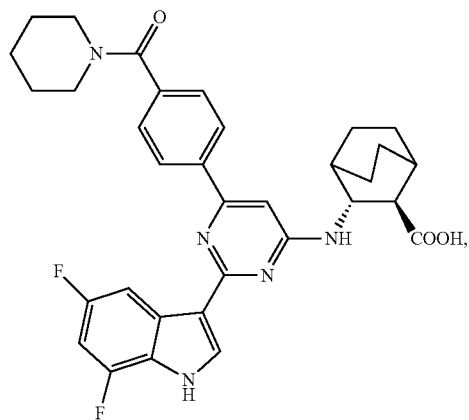
(26)
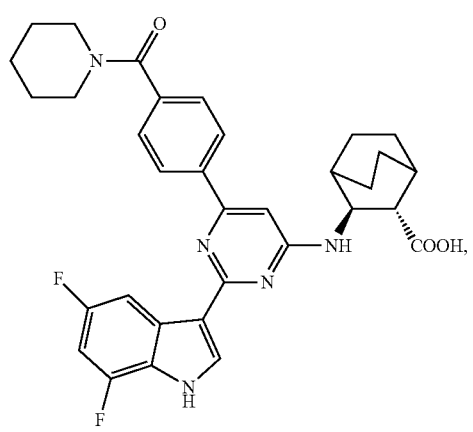
(27)
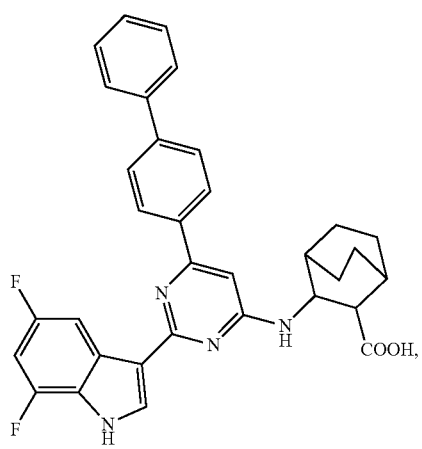
(28)
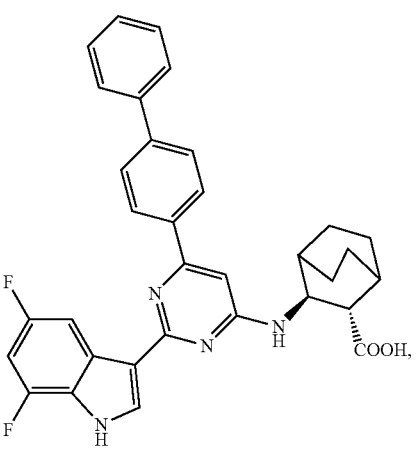
(29)
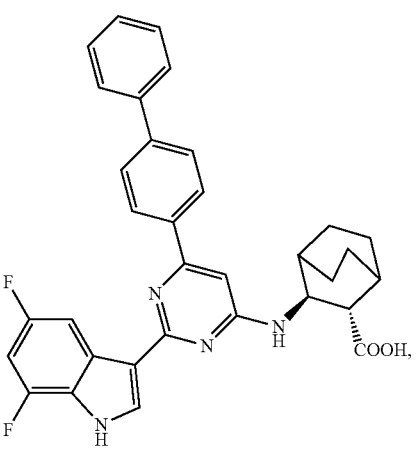
(30)
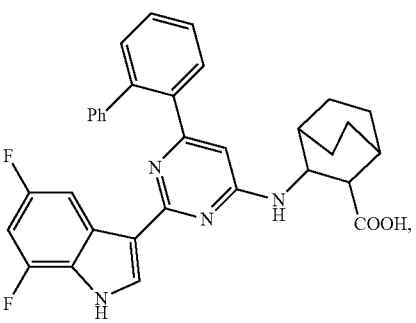
(31)
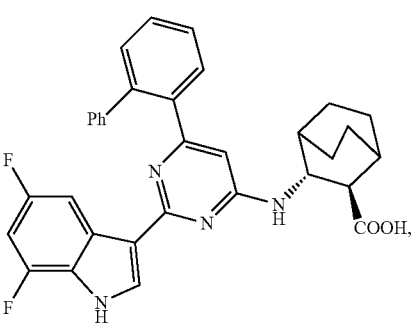
(32)

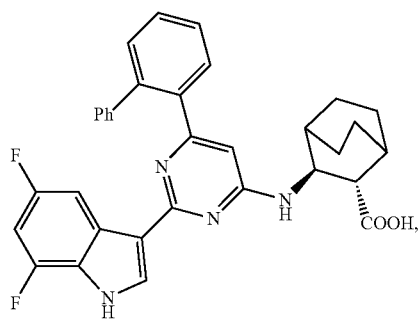
(33)
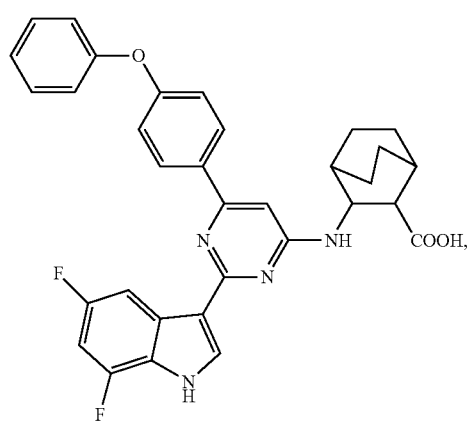
(34)
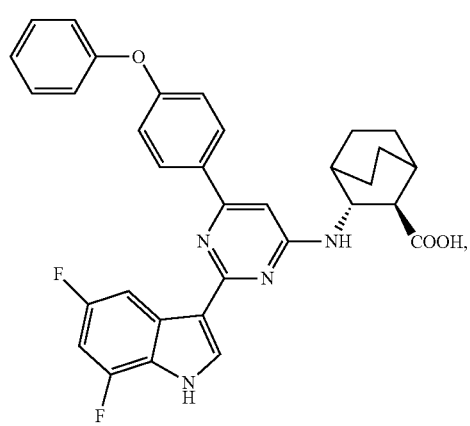
(35)
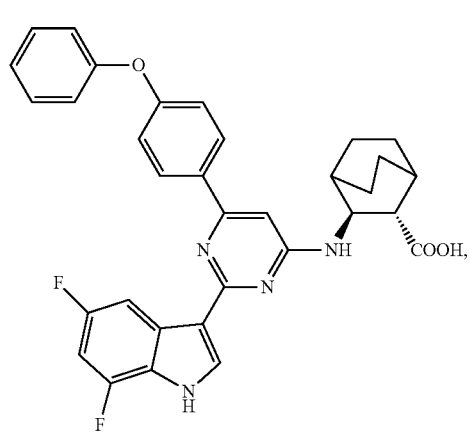
(36)
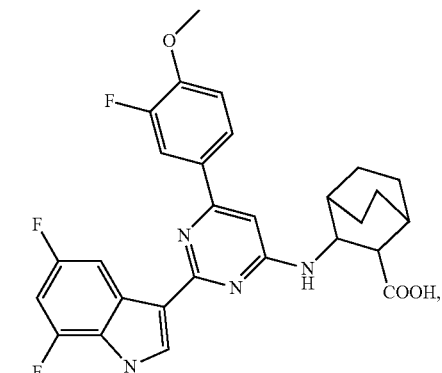
(37)
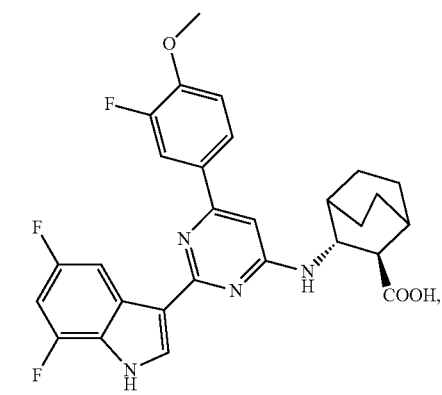
(38)
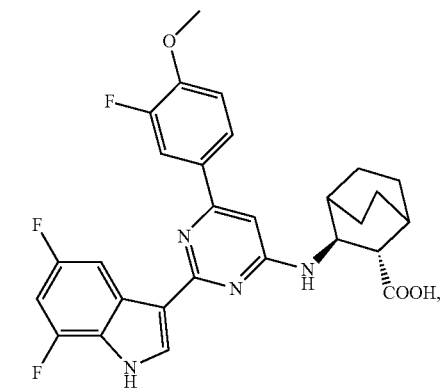
(39)
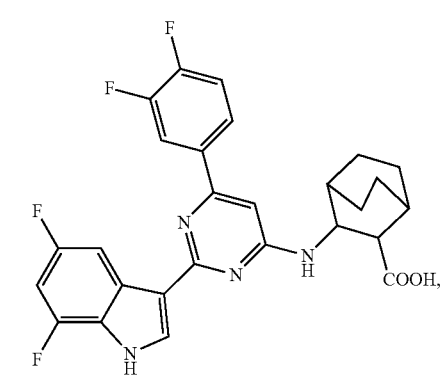
(40)

(41)
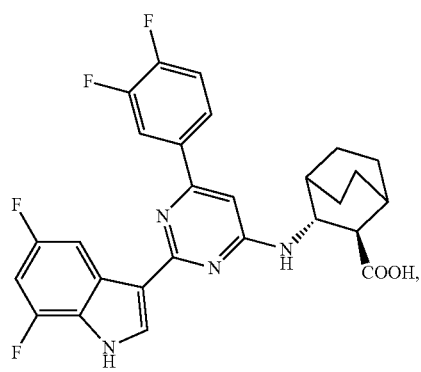
(42)
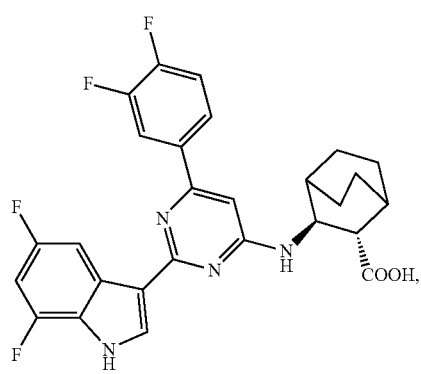
(43)
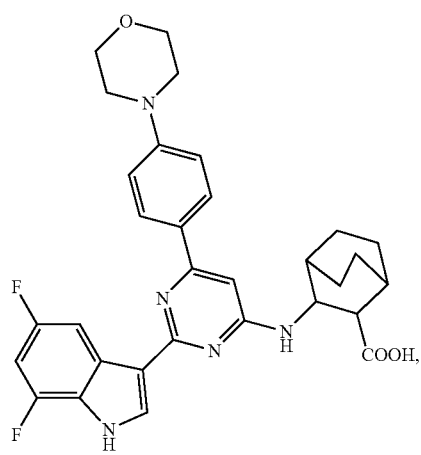
(44)
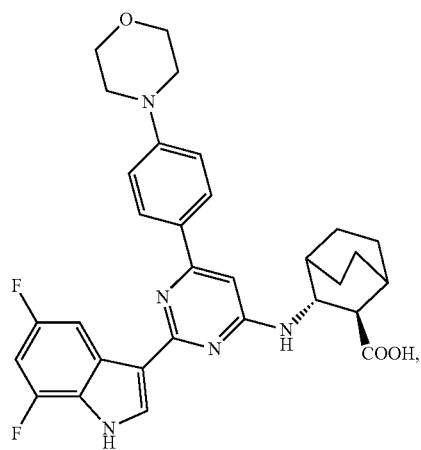
(45)
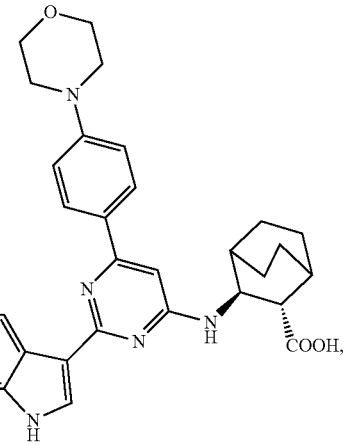
(46)
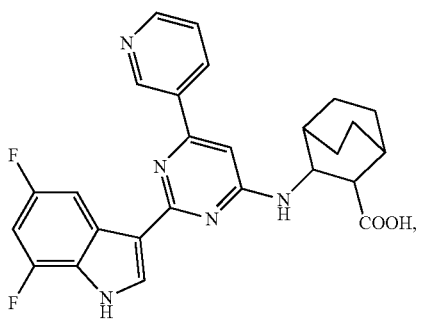
(47)
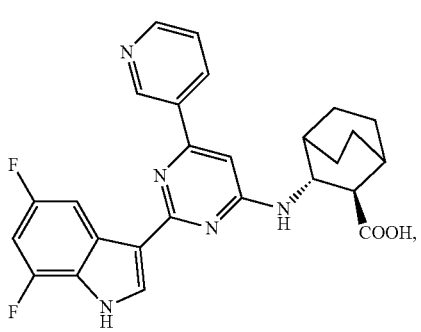
(48)
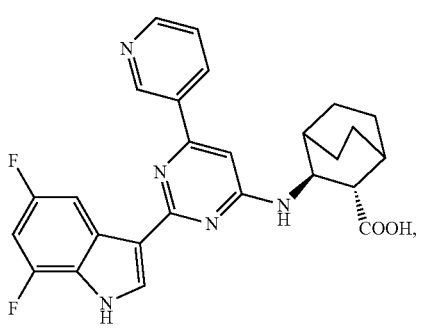

(49)
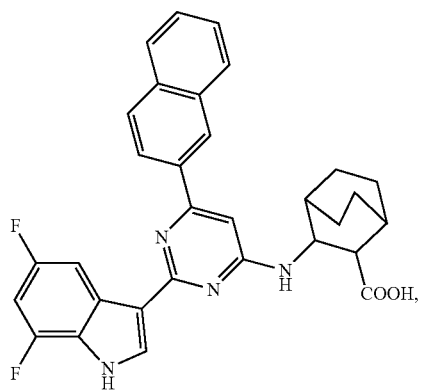
(50)
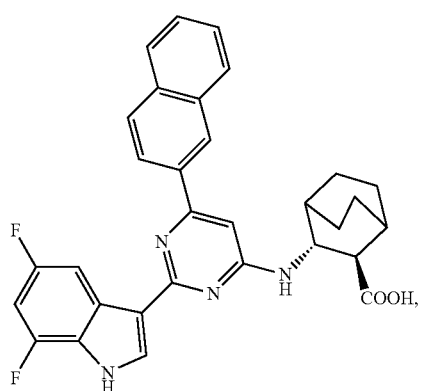
(51)
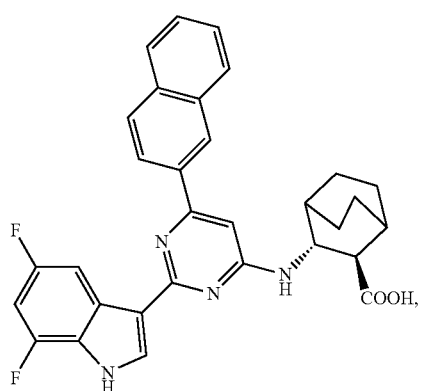
(52)
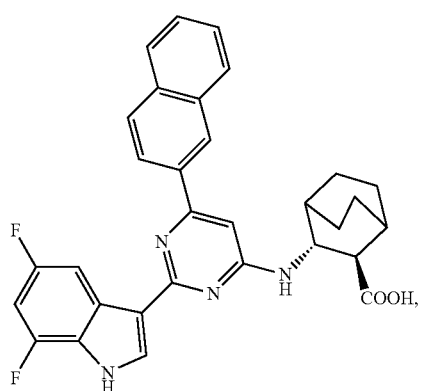
(53)
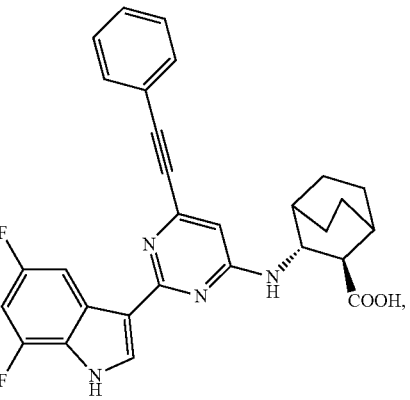
(54)
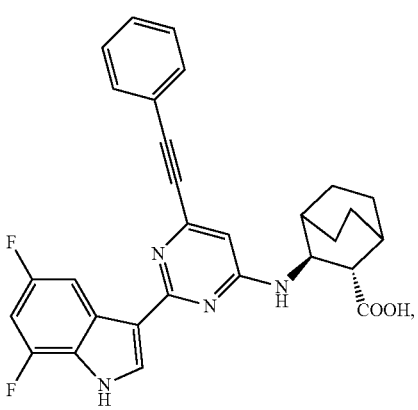
(55)
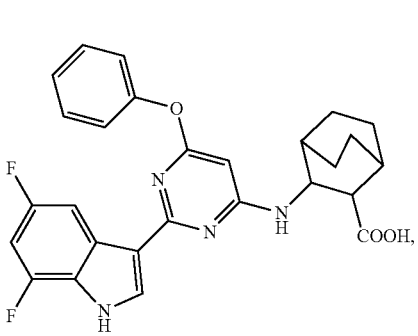
(56)
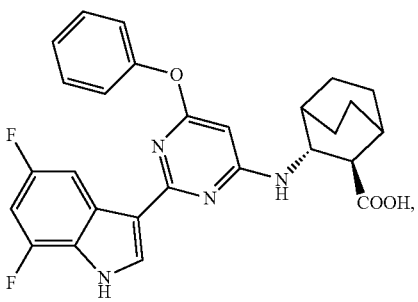

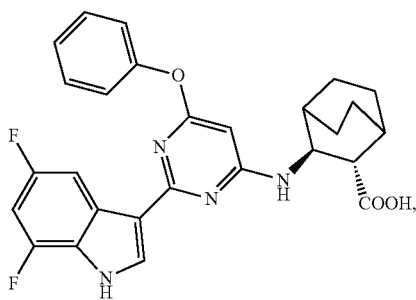
(57)
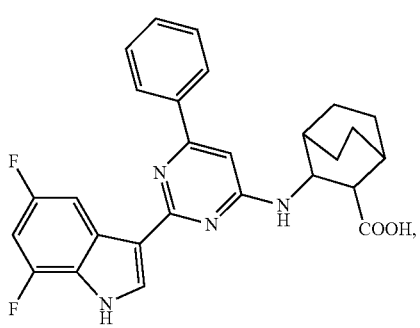
(58)
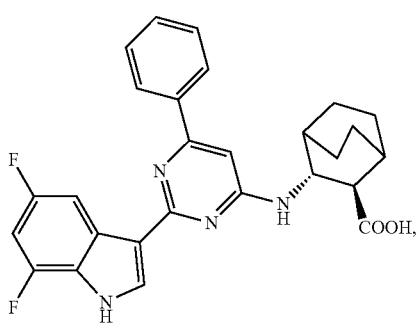
(59)
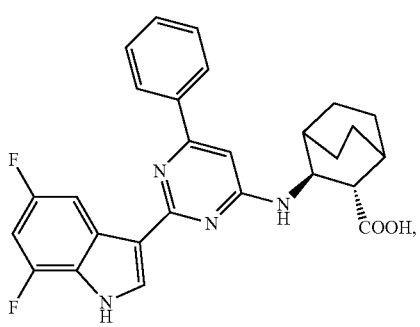
(60)
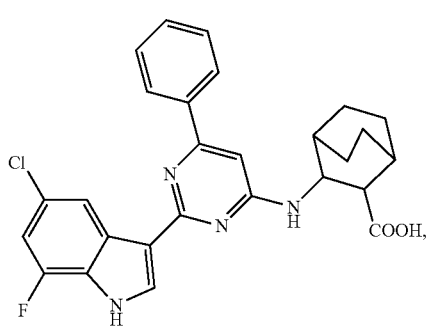
(61)
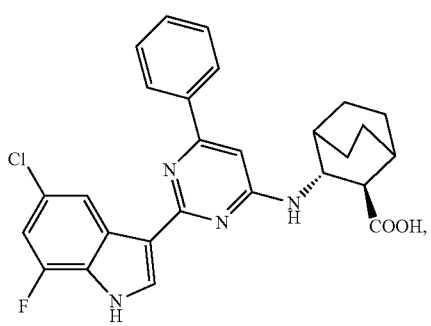
(62)
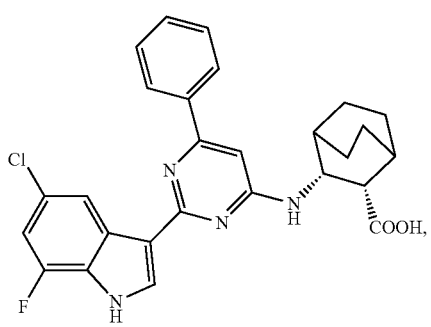
(63)
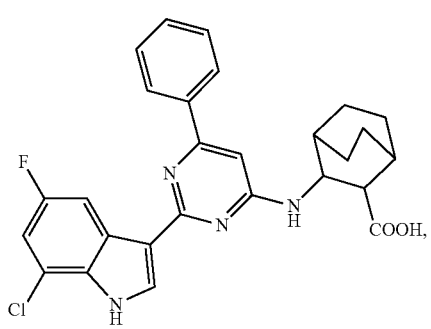
(64)
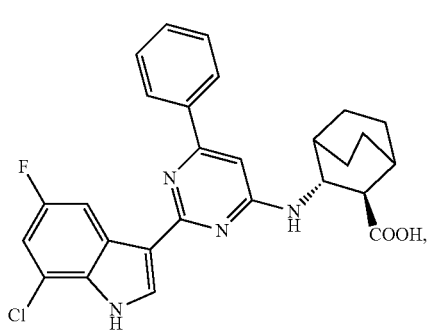
(65)
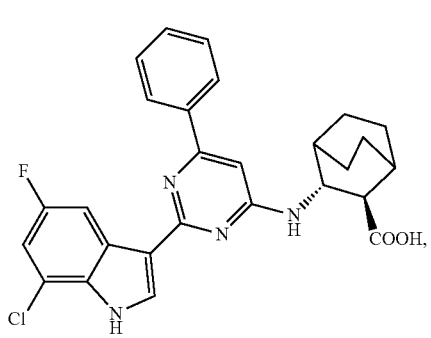
(66)

-continued
(67)
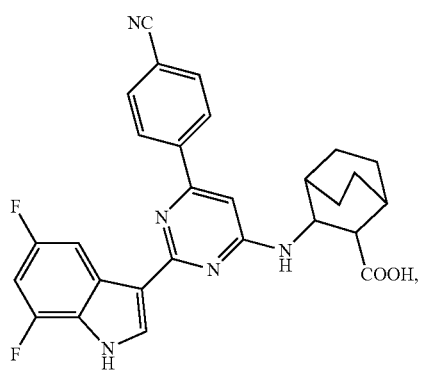
(68)
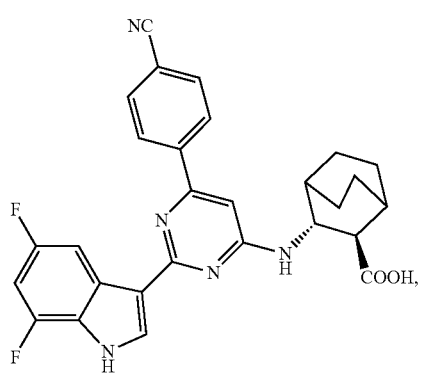
(69)
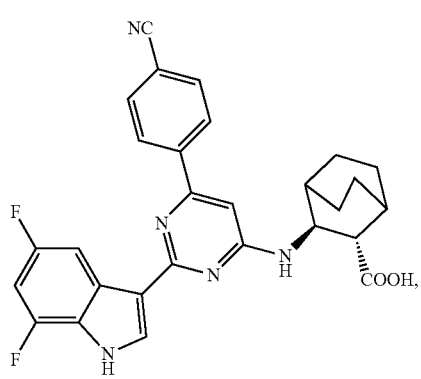
(70)
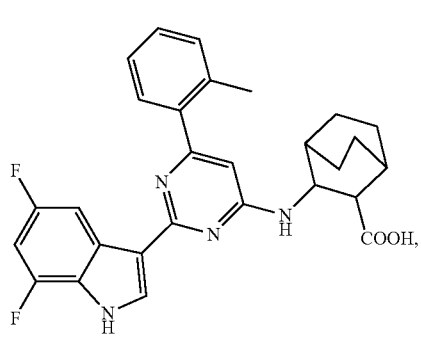
-continued
(71)
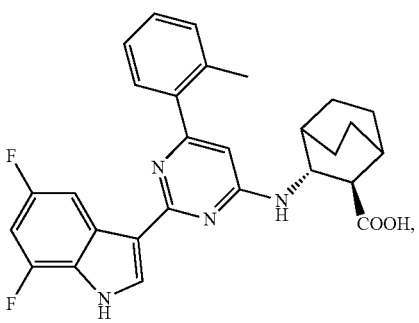
(72)
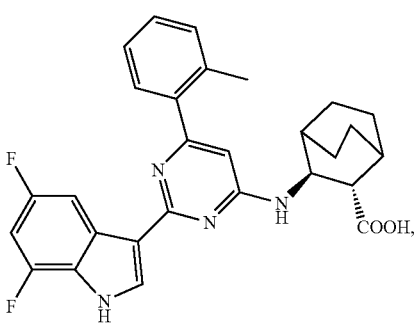
(73)
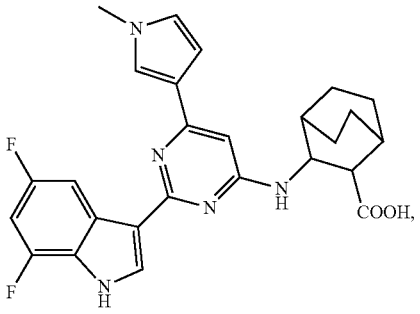
(74)
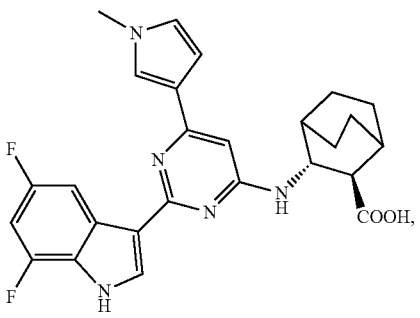
(75)
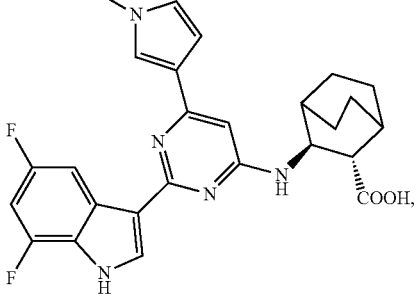

(76) 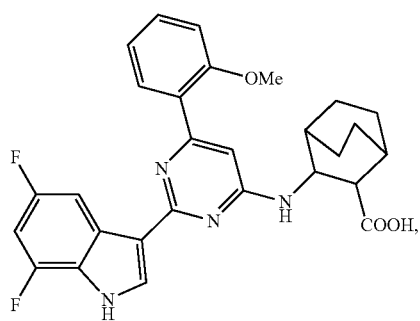
(77) 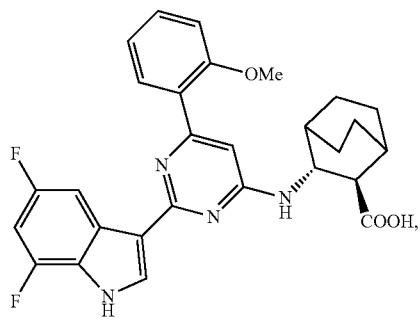
(78) 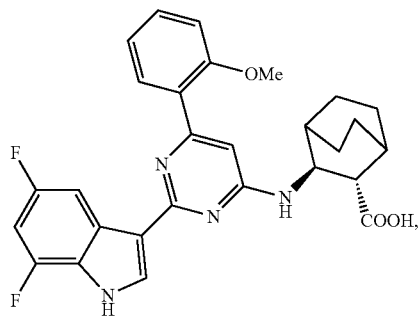
(79) 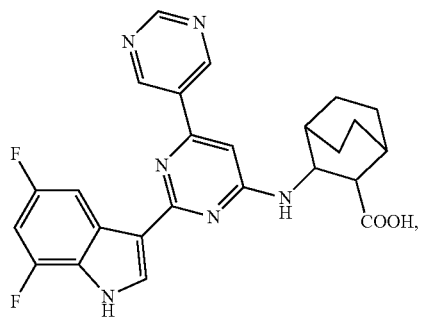
(80) 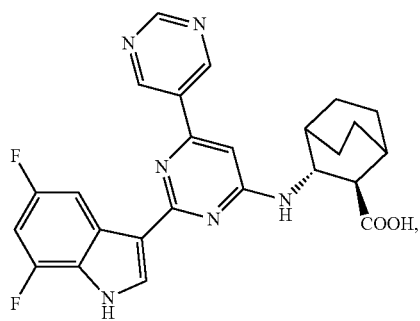
(81) 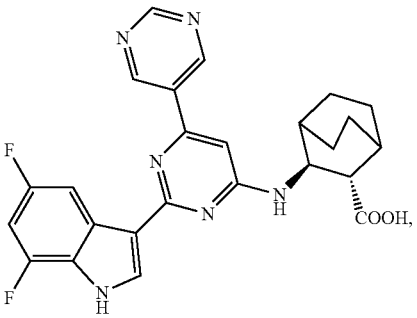
(82) 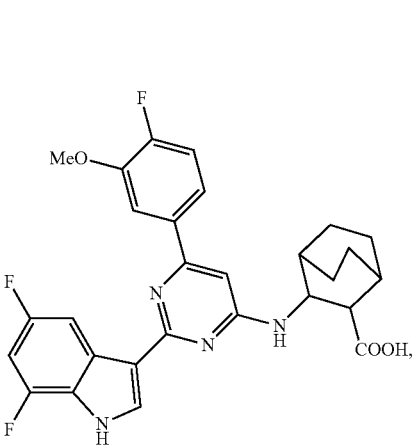
(83) 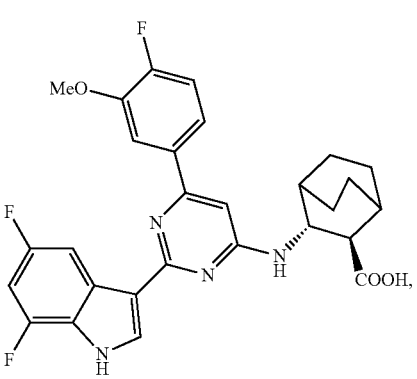
(84) 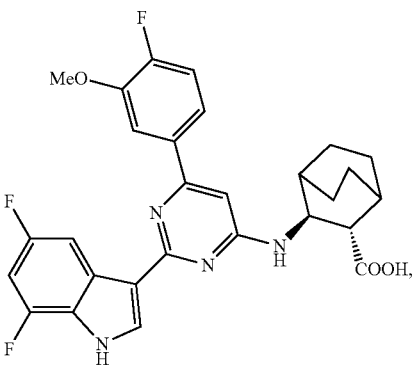

(85)
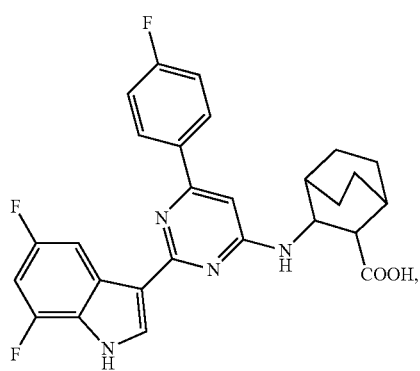
(86)
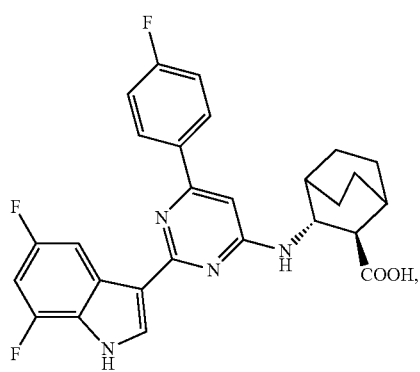
(87)
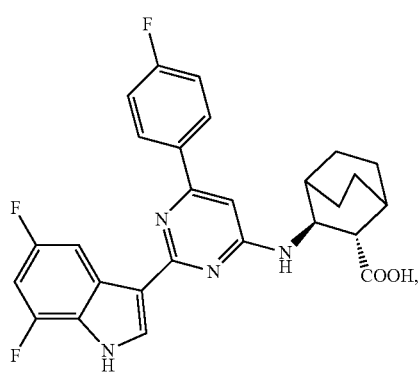
(88)
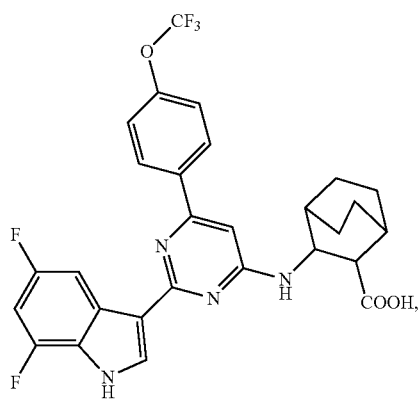
(89)
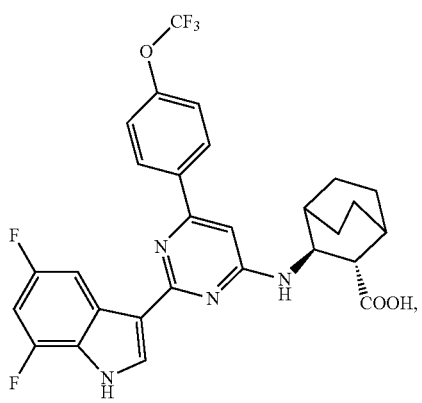
(90)
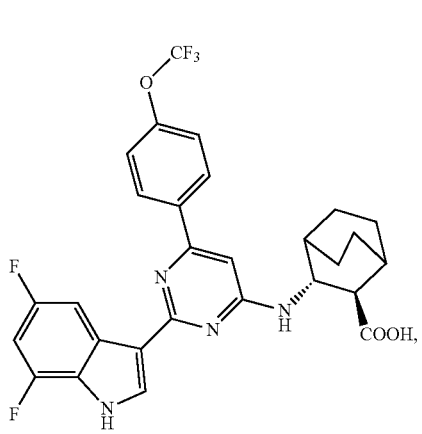
(91)
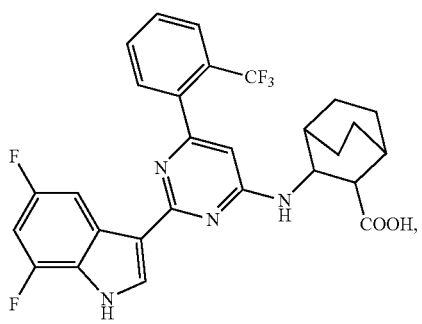
(92)
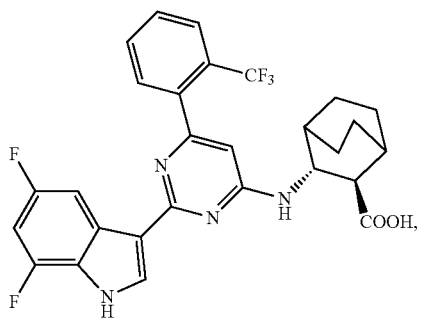

(93)
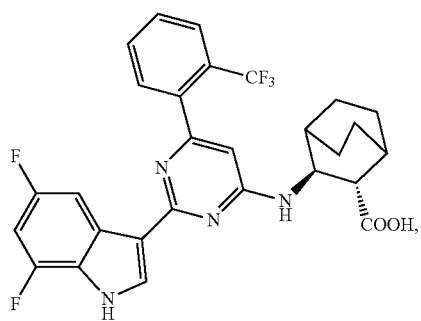
(94)
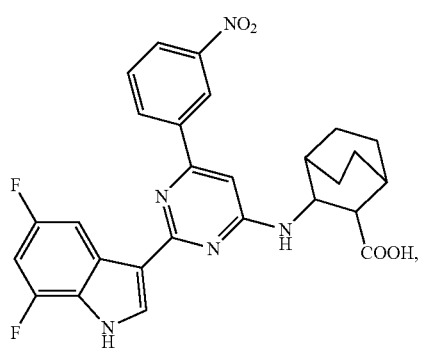
(95)
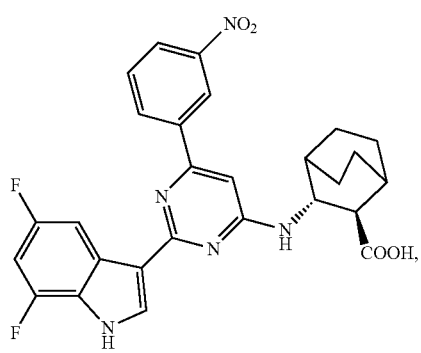
(96)
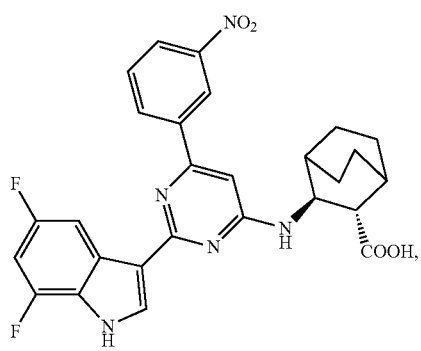
(97)
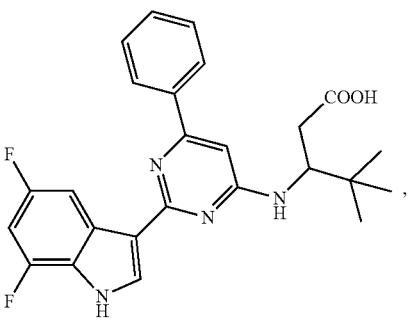
(98)
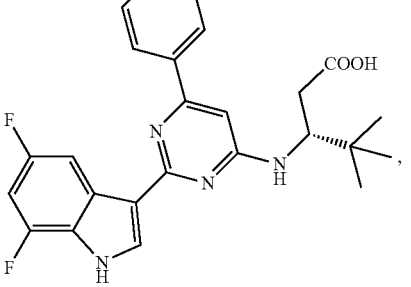
(99)
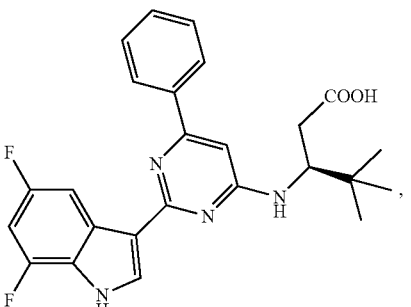
(100)
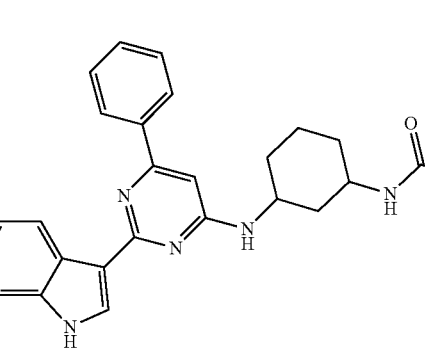
(101)
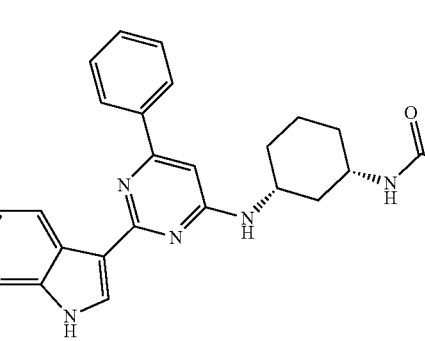

(102)
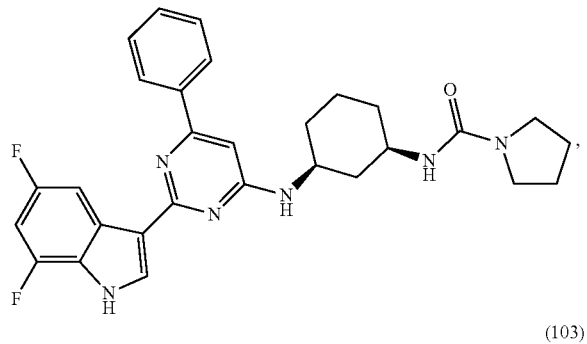
(103)
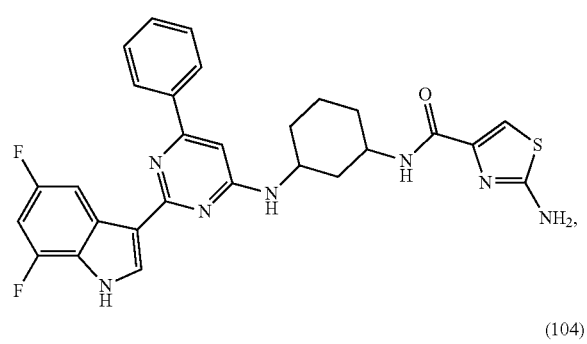
(104)
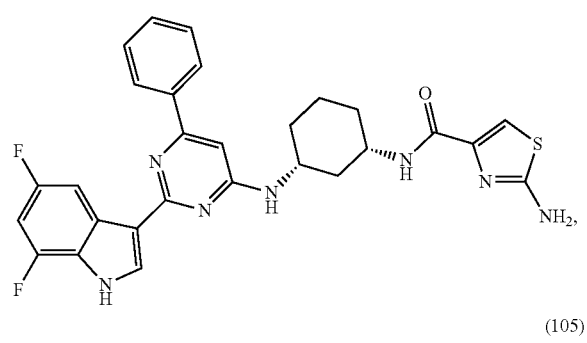
(105)
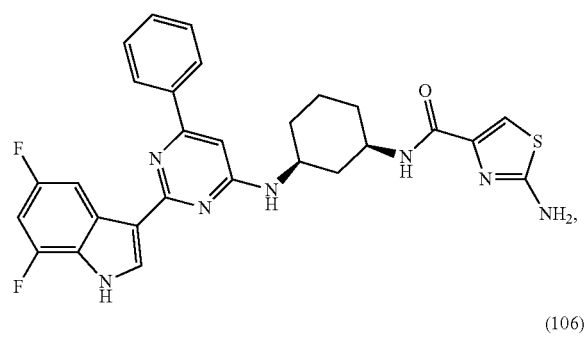
(106)
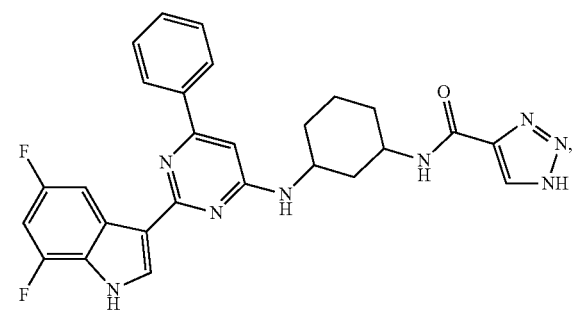
(107)
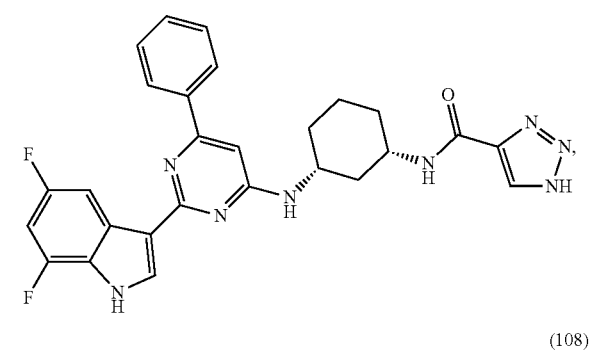
(108)
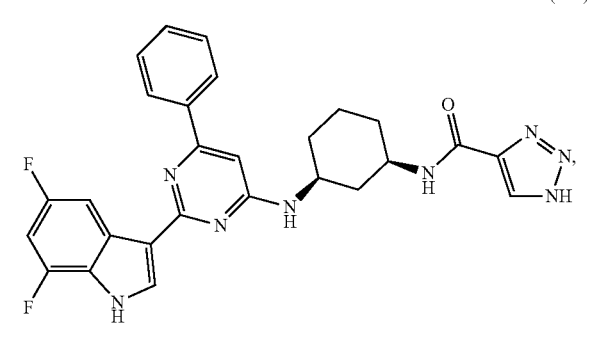
(109)
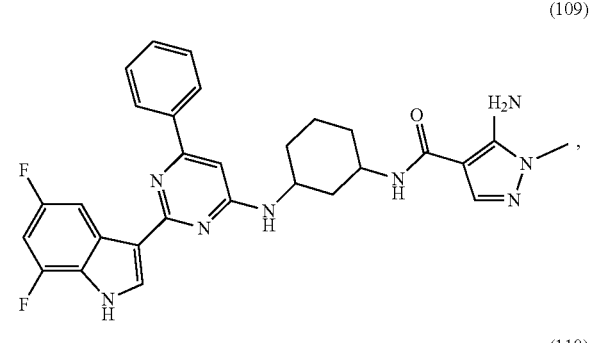
(110)
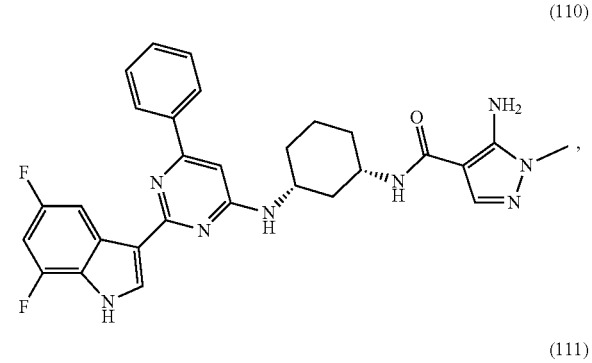
(111)
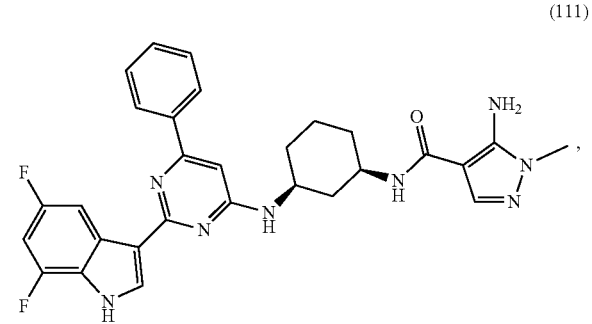

(112) 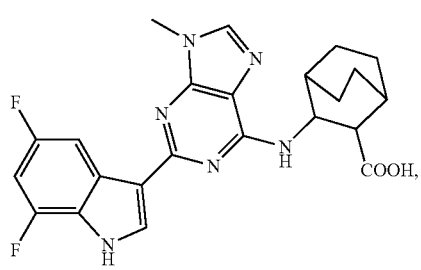
(113) 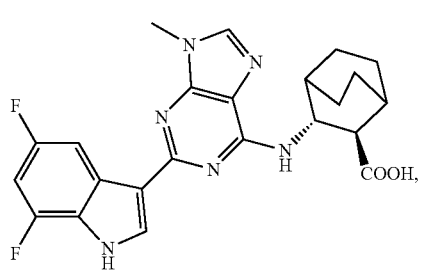
(114) 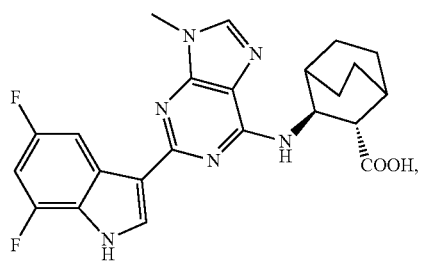
(115) 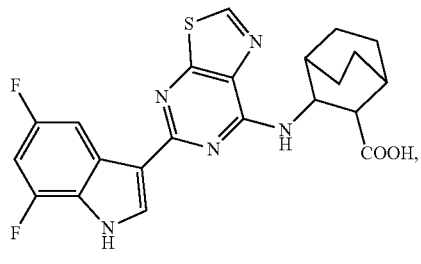
(116) 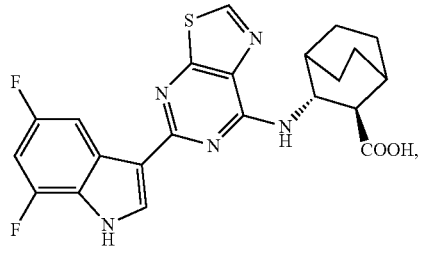
(117) 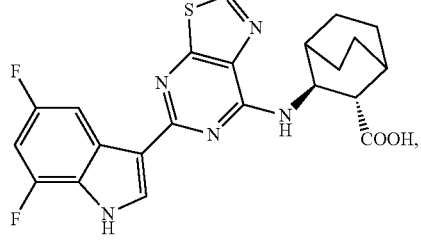
(118) 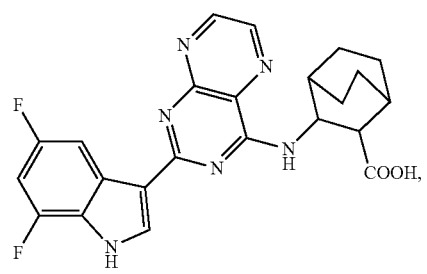
(119) 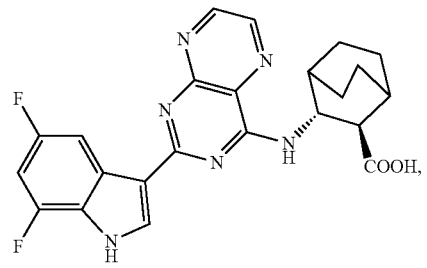
(120) 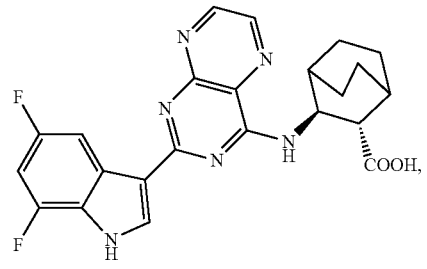
(121) 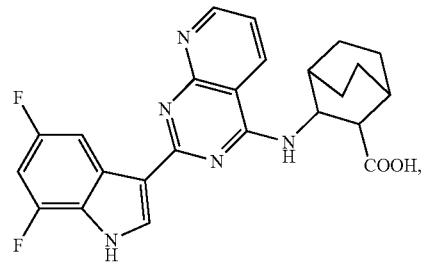
(122) 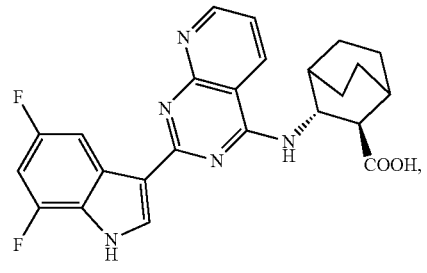
(123) 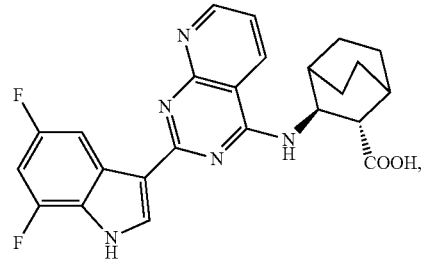

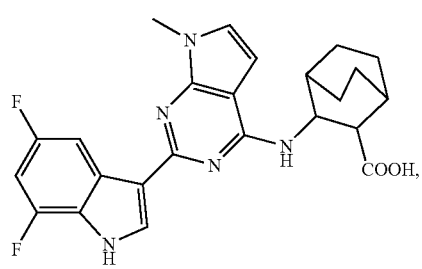
(124)
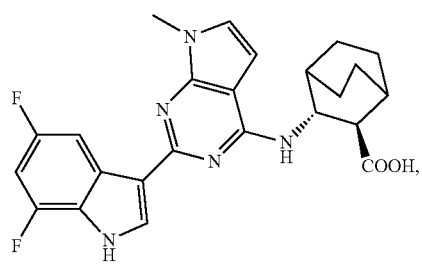
(125)
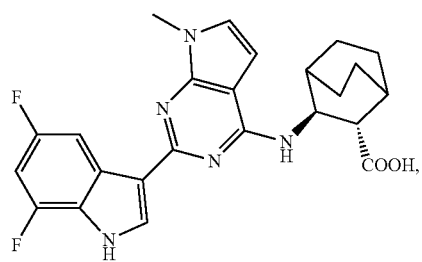
(126)
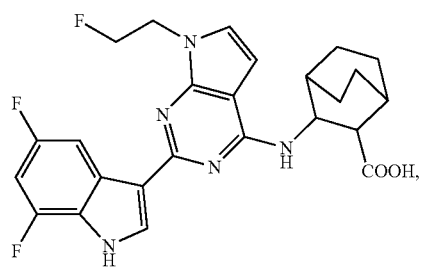
(127)
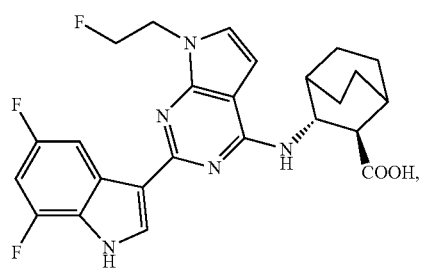
(128)
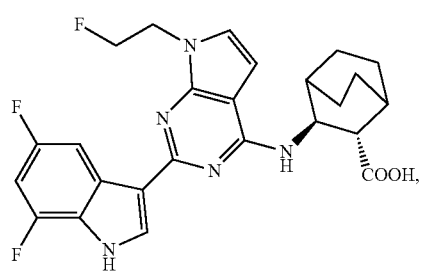
(129)
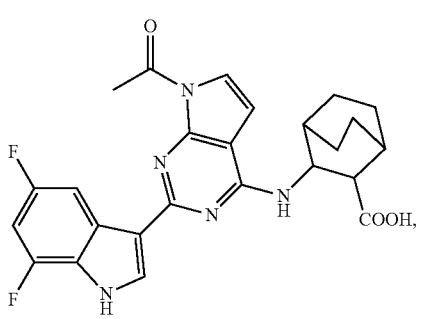
(130)
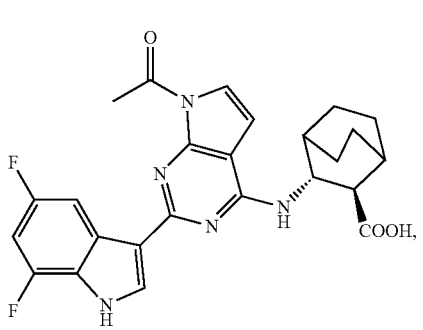
(131)
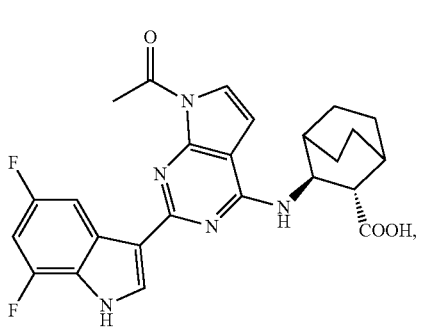
(132)
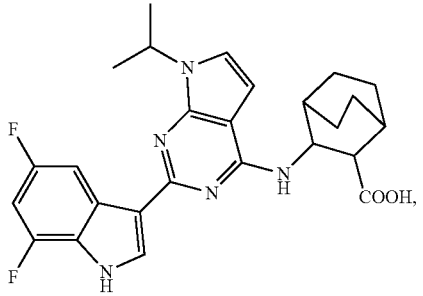
(133)
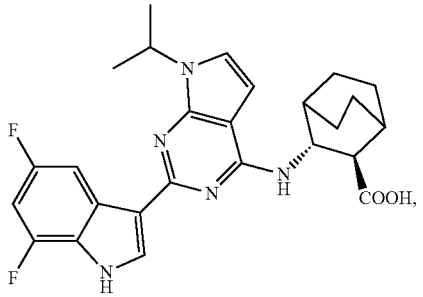
(134)

(135)
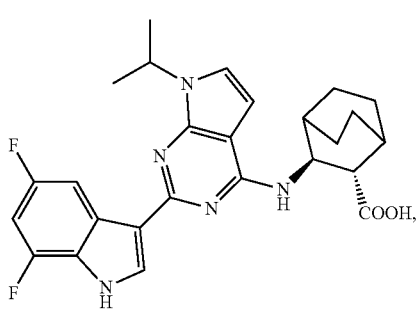
(136)
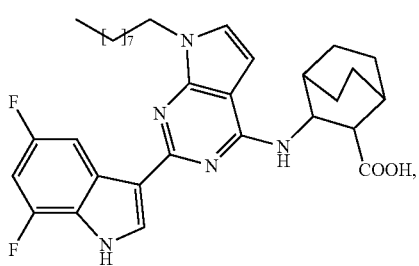
(137)
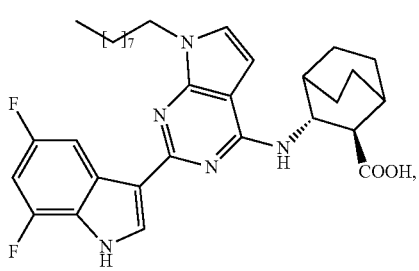
(138)
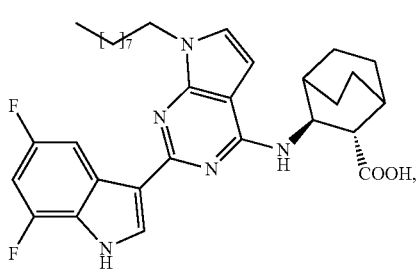
(139)
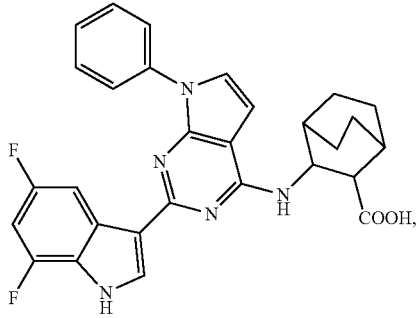
(140)
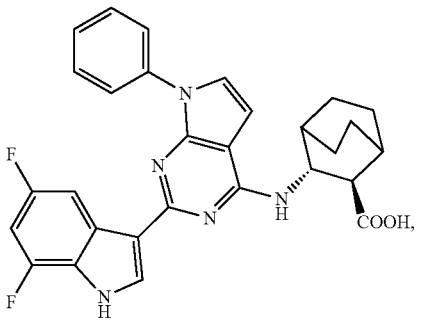
(141)
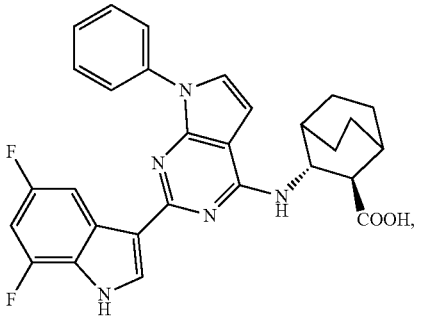
(142)
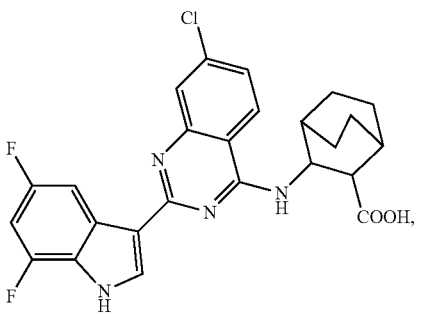
(143)
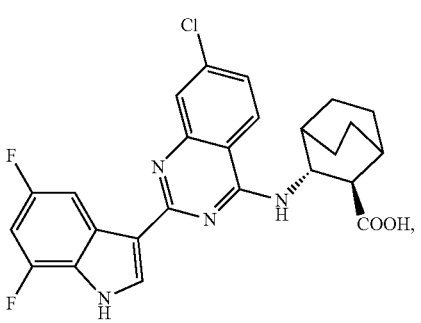
(144)
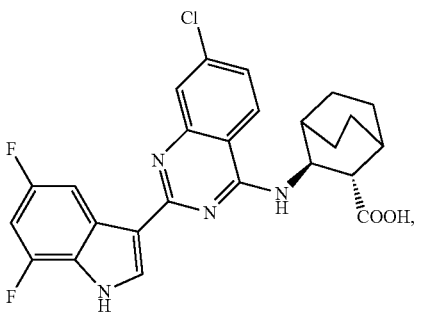

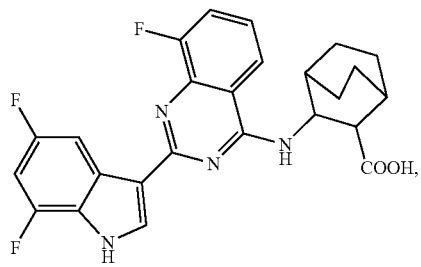 (145)
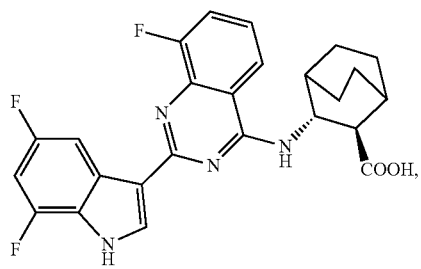 (146)
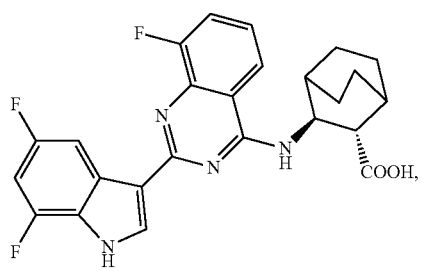 (147)
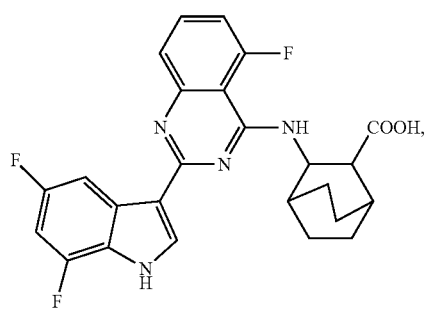 (148)
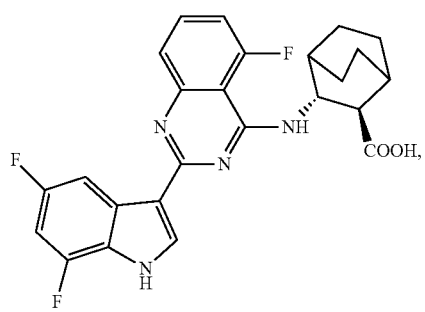 (149)
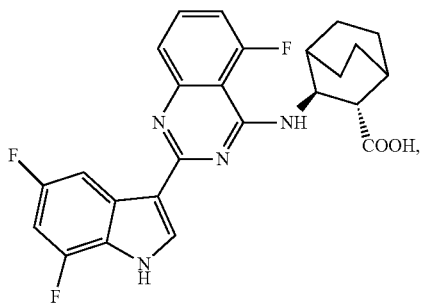 (150)
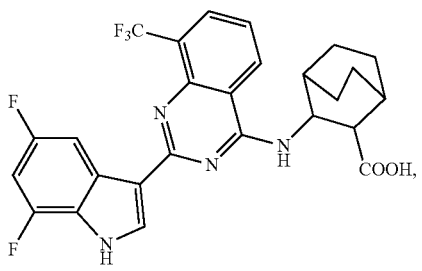 (151)
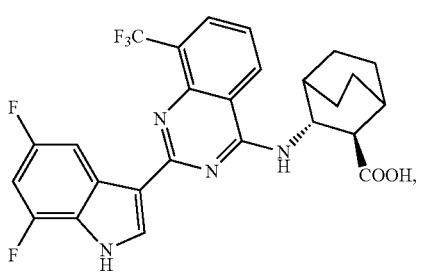 (152)
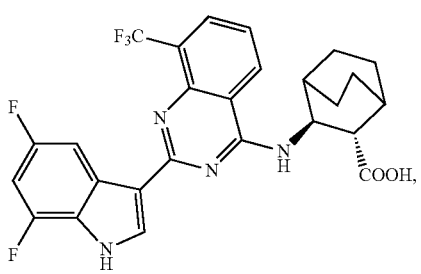 (153)
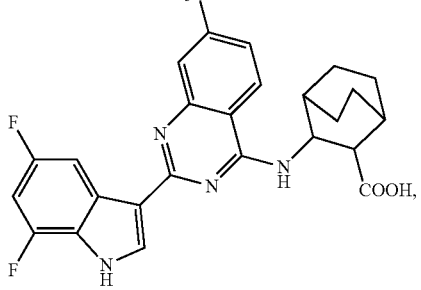 (154)

(155) 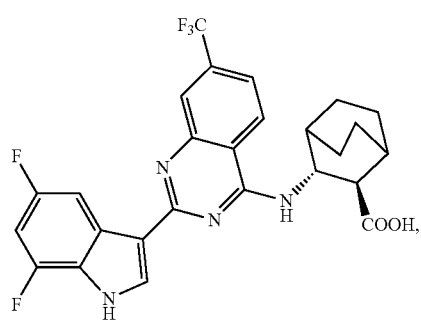
(156) 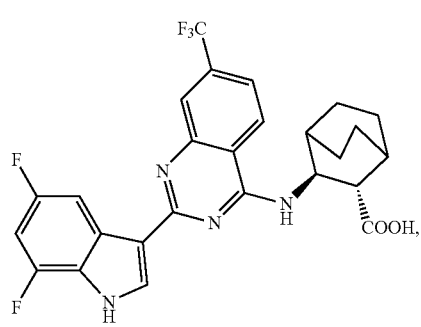
(157) 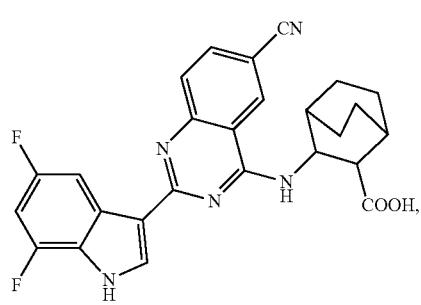
(158) 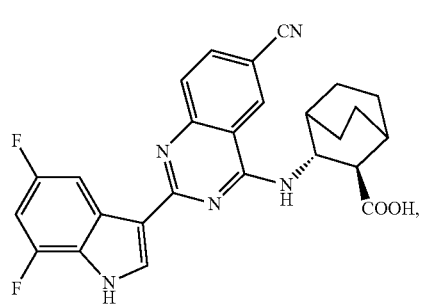
(159) 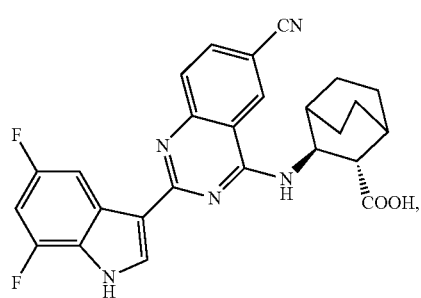
(160) 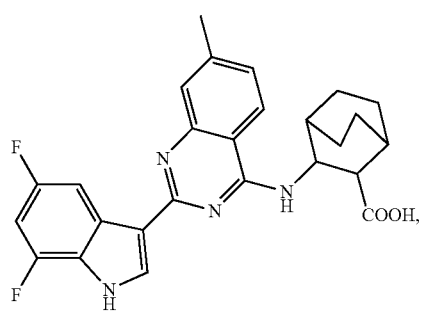
(161) 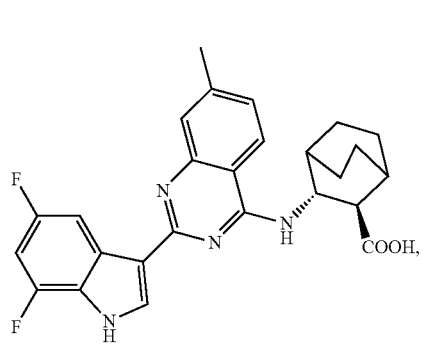
(162) 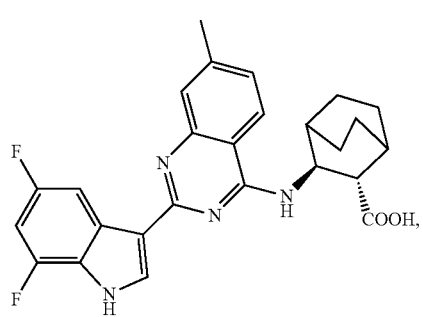
(163) 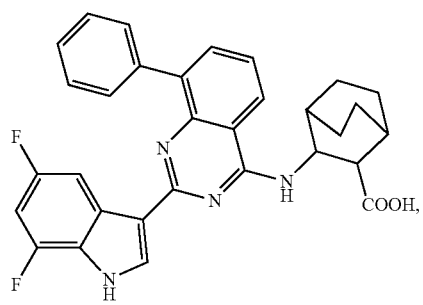
(164) 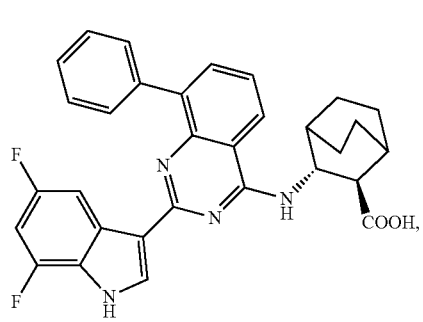

-continued
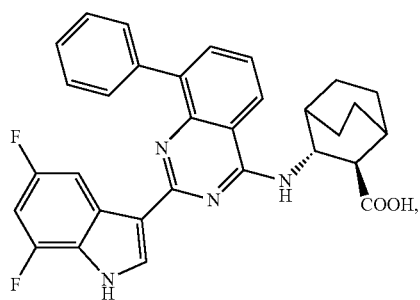 (165)
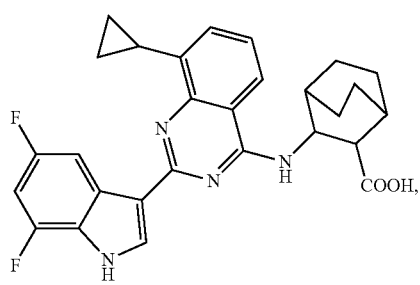 (166)
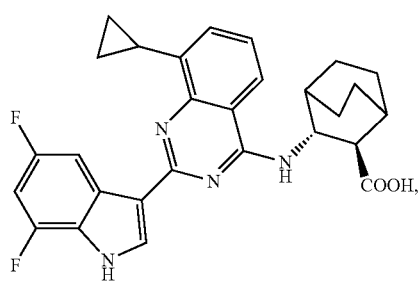 (167)
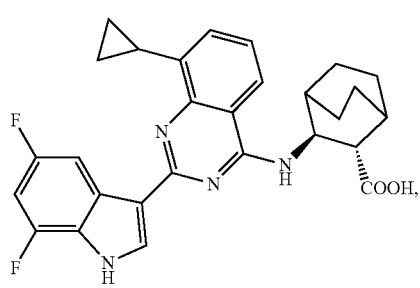 (168)
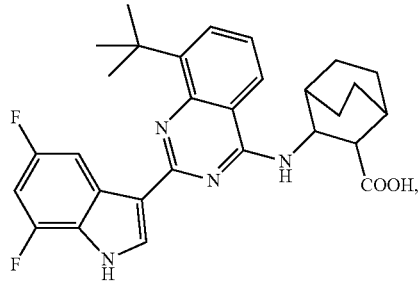 (169)
-continued
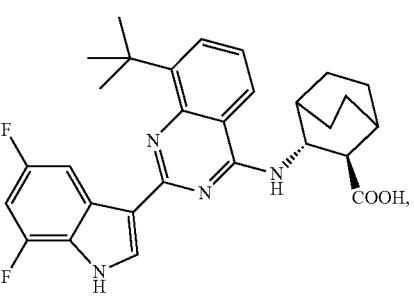 (170)
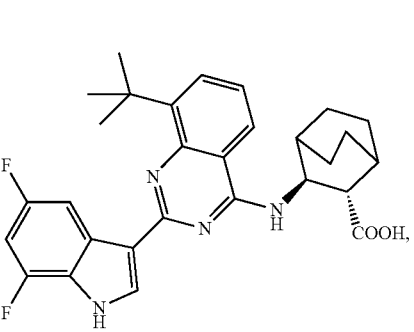 (171)
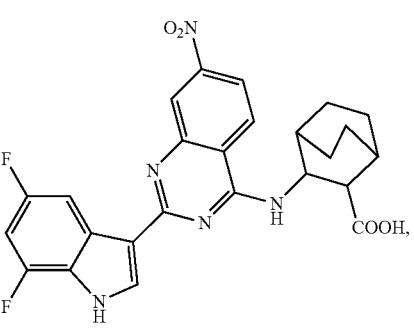 (172)
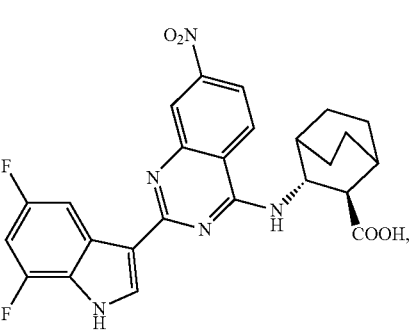 (173)
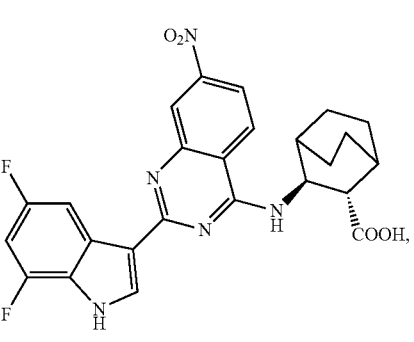 (174)

-continued
(175) 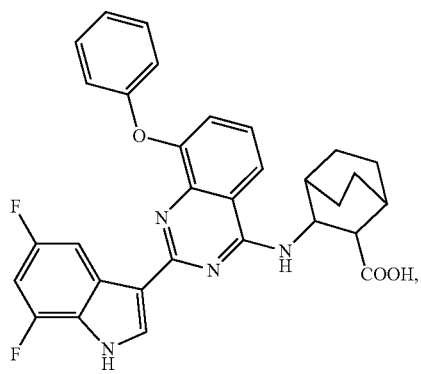
(176) 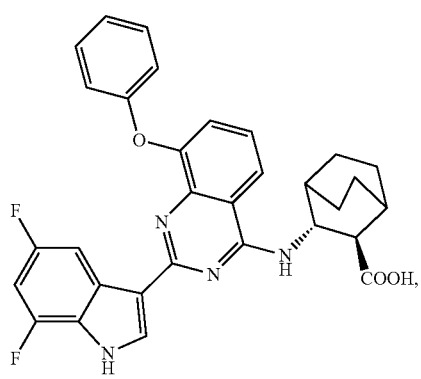
(177) 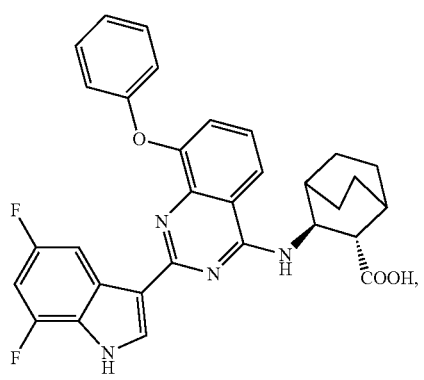
(178) 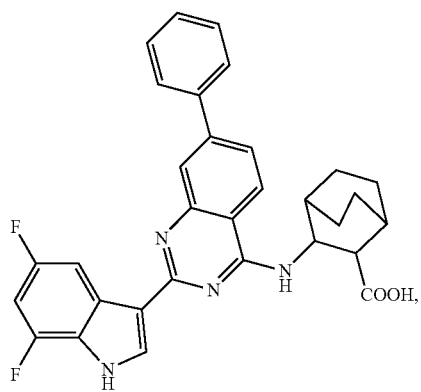
-continued
(179) 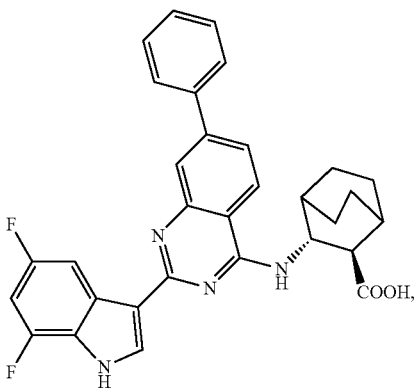
(180) 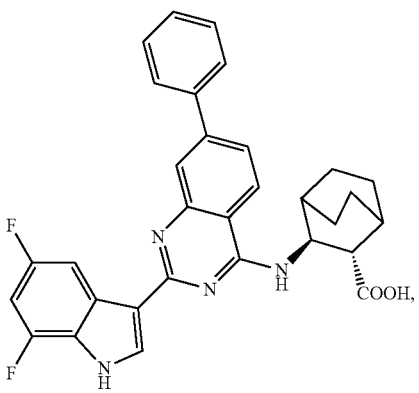
(181) 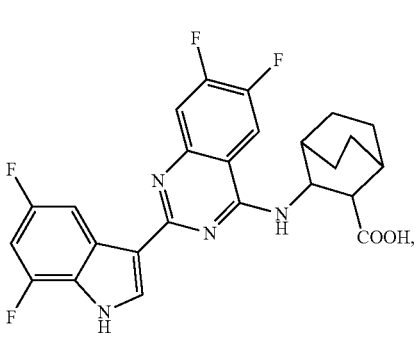
(182) 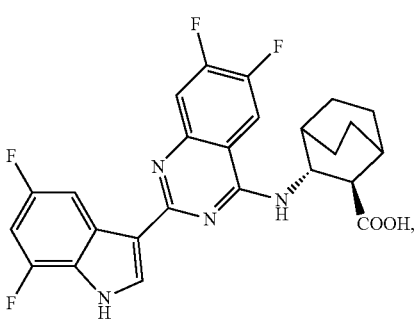

77
-continued
(183)
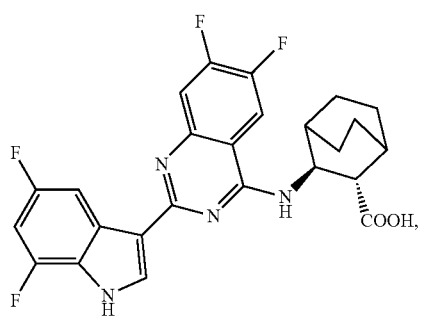
(184)
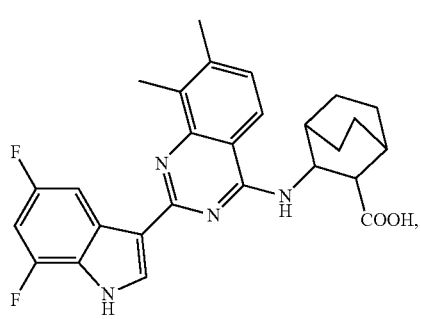
(185)
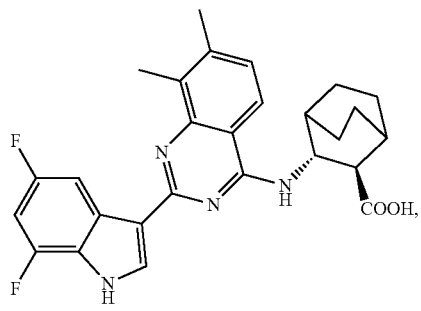
(186)
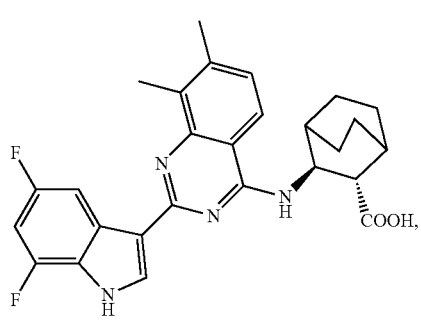
(187)
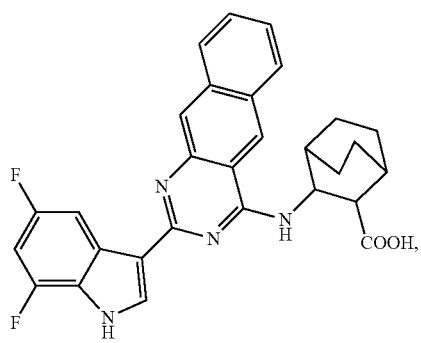
78
-continued
(188)
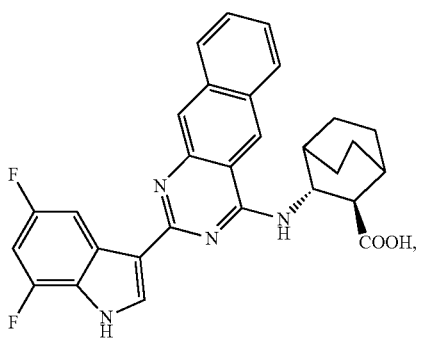
(189)
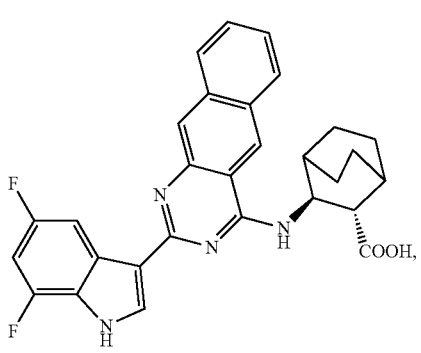
(190)
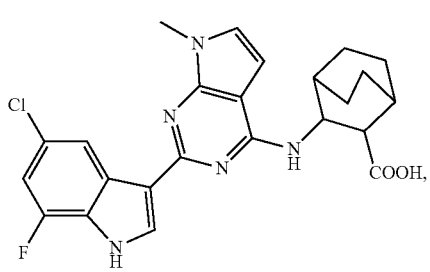
(191)
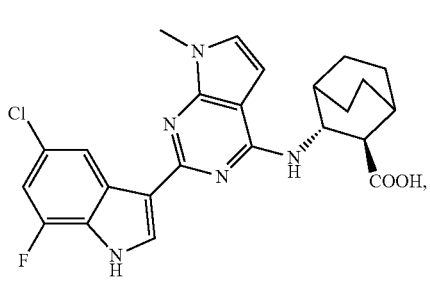
(192)
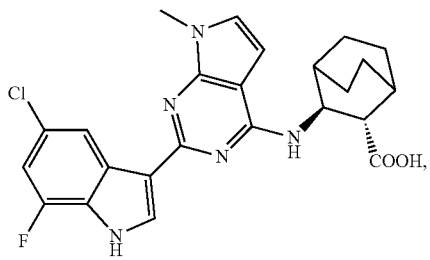

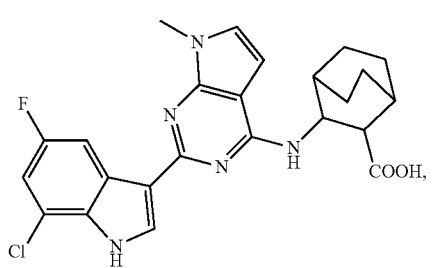
(193)
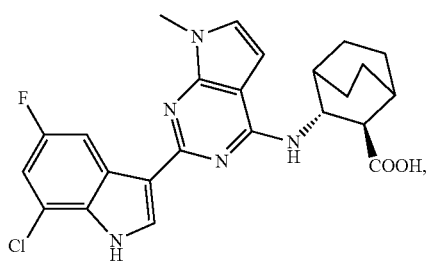
(194)
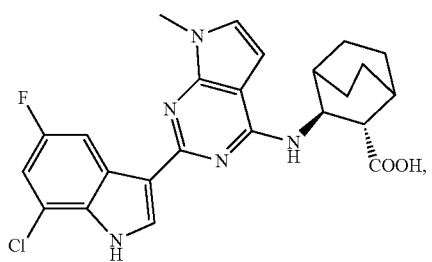
(195)
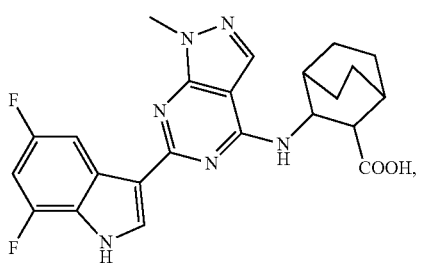
(196)
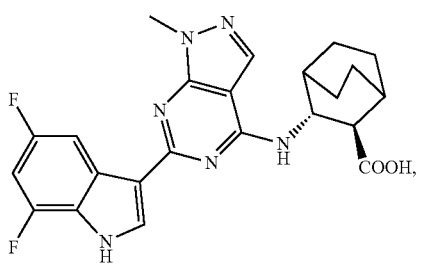
(197)
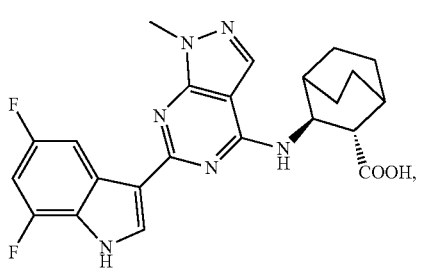
(198)
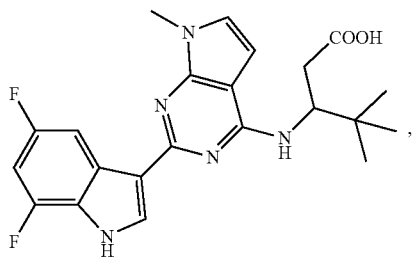
(199)
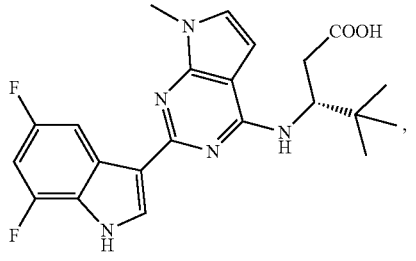
(200)
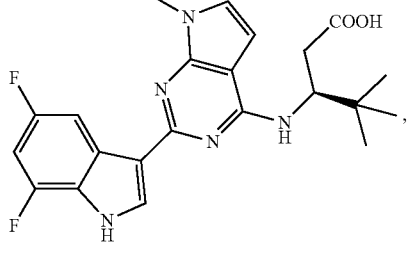
(201)
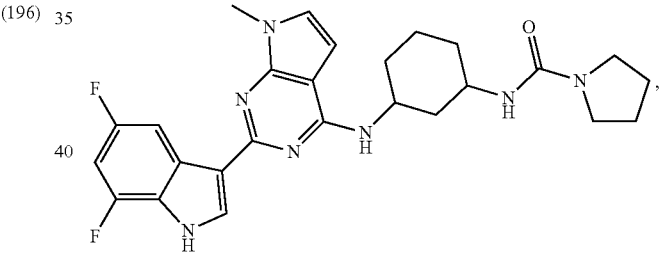
(202)
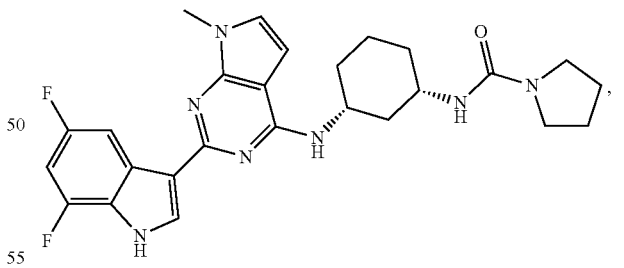
(203)
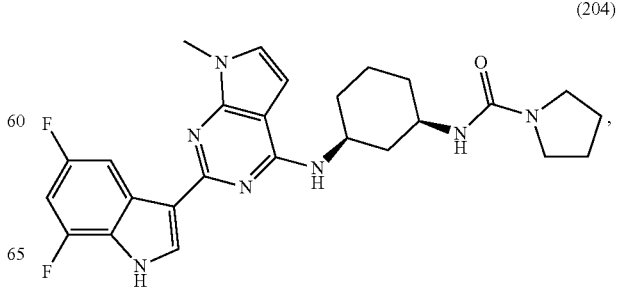
(204)

(205)
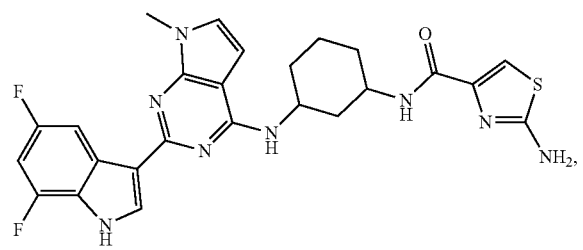
(206)
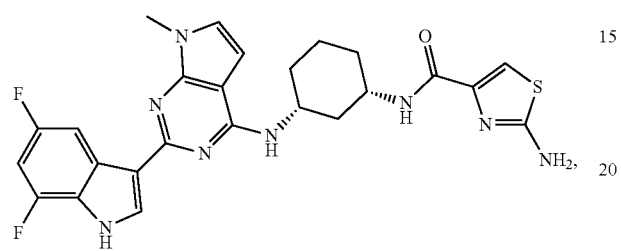
(207)
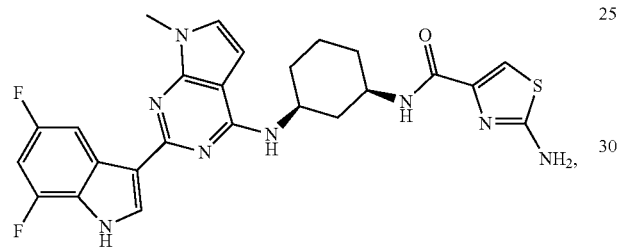
(208)
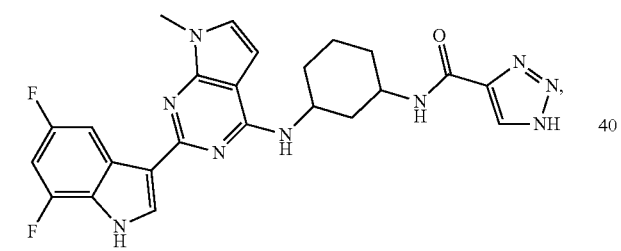
(209)
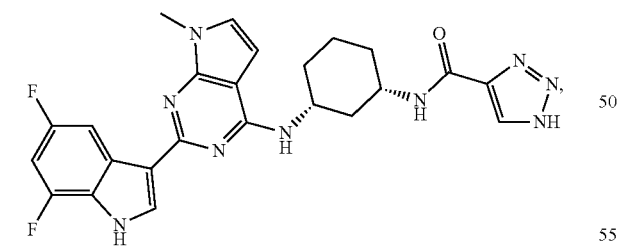
(210)
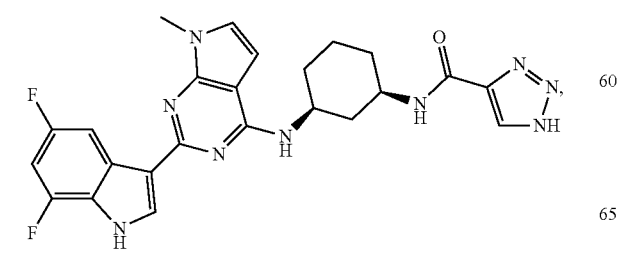
(211)
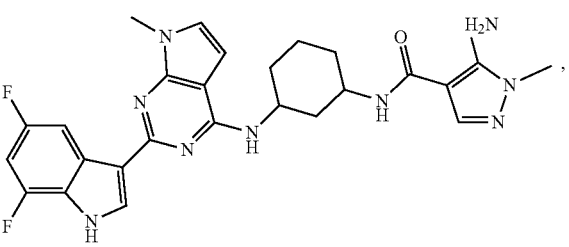
(212)
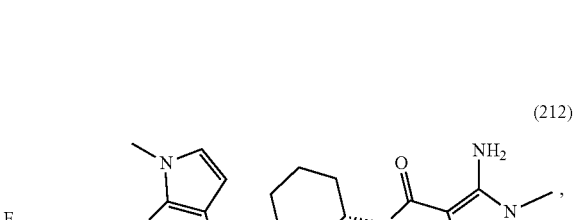
(213)
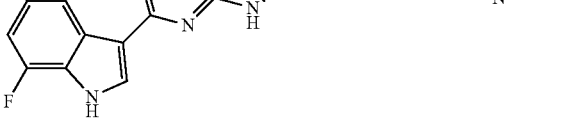
(214)
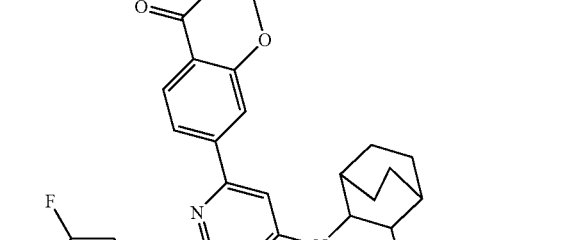

(215)
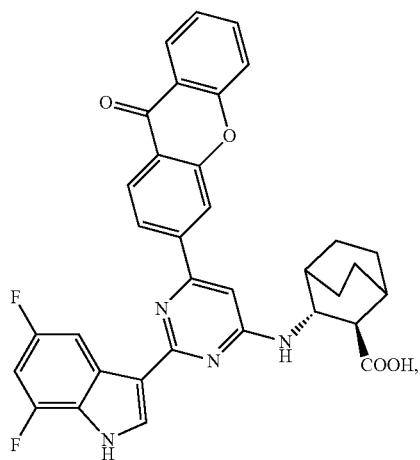
(216)
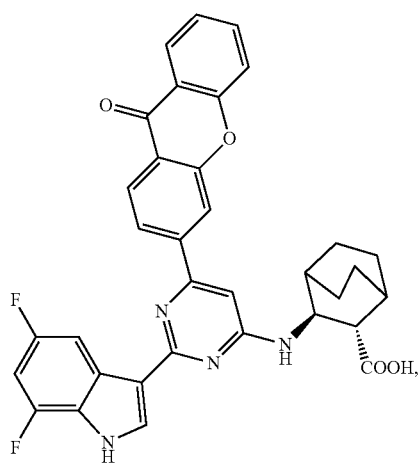
(217)
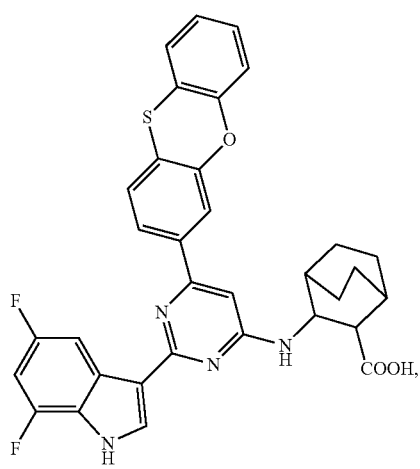
(218)
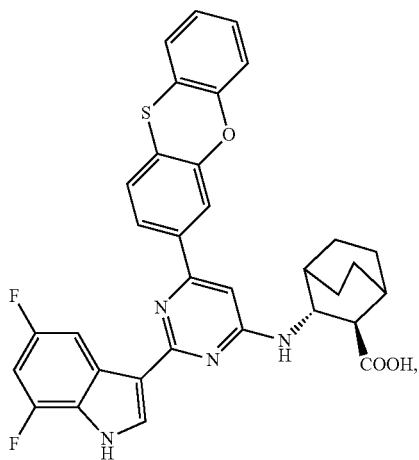
(219)
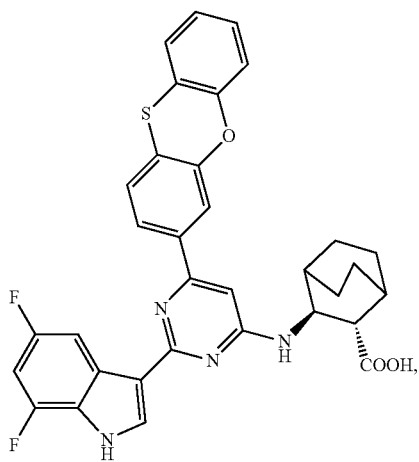
(220)
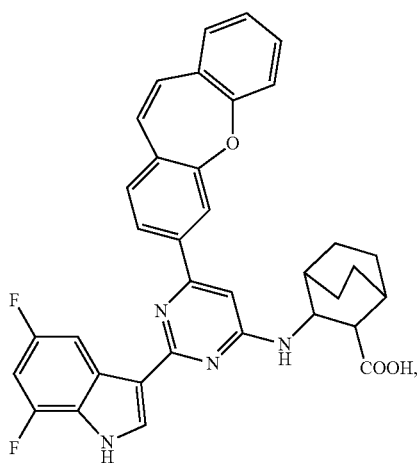

(221) 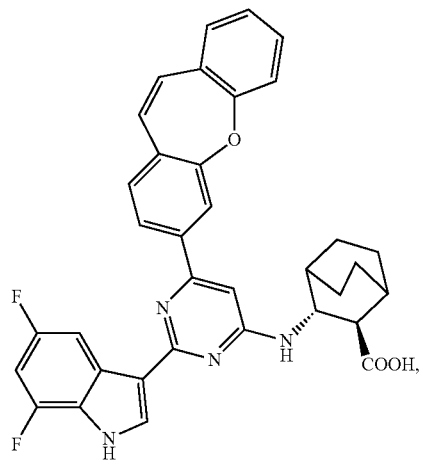
(222) 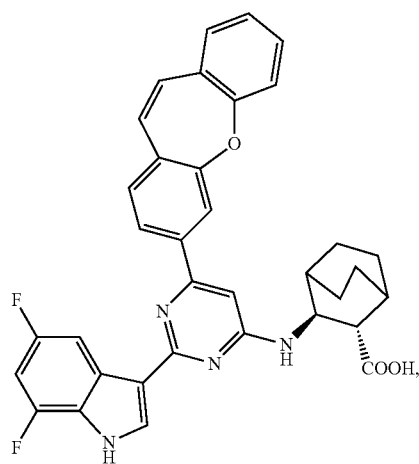
(223) 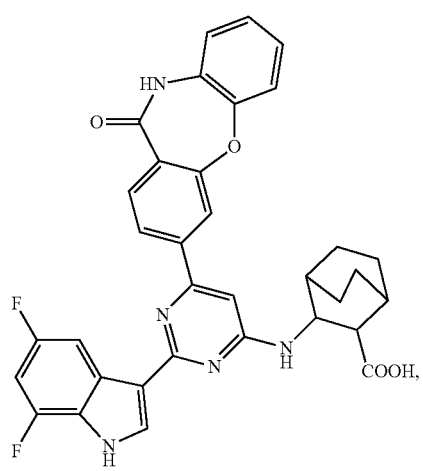
(224) 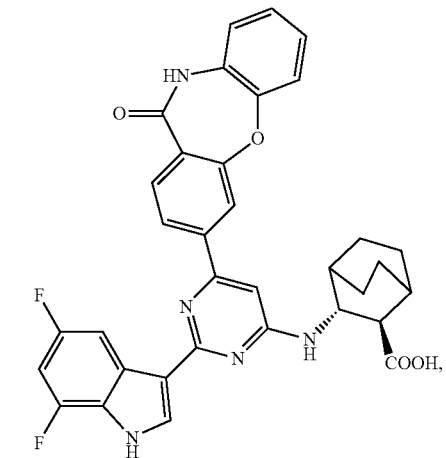
(225) 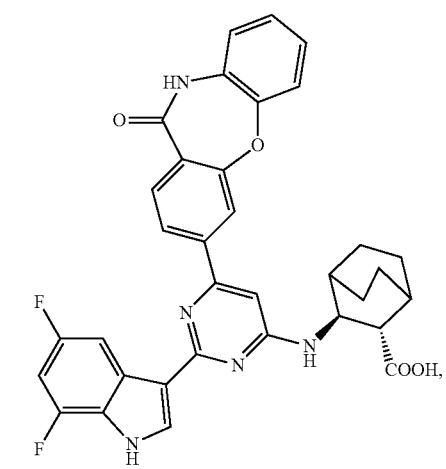
(226) 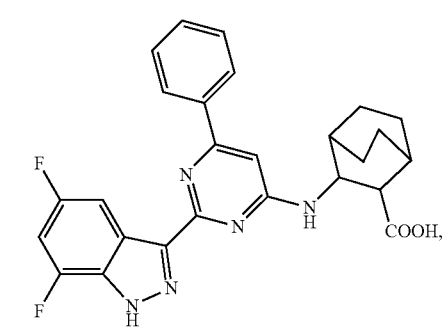
(227) 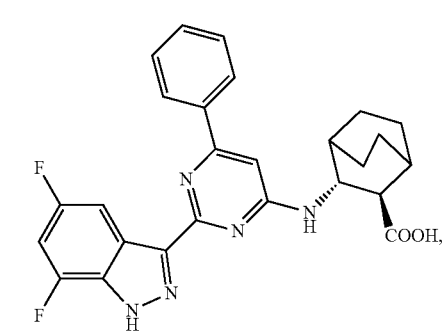

(228) 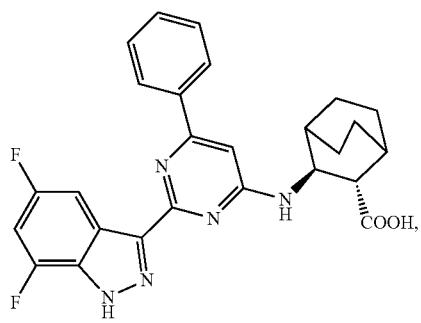
(229) 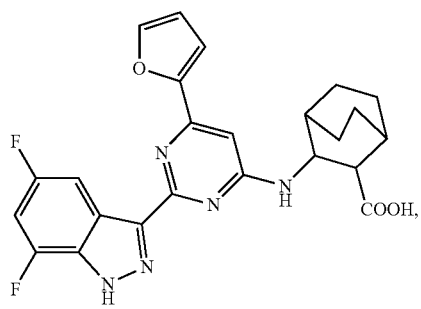
(230) 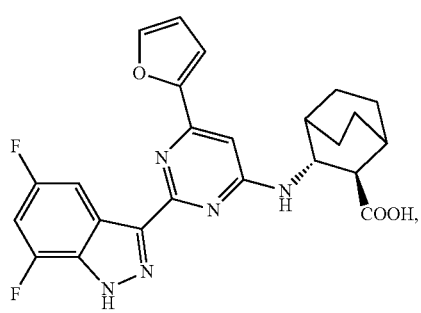
(231) 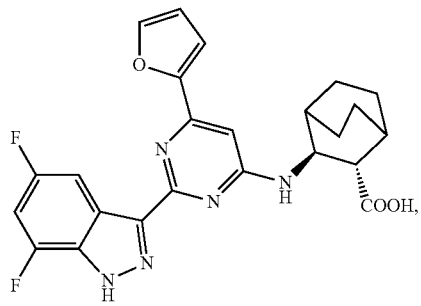
(232) 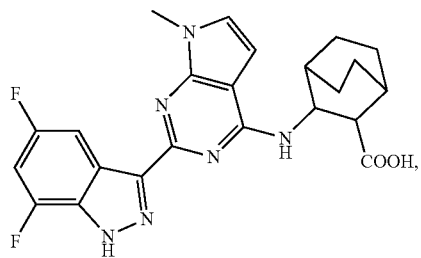
(233) 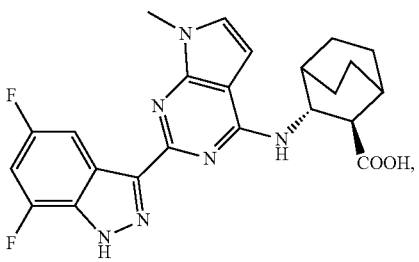
(234) 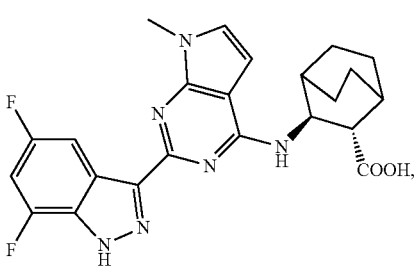
(235) 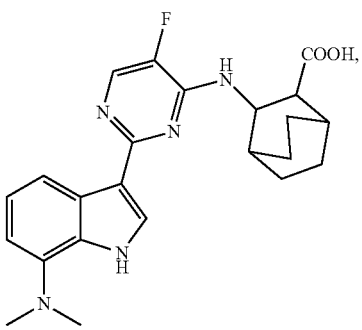
(236) 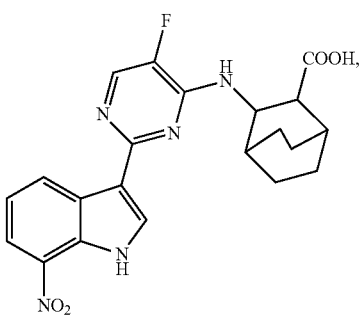
(237) 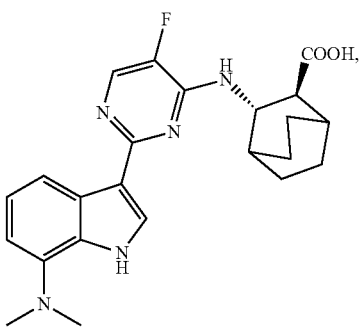

-continued
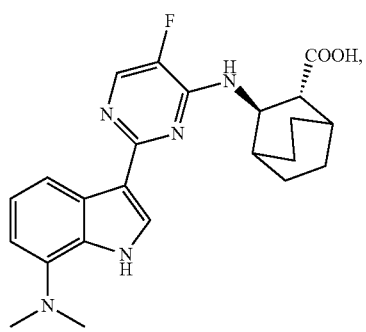 (238)
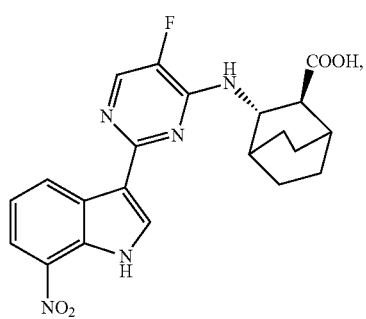 (239)
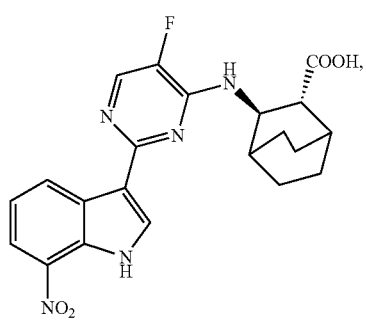 (240)
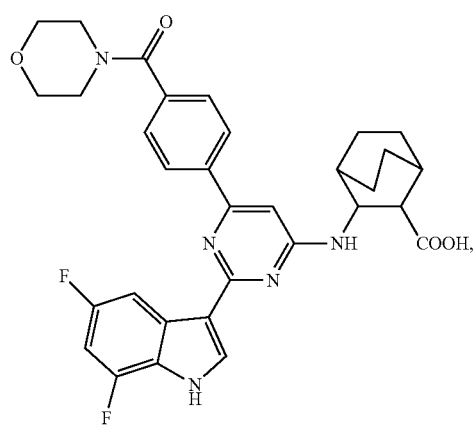 (241)
-continued
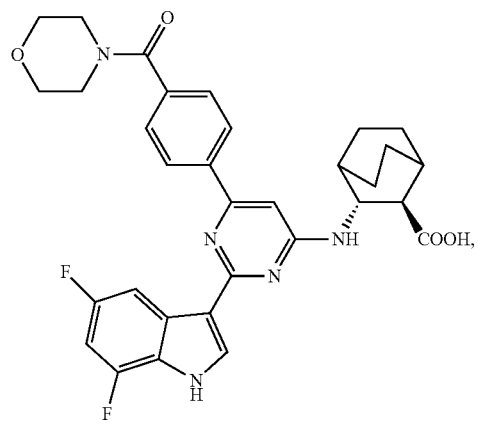 (242)
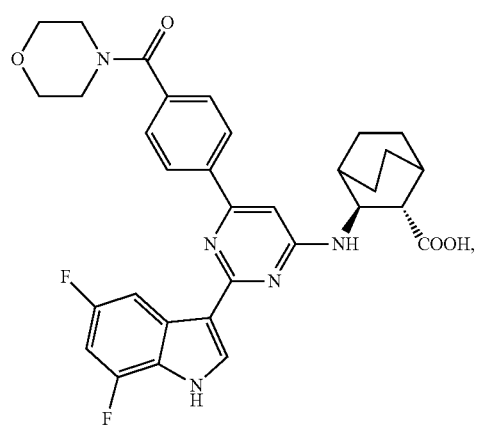 (243)
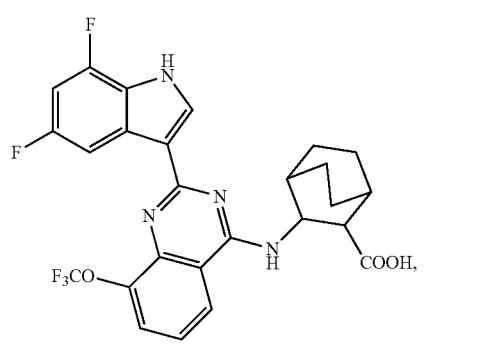 (244)
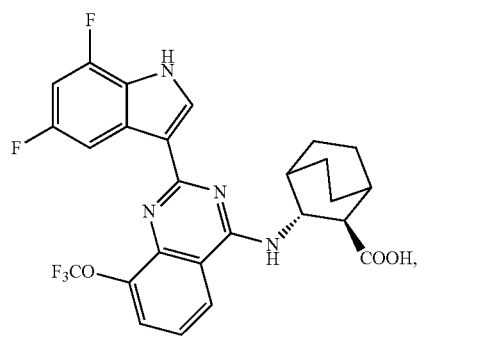 (245)

-continued
(246)
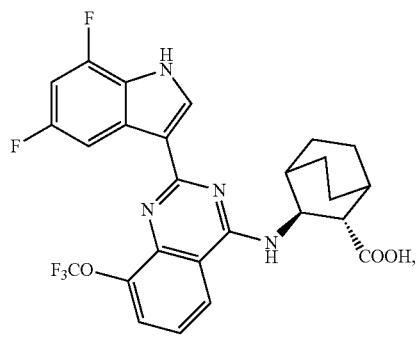
(247)
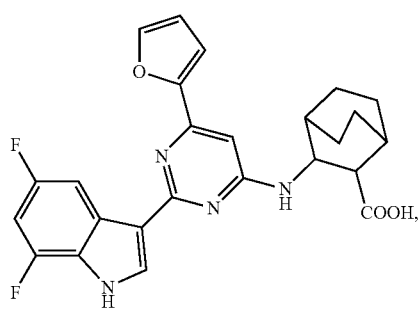
(248)
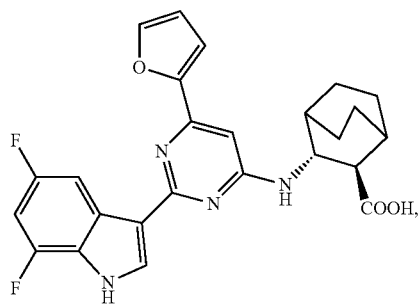
(249)
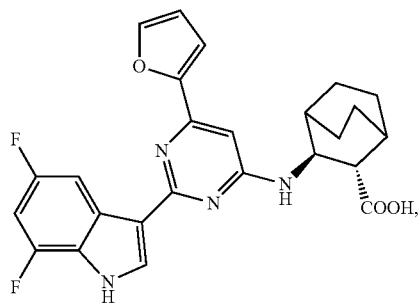
(250)
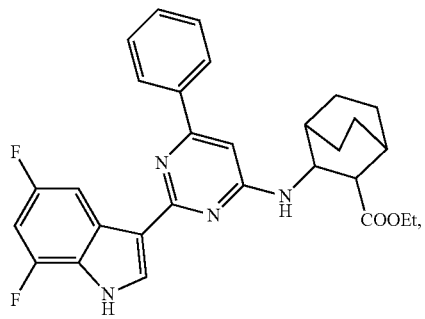
-continued
(251)
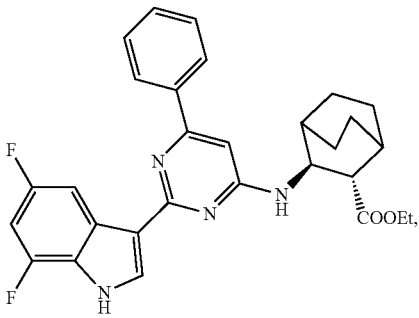
(252)
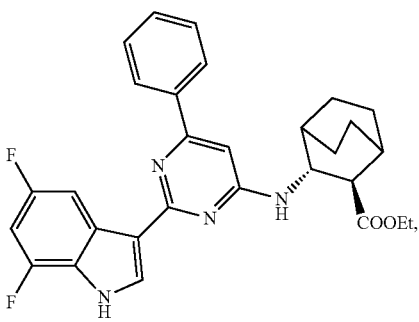
(253)
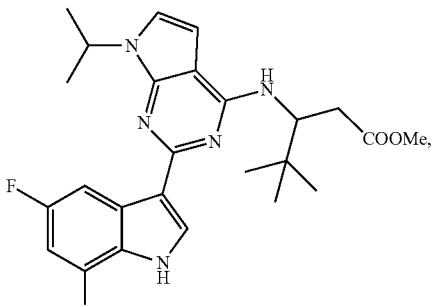
(254)
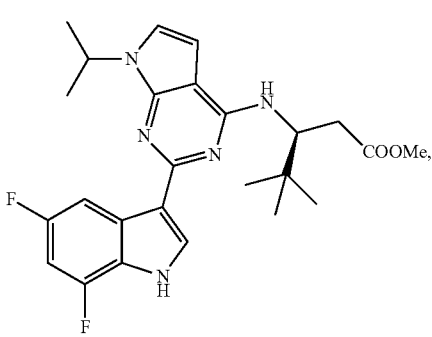
(255)
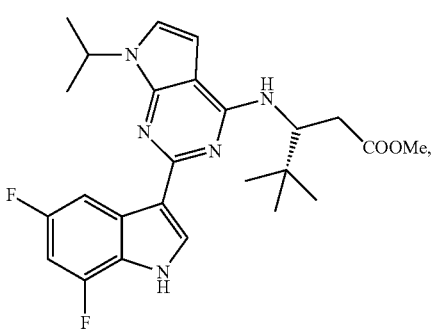

(256) 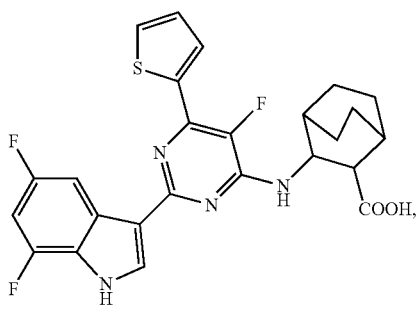

(257) 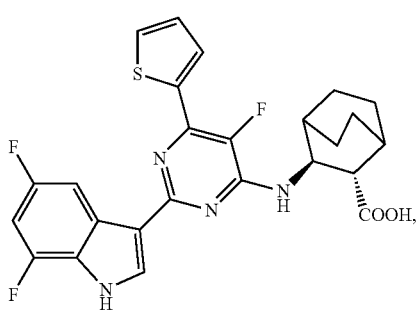

(258) 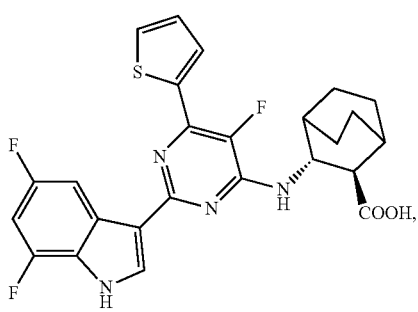

(259) 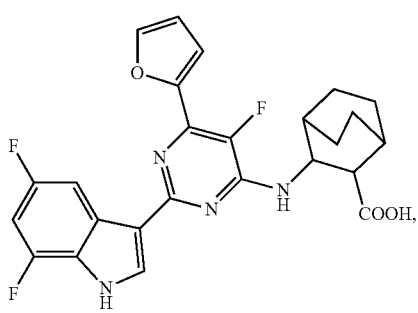

(260) 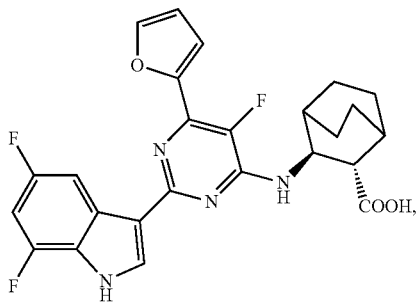

(261) 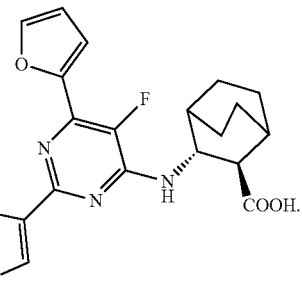

In another aspect, provided herein is a pharmaceutical composition comprising the compound of the invention.

In some embodiments, the pharmaceutical composition provided herein further comprises a pharmaceutically acceptable carrier, adjuvant, vehicle or a combination thereof.

In some embodiments, the pharmaceutical composition provided herein further comprises one or more therapeutic agents.

In other embodiments, the therapeutic agent disclosed herein is an anti-influenza virus agent or anti-influenza virus vaccine.

In other embodiments, the pharmaceutical composition is in the form of a liquid, solid, semi-solid, gel or spray.

In other embodiments, the pharmaceutical composition disclosed herein, wherein the therapeutic agent is amantadine, rimantadine, oseltamivir, zanamivir, peramivir, laninamivir, laninamivir octanoate hydrate, favipiravir, arbidol, ribavirin, stachyflin, ingavirin, fludase, CAS no. 1422050-75-6, JNJ-872, an influenza vaccine (FluMist Quadrivalent®, Fluarix® Quadrivalent, Fluzone® Quadrivalent, Flucelvax® or FluBlok®) or a combination thereof.

In another aspect, provided herein is use of the compound or the pharmaceutical composition disclosed herein in the manufacture of a medicament for preventing, managing, treating or lessening a disorder or disease caused by a virus infection in a patient.

In some embodiments, the virus infection disclosed herein is an influenza virus infection.

In another aspect, provided herein is use of the compound or the pharmaceutical composition disclosed herein in the manufacture of a medicament for inhibiting an influenza virus RNA polymerase.

In one embodiment, the salt is a pharmaceutically acceptable salt. The phrase "pharmaceutically acceptable" refers to that the substance or composition must be chemically and/or toxicologically compatible with the other ingredients comprising a formulation, and/or the mammal being treated therewith.

The compound of the invention also embraces the salts thereof, and the salts are not necessarily pharmaceutically acceptable salts, and which may be useful as intermediates for preparing and/or purifying compounds of the invention and/or for separating enantiomers of compounds of the invention.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, subsalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "*Remington's Pharmaceutical Sciences*", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds disclosed herein, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms.

Any formula given herein is also intended to represent isotopically unenriched forms as well as isotopically enriched forms of the compounds. Isotopically enriched compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, sulfur, fluorine and chlorine, such as $^2H$, $^3H$, $^{11}C$, $^{13}C$, $^{14}C$, $^{15}N$, $^{18}F$ $^{31}P$, $^{32}P$, $^{36}S$, $^{37}Cl$, $^{125}I$, respectively.

In another aspect, the compounds of the invention include isotopically enriched compounds as defined herein, for example those into which radioactive isotopes, such as $^3H$, $^{14}C$ and $^{18}F$, or those into which non-radioactive isotopes, such as $^2H$ and $^{13}C$ are present. Such isotopically enriched compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$-enriched compound may be particularly desirable for PET or SPECT studies. Isotopically-enriched compounds of Formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of Formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. $D_2O$, acetone-$d_6$ or DMSO-$d_6$.

Pharmaceutical Composition of the Compound of the Invention, Preparations and Administration The invention provides a pharmaceutical composition containing a therapeutic effective amount of the compound having formula (I) or a stereoisomer thereof, racemic mixture or non-racemic mixture of the stereoisomer thereof. In one embodiment, the pharmaceutical composition further comprises at least one pharmaceutically acceptable carriers, diluents, adjuvants or excipients, and optionally other treating and/or preventing ingredients. In one embodiment, the pharmaceutical composition comprises an effective amount of at least one pharmaceutically acceptable carriers, diluents, adjuvants or vehicles.

A pharmaceutically acceptable carrier may contain inert ingredients which do not unduly inhibit the biological activity of the compound(s) described herein. The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed.

As described above, the pharmaceutically acceptable compositions disclosed herein further comprise a pharmaceutically acceptable carrier, an adjuvant, or a vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington: The Science and Practice of Pharmacy,* 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium incompatible with the compounds disclosed herein, such as by producing any undesirable biological effect or otherwise interacting in a deleterious manner with any other components of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as tween 80, phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, methyl cellulose, hydroxypropyl methyl cellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening and perfuming agents, preservatives and antioxidants can also be present in the composition, according to the judgment of the formulator.

The pharmaceutically acceptable compositions can be administered to humans and other animals orally, rectally, parenterally, intracisternally, intravaginally, intraperitoneally, topically (as by powders, ointments, drops or patch), bucally, as an oral or nasal spray, or the like, depending on the severity of the infection being treated.

Liquid formulations for oral administration include, but not limited to, pharmaceutically acceptable emulsions, micro-emulsion, solution, suspension, syrup and elixir. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Addition to inert diluents, the oral compositions can also contain adjuvants such as wetting agents, emulsifiers or suspending agent, sweeteners, flavorings and fragrances.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound or a composition described herein, it is often desirable to slow the absorption of the compound from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolic acid. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

The solid dosage forms for oral administration include capsules, tablets, pills, powders and granules. In such solid dosage forms, the active compounds are mixed with at least one pharmaceutically acceptable inert excipients or carrier, such as sodium citrate or calcium phosphate and/or (a) fillers or swelling agents such as starch, lactose, sucrose, glucose, mannitol and silicic acid; (b) adhesives such as carboxymethylcellulose, alginates, gelatin, polyethylene pyrrole ketone, sucrose and gum arabic; (c) moisturizing agents such as glycerol; (d) disintegrating agents such as agar, calcium carbonate, potato starch or tapioca starch, alginic acid, certain silicates and sodium carbonate; (e) blocker solution, such as paraffin; (f) absorption promoter such as quaternary ammonium compounds; (g) wetting agents such as cetyl alcohol and glycerol monostearate; (h) absorbents such as kaolin and bentonite, (i) lubricants such as talc, calcium stearate, magnesium stearate, solid polyethylene glycol, laurylsodium sulfate, and mixtures thereof. In the case of capsules, tablets and pills, the pharmaceutical compositions may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, controlled release coatings and other coatings well known in the pharmaceutical formulating art. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the pharmaceutical compositions may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Specifically, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The compounds for use in the methods of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

Use of the Compounds and Pharmaceutical Compositions

The compounds and pharmaceutical compositions provided herein can be used in the manufacture of medicaments for preventing, treating or lessening a disorder or disease caused by virus infection in a patient. In some embodiment, the virus infection is influenza virus infection.

Also provided herein are the uses of the compounds and pharmaceutical compositions described above in the manufacture of medicaments which are inhibitors of influenza virus RNA polymerase.

Provided herein is a method of treating, preventing or delaying the infections caused by viruses, and wherein the method comprises administering to the patient a therapeutically effective amount of the compound or the pharmaceutical composition described herein to a patient in need of treatment. Wherein the virus is an influenza virus. And, the compounds or pharmaceutical compositions thereof can be co-administered with other therapies or therapeutic agents. The co-administration can be performed simultaneously, sequentially, or in a certain time interval.

Doses of the compound or pharmaceutical composition needed for implementing functions such as treating, preventing or delaying usually depend on the particular compound to be administered, patient, specific disease or disorder and severity thereof, route and frequency of administration and so on, and need to be determined by the doctor in accordance with specific conditions. For example, when the compound or pharmaceutical composition of the present invention is administrated intravenously, the administration may be once a week or even longer intervals.

As described above, the present invention provides a novel class of compounds, and wherein the compounds can be used as inhibitors of the influenza virus RNA polymerase. The compounds of the invention are suitable for preparing medicaments as various dosage forms, which can be used for treating seasonal flu, avian flu, swine flu as well as tamiflu-resistant influenza virus mutants.

Besides being useful for human treatment, these compounds are also useful for veterinary treatment of animals such as companion animals, exotic animals and farm animals. In other embodiments, the animals disclosed herein include horses, dogs, and cats. As used herein, the compounds disclosed herein include the pharmaceutically acceptable derivatives thereof.

General Synthetic Procedures

In the present specification, if the chemical name of the compound doesn't match the corresponding structure, the compound is characterized by the corresponding structure.

For the purpose of describing the invention, the following examples are listed. It should be understood that, the invention is not limited to these examples, and the present invention only provide the method to practice the invention.

Generally, the compounds disclosed herein may be prepared by methods described herein, wherein the substituents are as defined for Formula (I) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Tianjing Fuchen Chemical Reagent Factory, Wuhan XinHuayuan technology development co., LTD., Qingdao Tenglong Reagent Chemical Ltd., Qingdao Ocean Chemical Factory, Beijin Ouhe Technology Co., Ltd., Shanghai Topbiochem Technology Co., Ltd, and Accela ChemBio Co., Ltd.

Anhydrous THF, 1,4-dioxane, toluene, and ethyl ether were obtained by refluxing the solvent with sodium. Anhydrous $CH_2Cl_2$ and $CHCl_3$ were obtained by refluxing the solvent with CaH$_2$. EtOAc, PE, hexane, N,N-dimethylacetamide and N,N-dimethylformamide were treated with anhydrous Na$_2$SO$_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory.

$^1$H NMR spectra were recorded with a Bruker 400 MHz or 600 MHz spectrometer using CDCl$_3$, DMSO-d$_6$, CD$_3$OD or acetone-d$_6$ as solvent (reported in ppm), and using TMS (0 ppm) or chloroform (7.26 ppm) as the reference standard. When peak multiplicities were reported, the following abbreviations were used: s (singlet), d (doublet), t (triplet), m (multiplet), br (broadened), dd (doublet of doublets), and dt (doublet of triplets). Coupling constants, when given, are reported in Hertz (Hz).

Low-resolution mass spectral (MS) data were determined on an Agilent 6120 Quadrupole HPLC-MS spectrometer equipped with an Agilent Zorbax SB-C18 (2.1×30 mm, 3.5 μm, 6 min). The flow rate was 0.6 mL/min; the mobile phases consisted of a combination of A (0.1% formic acid in CH$_3$CN) and B (0.1% formic acid in H$_2$O) in gradient mode (5% to 95%), and an ESI source was used, the peak of HPLC was recorded with UV-Vis detection at 210/254 nm.

Purification of compound by preparative chromatography was implemented on Agilent 1260 Series high performance liquid chromatography (Pre-HPLC) or Calesep Pump 250 Series high performance liquid chromatography (Pre-HPLC) with UV detection at 210/254 nm (column type: NOVASEP, 50/80 mm. DAC).

The following abbreviations are used throughout the specification:
AcOH, HOAc, CH$_3$COOH acetic acid
AcOK, KOAc, CH$_3$COOK potassium acetate
BnOH phenylcarbinol
Bu$_4$NF tetrabutylammonium fluoride
BOC, Boc tert-butoxycarbonyl
(Boc)$_2$O di-tert-butyl dicarbonate ester
n-BuOH n-butyl alcohol
CHCl$_3$ chloroform
CDCl$_3$ deuterated chloroform
CD$_3$OD deuterated methyl alcohol
DCM, CH$_2$Cl$_2$ dichloromethane
CH$_3$CN, MeCN acetonitrile
CH$_3$Cl chloromethane
CH$_3$I iodomethane
CH$_3$SO$_2$Cl, MsCl methanesulfonyl chloride
Cbz carbobenzoxy
Cu(OAc)$_2$ copper acetate
DIEA, DIPEA, iPr$_2$Net N,N-diisopropylethylamine
DMF N,N-dimethylformamide, dimethylformamide
DME dimethyl ether
DMAP 4-dimethylaminopyridine
DMSO dimethylsulfoxide
DMSO-d$_6$ dimethyl sulfoxide-d$_6$, deuterated dimethyl sulfoxide
DPPA diphenylphosphoryl azide
EA, EtOAc ethyl acetate
Et$_3$N, TEA triethylamine
Et$_2$O ethyl ether
EtOH ethyl alcohol
g gram
h hour, hours
H$_2$ hydrogen
H$_2$O water
HCl hydrogen chloride
H$_2$O$_2$ hydrogen peroxide
H$_3$PO$_4$ phosphoric acid
H$_2$SO$_4$ sulfuric acid
HNO$_3$ nitric acid
HATU o-(7-azabenzotriazol-1-yl)-N,N,N',N'-te-tramethyluronium hexafluorophosphate
HCOOK potassium formate
HCOONH$_4$ ammonium formate
HPLC high performance liquid chromatography
HPTLC high performance thin layer chromatography
I$_2$ iodine
Fe iron
MgSO$_4$ magnesium sulfate
CH$_3$OH, MeOH methanol
MeI, CH$_3$I iodomethane
mL, ml milliliter
min minute, minutes
N$_2$ nitrogen
NH$_3$ ammonia
NMP N-methylpyrrolidone
NaHCO$_3$ sodium bicarbonate
NaBH$_4$ sodium borohydride
NaBH$_3$CN sodium cynaoborohydride
NaOMe, NaOCH$_3$, CH$_3$ONa sodium methoxide
NaOH sodium hydroxide
NaCl sodium chloride
NaH$_2$PO$_4$ sodium dihydrogen phosphate
NaH sodium hydride
NaI sodium iodide
Na$_2$SO$_4$ sodium sulfate
Na$_2$S$_2$O$_3$ sodium thiosulfate
NBS N-bromosuccinimide
NIS N-iodosuccinimide
NCS N-chlorosuccinimide
NH$_4$Cl ammonium chloride
NH$_2$OH.HCl hydroxylamine hydrochloride
psi pound per square inch
Pd/C Palladium on activated carbon
Pd(OAc)$_2$ Palladium diacetate
Pd(OH)$_2$ Palladium hydroxide
Pd(PPh$_3$)$_4$ tetrakis(triphenylphosphine)palladium(0)
Pd(PPh$_3$)$_2$Cl$_2$ bis(triphenylphosphine)palladium(II) chloride
Pd(dppf)Cl$_2$, PdCl$_2$(dppf) [1,1'-bis(diphenylphosphino)ferrocene]dichloropalladium(II)
Pd(dppf)Cl$_2$.CH$_2$Cl$_2$ 1,1'-bis(diphenylphosphino)ferrocene-palladium(II)dichloride dichloromethane complex
Pd$_2$(dba)$_3$ tris(dibenzylideneacetone)dipalladium
P(t-Bu)$_3$ tri-tert-butylphosphine
Pd(dtbpf)Cl$_2$ 1,1'-bis (di-t-butylphosphino)ferrocene palladium dichloride
PE petroleum ether (60-90° C.)
POCl$_3$ phosphorus oxychloride
K$_2$CO$_3$ potassium carbonate
K$_3$PO$_4$ potassium phosphate
KOH potassium hydroxide
RT, rt, r.t. room temperature
Rt retention time
SOCl$_2$ thionyl chloride
SI therapeutic index
t-BuOK potassium tert-butoxide
THF tetrahydrofuran
TFA trifluoroacetic acid
TBAI tetrabutylammonium iodide TBS tris(hydroxymethyl)methyl aminomethane buffer saline
TBAF tetrabutylammonium fluoride
TsCl tosyl chloride
Ts p-tosyl, (p-tolyl)sulphonyl
XPhos, X-phos 2-dicyclohexylphosphino-2',4',6'-triisopropylbiphenyl
Zn zinc
ZnCl-TMEDA dichloro(N,N,N',N'-tetramethylethylenediamine)zinc
μL microlitre
w.t mass percentage The following schemes list the synthetic steps of the compounds of the invention, and wherein each $R^1$, $R^2$, $R^3$, $R^4$, $R^6$, $R^7$, $R^b$, R', q and A is as defined herein. PG' is an alkynyl protecting group, and PG is an amino-protecting group.

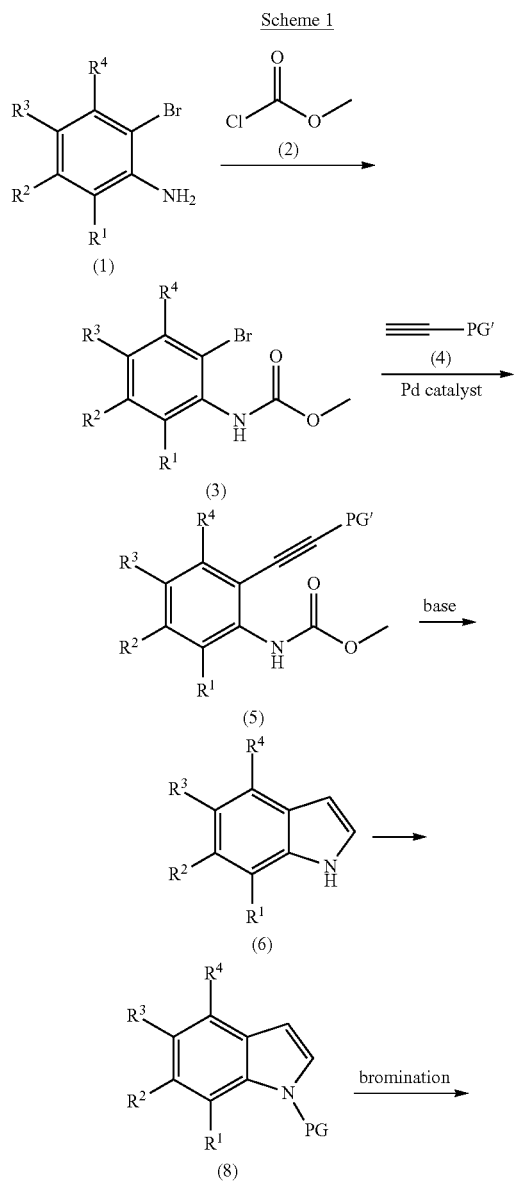

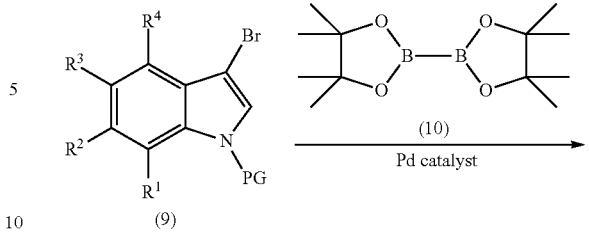

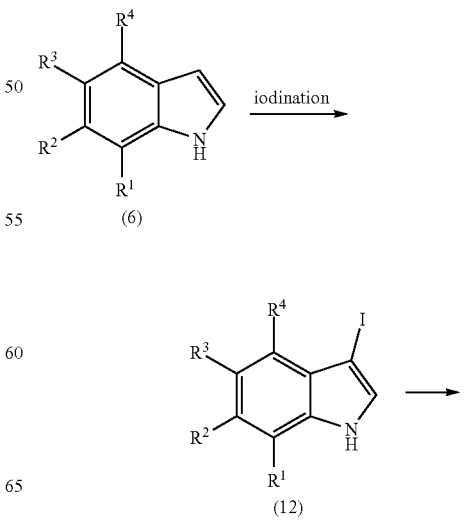

The intermediate having Formula (11) can be prepared by the process illustrated in scheme 1. Firstly, compound (1) can react with compound (2) under an alkaline condition to give compound (3). Then, compound (3) can react with alkynyl compound (4) in the presence of a palladium catalyst (such as Pd(dppf)Cl$_2$, Pd(PPh)$_2$Cl$_2$, and the like) to give compound (5). Compound (5) can undergo cyclization reaction in the presence of a base to give compound (6). The —NH— group of compound (6) can be pretected by a protecting group PG (such as -Ts) under an alkaline condition to give compound (8). Compound (8) with a brominating agent such as NBS can undergo bromination reaction to give compound (9). At last, compound (9) can react with compound (10) in the presence of a palladium catalyst (such as Pd(dppf)Cl$_2$, Pd(PPh)$_2$Cl$_2$, and the like) to give intermediate (11).

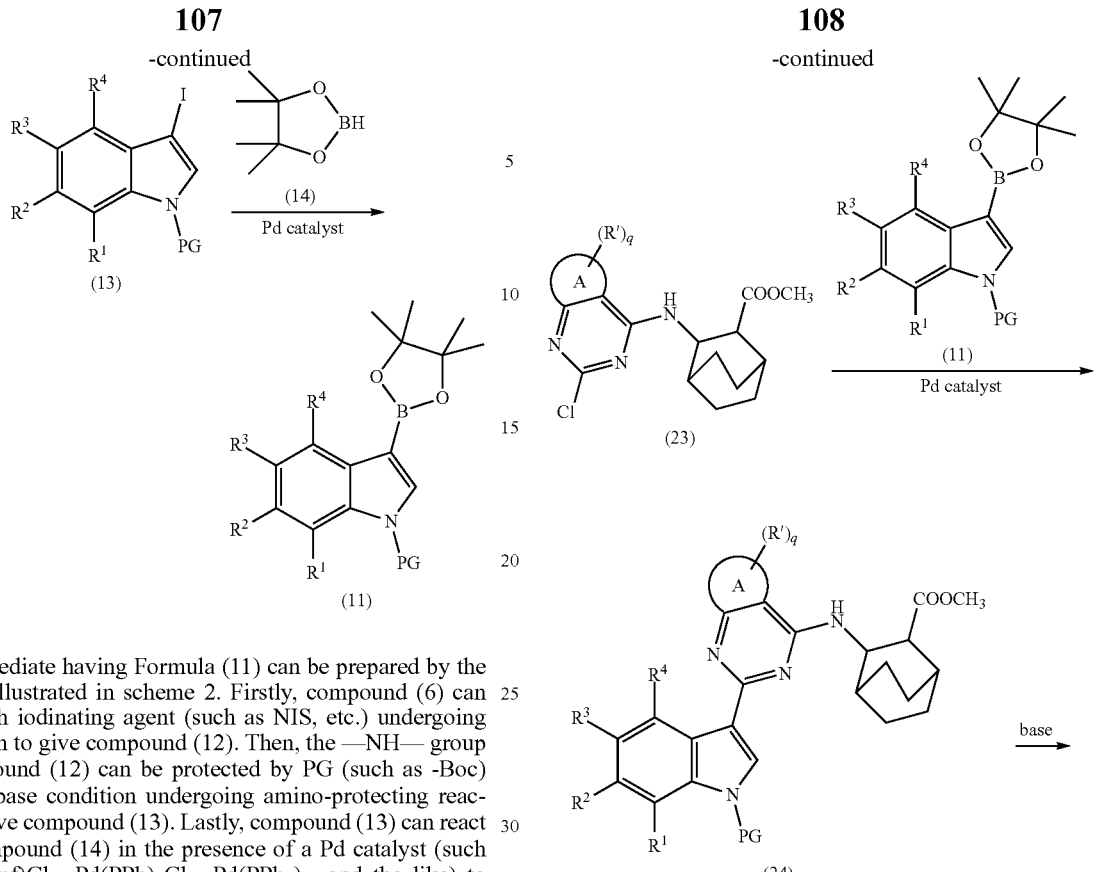

Intermediate having Formula (11) can be prepared by the process illustrated in scheme 2. Firstly, compound (6) can react with iodinating agent (such as NIS, etc.) undergoing iodination to give compound (12). Then, the —NH— group of compound (12) can be protected by PG (such as -Boc) under a base condition undergoing amino-protecting reaction to give compound (13). Lastly, compound (13) can react with compound (14) in the presence of a Pd catalyst (such as Pd(dppf)Cl$_2$, Pd(PPh)$_2$Cl$_2$, Pd(PPh$_3$)$_4$, and the like) to give intermediate (11).

Scheme 3

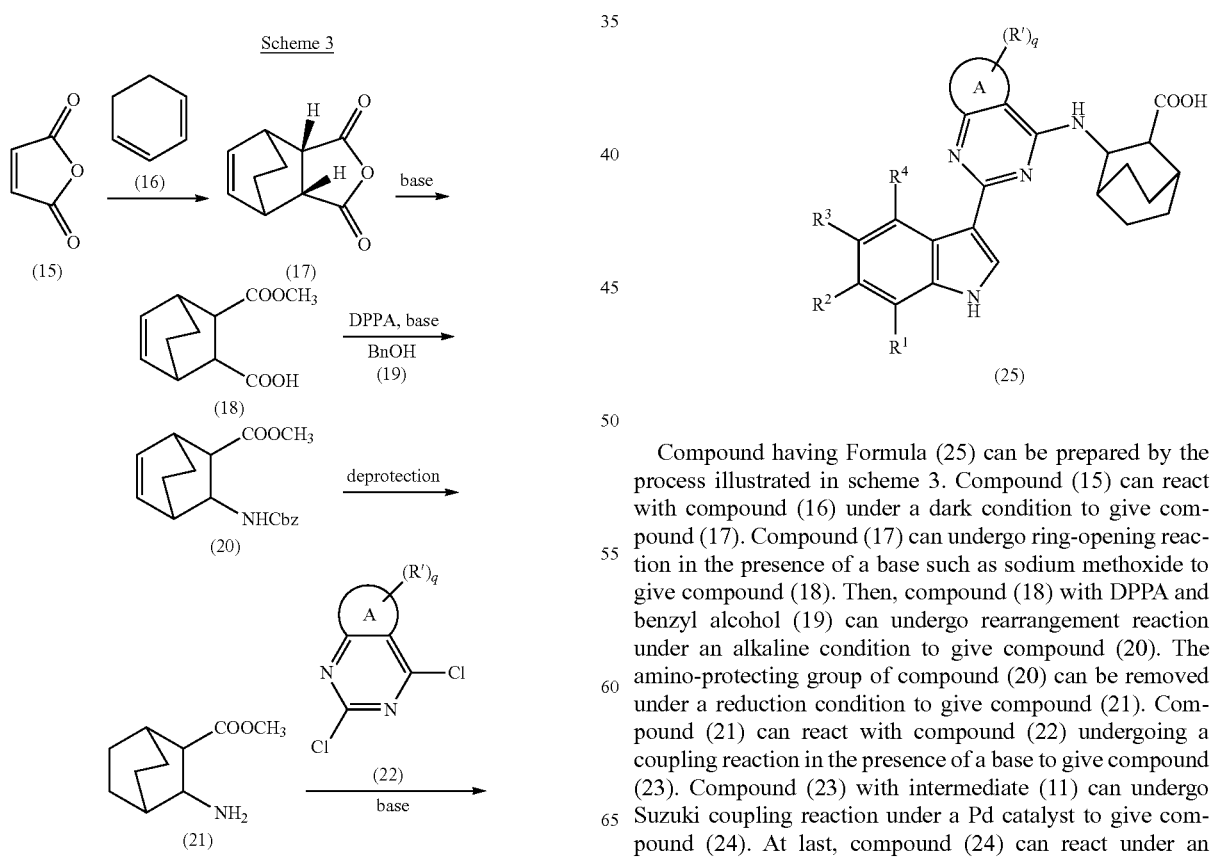

Compound having Formula (25) can be prepared by the process illustrated in scheme 3. Compound (15) can react with compound (16) under a dark condition to give compound (17). Compound (17) can undergo ring-opening reaction in the presence of a base such as sodium methoxide to give compound (18). Then, compound (18) with DPPA and benzyl alcohol (19) can undergo rearrangement reaction under an alkaline condition to give compound (20). The amino-protecting group of compound (20) can be removed under a reduction condition to give compound (21). Compound (21) can react with compound (22) undergoing a coupling reaction in the presence of a base to give compound (23). Compound (23) with intermediate (11) can undergo Suzuki coupling reaction under a Pd catalyst to give compound (24). At last, compound (24) can react under an alkaline condition to give compound (25).

Scheme 4

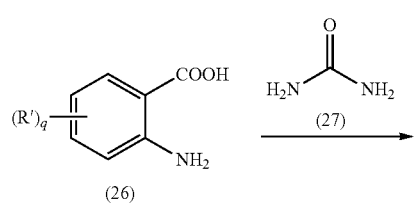

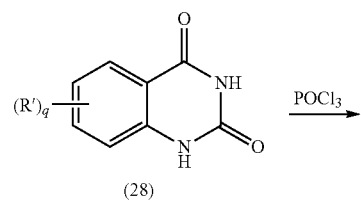

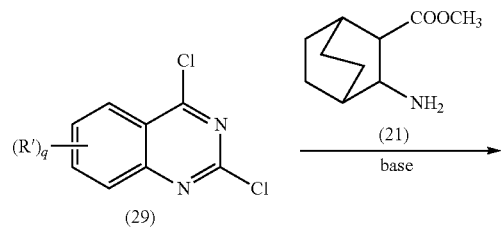

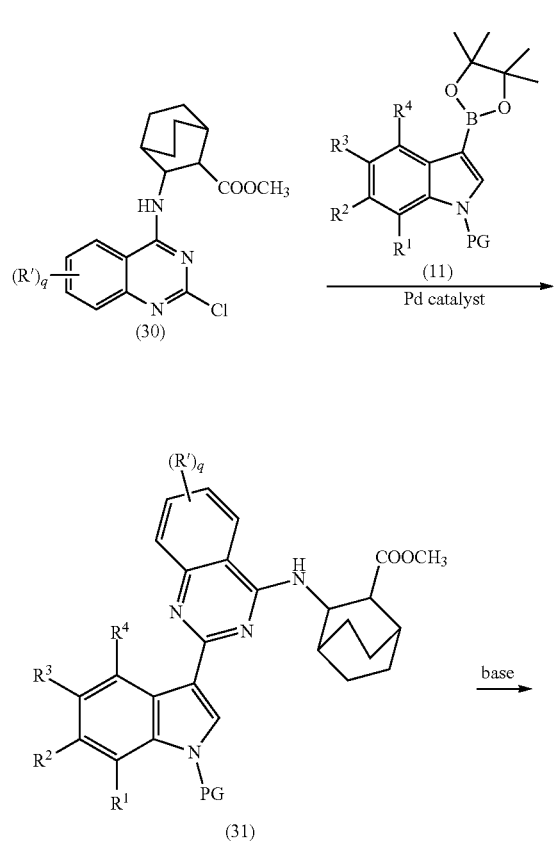

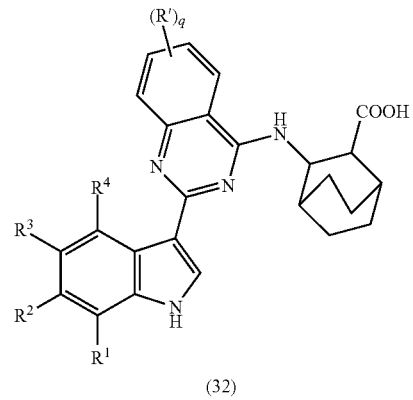

Compound having Formula (32) can be prepared by the process illustrated in scheme 4. Firstly, compound (26) can react with urea (27) under a heating condition to give compound (28). Compound (28) can undergo chlorination reaction in the presence of phosphorus oxychloride to give compound (29). Then, compound (29) can react with compound (21) under an alkaline condition to give compound (30). Compound (30) with compound (11) can undergo Suzuki coupling reaction in the presence of a Pd catalyst to give compound (31). At last, compound (31) can react under an alkaline condition to give compound (32).

Scheme 5

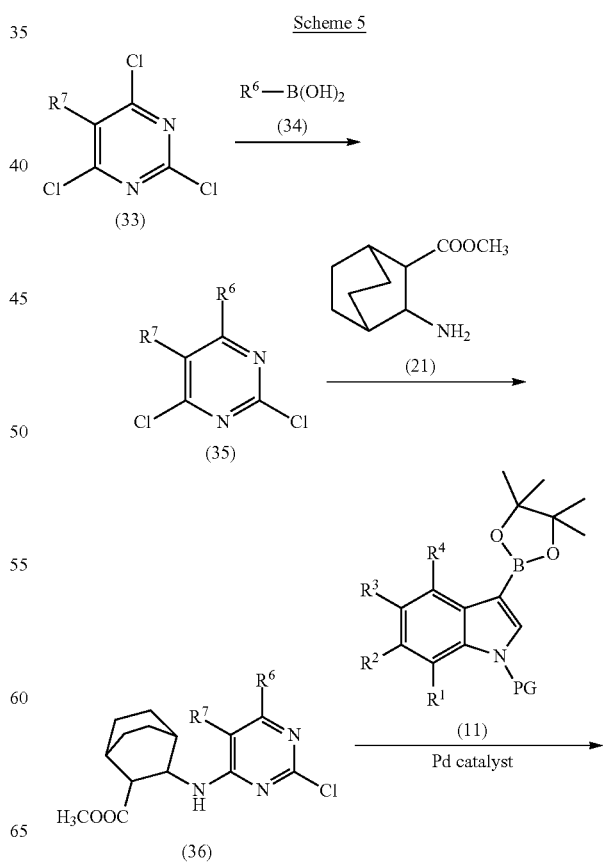

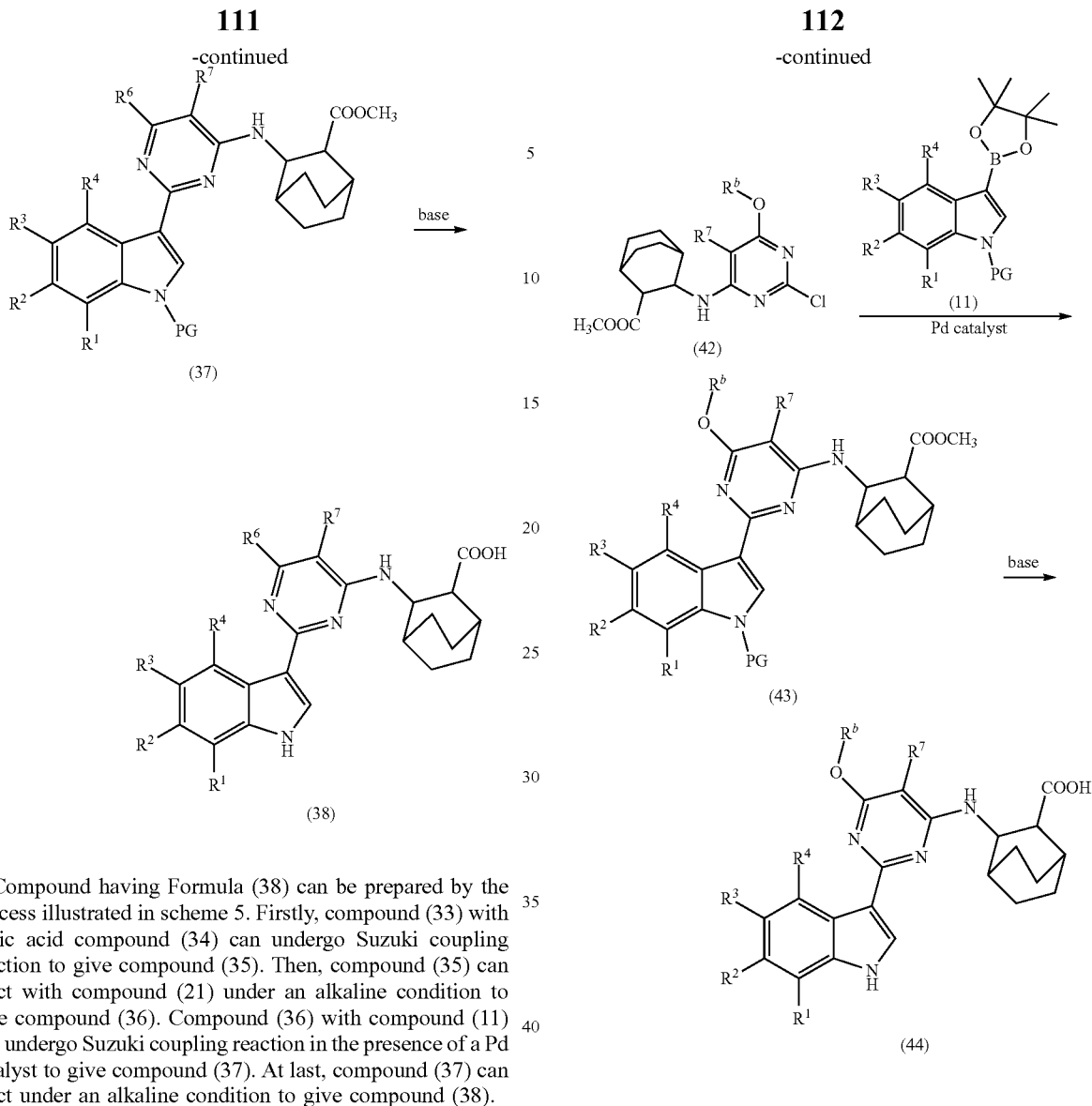

Compound having Formula (38) can be prepared by the process illustrated in scheme 5. Firstly, compound (33) with boric acid compound (34) can undergo Suzuki coupling reaction to give compound (35). Then, compound (35) can react with compound (21) under an alkaline condition to give compound (36). Compound (36) with compound (11) can undergo Suzuki coupling reaction in the presence of a Pd catalyst to give compound (37). At last, compound (37) can react under an alkaline condition to give compound (38).

Compound having Formula (44) can be prepared by the process illustrated in scheme 6. Firstly, compound (39) can react with compound (40) under an alkaline condition to give compound (41). Then, compound (41) can react with compound (21) under an alkaline condition to give compound (42). Then, compound (42) with compound (11) can undergo Suzuki coupling reaction in the presence of a Pd catalyst to give compound (43). At last, compound (43) can react under an alkaline condition to give compound (44).

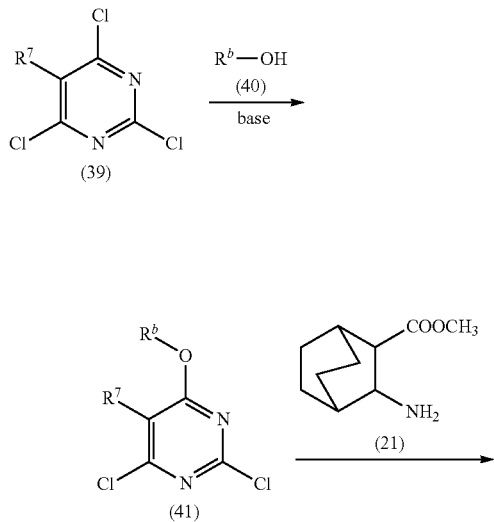

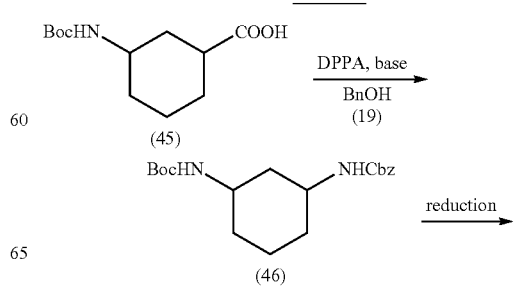

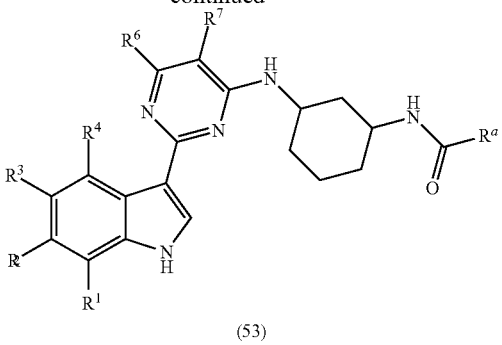

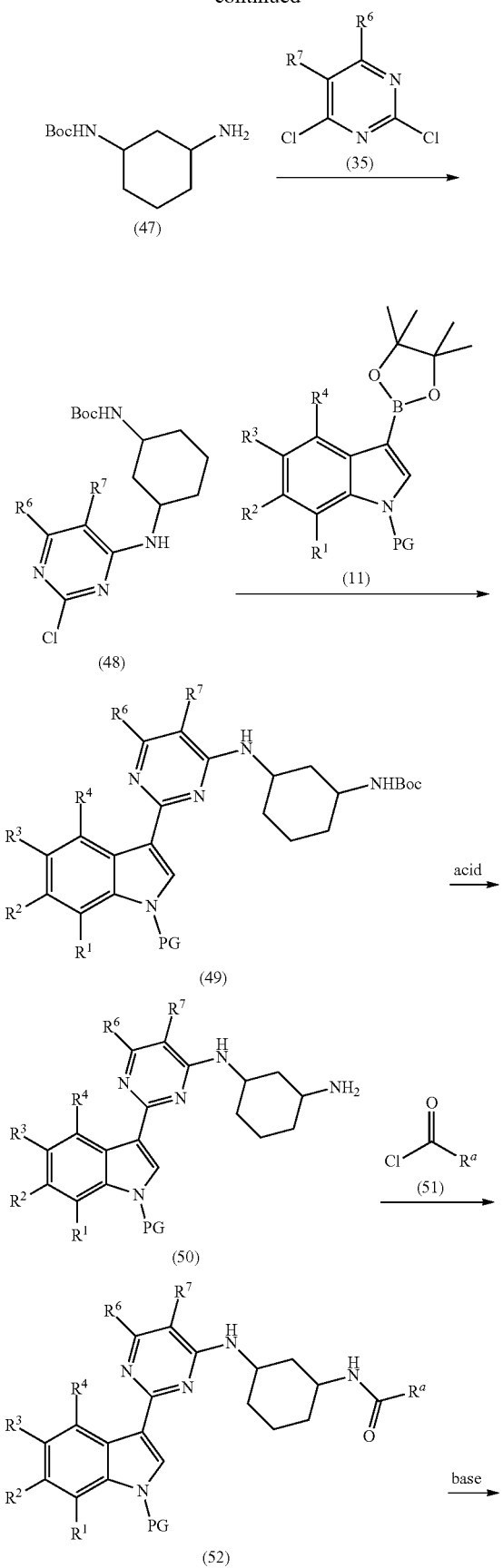

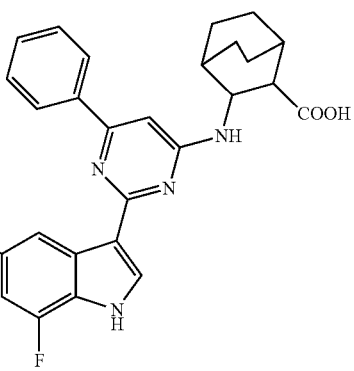

Compound having Formula (53) can be prepared by the process illustrated in scheme 7. Firstly, compound (45) can react with DPPA, compound (19) under an alkaline condition to give compound (46). Then, compound (46) can undergo reduction reaction under a condition (such as in the presence of Pd/C catalyst and hydrogen atmosphere) to give compound (47). Compound (47) can react with compound (35) under an alkaline condition to give compound (48). Then, compound (48) with compound (11) can undergo Suzuki coupling reaction in the presence of a Pd catalyst to give compound (49). The amino-protecting group -Boc of compound (49) can be removed under an acid condition to give compound (50). Compound (50) can react with acyl chloride compound (51) under an alkaline condition to give compound (52). At last, the protection group of compound (52) can be removed under an alkaline condition to give compound (53).

EXAMPLES

The following examples are used for illustrating the invention, but can not be construed to limit the scope of the invention.

Example 1: (+/−)-trans-3-((2-(5,7-difluoro-1H-indol-3-yl)-6-phenylpyrimidin-4-yl)amino)bicyclo[2.2.2]octane-2-carboxylic Acid

Step 1: meso-endo-tetrahydro-4,7-ethanoisobenzo-furan-1,3-dione

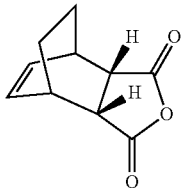

To a 2000 mL dried flask were added maleic anhydride (100 g, 1.02 mol) and chloroform (1000.0 mL) in turn, then the mixture was cooled to 0° C., and 1,3-cyclohexadiene (112.5 mL, 1.12 mol) was added dropwise. After the addition, the mixture was warmed to rt, and stirred overnight in the absence of light. After the reaction was completed, the mixture was concentrated in vacuo to remove the solvent. To the residue was added methanol (700.0 mL), and the resulting mixture was heated to 50° C. and stirred for 10 min, then cooled to 0° C. and stirred for 30 min. The mixture was filtered by suction, and the filter cake was dried in vacuo at 45° C. to give the title compound as a white solid (147 g, 81%).

MS (ESI, pos. ion) m/z: 179.1 [M+H]$^+$;

$^1$H NMR (400 MHz, DMSO-$d_6$) δ (ppm): 6.28 (dd, J=4.2, 3.4 Hz, 2H), 3.29 (s, 2H), 3.04 (s, 2H), 1.61 (d, J=7.9 Hz, 2H), 1.22 (d, J=7.6 Hz, 2H).

Step 2: (+/−)-trans-3-(methoxycarbonyl)bicyclo[2.2.2]oct-5-ene-2-carboxylic Acid

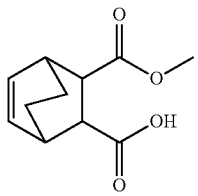

To a dried flask was added meso-endo-tetrahydro-4,7-ethanoisobenzofuran-1,3-dione (33.50 g, 188.01 mmol), then a solution of sodium methoxide in methanol (5 M, 300.8 mL) was added dropwise at 0° C. After the addition, the mixture was warmed to rt and stirred for 4 days, then concentrated in vacuo to remove part of the methanol (about 120 mL). The residue was added slowly into 0° C. aqueous hydrochloric acid solution (277 mL, 18% w.t.), and there was a white solid precipitated out. The mixture was concentrated in vacuo to remove methanol, and the residue was stirred at 0° C. for 30 min, then filtered by suction. The filter cake was washed with water three times and dried in vacuo to give the title compound as a white solid (37.19 g, 94%).

MS (ESI, neg. ion) m/z: 209.0 [M−H]$^-$;

$^1$H NMR (600 MHz, DMSO-$d_6$) δ (ppm): 12.28 (s, 1H), 6.34 (s, 1H), 6.17 (s, 1H), 3.65 (s, 3H), 2.94 (s, 1H), 2.91 (d, J=4.4 Hz, 1H), 2.86 (d, J=2.4 Hz, 1H), 2.72 (s, 1H), 1.48-1.58 (m, 1H), 1.34-1.44 (m, 1H), 1.26-1.16 (m, 1H), 1.09-0.99 (m, 1H).

Step 3: methyl (+/−)-trans-3-(((benzyloxy)carbonyl)amino)bicyclo[2.2.2]oct-5-ene-2-carboxylate

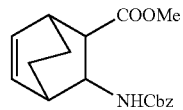

A solution of (+/−)-trans-3-(methoxycarbonyl)bicyclo[2.2.2]oct-5-ene-2-carboxylic acid (6.0 g, 29 mmol) in toluene (50 mL) was degassed and filled with nitrogen for three times, then diphenyl azidophosphate (7.0 mL, 32 mmol) and triethylamine (4.0 mL, 29 mmol) were added in turn by syringe. The mixture was heated to 90° C. and stirred for 2 hours, then phenylcarbinol (3.0 mL, 29 mmol) was added dropwise by syringe. The mixture was stirred for further 3 days maintaining at this temperature. The reaction mixture was cooled to rt, and ethyl acetate (60 mL) was added to dilute the mixture. The resulting mixture was washed with saturated aqueous sodium bicarbonate (60 mL×2) and saturated brine (50 mL) in turn, and the organic layer was dried over anhydrous sodium sulfate, filtered, then the filtrate concentrated in vacuo. The residue was purified by silica gel column chromatography (PE/EtOAc (v/v)=8/1) to give the title compound as yellow oil (8.25 g, 92%).

MS (ESI, pos. ion) m/z: 316.1 [M+H]$^+$.

Step 4: methyl (+/−)-trans-methyl 3-aminobicyclo[2.2.2]octane-2-carboxylate

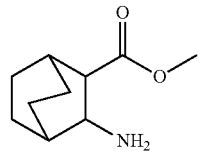

To an autoclave were added (+/−)-trans-methyl 3-(((benzyloxy)carbonyl)amino)bicyclo[2.2.2]oct-5-ene-2-carboxylate (8.21 g, 26.0 mmol), tetrahydrofuran (20 mL) and methanol (20 mL) in turn. To the solution was added Pd/C (10% w.t of Pd, 1.40 g), and the mixture was stirred at rt overnight under a hydrogen pressure of 40 psi. The reaction mixture was filtered through a celite pad to remove the catalyst, then the filter cake was washed with methanol (20 mL) and ethyl acetate (20 mL) in turn. The combined filtrates were concentrated in vacuo to give colourless oil, which was purified by silica-gel column chromatography (DCM/MeOH (v/v)=20/1-10/1) to give the title compound as colourless oil (3.95 g, 83%).

MS (ESI, pos. ion) m/z: 184.2 [M+H]$^+$;

$^1$H NMR (400 MHz, CDCl$_3$) δ (ppm): 3.68 (s, 3H), 3.31 (d, J=6.7 Hz, 1H), 2.11 (d, J=6.7 Hz, 1H), 1.98-1.91 (m, 1H), 1.83-1.71 (m, 1H), 1.60-1.33 (m, 10H).

Step 5: methyl (2-bromo-4,6-difluorophenyl)carbamate

To a suspension of 2-bromo-4,6-difluorophenylamino (10.00 g, 48.07 mmol) and potassium carbonate (19.93 g, 144.20 mmol) in acetonitrile (80 mL) was added dropwise slowly methylchloroformate (22.29 mL, 288.46 mmol).

After the addition, the mixture was stirred at rt for 10 min, then heated to 60° C. and stirred for 1 h. After the reaction, to the reaction mixture was added water (80 mL). The resulting mixture was partitioned, and the aqueous layer was extracted with ethyl acetate (80 mL). The combined organic layers were washed with saturated brine (120 mL), dried over anhydrous sodium sulfate and filtered. The filtrate was concentrated in vacuo, and the residue was purified by silica gel column chromatography (PE/EtOAc (v/v)=10/1~3/1) to give the title compound as a white solid (11.68 g, 50.0%).

MS (ESI, pos. ion) m/z: 267.9 [M+H]$^+$;
$^1$H NMR (400 MHz, CDCl$_3$) δ (ppm): 7.24-7.17 (m, 1H), 6.93 (td, J=9.3, 2.7 Hz, 1H), 6.10 (s, 1H), 3.81 (s, 3H).

Step 6: methyl (2,4-difluoro-6-((trimethylsilyl)ethynl)phenyl)carbamate

To a solution of methyl (2-bromo-4,6-difluorophenyl) carbamate (10.8 g, 40.6 mmol) in acetonitrile (11.6 mL) were added triethylamine (11.3 mL), Pd(PPh$_3$)$_2$Cl$_2$ (5.76 g, 8.12 mmol) and cuprous iodide (773 mg, 4.06 mmol). Then to the mixture was added slowly trimethylsilylacetylene (11.5 mL, 81.2 mmol) under nitrogen protection. After the addition, the mixture was stirred at 80° C. overnight under nitrogen protection, then the mixture was diluted with saturated aqueous ammonium chloride (100 mL). The resulting mixture was extracted with ethyl acetate (100 mL×3). The combined organic layers were washed with saturated brine (250 mL), dried over anhydrous sodium sulfate, then filtered. The filtrate was concentrated in vacuo to dry and the residue was purified by silica gel column chromatography (PE/EtOAc (v/v)=10/1) to give the title compound as a brown solid (9.53 g, 83%).

$^1$H NMR (400 MHz, CDCl$_3$) δ (ppm): 7.03-6.97 (m, 1H), 6.93-6.86 (m, 1H), 6.27 (s, 1H), 3.80 (s, 3H), 0.28 (s, 9H).

Step 7: 5,7-difluoro-1H-indole

To a solution of methyl (2,4-difluoro-6-((trimethylsilyl)ethynyl)phenyl)carbamate (11.02 g, 38.88 mmol) in ethanol (100 mL) was added a solution of sodium ethoxide in ethanol (61 mL, 155.5 mmol). The mixture was stirred at rt for 1.5 h under nitrogen protection, then heated to 80° C. and stirred for further 3 h. The mixture was cooled to rt, and concentrated in vacuo to remove the solvent. The residue was dissolved in ethyl acetate (100 mL), and the mixture was washed with water (100 mL) and saturated brine (100 mL), dried over anhydrous sodium sulfate and filtered. The filtrate was concentrated in vacuo to dry and the residue was purified by silica gel column chromatography (PE/EA (v/v)=10/1) to give the title compound as a white solid (4.76 g, 80%).

$^1$H NMR (600 MHz, CDCl$_3$) δ (ppm): 9.62 (s, 1H), 8.16 (d, J=2.2 Hz, 1H), 7.42-7.33 (m, 1H), 6.53 (dd, J=3.1, 2.1 Hz, 1H), 2.53 (d, J=1.0 Hz, 3H).

Step 8: 5,7-difluoro-1-tosyl-1H-indole

To a solution of 5,7-difluoro-1H-indole (4.76 g, 31.1 mmol) in toluene (120 mL) were added sodium hydride (50% w.t, 2.6 mg, 622 mmol), paratoluensulfonyl chloride (8.89 g, 46.6 mmol) and tetrabutylammonium hydrogen sulfate (1.06 g, 3.11 mmol), and the mixture was stirred at rt overnight. The mixture was diluted with ethyl acetate (100 mL), and the resulting mixture was washed with water (100 mL) and saturated brine (100 mL), dried over anhydrous sodium sulfate, filtered. The filtrate was concentrated in vacuo to dry and the residue was purified by silica gel column chromatography (n-hexane/EtOAc (v/v)=10/1) to give the title compound as a yellow solid (8.31 g, 87%).

MS (ESI, pos. ion) m/z: 308.0 [M+H]$^+$;
$^1$H NMR (400 MHz, CDCl$_3$) δ (ppm): 8.24 (s, 1H), 8.06 (d, J=8.3 Hz, 2H), 7.81 (s, 1H), 7.31 (d, J=8.2 Hz, 2H), 2.68 (d, J=1.3 Hz, 3H), 2.40 (s, 3H).

Step 9: 3-bromo-5,7-difluoro-1-tosyl-1H-indole

To a solution of 5,7-difluoro-1-tosyl-1H-indole (4.3 g, 14.0 mmol) in dichloromethane (100 mL) was added NBS (3.3 g, 18.0 mmol) in portions, and the mixture was stirred at rt overnight. The reaction was quenched with saturated aqueous sodium bicaronbate (100 mL), and the organic layer was washed with saturated brine (100 mL×3), dried over anhydrous sodium sulfate and filtered. The filtrate was concentrated in vacuo to dry and the residue was purified by silica gel column chromatography (n-hexane/EtOAc (v/v)=10/1) to give the title compound as a brown solid (5.23 g, 97%).

MS (ESI, pos. ion) m/z: 386.0 [M+H]$^+$;
$^1$H NMR (400 MHz, CDCl$_3$) δ (ppm): 7.90-7.81 (m, 3H), 7.33 (d, J=8.2 Hz, 2H), 7.03 (dd, J=7.8, 2.1 Hz, 1H), 6.84 (ddd, J=11.5, 9.1, 2.2 Hz, 1H), 2.42 (s, 3H).

Step 10: 5,7-difluoro-3-(4,4,5,5-tetramethyl-1,3,2-dioxaborolan-2-yl)-1-tosyl-1H-indole To a single-neck flask were added 3-bromo-5,7-difluoro-1-tosyl-1H-indole (5.23 g, 13.5 mmol), bis(pinacolato)diboron (5.16 g, 20.3 mmol), potassium acetate (3.99 g, 40.6 mmol), Pd(dppf)Cl$_2$.CH$_2$Cl$_2$ (2.21 g, 2.71 mmol) and 1,4-dioxane (20 mL). The mixture was stirred at 80° C. for 16 h under nitrogen protection. The reaction mixture was cooled to rt and filtered through a celite pad, and the filter cake was washed with ethyl acetate (50 mL). The filtrate was concentrated in vacuo to dry, and the residue was purified by silica gel column chromatography (n-hexane/EtOAc (v/v)=10/1) to give the title compound as a white solid (4.89 g, 83%).

MS (ESI, pos. ion) m/z: 434.0 [M+H]$^+$;
$^1$H NMR (400 MHz, CDCl$_3$) δ (ppm): 8.21 (s, 1H), 7.82 (t, J=7.9 Hz, 4H), 7.30 (s, 2H), 2.40 (s, 3H), 1.38 (s, 12H).

Step 11: 2,4-dichloro-6-phenylpyrimidine

To a solution of 2,4,6-trichloropyrimidine (0.29 mL, 2.5 mmol) in tetrahydrofuran (5 mL) were added palladium acetate (8 mg, 0.035 mmol), triphenylphosphine (18 mg, 0.065 mmol), phenylboronic acid (0.20 g, 1.6 mmol) and an aqueous sodium carbonate solution (1 M, 3.3 mL, 3.3 mmol). The mixture was heated to 60° C. and stirred for 6 h. The mixture was cooled to rt, and concentrated in vacuo to remove organic solvent. To the residue was added H$_2$O (10 mL), and the mixture was extracted with EtOAc (10 mL×3). The combined organic layers were washed with saturated brine (10 mL), dried over anhydrous sodium sulfate, and filtered. The filtrate was concentrated in vacuo to dryness, and the residue was purified by silica gel column chromatography (PE) to give the title compound as a white solid (0.225 g, 61%).

MS: (ESI, pos. ion) m/z: 224.95 [M+H]$^+$;
$^1$H NMR (400 MHz, CDCl$_3$) δ (ppm): 8.15-8.04 (m, 2H), 7.70 (s, 1H), 7.63-7.50 (m, 3H).

Step 12: (+/−)-trans-methyl 3-((2-chloro-6-phenylpyrimidin-4-yl)amino)bicyclo[2.2.2]octane 2-carboxylate To a solution of 2,4-dichloro-6-phenylpyrimidine (1.52 g, 6.7 mmol) and (+/−)-trans-methyl 3-aminobicyclo[2.2.2]octane-2-carboxylate (1.84 g, 10.0 mmol) in N,N-dimethylformamide (10 mL) was added potassium carbonate (0.92 g, 6.7 mmol). The mixture was stirred at rt overnight. To the reaction mixture was added H$_2$O (50 mL), and the mixture was extracted with EtOAc (40 mL×3). The combined organic layers were washed with saturated brine (50 mL), dried over anhydrous sodium sulfate, and filtered. The filtrate was concentrated in vacuo to dry, and the residue was purified by silica gel column chromatography (n-hexane/EtOAc (v/v)=20/1~10/1) to give the title compound as a white solid (1.65 g, 66%).

MS (ESI, pos. ion) m/z: 372.20 [M+H]$^+$;
$^1$H NMR (400 MHz, CDCl$_3$) δ (ppm): 8.04-7.91 (m, 2H), 7.51-7.41 (m, 3H), 6.78 (s, 1H), 5.41 (s, 1H), 4.32 (s, 1H), 3.73 (s, 3H), 2.38 (d, J=5.1 Hz, 1H), 2.07 (s, 1H), 1.86 (m, 1H), 1.73 (m, 1H), 1.70-1.60 (m, 4H), 1.57 (m, 2H), 1.51-1.41 (m, 1H).

Step 13: (+/−)-trans-methyl 3-((2-(5,7-difluoro-1-tosyl-1H-indol-3-yl)-6-phenylpyrimidin-4-yl)mino)bicyclo[2.2.2]octane-2-carboxylate To a mixed solvent of 1,4-dioxane (3 mL) and water (0.2 mL) were added 5,7-difluoro-3-(4,4,5,5-tetramethyl-1,3,2-dioxaborolan-2-yl)-1-tosyl-1H-indole (119 mg, 0.32 mmol), (+/−)-trans-methyl 3-((2-chloro-6-phenylpyrimidin-4-yl)amino)bicyclo[2.2.2]octane 2-carboxylate (100 mg, 0.27 mmol), potassium phosphate (171 mg, 0.81 mmol) and Pd(dtbpf)Cl$_2$ (17 mg, 0.03 mmol). The mixture was stirred at 100° C. for 30 min under nitrogen protection, and then filtered through a celite pad. The filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (114 mg, 66%).

$^1$H NMR (400 MHz, CDCl$_3$) δ (ppm): 8.77 (s, 1H), 8.36 (d, J=7.4 Hz, 1H), 8.13 (d, J=7.0 Hz, 2H), 7.90 (d, J=8.0 Hz, 2H), 7.58-7.49 (m, 3H), 7.31 (d, J=8.4 Hz, 2H), 6.85-6.75 (m, 2H), 5.20 (s, 1H), 4.55 (s, 1H), 3.75 (s, 3H), 2.46 (d, J=5.3 Hz, 1H), 2.41 (s, 3H), 2.11 (s, 1H), 2.02 (s, 1H), 1.91-1.62 (m, 8H).

Step 14: (+/−)-trans-3-((2-(5,7-difluoro-1H-indol-3-yl)-6-phenylpyrimidin-4-yl)amino)bicyclo[2.2.2]octane-2-carboxylic Acid To a solution of (+/−)-trans-methyl 3-((2-(5,7-difluoro-1-tosyl-1H-indol-3-yl) 6-phenylpyrimidin-4-yl)amino)bicyclo[2.2.2]octane-2-carboxylate (114 mg, 0.18 mmol) in a mixed solvent of THF and MeOH (v/v=1/1, 2 mL) was added an aqueous sodium hydroxide solution (4 M, 0.45 mL, 1.80 mmol). The mixture was stirred at 30° C. overnight. To the reaction mixture was added water (10 mL), and the mixture was acidified with hydrochloric acid (1 M) to pH about 5.5. The resulting mixture was extracted with EtOAc (20 mL×3). The combined organic layers were washed with saturated brine (50 mL), dried over anhydrous sodium sulfate, and filtered. The filtrate was concentrated in vacuo and the residue was purified by silica gel column chromatography (dichloromethane/methanol (v/v)=10/1) to give the title compound as a yellow solid (18 mg, 21%).

MS (ESI, pos. ion) m/z: 414.1 [M+H]$^+$;
$^1$H NMR (600 MHz, DMSO-d$_6$) δ (ppm): 12.22 (s, 1H), 8.30 (s, 1H), 8.23 (s, 1H), 8.10 (s, 2H), 7.52 (dt, J=38.5, 12.6 Hz, 4H), 7.06 (t, J=9.8 Hz, 1H), 6.75 (s, 1H), 4.65 (s, 1H), 3.96 (s, 1H), 2.00 (s, 2H), 1.60 (m, 8H).

Example 2: (+/−)-trans-3-((2-(5,7-difluoro-1H-indol-3-yl)-6-(p-tolyl)pyrimidin-4-yl)amino) icyclo[2.2.2]octane-2-carboxylic Acid

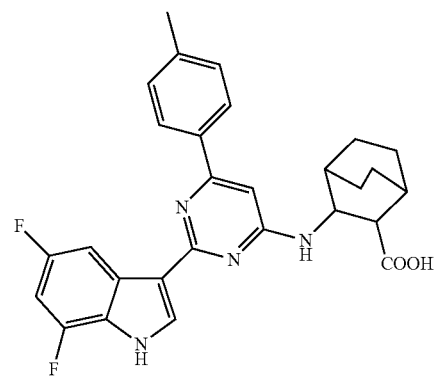 [SMILES: Cc1ccc(-c2cc(NC3C4CCC(CC4)C3C(=O)O)nc(-c3c[nH]c4c(F)cc(F)cc34)n2)cc1]

Step 1: 2,4-dichloro-6-(p-tolyl)pyrimidine

To a solution of 2,4,6-trichloropyrimidine (1.01 g, 5.51 mmol) in tetrahydrofuran (16 mL) were added palladium acetate (0.1 g, 0.4 mmol), triphenylphosphine (0.24 g, 0.87 mmol), p-tolylboronic acid (749 mg, 5.51 mol) and an aqueous sodium carbonate solution (1 M, 16.35 mL, 16.35 mmol). The mixture was heated to 70° C. and stirred for 6 h. To the reaction mixture was added water (50 mL), and the mixture was extracted with ethyl acetate (50 mL×3). The combined organic layer was washed with saturated brine (50 mL), dried over anhydrous sodium sulfate, and filtered. The filtrate was concentrated in vacuo to dry and the residue was purified by silica gel column chromatography (PE) to give the title compound as a white solid (815 mg, 62%).

MS (ESI, pos. ion) m/z: 239.0 [M+H]$^+$;
$^1$H NMR (400 MHz, CDCl$_3$) δ (ppm): 8.00 (d, J=8.1 Hz, 2H), 7.66 (s, 1H), 7.34 (d, J=8.1 Hz, 2H), 2.46 (s, 3H).

Step 2: (+/−)-trans-methyl 3-((2-chloro-6-(p-tolyl)pyrimidin-4-yl)amino)bicyclo[2.2.2]octane 2-carboxylate To a solution of (+/−)-trans-methyl 3-aminobicyclo[2.2.2]octane-2-carboxylate (337 mg, 1.84 mmol) and 2,4-dichloro-6-(p-tolyl)pyrimidine (400 mg, 1.67 mmol) in tetrahydrofuran (5 mL) was added DIPEA (1.23 mL, 8.36 mmol). The mixture was stirred at rt overnight, and the reaction mixture was concentrated in vacuo to dry. The residue was purified by silica gel column chromatography (PE/EtOAc (v/v)=20/1) to give the title compound as a white solid (115 mg, 18%).

MS (ESI, pos. ion) m/z: 386.1 [M+H]$^+$;
$^1$H NMR (400 MHz, CDCl$_3$) δ (ppm): 7.91 (d, J=8.0 Hz, 2H), 7.39 (d, J=4.3 Hz, 1H), 7.29 (d, J=3.5 Hz, 2H), 6.77 (s, 1H), 5.44 (s, 1H), 4.33 (s, 1H), 3.75 (s, 3H), 2.42 (s, 3H), 2.39 (d, J=5.1 Hz, 1H), 2.07 (s, 1H), 1.90-1.84 (m, 1H), 1.74 (d, J=8.6 Hz, 2H), 1.69 (d, J=2.5 Hz, 4H), 1.58 (d, J=10.3 Hz, 2H).

Step 3: (+/−)-trans-methyl 3-((2-(5,7-difluoro-1-tosyl-1H-indol-3-yl)-6-(p-tolyl)pyrimidin-4-yl)amino)bicyclo[2.2.2]octane-2-carboxylate To a microwave tube were added 5,7-difluoro-3-(4,4,5,5-tetramethyl-,3,2-dioxaborolan-2-yl)-1-tosyl-1H-indole (359 mg, 0.58 mmol), (+/−)-trans-methyl 3-((2-chloro-6-(p-tolyl)lpyrimidin-4-yl)amino)bicyclo[2.2.2]octane-2-carboxylate (187 mg, 0.48 mmol), potassium phosphate (308 mg, 1.45 mmol), Pd(dtbpf)Cl$_2$ (31 mg, 0.05 mmol), 1,4-dioxane (3 mL) and water (0.2 mL). A stream of nitrogen was bubbled through the mixture for 3 min to remove the air, and the mixture was stirred at 100° C. for 10 min, and then the mixture was filtered through a celite pad. The filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (195 mg, 61%).

MS (ESI, pos. ion) m/z: 657.7 [M+H]$^+$;
$^1$H NMR (400 MHz, CDCl$_3$) δ (ppm): 8.76 (s, 1H), 8.37 (d, J=7.3 Hz, 1H), 8.03 (d, J=8.0 Hz, 2H), 7.89 (d, J=8.0 Hz, 2H), 7.39 (d, J=4.5 Hz, 2H), 7.35 (d, J=8.1 Hz, 2H), 6.84-6.77 (m, 1H), 6.74 (s, 1H), 4.73 (d, J=5.7 Hz, 1H), 4.54 (s, 1H), 3.74 (s, 3H), 2.46 (s, 4H), 2.41 (s, 3H), 2.11 (s, 1H), 2.01 (s, 1H), 1.90-1.64 (m, 8H).

Step 4: (+/−)-trans-3-((2-(5,7-difluoro-1H-indol-3-yl)-6-(p-tolyl)pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-6-(p-tolyl)pyrimidin-4-yl)amino)bicyclo[2.2.2]octane-2-carboxylate (195 mg, 0.30 mmol) in a mixed solvent of THF and MeOH (v/v=1/1, 4 mL) was added an aqueous sodium hydroxide solution (4 M, 0.75 mL, 3.00 mmol). The mixture was stirred at 30° C. overnight. To the reaction mixture was added water (10 mL), and the mixture was acidified with hydrochloric acid (1 M) to pH about 5.5. The resulting mixture was extracted with EtOAc (20 mL×3). The combined organic layers were washed with saturated brine (50 mL), dried over anhydrous sodium sulfate, and filtered. The filtrate was concentrated in vacuo and the residue was purified by silica gel column chromatography (dichloromethane/methanol (v/v)=10/1) to give the title compound as a yellow solid (56 mg, 39%).

MS (ESI, pos. ion) m/z: 489.6 [M+H]$^+$;
$^1$H NMR (400 MHz, DMSO-d$_6$) δ (ppm): 12.22 (s, 1H), 8.29 (s, 1H), 8.23 (s, 1H), 8.00 (s, 1H), 7.47 (s, 1H), 7.35 (d, J=7.4 Hz, 3H), 7.06 (t, J=10.0 Hz, 1H), 6.74 (s, 1H), 4.64 (s, 1H), 2.89 (s, 1H), 2.73 (s, 1H), 2.39 (s, 3H), 1.99 (s, 2H), 1.90-1.48 (m, 8H).

Example 3: (+/−)-trans-3-((2-(5,7-difluoro-1H-indol-3-yl)-6-(3-fluoro-4-methoxyphenyl)pyrimidin-4-yl)amino)bicyclo[2.2.2]octane-2-carboxylic Acid

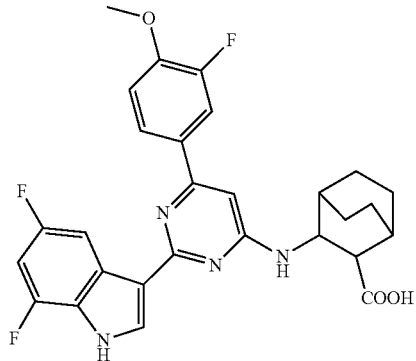 [SMILES: COc1ccc(-c2cc(NC3C4CCC(CC4)C3C(=O)O)nc(-c3c[nH]c4c(F)cc(F)cc34)n2)cc1F]

Step 1: 2,4-dichloro-6-(3-fluoro-4-methoxyphenyl)pyrimidine

To a solution of 2,4,6-trichloropyrimidine (1.01 g, 5.45 mmol) in tetrahydrofuran (16 mL) were added palladium acetate (125 mg, 0.55 mmol), triphenylphosphine (302 mg, 1.09 mmol), (3-fluoro-4-methoxyphenyl)boronic acid (1.18 g, 6.94 mol) and an aqueous sodium carbonate solution (1 M, 16.35 mL, 16.35 mmol). The mixture was heated to 70° C. and stirred for 6 h. To the reaction mixture was added water (50 mL), and the mixture was extracted with ethyl acetate (50 mL×3). The combined organic layer was washed with saturated brine (50 mL), dried over anhydrous sodium sulfate, and filtered. The filtrate was concentrated in vacuo to dry and the residue was purified by silica gel column chromatography (PE) to give the title compound as a white solid (1.03 g, 69%).

MS (ESI, pos. ion) m/z: 273.1 [M+H]$^+$;
$^1$H NMR (400 MHz, CDCl$_3$) δ (ppm): 7.91-7.88 (m, 1H), 7.87 (s, 1H), 7.59 (s, 1H), 7.09 (t, J=8.5 Hz, 1H), 4.00 (s, 3H).

Step 2: (+/−)-trans-methyl 3-((2-chloro-6-(3-fluoro-4-methoxyphenyl)pyrimidin-4-yl)amino)bicyclo[2.2.2]octane-2-carboxylate To a solution of (+/−)-trans-methyl 3-aminobicyclo[2.2.2]octane-2-carboxylate (369 mg, 2.01 mmol) and 2,4-dichloro-6-(3-fluoro-4-methoxyphenyl)pyrimidine (500 mg, 1.83 mmol) in tetrahydrofuran (5 mL) was added DIPEA (3 mL, 20.4 mmol). The mixture was stirred at rt overnight, and the reaction mixture was concentrated in vacuo to dry. The residue was purified by silica gel column chromatography (PE/EtOAc (v/v)=20/1) to give the title compound as a white solid (206 mg, 27%).

MS (ESI, pos. ion) m/z: 420.1 [M+H]$^+$;
$^1$H NMR (400 MHz, CDCl$_3$) δ (ppm): 7.79 (t, J=9.6 Hz, 2H), 7.04 (t, J=8.7 Hz, 1H), 6.73 (s, 1H), 5.46 (s, 1H), 4.33 (s, 1H), 3.97 (s, 3H), 3.76 (s, 3H), 2.40 (s, 1H), 2.09 (s, 1H), 1.88 (d, J=2.8 Hz, 1H), 1.78-1.65 (m, 6H), 1.50 (d, J=11.5 Hz, 2H).

Step 3: (+/−)-trans-methyl 3-((2-(5,7-difluoro-1-tosyl-1H-indol-3-yl)-6-(3-fluoro-4-methoxyphenyl)pyrimidin-4-yl)amino)bicyclo[2.2.2]octane-2-carboxylate To a microwave tube were added 5,7-difluoro-3-(4,4,5,5-tetramethyl-1,3,2-dioxaborolan-2-yl)-1-tosyl-1H-indole (172 mg, 0.28 mmol), (+/−)-trans-methyl 3-((2-chloro-6-(3-fluoro-4-methoxyphenyl)pyrimidin-4-yl)amino)bicyclo[2.2.2]octane-2-carboxylate (90 mg, 0.21 mmol), potassium phosphate (147 mg, 0.69 mmol), Pd(dtbpf)Cl$_2$ (15 mg, 0.02 mmol), 1,4-dioxane (3 mL) and water (0.2 mL). A stream of nitrogen was bubbled through the mixture for 3 min to remove the air, and the mixture was stirred at 100° C. for 10 min under a microwave condition, and then filtered through a celite pad. The filter cake was washed with ethyl acetate (50 mL). The filtrate was washed with saturated brine (50 mL), dried over anhydrous sodium sulfate, and filtered. The filtrate was concentrated in vacuo and the residue was purified by silica gel column chromatography (n-hexane/EtOAc (v/v)=5/1) to give the title compound as a yellow solid (100 mg, 68%).

MS (ESI, pos. ion) m/z: 691.7 [M+H]$^+$;
$^1$H NMR (400 MHz, CDCl$_3$) δ (ppm): 8.76 (s, 1H), 8.32 (d, J=8.5 Hz, 1H), 7.88 (d, J=12.3 Hz, 4H), 7.32 (s, 1H), 7.12 (s, 1H), 6.82 (s, 1H), 6.68 (s, 1H), 4.53 (s, 1H), 4.00 (s, 3H), 3.75 (s, 3H), 2.46 (s, 1H), 2.41 (s, 3H), 2.12 (s, 1H), 1.99 (d, J=19.2 Hz, 2H), 1.77 (m, 8H).

Step 4: (+/−)-trans-3-((2-(5,7-difluoro-1H-indol-3-yl)-6-(3-fluoro-4-methoxyphenyl)pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-6-(3-fluoro-4-methoxyphenyl)pyrimidin-4-yl)amino)bicyclo[2.2.2]octane-2-carboxylate (100 mg, 0.14 mmol) in a mixed solvent of THF and MeOH (v/v=1/1, 4 mL) was added an aqueous sodium hydroxide solution (4 M, 0.33 mL, 1.40 mmol). The mixture was stirred at 30° C. overnight. To the reaction mixture was added water (10 mL), and the mixture was acidified with hydrochloric acid (1 M) to pH about 5.5. The resulting mixture was extracted with EtOAc (20 mL×3). The combined organic layers were washed with saturated brine (50 mL), dried over anhydrous sodium sulfate, and filtered. The filtrate was concentrated in vacuo and the residue was purified by silica gel column chromatography (dichloromethane/methanol (v/v)=10/1) to give the title compound as a yellow solid (37 mg, 49%).

MS (ESI, pos. ion) m/z: 523.1 [M+H]$^+$;
$^1$H NMR (400 MHz, DMSO-d$_6$) δ (ppm): 12.26 (s, 1H), 8.32 (d, J=2.2 Hz, 1H), 8.21 (s, 1H), 7.92 (d, J=30.9 Hz, 2H), 7.51 (s, 1H), 7.33 (t, J=8.7 Hz, 1H), 7.07 (dd, J=15.1, 5.7 Hz, 1H), 6.72 (s, 1H), 4.64 (s, 1H), 3.93 (s, 3H), 3.60 (s, 1H), 2.89 (s, 1H), 2.73 (s, 1H), 2.00 (s, 2H), 1.47 (m, 6H);
$^{13}$C NMR (101 MHz, DMSO-d$_6$) δ (ppm): 175.98, 163.13, 162.78, 153.28, 150.86, 148.93, 131.77, 131.37, 123.15, 122.10, 117.47, 97.21, 74.01, 67.48, 56.63, 50.59, 49.71, 36.24, 31.25, 28.80, 28.59, 26.02, 25.59, 25.42, 24.06, 21.43, 19.45.

Example 4: (+/−)-trans-3-((2-(5,7-difluoro-1H-indol-3-yl)-6-(4-morpholinophenyl)pyrimidin-4-yl)amino)bicyclo[2.2.2]octane-2-carboxylic Acid

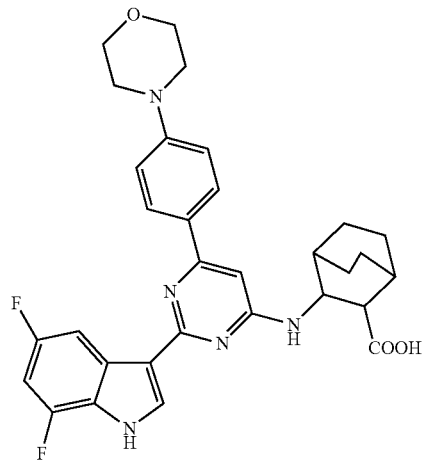 [SMILES: O=C(O)C1C2CCC(CC2)C1Nc1cc(-c2ccc(N3CCOCC3)cc2)nc(-c2c[nH]c3c(F)cc(F)cc23)n1]

Step 1:
4-(4-(2,6-dichloropyrimidin-4-yl)phenyl)morpholine

To a solution of 2,4,6-trichloropyrimidine (500 mg, 2.73 mmol) in tetrahydrofuran (8.18 mL) were added palladium acetate (63 mg, 0.28 mmol), triphenylphosphine (150 mg, 0.548 mmol), (4-morpholinophenyl)boronic acid (570 mg, 2.75 mmol) and an aqueous sodium carbonate solution (1 M, 8.18 mL, 8.18 mmol). The mixture was heated to 70° C. and stirred for 6 h. To the reaction mixture was added water (50 mL), and the mixture was extracted with EtOAc (50 mL×3). The combined organic layers were washed with saturated brine (50 mL), dried over anhydrous sodium sulfate, and filtered. The filtrate was concentrated in vacuo to dry, and the residue was purified by silica gel column chromatography (PE) to give the title compound as a white solid (374 mg, 44%).

MS (ESI, pos. ion) m/z: 310.0 [M+H]$^+$;
$^1$H NMR (400 MHz, CDCl$_3$) δ (ppm): 8.04 (d, J=9.1 Hz, 2H), 7.56 (s, 1H), 6.96 (d, J=9.1 Hz, 2H), 3.92-3.88 (m, 4H), 3.37-3.33 (m, 4H).

Step 2: (+/−)-trans-methyl 3-((2-chloro-6-(4-morpholinophenyl)pyrimidin-4-yl)amino)bicyclo[2.2.2]octane-2-carboxylate To a solution of (+/−)-trans-methyl 3-aminobicyclo[2.2.2]octane-2-carboxylate (230 mg, 1.25 mmol) and 4-(4-(2,6-dichloropyrimidin-4-yl)phenyl)morpholine (353 mg, 1.14 mmol) in DMF (5 mL) were added potassium carbonate (173 mg, 1.25 mmol). The mixture was stirred at rt overnight. To the reaction mixture was added water (40 mL), and the mixture was extracted with ethyl acetate (40 mL×3). The combined organic layer was washed with saturated brine (50 mL), dried over anhydrous sodium sulfate, and filtered. The filtrate was concentrated in vacuo to dry. The residue was purified by silica gel column chromatography (PE/EtOAc (v/v)=20/1) to give the title compound as a white solid (192 mg, 37%).

MS (ESI, pos. ion) m/z: 457.3 [M+H]$^+$;

¹H NMR (400 MHz, CDCl₃) δ (ppm): 7.96 (d, J=8.8 Hz, 2H), 6.96 (d, J=8.9 Hz, 2H), 6.71 (s, 1H), 5.41-5.34 (m, 1H), 4.32 (s, 1H), 3.92-3.86 (m, 4H), 3.75 (s, 3H), 3.32-3.25 (m, 4H), 2.39 (d, J=4.8 Hz, 1H), 2.07 (d, J=3.3 Hz, 1H), 1.88 (d, J=2.7 Hz, 1H), 1.81-1.62 (m, 6H), 1.53-1.41 (m, 2H).

Step 3: (+/−)-trans-methyl 3-((2-(5,7-difluoro-1-tosyl-1H-indol-3-yl)-6-(4-morpholinophenyl)pyrimidin-4-yl)amino)bicyclo[2.2.2]octane-2-carboxylate To a microwave tube were added 5,7-difluoro-3-(4,4,5,5-tetramethyl-1,3,2-dioxaborolan-2-yl)-1-tosyl-1H-indole (130 mg, 0.21 mmol), (+/−)-trans-methyl 3-((2-chloro-6-(4-morpholinophenyl)pyrimidin-4-yl)amino)bicyclo[2.2.2]octane-2-carboxylate (80 mg, 0.18 mmol), potassium phosphate (111 mg, 0.52 mmol), Pd(dtbpf)Cl₂ (11 mg, 0.02 mmol), 1,4-dioxane (3 mL) and water (0.2 mL). A stream of nitrogen was bubbled through the mixture for 3 min to remove the air, and the mixture was stirred at 100° C. for 10 min under nitrogen protection, and then filtered through a celite pad. The filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (68 mg, 53%).

¹H NMR (400 MHz, CDCl₃) δ (ppm): 8.75 (s, 1H), 8.37 (d, J=9.0 Hz, 1H), 8.09 (d, J=8.7 Hz, 2H), 7.89 (d, J=8.2 Hz, 2H), 7.31 (s, 1H), 7.04 (d, J=8.8 Hz, 2H), 6.80 (t, J=9.4 Hz, 1H), 6.69 (s, 1H), 5.16 (s, 1H), 4.52 (s, 1H), 4.00-3.86 (m, 4H), 3.74 (s, 3H), 3.36-3.24 (m, 4H), 2.45 (s, 1H), 2.41 (s, 3H), 2.10 (s, 1H), 2.02 (d, J=14.1 Hz, 2H), 1.74 (m, 6H).

Step 4: (+/−)-trans-3-((2-(5,7-difluoro-1H-indol-3-yl)-6-(4-morpholinophenyl)pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-6-(4-morpholinophenyl)pyrimidin-4-yl)amino)bicyclo[2.2.2]octane-2-carboxylate (68 mg, 0.09 mmol) in a mixed solvent of THF and MeOH (v/v=1/1, 4 mL) was added an aqueous sodium hydroxide solution (4 M, 0.23 mL, 0.90 mmol). The mixture was stirred at 30° C. overnight. The reaction mixture was diluted with water (10 mL), and the mixture was acidified with hydrochloric acid (1 M) to pH about 5.5. The resulting mixture was extracted with EtOAc (20 mL×3). The combined organic layers were washed with saturated brine (50 mL), dried over anhydrous sodium sulfate, and filtered. The filtrate was concentrated in vacuo to dry, and the residue was purified by silica gel column chromatography (dichloromethane/methanol (v/v)=10/1) to give the title compound as a yellow solid (17 mg, 33%).

MS (ESI, pos. ion) m/z: 489.6 [M+H]⁺;

¹H NMR (400 MHz, DMSO-d₆) δ (ppm): 12.22 (s, 1H), 8.29 (s, 1H), 8.23 (s, 1H), 8.00 (s, 1H), 7.47 (s, 1H), 7.35 (d, J=7.4 Hz, 3H), 7.06 (t, J=10.0 Hz, 1H), 6.74 (s, 1H), 4.64 (s, 1H), 2.89 (s, 1H), 2.73 (s, 1H), 2.39 (s, 3H), 1.99 (s, 2H), 1.90-1.48 (m, 8H).

Example 4a: (2S,3S)-3-((2-(5,7-difluoro-1H-indol-3-yl)-6-(4-morpholinophenyl)pyrimidin-4-yl)amino)bicyclo[2.2.2]octane-2-carboxylic Acid

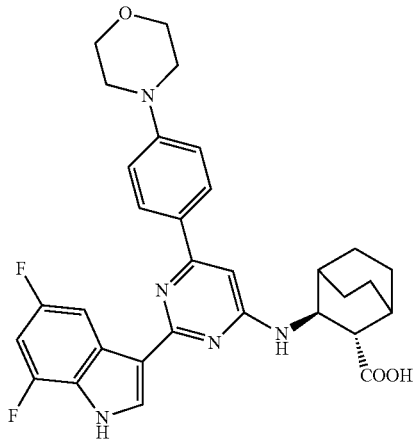 [SMILES: O=C(O)[C@H]1C2CCC(CC2)[C@@H]1Nc1cc(-c2ccc(N3CCOCC3)cc2)nc(-c2c[nH]c3c(F)cc(F)cc23)n1]

Step 1: (2S,3S)-methyl 3-aminobicyclo[2.2.2]octane-2-carboxylate hydrochloride

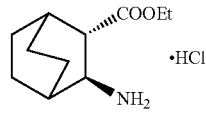 [SMILES: CCOC(=O)[C@H]1C2CCC(CC2)[C@@H]1N ; Cl]

The title compound was prepared according to the synthetic method disclosed in patent application WO 2015073491.

Step 2: (2S,3S)-ethyl 3-((2-chloro-6-(4-morpholinophenyl)pyrimidin-4-yl)amino) bicyclo[2.2.2]octane-2-carboxylate The title compound was prepared according to the procedure described in step 2 of example 4 by using (2S,3S)-methyl 3-aminobicyclo[2.2.2]octane-2-carboxylate hydrochloride (283 mg, 1.21 mmol), 4-(4-(2,6-dichloropyrimidin-4-yl)phenyl)morpholine (343 mg, 1.11 mmol), potassium carbonate (307 mg, 2.22 mmol) and solvent DMF (5 mL). The obtained title compound was a white solid (192 mg, 37%).

MS (ESI, pos. ion) m/z: 471.3 [M+H]⁺.

Step 3: (2S,3S)-ethyl 3-((2-(5,7-difluoro-1-tosyl-1H-indol-3-yl)-6-(4-morpholinophenyl)pyrimidin-4-yl)amino)bicyclo[2.2.2]octane-2-carboxylate The title compound was prepared according to the procedure described in step 3 of example 4 by using 5,7-difluoro-3-(4,4,5,5-tetramethyl-1,3,2-dioxaborolan-2-yl)-1-tosyl-1H-indole (130 mg, 0.21 mmol), (2S,3S)-ethyl 3-((2-chloro-6-(4-morpholinophenyl)pyrimidin-4-yl)amino)bicyclo[2.2.2]octane-2-carboxylate (86 mg, 0.18 mmol), potassium phosphate (111 mg, 0.52 mmol), Pd(dtbpf)Cl₂ (11 mg, 0.02 mmol), dioxane (3 mL) and water (0.2 mL). The obtained title compound was a yellow solid (68 mg, 51%).

MS (ESI, pos. ion) m/z: 742.3 [M+H]⁺.

Step 4

(2S,3S)-3-((2-(5,7-difluoro-1H-indol-3-yl)-6-(4-morpholinophenyl)pyrimidin-4-yl)amino) bicyclo[2.2.2]octane-2-carboxylic Acid The title compound was prepared according to the procedure described in step 4 of example 4 by using (2S,3S)-ethyl 3-((2-(5,7-difluoro-1-tosyl-1H-indol-3-yl)-6-(4-morpholinophenyl)pyrimidin-4-yl)amino)bicyclo[2.2.2]octane-2-carboxylate (68 mg, 0.09 mmol), an aqueous NaOH solution (4 M, 0.23 mL, 0.90 mmol) and a mixed solvent THF/EtOH (v/v=1/1, 4 mL). The obtained title compound was a yellow solid (21 mg, 41%).

MS (ESI, pos. ion) m/z: 489.6 [M+H]$^+$.

Example 5: (+/−)-trans-3-((2-(5,7-difluoro-1H-indol-3-yl)-6-phenoxypyrimidin-4-yl)amino)bicyclo[2.2.2]octane-2-carboxylic Acid

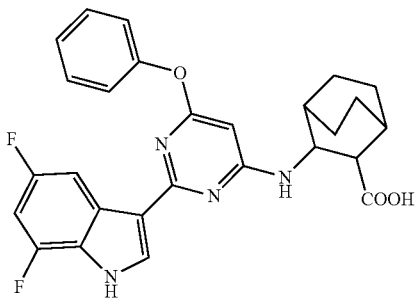 [SMILES: O=C(O)C1C2CCC(CC2)C1Nc1cc(Oc2ccccc2)nc(-c2c[nH]c3c(F)cc(F)cc23)n1]

Step 1: 2,4-dichloro-6-phenoxypyrimidine

To a 0° C. solution of 2,4,6-trichloropyrimidine (500 mg, 2.73 mmol) in acetone (6 mL) were added dropwise slowly a mixed solution of phenol (257 mg, 2.73 mmol) and sodium hydroxide (112 mg, 2.78 mmol). The mixture was stirred at rt for 3 h. The reaction mixture was diluted with water (30 mL), and the mixture was extracted with EtOAc (30 mL×3). The combined organic layers were washed with saturated brine (60 mL), dried over anhydrous sodium sulfate, and filtered. The filtrate was concentrated in vacuo to dry, and the residue was purified by silica gel column chromatography (PE/EtOAc (v/v)=20/1) to give the title compound as colorless oil (569 mg, 87%).

MS (ESI, pos. ion) m/z: 249.3 [M+H]$^+$;

$^1$H NMR (400 MHz, CDCl$_3$) δ (ppm): 7.48 (t, J=8.0 Hz, 2H), 7.34 (t, J=7.5 Hz, 1H), 7.18-7.14 (m, 2H), 6.80 (s, 1H).

Step 2: (+/−)-trans-methyl 3-((2-chloro-6-phenoxypyrimidin-4-yl)amino)bicyclo[2.2.2]octane-2-carboxylate To a solution of (+/−)-trans-methyl 3-aminobicyclo[2.2.2]octane-2-carboxylate (460 mg, 2.51 mmol) and 2,4-dichloro-6-phenoxypyrimidine (550 mg, 2.28 mmol) in DMF (5 mL) was added potassium carbonate (346 mg, 2.51 mmol). The mixture was stirred at rt overnight. To the reaction mixture was added water (40 mL), and the mixture was extracted with EtOAc (40 mL×3). The combined organic layers were washed with saturated brine (50 mL), dried over anhydrous sodium sulfate, and filtered. The filtrate was concentrated in vacuo to dry. The residue was purified by silica gel column chromatography (PE/EtOAc (v/v)=1/1) to give the title compound as a white solid (386 mg, 44%).

MS (ESI, pos. ion) m/z: 388.1 [M+H]$^+$;

$^1$H NMR (400 MHz, CDCl$_3$) δ (ppm): 7.59 (d, J=6.8 Hz, 2H), 7.41-7.37 (m, 3H), 6.55 (s, 1H), 5.50 (s, 1H), 3.76 (s, 3H), 2.36 (d, J=5.3 Hz, 1H), 1.84 (s, 1H), 1.70-1.42 (m, 10H).

Step 3: (+/−)-trans-methyl 3-((2-(5,7-difluoro-1-tosyl-1H-indol-3-yl)-6-phenoxypyrimidin-4-yl)amino)bicyclo[2.2.2]octane-2-carboxylate To a microwave tube were added 5,7-difluoro-3-(4,4,5,5-tetramethyl-1,3,2-dioxaborolan-2-yl)-1-tosyl-1H-indole (181 mg, 0.29 mmol), (+/−)-trans-methyl 3-((2-chloro-6-phenoxypyrimidin-4-yl)amino)bicyclo[2.2.2]octane-2-carboxylate (95 mg, 0.24 mmol), potassium phosphate (156 mg, 0.73 mmol), Pd(dtbpf)Cl$_2$ (15 mg, 0.02 mmol), 1,4-dioxane (3 mL) and water (0.2 mL). A stream of nitrogen was bubbled through the mixture for 3 min to remove the air, and then the mixture was stirred at 100° C. for 10 min under a microwave condition. The reaction mixture was filtered through a celite pad. The filter cake was washed with ethyl acetate (50 mL). The filtrate was concentrated in vacuo to dry and the residue was purified by silica gel column chromatography (n-hexane/EtOAc (v/v)=5/1) to give the title compound as a yellow solid (86 mg, 53%).

MS (ESI, pos. ion) m/z: 659.1 [M+H]$^+$;

$^1$H NMR (400 MHz, CDCl$_3$) δ (ppm): 8.30 (s, 1H), 7.99 (s, 1H), 7.85 (d, J=7.8 Hz, 2H), 7.46 (t, J=7.7 Hz, 2H), 7.32 (d, J=7.8 Hz, 2H), 7.21 (d, J=7.9 Hz, 2H), 6.81 (t, J=9.5 Hz, 1H), 6.42 (s, 1H), 5.18 (s, 1H), 3.65 (s, 3H), 2.42 (s, 3H), 2.33 (d, J=6.5 Hz, 1H), 2.01 (s, 2H), 1.85-1.60 (m, 8H).

Step 4: (+/−)-trans-3-((2-(5,7-difluoro-1H-indol-3-yl)-6-phenoxypyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-6-phenoxypyrimidin-4-yl)amino)bicyclo[2.2.2]octane-2-carboxylate (86 mg, 0.13 mmol) in a mixed solvent of THF and MeOH (v/v=1/1, 4 mL) was added an aqueous sodium hydroxide solution (4 M, 0.33 mL, 1.30 mmol). The mixture was stirred at 30° C. overnight. The reaction mixture was diluted with water (10 mL), and the mixture was acidified with hydrochloric acid (1 M) to pH about 5.5. The resulting mixture was extracted with EtOAc (20 mL×3). The combined organic layers were washed with saturated brine (50 mL), dried over anhydrous sodium sulfate, and filtered. The filtrate was concentrated in vacuo, and the residue was purified by silica gel column chromatography (dichloromethane/methanol (v/v)=10/1) to give the title compound as a yellow solid (50 mg, 78%).

MS (ESI, pos. ion) m/z: 491.1 [M+H]$^+$;

$^1$H NMR (400 MHz, DMSO-d$_6$) δ (ppm): 12.37 (s, 1H), 12.18 (s, 1H), 8.41 (s, 1H), 8.19 (d, J=9.6 Hz, 1H), 7.43 (t, J=7.3 Hz, 2H), 7.22 (dd, J=15.5, 7.6 Hz, 3H), 7.08 (d, J=9.3 Hz, 1H), 6.71 (d, J=26.3 Hz, 1H), 4.54 (s, 1H), 2.68 (s, 1H), 1.94 (d, J=19.1 Hz, 2H), 1.43 (m, 8H);

$^{13}$C NMR (101 MHz, DMSO-d$_6$) δ (ppm): 176.23, 170.15, 164.31, 162.19, 155.88, 153.47, 131.06, 130.07, 125.19, 122.12, 121.98, 115.63, 97.78, 97.58, 97.27, 51.22, 48.19, 28.84, 25.78, 25.43, 24.01, 21.61, 19.51, 14.39.

Example 5a: (2S,3S)-3-((2-(5,7-difluoro-1H-indol-3-yl)-6-phenoxypyrimidin-4-yl)amino)bicyclo[2.2.2]octane-2-carboxylic Acid

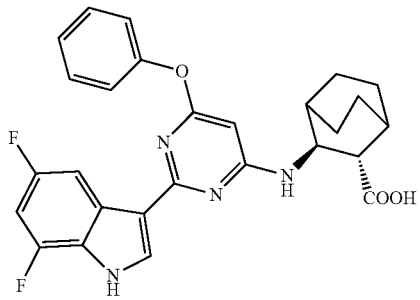

Step 1: (2S,3S)-ethyl 3-((2-chloro-6-phenoxypyrimidin-4-yl)amino)bicyclo[2.2.2]octane-2-carboxylate The title compound was prepared according to the procedure described in step 2 of example 5 by using (2S,3S)-methyl 3-aminobicyclo[2.2.2]octane-2-carboxylate hydrochloride (587 mg, 2.51 mmol), 2,4-dichloro-6-phenoxypyrimidine (550 mg, 2.28 mmol), potassium carbonate (694 mg, 5.02 mmol) and solvent DMF (5 mL). The obtained title compound was a white solid (386 mg, 44%).

MS (ESI, pos. ion) m/z: 402.1 [M+H]$^+$.

Step 2: (2S,3S)-ethyl 3-((2-(5,7-difluoro-1-tosyl-1H-indol-3-yl)-6-phenoxypyrimidin-4-yl)amino)bicyclo[2.2.2]octane-2-carboxylate The title compound was prepared according to the procedure described in step 3 of example 5 by using 5,7-difluoro-3-(4,4,5,5-tetramethyl-1,3,2-dioxaborolan-2-yl)-1-tosyl-1H-indole (181 mg, 0.29 mmol), (2S,3S)-ethyl 3-((2-chloro-6-phenoxypyrimidin-4-yl)amino)bicyclo[2.2.2]octane-2-carboxylate (96 mg, 0.24 mmol), potassium phosphate (156 mg, 0.73 mmol), Pd(dtbpf)Cl$_2$ (15 mg, 0.02 mmol), 1,4-dioxane (3 mL) and water (0.2 mL). The obtained title compound was a yellow solid (82 mg, 51%).

MS (ESI, pos. ion) m/z: 673.3 [M+H]$^+$.

Step 3: (2S,3S)-3-((2-(5,7-difluoro-1H-indol-3-yl)-6-phenoxypyrimidin-4-yl)amino)bicyclo[2.2.2]octane-2-carboxylic Acid The title compound was prepared according to the procedure described in step 4 of example 5 by using (2S,3S)-ethyl 3-((2-(5,7-difluoro-1-tosyl-1H-indol-3-yl)-6-phenoxypyrimidin-4-yl)amino)bicyclo[2.2.2]octane-2-carboxylate (82 mg, 0.12 mmol), an aqueous NaOH solution (4 M, 0.30 mL, 1.20 mmol) and mixed solvent THF/EtOH (v/v=1/1, 4 mL). The obtained title compound was a yellow solid (33 mg, 56%).

MS (ESI, pos. ion) m/z: 491.1 [M+H]$^+$.

Example 6: (+/−)-trans-3-((6-(4-cyanophenyl)-2-(5,7-difluoro-1H-indol-3-yl)pyrimidin-4-yl)amino)bicyclo[2.2.2]octane-2-carboxylic Acid

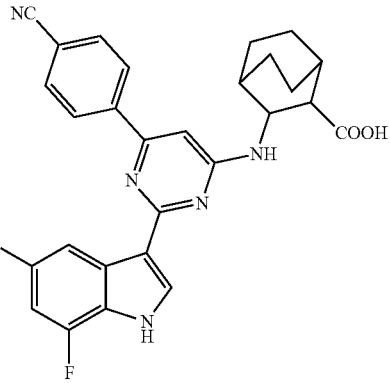

Step 1: 4-(2,6-dichloropyrimidin-4-yl)benzonitrile

To a solution of 2,4,6-trichloropyrimidine (500 mg, 2.73 mmol) in tetrahydrofuran (8.18 mL) were added palladium acetate (63 mg, 0.27 mmol), triphenylphosphine (150 mg, 0.55 mmol), 4-cyanophenylboronic acid (404 mg, 2.75 mol) and an aqueous sodium carbonate solution (1 M, 16.35 mL, 16.35 mmol). The mixture was heated to 70° C. and stirred for 6 h. The reaction mixture was diluted with water (50 mL), and the mixture was extracted with ethyl acetate (50 mL×3). The combined organic layer was washed with saturated brine (50 mL), dried over anhydrous sodium sulfate, and filtered. The filtrate was concentrated in vacuo to dry and the residue was purified by silica gel column chromatography (PE) to give the title compound as a white solid (376 mg, 55%).

MS (ESI, pos. ion) m/z: 252.1 [M+H]$^+$;

$^1$H NMR (400 MHz, CDCl$_3$) δ (ppm): 8.22 (d, J=8.3 Hz, 2H), 7.85 (d, J=8.3 Hz, 2H), 7.74 (s, 1H).

Step 2: (+/−)-trans-methyl 3-((2-chloro-6-(4-cyanophenyl)pyrimidin-4-yl)amino) bicyclo[2.2.2]octane-2-carboxylate To a solution of 4-(2,6-dichloropyrimidin-4-yl)benzonitrile (376 mg, 1.50 mmol) in DMF (5 mL) were added potassium carbonate (228 mg, 1.65 mmol) and (+/−)-trans-methyl 3-aminobicyclo[2.2.2]octane-2-carboxylate (303 mg, 1.65 mmol). The mixture was stirred at rt overnight. To the reaction mixture was added water (40 mL), and the mixture was extracted with EtOAc (40 mL×3). The combined organic layers were washed with saturated brine (50 mL), dried over anhydrous sodium sulfate, and filtered. The filtrate was concentrated in vacuo to dry. The residue was purified by silica gel column chromatography (PE/EtOAc (v/v)=20/1) to give the title compound as a white solid (300 mg, 50%).

MS (ESI, pos. ion) m/z: 397.1 [M+H]$^+$;

$^1$H NMR (400 MHz, CDCl$_3$) δ (ppm): 8.13 (d, J=7.8 Hz, 2H), 7.78 (d, J=8.3 Hz, 2H), 6.91 (s, 1H), 5.62 (s, 1H), 4.36

(s, 1H), 3.76 (s, 3H), 2.41 (d, J=3.3 Hz, 1H), 2.11 (s, 1H), 1.88 (s, 1H), 1.67 (dd, J=18.8, 14.2 Hz, 6H), 1.51 (d, J=11.5 Hz, 2H).

Step 3: (+/−)-trans-methyl 3-((6-(4-cyanophenyl)-2-(5,7-difluoro-1-tosyl-1H-indol-3-yl)pyrimidin-4-yl)amino)bicyclo[2.2.2]octane-2-carboxylate To a microwave tube were added 5,7-difluoro-3-(4,4,5,5-tetramethyl-1,3,2-dioxaborolan-2-yl)-1-tosyl-1H-indole (129 mg, 0.21 mmol), (+/−)-trans-methyl 3-((2-chloro-6-(4-cyanophenyl)pyrimidin-4-yl)amino)bicyclo[2.2.2]octane-2-carboxylate (69 mg, 0.17 mmol), potassium phosphate (110 mg, 0.52 mmol), Pd(dtbpf)Cl$_2$ (11 mg, 0.02 mmol), 1,4-dioxane (3 mL) and water (0.2 mL). A stream of nitrogen was bubbled through the mixture for 3 min to remove the air, and then the mixture was stirred at 100° C. for 10 min under a microwave condition. The reaction mixture was filtered through a celite pad. The filter cake was washed with ethyl acetate (50 mL). The filtrate was concentrated in vacuo to dry and the residue was purified by silica gel column chromatography (n-hexane/EtOAc (v/v)=5/1) to give the title compound as a yellow solid (78 mg, 67%).

MS (ESI, pos. ion) m/z: 668.1 [M+H]$^+$;
$^1$H NMR (400 MHz, CDCl$_3$) δ (ppm): 8.78 (s, 1H), 8.26 (dd, J=18.3, 8.3 Hz, 3H), 7.87 (dd, J=22.2, 8.1 Hz, 4H), 7.32 (d, J=8.0 Hz, 2H), 6.86-6.77 (m, 2H), 5.37 (s, 1H), 3.75 (s, 3H), 2.46 (s, 1H), 2.42 (s, 3H), 2.13 (s, 1H), 2.01 (s, 1H), 1.94 (s, 1H), 1.88-1.62 (m, 8H).

Step 4: (+/−)-trans-3-((6-(4-cyanophenyl)-2-(5,7-difluoro-1H-indol-3-yl)pyrimidin-4-yl)amino)bicyclo[2.2.2]octane-2-carboxylic Acid To a solution of (+/−)-trans-methyl 3-((6-(4-cyanophenyl)-2-(5,7-difluoro-1-tosyl-1H-indol-3-yl)pyrimidin-4-yl)amino)bicyclo[2.2.2]octane-2-carboxylate (79 mg, 0.12 mmol) in a mixed solvent of THF and MeOH (v/v=1/1, 2 mL) was added an aqueous sodium hydroxide solution (4 M, 0.30 mL, 1.20 mmol). The mixture was stirred at 30° C. overnight. The reaction mixture was diluted with water (10 mL), and the mixture was acidified with hydrochloric acid (1 M) to pH about 5.5. The resulting mixture was extracted with EtOAc (20 mL×3). The combined organic layers were washed with saturated brine (50 mL), dried over anhydrous sodium sulfate, and filtered. The filtrate was concentrated in vacuo to remove the solvent, and the residue was purified by silica gel column chromatography (dichloromethane/methanol (v/v)=10/1) to give the title compound as a yellow solid (34 mg, 58%).

MS (ESI, pos. ion) m/z: 500.5 [M+H]$^+$;
$^1$H NMR (600 MHz, DMSO-d$_6$) δ (ppm): 8.30 (s, 1H), 7.99 (s, 1H), 7.85 (d, J=7.8 Hz, 2H), 7.46 (t, J=7.7 Hz, 2H), 7.32 (d, J=7.8 Hz, 2H), 7.21 (d, J=7.9 Hz, 2H), 6.81 (t, J=9.5 Hz, 1H), 6.42 (s, 1H), 5.18 (s, 1H), 3.65 (s, 3H), 2.42 (s, 3H), 2.33 (d, J=6.5 Hz, 1H), 2.01 (s, 2H), 1.85-1.60 (m, 8H).

Example 7: (+/−)-trans-3-((2-(5,7-difluoro-1H-indol-3-yl)-6-(o-tolyl)pyrimidin-4-yl)amino)bicyclo[2.2.2]octane-2-carboxylic Acid

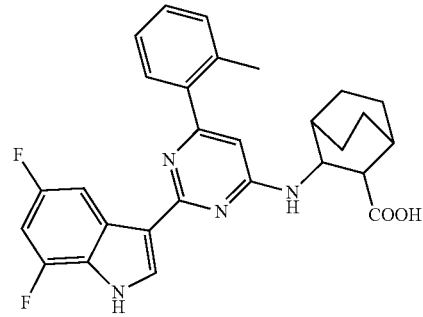 [SMILES: Cc1ccccc1-c1cc(NC2C3CCC(CC3)C2C(=O)O)nc(-c2c[nH]c3c(F)cc(F)cc23)n1]

Step 1: 2,4-dichloro-6-(o-tolyl)pyrimidine

To a solution of 2,4,6-trichloropyrimidine (1.01 g, 5.51 mmol) in tetrahydrofuran (16 mL) were added palladium acetate (0.1 g, 0.4 mmol), triphenylphosphine (0.24 g, 0.87 mmol), (4-(o-tolyl))boronic acid (749 mg, 5.51 mol) and an aqueous sodium carbonate solution (1 M, 16.35 mL, 16.35 mmol). The mixture was heated to 70° C. and stirred for 6 h. To the reaction mixture was added water (50 mL), and the mixture was extracted with EtOAc (50 mL×3). The combined organic layers were washed with saturated brine (50 mL), dried over anhydrous sodium sulfate, and filtered. The filtrate was concentrated in vacuo to dry, and the residue was purified by silica gel column chromatography (PE) to give the title compound as a white solid (671 mg, 51%).

MS (ESI, pos. ion) m/z: 238.9 [M+H]$^+$;
$^1$H NMR (400 MHz, CDCl$_3$) δ (ppm): 7.50-7.47 (m, 1H), 7.45 (s, 1H), 7.42 (d, J=7.4 Hz, 1H), 7.34 (dd, J=7.1, 3.5 Hz, 2H), 2.49 (s, 3H).

Step 2: (+/−)-trans-methyl 3-((2-chloro-6-(o-tolyl)pyrimidin-4-yl)amino)bicyclo[2.2.2]octane-2-carboxylate To a solution of (+/−)-trans-methyl 3-aminobicyclo[2.2.2]octane-2-carboxylate (469 mg, 2.56 mmol) and 2,4-dichloro-6-(o-tolyl)pyrimidine (557 mg, 2.33 mmol) in DMF (5 mL) was added potassium carbonate (354 mg, 2.56 mmol). The mixture was stirred at rt overnight. To the reaction mixture was added water (40 mL), and the mixture was extracted with EtOAc (40 mL×3). The combined organic layers were washed with saturated brine (50 mL), dried over anhydrous sodium sulfate, and filtered. The filtrate was concentrated in vacuo to dry, and the residue was purified by silica gel column chromatography (n-hexane) to give the title compound as a white solid (710 mg, 79%).

MS (ESI, pos. ion) m/z: 384.1 [M+H]$^+$;
$^1$H NMR (400 MHz, CDCl$_3$) δ (ppm): 7.39 (d, J=5.9 Hz, 1H), 7.32 (d, J=6.5 Hz, 1H), 7.28 (s, 1H), 7.26 (d, J=6.9 Hz, 1H), 6.42 (s, 1H), 5.43 (s, 1H), 4.27 (s, 1H), 3.74 (s, 3H), 2.42 (s, 3H), 2.39 (d, J=5.3 Hz, 1H), 2.06 (s, 1H), 1.85 (d, J=2.4 Hz, 1H), 1.81-1.65 (m, 6H), 1.59 (dd, J=10.7, 7.3 Hz, 2H).

Step 3: (+/−)-trans-methyl 3-((2-(5,7-difluoro-1-tosyl-1H-indol-3-yl)-6-(o-tolyl)pyrimidin-4-yl)amino)bicyclo[2.2.2]octane-2-carboxylate To a microwave tube were added 5,7-difluoro-3-(4,4,5,5-tetramethyl-1,3,2-dioxaborolan-2-yl)-1-tosyl-1H-indole (202 mg, 0.33 mmol), (+/−)-trans-methyl 3-((2-chloro-6-(o-tolyl)pyrimidin-4-yl)amino) bicyclo[2.2.2]octane-2-carboxylate (105 mg, 0.27 mmol), potassium phosphate (173 mg, 0.82 mmol), Pd(dtbpf)Cl$_2$ (17 mg, 0.03 mmol), 1,4-dioxane (3 mL) and water (0.2 mL). A stream of nitrogen was bubbled through the mixture for 3 min to remove the air, and then the mixture was stirred at 100° C. for 10 min under a microwave condition. The reaction mixture was filtered through a celite pad. The filter cake was washed with ethyl acetate (50 mL). The filtrate was washed with saturated brine (50 mL), dried over anhydrous sodium sulfate, and filtered. The filtrate was concentrated in vacuo to dry and the residue was purified by silica gel column chromatography (PE/EtOAc (v/v)=5/1) to give the title compound as a yellow solid (90 mg, 50%).

$^1$H NMR (400 MHz, CDCl$_3$) δ (ppm): 8.72 (s, 1H), 8.29 (d, J=7.7 Hz, 1H), 7.88 (d, J=7.9 Hz, 2H), 7.51 (d, J=7.2 Hz, 1H), 7.41-7.29 (m, 5H), 6.78 (t, J=10.4 Hz, 1H), 6.40 (s, 1H), 5.15 (s, 1H), 4.51 (s, 1H), 3.74 (s, 3H), 2.52 (s, 3H), 2.45 (d, J=5.3 Hz, 1H), 2.41 (s, 3H), 2.11 (s, 1H), 2.00 (s, 1H), 1.92-1.61 (m, 8H).

Step 4: (+/−)-trans-3-((2-(5,7-difluoro-1H-indol-3-yl)-6-(o-tolyl)pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-6-(o-tolyl)pyrimidin-4-yl)amino)bicyclo[2.2.2]octane-2-carboxylate (110 mg, 0.17 mmol) in a mixed solvent of THF and MeOH (v/v=1/1, 4 mL) was added an aqueous sodium hydroxide solution (4 M, 0.43 mL, 1.70 mmol). The mixture was stirred at 30° C. overnight. The reaction mixture was diluted with water (10 mL), and the mixture was acidified with hydrochloric acid (1 M) to pH about 5.5. The resulting mixture was extracted with EtOAc (20 mL×3). The combined organic layers were washed with saturated brine (50 mL), dried over anhydrous sodium sulfate, and filtered. The filtrate was concentrated in vacuo to dry, and the residue was purified by silica gel column chromatography (dichloromethane/methanol (v/v)=10/1) to give the title compound as a yellow solid (26 mg, 32%).

MS (ESI, pos. ion) m/z: 489.1 [M+H]$^+$;

$^1$H NMR (400 MHz, DMSO-d$_6$) δ (ppm): 12.18 (s, 1H), 8.18 (s, 2H), 7.45 (s, 2H), 7.33 (s, 3H), 7.05 (s, 1H), 6.35 (s, 1H), 4.66 (s, 1H), 2.44 (s, 3H), 2.00 (s, 2H), 1.88-1.39 (m, 8H).

Example 8: (+/−)-trans-3-((2-(5,7-difluoro-1H-indol-3-yl)-6-(2-methoxyphenyl)pyrimidin-4-yl)amino)bicyclo[2.2.2]octane-2-carboxylic Acid

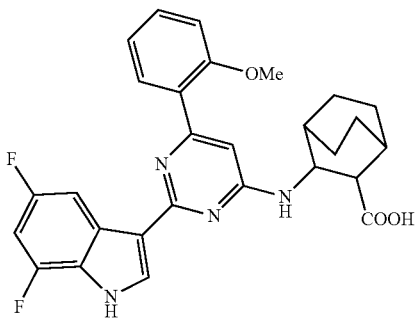 [SMILES: COc1ccccc1-c1cc(NC2C3CCC(CC3)C2C(=O)O)nc(-c2c[nH]c3c(F)cc(F)cc23)n1]

Step 1: 2,4-dichloro-6-(2-methoxyphenyl)pyrimidine

To a solution of 2,4,6-trichloropyrimidine (500 mg, 2.73 mmol) in tetrahydrofuran (8.5 mL) were added palladium acetate (63 mg, 0.27 mmol), triphenylphosphine (150 mg, 0.55 mmol), (2-methoxyphenyl)boronic acid (418 mg, 2.75 mol) and an aqueous sodium carbonate solution (1 M, 8.18 mL, 8.18 mmol). The mixture was heated to 70° C. and stirred for 6 h. To the reaction mixture was added water (50 mL), and the mixture was extracted with EtOAc (50 mL×3). The combined organic layers were washed with saturated brine (50 mL), dried over anhydrous sodium sulfate, and filtered. The filtrate was concentrated in vacuo to dry, and the residue was purified by silica gel column chromatography (PE) to give the title compound as a white solid (438 mg, 63%).

MS (ESI, pos. ion) m/z: 255.1[M+H]$^+$;

$^1$H NMR (400 MHz, CDCl$_3$) δ (ppm): 8.15 (dd, J=7.8, 1.6 Hz, 1H), 8.07 (s, 1H), 7.55-7.49 (m, 1H), 7.14 (t, J=7.6 Hz, 1H), 7.05 (d, J=8.4 Hz, 1H), 3.98 (s, 3H).

Step 2: (+/−)-trans-methyl 3-((2-chloro-6-(2-methoxyphenyl)pyrimidin-4-yl)amino)bicyclo[2.2.2]octane-2-carboxylate To a solution of (+/−)-trans-methyl 3-aminobicyclo[2.2.2]octane-2-carboxylate (346 mg, 1.89 mmol) and 2,4-dichloro-6-(2-methoxyphenyl)pyrimidine (438 mg, 1.72 mmol) in DMF (5 mL) was added potassium carbonate (261 mg, 1.89 mmol). The mixture was stirred at rt overnight. To the reaction mixture was added water (40 mL), and the mixture was extracted with EtOAc (40 mL×3). The combined organic layers were washed with saturated brine (50 mL), dried over anhydrous sodium sulfate, and filtered. The filtrate was concentrated in vacuo to dry, and the residue was purified by silica gel column chromatography (n-hexane) to give the title compound as a white solid (503 mg, 73%).

MS (ESI, pos. ion) m/z: 402.3 [M+H]$^+$;

$^1$H NMR (400 MHz, CDCl$_3$) δ (ppm): 7.95 (s, 1H), 7.42 (dd, J=11.5, 4.1 Hz, 1H), 7.27 (s, 1H), 7.08 (t, J=7.5 Hz, 1H), 6.99 (d, J=8.3 Hz, 1H), 5.43 (s, 1H), 4.46 (s, 1H), 3.91 (s, 3H), 3.60 (s, 3H), 2.41 (d, J=5.0 Hz, 1H), 1.96-1.88 (m, 2H), 1.79 (d, J=12.2 Hz, 1H), 1.64 (d, J=7.5 Hz, 4H), 1.55 (dd, J=19.5, 10.6 Hz, 2H).

Step 3: (+/−)-trans-methyl 3-((2-(5,7-difluoro-1-tosyl-1H-indol-3-yl)-6-(2-methoxyphenyl)pyrimidin-4-yl)amino)bicyclo[2.2.2]octane-2-carboxylate To a microwave tube were added 5,7-difluoro-3-(4,4,5,5-tetramethyl-1,3,2-dioxaborolan-2-yl)-1-tosyl-1H-indole (157 mg, 0.25 mmol), (+/−)-trans-methyl 3-((2-chloro-6-(2-methoxyphenyl)pyrimidin-4-yl)amino) bicyclo[2.2.2]octane-2-carboxylate (85 mg, 0.21 mmol), potassium phosphate (134 mg, 0.63 mmol), Pd(dtbpf)Cl$_2$ (13 mg, 0.02 mmol), 1,4-dioxane (3 mL) and water (0.2 mL). A stream of nitrogen was bubbled through the mixture for 3 min to remove the air, and then the mixture was stirred at 100° C. for 10 min under a microwave condition. The reaction mixture was filtered through a celite pad. The filter cake was washed with ethyl acetate (50 mL). The filtrate washed with saturated brine (50 mL), and dried over anhydrous sodium sulfate, filtered. The filtrate was was concentrated in vacuo to dry and the residue was purified by silica gel column chromatography (n-hexane/EtOAc (v/v)=5/1) to give the title compound as a yellow solid (76 mg, 53%).

MS (ESI, pos. ion) m/z: 673.7[M+H]+;

¹H NMR (400 MHz, CDCl₃) δ (ppm): 8.73 (s, 1H), 8.35 (d, J=9.0 Hz, 1H), 8.12 (d, J=7.7 Hz, 1H), 7.89 (d, J=8.1 Hz, 2H), 7.45 (t, J=7.8 Hz, 1H), 7.30 (s, 1H), 7.17 (t, J=7.5 Hz, 1H), 7.06 (d, J=8.3 Hz, 1H), 7.00 (s, 1H), 6.82-6.74 (m, 1H), 5.09 (s, 1H), 4.54 (s, 1H), 3.96 (s, 3H), 3.73 (s, 3H), 2.45 (d, J=5.0 Hz, 1H), 2.41 (s, 3H), 2.10 (s, 1H), 2.04 (s, 1H), 1.74 (dd, J=60.7, 26.3 Hz, 8H).

Step 4: (+/−)-trans-3-((2-(5,7-difluoro-1H-indol-3-yl)-6-(2-methoxyphenyl)pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-6-(2-methoxyphenyl)pyrimidin-4-yl)amino)bicyclo[2.2.2]octane-2-carboxylate (76 mg, 0.11 mmol) in a mixed solvent of THF and MeOH (v/v=1/1, 4 mL) was added an aqueous sodium hydroxide solution (4 M, 0.28 mL, 1.10 mmol). The mixture was stirred at 30° C. overnight. The reaction mixture was diluted with water (10 mL), and the mixture was acidified with hydrochloric acid (1 M) to pH about 5.5. The resulting mixture was extracted with EtOAc (20 mL×3). The combined organic layers were washed with saturated brine (50 mL), dried over anhydrous sodium sulfate, and filtered. The filtrate was concentrated in vacuo to dry, and the residue was purified by silica gel column chromatography (dichloromethane/methanol (v/v) =10/1) to give the title compound as a yellow solid (10 mg, 18%).

MS (ESI, pos. ion) m/z: 505.1 [M+H]+;

¹H NMR (400 MHz, DMSO-d₆) δ (ppm): 12.29 (s, 1H), 12.16 (s, 1H), 8.20 (d, J=2.3 Hz, 2H), 8.03 (d, J=7.7 Hz, 1H), 7.49-7.34 (m, 2H), 7.10 (ddd, J=30.7, 20.2, 9.0 Hz, 3H), 6.89 (s, 1H), 4.62 (s, 1H), 3.89 (s, 3H), 2.68 (s, 1H), 2.33 (s, 1H), 1.86-1.38 (m, 8H).

Example 9: (+/−)-trans-3-((2-(5,7-difluoro-1H-indol-3-yl)-7-methyl-7H-pyrrolo[2,3-d]pyrimidin-4-yl)amino)bicyclo[2.2.2]octane-2-carboxylic Acid

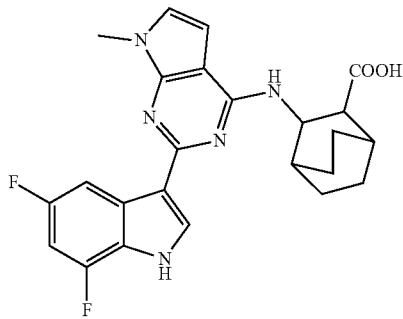 [SMILES: Cn1ccc2c(NC3C4CCC(CC4)C3C(=O)O)nc(-c3c[nH]c4c(F)cc(F)cc34)nc21]

Step 1: 2,4-dichloro-7-methyl-7H-pyrrolo[2,3-d]pyrimidine

A 0° C. solution of 2,4-dichloro-7H-pyrrolo[2,3-d]pyrimidine (1.00 g, 5.32 mmol) in THF (8 mL) was stirred for 5 min, then to the solution was added sodium hydroxide (255 mg, 6.38 mmol). The mixture was stirred for further 15 min, and iodomethane (8.50 g, 53.20 mmol) was added. The mixture was stirred at rt overnight. To the reaction mixture was added H₂O (100 mL), and the mixture was extracted with EtOAc (50 mL×3). The combined organic layers were washed with saturated brine (80 mL), dried over anhydrous sodium sulfate, and filtered. The filtrate was concentrated in vacuo dry, and the residue was purified by silica gel column chromatography (PE/EtOAc (v/v)=10/1) to give the title compound as a white solid (1.00 g, 93%).

MS (ESI, pos. ion) m/z: 202.95 [M+H]+.

Step 2: (+/−)-trans-methyl 3-((2-chloro-7-methyl-7H-pyrrolo[2,3-d]pyrimidin-4-yl)amino)bicyclo[2.2.2]octane-2-carboxylate A suspension of 2,4-dichloro-7-methyl-7H-pyrrolo[2,3-d]pyrimidine (200 mg, 0.99 mmol), (+/−)-trans-methyl 3-aminobicyclo[2.2.2]octane-2-carboxylate (200 mg, 1.09 mmol) and K₂CO₃ (273 mg, 1.98 mmol) in DMF (10 mL) was stirred at rt overnight. To the reaction mixture was added H₂O (100 mL) to quench the reaction, and the mixture was extracted with EtOAc (50 mL×3). The combined organic layers were washed with saturated brine (80 mL×3), dried over anhydrous sodium sulfate, and filtered. The filtrate was concentrated in vacuo, and the residue was purified by silica gel column chromatography (PE/EtOAc (v/v)=3/1) to give the title compound as a white solid (144 mg, 42%).

MS (ESI, pos. ion) m/z: 349.10 [M+H]+.

Step 3: (+/−)-trans-methyl 3-((2-(5,7-difluoro-1-tosyl-1H-indol-3-yl)-7-methyl-7H-pyrrolo[2,3-d]pyrimidin-4-yl)amino)bicyclo[2.2.2]octane-2-carboxylate To 1,4-dioxane (8 mL) were added 5,7-difluoro-3-(4,4,5,5-tetramethyl-1,3,2-dioxaborolan-2-yl)-1-tosyl-1H-indole (190 mg, 0.44 mmol), K₂CO₃ (167 mg, 1.20 mmol), Pd(dppf)Cl₂ (33 mg, 0.04 mmol), (+/−)-trans-methyl 3-((2-chloro-7-methyl-7H-pyrrolo[2,3-d]pyrimidin-4-yl)amino)bicyclo[2.2.2]octane-2-carboxylate (140 mg, 0.40 mmol), then H₂O (1 mL) was added to the mixture. A stream of nitrogen was bubbled through the mixture for 5 min to remove the air, then the mixture was stirred at 115° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give the title compound as a white solid (98 mg, 39%).

Step 4: (+/−)-trans-3-((2-(5,7-difluoro-1H-indol-3-yl)-7-methyl-7H-pyrrolo[2,3-d]pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-7-methyl-7H-pyrrolo[2,3-d]pyrimidin-4-yl)amino)bicyclo[2.2.2]octane-2-carboxylate (100 mg, 0.16 mmol) in a mixed solvent THF/MeOH (v/v=5 mL/5 mL) was added a solution of NaOH (66 mg, 1.61 mmol) in water (1 mL). The mixture was stirred at rt overnight. The reaction mixture was quenched with water (10 mL), and the mixture was acidified with hydrochloric Acid (1 M) to pH about 6. The resulting mixture was extracted with EtOAc (15 mL×3). The combined organic layers were washed with saturated brine (50 mL), dried over anhydrous sodium sulfate, and filtered. The filtrate was concentrated in vacuo to remove the solvent, and the residue was purified by silica gel column chromatography (DCM/MeOH (v/v)=10/1~5/1) to give the title compound as a white solid (38 mg, 52%).

HRMS (ESI, pos. ion) m/z: 452.1901 [M+H]+, (C₂₄H₂₃F₂N₅O₂) [M+H]+ theoretical value: 452.1898;

$^1$H NMR (600 MHz, DMSO-d$_6$) δ (ppm) 12.03 (s, 1H), 8.30 (d, J=9.6 Hz, 1H), 8.15 (s, 1H), 7.21 (d, J=5.5 Hz, 1H), 7.07 (d, J=2.3 Hz, 1H), 7.03 (t, J=10.0 Hz, 1H), 6.62 (s, 1H), 4.79 (s, 1H), 3.77 (s, 3H), 2.73 (d, J=6.5 Hz, 1H), 2.04 (d, J=20.1 Hz, 2H), 1.92-1.34 (m, 9H);

$^{13}$C NMR (101 MHz, DMSO-d$_6$) δ(ppm) 176.14, 157.48, 156.30, 155.93, 149.54, 149.45, 147.91, 147.82, 130.15, 128.96, 124.72, 121.98, 121.89, 118.40, 103.69, 103.50, 101.05, 98.87, 97.10, 96.96, 96.76, 50.55, 48.96, 31.05, 28.97, 28.83, 26.07, 24.13, 21.59, 19.52.

Example 10: (+/−)-trans-3-((2-(5,7-difluoro-1H-indol-3-yl)-8-fluoroquinazolin-4-yl)amino)bicyclo[2.2.2]octane-2-carboxylic Acid

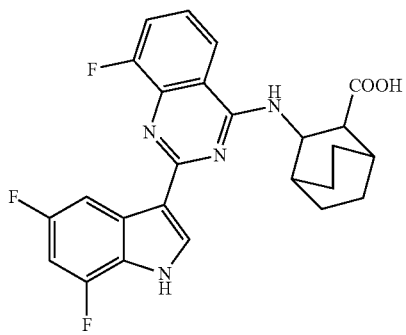 [SMILES: O=C(O)C1C2CCC(CC2)C1Nc1nc(-c2c[nH]c3c(F)cc(F)cc23)nc2c(F)cccc12]

Step 1: (+/−)-trans-Methyl 3-((2-chloro-8-fluoroquinazolin-4-yl)amino)bicyclo[2.2.2]octane-2-carboxylate A suspension of 2,4-dichloro-8-fluoroquinazoline (400 mg, 1.84 mmol), (+/−)-trans-methyl 3-aminobicyclo[2.2.2]octane-2-carboxylate (371 mg, 2.03 mmol) and DIPEA (3.2 mL, 18.43 mmol) in THF (10 mL) was stirred at rt overnight. The reaction was quenched with H$_2$O (100 mL), and the mixture was extracted with EtOAc (50 mL×3). The combined organic layers were washed with saturated brine (80 mL), dried over anhydrous sodium sulfate, and filtered. The filtrate was concentrated in vacuo, and the residue was purified by silica gel column chromatography (PE/EtOAc (v/v)=3/1) to give the title compound as a white solid (662 mg, 99%).

$^1$H NMR (400 MHz, CDCl$_3$) δ (ppm): 7.50-7.37 (m, 3H), 6.01 (d, J=4.8 Hz, 1H), 4.65 (s, 1H), 3.81 (s, 3H), 2.50 (d, J=5.6 Hz, 1H), 2.05-1.98 (m, 2H), 1.78 (dd, J=11.2, 2.7 Hz, 2H), 1.69 (ddd, J=11.4, 6.4, 1.8 Hz, 4H), 1.56-1.46 (m, 2H).

Step 2: (+/−)-trans-methyl 3-((2-(5,7-difluoro-1-tosyl-1H-indol-3-yl)-8-fluoroquinazolin-4-yl)amino)bicyclo[2.2.2]octane-2-carboxylate To 1,4-dioxane (8 mL) were added 5,7-difluoro-3-(4,4,5,5-tetramethyl-1,3,2-dioxaborolan-2-yl)-1-tosyl-1H-indole (182 mg, 0.45 mmol), K$_2$CO$_3$ (110 mg, 0.83 mmol), Pd(dppf)Cl$_2$ (30 mg, 0.04 mmol), (+/−)-trans-methyl 3-((2-chloro-8-fluoroquinazolin-4-yl)amino)bicyclo[2.2.2]octane-2-carboxylate (150 mg, 0.41 mmol), then H$_2$O (1 mL) was added to the mixture. A stream of nitrogen was bubbled through the mixture for 5 min to remove air, then the mixture was stirred at 115° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give the title compound as a white solid (130 mg, 50%).

MS (ESI, pos. ion) m/z: 636.10 [M+H]$^+$;

$^1$H NMR (400 MHz, CDCl$_3$) δ (ppm) 8.84 (s, 1H), 8.54 (dd, J=9.0, 2.1 Hz, 1H), 7.92 (d, J=8.1 Hz, 2H), 7.52-7.44 (m, 2H), 7.41-7.35 (m, 1H), 7.31 (d, J=8.2 Hz, 2H), 6.86-6.78 (m, 1H), 5.88 (d, J=6.4 Hz, 1H), 4.99 (s, 1H), 3.76 (s, 3H), 2.53 (d, J=5.5 Hz, 1H), 2.41 (s, 3H), 2.16 (d, J=2.5 Hz, 1H), 2.12 (d, J=2.4 Hz, 1H), 2.07 (s, 1H), 2.01 (t, J=12.1 Hz, 1H), 1.87-1.72 (m, 5H), 1.67 (s, 1H).

Step 3: (+/−)-trans-3-((2-(5,7-difluoro-1H-indol-3-yl)-8-fluoroquinazolin-4-yl)amino)bicyclo[2.2.2]octane-2-carboxylic Acid To a solution of (+/−)-trans-methyl 3-((2-(5,7-difluoro-1-tosyl-1H-indol-3-yl)-8-fluoroquinazolin-4-yl)amino)bicyclo[2.2.2]octane-2-carboxylate (130 mg, 0.20 mmol) in a mixed solvent THF/MeOH (v/v=5 mL/5 mL) was added a solution of NaOH (90 mg, 2.05 mmol) in water (1 mL). The mixture was stirred at rt overnight. The reaction was quenched with water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to dry, and the residue was purified by silica gel column chromatography (dichloromethane/methanol (v/v)=10/1~5/1) to give the title compound as a white solid (46 mg, 48%).

HRMS (ESI, pos. ion) m/z: 467.1695 [M+H]$^+$, (C$_{25}$H$_{21}$F$_3$N$_4$O) [M+H]$^+$ theoretical value: 467.1695;

$^1$H NMR (600 MHz, DMSO-d$_6$) δ (ppm) 12.37 (s, 1H), 8.32 (dd, J=14.6, 9.2 Hz, 2H), 8.24 (s, 1H), 8.10 (d, J=6.3 Hz, 1H), 7.60-7.52 (m, 1H), 7.35 (dd, J=12.9, 7.8 Hz, 1H), 7.06 (t, J=9.6 Hz, 1H), 4.90 (s, 1H), 3.07 (d, J=6.5 Hz, 1H), 2.06 (s, 2H), 1.92-1.79 (m, 3H), 1.51 (m, 6H);

$^{13}$C NMR (151 MHz, DMSO-d$_6$) δ(ppm) 176.28, 159.52, 158.97, 158.95, 157.63, 156.32, 156.25, 155.96, 147.99, 147.90, 140.76, 140.68, 139.73, 131.91, 129.12, 129.08, 129.04, 125.36, 123.75, 123.69, 122.11, 122.02, 119.72, 117.57, 117.45, 117.33, 115.51, 115.49, 103.69, 103.53, 97.52, 97.38, 97.31, 97.18, 51.71, 48.04, 30.89, 28.84, 28.40, 25.81, 24.29, 21.70, 19.81.

Example 11: (+/−)-trans-3-((2-(5,7-difluoro-1H-indol-3-yl)-8-phenylquinazolin-4-yl)amino)bicyclo[2.2.2]octane-2-carboxylic Acid

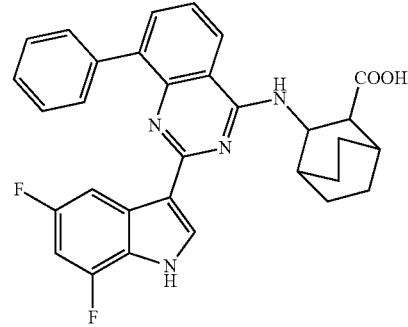 [SMILES: O=C(O)C1C2CCC(CC2)C1Nc1nc(-c2c[nH]c3c(F)cc(F)cc23)nc2c(-c3ccccc3)cccc12]

Step 1: (+/−)-trans-methyl 3-((8-bromo-2-chloro-quinazolin-4-yl)amino)bicyclo[2.2.2]octane-2-carboxylate A suspension of 2,4-dichloro-8-bromo-quinazoline (1.51 g, 5.43 mmol), (+/−)-trans-methyl 3-aminobicyclo[2.2.2]octane-2-carboxylate (1.10 g, 5.98 mmol) and $K_2CO_3$ (1.50 g, 10.9 mmol) in DMF (10 mL) was stirred at rt overnight. To the reaction mixture was added $H_2O$ (100 mL), and the mixture was extracted with EtOAc (50 mL×3). The combined organic layers were washed with saturated brine (80 mL), dried over anhydrous sodium sulfate, and filtered. The filtrate was concentrated in vacuo, and the residue was purified by silica gel column chromatography (PE/EtOAc (v/v)=5/1~2/1) to give the title compound as a white solid (1.04 g, 45%).

MS (ESI, pos. ion) m/z: 426.00 [M+H]$^+$.

Step 2: (+/−)-trans-methyl 3-((2-chloro-8-phenylquinazolin-4-yl)amino)bicyclo[2.2.2]octane-2-carboxylate (+/−)-trans-Methyl 3-((8-bromo-2-chloro-quinazolin-4-yl)amino)bicyclo[2.2.2]octane-2-carboxylate (300 mg, 0.71 mmol) and phenylboronic acid (105 mg, 0.85 mmol) were dissolved in tolene (8 mL), and the mixture was bubbled with nitrogen for 5 min to remove the air. Then palladium acetate (20 mg, 0.07 mmol) and triphenyl phosphine (39 mg, 0.14 mmol) were added to the mixture, and the mixture was stirred at 110° C. overnight. The reaction was stopped, and the mixture was diluted with ethyl acetate (40 mL). The resulting mixture was filtered, and the filtrate was concentrated in vacuo. The residue was purified by silica gel column chromatography (PE/EtOAc (v/v)=10/1) to give the title compound as white powder (149 mg, 50%).

MS (ESI, pos. ion) m/z: 423.05 [M+H]$^+$;
$^1$H NMR (400 MHz, CDCl$_3$) δ (ppm) 7.80 (d, J=6.3 Hz, 1H), 7.68 (t, J=7.3 Hz, 3H), 7.56-7.45 (m, 3H), 7.41 (t, J=7.4 Hz, 1H), 5.98 (d, J=5.1 Hz, 1H), 4.65 (s, 1H), 3.81 (s, 3H), 2.51 (d, J=5.6 Hz, 1H), 2.06-2.00 (m, 2H), 1.81 (m, 7H), 1.53-1.46 (m, 1H).

Step 3: (+/−)-trans-methyl 3-((2-(5,7-difluoro-1-tosyl-1H-indol-3-yl)-8-phenylquinazolin-4-yl)amino)bicyclo[2.2.2]octane-2-carboxylate To 1,4-dioxane (8 mL) were added 5,7-difluoro-3-(4,4,5,5-tetramethyl-1,3,2-dioxaborolan-2-yl)-1-tosyl-1H-indole (170 mg, 0.39 mmol), $K_2CO_3$ (150 mg, 1.07 mmol), Pd(dppf)Cl$_2$ (26 mg, 0.04 mmol), (+/−)-trans-methyl 3-((2-chloro-8-phenylquinazolin-4-yl)amino)bicyclo[2.2.2]octane-2-carboxylate (150 mg, 0.36 mmol), then $H_2O$ (1 mL) was added to the mixture. A stream of nitrogen was bubbled through the mixture for 5 min to remove air, then the mixture was stirred at 115° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give the title compound as a white solid (96 mg, 39%).

$^1$H NMR (400 MHz, CDCl$_3$) δ (ppm): 8.80 (s, 1H), 8.05 (dd, J=9.4, 2.3 Hz, 1H), 7.89 (d, J=7.7 Hz, 2H), 7.80 (d, J=6.2 Hz, 1H), 7.72 (t, J=7.6 Hz, 3H), 7.59-7.46 (m, 5H), 7.27 (s, 1H), 6.74-6.68 (m, 1H), 5.92 (d, J=6.4 Hz, 1H), 4.99 (s, 1H), 3.77 (s, 3H), 2.54 (d, J=5.2 Hz, 1H), 2.39 (s, 3H), 2.16 (s, 1H), 2.11 (s, 1H), 1.78 (m, 6H), 1.28 (s, 2H).

Step 4: (+/−)-trans-3-((2-(5,7-difluoro-1H-indol-3-yl)-8-phenylquinazolin-4-yl)amino)bicyclo[2.2.2]octane-2-carboxylic Acid To a solution of (+/−)-trans-methyl 3-((2-(5,7-difluoro-1-tosyl-1H-indol-3-yl)-8-phenylquinazolin-4-yl)amino)bicyclo[2.2.2]octane-2-carboxylate (100 mg, 0.14 mmol) in a mixed solvent THF/MeOH (v/v=5 mL/5 mL) was added a solution of NaOH (59 mg, 1.44 mmol) in water (1 mL). The mixture was stirred at rt overnight. The reaction was quenched with water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to dry, and the residue was purified by silica gel column chromatography (dichloromethane/methanol (v/v)=10/1~5/1) to give the title compound as a white solid (36 mg, 48%).

HRMS (ESI, pos. ion) m/z: 525.2109 [M+H]$^+$, ($C_{31}H_{26}F_4N_4O_2$) [M+H]$^+$ theoretical value: 525.2102;
$^1$H NMR (600 MHz, DMSO-d$_6$) δ (ppm): 12.10 (s, 1H), 8.38 (d, J=7.2 Hz, 1H), 8.12 (s, 1H), 7.98 (d, J=8.6 Hz, 1H), 7.77 (d, J=20.0 Hz, 4H), 7.50 (dd, J=15.9, 6.5 Hz, 4H), 6.98 (s, 1H), 4.87 (s, 1H), 2.96 (s, 1H), 2.08 (d, J=19.2 Hz, 2H), 1.59 (m, 9H);
$^{13}$C NMR (151 MHz, DMSO-d$_6$) δ(ppm): 176.14, 159.66, 158.73, 155.75, 148.15, 139.92, 138.64, 133.28, 131.60, 130.92, 130.10, 128.80, 128.20, 127.42, 124.11, 122.93, 122.08, 121.95, 118.17, 114.28, 104.00, 103.80, 97.25, 51.52, 48.33, 28.87, 28.30, 25.98, 24.36, 21.66, 19.76.

Example 12: (+/−)-trans-3-((8-cyclopropyl-2-(5,7-difluoro-1H-indol-3-yl)quinazolin-4-yl)amino)bicyclo[2.2.2]octane-2-carboxylic Acid

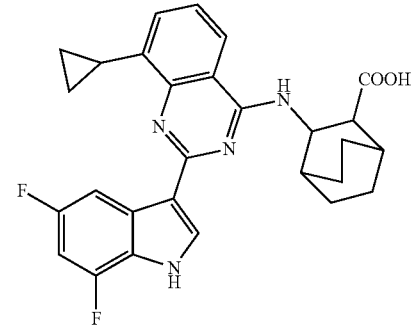 [SMILES: O=C(O)C1C2CCC(CC2)C1Nc1nc(-c2c[nH]c3c(F)cc(F)cc23)nc2c(C3CC3)cccc12]

Step 1: (+/−)-trans-methyl 3-((8-bromo-2-chloro-quinazolin-4-yl)amino)bicyclo[2.2.2]octane-2-carboxylate A suspension of 2,4-dichloro-8-bromo-quinazoline (1.51 g, 5.43 mmol), (+/−)-trans-methyl 3-aminobicyclo[2.2.2]octane-2-carboxylate (1.10 g, 5.98 mmol) and $K_2CO_3$ (1.50 g, 10.9 mmol) in DMF (10 mL) was stirred at rt overnight. To the reaction mixture was added $H_2O$ (100 mL), and the mixture was extracted with EtOAc (50 mL×3). The combined organic layers were washed with saturated brine (80 mL), dried over anhydrous sodium sulfate, and filtered. The filtrate was concentrated in vacuo, and the residue was purified by silica gel column chromatography (PE/EtOAc (v/v)=5/1~2/1) to give the title compound as a white solid (1.04 g, 45%).

MS (ESI, pos. ion) m/z: 426.00 [M+H]+.

Step 2: (+/−)-trans-methyl 3-((2-chloro-8-cyclopropylquinazolin-4-yl)amino)bicyclo[2.2.2]octane-2-carboxylate (+/−)-trans-Methyl 3-((8-bromo-2-chloro-quinazolin-4-yl)amino)bicyclo[2.2.2]octane-2-carboxylate (300 mg, 0.71 mmol) and cyclopropylboronic acid (73 mg, 0.85 mmol) were dissolved in tolene (8 mL), and the mixture was bubbled with nitrogen for 5 min to remove the air. Then palladium acetate (20 mg, 0.07 mmol) and triphenyl phosphine (39 mg, 0.14 mmol) were added to the mixture under nitrogen protection, and the mixture was stirred at 110° C. overnight. The reaction was stopped, and the mixture was diluted with ethyl acetate (50 mL). The resulting mixture was filtered, and the filtrate was concentrated in vacuo. The residue was purified by silica gel column chromatography (PE/EtOAc (v/v)=10/1) to give the title compound as white powder (123 mg, 45%).

MS (ESI, pos. ion) m/z: 386.10 [M+H]+;
1H NMR (400 MHz, CDCl3) δ (ppm): 7.45 (d, J=7.5 Hz, 1H), 7.39-7.33 (m, 1H), 7.14 (d, J=7.3 Hz, 1H), 5.93 (d, J=5.2 Hz, 1H), 4.62 (s, 1H), 3.81 (s, 3H), 3.02 (m, 1H), 2.48 (d, J=5.5 Hz, 1H), 1.99 (dd, J=5.7, 2.8 Hz, 2H), 1.95-1.59 (m, 11H), 1.46 (dd, J=15.3, 7.8 Hz, 1H).

Step 3: (+/−)-trans-methyl 3-((8-cyclopropyl-2-(5,7-difluoro-1-tosyl-1H-indol-3-yl)quinazolin-4-yl)amino)bicyclo[2.2.2]octane-2-carboxylate To 1,4-dioxane (8 mL) were added 5,7-difluoro-3-(4,4,5,5-tetramethyl-1,3,2-dioxaborolan-2-yl)-1-tosyl-1H-indole (125 mg, 0.29 mmol), K2CO3 (110 mg, 0.78 mmol), Pd(dppf)Cl2 (22 mg, 0.03 mmol), (+/−)-trans-methyl 3-((2-chloro-8-cyclopropylquinazolin-4-yl)amino)bicyclo[2.2.2]octane-2-carboxylate (100 mg, 0.26 mmol), then H2O (1 mL) was added to the mixture. A stream of nitrogen was bubbled through the mixture for 5 min to remove air, then the mixture was stirred at 115° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give the title compound as a white solid (66 mg, 39%).

1H NMR (400 MHz, CDCl3) δ (ppm): 8.84 (s, 1H), 8.61 (d, J=9.4 Hz, 1H), 7.93 (d, J=7.9 Hz, 2H), 7.52 (d, J=7.5 Hz, 1H), 7.35 (dd, J=15.5, 7.6 Hz, 3H), 6.81 (t, J=9.2 Hz, 1H), 5.83 (d, J=6.3 Hz, 1H), 4.97 (s, 1H), 3.76 (s, 3H), 3.07 (s, 1H), 2.51 (s, 1H), 2.41 (s, 3H), 2.08 (dd, J=30.1, 19.2 Hz, 4H), 1.86-1.65 (m, 5H), 1.28 (s, 6H), 0.85 (d, J=3.1 Hz, 2H).

Step 4: (+/−)-trans-3-((8-cyclopropyl-2-(5,7-difluoro-1H-indol-3-yl)quinazolin-4-yl)amino)bicyclo[2.2.2]octane-2-carboxylic Acid To a solution of (+/−)-trans-methyl 3-((8-cyclopropyl-2-(5,7-difluoro-1-tosyl-1H-indol-3-yl)quinazolin-4-yl)amino)bicyclo[2.2.2]octane-2-carboxylate (96 mg, 0.15 mmol) in a mixed solvent THF/MeOH (v/v=5 mL/5 mL) was added a solution of NaOH (59 mg, 1.44 mmol) in water (1 mL). The mixture was stirred at rt overnight. The reaction mixture was quenched with water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1~5/1) to give the title compound as a white solid (36 mg, 50%).

HRMS (ESI, pos. ion) m/z: 489.2111 [M+H]+, (C28H26F2N4O2) [M+H]+ theoretical value: 489.2102;
1H NMR (600 MHz, DMSO-d6) δ (ppm): 12.33 (s, 1H), 8.21 (s, 3H), 7.43 (s, 2H), 7.16 (s, 1H), 5.01 (s, 1H), 2.09 (s, 2H), 1.85 (dd, J=21.8, 10.1 Hz, 4H), 1.65-1.43 (m, 6H), 1.23 (s, 1H), 1.16 (d, J=7.9 Hz, 2H), 0.84 (s, 2H).

Example 13: (+/−)-trans-3-((2-(5,7-difluoro-1H-indol-3-yl)-7-phenylquinazolin-4-yl)amino)bicyclo[2.2.2]octane-2-carboxylic Acid

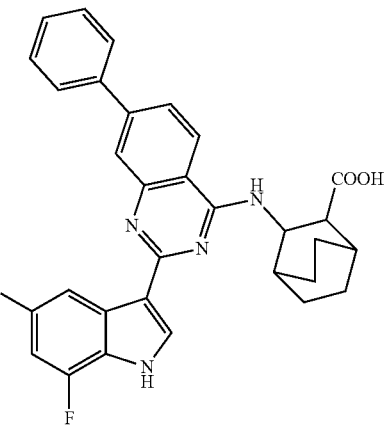

Step 1: (+/−)-trans-methyl 3-((7-bromo-2-chloroquinazolin-4-yl)amino)bicyclo[2.2.2]octane-2-carboxylate A suspension of 2,4-dichloro-7-bromo-quinazoline (811 mg, 2.88 mmol), (+/−)-trans-methyl 3-aminobicyclo[2.2.2]octane-2-carboxylate (635 mg, 3.45 mmol) and DIPEA (3.80 g, 28.78 mmol) in THF (8 mL) was stirred at rt overnight. To the reaction mixture was added H2O (100 mL) to quench the reaction, and the mixture was extracted with EtOAc (50 mL×3). The combined organic layers were washed with saturated brine (80 mL), dried over anhydrous sodium sulfate, and filtered. The filtrate was concentrated in vacuo, and the residue was purified by silica gel column chromatography (PE/EtOAc (v/v)=5/1~2/1) to give the title compound as a white solid (563 mg, 45%).

MS (ESI, neg. ion) m/z: 423.30 [M−H]−;
1H NMR (400 MHz, CDCl3) δ (ppm): 7.94 (s, 1H), 7.55 (s, 2H), 5.95 (d, J=5.0 Hz, 1H), 4.63 (s, 1H), 3.81 (s, 3H), 2.49 (d, J=5.5 Hz, 1H), 2.01 (dd, J=13.4, 2.4 Hz, 2H), 1.76 (m, 8H).

Step 2: (+/−)-trans-methyl 3-((2-chloro-7-phenylquinazolin-4-yl)amino)bicyclo[2.2.2]octane-2-carboxylate (+/−)-trans-Methyl 3-((7-bromo-2-chloro-quinazolin-4-yl)amino)bicyclo[2.2.2]octane-2-carboxylate (480 mg, 1.13 mmol) and phenylboronic acid (175 mg, 1.36 mmol) were dissolved in tolene (8 mL), and the mixture was bubbled with nitrogen for 5 min to remove the air. Then palladium acetate (26 mg, 0.11 mmol) and triphenyl phosphine (60 mg, 0.23 mmol) were added to the mixture, and the mixture was stirred at 110° C. overnight. The reaction was stopped, and the mixture was diluted with ethyl acetate (40 mL). The resulting mixture was filtered, and the filtrate was concentrated in vacuo. The residue was purified by silica gel column chromatography (PE/EtOAc (v/v)=10/1) to give the title compound as white powder (250 mg, 52%).

MS (ESI, pos. ion) m/z: 423.10 [M+H]$^+$;

$^1$H NMR (400 MHz, CDCl$_3$) δ (ppm): 8.01 (s, 1H), 7.74 (s, 2H), 7.70 (d, J=7.2 Hz, 2H), 7.52 (t, J=7.4 Hz, 2H), 7.46 (d, J=7.2 Hz, 1H), 5.96 (d, J=5.0 Hz, 1H), 4.66 (s, 1H), 3.83 (s, 3H), 2.52 (d, J=5.5 Hz, 1H), 2.05-2.00 (m, 2H), 1.95-1.67 (m, 8H).

Step 3: (+/−)-trans-methyl 3-((2-(5,7-difluoro-1-tosyl-1H-indol-3-yl)-7-phenylquinazolin-4-yl)amino)bicyclo[2.2.2]octane-2-carboxylate To 1,4-dioxane (8 mL) were added 5,7-difluoro-3-(4,4,5,5-tetramethyl-1,3,2-dioxaborolan-2-yl)-1-tosyl-1H-indole (120 mg, 0.26 mmol), K$_2$CO$_3$ (100 mg, 0.71 mmol), Pd(dppf)Cl$_2$ (21 mg, 0.02 mmol) and (+/−)-trans-methyl 3-((2-chloro-7-phenylquinazolin-4-yl)amino)bicyclo[2.2.2]octane-2-carboxylate (100 mg, 0.24 mmol), then H$_2$O (1 mL) was added to the mixture. A stream of nitrogen was bubbled through the mixture for 5 min to remove air, then the mixture was stirred at 115° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give the title compound as a white solid (86 mg, 52%).

Step 4: (+/−)-trans-3-((2-(5,7-difluoro-1H-indol-3-yl)-7-phenylquinazolin-4-yl)amino)bicyclo[2.2.2]octane-2-carboxylic Acid To a solution of (+/−)-trans-methyl 3-((2-(5,7-difluoro-1-tosyl-1H-indol-3-yl)-7-phenylquinazolin-4-yl)amino)bicyclo[2.2.2]octane-2-carboxylate (86 mg, 0.12 mmol) in a mixed solvent THF/MeOH (v/v=5 mL/5 mL) was added a solution of NaOH (50 mg, 1.24 mmol) in water (1 mL). The mixture was stirred at rt overnight. The reaction was quenched with water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to dry, and the residue was purified by silica gel column chromatography (dichloromethane/methanol (v/v)=10/1~5/1) to give the title compound as a white solid (45 mg, 69%).

HRMS (ESI, pos. ion) m/z: 525.2122 [M+H]$^+$, (C$_{31}$H$_{26}$F$_2$N$_4$O$_2$) [M+H]$^+$ theoretical value: 525.2102;

$^1$H NMR (600 MHz, DMSO-d$_6$) δ (ppm): 12.43 (s, 1H), 8.54 (d, J=8.6 Hz, 1H), 8.48 (s, 1H), 8.32 (d, J=8.6 Hz, 1H), 8.27 (s, 1H), 8.06 (s, 1H), 7.87 (d, J=7.4 Hz, 2H), 7.82 (d, J=8.2 Hz, 1H), 7.55 (t, J=7.5 Hz, 2H), 7.47 (t, J=7.3 Hz, 1H), 7.11 (t, J=9.6 Hz, 1H), 4.98 (s, 1H), 3.17 (s, 1H), 3.05 (d, J=6.6 Hz, 1H), 2.10 (s, 2H), 1.98-1.78 (m, 3H), 1.72-1.34 (m, 5H);

$^{13}$C NMR (101 MHz, DMSO-d$_6$) δ (ppm): 175.92, 159.55, 156.29, 147.70, 145.05, 139.36, 132.49, 129.59, 129.06, 128.95, 127.60, 124.62, 123.87, 122.20, 122.07, 112.44, 103.79, 103.51, 97.92, 97.61, 97.44, 51.85, 48.00, 28.80, 28.60, 25.85, 24.25, 21.63, 19.76.

Example 14: (+/−)-trans-3-((2-(5,7-difluoro-1H-indol-3-yl)-7,8-dimethylquinazolin-4-yl)amino)bicyclo[2.2.2]octane-2-carboxylic Acid

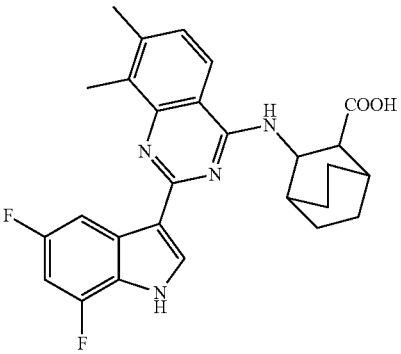 [SMILES: Cc1ccc2c(NC3C4CCC(CC4)C3C(=O)O)nc(-c3c[nH]c4c(F)cc(F)cc34)nc2c1C]

Step 1: 7,8-dimethylquinazoline-2,4(1H,3H)-dione

2-Amino-3,4-dimethylbenzoic acid (3.00 g, 18.16 mmol) and urea (10.90 g, 181.61 mmol) were mixed homogeneously, and the mixture was reacted at 160° C. 10 Hours later, the mixture was cooled to 100° C., and to the mixture was added water (100 mL). The resulting mixture was stirred for 5 min and then filtered. The filter cake was washed with water (100 mL). The filter cake was added into an aqueous sodium hydroxide solution (0.5 M, 100 mL), and the mixture was kept boiling for 10 min. Then the mixture was cooled to rt, and acidified with diluted hydrochloric acid (1 M) to pH about 1 to 2. The resulting mixture was filtered, and the filter cake was washed with water to give a yellow solid (2.99 g, 87%).

MS (ESI, pos. ion) m/z: 191.10 [M+H]$^+$;

$^1$H NMR (400 MHz, DMSO-d$_6$) δ (ppm): 11.24 (s, 1H), 10.32 (s, 1H), 7.66 (s, 1H), 7.03 (s, 1H), 2.31 (s, 3H), 2.23 (s, 3H).

Step 2: 2,4-dichloro-7,8-dimethylquinazoline

A solution of 7,8-dimethylquinazoline-2,4(1H,3H)-dione (2.99 g, 15.70 mmol) in phosphorus oxychloride (10 mL) was stirred at 115° C. overnight. The reaction was stopped, and the mixture was concentrated in vacuo to remove phosphorus oxychloride. The residue was purified by silica gel column chromatography (PE/EtOAc (v/v)=15/1) to give the title compound as white powder (1.25 g, 35%).

MS (ESI, pos. ion) m/z: 227.95 [M+H]$^+$;

$^1$H NMR (400 MHz, CDCl$_3$) δ (ppm): 7.98 (d, J=8.5 Hz, 1H), 7.52 (d, J=8.5 Hz, 1H), 2.67 (s, 3H), 2.56 (s, 3H).

Step 3: (+/−)-trans-methyl 3-((2-chloro-7,8-dimethylquinazolin-4-yl)amino)bicyclo[2.2.2]octane-2-carboxylate A suspension of 2,4-dichloro-7,8-dimethylquinazoline (300 mg, 1.32 mmol), (+/−)-trans-methyl 3-aminobicyclo[2.2.2]octane-2-carboxylate (290 mg, 1.45 mmol) and DIPEA (1.72 g, 13.21 mmol) in THF (10 mL) was stirred at rt overnight. To the reaction mixture was added H$_2$O (100 mL) to quench the reaction, and the mixture was extracted with EtOAc (50 mL×3). The combined organic layers were washed with saturated brine (80 mL), dried over anhydrous sodium sulfate, and filtered. The filtrate was concentrated in vacuo, and the residue was purified by silica gel column chromatography (PE/EtOAc (v/v)=5/1~2/1) to give the title compound as a white solid (354 mg, 72%).

MS (ESI, pos. ion) m/z: 374.50 [M+H]$^+$;

$^1$H NMR (400 MHz, CDCl$_3$) δ (ppm): 7.41 (d, J=8.4 Hz, 1H), 7.26 (d, J=8.4 Hz, 1H), 5.85 (d, J=4.8 Hz, 1H), 4.60 (s, 1H), 3.81 (s, 3H), 2.58 (s, 3H), 2.45 (s, 3H), 1.99 (dd, J=6.5, 2.8 Hz, 2H), 1.90 (dd, J=18.9, 7.8 Hz, 1H), 1.83-1.75 (m, 2H), 1.72-1.57 (m, 5H), 1.46 (t, J=12.1 Hz, 1H).

Step 4: (+/−)-trans-methyl 3-((2-(5,7-difluoro-1-tosyl-1H-indol-3-yl)-7,8-dimethylquinazolin-4-yl)amino)bicyclo[2.2.2]octane-2-carboxylate To 1,4-dioxane (8 mL) were added 5,7-difluoro-3-(4,4,5,5-tetramethyl-1,3,2-dioxaborolan-2-yl)-1-tosyl-1H-indole (160 mg, 0.35 mmol), K$_2$CO$_3$ (135 mg, 0.96 mmol), Pd(dppf)Cl$_2$ (26 mg, 0.03 mmol) and (+/−)-trans-methyl 3-((2-chloro-7,8-dimethylquinazolin-4-yl)amino)bicyclo[2.2.2]octane-2-carboxylate (120 mg, 0.32 mmol), then H$_2$O (1 mL) was added to the mixture. A stream of nitrogen was bubbled through the mixture for 5 min to remove air, then the mixture was stirred at 115° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give the title compound as a white solid (120 mg, 58%).

$^1$H NMR (400 MHz, CDCl$_3$) δ (ppm): 8.83 (s, 1H), 8.58-8.51 (m, 1H), 7.93 (d, J=8.2 Hz, 2H), 7.47 (d, J=8.3 Hz, 1H), 7.31 (d, J=8.3 Hz, 2H), 7.26 (s, 1H), 6.82 (t, J=10.4 Hz, 1H), 5.79 (d, J=6.3 Hz, 1H), 4.96 (s, 1H), 3.75 (s, 3H), 2.76 (s, 2H), 2.51 (s, 3H), 2.41 (s, 3H), 2.15 (d, J=2.6 Hz, 1H), 2.09 (d, J=2.5 Hz, 1H), 2.05-1.99 (m, 1H), 1.89-1.72 (m, 5H), 1.55-1.48 (m, 1H), 1.29 (d, J=6.8 Hz, 2H).

Step 5: (+/−)-trans-3-((2-(5,7-difluoro-1H-indol-3-yl)-7,8-dimethylquinazolin-4-yl)amino)bicyclo[2.2.2]octane-2-carboxylic Acid To a solution of (+/−)-trans-methyl 3-((2-(5,7-difluoro-1-tosyl-1H-indol-3-yl)-7,8-dimethylquinazolin-4-yl)amino)bicyclo[2.2.2]octane-2-carboxylate (100 mg, 0.16 mmol) in a mixed solvent THF/MeOH (v/v=5 mL/5 mL) was added a solution of NaOH (59 mg, 1.55 mmol) in water (1 mL). The mixture was stirred at rt overnight. The reaction was quenched with water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to dry, and the residue was purified by silica gel column chromatography (dichloromethane/methanol (v/v)=10/1~5/1) to give the title compound as a white solid (41 mg, 55%).

HRMS (ESI, pos. ion) m/z: 477.2109 [M+H]$^+$, (C$_{27}$H$_{26}$F$_2$N$_4$O$_2$) [M+H]$^+$ theoretical value: 477.2102;

$^1$H NMR (600 MHz, DMSO-d$_6$) δ (ppm): 12.32 (s, 1H), 8.17 (s, 3H), 7.37 (s, 1H), 7.14 (s, 2H), 5.02 (s, 1H), 2.62 (s, 3H), 2.45 (s, 3H), 2.07 (s, 2H), 1.86 (s, 4H), 1.65-1.42 (m, 6H).

Example 15: (+/−)-trans-3-((2-(5,7-difluoro-1H-indol-3-yl)benzo[g]quinazolin-4-yl)amino)bicyclo[2.2.2]octane-2-carboxylic Acid

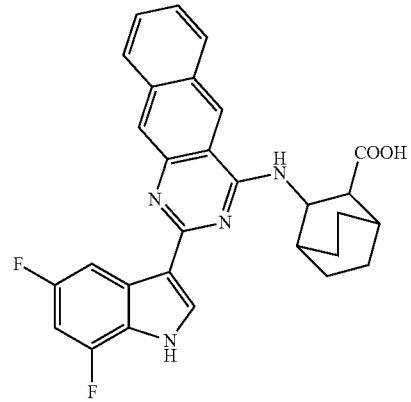 [SMILES: O=C(O)C1C2CCC(CC2)C1Nc1nc(-c2c[nH]c3c(F)cc(F)cc23)nc2cc3ccccc3cc12]

Step 1: benzo[g]quinazoline-2,4(1H,3H)-dione

3-Amino-2-naphthoic acid (3.00 g, 16.03 mmol) and urea (9.63 g, 160.00 mmol) were mixed homogeneously, and the mixture was reacted at 160° C. 10 Hours later, the mixture was cooled to 100° C., and to the mixture was added water (100 mL). The resulting mixture was stirred for 5 min and then filtered. The filter cake was washed with water (100 mL). The filter cake was added into sodium hydroxide solution (0.5 M, 100 mL), and the mixture was kept boiling for 10 min. Then the mixture was cooled, and acidified with diluted hydrochloric acid (1 M) to pH about 1 to 2. The resulting mixture was filtered, and the filter cake was washed with water to give the title compound as a yellow solid (3.30 g, 97.0%).

MS (ESI, pos. ion) m/z: 213.10 [M+H]$^+$.

Step 2: 2,4-dichlorobenzo[g]quinazoline

A solution of benzo[g]quinazoline-2,4(1H,3H)-dione (3.30 g, 15.60 mmol) in phosphorus oxychloride (10 mL) was stirred at 115° C. overnight. The reaction was stopped, and the mixture was concentrated in vacuo to remove phosphorus oxychloride. The residue was purified by silica gel column chromatography (PE/EtOAc (v/v)=15/1) to give the title compound as white powder (245 mg, 6.32%).

MS (ESI, pos. ion) m/z: 250.95 [M+H]$^+$;

$^1$H NMR (400 MHz, CDCl$_3$) δ (ppm): 8.88 (s, 1H), 8.54 (s, 1H), 8.13 (dd, J=19.0, 8.4 Hz, 2H), 7.71 (dt, J=14.8, 7.0 Hz, 2H).

Step 3: (+/−)-trans-methyl 3-((2-chlorobenzo[g]quinazolin-4-yl)amino)bicyclo[2.2.2]octane-2-carboxylate A suspension of 2,4-dichlorobenzo[g]quinazoline (500 mg, 2.30 mmol), (+/−)-trans-methyl 3-aminobicyclo[2.2.2]octane-2-carboxylate (506 mg, 2.76 mmol) and DIPEA (4.0 mL, 24.00 mmol) in THF (10 mL) was stirred at rt overnight. To the reaction mixture was added H$_2$O (100 mL) to quench the reaction, and the mixture was extracted with EtOAc (50 mL×3). The combined organic layers were washed with saturated brine (80 mL), dried over anhydrous sodium sulfate, and filtered. The filtrate was concentrated in vacuo, and the residue was purified by silica gel column chromatography (PE/EtOAc (v/v)=5/1~2/1) to give the title compound as a white solid (807 mg, 96%).

MS (ESI, pos. ion) m/z: 396.05 [M+H]$^+$;

$^1$H NMR (400 MHz, CDCl$_3$) δ (ppm): 8.26 (d, J=19.0 Hz, 2H), 7.95 (d, J=8.4 Hz, 2H), 7.53 (dt, J=14.9, 6.9 Hz, 2H), 6.42 (s, 1H), 4.73 (d, J=3.9 Hz, 1H), 3.81 (s, 3H), 2.60 (d, J=5.2 Hz, 1H), 2.10-2.02 (m, 2H), 1.90 (d, J=11.5 Hz, 2H), 1.76 (dd, J=25.6, 12.4 Hz, 5H), 1.48 (t, J=12.1 Hz, 1H).

Step 4: (+/−)-trans-methyl 3-((2-(5,7-difluoro-1-tosyl-1H-indol-3-yl)benzo[g]quinazolin-4-yl)amino)bicyclo[2.2.2]octane-2-carboxylate To 1,4-dioxane (8 mL) were added 5,7-difluoro-3-(4,4,5,5-tetramethyl-1,3,2-dioxaborolan-2-yl)-1-tosyl-1H-indole (66 mg, 0.14 mmol), K$_2$CO$_3$ (53 mg, 0.38 mmol), Pd(dppf)Cl$_2$ (12 mg, 0.01 mmol) and (+/−)-trans-methyl 3-((2-chlorobenzo[g]quinazolin-4-yl)amino)bicyclo[2.2.2]octane-2-carboxylate (50 mg, 0.13 mmol), then H$_2$O (1 mL) was added to the mixture. A stream of nitrogen was bubbled through the mixture for 5 min to remove air, then the mixture was stirred at 115° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give the title compound as a white solid (38 mg, 45%).

Step 5: (+/−)-trans-3-((2-(5,7-difluoro-1H-indol-3-yl)benzo[g]quinazolin-4-yl)amino) bicyclo[2.2.2]octane-2-carboxylic Acid To a solution of (+/−)-trans-methyl 3-((2-(5,7-difluoro-1-tosyl-1H-indol-3-yl)benzo[g]quinazolin-4-yl)amino)bicyclo[2.2.2]octane-2-carboxylate (35 mg, 0.05 mmol) in a mixed solvent THF/MeOH (v/v=5 mL/5 mL) was added a solution of NaOH (26 mg, 0.53 mmol) in water (1 mL). The mixture was stirred at rt overnight. The reaction was quenched with water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (dichloromethane/methanol (v/v)=10/1~5/1) to give the title compound as a white solid (15 mg, 57%).

HRMS (ESI, pos. ion) m/z: 499.1965 [M+H]$^+$, (C$_{29}$H$_{24}$F$_2$N$_4$O$_2$) [M+H]$^+$ theoretical value: 499.1946;

$^1$H NMR (600 MHz, DMSO-d$_6$) δ (ppm): 12.46 (s, 1H), 9.16 (s, 1H), 8.34 (s, 2H), 8.08 (t, J=9.5 Hz, 2H), 7.63 (t, J=7.2 Hz, 1H), 7.55 (t, J=7.4 Hz, 1H), 7.13 (t, J=10.0 Hz, 1H), 6.87 (s, 1H), 6.65 (s, 1H), 5.03 (s, 1H), 3.10 (d, J=6.6 Hz, 1H), 2.18 (s, 2H), 2.12 (s, 1H), 2.07 (s, 1H), 1.96-1.87 (m, 3H), 1.63-1.48 (m, 4H).

Example 16: (+/−)-trans-3-((2-(5,7-difluoro-1H-indol-3-yl)-5-fluoroquinazolin-4-yl)amino)bicyclo[2.2.2]octane-2-carboxylic Acid

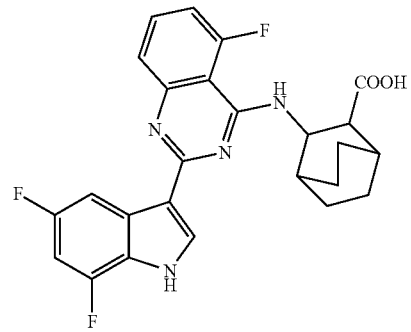 [SMILES: O=C(O)C1C2CCC(CC2)C1Nc1nc(-c2c[nH]c3c(F)cc(F)cc23)nc2cccc(F)c12]

Step 1: (+/−)-trans-methyl 3-((2-chloro-5-fluoroquinazolin-4-yl)amino)bicyclo[2.2.2]octane-2-carboxylate A suspension of 2,4-dichloro-5-fluoroquinazoline (465 mg, 2.14 mmol), (+/−)-trans-methyl 3-aminobicyclo[2.2.2]octane-2-carboxylate (700 mg, 3.82 mmol) and DIPEA (3.2 mL, 19.00 mmol) in THF (10 mL) was stirred at rt overnight. To the reaction mixture was added H$_2$O (100 mL), and the mixture was extracted with EtOAc (50 mL×3). The combined organic layers were washed with saturated brine (80 mL), dried over anhydrous sodium sulfate, and filtered. The filtrate was concentrated in vacuo, and the residue was purified by silica gel column chromatography (PE/EtOAc (v/v)=5/1~2/1) to give the title compound as a white solid (400 mg, 51%).

$^1$H NMR (400 MHz, CDCl$_3$) δ (ppm): 7.68-7.59 (m, 1H), 7.55 (d, J=8.4 Hz, 1H), 7.10 (dd, J=12.4, 7.9 Hz, 1H), 4.61 (s, 1H), 3.81 (s, 3H), 2.47 (dd, J=3.2, 2.0 Hz, 1H), 1.98 (dd, J=16.1, 2.6 Hz, 2H), 1.90-1.82 (m, 1H), 1.80-1.59 (m, 7H), 1.50-1.42 (m, 1H).

Step 2: (+/−)-trans-methyl 3-((2-(5,7-difluoro-1-tosyl-1H-indol-3-yl)-5-fluoroquinazolin-4-yl)amino)bicyclo[2.2.2]octane-2-carboxylate To 1,4-dioxane (8 mL) were added 5,7-difluoro-3-(4,4,5,5-tetramethyl-1,3,2-dioxaborolan-2-yl)-1-tosyl-1H-indole (182 mg, 0.45 mmol), K$_2$CO$_3$ (110 mg, 0.83 mmol), Pd(dppf)Cl$_2$ (30 mg, 0.04 mmol) and (+/−)-trans-methyl 3-((2-chloro-5-fluoroquinazolin-4-yl)amino)bicyclo[2.2.2]octane-2-carboxylate (150 mg, 0.41 mmol), then H$_2$O (1 mL) was added to the mixture. A stream of nitrogen was bubbled through the mixture for 5 min to remove air, then the mixture was stirred at 115° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give the title compound as a white solid (46 mg, 18%).

MS (ESI, pos. ion) m/z: 636.10 [M+H]$^+$.

Step 3: (+/−)-trans-3-((2-(5,7-difluoro-1H-indol-3-yl)-5-fluoroquinazolin-4-yl)amino)bicyclo[2.2.2]octane-2-carboxylic Acid To a solution of (+/−)-trans-methyl 3-((2-(5,7-difluoro-1-tosyl-1H-indol-3-yl)-5-fluoroquinazolin-4-yl)amino)bicyclo[2.2.2]octane-2-carboxylate (36 mg, 0.06 mmol) in a mixed solvent THF/MeOH (v/v=5 mL/5 mL) was added a solution of NaOH (25 mg, 0.57 mmol) in water (1 mL). The mixture was stirred at rt overnight. The reaction was quenched with water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to dry, and the residue was purified by silica gel column chromatography (dichloromethane/methanol (v/v)=10/1~5/1) to give the title compound as a white solid (13 mg, 49%).

HRMS (ESI, pos. ion) m/z: 467.1699 [M+H]$^+$, ($C_{25}H_{21}F_3N_4O_2$) [M+H]$^+$ theoretical value: 467.1695;

$^1$H NMR (600 MHz, DMSO-d$_6$) δ (ppm): 13.18 (s, 1H), 9.21 (s, 1H), 8.52 (s, 1H), 8.12 (dd, J=9.5, 1.8 Hz, 1H), 7.98 (d, J=10.7 Hz, 2H), 7.54-7.45 (m, 1H), 7.25 (t, J=9.3 Hz, 1H), 5.21 (s, 1H), 3.17 (t, J=5.7 Hz, 1H), 2.11 (s, 2H), 1.85 (m, 3H), 1.70-1.40 (m, 6H);

$^{13}$C NMR (151 MHz, DMSO-d$_6$) δ (ppm) 175.46, 159.58, 158.26, 157.90, 149.89, 148.28, 136.93, 136.24, 128.56, 125.96, 122.29, 122.20, 112.95, 109.60, 103.39, 103.23, 102.38, 98.94, 53.20, 47.74, 28.85, 28.49, 25.24, 24.16, 21.42, 19.67.

Example 17: (+/−)-trans-3-((2-(5,7-difluoro-1H-indol-3-yl)-6-(4-(trifluoromethyl)phenyl)pyrimidin-4-yl)amino)bicyclo[2.2.2]octane-2-carboxylic Acid

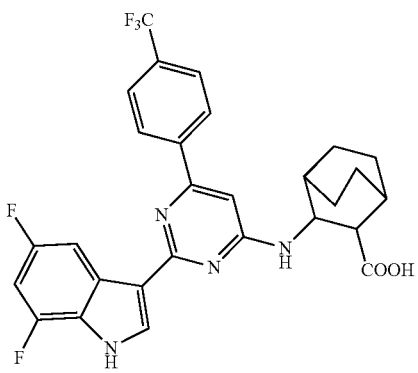 [SMILES: O=C(O)C1C2CCC(CC2)C1Nc1cc(-c2ccc(C(F)(F)F)cc2)nc(-c2c[nH]c3c(F)cc(F)cc23)n1]

Step 1: 2,4-dichloro-6-(3-fluoro-4-methoxyphenyl)pyrimidine

To a solution of 2,4,6-trichloropyrimidine (1 g, 5.45 mmol) in tetrahydrofuran (16 mL) were added palladium acetate (125 mg, 0.55 mmol), triphenylphosphine (302 mg, 1.09 mmol), (3-fluoro-4-methoxyphenyl)boronic acid (1.18 g, 5.51 mol) and an aqueous sodium carbonate solution (1 M, 16.35 mL, 16.35 mmol). The mixture was heated to 70° C. and stirred for 6 h. To the reaction mixture was added water (50 mL) to quench the reaction, and the mixture was extracted with ethyl acetate (50 mL×3). The combined organic layer was washed with saturated brine (50 mL), dried over anhydrous sodium sulfate, and filtered. The filtrate was concentrated in vacuo to dry. And the residue was purified by silica gel column chromatography (PE) to give the title compound as a white solid (1.03 g, 69%).

MS (ESI, pos. ion) m/z: 273.1 [M+H]$^+$;

$^1$H NMR (400 MHz, CDCl$_3$) δ (ppm): 7.91-7.88 (m, 1H), 7.87 (s, 1H), 7.59 (s, 1H), 7.09 (t, J=8.5 Hz, 1H), 4.00 (s, 3H).

Step 2: (+/−)-trans-methyl 3-((2-chloro-6-(3-fluoro-4-methoxyphenyl)pyrimidin-4-yl)amino)bicyclo[2.2.2]octane-2-carboxylate To a solution of (+/−)-trans-methyl 3-aminobicyclo[2.2.2]octane-2-carboxylate (369 mg, 2.01 mmol) and 2,4-dichloro-6-(3-fluoro-4-methoxyphenyl)pyrimidine (500 mg, 1.83 mmol) in tetrahydrofuran (5 mL) was added DIPEA (3 mL, 20.4 mmol). The mixture was stirred at rt overnight, and concentrated in vacuo to dry. The residue was purified by silica gel column chromatography (PE/EtOAc (v/v)=20/1) to give the title compound as a white solid (206 mg, 27%).

MS (ESI, pos. ion) m/z: 420.1 [M+H]$^+$;

$^1$H NMR (400 MHz, CDCl$_3$) δ (ppm): 7.79 (t, J=9.6 Hz, 2H), 7.04 (t, J=8.7 Hz, 1H), 6.73 (s, 1H), 5.46 (s, 1H), 4.33 (s, 1H), 3.97 (s, 3H), 3.76 (s, 3H), 2.40 (s, 1H), 2.09 (s, 1H), 1.88 (d, J=2.8 Hz, 1H), 1.78-1.65 (m, 6H), 1.50 (d, J=11.5 Hz, 2H).

Step 3: (+/−)-trans-methyl 3-((2-(5,7-difluoro-1-tosyl-1H-indol-3-yl)-6-(4-(trifluoromethyl)phenyl)pyrimidin-4-yl)amino)bicyclo[2.2.2]octane-2-carboxylate To a mixed solvent of 1,4-dioxane (3 mL) and water (0.2 mL) were added 5,7-difluoro-3-(4,4,5,5-tetramethyl-1,3,2-dioxaborolan-2-yl)-1-tosyl-1H-indole (236 mg, 0.27 mmol), (+/−)-trans-methyl 3-((2-chloro-6-(3-fluoro-4-methoxyphenyl)pyrimidin-4-yl)amino)bicyclo[2.2.2]octane-2-carboxylate (100 mg, 0.23 mmol), potassium phosphate (144 mg, 0.68 mmol) and Pd(dtbpf)Cl$_2$ (14 mg, 0.02 mmol). The mixture was stirred at 100° C. for 30 min under nitrogen protection, and then filtered through a celite pad. The filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (114 mg, 71%).

$^1$H NMR (400 MHz, CDCl$_3$) δ (ppm): 8.78 (s, 1H), 8.31 (d, J=7.3 Hz, 1H), 8.23 (d, J=8.1 Hz, 2H), 7.90 (d, J=8.0 Hz, 2H), 7.81 (d, J=8.2 Hz, 2H), 7.31 (d, J=8.2 Hz, 2H), 6.86-6.76 (m, 2H), 4.57 (s, 1H), 3.75 (s, 3H), 2.46 (s, 1H), 2.41 (s, 3H), 2.12 (s, 1H), 2.02 (s, 1H), 1.78 (dd, J=36.1, 17.6 Hz, 8H).

Step 4: (+/−)-trans-3-((2-(5,7-difluoro-1H-indol-3-yl)-6-(4-(trifluoromethyl)phenyl)pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-6-(4-(trifluoromethyl)phenyl)pyrimidin-4-yl)amino)bicyclo[2.2.2]octane-2-carboxylate (114 mg, 0.14 mmol) in a mixed solvent of THF and MeOH (v/v=1/1, 4 mL) was added an aqueous sodium hydroxide solution (4 M, 0.40 mL, 1.60 mmol). The mixture was stirred at 30° C. overnight. The reaction mixture was diluted with water (10 mL), and the mixture was acidified with hydrochloric acid (1 M) to pH about 5.5. The resulting mixture was extracted with EtOAc (20 mL×3). The combined organic layers were washed with saturated brine (40 mL), dried over anhydrous sodium sulfate, and filtered. The filtrate was concentrated in vacuo to dry, and the residue was purified by silica gel column chromatography (dichloromethane/methanol (v/v)=10/1) to give the title compound as a yellow solid (40 mg, 46%).

MS (ESI, pos. ion) m/z: 543.1 [M+H]$^+$;

$^1$H NMR (400 MHz, DMSO-d$_6$) δ (ppm): 12.29 (s, 1H), 8.40-8.25 (m, 3H), 8.20 (d, J=8.9 Hz, 1H), 7.91 (d, J=8.2 Hz, 2H), 7.67 (s, 1H), 7.08 (dd, J=15.0, 5.6 Hz, 1H), 6.85 (s, 1H), 4.67 (s, 1H), 2.01 (s, 2H), 1.62 (m, 8H);

$^{13}$C NMR (101 MHz, DMSO-d$_6$) δ (ppm): 175.91, 163.16, 163.01, 155.94, 155.84, 150.09, 147.49, 142.44, 131.85, 130.44, 128.91, 127.59, 126.12, 123.36, 122.13, 122.00, 117.38, 103.54, 99.03, 97.31, 97.21, 60.20, 50.63, 49.70, 28.78, 28.54, 26.01, 24.08, 21.42, 21.21, 19.47, 14.54.

Example 18: (+/−)-trans-3-((6-([1,1'-biphenyl]-4-yl)-2-(5,7-difluoro-1H-indol-3-yl)pyrimidin-4-yl)amino)bicyclo[2.2.2]octane-2-carboxylic Acid

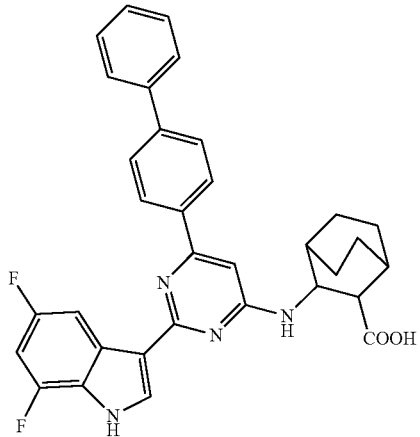 [SMILES: O=C(O)C1C2CCC(CC2)C1Nc1cc(-c2ccc(-c3ccccc3)cc2)nc(-c2c[nH]c3c(F)cc(F)cc23)n1]

Step 1: 4-([1,1'-biphenyl]-4-yl)-2,6-dichloropyrimidine

To a solution of 2,4,6-trichloropyrimidine (500 mg, 2.73 mmol) in tetrahydrofuran (8.5 mL) were added palladium acetate (63 mg, 0.28 mmol), triphenylphosphine (150 mg, 0.54 mmol), [1,1'-biphenyl]-4-ylboronic acid (545 mg, 2.75 mmol) and an aqueous sodium carbonate solution (1 M, 8.5 mL, 8.5 mmol). The mixture was heated to 70° C. and stirred for 6 h. To the reaction mixture was added water (50 mL), and the mixture was extracted with EtOAc (50 mL×3). The combined organic layers were washed with saturated brine (50 mL), dried over anhydrous sodium sulfate, and filtered. The filtrate was concentrated in vacuo to dry, and the residue was purified by silica gel column chromatography (PE) to give the title compound as a white solid (548 mg, 68%).

MS (ESI, pos. ion) m/z: 301.0 [M+H]$^+$;

$^1$H NMR (400 MHz, CDCl$_3$) δ (ppm): 8.18 (d, J=8.3 Hz, 2H), 7.78 (d, J=8.3 Hz, 2H), 7.73 (s, 1H), 7.68 (d, J=7.5 Hz, 2H), 7.51 (t, J=7.5 Hz, 2H), 7.44 (t, J=7.3 Hz, 1H).

Step 2: (+/−)-trans-methyl 3-((6-([1,1'-biphenyl]-4-yl)-2-chloropyrimidin-4-yl)amino)bicyclo[2.2.2]octane-2-carboxylate To a solution of (+/−)-trans-methyl 3-aminobicyclo[2.2.2]octane-2-carboxylate (366 mg, 2.00 mmol) and 4-([1,1'-biphenyl]-4-yl)-2,6-dichloropyrimidine (548 mg, 1.82 mmol) in DMF (5 mL) was added potassium carbonate (277 mg, 2.01 mmol). The mixture was stirred at rt overnight. To the reaction mixture was added water (50 mL), and the mixture was extracted with EtOAc (50 mL×2). The combined organic layers were washed with saturated brine (40 mL), dried over anhydrous Na$_2$SO$_4$ and filtered. The filtrate was concentrated in vacuo. The residue was purified by silica gel column chromatography (PE/EtOAc (v/v)=20/1) to give the title compound as a white solid (546 mg, 67%).

MS (ESI, pos. ion) m/z: 448.3 [M+H]$^+$;

$^1$H NMR (400 MHz, CDCl$_3$) δ (ppm): 8.09 (d, J=8.1 Hz, 2H), 7.72 (d, J=8.3 Hz, 2H), 7.67 (d, J=7.3 Hz, 2H), 7.49 (t, J=7.5 Hz, 2H), 7.40 (dd, J=8.3, 6.1 Hz, 1H), 6.85 (s, 1H), 5.48 (s, 1H), 4.36 (s, 1H), 3.76 (s, 3H), 2.42 (d, J=5.1 Hz, 1H), 2.09 (s, 1H), 1.89 (d, J=2.6 Hz, 1H), 1.83-1.65 (m, 6H), 1.60 (d, J=9.9 Hz, 2H).

Step 3: (+/−)-trans-methyl 3-((6-([1,1'-biphenyl]-4-yl)-2-(5,7-difluoro-1-tosyl-1H-indol-3-yl)pyrimidin-4-yl)amino)bicyclo[2.2.2]octane-2-carboxylate To a sealed tube were added 5,7-difluoro-3-(4,4,5,5-tetramethyl-1,3,2-dioxaborolan-2-yl)-1-tosyl-1H-indole (206 mg, 0.24 mmol), (+/−)-trans-methyl 3-((6-([1,1'-biphenyl]-4-yl)-2-chloropyrimidin-4-yl) amino)bicyclo[2.2.2]octane-2-carboxylate (89 mg, 0.20 mmol), potassium phosphate (126 mg, 0.59 mmol), Pd(dtbpf)Cl$_2$ (12 mg, 0.02 mmol), 1,4-dioxane (3 mL) and water (0.2 mL). The mixture was stirred at 100° C. for 10 min under nitrogen protection, and then filtered through a celite pad. The filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (92 mg, 64%).

$^1$H NMR (400 MHz, CDCl$_3$) δ (ppm): 8.79 (s, 1H), 8.38 (d, J=7.2 Hz, 1H), 8.22 (d, J=8.2 Hz, 2H), 7.90 (d, J=8.0 Hz, 2H), 7.79 (d, J=8.3 Hz, 2H), 7.71 (d, J=7.3 Hz, 2H), 7.52 (dd, J=14.4, 6.9 Hz, 2H), 7.41 (t, J=7.1 Hz, 1H), 7.31 (d, J=8.5 Hz, 2H), 6.82 (t, J=9.3 Hz, 2H), 5.24 (s, 1H), 4.56 (s, 1H), 3.76 (s, 3H), 2.47 (s, 1H), 2.41 (s, 3H), 2.12 (s, 1H), 2.03 (s, 1H), 1.93-1.61 (m, 8H).

Step 4: (+/−)-trans-3-((6-([1,1'-biphenyl]-4-yl)-2-(5,7-difluoro-1H-indol-3-yl)pyrimidin-4-yl)amino)bicyclo[2.2.2]octane-2-carboxylic Acid To a solution of (+/−)-trans-methyl 3-((6-([1,1'-biphenyl]-4-yl)-2-(5,7-difluoro-1-tosyl-1H-indol-3-yl)pyrimidin-4-yl)amino)bicyclo[2.2.2]octane-2-carboxylate (92 mg, 0.13 mmol) in a mixed solvent of THF and MeOH (v/v=1/1, 4 mL) was added an aqueous sodium hydroxide solution (4 M, 0.23 mL, 1.30 mmol). The mixture was stirred at 30° C. overnight. The reaction mixture was diluted with water (10 mL), and the mixture was acidified with hydrochloric acid (1 M) to pH about 5.5. The resulting mixture was extracted with EtOAc (20 mL×3). The combined organic layers were washed with saturated brine (50 mL), dried over anhydrous sodium sulfate, and filtered. The filtrate was concentrated in vacuo to remove the solvent, and the residue was purified by silica gel column chromatography (dichloromethane/methanol (v/v)=10/1) to give the title compound as a yellow solid (44 mg, 62%).

MS (ESI, pos. ion) m/z: 551.2 [M+H]$^+$;

¹H NMR (400 MHz, DMSO-d₆) δ (ppm): 12.27 (s, 1H), 8.32 (s, 1H), 8.20 (s, 3H), 7.86 (d, J=8.3 Hz, 2H), 7.78 (d, J=7.5 Hz, 2H), 7.52 (t, J=7.6 Hz, 3H), 7.41 (t, J=7.3 Hz, 1H), 7.07 (t, J=9.6 Hz, 1H), 6.84 (s, 1H), 4.66 (s, 1H), 2.01 (s, 2H), 1.88-1.51 (m, 8H).

Example 19: (+/−)-trans-3-((2-(5,7-difluoro-1H-indol-3-yl)-6-(3,4-difluorophenyl)pyrimidin-4-yl)amino)bicyclo[2.2.2]octane-2-carboxylic Acid

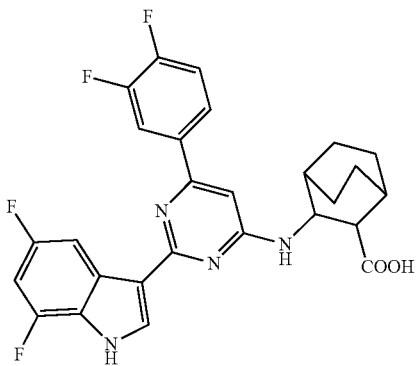 [SMILES: O=C(O)C1C2CCC(CC2)C1Nc1cc(-c2ccc(F)c(F)c2)nc(-c2c[nH]c3c(F)cc(F)cc23)n1]

Step 1:
2,4-dichloro-6-(3,4-difluorophenyl)pyrimidine

To a solution of 2,4,6-trichloropyrimidine (500 mg, 2.73 mmol) in tetrahydrofuran (8.5 mL) were added palladium acetate (63 mg, 0.28 mmol), triphenylphosphine (150 mg, 0.54 mmol), (3,4-difluorophenyl)boronic acid (434 mg, 2.75 mmol) and an aqueous sodium carbonate solution (1 M, 8.18 mL, 8.18 mmol). The mixture was heated to 70° C. and stirred for 6 h. To the reaction mixture was added water (50 mL), and the mixture was extracted with EtOAc (50 mL×3). The combined organic layers were washed with saturated brine (50 mL), dried over anhydrous sodium sulfate, and filtered. The filtrate was concentrated in vacuo to dry, and the residue was purified by silica gel column chromatography (PE) to give the title compound as a white solid (322 mg, 45%).

MS (ESI, pos. ion) m/z: 261.1 [M+H]⁺;

¹H NMR (400 MHz, CDCl₃) δ (ppm): 8.03-7.98 (m, 1H), 7.89-7.84 (m, 1H), 7.64 (s, 1H), 7.37-7.33 (m, 1H).

Step 2: (+/−)-trans-methyl 3-((2-chloro-6-(3,4-difluorophenyl)pyrimidin-4-yl)amino)bicyclo[2.2.2]octane-2-carboxylate To a solution of (+/−)-trans-methyl 3-aminobicyclo[2.2.2]octane-2-carboxylate (248 mg, 1.35 mmol) and 2,4-dichloro-6-(3,4-difluorophenyl)pyrimidine (322 mg, 1.23 mmol) in DMF (5 mL) was added potassium carbonate (187 mg, 1.36 mmol). The mixture was stirred at rt overnight. To the reaction mixture was added water (50 mL), and the mixture was extracted with EtOAc (50 mL×2). The combined organic layers were washed with saturated brine (80 mL), dried over anhydrous Na₂SO₄ and filtered. The filtrate was concentrated in vacuo. The residue was purified by silica gel column chromatography (PE/EtOAc (v/v)=20/1) to give the title compound as a white solid (265 mg, 53%).

MS (ESI, pos. ion) m/z: 408.0 [M+H]⁺;

¹H NMR (400 MHz, CDCl₃) δ (ppm): 7.94-7.84 (m, 1H), 7.77 (s, 1H), 7.40 (d, J=4.3 Hz, 1H), 6.78 (s, 1H), 5.53 (s, 1H), 4.35 (s, 1H), 3.76 (s, 3H), 2.40 (d, J=4.6 Hz, 1H), 2.10 (s, 1H), 1.88 (s, 1H), 1.82-1.60 (m, 6H), 1.50 (d, J=10.5 Hz, 2H).

Step 3: (+/−)-trans-methyl 3-((2-(5,7-difluoro-1-tosyl-1H-indol-3-yl)-6-(3,4-difluorophenyl)pyrimidin-4-yl)amino)bicyclo[2.2.2]octane-2-carboxylate To a mixed solvent of 1,4-dioxane (3 mL) and water (0.2 mL) were added 5,7-difluoro-3-(4,4,5,5-tetramethyl-1,3,2-dioxaborolan-2-yl)-1-tosyl-1H-indole (306 mg, 0.32 mmol), (+/−)-trans-methyl 3-((2-chloro-6-(3,4-difluorophenyl)pyrimidin-4-yl)amino)bicyclo[2.2.2]octane-2-carboxylate (108 mg, 0.26 mmol), potassium phosphate (168 mg, 0.79 mmol) and Pd(dtbpf)Cl₂ (17 mg, 0.03 mmol). The mixture was stirred at 100° C. for 30 min under nitrogen protection, and then filtered through a celite pad. The filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (120 mg, 68%).

MS (ESI, pos. ion) m/z: 679.1 [M+H]⁺;

¹H NMR (400 MHz, CDCl₃) δ (ppm): 8.76 (s, 1H), 8.29 (d, J=9.3 Hz, 1H), 8.00-7.94 (m, 1H), 7.90 (d, J=7.9 Hz, 3H), 7.33 (dd, J=15.3, 8.3 Hz, 3H), 6.82 (t, J=10.4 Hz, 1H), 6.71 (s, 1H), 4.55 (s, 1H), 3.75 (s, 3H), 2.45 (s, 1H), 2.42 (s, 3H), 2.12 (s, 1H), 2.02 (d, J=12.5 Hz, 2H), 1.93-1.64 (m, 8H).

Step 4: (+/−)-trans-3-((2-(5,7-difluoro-1H-indol-3-yl)-6-(3,4-difluorophenyl)pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-6-(3,4-difluorophenyl)pyrimidin-4-yl)amino)bicyclo[2.2.2]octane-2-carboxylate (80 mg, 0.12 mmol) in a mixed solvent of THF and MeOH (v/v=1/1, 4 mL) was added an aqueous sodium hydroxide solution (4 M, 0.30 mL, 1.20 mmol). The mixture was stirred at 30° C. overnight. The reaction mixture was diluted with water (10 mL), and the mixture was acidified with hydrochloric acid (1 M) to pH about 5.5. The resulting mixture was extracted with EtOAc (20 mL×3). The combined organic layers were washed with saturated brine (50 mL), dried over anhydrous sodium sulfate, and filtered. The filtrate was concentrated in vacuo to remove the solvent, and the residue was purified by silica gel column chromatography (dichloromethane/methanol (v/v)=10/1) to give the title compound as a yellow solid (49 mg, 81%).

MS (ESI, pos. ion) m/z: 511.6 [M+H]⁺;

¹H NMR (400 MHz, DMSO-d₆) δ (ppm): 12.29 (s, 1H), 8.36 (s, 1H), 8.17 (s, 2H), 7.92 (s, 1H), 7.61 (s, 2H), 7.06 (s, 1H), 6.77 (s, 1H), 4.66 (s, 1H), 2.90 (s, 1H), 2.00 (s, 2H), 1.61 (m, 8H);

¹³C NMR (101 MHz, DMSO-d₆) δ (ppm): 176.07, 172.51, 162.86, 158.24, 149.05, 136.13, 131.98, 128.84, 122.11, 121.98, 118.37, 117.30, 97.26, 56.49, 50.70, 49.66, 45.92, 28.79, 28.57, 26.02, 24.05, 21.57, 21.45, 19.47, 9.73.

Example 20: (+/−)-trans-3-((2-(5,7-difluoro-1H-indol-3-yl)-[4,5'-bipyrimidin]-6-yl)amino)bicyclo[2.2.2]octane-2-carboxylic Acid

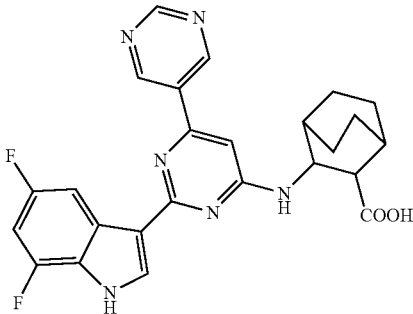 [SMILES: O=C(O)C1C2CCC(CC2)C1Nc1cc(-c2cncnc2)nc(-c2c[nH]c3c(F)cc(F)cc23)n1]

Step 1: 2,6-dichloro-4,5'-bipyrimidine

To a solution of 2,4,6-trichloropyrimidine (100 mg, 0.55 mmol) in acetonitrile (4 mL) were added Pd(dppf)Cl$_2$ (89 mg, 0.11 mmol), pyrimidin-5-ylboronic acid (67 mg, 0.55 mol), cesium carbonate (266 mg, 0.82 mmol) and water (0.5 mL). The mixture was heated to 95° C. under nitrogen protection and stirred for 5 h. To the reaction mixture was added water (50 mL), and the mixture was extracted with EtOAc (50 mL×3). The combined organic layers were washed with saturated brine (50 mL), dried over anhydrous sodium sulfate, and filtered. The filtrate was concentrated in vacuo to dry. The residue was purified by silica gel column chromatography (PE/EtOAc (v/v)=5/1) to give the title compound as a red solid (44 mg, 36%).

MS (ESI, pos. ion) m/z: 228.0 [M+H]$^+$;

$^1$H NMR (400 MHz, CDCl$_3$) δ (ppm): 9.41 (s, 3H), 7.76 (s, 1H).

Step 2: (+/−)-trans-methyl 3-((2-chloro-[4,5'-bipyrimidin]-6-yl)amino)bicyclo[2.2.2]octane-2-carboxylate To a solution of (+/−)-trans-methyl 3-aminobicyclo[2.2.2]octane-2-carboxylate (73 mg, 0.40 mmol) and 2,6-dichloro-4,5'-bipyrimidine (76 mg, 0.33 mmol) in DMF (2 mL) was added potassium carbonate (138 mg, 1.00 mmol). The mixture was stirred at rt overnight. To the reaction mixture was added water (40 mL), and the mixture was extracted with EtOAc (40 mL×3). The combined organic layers were washed with saturated brine (50 mL), dried over anhydrous sodium sulfate, and filtered. The filtrate was concentrated in vacuo to dry. The residue was purified by silica gel column chromatography (PE/EtOAc (v/v)=1/1) to give the title compound as a colorless solid (65 mg, 52%).

MS (ESI, pos. ion) m/z: 374.4 [M+H]$^+$;

$^1$H NMR (400 MHz, CDCl$_3$) δ (ppm): 9.32 (s, 3H), 6.95 (s, 1H), 5.77 (s, 1H), 4.36 (s, 1H), 3.77 (s, 3H), 2.41 (d, J=3.4 Hz, 1H), 1.88 (s, 1H), 1.83-1.65 (m, 8H).

Step 3: (+/−)-trans-methyl 3-((2-(5,7-difluoro-1-tosyl-1H-indol-3-yl)-[4,5'-bipyrimidin]-6-yl)amino)bicyclo[2.2.2]octane-2-carboxylate To a mixed solvent of 1,4-dioxane (3 mL) and water (0.2 mL) were added 5,7-difluoro-3-(4,4,5,5-tetramethyl-1,3,2-dioxaborolan-2-yl)-1-tosyl-1H-indole (154 mg, 0.16 mmol), (+/−)-trans-methyl 3-((2-chloro-[4,5'-bipyrimidin]-6-yl)amino)bicyclo[2.2.2]octane-2-carboxylate (50 mg, 0.13 mmol), potassium phosphate (85 mg, 0.40 mmol) and Pd(dt-bpf)Cl$_2$ (8 mg, 0.01 mmol). The mixture was stirred at 100° C. for 30 min under nitrogen protection, and then filtered through a celite pad. The filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (56 mg, 65%).

MS (ESI, pos. ion) m/z: 645.1[M+H]$^+$;

$^1$H NMR (400 MHz, CDCl$_3$) δ (ppm): 9.43 (s, 2H), 9.35 (s, 1H), 8.78 (s, 1H), 8.26 (d, J=7.7 Hz, 1H), 7.90 (d, J=7.7 Hz, 2H), 7.32 (d, J=8.2 Hz, 2H), 6.82 (t, J=9.1 Hz, 2H), 5.37 (s, 1H), 3.76 (s, 3H), 2.46 (s, 1H), 2.42 (s, 3H), 2.15 (s, 1H), 2.02 (s, 2H), 1.88-1.64 (m, 8H).

Step 4: (+/−)-trans-3-((2-(5,7-difluoro-1H-indol-3-yl)-[4,5'-bipyrimidin]-6-yl)amino)bicyclo[2.2.2]octane-2-carboxylic Acid To a solution of (+/−)-trans-methyl 3-((2-(5,7-difluoro-1-tosyl-1H-indol-3-yl)-[4,5'-bipyrimidin]-6-yl)amino)bicyclo[2.2.2]octane-2-carboxylate (56 mg, 0.09 mmol) in a mixed solvent of THF and MeOH (v/v=1/1, 4 mL) was added an aqueous sodium hydroxide solution (4 M, 0.13 mL, 0.90 mmol). The mixture was stirred at 30° C. overnight. The reaction mixture was diluted with water (10 mL), and the mixture was acidified with hydrochloric acid (1 M) to pH about 5.5. The resulting mixture was extracted with EtOAc (20 mL×3). The combined organic layers were washed with saturated brine (50 mL), dried over anhydrous sodium sulfate, and filtered. The filtrate was concentrated in vacuo to dry, and the residue was purified by silica gel column chromatography (dichloromethane/methanol (v/v)=10/1) to give the title compound as a yellow solid (38 mg, 92%).

MS (ESI, pos. ion) m/z: 477.5 [M+H]$^+$;

$^1$H NMR (400 MHz, DMSO-d$_6$) δ (ppm): 12.36 (s, 2H), 9.43 (s, 2H), 9.31 (s, 1H), 8.39 (s, 1H), 8.18 (d, J=8.5 Hz, 1H), 7.87 (s, 1H), 7.06 (t, J=9.9 Hz, 1H), 6.90 (s, 1H), 4.68 (s, 1H), 2.59 (s, 1H), 2.00 (d, J=7.8 Hz, 2H), 1.71 (m, 8H);

$^{13}$C NMR (151 MHz, DMSO-d$_6$) δ (ppm): 175.89, 163.19, 162.87, 159.51, 157.88, 156.33, 156.26, 155.83, 155.33, 132.27, 131.62, 131.07, 130.03, 128.96, 122.09, 122.01, 117.12, 103.39, 103.23, 98.89, 97.45, 97.31, 97.25, 97.11, 50.64, 49.43, 28.76, 28.51, 25.96, 24.07, 21.44, 19.49.

Example 21: (+/−)-trans-3-((2-(5,7-difluoro-1H-indol-3-yl)-6-(4-fluoro-3-methoxyphenyl)pyrimidin-4-yl)amino)bicyclo[2.2.2]octane-2-carboxylic Acid

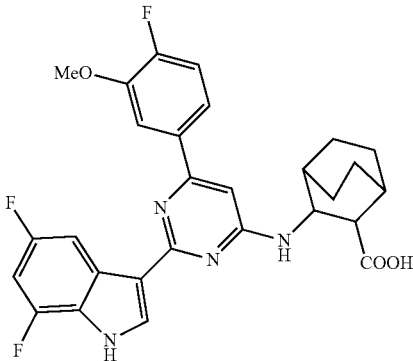 [SMILES: COc1cc(-c2cc(NC3C4CCC(CC4)C3C(=O)O)nc(-c3c[nH]c4c(F)cc(F)cc34)n2)ccc1F]

Step 1: 2,4-dichloro-6-(4-fluoro-3-methoxyphenyl)pyrimidine

To a solution of 2,4,6-trichloropyrimidine (1 g, 5.45 mmol) in tetrahydrofuran (16 mL) were added palladium acetate (125 mg, 0.55 mmol), triphenylphosphine (302 mg, 1.09 mmol), (4-fluoro-3-methoxyphenyl)boronic acid (935 mg, 5.51 mol) and an aqueous sodium carbonate solution (1 M, 16.35 mL, 16.35 mmol). The mixture was heated to 70° C. and stirred for 6 h. To the reaction mixture was added water (50 mL), and the mixture was extracted with EtOAc (50 mL×3). The combined organic layers were washed with saturated brine (50 mL), dried over anhydrous sodium sulfate, and filtered. The filtrate was concentrated in vacuo to dry, and the residue was purified by silica gel column chromatography (PE) to give the title compound as a white solid (840 mg, 56%).

MS (ESI, pos. ion) m/z: 428.2 [M+H]$^+$;

$^1$H NMR (400 MHz, CDCl$_3$) δ (ppm): 7.79 (dd, J=8.1, 1.9 Hz, 1H), 7.65 (s, 1H), 7.60 (ddd, J=8.3, 4.0, 2.1 Hz, 1H), 7.22 (dd, J=10.4, 8.6 Hz, 1H), 4.03 (s, 3H).

Step 2: (+/−)-trans-methyl 3-((2-chloro-6-(4-fluoro-3-methoxyphenyl)pyrimidin-4-yl)amino) bicyclo[2.2.2]octane-2-carboxylate To a solution of (+/−)-trans-methyl 3-aminobicyclo[2.2.2]octane-2-carboxylate (369 mg, 2.01 mmol) and 2,4-dichloro-6-(4-fluoro-3-methoxyphenyl)pyrimidine (500 mg, 1.83 mmol) in DMF (5 mL) was added potassium carbonate (278 mg, 2.01 mmol). The mixture was stirred at rt overnight. To the reaction mixture was added water (50 mL), and the mixture was extracted with EtOAc (50 mL×2). The combined organic layers were washed with saturated brine (80 mL), dried over anhydrous Na$_2$SO$_4$ and filtered. The filtrate was concentrated in vacuo to dry. The residue was purified by silica gel column chromatography (PE/EtOAc (v/v)=20/1) to give the title compound as a white solid (326 mg, 42%).

MS (ESI, pos. ion) m/z: 420.1 [M+H]$^+$;

$^1$H NMR (400 MHz, CDCl$_3$) δ (ppm): 7.72 (d, J=8.1 Hz, 1H), 7.52 (s, 1H), 7.20-7.13 (m, 1H), 6.81 (s, 1H), 5.49 (s, 1H), 4.34 (s, 1H), 4.03 (s, 3H), 3.75 (s, 3H), 3.51 (d, J=5.0 Hz, 1H), 2.41 (s, 1H), 2.10 (s, 1H), 1.88 (s, 1H), 1.70 (m, 6H), 1.55-1.44 (m, 2H).

Step 3: (+/−)-trans-methyl 3-((2-(5,7-difluoro-1-tosyl-1H-indol-3-yl)-6-(4-fluoro-3-methoxyphenyl)pyrimidin-4-yl)amino)bicyclo[2.2.2]octane-2-carboxylate To a sealed tube were added 5,7-difluoro-3-(4,4,5,5-tetramethyl-1,3,2-dioxaborolan-2-yl)-1-tosyl-1H-indole (220 mg, 0.23 mmol), (+/−)-trans-methyl 3-((2-chloro-6-(4-fluoro-3-methoxyphenyl)pyrimidin-4-yl)amino)bicyclo[2.2.2]octane-2-carboxylate (80 mg, 0.19 mmol), potassium phosphate (121 mg, 0.57 mmol) Pd(dtbpf)Cl$_2$ (12 mg, 0.12 mmol), 1,4-dioxane (3 mL) and water (0.2 mL). The mixture was stirred at 100° C. for 10 min under nitrogen protection, and then filtered through a celite pad. The filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (60 mg, 46%).

MS (ESI, pos. ion) m/z: 691.1 [M+H]$^+$;

$^1$H NMR (400 MHz, CDCl$_3$) δ (ppm): 8.75 (s, 1H), 8.39 (d, J=7.7 Hz, 1H), 7.95-7.87 (m, 3H), 7.62 (s, 1H), 7.31 (d, J=8.2 Hz, 2H), 7.25-7.19 (m, 1H), 6.80 (dd, J=20.1, 8.6 Hz, 2H), 4.55 (s, 1H), 4.08 (s, 3H), 3.75 (s, 3H), 2.46 (s, 1H), 2.41 (s, 3H), 2.12 (s, 1H), 2.05-1.97 (m, 2H), 1.78 (m, 8H).

Step 4: (+/−)-trans-3-((2-(5,7-difluoro-1H-indol-3-yl)-6-(4-fluoro-3-methoxyphenyl)pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-6-(4-fluoro-3-methoxyphenyl)pyrimidin-4-yl)amino)bicyclo[2.2.2]octane-2-carboxylate (120 mg, 0.17 mmol) in a mixed solvent of THF and MeOH (v/v=1/1, 4 mL) was added aqueous sodium hydroxide (4 M, 0.43 mL, 1.70 mmol). The mixture was stirred at 30° C. overnight. The reaction mixture was diluted with water (10 mL), and the mixture was acidified with hydrochloric acid (1 M) to pH about 5.5. The resulting mixture was extracted with EtOAc (20 mL×3). The combined organic layers were washed with saturated brine (50 mL), dried over anhydrous sodium sulfate, and filtered. The filtrate was concentrated in vacuo to dry, and the residue was purified by silica gel column chromatography (dichloromethane/methanol (v/v)=10/1) to give the title compound as a yellow solid (26 mg, 29%).

MS (ESI, pos. ion) m/z: 523.2 [M+H]$^+$;

$^1$H NMR (400 MHz, DMSO-d$_6$) δ (ppm): 12.26 (s, 1H), 8.28 (d, J=20.6 Hz, 2H), 7.92 (s, 1H), 7.61 (d, J=33.2 Hz, 2H), 7.42-7.31 (m, 1H), 7.06 (t, J=10.2 Hz, 1H), 6.79 (s, 1H), 4.64 (s, 1H), 4.00 (s, 3H), 1.99 (s, 2H), 1.89-1.46 (m, 8H);

$^{13}$C NMR (101 MHz, DMSO-d$_6$) δ (ppm): 175.97, 163.13, 162.70, 154.28, 151.82, 147.76, 147.66, 135.34, 131.72, 129.11, 122.11, 121.98, 119.33, 116.64, 116.45, 112.16, 103.60, 97.44, 96.93, 56.34, 50.60, 49.76, 28.79, 28.56, 26.01, 24.10, 21.41, 19.45, 19.11.

Example 22: (+/−)-trans-3-((2-(5,7-difluoro-1H-indol-3-yl)-6-(4-fluorophenyl)pyrimidin-4-yl)amino)bicyclo[2.2.2]octane-2-carboxylic Acid

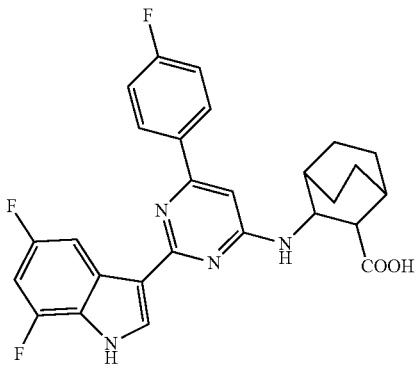 [SMILES: O=C(O)C1C2CCC(CC2)C1Nc1cc(-c2ccc(F)cc2)nc(-c2c[nH]c3c(F)cc(F)cc23)n1]

Step 1: 2,4-dichloro-6-(4-fluorophenyl)pyrimidine

To a solution of 2,4,6-trichloropyrimidine (6.3 mL, 54 mmol) in tetrahydrofuran (35 mL) were added palladium acetate (0.16 g, 0.70 mmol), triphenylphosphine (0.39 g, 1.4 mmol), p-fluorophenylboronic acid (5 g, 36 mmol) and an aqueous sodium carbonate solution (1 mol/L, 71 mL, 71 mmol). The mixture was heated to 60° C. and stirred for 6 h. The reaction mixture was cooled to rt and concentrated to remove the organic solvent. The residue was diluted with H$_2$O (100 mL), and the mixture was extracted with EtOAc (10 mL×3). The combined organic layers were washed with saturated brine (300 mL), dried over anhydrous sodium sulfate, and filtered. The filtrate was concentrated in vacuo dry, and the residue was purified by silica gel column chromatography (PE) to give the title compound as a white solid (8.01 g, 92%).

$^1$H NMR (400 MHz, CDCl$_3$) δ (ppm): 8.10 (dd, J=8.7 Hz, 5.3 Hz, 2H), 7.63 (s, 1H), 7.21 (t, J=8.5 Hz, 2H).

Step 2: (+/−)-trans-methyl 3-((2-chloro-6-(4-fluorophenyl)pyrimidin-4-yl)amino)bicyclo[2.2.2]octane-2-carboxylate To a solution of 2,4-dichloro-6-(4-fluorophenyl)pyrimidine (2 g, 8.2 mmol) and (+/−)-trans-methyl 3-aminobicyclo[2.2.2]octane-2-carboxylate (1.5 g, 8.2 mmol) in N,N-dimethylformamide (10 mL) was added potassium carbonate (1.1 g, 8 mmol). The mixture was stirred at rt overnight. To the reaction mixture was added water (40 mL) to quench the reaction, and the mixture was extracted with EtOAc (40 mL×3). The combined organic layers were washed with saturated brine (50 mL), dried over anhydrous sodium sulfate, and filtered. The filtrate was concentrated in vacuo to dry, and the residue was purified by silica gel column chromatography (n-hexane) to give the title compound as a white solid (1.75 g, 55%).

$^1$H NMR (400 MHz, CDCl$_3$) δ (ppm): 8.01 (dd, J=7.8, 5.7 Hz, 2H), 7.16 (t, J=8.6 Hz, 2H), 6.76 (s, 1H), 5.49 (s, 1H), 4.34 (s, 1H), 3.75 (s, 3H), 2.40 (d, J=4.9 Hz, 1H), 2.08 (s, 1H), 1.87 (d, J=2.6 Hz, 1H), 1.71 (m, 5H), 1.59 (d, J=10.2 Hz, 2H), 1.49 (d, J=11.4 Hz, 1H).

Step 3: (+/−)-trans-methyl 3-((2-(5,7-difluoro-1-tosyl-1H-indol-3-yl)-6-(4-fluorophenyl)pyrimidin-4-yl)amino)bicyclo[2.2.2]octane-2-carboxylate To a mixed solvent of 1,4-dioxane (3 mL) and water (0.2 mL) were added 5,7-difluoro-3-(4,4,5,5-tetramethyl-1,3,2-dioxaborolan-2-yl)-1-tosyl-1H-indole (305 mg, 0.32 mmol), (+/−)-trans-methyl 3-((2-chloro-6-(4-fluorophenyl)pyrimidin-4-yl)amino)bicyclo[2.2.2]octane-2-carboxylate (103 mg, 0.26 mmol), potassium phosphate (168 mg, 0.79 mmol) and Pd(dtbpf)Cl$_2$ (17 mg, 0.03 mmol). The mixture was stirred at 100° C. for 30 min under nitrogen protection, and then filtered through a celite pad. The filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (110 mg, 63%).

$^1$H NMR (400 MHz, CDCl$_3$) δ (ppm): 8.77 (s, 1H), 8.32 (d, J=7.1 Hz, 1H), 8.14 (dd, J=8.5, 5.5 Hz, 2H), 7.90 (d, J=7.9 Hz, 2H), 7.31 (d, J=8.3 Hz, 2H), 7.23 (t, J=8.7 Hz, 2H), 6.82 (dd, J=15.1, 5.8 Hz, 1H), 6.73 (s, 1H), 5.21 (s, 1H), 4.54 (s, 1H), 3.74 (s, 3H), 2.46 (d, J=6.5 Hz, 1H), 2.42 (d, J=6.1 Hz, 3H), 2.12 (s, 1H), 2.01 (s, 1H), 1.92-1.58 (m, 8H).

Step 4: (+/−)-trans-3-((2-(5,7-difluoro-1H-indol-3-yl)-6-(4-fluorophenyl)pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-6-(4-fluorophenyl)pyrimidin-4-yl)amino)bicyclo[2.2.2]octane-2-carboxylate (110 mg, 0.17 mmol) in a mixed solvent of THF and MeOH (v/v=1/1, 3 mL) was added an aqueous sodium hydroxide solution (4 M, 0.43 mL, 1.70 mmol). The mixture was stirred at 30° C. overnight. The reaction mixture was diluted with water (10 mL), and the mixture was acidified with hydrochloric acid (1 M) to pH about 5.5. The resulting mixture was extracted with EtOAc (20 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (dichloromethane/methanol (v/v)=10/1) to give the title compound as a yellow solid (58 mg, 71%).

MS (ESI, pos. ion) m/z: 493.1 [M+H]$^+$;

$^1$H NMR (400 MHz, DMSO-d$_6$) δ (ppm): 12.27 (s, 1H), 8.30 (d, J=2.2 Hz, 1H), 8.27-8.10 (m, 3H), 7.58 (s, 1H), 7.37 (t, J=8.7 Hz, 2H), 7.06 (t, J=10.3 Hz, 1H), 6.76 (s, 1H), 4.66 (s, 1H), 2.00 (s, 2H), 1.85-1.42 (m, 8H);

$^{13}$C NMR (101 MHz, DMSO-d$_6$) δ (ppm): 175.96, 164.51, 163.11, 162.87, 162.78, 159.43, 157.81, 157.74, 156.26, 156.19, 149.63, 149.54, 148.00, 147.90, 134.85, 131.75, 131.16, 129.96, 129.01, 128.96, 122.07, 121.98, 117.45, 116.14, 116.00, 103.30, 97.84, 97.38, 97.25, 97.18, 97.04, 74.03, 50.54, 49.69, 29.48, 28.80, 28.54, 25.99, 25.41, 24.07, 21.42, 19.45.

Example 23: (+/−)-trans-3-((2-(5,7-difluoro-1H-indol-3-yl)-6-(4-(trifluoromethoxy)phenyl)pyrimidin-4-yl)amino)bicyclo[2.2.2]octane-2-carboxylic Acid

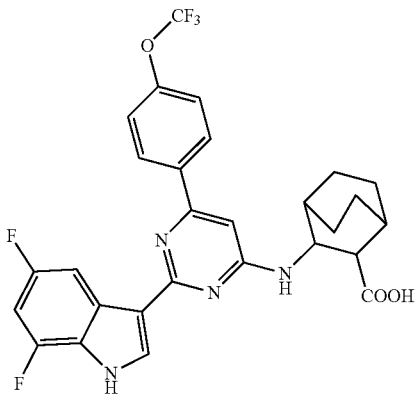 [SMILES: O=C(O)C1C2CCC(CC2)C1Nc1cc(-c2ccc(OC(F)(F)F)cc2)nc(-c2c[nH]c3c(F)cc(F)cc23)n1]

Step 1: 2,4-dichloro-6-(4-(trifluoromethoxy)phenyl)pyrimidine

To a solution of 2,4,6-trichloropyrimidine (500 mg, 2.73 mmol) in tetrahydrofuran (8.5 mL) were added palladium acetate (63 mg, 0.27 mmol), triphenylphosphine (150 mg, 0.55 mmol), (4-(trifluoromethoxy)phenyl)boronic acid (749 mg, 5.51 mol) and an aqueous sodium carbonate solution (1 M, 8.5 mL, 8.5 mmol). The mixture was heated to 70° C. and stirred for 6 h. To the reaction mixture was added water (50 mL) to quench the reaction, and the mixture was extracted with EtOAc (50 mL×3). The combined organic layers were washed with saturated brine (50 mL), dried over anhydrous sodium sulfate, and filtered. The filtrate was concentrated in vacuo to dry, and the residue was purified by silica gel column chromatography (PE) to give the title compound as a white solid (620 mg, 74%).

MS (ESI, pos. ion) m/z: 309.0 [M+H]$^+$;
$^1$H NMR (400 MHz, CDCl$_3$) δ (ppm): 8.15 (d, J=8.8 Hz, 2H), 7.68 (s, 1H), 7.39 (d, J=8.3 Hz, 2H).

Step 2: (+/−)-trans-methyl 3-((2-chloro-6-(4-(trifluoromethoxy)phenyl)pyrimidin-4-yl)amino)bicyclo[2.2.2]octane-2-carboxylate To a solution of (+/−)-trans-methyl 3-aminobicyclo[2.2.2]octane-2-carboxylate (404 mg, 2.21 mmol) and 2,4-dichloro-6-(4-(trifluoromethoxy)phenyl)pyrimidine (620 mg, 2.01 mmol) in DMF (5 mL) was added potassium carbonate (304 mg, 2.21 mmol). The mixture was stirred at rt overnight. To the reaction mixture was added water (40 mL), and the mixture was extracted with EtOAc (50 mL×2). The combined organic layers were washed with saturated brine (80 mL), dried over anhydrous Na$_2$SO$_4$ and filtered. The filtrate was concentrated in vacuo. The residue was purified by silica gel column chromatography (PE/EtOAc (v/v)=20/1) to give the title compound as a white solid (471 mg, 52%).

MS (ESI, pos. ion) m/z: 454.1 [M+H]$^+$;
$^1$H NMR (400 MHz, CDCl$_3$) δ (ppm): 8.05 (d, J=8.4 Hz, 2H), 7.39 (d, J=4.3 Hz, 1H), 7.32 (d, J=8.4 Hz, 2H), 6.81 (s, 1H), 5.50 (s, 1H), 4.35 (s, 1H), 3.76 (s, 3H), 2.40 (d, J=4.0 Hz, 1H), 2.10 (s, 1H), 1.88 (d, J=2.4 Hz, 1H), 1.67 (m, 7H).

Step 3: (+/−)-trans-methyl 3-((2-(5,7-difluoro-1-tosyl-1H-indol-3-yl)-6-(4-(trifluoromethoxy)phenyl)pyrimidin-4-yl)amino)bicyclo[2.2.2]octane-2-carboxylate To a mixed solvent of 1,4-dioxane (3 mL) and water (0.2 mL) were added 5,7-difluoro-3-(4,4,5,5-tetramethyl-1,3,2-dioxaborolan-2-yl)-1-tosyl-1H-indole (258 mg, 0.27 mmol), (+/−)-trans-methyl 3-((2-chloro-6-(4-(trifluoromethoxy)phenyl)pyrimidin-4-yl)amino)bicyclo[2.2.2]octane-2-carboxylate (102 mg, 0.22 mmol), potassium phosphate (142 mg, 0.67 mmol) and Pd(dtbpf)Cl$_2$ (14 mg, 0.02 mmol). The mixture was stirred at 100° C. for 30 min under nitrogen protection, and then filtered through a celite pad. The filter cake was washed with ethyl acetate (50 mL). The filtrate was washed with saturated brine (50 mL), dried over anhydrous sodium sulfate, and concentrated in vacuo to dry. The residue was purified by silica gel column chromatography (n-hexane/EtOAc (v/v)=5/1) to give the title compound as a yellow solid (135 mg, 83%).

MS (ESI, pos. ion) m/z: 727.1 [M+H]$^+$;
$^1$H NMR (400 MHz, CDCl$_3$) δ (ppm): 8.77 (s, 1H), 8.32 (d, J=9.3 Hz, 1H), 8.17 (d, J=8.7 Hz, 2H), 7.90 (d, J=8.0 Hz, 2H), 7.39 (d, J=8.2 Hz, 2H), 7.31 (d, J=8.3 Hz, 2H), 6.80 (dd, J=22.1, 13.0 Hz, 2H), 5.24 (s, 1H), 4.55 (s, 1H), 3.75 (s, 3H), 2.46 (s, 1H), 2.42 (s, 3H), 2.12 (s, 1H), 2.01 (s, 1H), 1.95-1.57 (m, 8H).

Step 4: (+/−)-trans-3-((2-(5,7-difluoro-1H-indol-3-yl)-6-(4-(trifluoromethoxy)phenyl)pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-6-(4-(trifluoromethoxy)phenyl)pyrimidin-4-yl)amino)bicyclo[2.2.2]octane-2-carboxylate (132 mg, 0.19 mmol) in a mixed solvent of THF and MeOH (v/v=1/1, 4 mL) was added an aqueous sodium hydroxide solution (4 M, 0.48 mL, 1.90 mmol). The mixture was stirred at 30° C. overnight. The reaction mixture was diluted with water (10 mL), and the mixture was acidified with hydrochloric acid (1 M) to pH about 5.5. The resulting mixture was extracted with EtOAc (20 mL×3). The combined organic layers were washed with saturated brine (50 mL), dried over anhydrous sodium sulfate, and filtered. The filtrate was concentrated in vacuo to dry, and the residue was purified by silica gel column chromatography (dichloromethane/methanol (v/v)=10/1) to give the title compound as a yellow solid (72 mg, 69%).

MS (ESI, pos. ion) m/z: 559.6 [M+H]$^+$;
$^1$H NMR (400 MHz, DMSO-d$_6$) δ (ppm): 12.27 (s, 1H), 8.31 (s, 1H), 8.22 (s, 3H), 7.63 (s, 1H), 7.53 (d, J=8.1 Hz, 2H), 7.06 (t, J=10.2 Hz, 1H), 6.79 (s, 1H), 4.66 (s, 1H), 2.00 (s, 2H), 1.91-1.46 (m, 8H);
$^{13}$C NMR (101 MHz, DMSO-d$_6$) δ (ppm): 175.98, 163.12, 162.89, 162.83, 159.11, 157.77, 156.28, 156.21, 149.86, 149.64, 149.54, 148.01, 147.91, 137.63, 131.81, 128.81, 122.08, 121.99, 121.59, 121.41, 119.71, 117.42, 103.46, 98.32, 97.41, 97.28, 97.21, 97.07, 67.48, 50.58, 49.68, 36.26, 31.24, 29.48, 28.80, 28.52, 26.00, 25.58, 24.06, 21.42, 19.46.

Example 24: (+/−)-trans-3-((2-(5,7-difluoro-1H-indol-3-yl)-6-(phenylethynyl)pyrimidin-4-yl)amino)bicyclo[2.2.2]octane-2-carboxylic Acid

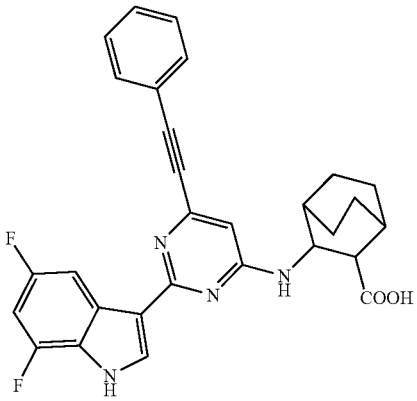 [SMILES: O=C(O)C1C2CCC(CC2)C1Nc1cc(C#Cc2ccccc2)nc(-c2c[nH]c3c(F)cc(F)cc23)n1]

Step 1: 2,4-dichloro-6-(phenylethynyl)pyrimidine

To a solution of 2,4,6-trichloropyrimidine (101 mg, 0.55 mmol) in toluene (3 mL) were added tributyl(2-phenylethynyl)stannane (259 mg, 0.66 mmol), arsenic triphenyl (67 mg, 0.22 mmol) and Pd(PPh$_3$)Cl$_2$ (40 mg, 0.06 mmol). The mixture was heated to 80° C. and stirred for 6 h. The mixture was concentrated in vacuo to dry, and the residue was purified by silica gel column chromatography (PE) to give the title compound as a white solid (129 mg, 94%).

MS (ESI, pos. ion) m/z: 249.3 [M+H]$^+$;
$^1$H NMR (400 MHz, CDCl$_3$) δ (ppm): 8.40 (t, J=7.9 Hz, 2H), 8.29 (d, J=8.7 Hz, 1H), 7.88-7.74 (m, 2H).

Step 2: (+/−)-trans-methyl 3-((2-chloro-6-(phenylethynyl)pyrimidin-4-yl)amino)bicyclo[2.2.2]octane-2-carboxylate To a solution of (+/−)-trans-methyl 3-aminobicyclo[2.2.2]octane-2-carboxylate (405 mg, 2.21 mmol) and 2,4-dichloro-6-(phenylethynyl)pyrimidine (500 mg, 2.01 mmol) in DMF (5 mL) was added potassium carbonate (306 mg, 2.21 mmol). The mixture was stirred at rt overnight. To the reaction mixture was added water (40 mL), and the mixture was extracted with EtOAc (40 mL×3). The combined organic layers were washed with saturated brine (50 mL), dried over anhydrous sodium sulfate, and filtered. The filtrate was concentrated in vacuo to dry, and the residue was purified by silica gel column chromatography (PE/EtOAc (v/v)=5/1) to give the title compound as a white solid (470 mg, 59%).

MS (ESI, pos. ion) m/z: 396.1 [M+H]$^+$;
$^1$H NMR (400 MHz, CDCl$_3$) δ (ppm): 7.59 (d, J=6.8 Hz, 2H), 7.41-7.37 (m, 3H), 6.55 (s, 1H), 5.50 (s, 1H), 3.76 (s, 3H), 2.36 (d, J=5.3 Hz, 1H), 1.84 (s, 1H), 1.70-1.42 (m, 10H).

Step 3: (+/−)-trans-methyl 3-((2-(5,7-difluoro-1-tosyl-1H-indol-3-yl)-6-(phenylethynyl)pyrimidin-4-yl)amino)bicyclo[2.2.2]octane-2-carboxylate To a sealed tube were added 5,7-difluoro-3-(4,4,5,5-tetramethyl-1,3,2-dioxaborolan-2-yl)-1-tosyl-1H-indole (336 mg, 0.39 mmol), (+/−)-trans-methyl 3-((2-chloro-6-(phenylethynyl)pyrimidin-4-yl)amino)bicyclo[2.2.2]octane-2-carboxylate (128 mg, 0.32 mmol), potassium phosphate (205 mg, 0.95 mmol), Pd(dtbpf)Cl$_2$ (21 mg, 0.03 mmol), dioxane (3 mL) and water (0.2 mL). The mixture was stirred at 100° C. for 10 min under nitrogen protection, and then filtered through a celite pad. The filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (200 mg, 93%).

MS (ESI, pos. ion) m/z: 667.2 [M+H]$^+$;
$^1$H NMR (400 MHz, CDCl$_3$) δ (ppm): 8.71 (s, 1H), 8.23 (dd, J=9.2, 2.1 Hz, 1H), 7.88 (d, J=7.9 Hz, 2H), 7.82 (d, J=7.8 Hz, 1H), 7.71-7.65 (m, 1H), 7.61 (d, J=8.0 Hz, 2H), 7.31 (s, 1H), 6.80-6.74 (m, 1H), 6.43 (s, 1H), 5.21 (s, 1H), 4.47 (s, 1H), 3.73 (s, 3H), 2.45 (d, J=5.1 Hz, 1H), 2.41 (s, 3H), 2.10 (s, 1H), 1.99 (s, 1H), 1.76 (dd, J=34.9, 19.5 Hz, 8H).

Step 4: (+/−)-trans-3-((2-(5,7-difluoro-1H-indol-3-yl)-6-(2-phenylethynyl)pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-6-(phenylethynyl)pyrimidin-4-yl)amino)bicyclo[2.2.2]octane-2-carboxylate (250 mg, 0.38 mmol) in a mixed solvent of THF and MeOH (v/v=1/1, 4 mL) was added an aqueous sodium hydroxide solution (4 M, 0.95 mL, 3.80 mmol). The mixture was stirred at 30° C. overnight. The reaction mixture was diluted with water (10 mL), and the mixture was acidified with hydrochloric acid (1 M) to pH about 5.5. The resulting mixture was extracted with EtOAc (20 mL×3). The combined organic layers were washed with saturated brine (50 mL), dried over anhydrous sodium sulfate, and filtered. The filtrate was concentrated in vacuo to dry, and the residue was purified by silica gel column chromatography (dichloromethane/methanol (v/v)=10/1) to give the title compound as a yellow solid (36 mg, 19%).

MS (ESI, pos. ion) m/z: 499.1 [M+H]$^+$;
$^1$H NMR (400 MHz, DMSO-d$_6$) δ (ppm): 12.27 (s, 1H), 8.20 (s, 1H), 8.14 (d, J=9.7 Hz, 1H), 7.67 (d, J=20.0 Hz, 3H), 7.49 (d, J=5.7 Hz, 2H), 7.05 (t, J=10.3 Hz, 1H), 6.50 (s, 1H), 5.75 (s, 1H), 4.63 (s, 1H), 1.98 (d, J=10.5 Hz, 2H), 1.83-1.38 (m, 8H).

Example 25: (+/−)-trans-3-((2-(7-(dimethylamino)-1H-indol-3-yl)-5-fluoropyrimidin-4-yl)amino)bicyclo[2.2.2]octane-2-carboxylic Acid

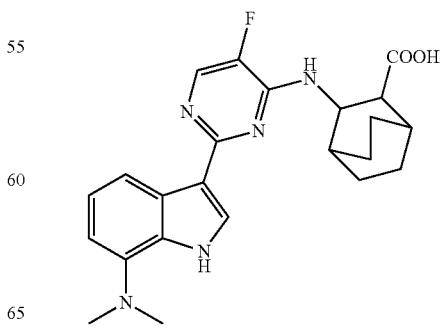

Step 1: (+/−)-trans-methyl 3-((2-chloro-5-fluoropyrimidin-4-yl)amino)bicyclo[2.2.2]octane-2-carboxylate (+/−)-trans-Methyl 3-aminobicyclo[2.2.2]octane-2-carboxylate (1.83 g, 9.99 mmol), 2,4-dichloro-5-fluoropyrimidine (2.5 g, 15 mmol) and DIPEA (8.7 mL, 50 mmol) were mixed in tetrahydrofuran (20 mL). The mixture was stirred at rt overnight. The reaction was quenched with $H_2O$ (100 mL), and the mixture was extracted with EtOAc (50 mL×2). The combined organic layers were dried over anhydrous sodium sulfate, and filtered. The filtrate was concentrated in vacuo, and the residue was purified by silica gel column chromatography (PE/EtOAc (v/v)=4/1) to give the title compound as a white solid (3.13 g, 95%).

MS (ESI, pos. ion) m/z: 314.10 [M+H]$^+$;
$^1$H NMR (600 MHz, CDCl$_3$) δ (ppm): 7.83 (d, J=2.8 Hz, 1H), 5.40 (s, 1H), 4.45 (dd, J=7.9, 3.6 Hz, 1H), 3.73 (s, 3H), 2.40 (d, J=5.9 Hz, 1H), 1.97 (d, J=2.5 Hz, 1H), 1.86 (d, J=2.6 Hz, 1H), 1.77 (dd, J=17.7, 6.5 Hz, 1H), 1.72-1.56 (m, 6H), 1.57-1.49 (m, 1H), 1.41 (t, J=11.7 Hz, 1H).

Step 2: 3-bromo-7-nitro-1H-indole

To a solution of 7-nitro-indole (5.00 g, 30.84 mmol) in DMF (30 mL) was added bromine (1.6 mL, 33 mmol), and the mixture was stirred at rt for 8 h. Then the reaction mixture was quenched with a saturated aqueous sodium thiosulfate solution (100 mL), and the mixture was extracted with EtOAc (150 mL×3). The combined organic layers were washed with saturated brine (100 mL×3), dried over anhydrous sodium sulfate, and filtered. The filtrate was concentrated in vacuo, and the residue was purified by silica gel column chromatography (PE/EtOAc (v/v)=10/1) to give the title compound as yellow powder (7.21 g, 97%).

MS (ESI, pos. ion) m/z: 242.95 [M+H]$^+$.

Step 3: 3-bromo-7-nitro-1-tosyl-1H-indole

To a 0° C. solution of 3-bromo-7-nitro-1H-indole (769 mg, 3.19 mmol) in DMF (8 mL) was added NaH (153 mg, 3.83 mmol). The mixture was stirred at 0° C. for 30 min, then TsCl (729 mg, 3.82 mmol) was added. The reaction mixture was warmed to rt and stirred overnight. The reaction was quenched with diluted hydrochloric acid (1 M, 20 mL), and the mixture was partitioned. The aqueous layer was extracted with EtOAc (20 mL×2). The combined organic layers were washed with saturated brine (50 mL×3), dried over anhydrous sodium sulfate, and filtered. The filtrate was concentrated in vacuo, and the residue was purified by silica gel column chromatography (PE/EtOAc (v/v)=40/1-5/1) to give the title compound as a yellow solid (321 mg, 26%).

MS (ESI, pos. ion) m/z: 417.05 [M+Na]$^+$;
$^1$H NMR (400 MHz, DMSO-d$_6$) δ (ppm): 8.46 (d, J=1.6 Hz, 1H), 7.95 (s, 3H), 7.87 (d, J=8.2 Hz, 2H), 7.48 (d, J=7.9 Hz, 2H), 2.40 (s, 3H).

Step 4: 3-bromo-1-tosyl-1H-indol-7-amine

To a solution of 3-bromo-7-nitro-1-tosyl-1H-indole (2.00 g, 5.06 mmol) in a mixed solvent of MeOH (15 mL), THF (15 mL) and $H_2O$ (2 mL) was added ammonium chloride (296 mg, 5.06 mmol), and the mixture was heated to 85° C. and stirred vigorously, then iron powder (2.83 g, 50.6 mmol) was added. The mixture was stirred for further 4 h at 85° C., then the reaction was stopped. The reaction mixture was filtered, and the filter cake was washed with ethyl acetate. The filtrate was added into a saturated aqueous sodium carbonate solution (40 mL), and the mixture was extrated with ethyl acetate (40 mL×3). The combined organic layers were washed with saturated brine (100 mL), dried over anhydrous sodium sulfate, and filtered. The filtrated was concentrated in vacuo, and the residue was purified by silica gel column chromatography (PE/EtOAc (v/v)=30/1) to give the title compound as a light yellow solid (1.76 g, 95%).

Step 5: 3-bromo-N-methyl-1-tosyl-1H-indol-7-amine

To a solution of 3-bromo-1-tosyl-1H-indol-7-amine (1.76 g, 4.81 mmol) in CCl$_4$ (15 mL) were added iodomethane (2.73 g, 19.23 mmol), tetra-n-butylammonium iodide (184 mg, 0.48 mmol) and a solution of KOH (674 mg, 12.0 mmol) in water (1 mL). The mixture was stirred for 7 h at rt, then the reaction was stopped. The reaction mixture was added into a saturated aqueous sodium carbonate solution (50 mL), and the mixture was extrated with ethyl acetate (100 mL×3). The combined organic layers were washed with saturated brine (150 mL), dried over anhydrous sodium sulfate, and filtered. The filtrated was concentrated in vacuo, and the residue was purified by silica gel column chromatography (PE/EtOAc (v/v)=20/1) to give the title compound as a light yellow solid (475 mg, 26%).

MS (ESI, pos. ion) m/z: 381.0 [M+H]$^+$;
$^1$H NMR (400 MHz, CDCl$_3$) δ (ppm): 7.68-7.60 (m, 3H), 7.21 (dd, J=16.0, 8.1 Hz, 3H), 6.80 (dd, J=7.7, 0.7 Hz, 1H), 6.60 (d, J=8.0 Hz, 1H), 6.46 (s, 1H), 2.98 (s, 3H), 2.33 (s, 3H).

Step 6: 3-bromo-N,N-dimethyl-1-tosyl-1H-indol-7-amine

To a solution of 3-bromo-N-methyl-1-tosyl-1H-indol-7-amine (434 mg, 1.14 mmol) in methanol (15 mL) were added NaBH$_3$CN (69 mg, 1.14 mmol), zinc chloride (85 mg, 0.57 mmol) and 36% formaldehyde solution (176 mg, 2.12 mmol). The reaction mixture was stirred overnight at rt, then the reaction mixture was added into a saturated aqueous sodium carbonate solution (50 mL), and the mixture was extracted with ethyl acetate (100 mL×3). The combined organic layers were washed with saturated brine (150 mL), dried over anhydrous sodium sulfate, and filtered. The filtrated was concentrated in vacuo, and the residue was purified by silica gel column chromatography (PE/EtOAc (v/v)=3/1) to give the title compound as a light yellow solid (390 mg, 86%).

MS (ESI, pos. ion) m/z: 394.20 [M+H]$^+$;
$^1$H NMR (600 MHz, CDCl$_3$) δ (ppm): 7.94 (s, 1H), 7.61 (d, J=8.4 Hz, 2H), 7.29 (dd, J=8.0, 1.4 Hz, 1H), 7.28-7.22 (m, 3H), 7.12 (dd, J=7.5, 0.9 Hz, 1H), 2.36 (s, 6H).

Step 7) N,N-dimethyl-3-(4,4,5,5-tetramethyl-1,3,2-dioxaborolan-2-yl)-1-tosyl-1H-indol-7-amine 3-Bromo-N,N-dimethyl-1-tosyl-1H-indol-7-amine (310 mg, 0.79 mmol), Pd(dppf)Cl$_2$ (59 mg, 0.08 mmol), potassium acetate (232 mg, 2.37 mmol) and bis(pinacolato)diboron (240 mg, 0.95 mmol) were mixed in DME (8 mL). The air in the mixture was removed by exchanging with nitrogen, then the mixture in the tube was sealed, and reacted for 2 h at 105° C. under a microwave condition (10 bar). After the reaction was completed, the mixture was filtered to remove the solid impurities. The filtrate was concentrated to remove the solvent, and the residue was purified by silica gel column chromatography (PE/EtOAc (v/v)=20/1) to give the title compound as a yellow solid (275 mg, 79%).
MS (ESI, pos. ion) m/z: 441.25 [M+H]⁺.

Step 8: (+/−)-trans-methyl 3-((2-(7-(dimethyl-amino)-1-tosyl-1H-indol-3-yl)-5-fluoropyrimidin-4-yl)amino)bicyclo[2.2.2]octane-2-carboxylate To 2-methyltetrahydrofuran (8 mL) were added N,N-dimethyl-3-(4,4,5,5-tetramethyl-1,3,2-dioxaborolan-2-yl)-1-tosyl-1H-indol-7-amine (340 mg, 0.77 mmol), potassium phosphate (522 mg, 2.32 mmol), Pd$_2$(dba)$_3$ (80 mg, 0.08 mmol), (+/−)-trans-methyl 3-((2-chloro-5-fluoropyrimidin-4-yl)amino)bicyclo[2.2.2]octane-2-carboxylate (161 mg, 0.46 mmol) and X-phos (42 mg, 0.08 mmol), then H$_2$O (1 mL) was added to the mixture. The air in the mixture was removed by purging nitrogen, then the mixture was stirred at 110° C. for 3 h under a sealed-tube condition. The mixture was filtered to remove the solid impurities, and the filtrate was concentrated to remove the solvent. The residue was purified by silica gel column chromatography (PE/EtOAc (v/v)=20/1~10/1) to give the title compound as a white solid (174 mg, 38%).
MS (ESI, pos. ion) m/z: 592.40 [M+H]⁺.

Step 9: (+/−)-trans-3-((2-(7-(dimethylamino)-1H-indol-3-yl)-5-fluoropyrimidin-4-yl)amino)bicyclo[2.2.2]octane-2-carboxylic Acid To a solution of (+/−)-trans-methyl 3-((2-(7-(dimethyl-amino)-1-tosyl-1H-indol-3-yl)-5-fluoropyrimidin-4-yl)amino)bicyclo[2.2.2]octane-2-carboxylate (174 mg, 0.29 mmol) in THF/MeOH (v/v=1/1, 10 mL) was added a solution of NaOH (120 mg, 2.94 mmol) in water (1 mL). The mixture was stirred at 65° C. overnight. The mixture was acidified with hydrochloric acid (1 M) to pH about 6, and the mixture was concentrated in vacuo. The residue was purified by silica gel column chromatography (PE/EtOAc (v/v)=2/1~1/2) to give the title compound as a white solid (31 mg, 25%).
MS (ESI, pos. ion) m/z: 424.30 [M+H]⁺;
HRMS (ESI, pos. ion) m/z: 424.2119. [M+H]⁺, (C$_{23}$H$_{26}$FN$_5$O$_{52}$) [M+H]⁺ theoretical value: 424.2149;
¹H NMR (600 MHz, CD$_3$OD) δ (ppm): 8.29 (d, J=7.9 Hz, 1H), 8.00 (s, 1H), 7.96 (d, J=3.9 Hz, 1H), 7.08 (t, J=7.7 Hz, 1H), 6.83 (d, J=7.3 Hz, 1H), 3.78 (s, 1H), 2.88 (s, 6H), 2.78 (d, J=5.7 Hz, 1H), 2.11 (d, J=13.2 Hz, 2H), 1.85 (d, J=7.2 Hz, 2H), 1.78-1.64 (m, 3H), 1.33 (d, J=32.1 Hz, 3H).

Example 26: (+/−)-trans-3-((5-fluoro-2-(7-nitro-1H-indol-3-yl)pyrimidin-4-yl)amino)bicyclo[2.2.2]oc-tane-2-carboxylic Acid

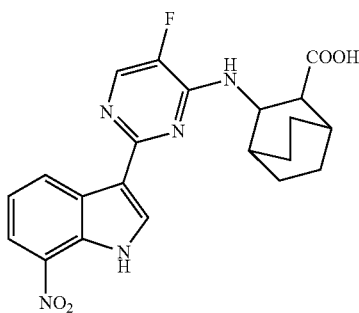 [SMILES: O=C(O)C1C2CCC(CC2)C1Nc1nc(-c2c[nH]c3c([N+](=O)[O-])cccc23)ncc1F]

Step 1: 7-nitro-3-(4,4,5,5-tetramethyl-1,3,2-dioxa-borolan-2-yl)-1-tosyl-1H-indole 3-Bromo-7-nitro-1-tosyl-1H-indole (321 mg, 0.78 mmol), Pd(dppf)Cl$_2$ (58 mg, 0.08 mmol), potassium acetate (228 mg, 2.33 mmol) and bis(pinacolato)diboron (295 mg, 1.17 mmol) were mixed in DME (5 mL). The air in the mixture was removed by purging nitrogen, then the mixture in the tube was sealed, and reacted for 2 h at 105° C. under a microwave condition (5 bar). After the reaction was completed, the mixture was filtered to remove the solid impurities. The filtrate was concentrated to remove the solvent, and the residue was purified by silica gel column chromatography (PE/EtOAc (v/v)=4/1) to give the title compound as a yellow solid (330 mg, 92%).
MS (ESI, pos. ion) m/z: 461.4 [M+H]⁺.

Step 2: (+/−)-trans-methyl 3-((5-fluoro-2-(7-nitro-1-tosyl-1H-indol-3-yl)pyrimidin-4-yl)amino)bicyclo[2.2.2]octane-2-carboxylate To 2-methyltetrahydrofuran (8 mL) were added 7-nitro-3-(4,4,5,5-tetramethyl-1,3,2-dioxaborolan-2-yl)-1-tosyl-1H-indole (350 mg, 0.79 mmol), potassium phosphate (484 mg, 2.37 mmol), Pd$_2$(dba)$_3$ (71 mg, 0.08 mmol), (+/−)-trans-methyl 3-((2-chloro-5-fluoropyrimidin-4-yl)amino)bicyclo[2.2.2]octane-2-carboxylate (262 mg, 0.87 mmol) and X-phos (36 mg, 0.08 mmol), then H$_2$O (1 mL) was added to the mixture. The air in the mixture was removed by purging nitrogen, then the mixture was stirred at 110° C. for 3 h under a sealed-tube condition. After the reaction, the mixture was filtered to remove the solid impurities. The solvent of the filtrate was removed, and the residue was purified by silica gel column chromatography (PE/EtOAc (v/v)=10/1~5/1) to give the title compound as a yellow solid (197 mg, 42%).
MS (ESI, pos. ion) m/z: 594.4[M+H]⁺;
¹H NMR (400 MHz, CDCl$_3$) δ (ppm): 9.01 (d, J=8.0 Hz, 1H), 8.59 (s, 1H), 8.13 (d, J=2.6 Hz, 1H), 7.99 (d, J=8.3 Hz, 2H), 7.73 (d, J=7.1 Hz, 1H), 7.45-7.36 (m, 3H), 5.23 (d, J=6.4 Hz, 1H), 4.82 (s, 1H), 3.69 (s, 3H), 2.46 (s, 3H), 2.12-2.06 (m, 3H), 1.76-1.68 (m, 8H).

Step 3: (+/−)-trans-3-((5-fluoro-2-(7-nitro-1H-indol-3-yl)pyrimidin-4-yl)amino) bicyclo[2.2.2]octane-2-carboxylic Acid To a solution of (+/−)-trans-methyl 3-((5-fluoro-2-(7-nitro-1-tosyl-1H-indol-3-yl)pyrimidin-4-yl)amino)bicyclo[2.2.2]octane-2-carboxylate (100 mg, 0.17 mmol) in a mixed solvent THF/MeOH/H$_2$O (v/v/v=3/3/1, 7 mL) was added sodium hydroxide (67 mg, 1.69 mmol). The mixture was stirred at rt overnight. The reaction mixture was acidified with hydrochloric acid (1 M) to pH about 6. The resulting mixture was extracted with EtOAc (20 mL×3). The combined organic layers were washed with saturated brine (50 mL), dried over anhydrous sodium sulfate, and filtered. The filtrate was concentrated in vacuo and the residue was purified by silica gel column chromatography (PE/EtOAc (v/v)=2/1) to give the title compound as a yellow solid (55 mg, 77%).
MS (ESI, pos. ion) m/z: 426.20 [M+H]⁺;
HRMS (ESI, pos. ion) m/z: 426.1572 [M+H]⁺; (C$_{24}$H$_{26}$FN$_5$O$_{52}$) [M+H]⁺ theoretical value: 426.1578;
¹H NMR (600 MHz, DMSO-d$_6$) δ (ppm): 12.20 (s, 1H), 9.03 (d, J=7.4 Hz, 1H), 8.17 (d, J=8.2 Hz, 1H), 8.10 (s, 1H), 7.76-7.65 (m, 1H), 7.62 (d, J=5.3 Hz, 1H), 7.36 (t, J=7.6 Hz, 1H), 4.70 (s, 1H), 4.22 (t, J=6.0 Hz, 1H), 2.86 (d, J=4.1 Hz, 1H), 1.99 (d, J=31.0 Hz, 2H), 1.75 (t, J=19.9 Hz, 3H), 1.68-1.62 (m, 2H), 1.59-1.48 (m, 3H).

Example 27: (+/−)-cis-N-(3-((2-(5,7-difluoro-1H-indol-3-yl)-6-phenylpyrimidin-4-yl)amino)cyclohexyl)pyrrolidine-1-carboxamide

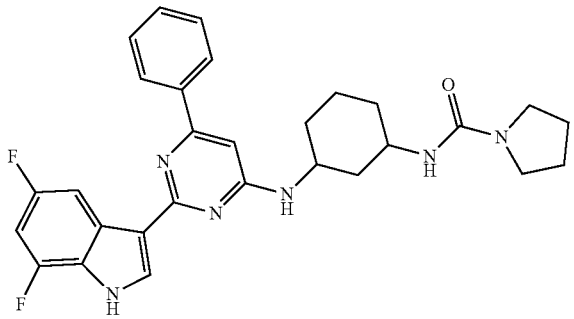 [SMILES: O=C(NC1CCCC(Nc2cc(-c3ccccc3)nc(-c3c[nH]c4c(F)cc(F)cc34)n2)C1)N1CCCC1]

Step 1: (+/−)-cis-3-((tert-butoxycarbonyl)amino)-1-benzoxyformamidocyclohexane

To a solution of (+/−)-cis-3-((tert-butoxycarbonyl)amino)cyclohexanecarboxylic acid (5.01 g, 20.6 mmol) in toluene (80 mL) were added triethylamino (4.70 mL, 33.4 mmol) and diphenylphosphoryl azide (5.45 mL, 24.8 mmol). The mixture was stirred at rt for 3 h under nitrogen protection, then benzyl alcohol (4.32 mL, 41.3 mmol) was added dropwise to the reaction mixture. After the addition, the mixture was heated to 100° C. and stirred overnight under nitrogen protection. After the reaction mixture was cooled, ethyl acetate (60 mL) was added into the mixture, and the resulting mixture was partitioned. The organic layer was washed with water (100 mL) and a saturated aqueous sodium chloride solution (100 mL) in turn, dried over anhydrous sodium sulfate, and filtered. The filtrate was concentrated in vacuo to give a humid light yellow solid, and then the solid was mixed with petroleum ether (80 mL). The mixture was stirred at rt for 30 min, and then filtered. The filter cake was dried in vacuo to give the title compound as a light yellow solid (6.82 g, 95%).

MS (ESI, pos. ion) m/z: 371.1[M+Na]$^+$;
$^1$H NMR (400 MHz, CDCl$_3$) δ (ppm): 7.37 (m, 5H), 5.10 (s, 1H), 4.71 (s, 1H), 4.44 (s, 1H), 3.53 (d, J=10.5 Hz, 2H), 2.30 (d, J=11.4 Hz, 1H), 1.99 (s, 2H), 1.86 (s, 1H), 1.78 (dd, J=10.8, 3.1 Hz, 1H), 1.45 (s, 9H). 0.99 (m, 3H).

Step 2: (+/−)-cis-N-(tert-butoxycarbonyl)-1,3-cyclohexanediamine

To a solution of (+/−)-cis-3-((tert-butoxycarbonyl)amino)-1-benzoxy formamidocyclohexane (3.55 g, 10.2 mmol) in methanol (20 mL) was added Pd/C (weight content 10%, 1.72 g), and the mixture was stirred at rt overnight in a hydrogen atmosphere at a pressure of 2 MPa. The reaction mixture was filtered through a celite pad, and the filter cake was washed with ethanol (20 mL). The filtrate was concentrated in vacuo to give the title compound as a white solid (3.16 g), which was used directly in the next step without further purification.

MS (ESI, pos. ion) m/z: 215.2 [M+H]$^+$.

Step 3: 2,4-dichloro-6-phenylpyrimidine

To a solution of 2,4,6-trichloropyrimidine (0.29 mL, 2.5 mmol) in tetrahydrofuran (5 mL) were added palladium acetate (8 mg, 0.035 mmol), triphenylphosphine (18 mg, 0.065 mmol), phenylboronic acid (0.20 g, 1.6 mmol) and an aqueous sodium carbonate solution (1 M, 3.3 mL, 3.3 mmol). The mixture was heated to 60° C. and stirred for 6 h. The reaction mixture was cooled to rt and concentrated in vacuo to remove the organic solvent. To the residue was added H$_2$O (10 mL), and the mixture was extracted with EtOAc (10 mL×3). The combined organic layers were washed with saturated brine (10 mL), dried over anhydrous sodium sulfate, and filtered. The filtrate was concentrated in vacuo to dry, and the residue was purified by silica gel column chromatography (PE) to give the title compound as a white solid (0.225 g, 61%).

MS (ESI, pos. ion) m/z: 224.9 [M+H]$^+$;
$^1$H NMR (400 MHz, CDCl$_3$) δ (ppm): 8.15-8.05 (m, 2H), 7.70 (s, 1H), 7.63-7.50 (m, 3H).

Step 4: (+/−)-cis-tert-butyl (3-((2-chloro-6-phenylpyrimidin-4-yl)amino)cyclohexyl)carbamate To a solution of 2,4-dichloro-6-phenylpyrimidine (760 mg, 3.38 mmol) and (+/−)-cis-N-(tert-butoxycarbonyl)-1,3-cyclohexanediamine (1.84 g, 10.0 mmol) in N,N-dimethylformamide (12 mL) was added potassium carbonate (1.41 g, 10.2 mmol). The mixture was stirred at 50° C. overnight. To the reaction mixture was added water (30 mL), and the mixture was extracted with EtOAc (30 mL×3). The combined organic layers were washed with a saturated aqueous sodium chloride solution (60 mL), dried over anhydrous sodium sulfate, and filtered. The filtrate was concentrated in vacuo, and the residue was purified by silica gel column chromatography (PE/EtOAc (v/v)=10/1-1/3) to give the title compound as a white solid (588 mg, 43%).

$^1$H NMR (400 MHz, CDCl$_3$) δ (ppm): 7.97 (d, J=3.7 Hz, 2H), 7.48 (m, 3H), 6.59 (s, 1H), 5.15 (s, 1H), 4.47 (s, 1H), 3.60 (s, 2H), 2.43 (d, J=11.8 Hz, 1H), 2.10 (d, J=14.5 Hz, 2H), 1.88 (d, J=13.9 Hz, 1H), 1.46 (s, 9H), 1.10 (m, 3H).

Step 5: (+/−)-cis-tert-butyl (3-((2-(5,7-difluoro-1-tosyl-1H-indol-3-yl)-6-phenylpyrimidin-4-yl)amino)cyclohexyl)carbamate To a mixed solvent of 1,4-dioxane (5 mL) and water (0.5 mL) were added 5,7-difluoro-3-(4,4,5,5-tetramethyl-1,3,2-dioxaborolan-2-yl)-1-tosyl-1H-indole (670 mg, 0.77 mmol), (+/−)-cis-tert-butyl (3-((2-chloro-6-phenylpyrimidin-4-yl)amino)cyclohexyl)carbamate (260 mg, 0.65 mmol), potassium phosphate (413 mg, 1.95 mmol) and Pd(dtbpf)Cl$_2$ (45 mg, 0.07 mmol). The mixture was stirred at 100° C. for 30 min under nitrogen protection, and then filtered through a celite pad. The filter cake was washed with ethyl acetate (40 mL). The filtrate was washed with saturated brine (50 mL), dried over anhydrous sodium sulfate and filtered. The filtrate was concentrated in vacuo and the residue was purified by silica gel column chromatography (n-hexane/EtOAc (v/v)= 10/1~2/1) to give the title compound as brown oil (374 mg, 86%).

MS (ESI, pos. ion) m/z: 674.8 [M+H]$^+$;
$^1$H NMR (400 MHz, CDCl$_3$) δ (ppm): 8.75 (s, 1H), 8.30 (dd, J=9.1, 2.0 Hz, 1H), 8.10 (d, J=6.7 Hz, 2H), 7.88 (d, J=7.9 Hz, 2H), 7.53 (m, 3H), 7.29 (d, J=7.7 Hz, 2H), 6.80

(m, 1H), 6.62 (s, 1H), 5.67 (s, 1H), 5.08 (s, 1H), 4.59 (d, J=7.9 Hz, 1H), 3.90 (s, 1H), 3.64 (s, 1H), 2.48 (d, J=11.7 Hz, 1H), 2.39 (s, 3H), 2.07 (d, J=14.0 Hz, 1H), 1.99 (s, 2H), 1.91 (d, J=14.1 Hz, 1H), 1.55 (d, J=13.4 Hz, 1H), 1.46 (s, 9H).

Step 6: (+/−)-cis-N$^1$-(2-(5,7-difluoro-1-tosyl-1H-indol-3-yl)-6-phenylpyrimidin-4-yl)cyclohexane-1,3-diamine The suspension of (+/−)-cis-tert-butyl (3-((2-(5,7-difluoro-1-tosyl-1H-indol-3-yl)-6-phenylpyrimidin-4-yl)amino)cyclohexyl)carbamate (426 mg, 0.63 mmol) in a solution of hydrochloric acid in 1,4-dioxane (3.5 M, 5 mL) was stirred at rt overnight. The reaction mixture was concentrated in vacuo, and to the residue was added a saturated aqueous sodium bicarbonate solution (20 mL). The mixture was extracted with EtOAc (20 mL×3). The combined organic layers were washed with saturated aqueous sodium chloride (60 mL), dried over anhydrous sodium sulfate, and filtered. The filtrate was concentrated in vacuo, and the residue was purified by silica gel column chromatography (DCM/MeOH=100/1~10/1) to give the title compound as a light yellow solid (265 mg, 73%).

MS (ESI, pos. ion) m/z: 574.2 [M+H]$^+$;
$^1$H NMR (600 MHz, DMSO-d$_6$) δ (ppm): 8.67 (s, 1H), 8.30 (s, 1H), 8.10 (s, 1H), 7.91 (d, J=7.9 Hz, 2H), 7.56 (m, 4H), 7.46 (d, J=8.2 Hz, 2H), 7.29 (t, J=9.9 Hz, 1H), 6.85 (s, 1H), 3.99 (s, 1H), 2.76 (s, 1H), 2.37 (s, 3H), 2.17 (s, 1H), 2.08 (s, 1H), 1.80 (s, 2H), 1.41 (d, J=13.4 Hz, 1H), 1.07 (m, 3H).

Step 7: (+/−)-cis-N-(3-((2-(5,7-difluoro-1-tosyl-1H-indol-3-yl)-6-phenylpyrimidin-4-yl)amino)cyclohexyl)pyrrolidine-1-carboxamide To a solution of (+/−)-cis-N$^1$-(2-(5,7-difluoro-1-tosyl-1H-indol-3-yl)-6-phenylpyrimidin-4-yl)cyclohexane-1,3-diamine (46 mg, 0.08 mmol) in tetrahydrofuran (5 mL) were added pyrrolidine-1-carbonyl chloride (21 μL, 0.19 mmol) and DIPEA (0.10 mL, 0.60 mmol). The mixture was stirred at rt overnight. The reaction mixture was concentrated, and the residue was diluted with ethyl acetate (60 mL). The mixture was partitioned. The organic layer was washed with water (60 mL) and saturated aqueous sodium chloride (60 mL) in turn, dried over anhydrous sodium sulfate, and filtered. The filtrate was concentrated in vacuo to give the title compound as light yellow oil (106 mg), which was used in the next step without further purification.

Step 8: (+/−)-cis-N-(3-((2-(5,7-difluoro-1H-indol-3-yl)-6-phenylpyrimidin-4-yl)amino)cyclohexyl)pyrrolidine-1-carboxamide To a solution of (+/−)-cis-N-(3-((2-(5,7-difluoro-1-tosyl-1H-indol-3-yl)-6-phenylpyrimidin-4-yl)amino)cyclohexyl)pyrrolidine-1-carboxamide (54 mg, 0.08 mmol) in methanol (2 mL) was added a solution of sodium methoxide in methanol (5 M, 3 mL). The mixture was stirred overnight at rt. The reaction mixture was concentrated in vacuo, and the residue was adjusted with aqueous hydrochloric acid (2 M) to pH 8. The mixture was extracted with EtOAc (20 mL×3). The combined organic layers were washed with saturated aqueous sodium chloride (60 mL), dried over anhydrous sodium sulfate, and filtered. The filtrate was concentrated in vacuo, and the residue was purified by silica gel column chromatography (DCM/MeOH=100/1~15/1) to give the title compound as a light yellow solid (20 mg, 48%).

MS-ESI: (ESI, pos. ion) m/z: 517.2 [M+H]$^+$;
HRMS (ESI, pos. ion) m/z: 517.2544, (C$_{29}$H$_{31}$F$_2$N$_6$O) [M+H]$^+$ theoretical value: 517.2527;
$^1$H NMR (400 MHz, CD$_3$OD) δ (ppm): 8.25 (s, 1H), 8.21 (d, J=10.1 Hz, 1H), 8.07 (d, J=6.9 Hz, 2H), 7.52 (m, 3H), 6.82 (t, J=10.2 Hz, 1H), 6.66 (s, 1H), 4.16 (s, 1H), 3.82 (t, J=11.4 Hz, 1H), 2.38 (d, J=11.1 Hz, 1H), 2.26 (d, J=11.3 Hz, 1H), 2.00 (s, 1H), 1.91 (s, 5H), 1.63 (d, J=13.1 Hz, 1H), 1.33 (m, 7H);
$^{13}$C NMR (101 MHz, CD$_3$OD) δ (ppm): 162.91, 162.69, 157.38, 138.38, 130.38, 129.43, 128.92, 128.26, 126.59, 121.95, 121.82, 117.03, 103.05, 103.01, 102.81, 102.76, 96.45, 96.24, 96.14, 95.93, 48.96, 48.74, 45.27, 39.53, 32.57, 31.89, 29.31, 25.00, 23.02.

Example 28: (+/−)-cis-2-amino-N-(3-((2-(5,7-difluoro-1H-indol-3-yl)-6-phenylpyrimidin-4-yl)amino)cyclohexyl)thiazole-4-carboxamide

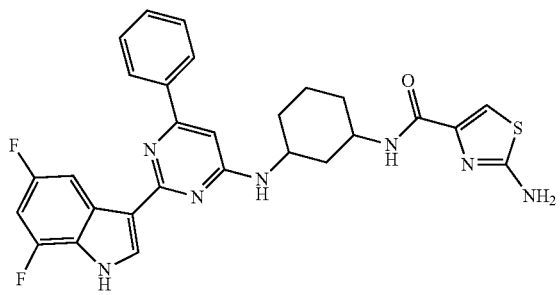 [SMILES: Nc1nc(C(=O)NC2CCCC(Nc3cc(-c4ccccc4)nc(-c4c[nH]c5c(F)cc(F)cc45)n3)C2)cs1]

Step 1: (+/−)-cis-2-amino-N-(3-((2-(5,7-difluoro-1-tosyl-1H-indol-3-yl)-6-phenylpyrimidin-4-yl)amino)cyclohexyl)thiazole-4-carboxamide To a solution of (+/−)-cis-N$^1$-(2-(5,7-difluoro-1-tosyl-1H-indol-3-yl)-6-phenylpyrimidin-4-yl)cyclohexane-1,3-diamine (50 mg, 0.09 mmol) and 2-aminothiazole-4-carboxylic acid (27 mg, 0.19 mmol) in a mixed solvent of dimethyl sulfoxide (2 mL) and tetrahydrofuran (4 mL) was added DIPEA (46 μL, 0.28 mmol). The mixture was stirred at rt for 10 min then HATU (68 mg, 0.18 mmol) was added. The resulting mixture was stirred at rt overnight. To the reaction mixture was added water (30 mL), and the mixture was extracted with ethyl acetate (30 mL×3). The combined organic layers were washed with a saturated aqueous sodium chloride solution (60 mL), dried over anhydrous sodium sulfate, and filtered. The filtrate was concentrated in vacuo to give the title compound as a light yellow solid (89 mg), which was used in the next step without further purification.

Step 2: (+/−)-cis-2-amino-N-(3-((2-(5,7-difluoro-1H-indol-3-yl)-6-phenylpyrimidin-4-yl)amino)cyclohexyl)thiazole-4-carboxamide To a solution of (+/−)-cis-2-amino-N-(3-((2-(5,7-difluoro-1-tosyl-1H-indol-3-yl)-6-phenylpyrimidin-4-yl)amino)cyclohexyl)thiazole-4-carboxamide (49 mg, 0.07 mmol) in methanol (2 mL) was added a solution of sodium methoxide in methanol (5 M, 3 mL). The mixture was stirred overnight at rt. The reaction mixture was concentrated in vacuo, and the residue was adjusted with aqueous hydrochloric acid (2 M) to pH 8. The mixture was extracted with EtOAc (20 mL×3). The combined organic layers were washed with saturated aqueous sodium chloride (60 mL), dried over anhydrous sodium sulfate, and filtered. The filtrate was concentrated in vacuo, and the residue was purified by silica gel column chromatography (DCM/MeOH (v/v)=100/1~15/1) to give the title compound as a light yellow solid (19 mg, 50%).

MS-ESI: (ESI, pos. ion) m/z: 546.6 [M+H]$^+$;

HRMS (ESI, pos. ion) m/z: 546.1893, ($C_{29}H_{31}F_2N_6O$) [M+H]$^+$ theoretical value: 546.1888;

$^1$H NMR (400 MHz, CD$_3$OD) δ (ppm): 8.26 (s, 1H), 8.22 (d, J=10.0 Hz, 1H), 8.07 (d, J=7.0 Hz, 2H), 7.50 (m, 3H), 7.27 (s, 1H), 6.82 (m, 1H), 6.67 (s, 1H), 4.22 (s, 1H), 4.08 (dd, J=18.8, 7.2 Hz, 1H), 2.46 (d, J=11.6 Hz, 1H), 2.29 (d, J=10.2 Hz, 1H), 2.07 (d, J=11.4 Hz, 1H), 1.97 (d, J=13.6 Hz, 1H), 1.68 (dd, J=26.9, 13.5 Hz, 1H), 1.37 (m, 4H);

$^{13}$C NMR (101 MHz, CD$_3$OD) δ (ppm): 170.61, 164.46, 164.15, 163.13, 159.98, 157.73, 149.05, 146.52, 139.91, 131.85, 130.87, 130.58, 130.51, 130.46, 130.39, 129.72, 128.04, 123.43, 123.30, 118.62, 118.57, 113.60, 104.52, 104.48, 104.27, 104.23, 97.90, 97.70, 97.60, 97.39, 50.14, 39.96, 33.25, 33.14, 30.78, 24.34.

Example 29: (+/−)-trans-3-((2-(5-chloro-7-fluoro-1H-indol-3-yl)-6-phenylpyrimidin-4-yl)amino) bicyclo[2.2.2]octane-2-carboxylic Acid

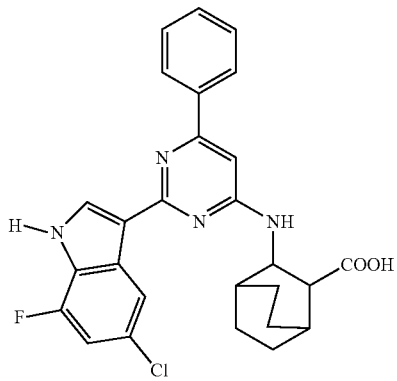 [SMILES: O=C(O)C1C2CCC(CC2)C1Nc1cc(-c2ccccc2)nc(-c2c[nH]c3c(F)cc(Cl)cc23)n1]

Step 1: methyl (2-bromo-4-chloro-6-fluorophenyl)carbamate

To a solution of 2-bromo-4-chloro-6-fluoroaniline (1.23 g, 5.49 mmol) in MeCN (10 mL) was added potassium carbonate (2.35 g, 17.0 mmol), then methyl carbonochloridate (2.5 mL, 32 mmol) was added dropwise in 20 min. After the addition, the mixture was heated to 85° C. and stirred overnight. After the reaction, the reaction mixture was concentrated in vacuo to remove the solvent. To the residue was added dichloromethane (90 mL). The organic layer was washed with water (80 mL) and a saturated aqueous sodium chloride solution (80 mL) in turn, dried over anhydrous sodium sulfate, and filtered. The filtrate was concentrated in vacuo to dry, and the residue was purified by silica gel column chromatography (PE/EtOAc (v/v)=20/1~8/1) to give the title compound as a light yellow solid (1.26 g, 85%).

MS: (ESI, pos. ion) m/z: 284.1 [M+H]$^+$;

$^1$H NMR (400 MHz, CDCl$_3$) δ (ppm): 7.47 (dt, J=15.8, 1.9 Hz, 1H), 7.19 (td, J=8.7, 2.2 Hz, 1H), 6.15 (s, 1H), 3.83 (s, 3H).

Step 2: methyl (4-chloro-2-fluoro-6-((trimethylsilyl)ethynyl)phenyl)carbamate

To a suspension of methyl (2-bromo-4-chloro-6-fluorophenyl)carbamate (1.28 g, 4.53 mmol), cuprous iodide (90 mg, 0.47 mmol), Pd(PPh$_3$)$_2$Cl$_2$ (740 mg, 1.0556 mmol) and triethylamine (5 mL) in acetonitrile (10 mL) was added slowly ethynyltrimethylsilane (1.30 mL, 9.20 mmol) under nitrogen protection. After the addition, the mixture was refluxed and stirred for 3 h. The reaction mixture was filtered through a celite pad, and the filter cake was washed with ethyl acetate (50 mL). The filtrate was washed with saturated aqueous sodium chloride (50 mL), dried over anhydrous sodium sulfate, and filtered. The filtrate was concentrated in vacuo, and the residue was purified by silica gel column chromatography (PE/EtOAc (v/v)=20/1~5/1) to give the title compound as a light yellow solid (800 mg, 60%).

MS: (ESI, pos. ion) m/z: 300.0 [M+H]$^+$;

$^1$H NMR: (600 MHz, CDCl$_3$) δ (ppm): 7.26 (s, 1H), 7.14 (dd, J=9.6, 2.1 Hz, 1H), 6.38 (s, 1H), 3.81 (s, 3H), 0.28 (s, 9H).

Step 3: 5-chloro-7-fluoro-1H-indole

To a mixture of sodium ethoxide (3.40 g, 10.0 mmol, weight content 20%) and anhydrous ethanol (10 mL) was added a solution of methyl (4-chloro-2-fluoro-6-((trimethylsilyl)ethynyl)phenyl)carbamate (0.603 g, 2.01 mmol) in anhydrous ethanol (10 mL) under nitrogen protection. The mixture was stirred at rt for 2 h, then reflued and stirred for 2 h. The reaction mixture was concentrated in vacuo to remove the solvent, and to the residue was added ethyl acetate (80 mL). The mixture was washed with water (60 mL) and saturated brine (60 mL), dried over anhydrous sodium sulfate and filtered. The filtrate was concentrated in vacuo to dry and the residue was purified by silica gel column chromatography (PE/EtOAc (v/v)=10/1) to give the title compound as a light yellow solid (119 mg, 40%).

$^1$H NMR (400 MHz, CDCl$_3$) δ (ppm): 8.47 (s, 1H), 7.43 (d, J=0.9 Hz, 1H), 7.26 (t, J=2.7 Hz, 1H), 6.97 (dd, J=10.6, 1.4 Hz, 1H), 6.56 (dd, J=5.4, 3.2 Hz, 1H).

Step 4: 5-chloro-7-fluoro-3-iodo-1H-indole

To a solution of 5-chloro-7-fluoro-1H-indole (245 mg, 1.44 mmol) in tetrahydrofuran (5 mL) was added NIS (390 mg, 1.73 mmol) in portions. The mixture was stirred at rt for 2 h. After the reaction, the reaction mixture was concentrated in vacuo to remove the solvent. To the residue was added dichloromethane (80 mL). The organic layers were washed with water (80 mL) and a saturated aqueous sodium chloride solution (80 mL) in turn, dried over anhydrous sodium sulfate, and filtered. The filtrate was concentrated in vacuo, and the residue was purified by silica gel column chromatography (PE/EtOAc (v/v)=20/1~8/1) to give the title compound as a light yellow solid (320 mg, 75%).

MS: (ESI, neg. ion) m/z: 293.9 [M−H]$^−$;

$^1$H NMR (400 MHz, CDCl$_3$) δ (ppm): 8.81 (s, 1H), 7.30 (d, J=2.4 Hz, 1H), 7.25 (s, 1H), 7.01 (dd, J=10.5, 1.3 Hz, 1H).

Step 5: tert-butyl 5-chloro-7-fluoro-3-iodo-1H-indole-1-carboxylate

To a solution of 5-chloro-7-fluoro-3-iodo-1H-indole (100 mg, 0.34 mmol), triethylamine (55 mg, 0.54 mmol) and DMAP (6 mg, 0.049 mmol) in DCM (6 mL) was added Boc₂O (141 mg, 0.63 mmol) in portions. The mixture was stirred at rt for 2 h. After the reaction, to the reaction mixture was added ethyl acetate (50 mL). The mixture wad washed with a saturated aqueous sodium thiosulfate solution (40 mL) and a saturated aqueous sodium chloride solution (40 mL) in turn, dried over anhydrous sodium sulfate, and filtered. The filtrate was concentrated in vacuo to dry, and the residue was purified by silica gel column chromatography (PE/EtOAc (v/v)=20/1~8/1) to give the title compound as a light yellow solid (95 mg, 71%).

$^1$H NMR (400 MHz, CDCl₃) δ (ppm): 7.80 (s, 1H), 7.24 (s, 1H), 7.15 (d, J=11.8 Hz, 1H), 1.66 (s, 9H).

Step 6: tert-butyl 5-chloro-7-fluoro-3-(4,4,5,5-tetramethyl-1,3,2-dioxaborolan-2-yl)-1H-indole-1-carboxylate To a suspension of tert-butyl 5-chloro-7-fluoro-3-iodo-1H-indole-1-carboxylate (414 mg, 1.05 mmol), triethylamine (0.44 mL, 3.14 mmol) and tetrakis(triphenylphosphine) palladium (247 mg, 0.21 mmol) in 1,4-dioxane (5 mL) was added slowly pinacolborane (0.90 mL, 6.20 mmol) under nitrogen protection. The mixture was heated to 80° C. and stirred for 3 h. The reaction mixture was filtered through a celite pad, and the filter cake was washed with EtOAc (60 mL). The filtrate was concentrated in vacuo, and the residue was purified by silica gel column chromatography (PE/EtOAc (v/v)=20/1~10/1) to give the title compound as a light yellow solid (75 mg, 18%).

MS (ESI, pos. ion) m/z: 418.2 [M+Na]⁺;

$^1$H NMR (400 MHz, CDCl₃) δ (ppm): 8.05 (s, 1H), 7.79 (d, J=1.6 Hz, 1H), 7.05 (dd, J=11.9, 1.7 Hz, 1H), 1.66 (s, 10H), 1.39 (s, 12H).

Step 7: tert-butyl 5-chloro-7-fluoro-3-(4-((3-(methoxycarbonyl)bicyclo[2.2.2]octan-2-yl)amino)-6-phenylpyrimidin-2-yl)-1H-indole-1-carboxylate A suspension of (+/−)-trans-methyl 3-((2-chloro-6-phenylpyrimidin-4-yl)amino)bicyclo[2.2.2]octane-2-carboxylate (76 mg, 0.204 mmol), tert-butyl 5-chloro-7-fluoro-3-(4,4,5,5-tetramethyl-1,3,2-dioxaborolan-2-yl)-1H-indole-1-carboxylate (74 mg, 0.19 mmol), potassium phosphate (120 mg, 0.565 mmol) and Pd(dtbpf)Cl₂ (20 mg, 0.0307 mmol) in a mixed solvent of 1,4-dioxane (5 mL) and water (0.5 mL) was stirred at 90° C. for 2 h under nitrogen protection. The reaction mixture was filtered through a celite pad, and the filter cake was washed with EtOAc (50 mL). The organic layer was washed with water (50 mL) and a saturated aqueous sodium chloride solution (50 mL), dried over anhydrous sodium sulfate, and filtered. The filtrate was concentrated in vacuo, and the residue was purified by silica gel column chromatography (PE/EtOAc (v/v)=15/1~5/1) to give the title compound as a light yellow solid (60 mg, 53%).

Step 8: (+/−)-trans-methyl 3-((2-(5-chloro-7-fluoro-1H-indol-3-yl)-6-phenylpyrimidin-4-yl)amino)bicyclo[2.2.2]octane-2-carboxylate To a solution of tert-butyl 5-chloro-7-fluoro-3-(4-((3-(methoxycarbonyl) bicyclo[2.2.2]octan-2-yl)amino)-6-phenylpyrimidin-2-yl)-1H-indole-1-carboxylate (74 mg, 0.12 mmol) in dichloromethane (5 mL) was added trifluoroacetic acid (2 mL). The mixture was stirred at rt for 2 h. The reaction mixture was concentrated in vacuo, and to the residue was added slowly a saturated aqueous sodium bicarbonate solution (20 mL). The mixture was extracted with EtOAc (20 mL×3). The combined organic layers were washed with saturated brine (50 mL), dried over anhydrous sodium sulfate, and filtered. The filtrate was concentrated in vacuo to give the title compound as a yellow solid (30 mg, 48%), which was used in the next step without further purification.

MS: (ESI, pos. ion) m/z: 505.3 [M+H]⁺.

Step 9: (+/−)-trans-3-((2-(5-chloro-7-fluoro-1H-indol-3-yl)-6-phenylpyrimidin-4-yl)amino)bicyclo[2.2.2]octane-2-carboxylic Acid To a solution of (+/−)-trans-methyl 3-((2-(5-chloro-7-fluoro-1H-indol-3-yl)-6-phenylpyrimidin-4-yl)amino)bicyclo[2.2.2]octane-2-carboxylate (100 mg, 0.20 mmol) in a mixed solvent THF/MeOH/H₂O (v/v/v=1/1/1, 6 mL) was added sodium hydroxide (63 mg, 1.58 mmol). The mixture was stirred at rt overnight. To the reaction mixture was added water (20 mL), and the mixture was acidified with hydrochloric acid (1 M) to pH about 5.5. The resulting mixture was extracted with EtOAc (20 mL×3). The combined organic layers were washed with saturated brine (50 mL), dried over anhydrous sodium sulfate, and filtered. The filtrate was concentrated in vacuo and the residue was purified by preparative TLC (dichloromethane/methanol (v/v)=15/1) to give the title compound as a light yellow solid (10 mg, 10%).

MS (ESI, pos. ion) m/z: 491.0[M+H]⁺;

$^1$H NMR (400 MHz, DMSO-d₆) δ (ppm): 12.20 (s, 1H), 8.27 (s, 1H), 8.21 (s, 1H), 8.07 (s, 2H), 7.56-7.38 (m, 4H), 7.05 (t, J=9.8 Hz, 1H), 6.73 (s, 1H), 4.65 (s, 1H), 3.96 (s, 1H), 2.00 (s, 2H), 1.81-1.37 (m, 8H).

Example 30: (+/−)-trans-3-((2-(7-chloro-5-fluoro-1H-indol-3-yl)-6-phenylpyrimidin-4-yl)amino)bicyclo[2.2.2]octane-2-carboxylic Acid

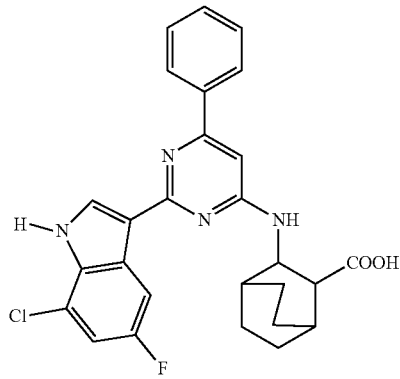 [SMILES: O=C(O)C1C2CCC(CC2)C1Nc1cc(-c2ccccc2)nc(-c2c[nH]c3c(Cl)cc(F)cc23)n1]

Step 1: methyl (2-bromo-6-chloro-4-fluorophenyl)carbamate

To a solution of 2-bromo-6-chloro-4-fluoroaniline (1.45 g, 6.46 mmol) in MeCN (10 mL) was added potassium carbonate (2.82 g, 20.4 mmol), then methyl carbonochloridate (4.0 mL, 51.7 mmol) was added dropwise in 20 minutes. After the addition, the mixture was heated to 85° C. and stirred overnight. After the reaction, the reaction mixture was concentrated in vacuo to remove the solvent. To the residue was added dichloromethane (90 mL). The organic layers were washed with water (80 mL) and a saturated aqueous sodium chloride solution (80 mL) in turn, dried over anhydrous sodium sulfate, and filtered. The filtrate was concentrated in vacuo, and the residue was purified by silica gel column chromatography (PE/EtOAc (v/v)=20/1~8/1) to give the title compound as a light yellow solid (1.52 g, 84%).

MS(ESI, pos. ion) m/z: 283.9 [M+H]$^+$;

$^1$H NMR (400 MHz, CDCl$_3$) δ (ppm): 7.33 (dd, J=7.6, 2.8 Hz, 1H), 7.21 (dd, J=7.8, 2.8 Hz, 1H), 6.27 (s, 1H), 3.81 (s, 3H).

Step 2: methyl (2-chloro-4-fluoro-6-((trimethylsilyl)ethynyl)phenyl)carbamate

To a suspension of methyl (2-bromo-6-chloro-4-fluorophenyl)carbamate (1.52 g, 5.39 mmol), cuprous iodide (108 mg, 0.567 mmol), Pd(PPh$_3$)$_2$Cl$_2$ (882 mg, 1.258 mmol) and triethylamine (6 mL) in acetonitrile (20 mL) was added slowly ethynyltrimethylsilane (2.5 mL, 18 mmol) under nitrogen protection. After the addition, the mixture was refluxed and stirred for 3 h under nitrogen protection. The reaction mixture was filtered through a celite pad, and the filter cake was washed with ethyl acetate (50 mL). The filtrate was washed with a saturated aqueous sodium chloride solution (50 mL), dried over anhydrous sodium sulfate, and filtered. The filtrate was concentrated in vacuo, and the residue was purified by silica gel column chromatography (PE/EtOAc (v/v)=20/1~5/1) to give the title compound as a light yellow solid (1.30 g, 80%).

MS (ESI, pos. ion) m/z: 300.0 [M+H]$^+$;

$^1$H NMR (600 MHz, CDCl$_3$) δ (ppm): 7.18 (dd, J=7.9, 2.8 Hz, 1H), 7.13 (dd, J=8.3, 2.8 Hz, 1H), 6.34 (s, 1H), 3.80 (s, 3H), 0.27 (s, 9H).

Step 3: 7-chloro-5-fluoro-1H-indole

To a mixture of sodium ethoxide (5.78 g, 17.0 mmol, weight content 20%) and anhydrous ethanol (10 mL) was added a solution of methyl (2-chloro-4-fluoro-6-((trimethylsilyl)ethynyl)phenyl)carbamate (1.30 g, 4.36 mmol) in anhydrous ethanol (5 mL) under nitrogen protection. The mixture was stirred at rt for 2 h, then refluxed and stirred for 2 h. The reaction mixture was concentrated in vacuo to remove the solvent, and to the residue was added ethyl acetate (80 mL). The mixture wad washed with water (60 mL) and saturated brine (60 mL) in turn, dried over anhydrous sodium sulfate, and filtered. The filtrate was concentrated in vacuo to dry, and the residue was purified by silica gel column chromatography (PE/EtOAc (v/v)=10/1) to give the title compound as a light yellow solid (589 mg, 80%).

$^1$H NMR (400 MHz, CDCl$_3$) δ (ppm): 8.43 (s, 1H), 7.31 (t, J=2.7 Hz, 1H), 7.24 (dd, J=9.1, 1.7 Hz, 1H), 7.04 (dd, J=9.0, 2.0 Hz, 1H), 6.60-6.57 (m, 1H).

Step 4: 7-chloro-5-fluoro-3-iodo-1H-indole

To a solution of 7-chloro-5-fluoro-1H-indole (743 mg, 4.38 mmol) in tetrahydrofuran (8 mL) was added NIS (1.20 g, 5.33 mmol) in portions. The mixture was stirred at rt for 2 h. The reaction mixture was concentrated in vacuo to remove the solvent. To the residue was added dichloromethane (80 mL). The organic layer was washed with water (80 mL) and a saturated aqueous sodium chloride solution (80 mL) in turn, dried over anhydrous sodium sulfate, and filtered. The filtrate was concentrated in vacuo, and the residue was purified by silica gel column chromatography (PE/EtOAc (v/v)=20/1~8/1) to give the title compound as a light yellow solid (1.00 g, 77%).

MS (ESI, neg. ion) m/z: 294.0 [M–H]$^-$;

$^1$H NMR (400 MHz, CDCl$_3$) δ (ppm): 8.57 (s, 1H), 7.40 (d, J=2.2 Hz, 1H), 7.09 (dd, J=8.8, 2.5 Hz, 2H).

Step 5) tert-butyl 7-chloro-5-fluoro-3-iodo-1H-indole-1-carboxylate

To a solution of 7-chloro-5-fluoro-3-iodo-1H-indole (112 mg, 0.38 mmol), triethylamine (58 mg, 0.57 mmol) and DMAP (6 mg, 0.05 mmol) in DCM (6 mL) was added Boc$_2$O (149 mg, 0.68 mmol) in portions. The mixture was stirred at rt for 2 h. After the reaction, to the reaction mixture was added ethyl acetate (50 mL). The mixture was washed with saturated aqueous sodium thiosulfate (40 mL) and saturated aqueous sodium chloride (40 mL) in turn, dried over anhydrous sodium sulfate, and filtered. The filtrate was concentrated in vacuo, and the residue was purified by silica gel column chromatography (PE/EtOAc (v/v)=20/1~8/1) to give the title compound as a light yellow solid (108 mg, 72%).

Step 6: tert-butyl 7-chloro-5-fluoro-3-(4,4,5,5-tetramethyl-1,3,2-dioxaborolan-2-yl)-1H-indole-1-carboxylate To a suspension of tert-butyl 7-chloro-5-fluoro-3-iodo-1H-indole-1-carboxylate (108 mg, 0.275 mmol), triethylamine (83 mg, 0.82 mmol) and tetrakis(triphenylphosphine)palladium (66 mg, 0.06 mmol) in 1,4-dioxane (5 mL) was added slowly pinacolborane (0.20 mL, 1.40 mmol) under nitrogen protection. The mixture was heated to 80° C. and stirred for 3 h. The reaction mixture was filtered through a celite pad, and the filter cake was washed with EtOAc (60 mL). The filtrate was concentrated in vacuo, and the residue was purified by silica gel column chromatography (PE/EtOAc (v/v)=20/1~10/1) to give the title compound as a light yellow solid (35 mg, 32%).

MS (ESI, pos. ion) m/z: 418.2 [M+Na]$^+$;

$^1$H NMR (400 MHz, CDCl$_3$) δ (ppm): 7.98 (s, 1H), 7.64 (dd, J=8.4, 2.3 Hz, 1H), 7.12 (dd, J=9.0, 2.3 Hz, 1H), 1.66 (s, 9H), 1.39 (s, 12H).

Step 7: tert-butyl 7-chloro-5-fluoro-3-(4-((3-(methoxycarbonyl)bicyclo[2.2.2]octan-2-yl)amino)-6-phenylpyrimidin-2-yl)-1H-indole-1-carboxylate A suspension of (+/−)-trans-methyl 3-((2-chloro-6-phenylpyrimidin-4-yl)amino)bicyclo[2.2.2]octane-2-carboxylate (290 mg, 0.779 mmol), tert-butyl 7-chloro-5-fluoro-3-(4,4,5,5-tetramethyl-1,3,2-dioxaborolan-2-yl)-1H-indole-1-carboxylate (286 mg, 0.72 mmol), potassium phosphate (460 mg, 2.17 mmol), XPhos (68 mg, 0.14 mmol) and Pd$_2$(dba)$_3$ (66 mg, 0.07 mmol) in a mixed solvent of 1,4-dioxane (5 mL) and water (0.5 mL) was stirred at 100° C. for 2.5 h under nitrogen protection. The reaction mixture was filtered through a celite pad, and the filter cake was washed with EtOAc (50 mL). The organic layer was washed with water (50 mL) and a saturated aqueous sodium chloride solution (50 mL), dried over anhydrous sodium sulfate, and filtered. The filtrate was concentrated in vacuo, and the residue was purified by silica gel column chromatography (PE/EtOAc (v/v)=15/1~5/1) to give the title compound as a light yellow solid (70 mg, 16%).

MS (ESI, pos. ion) m/z: 605.3 [M+H]$^+$.

Step 8: (+/−)-trans-methyl 3-((2-(7-chloro-5-fluoro-1H-indol-3-yl)-6-phenylpyrimidin-4-yl)amino)bicyclo[2.2.2]octane-2-carboxylate To a solution of tert-butyl 7-chloro-5-fluoro-3-(4-((3-(methoxycarbonyl) bicyclo[2.2.2]octan-2-yl)amino)-6-phenylpyrimidin-2-yl)-1H-indole-1-carboxylate (144 mg, 0.24 mmol) in dichloromethane (5 mL) was added trifluoroacetic acid (2 mL). The mixture was stirred at rt for 2 h. The reaction mixture was concentrated in vacuo, and to the residue was added slowly a saturated aqueous sodium bicarbonate solution (20 mL). The mixture was extracted with EtOAc (20 mL×3). The combined organic layers were washed with saturated brine (50 mL), dried over anhydrous sodium sulfate, and filtered. The filtrate was concentrated in vacuo to give the title compound as a yellow solid (90 mg, 70%), which was used in the next step without further purification.

Step 9: (+/−)-trans-3-((2-(7-chloro-5-fluoro-1H-indol-3-yl)-6-phenylpyrimidin-4-yl)amino)bicyclo[2.2.2]octane-2-carboxylic Acid To a solution of (+/−)-trans-methyl 3-((2-(5-chloro-7-fluoro-1H-indol-3-yl)-6-phenylpyrimidin-4-yl)amino)bicyclo[2.2.2]octane-2-carboxylate (126 mg, 0.25 mmol) in a mixed solvent THF/MeOH/H$_2$O (v/v/v=1/1/1, 6 mL) was added sodium hydroxide (80 mg, 2.00 mmol). The mixture was stirred at rt overnight. To the reaction mixture was added water (20 mL), and the mixture was acidified with hydrochloric acid (1 M) to pH about 6. The resulting mixture was extracted with EtOAc (20 mL×3). The combined organic layers were washed with saturated brine (50 mL), dried over anhydrous sodium sulfate, and filtered. The filtrate was concentrated in vacuo and the residue was purified by preparative TLC (dichloromethane/methanol (v/v)=15/1) to give the title compound as a light yellow solid (52 mg, 43%).

MS (ESI, pos. ion) m/z: 491.0[M+H]$^+$;

$^1$H NMR (400 MHz, DMSO-d$_6$) δ (ppm): 12.10 (s, 1H), 8.39 (s, 1H), 8.29 (s, 1H), 8.08 (s, 2H), 7.58-7.49 (m, 4H), 7.26 (d, J=8.9 Hz, 1H), 6.78 (s, 1H), 4.66 (s, 1H), 4.03 (s, 1H), 2.01 (s, 2H), 1.79-1.38 (m, 8H).

Example 31: (+/−)-trans-3-((6-(5,7-difluoro-1H-indol-3-yl)-1-methyl-1H-pyrazolo[3,4-d]pyrimidin-4-yl)amino)bicyclo[2.2.2]octane-2-carboxylic Acid

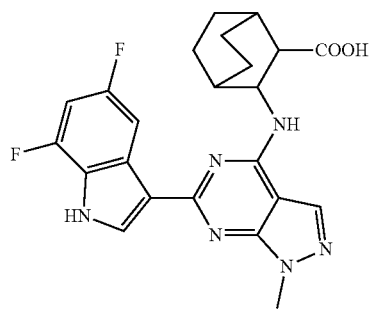 [SMILES: Cn1ncc2c(NC3C4CCC(CC4)C3C(=O)O)nc(-c3c[nH]c4c(F)cc(F)cc34)nc21]

Step 1: 4,6-dichloro-1-methyl-1H-pyrazolo[3,4-d]pyrimidine

To a solution of 4,6-dichloro-1H-pyrrolo[3,4-d]pyridine (110 mg, 0.58 mmol) in DMF (5 mL) was added K$_2$CO$_3$ (160 mg, 1.16 mmol). Then the reaction mixture was stirred for 30 min maintaining at temperature, then iodomethane (3.78 g, 26.60 mmol) was added. The reaction mixture was stirred at rt overnight. Water (50 mL) was added to quench the reaction, and the resulting mixture was extracted with EtOAc (50 mL×2). The combined organic phases were washed with saturated brine (80 mL), dried over anhydrous Na$_2$SO$_4$, filtered, and the filtrate was concentrated in vacuo. The residue was purified by silica gel chromatograph (PE/EtOAc (v/v)=10/1) to give the title compound as a yellow solid (48 mg, 41%).

$^1$H NMR (400 MHz, CDCl$_3$) δ (ppm): 8.16 (s, 1H), 4.13 (s, 3H).

Step 2: (+/−)-trans-methyl 3-((2-chloro-5-methyl-5H-pyrazolo[3,4-d]pyrimidin-4-yl)amino)bicyclo[2.2.2]octane-2-carboxylate To a solution of (+/−)-trans-methyl 3-aminobicyclo[2.2.2]octane-2-carboxylate (132 mg, 0.67 mmol) and 4,6-dichloro-1-methyl-1H-pyrazolo[3,4-d]pyrimidine (123 mg, 0.61 mmol) in tetrahydrofuran (5 mL) was added K$_2$CO$_3$ (167 mg, 1.21 mmol). The mixture was stirred at rt overnight. The reaction was stopped, and water (50 mL) was added to quench the reaction, and the resulting mixture was partitioned. The aqueous layer was extracted with EtOAc (50 mL×2). The combined organic phases were washed with saturated brine (80 mL), dried over anhydrous Na$_2$SO$_4$, filtered, and the filtrate was concentrated in vacuo to remove the solvent. The residue was purified by silica gel chromatograph (n-hexane/EtOAc (v/v)=10/1) to give the title compound as a yellow solid (201 mg, 95%).

MS (ESI, pos. ion) m/z: 351.1 [M+H]$^+$;

$^1$H NMR (400 MHz, CDCl$_3$) δ (ppm): 8.00 (s, 1H), 4.62 (t, J=6.3 Hz, 1H), 3.99 (s, 3H), 3.74 (s, 3H), 2.44 (s, 1H), 1.94 (s, 1H), 1.88-1.37 (m, 10H).

Step 3: (+/−)-trans-methyl 3-((6-(5,7-difluoro-1-tosyl-1H-indol-3-yl)-1-methyl-1H-pyrazolo[3,4-d]pyrimidin-4-yl)amino)bicyclo[2.2.2]octane-2-carboxylate To a mixed solvent of 1,4-dioxane (8 mL) and H$_2$O (1 mL) were added 5,7-difluoro-3-(4,4,5,5-tetramethyl-1,3,2-dioxaborolan-2-yl)-1-tosyl-1H-indole (177 mg, 0.41 mmol), K$_2$CO$_3$ (160 mg, 1.12 mmol), Pd(dppf)Cl$_2$ (30 mg, 0.04 mmol), (+/−)-trans-methyl 3-((2-chloro-5-methyl-5H-pyrazolo[3,4-d]pyrimidin-4-yl)amino)bicyclo[2.2.2]octane-2-carboxylate (130 mg, 0.37 mmol). A stream of nitrogen was bubbled through the mixture for 5 min to remove air, then the mixture was stirred at 110° C. for 1.5 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give the title compound as a white solid (153 mg, 66%).

MS (ESI, pos. ion) m/z: 621.60 [M+H]$^+$.

Step 4: (+/−)-trans-3-((6-(5,7-difluoro-1H-indol-3-yl)-1-methyl-1H-pyrazolo[3,4-d]pyrimidin-4-yl)amino)bicyclo[2.2.2]octane-2-carboxylic Acid To a solution of (+/−)-trans-methyl 3-((6-(5,7-difluoro-1-tosyl-1H-indol-3-yl)-1-methyl-1H-pyrazolo[3,4-d]pyrimidin-4-yl)amino)bicyclo[2.2.2]octane-2-carboxylate (107 mg, 0.17 mmol) in a mixed solvent THF/MeOH ((v/v=1/1, 10 mL) was added a solution of sodium hydroxide (71 mg, 1.72 mmol) in water (1 mL). The mixture was stirred at rt overnight. The reaction mixture was diluted with water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo, and the residue was purified by silica gel column chromatography (DCM/MeOH (v/v)=10/1~5/1) to give the title compound as a white solid (49 mg, 63%).

MS (ESI, pos. ion) m/z: 453.1 [M+H]$^+$;
HRMS (ESI, pos. ion) m/z: 453.1871 [M+H]$^+$, (C$_{23}$H$_{23}$F$_2$N$_6$O$_2$) [M+H]$^+$ theoretical value: 453.1851;
$^1$H NMR (600 MHz, DMSO-d$_6$) δ (ppm): 12.22 (s, 1H), 8.26 (d, J=8.3 Hz, 2H), 8.10 (s, 1H), 7.98 (d, J=6.5 Hz, 1H), 7.05 (t, J=9.6 Hz, 1H), 4.83 (s, 1H), 3.95 (s, 3H), 2.68 (d, J=6.3 Hz, 1H), 2.04 (s, 2H), 1.90-1.35 (m, 9H).

Example 32: (+/−)-trans-3-((5-(5,7-difluoro-1H-indol-3-yl)thiazolo[5,4-d]pyrimidin-7-yl)amino)bicyclo[2.2.2]octane-2-carboxylic Acid

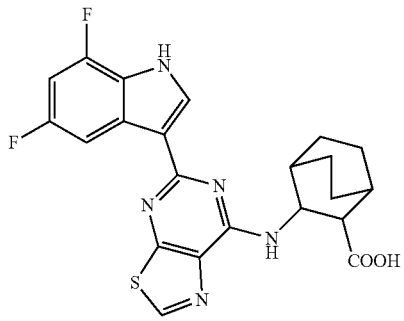 [SMILES: O=C(O)C1C2CCC(CC2)C1Nc1nc(-c2c[nH]c3c(F)cc(F)cc23)nc2scnc12]

Step 1: (+/−)-trans-methyl 3-((5-chlorothiazolo[5,4-d]pyrimidin-7-yl)amino)bicyclo[2.2.2]octane-2-carboxylate A suspension of 5,7-dichlorothiazolo[5,4-d]pyrimidine (115 mg, 0.56 mmol), (+/−)-trans-methyl 3-aminobicyclo[2.2.2]octane-2-carboxylate (25 mg, 0.14 mmol) and K$_2$CO$_3$ (155 mg, 1.12 mmol) in DMF (10 mL) was stirred at rt overnight. After the reaction, to the reaction mixture was added H$_2$O (100 mL), and the mixture was extracted with EtOAc (50 mL×3). The combined organic layers were washed with saturated brine (80 mL×3), dried over anhydrous sodium sulfate, and filtered. The filtrate was concentrated in vacuo, and the residue was purified by silica gel column chromatography (PE/EtOAc (v/v)=3/1) to give the title compound as a white solid (150 mg, 76%).

MS (ESI, pos. ion) m/z: 354.0 [M+H]$^+$.

Step 2: (+/−)-trans-methyl 3-((5-(5,7-difluoro-1-tosyl-1H-indol-3-yl)thiazolo[5,4-d]pyrimidin-7-yl)amino)bicyclo[2.2.2]octane-2-carboxylate To a mixed solvent of 1,4-dioxane (8 mL) and H$_2$O (1 mL) were added 5,7-difluoro-3-(4,4,5,5-tetramethyl-1,3,2-dioxaborolan-2-yl)-1-tosyl-1H-indole (202 mg, 0.47 mmol), K$_2$CO$_3$ (180 mg, 1.28 mmol), PdCl$_2$(dppf) (33 mg, 0.04 mmol), (+/−)-trans-methyl 3-((5-chlorothiazolo[5,4-d]pyrimidin-7-yl)amino)bicyclo[2.2.2]octane-2-carboxylate (150 mg, 0.43 mmol). A stream of nitrogen was bubbled through the mixture for 10 min to remove air, then the mixture was stirred at 110° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give a white solid (161 mg, 61%).

MS (ESI, pos. ion) m/z: 625.10 [M+H]$^+$.

Step 3: (+/−)-trans-3-((5-(5,7-difluoro-1H-indol-3-yl)thiazolo[5,4-d]pyrimidin-7-yl)amino)bicyclo[2.2.2]octane-2-carboxylic Acid To a solution of (+/−)-trans-methyl 3-((5-(5,7-difluoro-1-tosyl-1H-indol-3-yl) thiazolo[5,4-d]pyrimidin-7-yl)amino)bicyclo[2.2.2]octane-2-carboxylate (161 mg, 0.26 mmol) in a mixed solvent THF/MeOH ((v/v=1/1, 10 mL) was added a solution of NaOH (110 mg, 2.58 mmol) in water (1 mL). The mixture was stirred at rt overnight. The reaction mixture was diluted with water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1~5/1) to give the title compound as a white solid (78 mg, 66%).

MS (ESI, pos. ion) m/z: 456.1 [M+H]$^+$;
HRMS (ESI, pos. ion) m/z: 456.1329[M+H]$^+$, (C$_{22}$H$_{20}$F$_2$N$_5$O$_2$S) [M+H]$^+$ theoretical value: 456.1306;
$^1$H NMR (600 MHz, DMSO-d$_6$) δ (ppm): 12.29 (s, 1H), 9.11 (s, 1H), 8.22 (d, J=22.9 Hz, 3H), 7.06 (s, 1H), 4.89 (s, 1H), 3.94 (s, 1H), 3.05 (s, 1H), 2.50 (s, 2H), 2.04-1.79 (m, 4H), 1.49 (s, 4H);
$^{13}$C NMR (101 MHz, DMSO-d$_6$) δ (ppm): 176.10, 162.43, 159.62, 158.39, 156.05, 155.95, 155.58, 150.02, 131.85, 128.88, 128.76, 128.52, 122.15, 122.02, 116.92, 103.48, 103.20, 97.66, 97.45, 97.35, 97.15, 51.05, 47.87, 28.93, 28.79, 25.65, 24.25, 21.66, 19.61.

Example 33: (+/−)-trans-3-((2-(5,7-difluoro-1H-indol-3-yl)pteridin-4-yl)amino)bicyclo[2.2.2]octane-2-carboxylic Acid

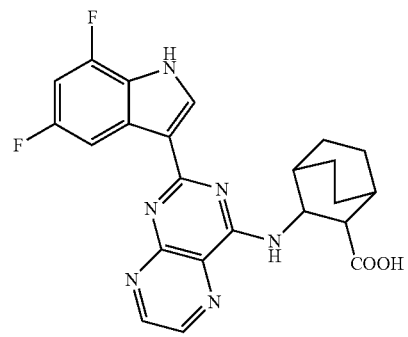 [SMILES: O=C(O)C1C2CCC(CC2)C1Nc1nc(-c2c[nH]c3c(F)cc(F)cc23)nc2nccnc12]

Step 1: (+/−)-trans-methyl 3-((2-chloropteridin-4-yl)amino)bicyclo[2.2.2]octane-2-carboxylate The suspension of 2,4-dichloropteridine (120 mg, 0.60 mmol), (+/−)-trans-methyl 3-aminobicyclo[2.2.2]octane-2- carboxylate (131 mg, 0.72 mmol) and DIPEA (1.1 mL, 5.97 mmol) in THF (5 mL) was stirred at rt overnight. To the reaction mixture was added H$_2$O (100 mL) to quench the reaction, and the mixture was extracted with EtOAc (50 mL×3). The combined organic layers were washed with saturated brine (80 mL×3), dried over anhydrous sodium sulfate, and filtered. The filtrate was concentrated in vacuo, and the residue was purified by silica gel column chromatography (PE/EtOAc (v/v)=3/1) to give the title compound as a white solid (156 mg, 75%).

MS (ESI, pos. ion) m/z: 348.10 [M+H]$^+$.

Step 2: (+/−)-trans-methyl 3-((2-(5,7-difluoro-1-tosyl-1H-indol-3-yl)pteridin-4-yl)amino)bicyclo[2.2.2]octane-2-carboxylate To a mixed solvent of 1,4-dioxane (8 mL) and H$_2$O (1 mL) were added 5,7-difluoro-3-(4,4,5,5-tetramethyl-1,3,2-dioxaborolan-2-yl)-1-tosyl-1H-indole (177 mg, 0.41 mmol), K$_2$CO$_3$ (160 mg, 1.12 mmol), Pd(dppf)Cl$_2$ (29 mg, 0.04 mmol) and (+/−)-trans-methyl 3-((2-chloropteridin-4-yl)amino)bicyclo[2.2.2]octane-2-carboxylate (130 mg, 0.37 mmol). A stream of nitrogen was bubbled through the mixture for 10 min to remove air, then the mixture was stirred at 110° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give the title compound as a white solid (150 mg, 65%).

Step 3: (+/−)-trans-3-((2-(5,7-difluoro-H-indol-3-yl)pteridin-4-yl)amino)bicyclo[2.2.2]octane-2-carboxylic Acid To a solution of (+/−)-trans-methyl 3-((2-(5,7-difluoro-1-tosyl-1H-indol-3-yl)pteridin-4-yl)amino)bicyclo[2.2.2]octane-2-carboxylate (120 mg, 0.19 mmol) in a mixed solvent THF/MeOH (v/v=1/1, 10 mL) was added a solution of NaOH (81 mg, 1.94 mmol) in water (1 mL). The mixture was stirred at rt overnight. The reaction mixture was diluted with water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo, and the residue was purified by silica gel column chromatography (DCM/MeOH (v/v)=10/1~5/1) to give the title compound as a white solid (41 mg, 47%).

MS (ESI, pos. ion) m/z: 451.5 [M+H]$^+$;

HRMS (ESI, pos. ion) m/z: 451.1692[M+H]$^+$, (C$_{23}$H$_{21}$F$_2$N$_6$O$_2$) [M+H]$^+$ theoretical value: 451.1694;

$^1$H NMR (600 MHz, DMSO-d$_6$) δ (ppm): 12.42 (s, 1H), 9.00 (s, 1H), 8.68 (s, 2H), 8.33 (d, J=16.3 Hz, 2H), 7.10 (s, 1H), 4.88 (s, 1H), 3.12 (s, 1H), 2.06 (s, 2H), 1.82 (s, 3H), 1.50 (m, 6H);

$^{13}$C NMR (101 MHz, DMSO-d$_6$) δ (ppm): 176.00, 163.16, 160.44, 158.56, 154.62, 151.44, 141.89, 133.21, 129.27, 129.09, 125.55, 122.17, 117.18, 103.53, 97.88, 97.58, 51.80, 47.91, 28.69, 28.60, 25.59, 24.34, 21.63, 19.74.

Example 34: (+/−)-trans-3-((2-(5,7-difluoro-1H-indol-3-yl)-7-(2-fluoroethyl)-7H-pyrrolo[2,3-d]pyrimidin-4-yl)amino)bicyclo[2.2.2]octane-2-carboxylic Acid

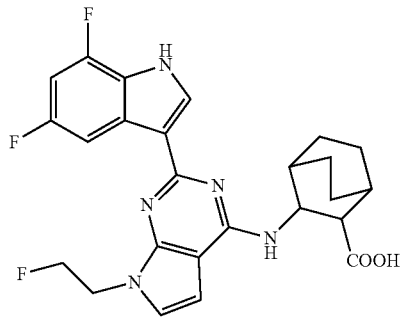 [SMILES: O=C(O)C1C2CCC(CC2)C1Nc1nc(-c2c[nH]c3c(F)cc(F)cc23)nc2c1ccn2CCF]

Step 1: 2,4-dichloro-7-(2-fluoroethyl)-7H-pyrrolo[2,3-d]pyrimidine

A solution of 2,4-dichloro-7H-pyrrolo[2,3-d]pyrimidine (500 mg, 2.66 mmol) in DMF (5 mL) was stirred at 0° C. for 5 min, then to the solution was added sodium hydride (130 mg, 3.25 mmol, weight content 60%). The mixture was stirred for further 15 min, and 1-fluoro-2-iodoethane (680 mg, 3.90 mmol) was added. The mixture was stirred at rt overnight. After the reaction, to the reaction mixture was added H$_2$O (100 mL) to quench the reaction, and the mixture was extracted with EtOAc (50 mL×3). The combined organic layers were washed with saturated brine (80 mL), dried over anhydrous sodium sulfate, and filtered. The filtrate was concentrated in vacuo, and the residue was purified by silica gel column chromatography (PE/EtOAc (v/v)=10/1) to give the title compound as a white solid (499 mg, 80%).

MS (ESI, pos. ion) m/z: 235.95 [M+H]$^+$;

$^1$H NMR (400 MHz, CDCl$_3$) δ (ppm): 7.35 (d, J=3.4 Hz, 1H), 6.66 (d, J=3.6 Hz, 1H), 4.83 (t, J=4.6 Hz, 1H), 4.71 (t, J=4.6 Hz, 1H), 4.61 (t, J=4.6 Hz, 1H), 4.54 (t, J=4.6 Hz, 1H).

Step 2: (+/−)-trans-methyl 3-((2-chloro-7-(2-fluoroethyl)-7H-pyrrolo[2,3-d]pyrimidin-4-yl)amino)bicyclo[2.2.2]octane-2-carboxylate A suspension of 2,4-dichloro-7-(2-fluoroethyl)-7H-pyrrolo[2,3-d]pyrimidine (210 mg, 0.90 mmol), (+/−)-trans-methyl 3-aminobicyclo[2.2.2]octane-2-carboxylate (185 mg, 0.99 mmol) and K$_2$CO$_3$ (250 mg, 1.79 mmol) in DMF (5 mL) was stirred at rt overnight. To the reaction mixture was added H$_2$O (50 mL) to quench the reaction, and the mixture was extracted with EtOAc (50 mL×3). The combined organic layers were washed with saturated brine (80 mL×3), dried over anhydrous sodium sulfate, and filtered. The filtrate was concentrated in vacuo, and the residue was purified by silica gel column chromatography (PE/EtOAc (v/v)=3/1) to give the title compound as a white solid (216 mg, 63%).

MS (ESI, pos. ion) m/z: 381.05 [M+H]$^+$.

Step 3: (+/−)-trans-methyl 3-((2-(5,7-difluoro-1-tosyl-1H-indol-3-yl)-7-(2-fluoroethyl)-7H-pyrrolo[2,3-d]pyrimidin-4-yl)amino)bicyclo[2.2.2]octane-2-carboxylate To a mixed solvent of 1,4-dioxane (8 mL) and H$_2$O (1 mL) were added 5,7-difluoro-3-(4,4,5,5-tetramethyl-1,3,2- dioxaborolan-2-yl)-1-tosyl-1H-indole (190 mg, 0.43 mmol), K₂CO₃ (166 mg, 1.18 mmol), PdCl₂(dppf) (30 mg, 0.04 mmol), (+/−)-trans-methyl 3-((2-chloro-7-(2-fluoroethyl)-7H-pyrrolo[2,3-d]pyrimidin-4-yl)amino)bicyclo[2.2.2]octane-2-carboxylate (150 mg, 0.39 mmol). A stream of nitrogen was bubbled through the mixture for 10 min to remove air, then the mixture was stirred at 110° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give the title compound as a white solid (127 mg, 49%).

¹H NMR (400 MHz, CDCl₃) δ (ppm): 8.71 (s, 1H), 8.37-8.29 (m, 1H), 7.90 (d, J=7.9 Hz, 2H), 7.31 (s, 2H), 7.09 (d, J=3.0 Hz, 1H), 6.80 (dd, J=15.2, 5.8 Hz, 1H), 6.44 (d, J=3.1 Hz, 1H), 5.16 (s, 1H), 4.90 (dd, J=9.5, 5.0 Hz, 2H), 4.60 (m, 2H), 3.72 (s, 3H), 2.48 (d, J=5.9 Hz, 1H), 2.41 (s, 3H), 2.11 (d, J=6.7 Hz, 2H), 1.70 (m, 9H).

Step 4: (+/−)-trans-3-((2-(5,7-difluoro-1H-indol-3-yl)-7-(2-fluoroethyl)-7H-pyrrolo[2,3-d]pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-7-(2-fluoroethyl)-7H-pyrrolo[2,3-d]pyrimidin-4-yl)amino)bicyclo[2.2.2]octane-2-carboxylate (126 mg, 0.19 mmol) in THF/MeOH (v/v=1/1, 10 mL) was added a solution of sodium hydroxide (81 mg, 1.93 mmol) in water (1 mL). The mixture was stirred at rt overnight. The reaction mixture was diluted with water (20 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1~5/1) to give the title compound as a white solid (59 mg, 63%).

MS (ESI, pos. ion) m/z: 484.6[M+H]⁺;
HRMS (ESI, pos. ion) m/z: 484.1972[M+H]⁺, (C₂₅H₂₅F₃N₅O₂) [M+H]⁺ theoretical value: 484.1960;
¹H NMR (600 MHz, DMSO-d₆) δ (ppm): 12.03 (s, 1H), 8.25 (d, J=10.1 Hz, 1H), 8.14 (d, J=2.4 Hz, 1H), 7.26 (d, J=6.6 Hz, 1H), 7.14 (d, J=3.2 Hz, 1H), 7.03 (t, J=10.4 Hz, 1H), 6.65 (s, 1H), 4.89 (t, J=4.7 Hz, 1H), 4.77 (t, J=4.8 Hz, 2H), 4.55 (d, J=3.4 Hz, 1H), 4.48 (d, J=3.5 Hz, 1H), 2.72 (d, J=6.4 Hz, 1H), 2.03 (d, J=11.8 Hz, 2H), 1.91-1.33 (m, 9H).

Example 35: (+/−)-trans-3-((2-(5,7-difluoro-1H-indol-3-yl)-7-isopropyl-7H-pyrrolo[2,3-d]pyrimidin-4-yl)amino)bicyclo[2.2.2]octane-2-carboxylic Acid

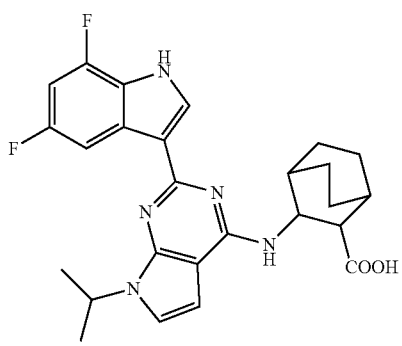 [SMILES: CC(C)n1ccc2c(NC3C4CCC(CC4)C3C(=O)O)nc(-c3c[nH]c4c(F)cc(F)cc34)nc21]

Step 1: 2,4-dichloro-7-isopropyl-7H-pyrrolo[2,3-d]pyrimidine

A solution of 2,4-dichloro-7H-pyrrolo[2,3-d]pyrimidine (500 mg, 2.66 mmol) in DMF (8 mL) was stirred at 0° C. for 5 min, then to the solution was added sodium hydroxide (130 mg, 3.19 mmol, weight content 60%). The mixture was stirred for further 15 min at 0° C., and iso-popyl iodide (904 mg, 5.32 mmol) was added. The mixture was stirred at rt overnight. To the reaction mixture was added H₂O (100 mL) to quench the reaction, and the mixture was extracted with EtOAc (50 mL×3). The combined organic layers were washed with saturated brine (80 mL), dried over anhydrous sodium sulfate, and filtered. The filtrate was concentrated in vacuo, and the residue was purified by silica gel column chromatography (PE/EtOAc (v/v)=10/1) to give the title compound as a white solid (460 mg, 75%).

MS (ESI, pos. ion) m/z: 231.05 [M+H]⁺.

Step 2: (+/−)-trans-methyl 3-((2-chloro-7-isopropyl-7H-pyrrolo[2,3-d]pyrimidin-4-yl)amino)bicyclo[2.2.2]octane-2-carboxylate A suspension of 2,4-dichloro-7-isopropyl-7H-pyrrolo[2,3-d]pyrimidine (460 mg, 2.00 mmol), (+/−)-trans-methyl 3-aminobicyclo[2.2.2]octane-2-carboxylate (440 mg, 2.20 mmol) and K₂CO₃ (553 mg, 4.00 mmol) in DMF (10 mL) was stirred at rt overnight. To the reaction mixture was added H₂O (50 mL) to quench the reaction, and the mixture was extracted with EtOAc (50 mL×3). The combined organic layers were washed with saturated brine (80 mL×3), dried over anhydrous sodium sulfate, and filtered. The filtrate was concentrated in vacuo, and the residue was purified by silica gel column chromatography (PE/EtOAc (v/v)=3/1) to give the title compound as a white solid (471 mg, 63%).

MS (ESI, pos. ion) m/z: 378.50 [M+H]⁺.

Step 3: (+/−)-trans-methyl 3-((2-(5,7-difluoro-1-tosyl-1H-indol-3-yl)-7-isopropyl-7H-pyrrolo[2,3-d]pyrimidin-4-yl)amino)bicyclo[2.2.2]octane-2-carboxylate To a mixed solvent of 1,4-dioxane (8 mL) and H₂O (1 mL) were added 5,7-difluoro-3-(4,4,5,5-tetramethyl-1,3,2-dioxaborolan-2-yl)-1-tosyl-1H-indole (190 mg, 0.44 mmol), K₂CO₃ (166 mg, 1.19 mmol), Pd(dppf)Cl₂ (21 mg, 0.04 mmol), (+/−)-trans-methyl 3-((2-chloro-7-isopropyl-7H-pyrrolo[2,3-d]pyrimidin-4-yl)amino)bicyclo[2.2.2]octane-2-carboxylate (150 mg, 0.40 mmol). A stream of nitrogen was bubbled through the mixture for 10 min to remove air, then the mixture was stirred at 115° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give a white solid (110 mg, 43%).

Step 4: (+/−)-trans-3-((2-(5,7-difluoro-1H-indol-3-yl)-7-isopropyl-7H-pyrrolo[2,3-d]pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-7-isopropyl-7H-pyrrolo[2,3-d]pyrimidin-4-yl)amino)bicyclo[2.2.2]octane-2-carboxylate (98 mg, 0.15 mmol) in THF/MeOH (v/v=1/1, 10 mL) was added a solution of sodium hydroxide (66 mg, 1.51 mmol) in water (1 mL). The mixture was stirred at rt overnight. The reaction mixture was diluted with water (20 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1~5/1) to give the title compound as a white solid (36 mg, 50%).

MS (ESI, pos. ion) m/z: 480.2[M+H]$^+$;

HRMS (ESI, pos. ion) m/z: 480.2220 [M+H]$^+$, ($C_{26}H_{28}F_2N_5O_2$) [M+H]$^+$ theoretical value: 480.2211;

$^1$H NMR (600 MHz, DMSO-d$_6$) δ (ppm): 12.02 (s, 1H), 8.26 (d, J=8.9 Hz, 1H), 8.14 (s, 1H), 7.19 (d, J=2.7 Hz, 2H), 7.02 (t, J=9.7 Hz, 1H), 6.63 (d, J=2.7 Hz, 1H), 5.00 (m, 1H), 4.78 (s, 1H), 2.72 (d, J=6.6 Hz, 1H), 2.02 (d, J=8.6 Hz, 2H), 1.93-1.67 (m, 4H), 1.58 (dd, J=13.7, 9.0 Hz, 3H), 1.50-1.46 (m, 6H), 1.36 (d, J=10.2 Hz, 1H);

$^{13}$C NMR (101 MHz, DMSO-d$_6$) δ (ppm): 176.13, 157.86, 155.93, 155.64, 155.54, 149.99, 149.79, 147.54, 147.40, 130.17, 129.04, 128.97, 128.85, 122.01, 121.88, 120.54, 118.48, 103.59, 103.36, 101.32, 99.07, 97.15, 96.94, 96.84, 96.64, 74.04, 50.56, 49.00, 45.73, 28.95, 26.05, 25.38, 24.16, 22.96, 21.58, 19.51.

Example 36: (+/−)-trans-3-((2-(5,7-difluoro-1H-indol-3-yl)-7-nonyl-7H-pyrrolo[2,3-d]pyrimidin-4-yl)amino)bicyclo[2.2.2]octane-2-carboxylic Acid

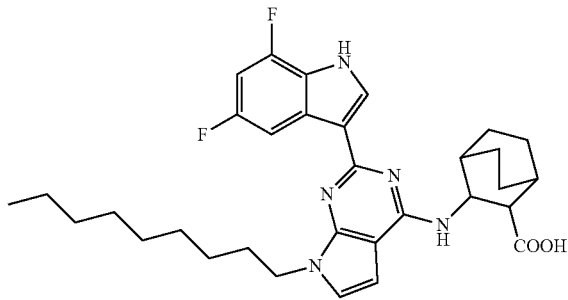 [SMILES: CCCCCCCCCn1ccc2c(NC3C4CCC(CC4)C3C(=O)O)nc(-c3c[nH]c4c(F)cc(F)cc34)nc21]

Step 1: 2,4-dichloro-7-nonyl-7H-pyrrolo[2,3-d]pyrimidine

A solution of 2,4-dichloro-7H-pyrrolo[2,3-d]pyrimidine (500 mg, 2.66 mmol) in THF (8 mL) was stirred at 0° C. for 5 min, then to the solution was added sodium hydroxide (130 mg, 3.24 mmol, weight content 60%). The mixture was stirred for further 15 min, and 1-bromononane (1.03 g, 5.32 mmol) was added. The mixture was stirred at rt overnight. To the reaction mixture was added H$_2$O (100 mL), and the mixture was extracted with EtOAc (50 mL×3). The combined organic layers were washed with saturated brine (80 mL), dried over anhydrous sodium sulfate, and filtered. The filtrate was concentrated in vacuo, and the residue was purified by silica gel column chromatography (PE/EtOAc (v/v)=10/1) to give the title compound as a white solid (821 mg, 98%).

MS (ESI, pos. ion) m/z: 314.05 [M+H]$^+$;

$^1$H NMR (600 MHz, CDCl$_3$) δ (ppm): 7.24 (d, J=3.6 Hz, 1H), 6.59 (d, J=3.5 Hz, 1H), 4.23 (t, J=7.3 Hz, 2H), 1.84 (m, 2H), 1.31-1.23 (m, 12H), 0.87 (t, J=7.0 Hz, 3H).

Step 2: (+/−)-trans-methyl 3-((2-chloro-7-nonyl-7H-pyrrolo[2,3-d]pyrimidin-4-yl)amino)bicyclo[2.2.2]octane-2-carboxylate A suspension of 2,4-dichloro-7-nonyl-7H-pyrrolo[2,3-d]pyrimidine (360 mg, 1.15 mmol), (+/−)-trans-methyl 3-aminobicyclo[2.2.2]octane-2-carboxylate (253 mg, 1.26 mmol) and K$_2$CO$_3$ (320 mg, 2.29 mmol) in DMF (10 mL) was stirred at rt overnight. To the reaction mixture was added H$_2$O (100 mL), and the mixture was extracted with EtOAc (50 mL×3). The combined organic layers were washed with saturated brine (80 mL×3), dried over anhydrous sodium sulfate, and filtered. The filtrate was concentrated in vacuo, and the residue was purified by silica gel column chromatography (PE/EtOAc (v/v)=3/1) to give the title compound as a white solid (200 mg, 38%).

Step 3: (+/−)-trans-methyl 3-((2-(5,7-difluoro-1-tosyl-1H-indol-3-yl)-7-nonyl-7H-pyrrolo[2,3-d]pyrimidin-4-yl)amino)bicyclo[2.2.2]octane-2-carboxylate To a mixed solvent of 1,4-dioxane (8 mL) and water (1 mL) were added 5,7-difluoro-3-(4,4,5,5-tetramethyl-1,3,2-dioxaborolan-2-yl)-1-tosyl-1H-indole (140 mg, 0.30 mmol), K$_2$CO$_3$ (120 mg, 0.83 mmol), Pd(dppf)Cl$_2$ (30 mg, 0.03 mmol), (+/−)-trans-methyl 3-((2-chloro-7-nonyl-7H-pyrrolo[2,3-d]pyrimidin-4-yl)amino)bicyclo[2.2.2]octane-2-carboxylate (120 mg, 0.28 mmol). A stream of nitrogen was bubbled through the mixture for 10 min to remove air, then the mixture was stirred at 115° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give a white solid (125 mg, 64%).

Step 4: (+/−)-trans-3-((2-(5,7-difluoro-1H-indol-3-yl)-7-nonyl-7H-pyrrolo[2,3-d]pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-7-nonyl-7H-pyrrolo[2,3-d]pyrimidin-4-yl)amino)bicyclo[2.2.2]octane-2-carboxylate (127 mg, 0.18 mmol) in a mixed solvent THF/MeOH (v/v=1/1, 10 mL) was added a solution of sodium hydroxide (75 mg, 1.85 mmol) in water (1 mL). The mixture was stirred at rt overnight. The reaction mixture was quenched with water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1~5/1) to give the title compound as a white solid (63 mg, 65%).

HRMS (ESI, pos. ion) m/z: 564.3156 [M+H]$^+$, ($C_{32}H_{40}F_2N_5O_2$) [M+H]$^+$ theoretical value: 564.3150;

$^1$H NMR (600 MHz, DMSO-d$_6$) δ (ppm): 12.00 (s, 1H), 8.29 (d, J=8.3 Hz, 1H), 8.12 (s, 1H), 7.08 (m, 3H), 6.61 (s, 1H), 4.78 (s, 1H), 4.18 (s, 2H), 2.72 (s, 1H), 2.02 (s, 2H), 1.81 (s, 5H), 1.60 (s, 3H), 1.17 (s, 10H), 0.78 (s, 3H);

$^{13}$C NMR (101 MHz, DMSO-d$_6$) δ (ppm): 176.12, 157.98, 156.14, 155.94, 150.42, 149.98, 147.39, 130.09, 129.01, 123.71, 122.02, 121.89, 118.50, 103.65, 103.43, 101.06, 98.91, 50.57, 49.06, 43.98, 31.66, 30.30, 29.35, 28.99, 28.92, 26.55, 26.09, 24.19, 22.47, 21.59, 19.54, 14.29.

Example 37: (+/−)-trans-3-((2-(5,7-difluoro-1H-indol-3-yl)-7-phenyl-7H-pyrrolo[2,3-d]pyrimidin-4-yl)amino)bicyclo[2.2.2]octane-2-carboxylic Acid

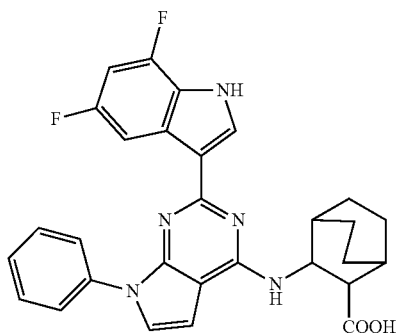 [SMILES: O=C(O)C1C2CCC(CC2)C1Nc1nc(-c2c[nH]c3c(F)cc(F)cc23)nc2c1ccn2-c1ccccc1]

Step 1: 2,4-dichloro-7-phenyl-7H-pyrrolo[2,3-d]pyrimidine

To a solution of 2,4-dichloro-7H-pyrrolo[2,3-d]pyrimidine (300 mg, 1.60 mmol) in DCM (5 mL) were added phenylboronic acid (215 mg, 1.76 mmol), Cu(OAc)$_2$ (580 mg, 3.19 mmol) and Et$_3$N (1.61 g, 15.95 mmol). The mixture was stirred at rt overnight under nitrogen protection. Water (50 mL) was added to quench the reaction, and the resulting mixture was extracted with EtOAc (50 mL×2). The combined organic phases were washed with saturated brine (80 mL), dried over anhydrous Na$_2$SO$_4$, filtered, and the filtrate was concentrated in vacuo. The residue was purified by silica gel chromatograph (PE/EtOAc (v/v)=10/1) to give the title compound as a yellow solid (296 mg, 70%).
MS (ESI, pos. ion) m/z: 265.35 [M+H]$^+$.

Step 2: (+/−)-trans-methyl 3-((2-chloro-7-phenyl-7H-pyrrolo[2,3-d]pyrimidin-4-yl)amino)bicyclo[2.2.2]octane-2-carboxylate To a solution of (+/−)-trans-methyl 3-aminobicyclo[2.2.2]octane-2-carboxylate (245 mg, 1.23 mmol) and 2,4-dichloro-7-phenyl-7H-pyrrolo[2,3-d]pyrimidine (296 mg, 1.12 mmol) in DMF (10 mL) was added K$_2$CO$_3$ (310 mg, 2.24 mmol). The mixture was stirred at rt overnight. Water (50 mL) was added to quench the reaction, and the resulting mixture was extracted with EtOAc (50 mL×2). The combined organic phases were washed with saturated brine (80 mL), dried over anhydrous Na$_2$SO$_4$, and the filtrate was concentrated in vacuo. The residue was purified by silica gel chromatograph (PE/EtOAc (v/v)=10/1) to give the title compound as a yellow solid (156 mg, 34%).
MS (ESI, pos. ion) m/z: 412.15 [M+H]$^+$.

Step 3: (+/−)-trans-methyl 3-((2-(5,7-difluoro-1-tosyl-1H-indol-3-yl)-7-phenyl-7H-pyrrolo[2,3-d]pyrimidin-4-yl)amino)bicyclo[2.2.2]octane-2-carboxylate To a mixed solvent of 1,4-dioxane (8 mL) and H$_2$O (1 mL) were added 5,7-difluoro-3-(4,4,5,5-tetramethyl-1,3,2-dioxaborolan-2-yl)-1-tosyl-1H-indole (150 mg, 0.33 mmol), K$_2$CO$_3$ (131 mg, 0.91 mmol), Pd(dppf)Cl$_2$ (21 mg, 0.03 mmol), (+/−)-trans-methyl 3-((2-chloro-7-phenyl-7H-pyrrolo[2,3-d]pyrimidin-4-yl)amino)bicyclo[2.2.2]octane-2-carboxylate (125 mg, 0.30 mmol). A stream of nitrogen was bubbled through the mixture for 10 min to remove air, then the mixture was stirred at 115° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give a white solid (89 mg, 43%).
MS (ESI, pos. ion) m/z: 682.6 [M+H]$^+$.

Step 4: (+/−)-trans-3-((2-(5,7-difluoro-1H-indol-3-yl)-7-phenyl-7H-pyrrolo[2,3-d]pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-7-phenyl-7H-pyrrolo[2,3-d]pyrimidin-4-yl)amino)bicyclo[2.2.2]octane-2-carboxylate (45 mg, 0.07 mmol) in a mixed solvent THF/MeOH (v/v=1/1, 10 mL) was added a solution of sodium hydroxide (66 mg, 1.51 mmol) in water (1 mL). The mixture was stirred at rt overnight. The reaction mixture was quenched with water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo, and the residue was purified by silica gel column chromatography (DCM/MeOH (v/v)=10/1~5/1) to give the title compound as a white solid (22 mg, 65%).
MS (ESI, pos. ion) m/z: 514.4[M+H]$^+$;
HRMS (ESI, pos. ion) m/z: 514.2060 [M+H]$^+$, (C$_{29}$H$_{26}$F$_2$N$_5$O$_2$) [M+H]$^+$ theoretical value: 514.2055;
$^1$H NMR (600 MHz, DMSO-d$_6$) δ (ppm): 12.05 (s, 1H), 8.22 (d, J=10.2 Hz, 1H), 8.12 (d, J=2.2 Hz, 1H), 7.95 (d, J=8.1 Hz, 2H), 7.59 (t, J=7.7 Hz, 2H), 7.51 (d, J=3.4 Hz, 1H), 7.40 (d, J=7.3 Hz, 2H), 7.02 (t, J=9.8 Hz, 1H), 6.89 (d, J=2.7 Hz, 1H), 4.81 (s, 1H), 2.74 (d, J=6.6 Hz, 1H), 2.04 (d, J=12.2 Hz, 2H), 1.88-1.36 (m, 9H).

Example 38: (+/−)-trans-3-((7-chloro-2-(5,7-difluoro-1H-indol-3-yl)quinazolin-4-yl)amino)bicyclo[2.2.2]octane-2-carboxylic Acid

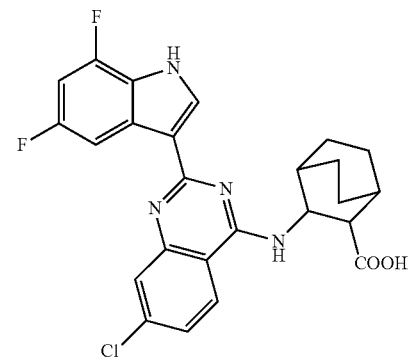 [SMILES: O=C(O)C1C2CCC(CC2)C1Nc1nc(-c2c[nH]c3c(F)cc(F)cc23)nc2cc(Cl)ccc12]

Step 1: (+/−)-trans-methyl 3-((2,7-dichloroquinazolin-4-yl)amino)bicyclo[2.2.2]octane-2-carboxylate A suspension of 2,4,7-trichloroquinazoline (120 mg, 0.60 mmol), (+/−)-trans-methyl 3-aminobicyclo[2.2.2]octane-2- carboxylate (131 mg, 0.72 mmol) and DIPEA (1.1 mL, 5.97 mmol) in THF (5 mL) was stirred at rt overnight. The reaction was quenched with H₂O (100 mL), and the mixture was partitioned. The aqueous layer was extracted with EtOAc (50 mL×3). The combined organic layers were washed with saturated brine (80 mL×3), dried over anhydrous sodium sulfate, and filtered. The filtrate was concentrated in vacuo, and the residue was purified by silica gel column chromatography (PE/EtOAc (v/v)=3/1) to give the title compound as a white solid (156 mg, 75%).

Step 2: (+/−)-trans-methyl 3-((7-chloro-2-(5,7-difluoro-1-tosyl-1H-indol-3-yl)quinazolin-4-yl)amino)bicyclo[2.2.2]octane-2-carboxylate To a mixed solvent of 1,4-dioxane (8 mL) and H₂O (1 mL) were added 5,7-difluoro-3-(4,4,5,5-tetramethyl-1,3,2-dioxaborolan-2-yl)-1-tosyl-1H-indole (50 mg, 0.11 mmol), K₂CO₃ (50 mg, 0.29 mmol), Pd(dppf)Cl₂ (9 mg, 0.01 mmol) and (+/−)-trans-methyl 3-((2,7-dichloroquinazolin-4-yl)amino)bicyclo[2.2.2]octane-2-carboxylate (37 mg, 0.10 mmol). A stream of nitrogen was bubbled through the mixture for 10 min to remove air, then the mixture was stirred at 115° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give a white solid (45 mg, 71%).

Step 3: (+/−)-trans-3-((7-chloro-2-(5,7-difluoro-1H-indol-3-yl)quinazolin-4-yl)amino)bicyclo[2.2.2]octane-2-carboxylic Acid To a solution of (+/−)-trans-methyl 3-((7-chloro-2-(5,7-difluoro-1-tosyl-1H-indol-3-yl) quinazolin-4-yl)amino)bicyclo[2.2.2]octane-2-carboxylate (45 mg, 0.07 mmol) in a mixed solvent THF/MeOH (v/v=1/1, 10 mL) was added a solution of NaOH (29 mg, 0.70 mmol) in water (1 mL). The mixture was stirred at rt overnight. The reaction mixture was quenched with water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo, and the residue was purified by silica gel column chromatography (DCM/MeOH (v/v)=10/1~5/1) to give the title compound as a white solid (18 mg, 54%).

MS (ESI, pos. ion) m/z: 483.5[M+H]⁺;
HRMS (ESI, pos. ion) m/z: 483.1419[M+H]⁺, (C₂₅H₂₂ClF₂N₄O₂) [M+H]⁺ theoretical value: 483.1399;
¹H NMR (600 MHz, DMSO-d₆) δ (ppm): 12.26 (s, 1H), 8.41 (d, J=8.8 Hz, 1H), 8.30 (d, J=10.0 Hz, 1H), 8.24 (s, 1H), 7.92 (d, J=6.3 Hz, 1H), 7.74 (d, J=2.0 Hz, 1H), 7.46 (d, J=8.7 Hz, 1H), 7.07 (t, J=10.5 Hz, 1H), 5.34-5.31 (m, 1H), 4.89 (s, 1H), 2.93 (s, 1H), 2.07 (s, 2H), 2.02-1.94 (m, 2H), 1.79 (s, 2H), 1.63-1.44 (m, 4H).

Example 39: (+/−)-trans-3-((2-(5,7-difluoro-1H-indol-3-yl)-8-(trifluoromethyl)quinazolin-4-yl)amino)bicyclo[2.2.2]octane-2-carboxylic Acid

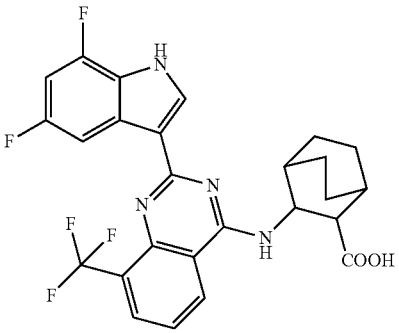 [SMILES: O=C(O)C1C2CCC(CC2)C1Nc1nc(-c2c[nH]c3c(F)cc(F)cc23)nc2c(C(F)(F)F)cccc12]

Step 1:
8-(trifluoromethyl)quinazoline-2,4(1H,3H)-dione

A mixture of 2-amino-3-(difluoromethyl)benzoic acid (3.00 g, 14.62 mmol) and urea (12.00 g, 199.80 mmol) was heated to 160° C. and stirred for 10 h, then cooled to 100° C. To the reaction mixture was added water (100 mL), and the resulting mixture was stirred for 5 min. After the reaction, the mixture was filtered and the filter cake was washed with water (100 mL). The filter cake was added into a sodium hydroxide solution (0.5 M, 100 mL), and the mixture was kept boiling for 10 min. Then the mixture was cooled, and acidified with diluted hydrochloric acid (1 M) to pH about 1 to 2. The resulting mixture was filtered, and the filter cake was washed with water to give the title compound as a yellow solid (2.14 g, 64%).

MS (ESI, pos. ion) m/z: 230.95 [M+H]⁺.

Step 2: 2,4-dichloro-8-(trifluoromethyl)quinazoline

A solution of 8-(trifluoromethyl)quinazoline-2,4(1H,3H)-dione (2.14 g, 9.30 mmol) in phosphorus oxychloride (10 mL) was stirred at 115° C. overnight. The reaction was stopped, and the mixture was concentrated in vacuo to remove phosphorus oxychloride. The residue was purified by silica gel column chromatography (PE/EtOAc (v/v)=15/1) to give the title compound as white powder (1.09 g, 44%).

MS (ESI, pos. ion) m/z: 267.0[M+H]⁺;
¹H NMR (400 MHz, CDCl₃) δ (ppm): 8.51 (d, J=8.4 Hz, 1H), 8.36 (d, J=7.4 Hz, 1H), 7.84 (t, J=7.9 Hz, 1H).

Step 3: (+/−)-trans-methyl 3-((2-chloro-8-(trifluoromethyl)quinazolin-4-yl)amino)bicyclo[2.2.2]octane-2-carboxylate A suspension of 2,4-dichloro-8-(trifluoromethyl)quinazoline (300 mg, 1.12 mmol), (+/−)-trans-methyl 3-aminobicyclo[2.2.2]octane-2-carboxylate (247 mg, 1.35 mmol) and DIPEA (1.90 mL, 11.23 mmol) in THF (10 mL) was stirred at rt overnight. To the reaction mixture was added H₂O (100 mL), and the mixture was partitioned. The aqueous layer was extracted with EtOAc (50 mL×3). The combined organic layers were washed with saturated brine (80 mL), dried over anhydrous sodium sulfate, and filtered. The filtrate was concentrated in vacuo, and the residue was purified by silica gel column chromatography (PE/EtOAc (v/v)=5/1~2/1) to give the title compound as a white solid (390 mg, 84%).

MS (ESI, pos. ion) m/z: 414.10 [M+H]$^+$;

$^1$H NMR (400 MHz, CDCl$_3$) δ (ppm): 8.09 (d, J=7.3 Hz, 1H), 7.89 (d, J=8.2 Hz, 1H), 7.52 (t, J=7.7 Hz, 1H), 6.01 (s, 1H), 4.66 (s, 1H), 3.81 (s, 3H), 2.47 (d, J=4.7 Hz, 1H), 2.07 (s, 1H), 2.02 (d, J=10.9 Hz, 2H), 1.89 (d, J=12.8 Hz, 1H), 1.75-1.66 (m, 6H).

Step 4: (+/−)-trans-methyl 3-((2-(5,7-difluoro-1-tosyl-1H-indol-3-yl)-8-(trifluoromethyl) quinazolin-4-yl)amino)bicyclo[2.2.2]octane-2-carboxylate To a mixed solvent of 1,4-dioxane (8 mL) and H$_2$O (1 mL) were added 5,7-difluoro-3-(4,4,5,5-tetramethyl-1,3,2-dioxaborolan-2-yl)-1-tosyl-1H-indole (120 mg, 0.27 mmol), K$_2$CO$_3$ (110 mg, 0.73 mmol), Pd(dppf)Cl$_2$ (20 mg, 0.02 mmol), (+/−)-trans-methyl 3-((2-chloro-8-(trifluoromethyl)quinazolin-4-yl)amino)bicyclo[2.2.2]octane-2-carboxylate (100 mg, 0.24 mmol). A stream of nitrogen was bubbled through the mixture for 10 min to remove air, then the mixture was stirred at 115° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give the title compound as a white solid (68 mg, 41%).

MS (ESI, pos. ion) m/z: 685.10 [M+H]$^+$;

$^1$H NMR (600 MHz, CDCl$_3$) δ (ppm): 8.87 (s, 1H), 8.61 (dd, J=9.3, 2.3 Hz, 1H), 8.10 (d, J=7.3 Hz, 1H), 7.92 (dd, J=7.6, 4.1 Hz, 2H), 7.49 (t, J=7.8 Hz, 1H), 7.31 (d, J=8.2 Hz, 2H), 6.82 (m, 1H), 5.94 (d, J=6.4 Hz, 1H), 4.99 (s, 1H), 3.77 (s, 3H), 2.52 (d, J=5.4 Hz, 1H), 2.42 (s, 3H), 2.15 (d, J=2.8 Hz, 1H), 2.13-2.10 (m, 1H), 2.02 (dd, J=15.1, 10.2 Hz, 2H), 1.91-1.64 (m, 6H), 1.56-1.51 (m, 1H).

Step 5: (+/−)-trans-3-((2-(5,7-difluoro-1H-indol-3-yl)-8-(trifluoromethyl)quinazolin-4-yl)amino)bicyclo[2.2.2]octane-2-carboxylic Acid To a solution of (+/−)-trans-methyl 3-((2-(5,7-difluoro-1-tosyl-1H-indol-3-yl)-8-(trifluoromethyl)quinazolin-4-yl)amino)bicyclo[2.2.2]octane-2-carboxylate (62 mg, 0.09 mmol) in THF/MeOH (v/v=1 mL/10 mL) was added a solution of NaOH (60 mg, 1.5 mmol) in water (1 mL). The mixture was stirred at rt overnight. The reaction mixture was quenched with water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo, and the residue was purified by silica gel column chromatography (DCM/MeOH (v/v)=10/1~5/1) to give the title compound as a white solid (36 mg, 77%).

MS (ESI, pos. ion) m/z: 517.2[M+H]$^+$;

HRMS (ESI, pos. ion) m/z: 517.1648 [M+H]$^+$, (C$_{26}$H$_{22}$F$_5$N$_4$O$_2$) [M+H]$^+$ theoretical value: 517.1663;

$^1$H NMR (600 MHz, DMSO-d$_6$) δ (ppm): 12.28 (s, 1H), 8.65 (d, J=8.1 Hz, 1H), 8.37 (d, J=9.9 Hz, 1H), 8.24 (d, J=2.0 Hz, 1H), 8.12 (d, J=7.3 Hz, 1H), 8.02 (d, J=6.0 Hz, 1H), 7.52 (t, J=7.7 Hz, 1H), 7.08 (t, J=9.9 Hz, 1H), 4.86 (s, 1H), 2.92 (d, J=6.4 Hz, 1H), 2.07 (d, J=9.0 Hz, 2H), 1.88-1.36 (m, 8H);

$^{13}$C NMR (101 MHz, DMSO-d$_6$) δ (ppm): 175.97, 159.80, 159.24, 156.12, 149.89, 147.92, 147.53, 132.45, 131.10, 129.05, 128.35, 126.20, 124.64, 124.39, 123.07, 122.28, 122.15, 117.51, 114.48, 103.71, 103.43, 97.74, 97.54, 97.45, 97.35, 97.24, 51.60, 48.27, 28.79, 28.27, 25.94, 24.34, 21.59, 19.73.

Example 40: (+/−)-trans-3-((6-cyano-2-(5,7-difluoro-1H-indol-3-yl)quinazolin-4-yl)amino)bicyclo[2.2.2]octane-2-carboxylic Acid

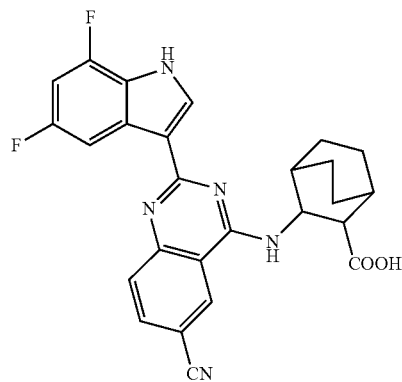 [SMILES: N#Cc1ccc2nc(-c3c[nH]c4c(F)cc(F)cc34)nc(NC3C4CCC(CC4)C3C(=O)O)c2c1]

Step 1: (+/−)-trans-methyl 3-((2-chloro-6-cyanoquinazolin-4-yl)amino)bicyclo[2.2.2]octane-2-carboxylate A suspension of 2,4-dichloroquinazoline-6-carbonitrile (120 mg, 0.60 mmol), (+/−)-trans-methyl 3-aminobicyclo[2.2.2]octane-2-carboxylate (131 mg, 0.72 mmol) and DIPEA (1.1 mL, 5.97 mmol) in THF (5 mL) was stirred at rt overnight. To the reaction mixture was added H$_2$O (100 mL) to quench the reaction, and the mixture was partitioned. The aqueous layer was extracted with EtOAc (50 mL×3). The combined organic layers were washed with saturated brine (80 mL×3), dried over anhydrous sodium sulfate, and filtered. The filtrate was concentrated in vacuo, and the residue was purified by silica gel column chromatography (PE/EtOAc (v/v)=3/1) to give the title compound as a white solid (156 mg, 75%).

Step 2: (+/−)-trans-methyl 3-((6-cyano-2-(5,7-difluoro-1-tosyl-1H-indol-3-yl)quinazolin-4-yl)amino) bicyclo[2.2.2]octane-2-carboxylate To a mixed solvent of 1,4-dioxane (8 mL) and H$_2$O (1 mL) were added 5,7-difluoro-3-(4,4,5,5-tetramethyl-1,3,2-dioxaborolan-2-yl)-1-tosyl-1H-indole (110 mg, 0.24 mmol), K$_2$CO$_3$ (61 mg, 0.43 mmol), PdCl$_2$(dppf) (22 mg, 0.02 mmol) and (+/−)-trans-methyl 3-((2-chloro-6-cyanoquinazolin-4-yl)amino)bicyclo[2.2.2]octane-2-carboxylate (80 mg, 0.22 mmol). A stream of nitrogen was bubbled through the mixture for 10 min to remove air, then the mixture was stirred at 115° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give the title compound as a white solid (96 mg, 69%).

MS (ESI, pos. ion) m/z: 642.10 [M+H].

Step 3: (+/−)-trans-3-((6-cyano-2-(5,7-difluoro-1H-indol-3-yl)quinazolin-4-yl)amino)bicyclo[2.2.2]octane-2-carboxylic Acid To a solution of (+/−)-trans-methyl 3-((6-cyano-2-(5,7-difluoro-1-tosyl-1H-indol-3-yl)quinazolin-4-yl)amino)bicyclo[2.2.2]octane-2-carboxylate (181 mg, 0.28 mmol) in THF/MeOH (v/v=1 mL/10 mL) was added a solution of NaOH (115 mg, 2.82 mmol) in water (1 mL). The mixture was stirred at rt overnight. To the reaction mixture was added water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo, and the residue was purified by silica gel column chromatography (DCM/MeOH (v/v)=10/1~5/1) to give the title compound as a white solid (23 mg, 17%).

MS (ESI, pos. ion) m/z: 474.5 [M+H];
HRMS (ESI, pos. ion) m/z: 474.1754 [M+H]$^+$, ($C_{26}H_{22}F_2N_5O_2$) [M+H]$^+$ theoretical value: 474.1742;
$^1$H NMR (600 MHz, DMSO-d$_6$) δ (ppm): 12.44 (s, 1H), 8.99 (s, 1H), 8.37 (s, 1H), 8.25 (d, J=8.9 Hz, 2H), 8.01 (d, J=6.9 Hz, 1H), 7.80 (d, J=6.9 Hz, 1H), 7.10 (s, 1H), 4.92 (s, 1H), 2.94 (s, 1H), 2.01-1.75 (m, 4H), 1.65-1.40 (m, 6H).

Example 41: (+/−)-trans-3-((2-(5,7-difluoro-1H-indol-3-yl)-7-methylquinazolin-4-yl) amino)bicyclo [2.2.2]octane-2-carboxylic Acid

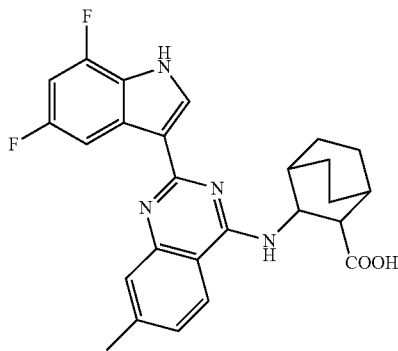 [SMILES: Cc1ccc2c(NC3C4CCC(CC4)C3C(=O)O)nc(-c3c[nH]c4c(F)cc(F)cc34)nc2c1]

Step 1: 7-methylquinazoline-2,4(1H,3H)-dione

A mixture of 4-methyl-2-aminobenzoic acid (2.00 g, 13.23 mmol) and urea (8.00 g, 133.21 mmol) was heated to 160° C. and stirred for 10 h, then cooled to 100° C. To the reaction mixture was added water (100 mL), and the resulting mixture was stirred for 5 min. After the reaction, the mixture was filtered and the filter cake was washed with water (100 mL). The filter cake was added into a sodium hydroxide solution (0.5 M, 100 mL), and the mixture was kept boiling for 10 min. Then the mixture was cooled, and acidified with diluted hydrochloric acid (1 M) to pH about 1 to 2. The resulting mixture was filtered, and the filter cake was washed with water (100 mL) to give the title compound as a yellow solid (2.30 g, 99%).

Step 2: 2,4-dichloro-7-methylquinazoline

A solution of 7-methylquinazoline-2,4(1H,3H)-dione (2.30 g, 13.00 mmol) in phosphorus oxychloride (10 mL) was stirred at 115° C. overnight. The reaction was stopped, and the mixture was concentrated in vacuo to remove phosphorus oxychloride. The residue was purified by silica gel column chromatography (PE/EtOAc (v/v)=15/1) to give the title compound as white powder (730 mg, 26%).

Step 3: (+/−)-trans-methyl 3-((2-chloro-7-methylquinazolin-4-yl)amino)bicyclo[2.2.2]octane-2-carboxylate A suspension of 2,4-dichloro-7-methylquinazoline (800 mg, 3.75 mmol), (+/−)-trans-methyl 3-aminobicyclo[2.2.2] octane-2-carboxylate (823 mg, 4.13 mmol) and DIPEA (3.1 mL, 19.00 mmol) in THF (10 mL) was stirred at rt overnight. To the reaction mixture was added H$_2$O (100 mL), and the mixture was partitioned. The aqueous layer was extracted with EtOAc (50 mL×3). The combined organic layers were washed with saturated brine (80 mL), dried over anhydrous sodium sulfate, and filtered. The filtrate was concentrated in vacuo, and the residue was purified by silica gel column chromatography (PE/EtOAc (v/v)=5/1~2/1) to give the title compound as a white solid (1.15 g, 85%).

MS (ESI, pos. ion) m/z: 360.20 [M+H]$^+$;
$^1$H NMR (400 MHz, CDCl$_3$) δ (ppm): 7.60 (d, J=8.4 Hz, 1H), 7.51 (s, 1H), 7.24 (d, J=8.4 Hz, 1H), 6.05 (s, 1H), 4.60 (s, 1H), 3.78 (s, 3H), 2.51 (d, J=5.6 Hz, 1H), 2.47 (s, 3H), 1.98 (s, 2H), 1.91-1.51 (m, 8H).

Step 4: (+/−)-trans-methyl 3-((2-(5,7-difluoro-1-tosyl-1H-indol-3-yl)-7-methylquinazolin-4-yl) amino)bicyclo[2.2.2]octane-2-carboxylate To a mixed solvent of 1,4-dioxane (8 mL) and H$_2$O (1 mL) were added 5,7-difluoro-3-(4,4,5,5-tetramethyl-1,3,2-dioxaborolan-2-yl)-1-tosyl-1H-indole (140 mg, 0.31 mmol), K$_2$CO$_3$ (120 mg, 0.83 mmol), PdCl$_2$(dppf) (20 mg, 0.03 mmol) and (+/−)-trans-methyl 3-((2-chloro-7-methylquinazolin-4-yl)amino)bicyclo[2.2.2]octane-2-carboxylate (100 mg, 0.28 mmol). A stream of nitrogen was bubbled through the mixture for 10 min to remove air, then the mixture was stirred at 115° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give the title compound as a white solid (85 mg, 48%).

$^1$H NMR (400 MHz, CDCl$_3$) δ (ppm): 8.81 (s, 1H), 8.52 (d, J=9.2 Hz, 1H), 7.92 (d, J=7.9 Hz, 2H), 7.73 (s, 1H), 7.60 (d, J=8.4 Hz, 1H), 7.31 (s, 2H), 6.80 (t, J=9.4 Hz, 1H), 5.75 (s, 1H), 4.98 (s, 1H), 3.74 (s, 3H), 2.56 (s, 3H), 2.53 (s, 1H), 2.41 (s, 3H), 2.16 (s, 1H), 2.11 (s, 1H), 2.05-1.96 (m, 2H), 1.75 (d, J=9.6 Hz, 5H), 1.45 (s, 2H).

Step 5: (+/−)-trans-3-((2-(5,7-difluoro-1H-indol-3-yl)-7-methylquinazolin-4-yl)amino)bicyclo[2.2.2] octane-2-carboxylic Acid To a solution of (+/−)-trans-methyl 3-((2-(5,7-difluoro-1-tosyl-1H-indol-3-yl)-7-methylquinazolin-4-yl)amino)bicyclo[2.2.2]octane-2-carboxylate (85 mg, 0.13 mmol) in THF/MeOH (v/v=1 mL/10 mL) was added a solution of NaOH (55 mg, 1.35 mmol) in water (1 mL). The mixture was stirred at rt overnight. The reaction mixture was diluted with water (20 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo, and the residue was purified by silica gel column chromatography (DCM/MeOH (v/v)=10/1~5/1) to give the title compound as a white solid (33 mg, 53%).

MS (ESI, pos. ion) m/z: 463.5[M+H]⁺;
HRMS (ESI, pos. ion) m/z: 463.1945 [M+H]⁺, ($C_{26}H_{25}F_2N_4O_2$) [M+H]⁺ theoretical value: 463.1946;
¹H NMR (600 MHz, DMSO-$d_6$) δ (ppm): 12.27 (s, 1H), 8.39-8.29 (m, 2H), 8.20 (s, 1H), 7.77 (d, J=5.7 Hz, 1H), 7.48 (s, 1H), 7.21 (d, J=8.0 Hz, 1H), 7.03 (t, J=10.0 Hz, 1H), 4.96 (s, 1H), 2.88 (d, J=5.5 Hz, 1H), 2.45 (s, 3H), 2.05 (s, 2H), 1.81 (d, J=7.8 Hz, 2H), 1.58-1.34 (m, 5H).

Example 42: (+/−)-trans-3-((8-(tert-butyl)-2-(5,7-difluoro-1H-indol-3-yl)quinazolin-4-yl)amino)bicyclo[2.2.2]octane-2-carboxylic Acid

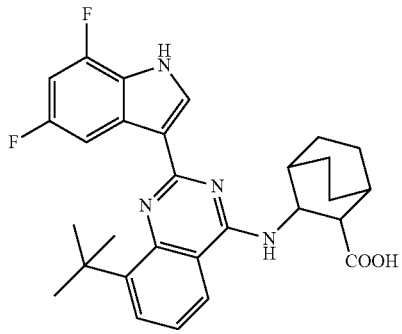 [SMILES: CC(C)(C)c1cccc2c(NC3C4CCC(CC4)C3C(=O)O)nc(-c3c[nH]c4c(F)cc(F)cc34)nc12]

Step 1: 8-(tert-butyl)quinazoline-2,4(1H,3H)-dione

A mixture of 2-amino-3-(tert-butyl)benzoic acid (3.00 g, 15.52 mmol) and urea (9.40 g, 155.20 mmol) was heated to 160° C. and stirred for 10 h, then cooled to 100° C. To the reaction mixture was added water (100 mL), and the resulting mixture was stirred for 5 min. After the reaction, the mixture was filtered and the filter cake was washed with water (100 mL). The filter cake was added into a sodium hydroxide solution (0.5 M, 100 mL), and the mixture was kept boiling for 10 min. Then the mixture was cooled, and acidified with diluted hydrochloric acid (1 M) to pH about 1 to 2. The resulting mixture was filtered, and the filter cake was washed with water (100 mL) to give the title compound as a yellow solid (2.82 g, 83%).

MS (ESI, pos. ion) m/z: 219.10 [M+H]⁺.

Step 2: 8-(tert-butyl)-2,4-dichloroquinazoline

A solution of 8-(tert-butyl)quinazoline-2,4(1H,3H)-dione (2.82 g, 12.90 mmol) in phosphorus oxychloride (10 mL) was stirred at 115° C. overnight. The reaction was stopped, and the mixture was concentrated in vacuo to remove phosphorus oxychloride. The residue was purified by silica gel column chromatography (PE/EtOAc (v/v)=15/1) to give the title compound as white powder (360 mg, 11%).

MS (ESI, pos. ion) m/z: 256.10 [M+H]⁺;
¹H NMR (400 MHz, CDCl₃) δ (ppm): 8.20 (dd, J=8.8, 1.7 Hz, 1H), 7.98 (s, 1H), 7.84 (dd, J=8.8, 1.8 Hz, 1H), 1.45 (d, J=2.0 Hz, 9H).

Step 3: (+/−)-trans-methyl 3-((8-(tert-butyl)-2-chloroquinazolin-4-yl)amino)bicyclo[2.2.2]octane-2-carboxylate A suspension of 8-(tert-butyl)-2,4-dichloroquinazoline (360 mg, 1.41 mmol), (+/−)-trans-methyl 3-aminobicyclo[2.2.2]octane-2-carboxylate (311 mg, 1.69 mmol) and DIPEA (2.50 mL, 14.11 mmol) in THF (10 mL) was stirred at rt overnight. To the reaction mixture was added H₂O (100 mL), and the mixture was partitioned. The aqueous layer was extracted with EtOAc (50 mL×3). The combined organic layers were washed with saturated brine (80 mL), dried over anhydrous sodium sulfate, and filtered. The filtrate was concentrated in vacuo, and the residue was purified by silica gel column chromatography (PE/EtOAc (v/v)=5/1~2/1) to give the title compound as a white solid (459 mg, 81%).

MS (ESI, pos. ion) m/z: 403.10 [M+H]⁺;
¹H NMR (400 MHz, CDCl₃) δ (ppm): 7.76 (d, J=1.7 Hz, 1H), 7.62 (d, J=8.7 Hz, 1H), 7.52 (dd, J=8.6, 1.9 Hz, 1H), 5.93 (d, J=5.2 Hz, 1H), 4.63 (d, J=5.3 Hz, 1H), 3.80 (s, 3H), 2.49 (dd, J=3.9, 1.7 Hz, 1H), 2.00 (m, 2H), 1.93-1.60 (m, 9H), 1.38 (s, 9H).

Step 4: (+/−)-trans-methyl 3-((8-(tert-butyl)-2-(5,7-difluoro-1-tosyl-1H-indol-3-yl)quinazolin-4-yl)amino)bicyclo[2.2.2]octane-2-carboxylate To a mixed solvent of 1,4-dioxane (8 mL) and H₂O (1 mL) were added 5,7-difluoro-3-(4,4,5,5-tetramethyl-1,3,2-dioxaborolan-2-yl)-1-tosyl-1H-indole (120 mg, 0.27 mmol), K₂CO₃ (110 mg, 0.75 mmol), PdCl₂(dppf) (20 mg, 0.02 mmol), (+/−)-trans-methyl 3-((8-(tert-butyl)-2-chloroquinazolin-4-yl)amino)bicyclo[2.2.2]octane-2-carboxylate (100 mg, 0.25 mmol). A stream of nitrogen was bubbled through the mixture for 10 min to remove air, then the mixture was stirred at 115° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give the title compound as a white solid (88 mg, 53%).

¹H NMR (600 MHz, CDCl₃) δ (ppm): 8.80 (s, 1H), 8.53 (d, J=7.2 Hz, 1H), 7.95-7.84 (m, 3H), 7.66 (d, J=8.6 Hz, 1H), 7.53 (d, J=6.9 Hz, 1H), 7.31 (s, 2H), 6.81 (t, J=9.4 Hz, 1H), 5.76 (d, J=6.4 Hz, 1H), 4.98 (s, 1H), 3.73 (s, 3H), 2.52 (d, J=5.6 Hz, 1H), 2.41 (s, 3H), 2.16 (s, 1H), 2.11 (s, 1H), 2.06-1.94 (m, 2H), 1.83-1.71 (m, 5H), 1.45 (s, 9H), 0.89 (m, 2H).

Step 5: (+/−)-trans-3-((8-(tert-butyl)-2-(5,7-difluoro-1H-indol-3-yl)quinazolin-4-yl)amino)bicyclo[2.2.2]octane-2-carboxylic Acid To a solution of (+/−)-trans-methyl 3-((2-(5,7-difluoro-1-tosyl-1H-indol-3-yl)-8-dimethylquinazolin-4-yl)amino)bicyclo[2.2.2]octane-2-carboxylate (96 mg, 0.14 mmol) in a mixed solvent THF/MeOH (v/v=1 mL/10 mL) was added a solution of NaOH (60 mg, 1.5 mmol) in water (1 mL). The mixture was stirred at rt overnight. The reaction mixture was quenched with water (20 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo, and the residue was purified by column chromatography (DCM/MeOH (v/v)=10/1~5/1) to give the title compound as a white solid (42 mg, 58%).

MS (ESI, pos. ion) m/z: 505.6[M+H]⁺;
HRMS (ESI, pos. ion) m/z: 505.2428[M+H]⁺, ($C_{29}H_{31}F_2N_4O_2$) [M+H]⁺ theoretical value: 505.2415;

¹H NMR (600 MHz, DMSO-d₆) δ (ppm): 12.68 (s, 1H), 8.66 (s, 2H), 8.47 (d, J=8.7 Hz, 1H), 8.21 (d, J=9.7 Hz, 1H), 7.83 (s, 1H), 7.64 (d, J=8.7 Hz, 1H), 7.14 (t, J=10.3 Hz, 1H), 5.03 (s, 1H), 3.09 (d, J=6.2 Hz, 1H), 2.07 (d, J=14.9 Hz, 2H), 1.98-1.71 (m, 4H), 1.69-1.46 (m, 4H), 1.38 (s, 9H), 1.20 (s, 1H);

¹³C NMR (101 MHz, DMSO-d₆) δ (ppm): 175.77, 159.70, 157.87, 156.37, 150.07, 147.79, 147.65, 133.37, 128.78, 124.23, 123.94, 122.16, 122.00, 110.55, 103.55, 103.30, 98.28, 98.05, 52.25, 47.65, 35.60, 31.08, 28.86, 28.69, 25.66, 24.21, 21.55, 19.71.

Example 43: (+/−)-trans-3-((2-(5,7-difluoro-1H-indol-3-yl)-6,7-difluoroquinazolin-4-yl)amino)bicyclo[2.2.2]octane-2-carboxylic Acid

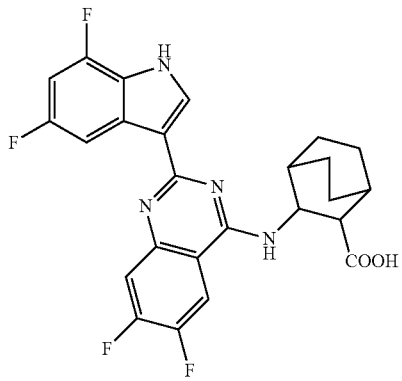 [SMILES: O=C(O)C1C2CCC(CC2)C1Nc1nc(-c2c[nH]c3c(F)cc(F)cc23)nc2cc(F)c(F)cc12]

Step 1: 6,7-difluoroquinazoline-2,4(1H,3H)-dione

A mixture of 2-amino-4,5-difluorobenzoic acid (1.00 g, 5.78 mmol) and urea (3.51 g, 57.76 mmol) was heated to 160° C. and stirred for 10 h, then cooled to 100° C. To the reaction mixture was added water (100 mL), and the resulting mixture was stirred for 5 min. After the reaction, the mixture was filtered and the filter cake was washed with water (100 mL). The filter cake was added into a sodium hydroxide solution (0.5 M, 100 mL), and the mixture was kept boiling for 10 min. Then the mixture was cooled, and acidified with diluted hydrochloric acid (1 M) to pH about 1 to 2. The resulting mixture was filtered, and the filter cake was washed with water (100 mL) to give the title compound as a yellow solid (835 mg, 73%).

MS (ESI, neg. ion) m/z: 197.0 [M−H]⁻.

Step 2: 2,4-dichloro-6,7-difluoroquinazoline

A solution of 6,7-difluoroquinazoline-2,4(1H,3H)-dione (3.34 g, 16.90 mmol) in phosphorus oxychloride (10 mL) was stirred at 115° C. overnight. The mixture was concentrated in vacuo to remove phosphorus oxychloride. The residue was purified by silica gel column chromatography (PE/EtOAc (v/v)=15/1) to give the title compound as white powder (185 mg, 5%).

¹H NMR (400 MHz, CDCl₃) δ (ppm): 8.10-7.99 (m, 1H), 7.80 (dd, J=9.9, 7.2 Hz, 1H).

Step 3: (+/−)-trans-methyl 3-((2-chloro-6,7-difluoroquinazolin-4-yl)amino)bicyclo[2.2.2]octane-2-carboxylate A suspension of 2,4-dichloro-6,7-difluoroquinazoline (184 mg, 0.78 mmol), (+/−)-trans-methyl 3-aminobicyclo[2.2.2]octane-2-carboxylate (180 mg, 0.94 mmol) and DIPEA (1.5 mL, 9.07 mmol) in THF (10 mL) was stirred at rt overnight. To the reaction mixture was added H₂O (100 mL) to quench the reaction, and the mixture was partitioned. The aqueous layer was extracted with EtOAc (50 mL×3). The combined organic layers were washed with saturated brine (80 mL), dried over anhydrous sodium sulfate, and filtered. The filtrate was concentrated in vacuo, and the residue was purified by silica gel column chromatography (PE/EtOAc (v/v)=5/1~2/1) to give the title compound as a white solid (254 mg, 85%).

MS (ESI, pos. ion) m/z: 382.0 [M+H]⁺;

¹H NMR (400 MHz, CDCl₃) δ (ppm): 7.53 (ddd, J=14.7, 10.3, 7.8 Hz, 2H), 5.97 (d, J=5.0 Hz, 1H), 4.63 (s, 1H), 3.79 (s, 3H), 2.52 (d, J=5.7 Hz, 1H), 2.03-1.97 (m, 3H), 1.91-1.63 (m, 7H).

Step 4: (+/−)-trans-methyl 3-((2-(5,7-difluoro-1-tosyl-1H-indol-3-yl)-6,7-difluoroquinazolin-4-yl)amino)bicyclo[2.2.2]octane-2-carboxylate To a mixed solvent of 1,4-dioxane (8 mL) and H₂O (1 mL) were added 5,7-difluoro-3-(4,4,5,5-tetramethyl-1,3,2-dioxaborolan-2-yl)-1-tosyl-1H-indole (124 mg, 0.29 mmol), K₂CO₃ (110 mg, 0.79 mmol), Pd(dppf)Cl₂ (20 mg, 0.03 mmol), (+/−)-trans-methyl 3-((2-chloro-6,7-difluoroquinazolin-4-yl)amino)bicyclo[2.2.2]octane-2-carboxylate (100 mg, 0.26 mmol). A stream of nitrogen was bubbled through the mixture for 10 min to remove air, then the mixture was stirred at 115° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give the title compound as a white solid (128 mg, 75%).

MS (ESI, pos. ion) m/z: 653.7 [M+H]⁺.

Step 5: (+/−)-trans-3-((2-(5,7-difluoro-1H-indol-3-yl)-6,7-difluoroquinazolin-4-yl)amino)bicyclo[2.2.2]octane-2-carboxylic Acid To a solution of (+/−)-trans-methyl 3-((2-(5,7-difluoro-1-tosyl-1H-indol-3-yl)-6,7-difluoroquinazolin-4-yl)amino)bicyclo[2.2.2]octane-2-carboxylate (128 mg, 0.20 mmol) in a mixed solvent THF/MeOH (v/v=1 mL/10 mL) was added a solution of NaOH (60 mg, 1.5 mmol) in water (1 mL). The mixture was stirred at rt overnight. The reaction mixture was quenched with water (20 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo, and the residue was purified by silica gel column chromatography (DCM/MeOH (v/v)=10/1~5/1) to give the title compound as a white solid (53 mg, 56%).

MS (ESI, pos. ion) m/z: 485.0[M+H]⁺;

HRMS (ESI, pos. ion) m/z: 485.1594 [M+H]⁺, (C₂₅H₂₁F₄N₄O₂) [M+H]⁺ theoretical value: 485.1601;

¹H NMR (600 MHz, DMSO-d₆) δ (ppm): 12.25 (s, 1H), 8.50 (dd, J=11.6, 8.9 Hz, 1H), 8.32-8.25 (m, 1H), 8.23 (d, J=2.5 Hz, 1H), 7.78 (d, J=6.2 Hz, 1H), 7.70 (dd, J=11.8, 7.9 Hz, 1H), 7.07 (t, J=9.5 Hz, 1H), 4.87 (d, J=6.0 Hz, 1H), 2.88 (d, J=6.6 Hz, 1H), 2.07 (s, 2H), 1.99-1.73 (m, 4H), 1.72-1.35 (m, 5H);

¹³C NMR (101 MHz, DMSO-d₆) δ (ppm): 175.88, 160.04, 158.89, 155.99, 152.24, 149.92, 148.73, 147.60, 147.47, 131.85, 128.89, 122.18, 117.29, 114.32, 114.16, 111.02, 110.82, 110.19, 110.13, 103.75, 103.51, 97.61, 97.40, 97.31, 51.54, 48.34, 28.82, 28.35, 25.95, 24.20, 21.58, 19.70.

Example 44: (+/−)-trans-3-((2-(5,7-difluoro-1H-indol-3-yl)-8-(trifluoromethoxy)quinazolin-4-yl)amino)bicyclo[2.2.2]octane-2-carboxylic Acid

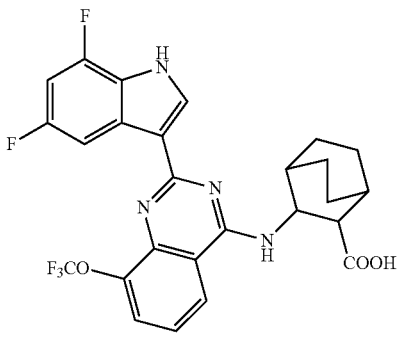 [SMILES: O=C(O)C1C2CCC(CC2)C1Nc1nc(-c2c[nH]c3c(F)cc(F)cc23)nc2c(OC(F)(F)F)cccc12]

Step 1: (+/−)-trans-methyl 3-((2-chloro-8-(trifluoromethoxy)quinazolin-4-yl)amino)bicyclo[2.2.2]octane-2-carboxylate A suspension of 2,4-dichloro-8-(trifluoromethoxy)quinazoline (900 mg, 3.01 mmol), (+/−)-trans-methyl 3-aminobicyclo[2.2.2]octane-2-carboxylate (660 mg, 3.61 mmol) and DIPEA (4.97 mL, 30.09 mmol) in THF (5 mL) was stirred at rt overnight. To the reaction mixture was added H$_2$O (100 mL), and the mixture was extracted with EtOAc (50 mL×3). The combined organic layers were washed with saturated brine (80 mL×3), dried over anhydrous sodium sulfate, and filtered. The filtrate was concentrated in vacuo, and the residue was purified by silica gel column chromatography (PE/EtOAc (v/v)=3/1) to give the title compound as a white solid (1.24 g, 96%).

MS (ESI, pos. ion) m/z: 431.0 [M+H];
$^1$H NMR (400 MHz, CDCl$_3$) δ (ppm): 7.86 (d, J=8.3 Hz, 1H), 7.61 (d, J=7.8 Hz, 1H), 7.40 (t, J=8.1 Hz, 1H), 6.45 (d, J=5.3 Hz, 1H), 4.64 (s, 1H), 3.76 (s, 3H), 2.52 (d, J=5.6 Hz, 1H), 1.98 (d, J=2.1 Hz, 2H), 1.88-1.75 (m, 2H), 1.73-1.46 (m, 6H).

Step 2: (+/−)-trans-methyl 3-((2-(5,7-difluoro-1-tosyl-1H-indol-3-yl)-8-(trifluoromethoxy) quinazolin-4-yl)amino)bicyclo[2.2.2]octane-2-carboxylate To a mixed solvent of 1,4-dioxane (8 mL) and H$_2$O (1 mL) were added 5,7-difluoro-3-(4,4,5,5-tetramethyl-1,3,2-dioxaborolan-2-yl)-1-tosyl-1H-indole (198 mg, 0.46 mmol), K$_2$CO$_3$ (181 mg, 1.24 mmol), Pd(dppf) Cl$_2$ (33 mg, 0.04 mmol), (+/−)-trans-methyl 3-((2-chloro-8-(trifluoromethoxy)quinazolin-4-yl)amino)bicyclo[2.2.2]octane-2-carboxylate (178 mg, 0.41 mmol). A stream of nitrogen was bubbled through the mixture for 10 min to remove air, then the mixture was stirred at 115° C. for 3 h under a sealed-tube condition. The mixture was filtered to remove the solid impurities, and the filtrate was concentrated to remove the solvent. The residue was purified by silica gel column chromatography (PE/EtOAc (v/v)=10/1~5/1) to give the title compound as a white solid (220 mg, 76%).

Step 3: (+/−)-trans-3-((2-(5,7-difluoro-1H-indol-3-yl)-8-(trifluoromethoxy)quinazolin-4-yl)amino)bicyclo[2.2.2]octane-2-carboxylic Acid To a solution of (+/−)-trans-methyl 3-((2-(5,7-difluoro-1-tosyl-1H-indol-3-yl)-8-(trifluoromethoxy)quinazolin-4-yl)amino)bicyclo[2.2.2]octane-2-carboxylate (218 mg, 0.31 mmol) in a mixed solvent THF/MeOH (v/v=1 mL/10 mL) was added a solution of NaOH (115 mg, 2.82 mmol) in water (1 mL). The mixture was stirred at rt overnight. To the reaction mixture was added water (20 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo, and the residue was purified by silica gel column chromatography (DCM/MeOH (v/v)=10/1~5/1) to give the title compound as a white solid (46 mg, 28%).

MS (ESI, pos. ion) m/z: 533.1[M+H];
HRMS (ESI, pos. ion) m/z: 533.1611 [M+H]$^+$, (C$_{26}$H$_{22}$F$_2$N$_5$O$_2$) [M+H]$^+$ theoretical value: 533.1612;
$^1$H NMR (600 MHz, DMSO-d$_6$) δ (ppm): 12.57 (s, 1H), 8.54 (s, 2H), 8.39 (s, 1H), 8.26 (s, 1H), 7.87 (s, 1H), 7.54 (s, 1H), 7.13 (s, 1H), 4.95 (s, 1H), 3.04 (s, 1H), 2.07 (s, 2H), 1.83 (s, 3H), 1.61-1.42 (m, 6H);
$^{13}$C NMR (101 MHz, DMSO-d$_6$) δ (ppm): 175.83, 159.22, 158.92, 156.37, 133.48, 130.09, 129.12, 125.99, 124.55, 123.52, 122.23, 122.10, 119.65, 115.11, 110.00, 103.40, 97.70, 52.18, 47.85, 28.70, 28.55, 25.75, 25.38, 24.28, 21.55, 19.75.

Example 45: (+/−)-trans-3-((6-(2-cyanophenyl)-2-(5,7-difluoro-1H-indol-3-yl)pyrimidin-4-yl)amino)bicyclo[2.2.2]octane-2-carboxylic Acid

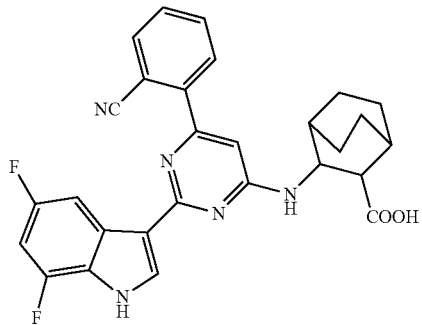 [SMILES: N#Cc1ccccc1-c1cc(NC2C3CCC(CC3)C2C(=O)O)nc(-c2c[nH]c3c(F)cc(F)cc23)n1]

Step 1: 2-(2,6-dichloropyrimidin-4-yl)benzonitrile

To a solution of 2,4,6-trichloropyrimidine (2 g, 10.90 mmol) in tetrahydrofuran (30 mL) were added tetrakis(triphenylphosphine)palladium (1.26 g, 1.09 mmol), (2-cyanophenyl)boronic acid (1.62 g, 11.00 mmol) and an aqueous sodium carbonate solution (1 M, 32.70 mL, 32.70 mmol). The mixture was heated to 70° C. and stirred for 6 h. To the reaction mixture was added water (50 mL), and the mixture was extracted with EtOAc (50 mL×3). The combined organic layers were washed with saturated brine (40 mL), dried over anhydrous sodium sulfate, and filtered. The filtrate was concentrated in vacuo to dry, and the residue was purified by silica gel column chromatography (PE) to give the title compound as brown oil (368 mg, 14%).

MS (ESI, pos. ion) m/z: 251.9[M+H]+.

Step 2: (+/−)-trans-methyl 3-((2-chloro-6-(2-cyanophenyl)pyrimidin-4-yl)amino)bicyclo[2.2.2]octane-2-carboxylate To a solution of (+/−)-trans-methyl 3-aminobicyclo[2.2.2]octane-2-carboxylate (365 mg, 1.99 mmol) and 2-(2,6-dichloropyrimidin-4-yl)benzonitrile (454 mg, 1.82 mmol) in DMF (5 mL) was added potassium carbonate (276 mg, 1.99 mmol). The mixture was stirred at rt overnight. To the reaction mixture was added water (40 mL), and the mixture was extracted with EtOAc (40 mL×3). The combined organic layers were washed with saturated brine (50 mL), dried over anhydrous sodium sulfate, and filtered. The filtrate was concentrated in vacuo to dry, and the residue was purified by silica gel column chromatography (PE/EtOAc (v/v)=5/1) to give the title compound as a white solid (537 mg, 75%).

MS (ESI, pos. ion) m/z: 397.1 [M+H]+;
$^1$H NMR (400 MHz, CDCl$_3$) δ (ppm): δ 7.94 (d, J=7.8 Hz, 1H), 7.80 (d, J=7.7 Hz, 1H), 7.72 (t, J=7.7 Hz, 1H), 7.56 (t, J=7.6 Hz, 1H), 6.90 (s, 1H), 5.63 (s, 1H), 4.32 (d, J=7.1 Hz, 1H), 3.75 (s, 3H), 2.40 (d, J=4.7 Hz, 1H), 1.91 (s, 1H), 1.76-1.52 (m, 8H).

Step 3: (+/−)-methyl 3-((6-(2-cyanophenyl)-2-(5,7-difluoro-1-tosyl-1H-indol-3-yl)pyrimidin-4-yl)amino)bicyclo[2.2.2]octane-2-carboxylate To a mixed solvent of 1,4-dioxane (3 mL) and water (0.2 mL) were added 5,7-difluoro-3-(4,4,5,5-tetramethyl-1,3,2-dioxaborolan-2-yl)-1-tosyl-1H-indole (267 mg, 0.61 mmol), (+/−)-trans-methyl 3-((2-chloro-6-(2-cyanophenyl)pyrimidin-4-yl)amino)bicyclo[2.2.2]octane-2-carboxylate (102 mg, 0.26 mmol), potassium phosphate (163 mg, 0.77 mmol) and Pd(dtbpf)Cl$_2$ (16 mg, 0.02 mmol). The mixture was stirred at 100° C. for 1 h under nitrogen protection, and then filtered through a celite pad. The filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (137 mg, 80%).

MS (ESI, pos. ion) m/z: 668.7[M+H]+;
$^1$H NMR (400 MHz, CDCl$_3$) δ (ppm): 8.83 (s, 1H), 8.35-8.25 (m, 1H), 8.00 (d, J=7.6 Hz, 1H), 7.88 (dd, J=16.1, 7.8 Hz, 3H), 7.76 (t, J=7.7 Hz, 1H), 7.58 (t, J=7.5 Hz, 1H), 7.31 (s, 1H), 6.83-6.75 (m, 2H), 5.40 (s, 1H), 4.57 (s, 1H), 3.80 (s, 1H), 3.73 (s, 3H), 2.46 (d, J=5.3 Hz, 2H), 2.40 (s, 3H), 2.11 (s, 1H), 1.74-1.44 (m, 8H).

Step 4: (+/−)-trans-3-((6-(2-cyanophenyl)-2-(5,7-difluoro-1H-indol-3-yl)pyrimidin-4-yl)amino)bicyclo[2.2.2]octane-2-carboxylic Acid To a solution of (+/−)-trans-methyl 3-((6-(2-cyanophenyl)-2-(5,7-difluoro-1-tosyl-1H-indol-3-yl)pyrimidin-4-yl)amino)bicyclo[2.2.2]octane-2-carboxylate (180 mg, 0.27 mmol) in a mixed solvent of THF and MeOH (v/v=1/1, 4 mL) was added an aqueous sodium hydroxide solution (4 M, 0.68 mL, 2.70 mmol). The mixture was stirred at 30° C. overnight. The reaction mixture was diluted with water (20 mL), and the mixture was acidified with hydrochloric acid (1 M) to pH about 5.5. The resulting mixture was extracted with EtOAc (20 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (dichloromethane/methanol (v/v)=10/1) to give the title compound as a yellow solid (57 mg, 42%).

MS (ESI, pos. ion) m/z: 500.1 [M+H]+;
HRMS (ESI, pos. ion) m/z: 500.1923 [M+H]+, (C$_{28}$H$_{24}$F$_2$N$_5$O$_2$) [M+H]+ theoretical value: 500.1898;
$^1$H NMR (400 MHz, DMSO-d$_6$) δ (ppm): 12.28 (s, 1H), 8.32 (d, J=2.4 Hz, 1H), 8.19 (d, J=9.2 Hz, 1H), 8.00 (d, J=7.6 Hz, 1H), 7.94 (d, J=6.8 Hz, 1H), 7.83 (dd, J=20.3, 12.7 Hz, 2H), 7.68 (t, J=7.5 Hz, 1H), 7.06 (t, J=9.6 Hz, 1H), 6.70 (s, 1H), 4.70 (s, 1H), 3.96 (s, 1H), 2.56 (s, 1H), 2.02 (s, 2H), 1.86-1.40 (m, 8H);
$^{13}$C NMR (151 MHz, DMSO-d$_6$) δ (ppm): 175.91, 162.89, 162.72, 159.21, 157.81, 156.32, 156.25, 147.88, 142.12, 135.36, 133.84, 132.21, 130.38, 129.36, 128.88, 122.02, 121.93, 119.34, 117.29, 110.48, 103.52, 100.42, 97.48, 97.34, 97.28, 97.14, 74.02, 50.66, 49.48, 29.49, 28.80, 28.49, 25.99, 25.41, 24.04, 22.55, 21.45, 19.48.

Example 46: (+/−)-trans-3-((2-(5,7-difluoro-1H-indol-3-yl)-6-(4-(morpholine-4-carbonyl)phenyl)pyrimidin-4-yl)amino)bicyclo[2.2.2]octane-2-carboxylic Acid

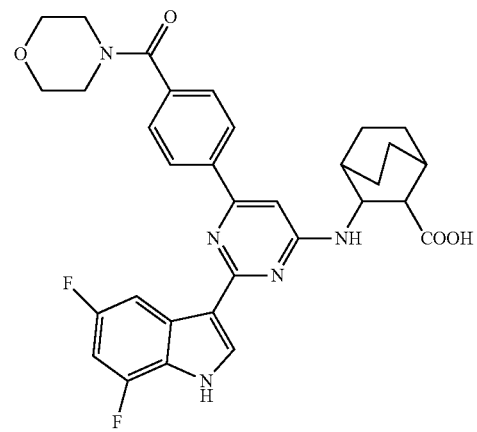 [SMILES: O=C(O)C1C2CCC(CC2)C1Nc1cc(-c2ccc(C(=O)N3CCOCC3)cc2)nc(-c2c[nH]c3c(F)cc(F)cc23)n1]

Step 1: (4-(2,6-dichloropyrimidin-4-yl)phenyl)(morpholino)methanone

To a solution of 2,4,6-trichloropyrimidine (400 mg, 2.18 mmol) in tetrahydrofuran (6.6 mL) were added palladium acetate (50 mg, 0.22 mmol), triphenylphosphine (120 mg, 0.43 mmol), (4-(morpholine-4-carbonyl)phenyl)boronic acid (517 mg, 2.20 mmol) and aqueous sodium carbonate (1 M, 6.6 mL, 6.6 mmol). The mixture was heated to 70° C. and stirred for 6 h. To the reaction mixture was added water (50 mL), and the mixture was extracted with EtOAc (50 mL×3). The combined organic layers were washed with saturated brine (50 mL), dried over anhydrous sodium sulfate, and filtered. The filtrate was concentrated in vacuo to dry, and the residue was purified by silica gel column chromatography (PE) to give the title compound as a white solid (371 mg, 50%).

MS (ESI, pos. ion) m/z: 340.0 [M+H]⁺;
¹H NMR (400 MHz, CDCl₃) δ (ppm): 8.16 (d, J=8.3 Hz, 2H), 7.72 (s, 1H), 7.59 (d, J=8.3 Hz, 2H), 3.75 (d, J=60.6 Hz, 6H), 3.46 (s, 2H).

Step 2: (+/−)-trans-methyl 3-((2-chloro-6-(4-(morpholine-4-carbonyl)phenyl)pyrimidin-4-yl)amino)bicyclo[2.2.2]octane-2-carboxylate To a solution of (+/−)-trans-methyl 3-aminobicyclo[2.2.2]octane-2-carboxylate (221 mg, 1.21 mmol) and (4-(2,6-dichloropyrimidin-4-yl)phenyl)(morpholino)methanone (371 mg, 1.10 mmol) in DMF (5 mL) was added potassium carbonate (166 mg, 1.21 mmol). The mixture was stirred at rt overnight. To the reaction mixture was added water (40 mL), and the mixture was extracted with EtOAc (40 mL×3). The combined organic layers were washed with saturated brine (50 mL), dried over anhydrous sodium sulfate, and filtered. The filtrate was concentrated in vacuo to dry, and the residue was purified by silica gel column chromatography (PE/EtOAc (v/v)=20/1) to give the title compound as a white solid (334 mg, 63%).
MS (ESI, pos. ion) m/z: 485.1 [M+H]⁺;
¹H NMR (400 MHz, CDCl₃) δ (ppm): 7.69 (dd, J=11.9, 7.7 Hz, 1H), 7.52 (d, J=8.2 Hz, 2H), 7.50-7.45 (m, 1H), 6.82 (s, 1H), 5.60 (s, 1H), 4.35 (s, 1H), 3.78 (d, J=21.6 Hz, 7H), 3.66 (s, 2H), 3.46 (s, 2H), 2.41 (d, J=4.3 Hz, 1H), 2.09 (s, 1H), 1.88 (s, 1H), 1.81-1.67 (m, 4H), 1.64-1.36 (m, 4H).

Step 3: (+/−)-trans-methyl 3-((2-(5,7-difluoro-1-tosyl-1H-indol-3-yl)-6-(4-(morpholine-4-carbonyl)phenyl)pyrimidin-4-yl)amino)bicyclo[2.2.2]octane-2-carboxylate To a mixed solvent of 1,4-dioxane (4 mL) and water (0.2 mL) were added 5,7-difluoro-3-(4,4,5,5-tetramethyl-1,3,2-dioxaborolan-2-yl)-1-tosyl-1H-indole (287 mg, 0.66 mmol), (+/−)-trans-methyl 3-((2-chloro-6-(4-(morpholine-4-carbonyl)phenyl)pyrimidin-4-yl)amino)bicyclo[2.2.2]octane-2-carboxylate (134 mg, 0.28 mmol), potassium phosphate (175 mg, 0.82 mmol) and Pd(dtbpf)Cl₂ (18 mg, 0.03 mmol). The mixture was stirred at 100° C. for 1 h under nitrogen protection, and then filtered through a celite pad. The filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (92 mg, 44%).
MS (ESI, pos. ion) m/z: 756.8[M+H]⁺;
¹H NMR (400 MHz, CDCl₃) δ (ppm): 8.77 (s, 1H), 8.33 (d, J=6.9 Hz, 1H), 8.17 (d, J=8.0 Hz, 2H), 7.90 (d, J=7.9 Hz, 2H), 7.69 (dd, J=11.9, 7.1 Hz, 1H), 7.59 (d, J=8.2 Hz, 2H), 7.50 (d, J=5.1 Hz, 1H), 7.31 (d, J=8.3 Hz, 2H), 5.27 (s, 1H), 4.56 (s, 1H), 3.75 (s, 9H), 3.54 (s, 2H), 2.46 (s, 1H), 2.41 (s, 3H), 2.11 (s, 1H), 2.02 (s, 1H), 1.86-1.65 (m, 8H).

Step 4: (+/−)-trans-3-((2-(5,7-difluoro-1H-indol-3-yl)-6-(4-(morpholine-4-carbonyl)phenyl)pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-6-(4-(morpholine-4-carbonyl)phenyl)pyrimidin-4-yl)amino)bicyclo[2.2.2]octane-2-carboxylate (93 mg, 0.12 mmol) in a mixed solvent of THF and MeOH (v/v=1/1, 4 mL) was added an aqueous sodium hydroxide solution (4 M, 0.30 mL, 1.20 mmol). The mixture was stirred at 30° C. overnight. The reaction mixture was diluted with water (20 mL), and the mixture was acidified with hydrochloric acid (1 M) to pH about 5.5. The resulting mixture was extracted with EtOAc (20 mL×3). The combined organic layers were washed with saturated brine (40 mL), dried over anhydrous sodium sulfate, and filtered. The filtrate was concentrated in vacuo to dry, and the residue was purified by silica gel column chromatography (dichloromethane/methanol (v/v)=10/1) to give the title compound as a yellow solid (44 mg, 61%).
MS (ESI, pos. ion) m/z: 588.2 [M+H]⁺;
HRMS (ESI, pos. ion) m/z: 588.2447 [M+H]⁺, (C₃₂H₃₂F₂N₅O₄) [M+H]⁺ theoretical value: 588.2422;
¹H NMR (400 MHz, DMSO-d₆) δ (ppm): 12.27 (s, 1H), 8.30 (d, J=2.2 Hz, 1H), 8.28-8.04 (m, 3H), 7.58 (d, J=8.1 Hz, 3H), 7.06 (t, J=10.4 Hz, 1H), 6.81 (s, 1H), 4.66 (s, 1H), 3.63 (s, 8H), 2.00 (s, 2H), 1.85-1.39 (m, 8H);
¹³C NMR (151 MHz, DMSO-d₆) δ (ppm): 175.96, 169.22, 163.12, 162.87, 159.71, 157.75, 156.27, 156.20, 149.54, 147.91, 139.49, 137.16, 131.77, 131.16, 128.96, 128.02, 126.81, 122.08, 121.99, 117.46, 103.45, 98.42, 97.21, 97.07, 66.59, 50.55, 49.70, 29.49, 28.80, 28.51, 26.00, 24.07, 22.56, 21.42, 19.46.

Example 47: (+/−)-trans-3-((2-(5,7-difluoro-1H-indol-3-yl)-6-(2-(trifluoromethyl)phenyl)pyrimidin-4-yl)amino)bicyclo[2.2.2]octane-2-carboxylic Acid

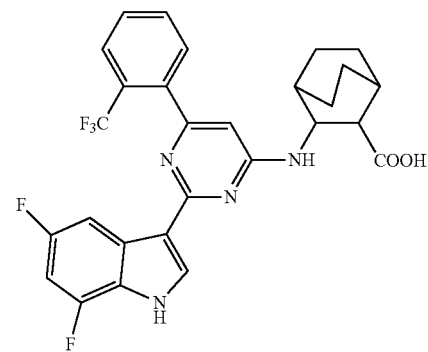 [SMILES: O=C(O)C1C2CCC(CC2)C1Nc1cc(-c2ccccc2C(F)(F)F)nc(-c2c[nH]c3c(F)cc(F)cc23)n1]

Step 1: 2,4-dichloro-6-(2-(trifluoromethyl)phenyl)pyrimidine

To a solution of 2,4,6-trichloropyrimidine (500 mg, 2.73 mmol) in tetrahydrofuran (8.18 mL) were added palladium acetate (63 mg, 0.27 mmol), triphenylphosphine (150 mg, 0.55 mmol), (2-(trifluoromethoxy)phenyl)boronic acid (522 mg, 2.75 mmol) and aqueous sodium carbonate (1 M, 8.18 mL, 8.18 mmol). The mixture was heated to 70° C. and stirred for 6 h under nitrogen protection. To the reaction mixture was added water (50 mL), and the mixture was extracted with EtOAc (50 mL×3). The combined organic layers were washed with saturated brine (50 mL), dried over anhydrous sodium sulfate, and filtered. The filtrate was concentrated in vacuo to dry, and the residue was purified by silica gel column chromatography (PE) to give the title compound as a white solid (408 mg, 51%).
MS (ESI, pos. ion) m/z: 294.9[M+H]⁺;
¹H NMR (400 MHz, CDCl₃) δ (ppm): 7.84 (d, J=7.4 Hz, 1H), 7.74-7.64 (m, 2H), 7.55 (d, J=7.3 Hz, 1H), 7.48 (s, 1H).

Step 2: (+/−)-trans-methyl 3-((2-chloro-6-(2-(trifluoromethyl)phenyl)pyrimidin-4-yl)amino)bicyclo[2.2.2]octane-2-carboxylate To a solution of (+/−)-trans-methyl 3-aminobicyclo[2.2.2]octane-2-carboxylate (280 mg, 1.53 mmol) and 2,4-dichloro-6-(2-(trifluoromethyl)phenyl)pyrimidine (408 mg, 1.39 mmol) in DMF (5 mL) was added potassium carbonate (211 mg, 1.53 mmol). The mixture was stirred at rt overnight. To the reaction mixture was added water (40 mL), and the mixture was extracted with EtOAc (40 mL×3). The combined organic layers were washed with saturated brine (40 mL), dried over anhydrous sodium sulfate, and filtered. The filtrate was concentrated in vacuo to dry, and the residue was purified by silica gel column chromatography (n-hexane) to give the title compound as a white solid (344 mg, 56%).

MS (ESI, pos. ion) m/z: 440.1 [M+H]$^+$;
$^1$H NMR (400 MHz, CDCl$_3$) δ (ppm): 7.77 (d, J=7.8 Hz, 1H), 7.64 (t, J=7.6 Hz, 1H), 7.59-7.50 (m, 2H), 6.47 (s, 1H), 5.46 (s, 1H), 4.25 (s, 1H), 3.73 (s, 3H), 2.39 (s, 1H), 2.07 (s, 1H), 1.85 (s, 1H), 1.69 (dd, J=18.0, 10.0 Hz, 8H).

Step 3: (+/−)-trans-methyl 3-((2-(5,7-difluoro-1-tosyl-1H-indol-3-yl)-6-(2-(trifluoromethyl)phenyl)pyrimidin-4-yl)amino)bicyclo[2.2.2]octane-2-carboxylate To a mixed solvent of 1,4-dioxane (3 mL) and water (0.2 mL) were added 5,7-difluoro-3-(4,4,5,5-tetramethyl-1,3,2-dioxaborolan-2-yl)-1-tosyl-1H-indole (189 mg, 0.22 mmol), (+/−)-trans-methyl 3-((2-chloro-6-(2-(trifluoromethyl)phenyl)pyrimidin-4-yl)amino)bicyclo[2.2.2]octane-2-carboxylate (80 mg, 0.18 mmol), potassium phosphate (175 mg, 0.82 mmol) and Pd(dtbpf)Cl$_2$ (11 mg, 0.02 mmol). The mixture was stirred at 100° C. for 1 h under nitrogen protection. After the reaction, the mixture was filtered through a celite pad, and the filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (110 mg, 85%).

$^1$H NMR (400 MHz, CDCl$_3$) δ (ppm): 8.74 (s, 1H), 8.27 (d, J=9.1 Hz, 1H), 7.88 (d, J=7.9 Hz, 2H), 7.70-7.63 (m, 2H), 7.43-7.41 (m, 2H), 7.31 (s, 1H), 6.80 (t, J=10.4 Hz, 1H), 6.53 (s, 1H), 4.39 (s, 1H), 3.81 (s, 1H), 3.75 (s, 3H), 2.41 (s, 4H), 2.11 (s, 1H), 1.75 (d, J=15.3 Hz, 2H), 1.64-1.48 (m, 6H).

Step 4: (+/−)-trans-3-((2-(5,7-difluoro-1H-indol-3-yl)-6-(2-(trifluoromethyl)phenyl)pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-6-(2-(trifluoromethyl)phenyl)pyrimidin-4-yl)amino)bicyclo[2.2.2]octane-2-carboxylate (109 mg, 0.15 mmol) in a mixed solvent of THF and MeOH (v/v=1/1, 4 mL) was added aqueous sodium hydroxide (4 M, 0.38 mL, 1.50 mmol). The mixture was stirred at 30° C. overnight. The reaction mixture was diluted with water (20 mL), and the mixture was acidified with hydrochloric acid (1 M) to pH about 5.5. The resulting mixture was extracted with EtOAc (20 mL×3). The combined organic layers were washed with saturated brine (40 mL), dried over anhydrous sodium sulfate, and filtered. The filtrate was concentrated in vacuo to dry, and the residue was purified by silica gel column chromatography (dichloromethane/methanol (v/v)=10/1) to give the title compound as a yellow solid (44 mg, 53%).

MS (ESI, pos. ion) m/z: 543.6 [M+H]$^+$;
HRMS (ESI, pos. ion) m/z: 543.1842 [M+H]$^+$, (C$_{28}$H$_{24}$F$_5$N$_4$O$_2$) [M+H]$^+$ theoretical value: 543.1819;
$^1$H NMR (400 MHz, DMSO-d$_6$) δ (ppm): 12.18 (s, 1H), 8.13 (d, J=2.2 Hz, 2H), 7.88 (d, J=7.8 Hz, 1H), 7.79 (t, J=7.4 Hz, 1H), 7.73-7.60 (m, 2H), 7.53 (d, J=6.7 Hz, 1H), 7.08-6.99 (m, 1H), 6.35 (s, 1H), 4.66 (s, 1H), 2.00 (s, 2H), 1.84-1.41 (m, 8H);
$^{13}$C NMR (151 MHz, DMSO-d$_6$) δ (ppm): 175.89, 162.24, 162.16, 155.87, 155.77, 147.41, 139.68, 132.93, 131.49, 129.51, 129.01, 127.33, 127.03, 126.98, 126.93, 126.01, 123.28, 122.06, 121.94, 117.32, 103.54, 101.87, 97.49, 97.29, 96.98, 50.52, 49.71, 28.81, 28.50, 26.02, 24.06, 21.40, 19.47.

Example 48: (+/−)-trans-3-((2-(5,7-difluoro-1H-indol-3-yl)-6-(naphthalen-2-yl)pyrimidin-4-yl)amino)bicyclo[2.2.2]octane-2-carboxylic Acid

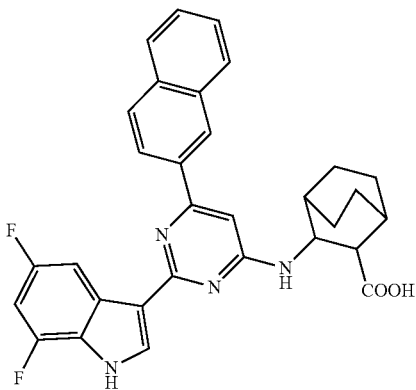 [SMILES: O=C(O)C1C2CCC(CC2)C1Nc1cc(-c2ccc3ccccc3c2)nc(-c2c[nH]c3c(F)cc(F)cc23)n1]

Step 1: 2,4-dichloro-6-(naphthalen-2-yl)pyrimidine

To a solution of 2,4,6-trichloropyrimidine (500 mg, 2.73 mmol) in tetrahydrofuran (8.18 mL) were added palladium acetate (63 mg, 0.27 mmol), triphenylphosphine (150 mg, 0.55 mmol), naphthalen-2-ylboronic acid (473 mg, 2.8 mmol) and an aqueous sodium carbonate solution (1 M, 8.18 mL, 8.18 mmol). The mixture was heated to 70° C. and stirred for 6 h under nitrogen protection. To the reaction mixture was added water (50 mL), and the mixture was extracted with EtOAc (50 mL×3). The combined organic layers were washed with saturated brine (50 mL), dried over anhydrous sodium sulfate, and filtered. The filtrate was concentrated in vacuo to dry, and the residue was purified by silica gel column chromatography (PE) to give the title compound as a white solid (530 mg, 71%).

MS (ESI, pos. ion) m/z: 275.0[M+H]$^+$;
$^1$H NMR (400 MHz, CDCl$_3$) δ (ppm): 8.67 (s, 1H), 8.13 (dd, J=8.6, 1.7 Hz, 1H), 8.01 (t, J=8.0 Hz, 2H), 7.92 (d, J=7.7 Hz, 1H), 7.84 (s, 1H), 7.62 (dq, J=6.9, 5.7 Hz, 2H).

Step 2: (+/−)-trans-methyl 3-((2-chloro-6-(naphthalen-2-yl)pyrimidin-4-yl)amino)bicyclo[2.2.2]octane-2-carboxylate To a solution of (+/−)-trans-methyl 3-aminobicyclo[2.2.2]octane-2-carboxylate (388 mg, 2.12 mmol) and 2,4-dichloro-6-(naphthalen-2-yl)pyrimidine (530 mg, 1.93 mmol) in DMF (5 mL) was added potassium carbonate (789 mg, 5.71 mmol). The mixture was stirred at rt overnight. To the reaction mixture was added water (40 mL), and the mixture was extracted with EtOAc (40 mL×3). The combined organic layers were washed with saturated brine (80 mL), dried over anhydrous sodium sulfate, and filtered. The filtrate was concentrated in vacuo to dry, and the residue was purified by silica gel column chromatography (n-hexane) to give the title compound as a white solid (330 mg, 41%).

MS (ESI, pos. ion) m/z: 422.0 [M+H]$^+$;

$^1$H NMR (400 MHz, CDCl$_3$) δ (ppm): 8.59 (s, 1H), 8.08-7.86 (m, 4H), 7.55 (p, J=6.9 Hz, 2H), 6.95 (s, 1H), 5.56 (s, 1H), 4.39 (s, 1H), 3.77 (s, 3H), 2.43 (d, J=4.6 Hz, 1H), 2.10 (s, 1H), 1.91 (s, 1H), 1.77-1.59 (m, 8H).

Step 3: (+/−)-trans-methyl 3-((2-(5,7-difluoro-1-tosyl-1H-indol-3-yl)-6-(naphthalen-2-yl)pyrimidin-4-yl)amino)bicyclo[2.2.2]octane-2-carboxylate To a mixed solvent of 1,4-dioxane (3 mL) and water (0.2 mL) were added 5,7-difluoro-3-(4,4,5,5-tetramethyl-1,3,2-dioxaborolan-2-yl)-1-tosyl-1H-indole (271 mg, 0.62 mmol), (+/−)-trans-methyl 3-((2-chloro-6-(naphthalen-2-yl)pyrimidin-4-yl)amino)bicyclo[2.2.2]octane-2-carboxylate (110 mg, 0.26 mmol), potassium phosphate (166 mg, 0.78 mmol) and Pd(dtbpf)Cl$_2$ (16 mg, 0.02 mmol). The mixture was stirred at 100° C. for 1 hour under nitrogen protection, and then filtered through a celite pad. The filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (142 mg, 79%).

$^1$H NMR (400 MHz, CDCl$_3$) δ (ppm): 8.82 (s, 1H), 8.66 (s, 1H), 8.43 (d, J=7.2 Hz, 1H), 8.24 (d, J=8.4 Hz, 1H), 8.06-8.00 (m, 2H), 7.91 (d, J=7.5 Hz, 3H), 7.58 (dd, J=6.2, 3.2 Hz, 2H), 7.31 (d, J=8.2 Hz, 2H), 6.92 (s, 1H), 6.86-6.79 (m, 1H), 4.60 (s, 1H), 3.76 (s, 3H), 3.07 (s, 1H), 2.50 (s, 1H), 2.42 (s, 3H), 2.13 (s, 1H), 2.04 (s, 1H), 1.76-1.62 (m, 8H).

Step 4: (+/−)-trans-3-((2-(5,7-difluoro-1H-indol-3-yl)-6-(naphthalen-2-yl)pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-6-(naphthalen-2-yl)pyrimidin-4-yl)amino)bicyclo[2.2.2]octane-2-carboxylate (142 mg, 0.21 mmol) in a mixed solvent of THF and MeOH (v/v=1/1, 4 mL) was added an aqueous sodium hydroxide solution (4 M, 0.53 mL, 2.10 mmol). The mixture was stirred at 30° C. overnight. The reaction mixture was diluted with water (20 mL), and the mixture was acidified with hydrochloric acid (1 M) to pH about 5.5. The resulting mixture was extracted with EtOAc (20 mL×3). The combined organic layers were washed with saturated brine (40 mL), dried over anhydrous sodium sulfate, and filtered. The filtrate was concentrated in vacuo to dry, and the residue was purified by silica gel column chromatography (dichloromethane/methanol (v/v)= 10/1) to give the title compound as a yellow solid (37 mg, 34%).

MS (ESI, pos. ion) m/z: 525.1 [M+H]$^+$;
HRMS (ESI, pos. ion) m/z: 525.2110 [M+H]$^+$, (C$_{31}$H$_{27}$F$_2$N$_4$O$_2$) [M+H]$^+$ theoretical value: 525.2102;

$^1$H NMR (400 MHz, DMSO-d$_6$) δ (ppm): 12.26 (s, 1H), 8.70 (s, 1H), 8.38 (s, 1H), 8.24 (d, J=13.3 Hz, 2H), 8.07 (d, J=8.9 Hz, 2H), 7.99 (s, 1H), 7.62-7.58 (m, 2H), 7.35 (s, 1H), 7.07 (t, J=9.6 Hz, 1H), 6.92 (s, 1H), 4.99 (s, 1H), 4.69 (s, 1H), 3.94 (s, 1H), 2.01 (s, 2H), 1.67-1.36 (m, 8H);

$^{13}$C NMR (151 MHz, DMSO-d$_6$) δ (ppm): 163.19, 162.85, 135.78, 134.16, 133.37, 131.81, 130.12, 129.22, 128.82, 128.72, 128.32, 128.07, 127.41, 127.02, 124.37, 122.10, 122.01, 65.62, 31.73, 29.47, 28.82, 28.56, 26.04, 25.71, 24.08, 22.54, 21.45, 19.46.

Example 49: (+/−)-trans-3-((6-(4-(tert-butyl)phenyl)-2-(5,7-difluoro-1H-indol-3-yl)pyrimidin-4-yl)amino)bicyclo[2.2.2]octane-2-carboxylic Acid

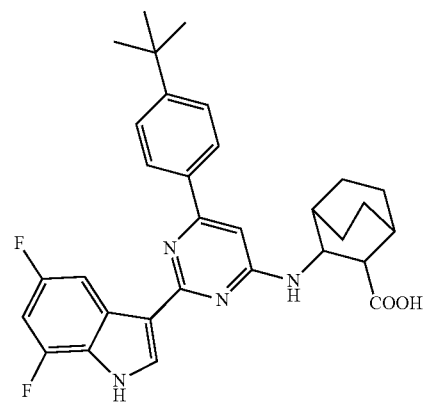 [SMILES: CC(C)(C)c1ccc(-c2cc(NC3C4CCC(CC4)C3C(=O)O)nc(-c3c[nH]c4c(F)cc(F)cc34)n2)cc1]

Step 1:
4-(4-(tert-butyl)phenyl)-2,6-dichloropyrimidine

To a solution of 2,4,6-trichloropyrimidine (500 mg, 2.73 mmol) in tetrahydrofuran (8.18 mL) were added palladium acetate (63 mg, 0.27 mmol), triphenylphosphine (150 mg, 0.55 mmol), (4-(tert-butyl)phenyl)boronic acid (490 mg, 2.75 mmol) and an aqueous sodium carbonate solution (1 M, 8.18 mL, 8.18 mmol). The mixture was heated to 70° C. and stirred for 6 h under nitrogen protection. To the reaction mixture was added water (50 mL), and the mixture was extracted with EtOAc (50 mL×3). The combined organic layers were washed with saturated brine (50 mL), dried over anhydrous sodium sulfate, and filtered. The filtrate was concentrated in vacuo to dry, and the residue was purified by silica gel column chromatography (PE) to give the title compound as a white solid (685 mg, 89%).

MS (ESI, pos. ion) m/z: 283.0[M+H]$^+$;
$^1$H NMR (400 MHz, CDCl$_3$) δ (ppm): 8.03 (d, J=8.6 Hz, 2H), 7.67 (s, 1H), 7.56 (d, J=8.5 Hz, 2H), 1.39 (s, 9H).

Step 2: (+/−)-trans-methyl 3-((6-(4-(tert-butyl)phenyl)-2-chloropyrimidin-4-yl)amino)bicyclo[2.2.2]octane-2-carboxylate To a solution of 4-(4-(tert-butyl)phenyl)-2,6-dichloropyrimidine (685 mg, 2.44 mmol) and (+/−)-trans-methyl 3-aminobicyclo[2.2.2]octane-2-carboxylate (492 mg, 2.68 mmol) in N,N-dimethylformamide (6 mL) was added potassium carbonate (1.01 g, 7.31 mmol). The mixture was stirred at rt overnight. To the reaction mixture was added water (40 mL), and the mixture was extracted with EtOAc (40 mL×3). The combined organic layers were washed with saturated brine (50 mL), dried over anhydrous sodium sulfate, and filtered. The filtrate was concentrated in vacuo to dry, and the residue was purified by silica gel column chromatography (n-hexane) to give the title compound as a white solid (334 mg, 32%).

MS (ESI, pos. ion) m/z: 428.2 [M+H]$^+$;

$^1$H NMR (400 MHz, CDCl$_3$) δ (ppm): 7.94 (d, J=8.2 Hz, 2H), 7.50 (d, J=8.4 Hz, 2H), 6.77 (s, 1H), 5.43 (s, 1H), 4.33 (s, 1H), 3.76 (s, 3H), 2.40 (d, J=4.9 Hz, 1H), 1.88 (d, J=2.6 Hz, 1H), 1.82-1.64 (m, 6H), 1.58 (d, J=10.1 Hz, 2H), 1.37 (s, 9H).

Step 3: (+/−)-trans-methyl 3-((6-(4-(tert-butyl)phenyl)-2-(5,7-difluoro-1-tosyl-1H-indol-3-yl)pyrimidin-4-yl)amino)bicyclo[2.2.2]octane-2-carboxylate To a mixed solvent of 1,4-dioxane (3 mL) and water (0.2 mL) were added 5,7-difluoro-3-(4,4,5,5-tetramethyl-1,3,2-dioxaborolan-2-yl)-1-tosyl-1H-indole (315 mg, 0.72 mmol), (+/−)-trans-methyl 3-((6-(4-(tert-butyl)phenyl)-2-chloropyrimidin-4-yl)amino)bicyclo[2.2.2]octane-2-carboxylate (130 mg, 0.30 mmol), potassium phosphate (193 mg, 0.91 mmol) and Pd(dtbpf)Cl$_2$ (15 mg, 0.03 mmol). The mixture was stirred at 100° C. for 1 h under nitrogen protection, and then filtered through a celite pad. The filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (194 mg, 91%).

$^1$H NMR (400 MHz, CDCl$_3$) δ (ppm): 8.76 (s, 1H), 8.41-8.35 (m, 1H), 8.07 (d, J=8.4 Hz, 2H), 7.89 (d, J=7.9 Hz, 2H), 7.57 (d, J=8.4 Hz, 2H), 7.31 (s, 2H), 6.84-6.78 (m, 1H), 6.74 (s, 1H), 4.54 (s, 1H), 3.75 (s, 3H), 2.46 (d, J=5.7 Hz, 1H), 2.41 (s, 3H), 2.11 (s, 1H), 2.01 (s, 1H), 1.92-1.60 (m, 8H).

Step 4: (+/−)-trans-3-((6-(4-(tert-butyl)phenyl)-2-(5,7-difluoro-1H-indol-3-yl)pyrimidin-4-yl)amino)bicyclo[2.2.2]octane-2-carboxylic Acid To a solution of (+/−)-trans-methyl 3-((6-(4-(tert-butyl)phenyl)-2-(5,7-difluoro-1-tosyl-1H-indol-3-yl)pyrimidin-4-yl)amino)bicyclo[2.2.2]octane-2-carboxylate (194 mg, 0.28 mmol) in a mixed solvent of THF and MeOH (v/v=1/1, 4 mL) was added aqueous sodium hydroxide solution (4 M, 0.70 mL, 2.80 mmol). The mixture was stirred at 30° C. overnight. The reaction mixture was diluted with water (20 mL), and the mixture was acidified with hydrochloric acid (1 M) to pH about 5.5. The resulting mixture was extracted with EtOAc (20 mL×3). The combined organic layers were washed with saturated brine (40 mL), dried over anhydrous sodium sulfate, and filtered. The filtrate was concentrated in vacuo to dry, and the residue was purified by silica gel column chromatography (dichloromethane/methanol (v/v)= 10/1) to give the title compound as a yellow solid (44 mg, 30%).

MS (ESI, pos. ion) m/z: 531.2 [M+H]$^+$;

HRMS (ESI, pos. ion) m/z: 531.2565 [M+H]$^+$, (C$_{26}$H$_{22}$F$_2$N$_5$O$_2$) [M+H]$^+$ theoretical value: 531.2572;

$^1$H NMR (400 MHz, DMSO-d$_6$) δ (ppm): 12.25 (s, 1H), 8.32-8.17 (m, 2H), 8.01 (d, J=6.7 Hz, 2H), 7.56 (d, J=8.4 Hz, 3H), 7.06 (t, J=10.3 Hz, 1H), 6.75 (s, 1H), 4.63 (s, 1H), 3.60 (s, 1H), 1.99 (s, 2H), 1.82-1.40 (m, 8H), 1.34 (s, 9H);

$^{13}$C NMR (151 MHz, DMSO-d$_6$) δ (ppm): 175.98, 167.36, 163.04, 152.98, 147.99, 131.17, 130.11, 129.95, 126.58, 126.00, 122.06, 121.97, 67.49, 34.98, 31.74, 31.52, 29.53, 29.48, 29.14, 29.02, 28.79, 28.55, 27.00, 26.01, 25.59, 24.10, 22.55, 21.41, 19.45, 14.40.

Example 50: (+/−)-trans-3-((2-(5,7-difluoro-1H-indol-3-yl)-6-(4-methoxyphenyl)pyrimidin-4-yl)amino)bicyclo[2.2.2]octane-2-carboxylic Acid

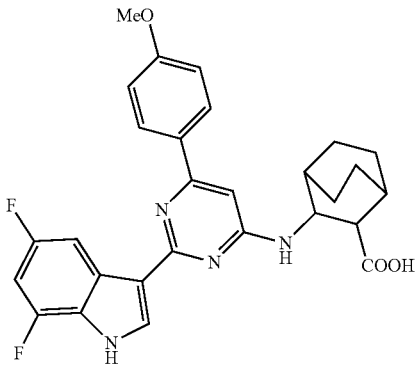 [SMILES: COc1ccc(-c2cc(NC3C4CCC(CC4)C3C(=O)O)nc(-c3c[nH]c4c(F)cc(F)cc34)n2)cc1]

Step 1:
2,4-dichloro-6-(4-methoxyphenyl)pyrimidine

To a solution of 2,4,6-trichloropyrimidine (5.5 mL, 48.0 mmol) in tetrahydrofuran (70 mL) were added palladium acetate (0.147 g, 0.64 mmol), triphenylphosphine (353 mg, 1.28 mmol), 4-methoxyphenylboronic acid (5 g, 31.9 mmol) and an aqueous sodium carbonate solution (1 M, 64 mL, 64 mmol). The mixture was heated to 60° C. and stirred overnight. After the reaction, the reaction mixture was cooled to rt and concentrated to remove the organic solvent. To the residue was added H$_2$O (100 mL), and the mixture was extracted with EtOAc (100 mL×3). The combined organic layers were washed with saturated brine (100 mL), dried over anhydrous sodium sulfate, and filtered. The filtrate was concentrated in vacuo to dry, and the residue was purified by silica gel column chromatography (PE) to give the title compound as a white solid (5.58 g, 68%).

MS (ESI, pos. ion) m/z: 255.0 [M+H]$^+$;

$^1$H NMR (400 MHz, CDCl$_3$) δ (ppm): 8.07 (dd, J=9.4, 2.4 Hz, 2H), 7.60 (s, 1H), 7.08-6.99 (m, 2H), 3.91 (s, 3H).

Step 2: (+/−)-trans-methyl 3-((2-chloro-6-(4-methoxyphenyl)pyrimidin-4-yl)amino)bicyclo[2.2.2]octane-2-carboxylate To a solution of 2,4-dichloro-6-(4-methoxyphenyl)pyrimidine (1.01 g, 3.96 mmol) and (+/−)-trans-methyl 3-aminobicyclo[2.2.2]octane-2-carboxylate (871 mg, 4.75 mmol) in N,N-dimethylformamide (20 mL) was added potassium carbonate (0.81 g, 5.88 mmol). The mixture was stirred at rt overnight. To the reaction mixture was added water (70 mL), and the mixture was extracted with EtOAc (100 mL×3). The combined organic layers were washed with saturated brine (100 mL), dried over anhydrous sodium sulfate, and filtered. The filtrate was concentrated in vacuo to dry. The residue was purified by silica gel column chromatography (PE/EtOAc (v/v)=20/1) to give the title compound as a white solid (1.01 g, 64%).

MS-ESI: (ESI, pos. ion) m/z: 402.2 [M+H]$^+$;

$^1$H NMR (400 MHz, CDCl$_3$) δ (ppm): 7.98 (d, J=8.7 Hz, 2H), 6.98 (d, J=8.9 Hz, 2H), 6.72 (s, 1H), 5.46 (d, J=6.3 Hz, 1H), 4.32 (s, 1H), 3.88 (s, 4H), 3.74 (s, 3H), 2.39 (d, J=5.1 Hz, 1H), 2.08 (s, 1H), 1.90-1.84 (m, 1H), 1.78-1.56 (m, 8H).

Step 3: (+/−)-trans-methyl 3-((2-(5,7-difluoro-1-tosyl-1H-indol-3-yl)-6-(4-methoxyphenyl)pyrimidin-4-yl)amino)bicyclo[2.2.2]octane-2-carboxylate To a mixed solvent of 1,4-dioxane (3 mL) and water (0.2 mL) were added 5,7-difluoro-3-(4,4,5,5-tetramethyl-1,3,2-dioxaborolan-2-yl)-1-tosyl-1H-indole (258 mg, 0.60 mmol), (+/−)-trans-methyl 3-((2-chloro-6-(4-methoxyphenyl)pyrimidin-4-yl)amino)bicyclo[2.2.2]octane-2-carboxylate (100 mg, 0.25 mmol), potassium phosphate (158 mg, 0.75 mmol) and Pd(dtbpf)Cl$_2$ (16 mg, 0.02 mmol). The mixture was stirred at 100° C. for 30 min under nitrogen protection, and then filtered through a celite pad. The filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (111 mg, 66%).

MS (ESI, pos. ion) m/z: 673.1[M+H]$^+$;

$^1$H NMR (400 MHz, CDCl$_3$) δ (ppm): 8.76 (s, 1H), 8.35 (d, J=7.1 Hz, 1H), 8.11 (d, J=8.8 Hz, 2H), 7.89 (d, J=8.0 Hz, 2H), 7.32 (d, J=9.3 Hz, 2H), 7.06 (d, J=8.8 Hz, 2H), 6.81 (t, J=10.5 Hz, 1H), 6.70 (s, 1H), 5.17 (s, 1H), 4.53 (s, 1H), 3.92 (s, 3H), 3.74 (s, 3H), 2.45 (s, 1H), 2.41 (s, 3H), 2.10 (s, 1H), 2.01 (s, 1H), 1.87-1.66 (m, 8H).

Step 4: (+/−)-trans-3-((2-(5,7-difluoro-1H-indol-3-yl)-6-(4-methoxyphenyl)pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-6-(4-methoxyphenyl)pyrimidin-4-yl)amino)bicyclo[2.2.2]octane-2-carboxylate (111 mg, 0.17 mmol) in a mixed solvent of THF and MeOH (v/v=1/1, 4 mL) was added an aqueous sodium hydroxide solution (4 M, 0.43 mL, 1.70 mmol). The mixture was stirred at 30° C. overnight. The reaction mixture was diluted with water (20 mL), and the mixture was acidified with hydrochloric acid (1 M) to pH about 5.5. The resulting mixture was extracted with EtOAc (20 mL×3). The combined organic layers were washed with saturated brine (40 mL), dried over anhydrous sodium sulfate, and filtered. The filtrate was concentrated in vacuo to dry, and the residue was purified by silica gel column chromatography (dichloromethane/methanol (v/v)=10/1) to give the title compound as a yellow solid (47 mg, 56%).

MS (ESI, pos. ion) m/z: 505.5 [M+H]$^+$;

HRMS (ESI, pos. ion) m/z: 505.2052 [M+H]$^+$, (C$_{28}$H$_{27}$F$_2$N$_4$O$_3$) [M+H]$^+$ theoretical value: 505.2051;

$^1$H NMR (400 MHz, DMSO-d$_6$) δ (ppm): 12.31 (s, 1H), 12.20 (s, 1H), 8.29 (d, J=2.2 Hz, 1H), 8.24 (s, 1H), 8.07 (s, 2H), 7.37 (s, 1H), 7.10 (d, J=8.7 Hz, 2H), 7.08-7.04 (m, 1H), 6.69 (s, 1H), 3.85 (s, 3H), 2.00 (s, 2H), 1.85-1.36 (m, 10H);

$^{13}$C NMR (151 MHz, DMSO-d$_6$) δ (ppm): 175.99, 163.07, 162.64, 161.20, 157.71, 156.23, 156.16, 147.99, 147.89, 131.57, 131.13, 130.70, 129.99, 129.00, 128.92, 128.20, 122.07, 121.98, 117.65, 114.56, 97.34, 97.20, 97.14, 97.00, 67.49, 55.74, 29.49, 28.81, 28.56, 26.05, 25.59, 24.09, 21.42, 19.44.

Example 51: (+/−)-trans-3-((2-(5,7-difluoro-1H-indol-3-yl)-6-(pyridin-3-yl)pyrimidin-4-yl)amino)bicyclo[2.2.2]octane-2-carboxylic Acid

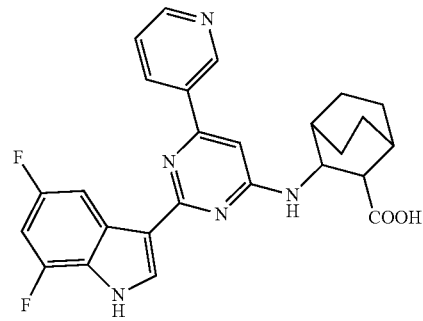 [SMILES: O=C(O)C1C2CCC(CC2)C1Nc1cc(-c2cccnc2)nc(-c2c[nH]c3c(F)cc(F)cc23)n1]

Step 1: 2,4-dichloro-6-(pyridin-3-yl)pyrimidine

To a solution of 2,4,6-trichloropyrimidine (2 g, 10.90 mmol) in tetrahydrofuran (30 mL) were added Pd(dppf)Cl$_2$ (797 mg, 1.09 mmol), pyridin-3-ylboronic acid (1.35 g, 11.01 mmol) and an aqueous sodium carbonate solution (1 M, 32.8 mL, 32.8 mmol). The mixture was heated to 70° C. and stirred for 6 h under nitrogen protection. To the reaction mixture was added water (50 mL), and the mixture was extracted with EtOAc (50 mL×3). The combined organic layers were washed with saturated brine (50 mL), dried over anhydrous sodium sulfate, and filtered. The filtrate was concentrated in vacuo to dry, and the residue was purified by silica gel column chromatography (PE) to give the title compound as a white solid (225 mg, 9%).

MS (ESI, pos. ion) m/z: 226.0 [M+H]$^+$;

$^1$H NMR (400 MHz, CDCl$_3$) δ (ppm): 9.28 (d, J=1.8 Hz, 1H), 8.81 (dd, J=4.8, 1.4 Hz, 1H), 8.49-8.39 (m, 1H), 7.75 (s, 1H), 7.52-7.48 (m, 1H).

Step 2: (+/−)-trans-methyl 3-((2-chloro-6-(pyridin-3-yl)pyrimidin-4-yl)amino)bicyclo[2.2.2]octane-2-carboxylate To a solution of (+/−)-trans-methyl 3-aminobicyclo[2.2.2]octane-2-carboxylate (200 mg, 1.09 mmol) and 2,4-dichloro-6-(pyridin-3-yl)pyrimidine (225 mg, 0.99 mmol) in DMF (5 mL) was added potassium carbonate (151 mg, 1.09 mmol). The mixture was stirred at rt overnight. To the reaction mixture was added water (40 mL), and the mixture was extracted with EtOAc (40 mL×3). The combined organic layers were washed with saturated brine (50 mL), dried over anhydrous sodium sulfate, and filtered. The filtrate was concentrated in vacuo to dry, and the residue was purified by silica gel column chromatography (PE/EtOAc (v/v)=20/1) to give the title compound as a white solid (124 mg, 33%).

MS (ESI, pos. ion) m/z: 373.1 [M+H]$^+$;

$^1$H NMR (400 MHz, CDCl$_3$) δ (ppm): 9.17 (s, 1H), 8.73 (d, J=4.2 Hz, 1H), 8.35 (d, J=7.9 Hz, 1H), 7.43 (dd, J=7.9, 4.8 Hz, 1H), 6.88 (s, 1H), 5.64 (s, 1H), 4.36 (s, 1H), 3.77 (s, 3H), 2.41 (d, J=4.0 Hz, 1H), 2.12 (s, 1H), 1.89 (d, J=2.6 Hz, 1H), 1.82-1.64 (m, 6H), 1.49 (s, 2H).

Step 3: (+/−)-trans-methyl 3-((2-(5,7-difluoro-1-tosyl-1H-indol-3-yl)-6-(pyridin-3-yl)pyrimidin-4-yl)amino)bicyclo[2.2.2]octane-2-carboxylate To a mixed solvent of 1,4-dioxane (3 mL) and water (0.2 mL) were added 5,7-difluoro-3-(4,4,5,5-tetramethyl-1,3,2- dioxaborolan-2-yl)-1-tosyl-1H-indole (278 mg, 0.32 mmol), (+/−)-trans-methyl 3-((2-chloro-6-(pyridin-3-yl)pyrimidin-4-yl)amino)bicyclo[2.2.2]octane-2-carboxylate (100 mg, 0.27 mmol), potassium phosphate (170 mg, 0.80 mmol) and Pd(dtbpf)Cl$_2$ (17 mg, 0.03 mmol). The mixture was stirred at 100° C. for 1 h under nitrogen protection, and then filtered through a celite pad. The filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (116 mg, 67%).

$^1$H NMR (400 MHz, CDCl$_3$) δ (ppm): 9.30 (s, 1H), 8.77 (s, 2H), 8.46 (d, J=7.8 Hz, 1H), 8.31 (d, J=7.3 Hz, 1H), 7.90 (d, J=7.8 Hz, 2H), 7.51 (d, J=7.6 Hz, 1H), 7.32 (t, J=6.9 Hz, 2H), 6.85-6.72 (m, 2H), 4.58 (s, 1H), 3.75 (s, 3H), 3.08 (d, J=11.6 Hz, 1H), 2.47 (d, J=5.0 Hz, 1H), 2.41 (s, 3H), 2.13 (s, 1H), 2.02 (s, 1H), 1.94-1.62 (m, 8H).

Step 4: (+/−)-trans-3-((2-(5,7-difluoro-1H-indol-3-yl)-6-(pyridin-3-yl)pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-6-(pyridin-3-yl)pyrimidin-4-yl)amino)bicyclo[2.2.2]octane-2-carboxylate (116 mg, 0.18 mmol) in a mixed solvent of THF and MeOH (v/v=1/1, 4 mL) was added an aqueous sodium hydroxide solution (4 M, 0.45 mL, 1.80 mmol). The mixture was stirred at 30° C. overnight. The reaction mixture was diluted with water (20 mL), and the mixture was acidified with hydrochloric acid (1 M) to pH about 5.5. The resulting mixture was extracted with EtOAc (20 mL×3). The combined organic layers were washed with saturated brine (40 mL), dried over anhydrous sodium sulfate, and filtered. The filtrate was concentrated in vacuo to dry, and the residue was purified by silica gel column chromatography (dichloromethane/methanol (v/v)=10/1) to give the title compound as a yellow solid (85 mg, 99%).

MS (ESI, pos. ion) m/z: 476.1 [M+H]$^+$;
HRMS (ESI, pos. ion) m/z: 476.1902 [M+H]$^+$, (C$_{26}$H$_{24}$F$_2$N$_5$O$_2$) [M+H]$^+$ theoretical value: 476.1898;
$^1$H NMR (400 MHz, DMSO-d$_6$) δ (ppm): 12.29 (s, 1H), 9.26 (s, 1H), 8.72-8.67 (m, 1H), 8.43 (d, J=5.4 Hz, 1H), 8.34 (d, J=2.4 Hz, 1H), 8.20 (d, J=8.6 Hz, 1H), 7.66 (s, 1H), 7.58 (dd, J=7.8, 4.8 Hz, 1H), 7.09-7.04 (m, 1H), 6.83 (s, 1H), 4.67 (s, 1H), 2.53 (s, 1H), 1.89-1.37 (m, 10H);
$^{13}$C NMR (151 MHz, DMSO-d$_6$) δ (ppm): 176.00, 163.01, 158.34, 157.78, 156.29, 156.23, 151.05, 149.55, 148.07, 134.32, 133.87, 131.95, 128.95, 124.31, 122.10, 122.01, 117.35, 98.53, 97.42, 97.29, 97.22, 97.09, 67.48, 50.59, 49.68, 29.49, 28.79, 28.52, 26.01, 24.08, 21.56, 21.43, 19.48.

Example 52: (+/−)-trans-3-((2-(5,7-difluoro-1H-indol-3-yl)-6-(furan-2-yl)pyrimidin-4-yl)amino)bicyclo[2.2.2]octane-2-carboxylic Acid

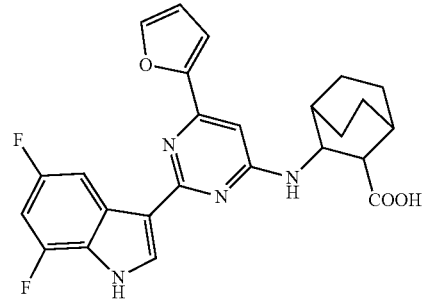 [SMILES: O=C(O)C1C2CCC(CC2)C1Nc1cc(-c2ccco2)nc(-c2c[nH]c3c(F)cc(F)cc23)n1]

Step 1: 2,4-dichloro-6-(furan-2-yl)pyrimidine

To a solution of 2,4,6-trichloropyrimidine (100 mg, 0.55 mmol) in tetrahydrofuran (4 mL) were added tetrakis(triphenylphosphine)palladium (43 mg, 0.05 mmol), furan-2-ylboronic acid (61 mg, 0.55 mol) and an aqueous sodium carbonate solution (1 M, 1.64 mL, 1.64 mmol). The mixture was heated to 80° C. and stirred overnight. To the reaction mixture was added water (50 mL), and the mixture was extracted with EtOAc (50 mL×3). The combined organic layers were washed with saturated brine (50 mL), dried over anhydrous sodium sulfate, and filtered. The filtrate was concentrated in vacuo to dry, and the residue was purified by silica gel column chromatography (PE) to give the title compound as a yellow solid (42 mg, 36%).

MS (ESI, pos. ion) m/z: 215.0 [M+H]$^+$;
$^1$H NMR (400 MHz, CDCl$_3$) δ (ppm): 7.67 (d, J=0.7 Hz, 1H), 7.58 (s, 1H), 7.43 (d, J=3.4 Hz, 1H), 6.65 (dd, J=3.4, 1.6 Hz, 1H).

Step 2: (+/−)-trans-methyl 3-((2-chloro-6-(furan-2-yl)pyrimidin-4-yl)amino)bicyclo[2.2.2]octane-2-carboxylate To a solution of (+/−)-trans-methyl 3-aminobicyclo[2.2.2]octane-2-carboxylate (429 mg, 2.34 mmol) and 2,4-dichloro-6-(furan-2-yl)pyrimidine (420 mg, 1.95 mmol) in DMF (6 mL) was added potassium carbonate (809 mg, 5.86 mmol). The mixture was stirred at rt overnight. To the reaction mixture was added water (40 mL), and the mixture was extracted with EtOAc (40 mL×3). The combined organic layers were washed with saturated brine (80 mL), dried over anhydrous sodium sulfate, and filtered. The filtrate was concentrated in vacuo to dry, and the residue was purified by silica gel column chromatography (PE/EtOAc (v/v)=5/1) to give the title compound as a white solid (383 mg, 54%).

MS (ESI, pos. ion) m/z: 362.1 [M+H]$^+$;
$^1$H NMR (400 MHz, CDCl$_3$) δ (ppm): 7.56 (s, 1H), 7.22 (s, 1H), 6.93 (s, 1H), 6.55 (d, J=1.6 Hz, 1H), 5.47 (d, J=5.5 Hz, 1H), 4.44 (s, 1H), 3.70 (s, 3H), 2.44-2.33 (m, 1H), 1.96 (d, J=2.5 Hz, 1H), 1.88 (s, 1H), 1.84-1.58 (m, 8H).

Step 3: (+/−)-trans-methyl 3-((2-(5,7-difluoro-1-tosyl-1H-indol-3-yl)-6-(furan-2-yl)pyrimidin-4-yl)amino)bicyclo[2.2.2]octane-2-carboxylate To a mixed solvent of 1,4-dioxane (3 mL) and water (0.2 mL) were added 5,7-difluoro-3-(4,4,5,5-tetramethyl-1,3,2- dioxaborolan-2-yl)-1-tosyl-1H-indole (307 mg, 0.70 mmol), (+/−)-trans-methyl 3-((2-chloro-6-(furan-2-yl)pyrimidin-4-yl)amino)bicyclo[2.2.2]octane-2-carboxylate (107 mg, 0.30 mmol), potassium phosphate (188 mg, 0.89 mmol) and Pd(dtbpf)Cl$_2$ (19 mg, 0.03 mmol). The mixture was stirred at 100° C. for 1 h under nitrogen protection, then filtered. The filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)= 5/1) to give the title compound as a yellow solid (130 mg, 69%).

$^1$H NMR (400 MHz, CDCl$_3$) δ (ppm): 8.71 (s, 1H), 8.32 (d, J=7.1 Hz, 1H), 7.89 (d, J=8.0 Hz, 2H), 7.59 (s, 1H), 7.31 (s, 3H), 6.80 (t, J=9.4 Hz, 1H), 6.68 (s, 1H), 6.61 (d, J=1.5 Hz, 1H), 5.19 (s, 1H), 4.51 (s, 1H), 3.75 (s, 3H), 2.44 (s, 1H), 2.41 (s, 3H), 2.10 (s, 1H), 2.00 (s, 1H), 1.94-1.61 (m, 8H).

Step 4: (+/−)-trans-3-((2-(5,7-difluoro-1H-indol-3-yl)-6-(furan-2-yl)pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-6-(furan-2-yl)pyrimidin-4-yl)amino)bicyclo[2.2.2]octane-2-carboxylate (130 mg, 0.21 mmol) in a mixed solvent of THF and MeOH (v/v=1/1, 4 mL) was added an aqueous sodium hydroxide solution (4 M, 0.53 mL, 2.10 mmol). The mixture was stirred at 30° C. overnight. The reaction mixture was diluted with water (20 mL), and the mixture was acidified with hydrochloric acid (1 M) to pH about 5.5. The resulting mixture was extracted with EtOAc (20 mL×3). The combined organic layers were washed with saturated brine (40 mL), dried over anhydrous sodium sulfate, and filtered. The filtrate was concentrated in vacuo to dry, and the residue was purified by silica gel column chromatography (dichloromethane/methanol (v/v)=10/1) to give the title compound as a yellow solid (54 mg, 57%).

MS (ESI, pos. ion) m/z: 465.1 [M+H]$^+$;
HRMS (ESI, pos. ion) m/z: 465.1744 [M+H]$^+$, (C$_{25}$H$_{23}$F$_2$N$_4$O$_3$) [M+H]$^+$ theoretical value: 465.1738;
$^1$H NMR (400 MHz, DMSO-d$_6$) δ (ppm): 12.21 (s, 1H), 8.25 (s, 1H), 8.20 (d, J=8.5 Hz, 1H), 7.88 (s, 1H), 7.49 (d, J=6.5 Hz, 1H), 7.22 (s, 1H), 7.07 (dd, J=14.9, 5.5 Hz, 1H), 6.70 (s, 1H), 6.61 (s, 1H), 4.63 (s, 1H), 2.47 (s, 1H), 1.82-1.39 (m, 10H);
$^{13}$C NMR (151 MHz, DMSO-d$_6$) δ (ppm): 175.92, 162.78, 157.81, 156.26, 156.19, 153.13, 152.62, 149.61, 149.51, 147.98, 147.88, 145.11, 131.69, 129.01, 122.06, 121.98, 117.25, 112.65, 110.53, 97.39, 97.26, 97.19, 97.05, 95.73, 74.00, 66.82, 50.47, 49.82, 29.49, 28.78, 28.49, 26.02, 25.41, 24.08, 21.38, 19.41.

Example 53: (2S,3S)-ethyl 3-((2-(5,7-difluoro-1H-indol-3-yl)-6-phenylpyrimidin-4-yl)amino)bicyclo[2.2.2]octane-2-carboxylate

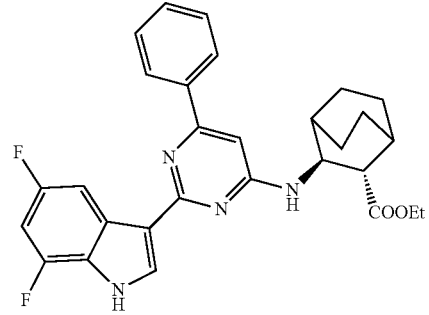 [SMILES: CCOC(=O)[C@H]1C2CCC(CC2)[C@@H]1Nc1cc(-c2ccccc2)nc(-c2c[nH]c3c(F)cc(F)cc23)n1]

Step 1: (2S,3S)-ethyl 3-aminobicyclo[2.2.2]octane-2-carboxylate hydrochloride

The title compound can be prepared according to the synthetic method disclosed in patent application WO 2015073491.

Step 2: (2S,3S)-ethyl 3-((2-chloro-6-phenylpyrimidin-4-yl)amino)bicyclo[2.2.2]octane-2-carboxylate To a solution of 2,4-dichloro-6-phenylpyrimidine (1.52 g, 6.7 mmol) and (2S,3S)-ethyl 3-aminobicyclo[2.2.2]octane-2-carboxylate hydrochloride (2.34 g, 10.0 mmol) in DMF (10 mL) was added potassium carbonate (1.85 g, 13.4 mmol). The mixture was stirred at rt overnight. To the reaction mixture was added H$_2$O (50 mL), and the mixture was extracted with EtOAc (40 mL×3). The combined organic layers were washed with saturated brine (50 mL), dried over anhydrous sodium sulfate, and filtered. The filtrate was concentrated in vacuo to dry, and the residue was purified by silica gel column chromatography (n-hexane/EtOAc (v/v)=20/1~10/1) to give the title compound as a white solid (1.65 g, 66%).

MS (ESI, pos. ion) m/z: 386.1 [M+H]$^+$.

Step 3: (2S,3S)-ethyl 3-((2-(5,7-difluoro-1-tosyl-1H-indol-3-yl)-6-phenylpyrimidin-4-yl)amino)bicyclo[2.2.2]octane-2-carboxylate To a mixed solvent of tetrahydrofuran (15 mL) and water (1 mL) were added 5,7-difluoro-3-(4,4,5,5-tetramethyl-1,3,2-dioxaborolan-2-yl)-1-tosyl-1H-indole (1.30 g, 3.00 mmol), (2S,3S)-ethyl 3-((2-chloro-6-phenoxypyrimidin-4-yl)amino)bicyclo[2.2.2]octane-2-carboxylate (1.00 g, 2.44 mmol), potassium phosphate (54 mg, 0.24 mmol) and X-Phos (233 mg, 0.49 mmol). The mixture was refuxed and stirred for 5 h under nitrogen protection, then filtered through a celite pad. The filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (1.10 g, 64%).

Step 4: (2S,3S)-ethyl 3-((2-(5,7-difluoro-1H-indol-3-yl)-6-phenylpyrimidin-4-yl)amino)bicyclo[2.2.2]octane-2-carboxylate To a reaction flask were added (2S,3S)-ethyl 3-((2-(5,7-difluoro-1-tosyl-1H-indol-3-yl)-6-phenylpyrimidin-4-yl)amino)bicyclo[2.2.2]octane-2-carboxylate (150 mg, 0.23 mmol) and a solution of TBAF in tetrahydrofuran (10 mL, 10.00 mmol, 1 M). The mixture was heated to reflux and stirred overnight. After the reaction, the mixture was concentrated in vacuo to remove the solvent, then a saturated aqueous sodium bicarbonate solution (30 mL) was added. The resulting mixture was extracted with EtOAc (30 mL×3). The combined organic phases were washed with saturated brine (60 mL), dried over anhydrous $Na_2SO_4$, filtered, and the filtrate was concentrated in vacuo to remove the solvent. The residue was purified by silica gel chromatograph (DCM/MeOH (v/v)=10/1) to give the title compound as a yellow solid (70 mg, 60%).

MS (ESI, pos. ion) m/z: 503.2 $[M+H]^+$;
HRMS (ESI, pos. ion) m/z: 503.2286 $[M+H]^+$, $(C_{29}H_{29}F_2N_4O_2)$ $[M+H]^+$ theoretical value: 503.2259;
$^1$H NMR (400 MHz, CDCl$_3$) δ (ppm): 8.97 (s, 1H), 8.30 (dd, J=10.3, 2.3 Hz, 2H), 8.16-8.10 (m, 2H), 7.56-7.47 (m, 3H), 6.84-6.75 (m, 1H), 6.69 (s, 1H), 5.24 (s, 1H), 4.55 (s, 1H), 4.27-4.10 (m, 2H), 2.44 (d, J=5.5 Hz, 1H), 2.08 (d, J=2.4 Hz, 1H), 2.00 (s, 1H), 1.68 (dd, J=15.6, 10.7 Hz, 4H), 1.62-1.47 (m, 3H), 1.21 (t, J=7.1 Hz, 3H).

Example 54: (R)-methyl 3-((2-(5,7-difluoro-1H-indol-3-yl)-7-isopropyl-7H-pyrrolo[2,3-d]pyrimidin-4-yl)amino)-4,4-dimethylpentanoate

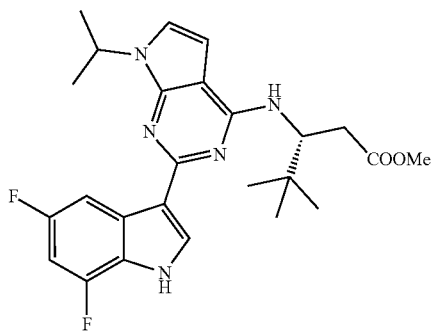 [SMILES: COC(=O)C[C@@H](Nc1nc(-c2c[nH]c3c(F)cc(F)cc23)nc2c1ccn2C(C)C)C(C)(C)C]

Step 1: (R)-methyl 3-amino-4,4-dimethylpentanoate

To a solution of (R)-3-amino-4,4-dimethylpentanoic acid (1.01 g, 6.96 mmol) in methanol (60 mL) was added dropwise slowly oxalyl chloride (0.9 mL, 10 mmol) at 0° C. The mixture was stirred for 1 h maintaining at this temperature, then heated to 65° C. and stirred for 2 h. The reaction mixture was concentrated in vacuo to dry, and the residue was washed with toluene (30 mL×3) and filtered to give the title compound as a white solid (1.11 g, 99%).

Step 2: (+/−)-trans-(R)-methyl 3-((2-chloro-7-isopropyl-7H-pyrrolo[2,3-d]pyrimidin-4-yl)amino)-4,4-dimethylpentanoate To a reaction flask were added 2,4-dichloro-7-isopropyl-7H-pyrrolo[2,3-d]pyrimidine (0.30 g, 1.30 mmol), potassium carbonate (0.36 g, 2.61 mmol), (R)-methyl 3-amino-4,4-dimethylpentanoate (0.42 g, 1.56 mmol) and DMF (10 mL). The mixture was heated to 80° C. and stirred for 24 h. After the reaction was completed, to the reaction mixture was added water (20 mL). The resulting mixture was extracted with ethyl acetate (30 mL×3). The combined organic layers were washed with saturated brine (60 mL), dried over anhydrous sodium sulfate and filtered. The filtrate was concentrated in vacuo, and the residue was purified by silica gel column chromatography (PE/EtOAc (v/v)=15/1) to give the title compound as a pale solid (260 mg, 56%).

Step 3: (R)-methyl 3-((2-(5,7-difluoro-1-tosyl-1H-indol-3-yl)-7-isopropyl-7H-pyrrolo[2,3-d]pyrimidin-4-yl)amino)-4,4-dimethylpentanoate To 1,4-dioxane (10 mL) were added 5,7-difluoro-3-(4,4,5,5-tetramethyl-1,3,2-dioxaborolan-2-yl)-1-tosyl-1H-indole (280 mg, 0.39 mmol), $K_2CO_3$ (83 mg, 0.60 mmol), Pd(dppf)Cl$_2$ (45 mg, 0.06 mmol) and (R)-methyl 3-((2-chloro-7-isopropyl-7H-pyrrolo[2,3-d]pyrimidin-4-yl)amino)-4,4-dimethylpentanoate (105 mg, 0.30 mmol), then H$_2$O (0.5 mL) was added to the mixture. The mixture was stirred at 110° C. for 4 h under nitrogen protection. The mixture was filtered through a celite pad to remove the solid impurity. The filtrate was concentrated in vacuo, and the residue was purified by silica gel column chromatography (PE/EtOAc (v/v)=10/1) to give the title compound as colorless oil (126 mg, 68%).

MS (ESI, pos. ion) m/z: 624.30 $[M+H]^+$.

Step 4: (R)-methyl 3-((2-(5,7-difluoro-1H-indol-3-yl)-7-isopropyl-7H-pyrrolo[2,3-d]pyrimidin-4-yl)amino)-4,4-dimethylpentanoate To a reaction flask were added (R)-methyl 3-((2-(5,7-difluoro-1-tosyl-1H-indol-3-yl)-7-isopropyl-7H-pyrrolo[2,3-d]pyrimidin-4-yl)amino)-4,4-dimethylpentanoate (130 mg, 0.20 mmol) and a solution of TBAF in tetrahydrofuran (10 mL, 10.00 mmol, 1 M). The mixture was heated to reflux and stirred overnight. The reaction mixture was concentrated to remove the solvent, and to the residue was added a saturated aqueous sodium bicarbonate solution (30 mL). The resulting mixture was extracted with EtOAc (20 mL×3). The combined organic layers were washed with saturated brine (50 mL), dried over anhydrous sodium sulfate, and filtered. The filtrate was concentrated in vacuo to dry, and the residue was purified by silica gel column chromatography (dichloromethane/methanol (v/v)=10/1) to give the title compound as a yellow solid (80 mg, 81%).

MS (ESI, pos. ion) m/z: 470.3 $[M+H]^+$;
HRMS (ESI, pos. ion) m/z: 470.2395 $[M+H]^+$, $(C_{25}H_{30}F_2N_5O_3)$ $[M+H]^+$ theoretical value: 470.2368;
$^1$H NMR (400 MHz, CDCl$_3$) δ (ppm): 8.57 (s, 1H), 8.33 (d, J=9.5 Hz, 1H), 8.26 (s, 1H), 7.03 (d, J=3.4 Hz, 1H), 6.85-6.75 (m, 1H), 6.42 (s, 1H), 5.19 (dt, J=12.4, 6.2 Hz, 1H), 4.99 (s, 1H), 3.52 (s, 3H), 2.79 (dd, J=14.5, 4.1 Hz, 1H), 2.55 (dd, J=14.4, 8.6 Hz, 1H), 1.80 (s, 1H), 1.60 (d, J=1.6 Hz, 3H), 1.58 (d, J=1.6 Hz, 3H), 1.08 (s, 9H).

Example 55: (2S,3S)-3-((2-(5,7-difluoro-1H-indol-3-yl)-5-fluoro-6-(thiophen-2-yl)pyrimidin-4-yl)amino)bicyclo[2.2.2]octane-2-carboxylic Acid

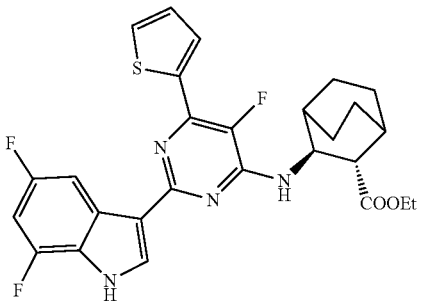 [SMILES: CCOC(=O)[C@H]1C2CCC(CC2)[C@@H]1Nc1nc(-c2c[nH]c3c(F)cc(F)cc23)nc(-c2cccs2)c1F]

Step 1: 2,4-dichloro-5-fluoro-6-(thiophen-2-yl)pyrimidine

To a −15° C. solution of thiophene (300 mg, 3.57 mmol) in anhydrous tetrahydrofuran (20 mL) was added n-butyllithium (1.4 mL, 3.57 mmol, 2.5 M). The mixture was stirred for 1 h maintaining at this temperature, then ZnCl-TMEDA (300 mg, 1.18 mmol) was added. The mixture was stirred for 1 h at rt, then palladium dichloride (65 mg, 0.36 mmol), triphenylphosphine (188 mg, 0.71 mmol) and 2,4,6-trichloro-5-fluoropyrimidine (790 mg, 3.92 mmol) were added. The mixture was heated to 55° C. and stirred overnight under nitrogen protection. To the reaction mixture was added water (50 mL), and the mixture was extracted with EtOAc (50 mL×3). The combined organic layers were washed with saturated brine (50 mL), dried over anhydrous sodium sulfate, and filtered. The filtrate was concentrated in vacuo to dry, and the residue was purified by silica gel column chromatography (PE) to give the title compound as a white solid (366 mg, 41%).

MS (ESI, pos. ion) m/z: 250.95 [M+H]$^+$.

Step 2: (2S,3S)-ethyl 3-aminobicyclo[2.2.2]octane-2-carboxylate hydrochloride The title compound can be prepared according to the synthetic method disclosed in patent application WO 2015073491.

Step 3: (2S,3S)-ethyl 3-((2-chloro-5-fluoro-6-(thiophen-2-yl)pyrimidin-4-yl)amino)bicyclo[2.2.2]octane-2-carboxylate A suspension of 2,4-dichloro-5-fluoro-6-(thiophen-2-yl)pyrimidine (366 mg, 1.47 mmol), (2S,3S)-ethyl 3-aminobicyclo[2.2.2]octane-2-carboxylate hydrochloride (412 mg, 1.76 mmol) and K$_2$CO$_3$ (406 mg, 2.94 mmol) in DMF (5 mL) was stirred at rt overnight. To the reaction mixture was added H$_2$O (100 mL), and the mixture was extracted with EtOAc (50 mL×3). The combined organic layers were washed with saturated brine (80 mL×3), dried over anhydrous sodium sulfate, and filtered. The filtrate was concentrated, and the residue was purified by silica gel column chromatography (PE/EtOAc (v/v)=5/1) to give the title compound as a white solid (388 mg, 64%).

MS (ESI, pos. ion) m/z: 410.20[M+H]$^+$;

$^1$H NMR (400 MHz, CDCl$_3$) δ (ppm) 7.84 (s, 1H), 7.57 (d, J=4.8 Hz, 1H), 7.18 (t, J=4.2 Hz, 1H), 5.34 (s, 1H), 4.53 (s, 1H), 4.24 (m, 2H), 2.41 (d, J=5.5 Hz, 1H), 2.05 (d, J=10.7 Hz, 2H), 1.93-1.77 (m, 3H), 1.69 (d, J=9.2 Hz, 5H), 1.29 (t, J=5.2 Hz, 3H).

Step 4: (2S,3S)-ethyl 3-((2-(5,7-difluoro-1-tosyl-1H-indol-3-yl)-5-fluoro-6-(thiophen-2-yl)pyrimidin-4-yl)amino)bicyclo[2.2.2]octane-2-carboxylate To a mixed solvent of 1,4-dioxane (15 mL) and H$_2$O (1 mL) were added 5,7-difluoro-1-tosyl-3-(4,4,5,5-tetramethyl-1,3,2-dioxaborolan-2-yl)indole (1.30 g, 3.00 mmol), potassium carbonate (1.35 g, 9.77 mmol), palladium acetate (54 mg, 0.25 mmol), (2S,3S)-ethyl 3-((2-chloro-5-fluoro-6-(thiophen-2-yl)pyrimidin-4-yl)amino)bicyclo[2.2.2]octane-2-carboxylate (1.00 g, 2.44 mmol) and X-phos (233 mg, 0.49 mmol). The mixture was refluxed and stirred for 5 h. The mixture was filtered through a celite pad to remove the solid impurities, and the filtrate was concentrated to remove the solvent. The residue was purified by silica gel column chromatography (PE/EtOAc (v/v)=15/1~5/1) to give the title compound as a light yellow solid (1.10 g, 66%).

Step 5: (2S,3S)-3-((2-(5,7-difluoro-1H-indol-3-yl)-5-fluoro-6-(thiophen-2-yl)pyrimidin-4-yl)amino)bicyclo[2.2.2]octane-2-carboxylic Acid To a solution of (2S,3S)-ethyl 3-((2-(5,7-difluoro-1-tosyl-1H-indol-3-yl)-5-fluoro-6-(thiophen-2-yl)pyrimidin-4-yl)amino)bicyclo[2.2.2]octane-2-carboxylate (600 mg, 0.88 mmol) in a mixed solvent of ethanol, THF and water (v/v/v=3 mL/3 mL/3 mL) was added sodium hydroxide (0.35 g, 8.80 mmol). The mixture was stirred at rt overnight. To the reaction mixture was added water (20 mL), and the mixture was acidified with hydrochloric acid (3 M) to pH about 6. The resulting mixture was extracted with EtOAc (30 mL×3). The combined organic layers were washed with saturated brine (60 mL), dried over anhydrous sodium sulfate, and filtered. The filtrate was concentrated in vacuo to remove the solvent, and the residue was purified by silica gel column chromatography (PE/EtOAc (v/v)=5/1-1/1) to give the title compound as a yellow solid (230 mg, 51%).

MS (ESI, pos. ion) m/z: 499.1 [M+H]$^+$;

HRMS (ESI, pos. ion) m/z: 499.1403 [M+H]$^+$, (C$_{25}$H$_{22}$F$_3$N$_4$O$_2$S) [M+H]$^+$ theoretical value: 499.1416;

$^1$H NMR (400 MHz, DMSO-d$_6$) δ (ppm): 12.27 (s, 1H), 12.24 (s, 1H), 8.18 (dd, J=10.0, 1.9 Hz, 1H), 8.13 (d, J=2.7 Hz, 1H), 7.86 (m, 2H), 7.64 (d, J=6.4 Hz, 1H), 7.30 (m, 1H), 7.09 (dd, J=15.2, 5.7 Hz, 1H), 4.68 (t, J=6.7 Hz, 1H), 2.87 (d, J=6.6 Hz, 1H), 2.00 (d, J=10.6 Hz, 2H), 1.86-1.71 (m, 3H), 1.65-1.45 (m, 5H).

Example 56: (+/−)-trans-3-((2-(5,7-difluoro-1H-indol-3-yl)-5-fluoro-6-(furan-2-yl)pyrimidin-4-yl)amino)bicyclo[2.2.2]octane-2-carboxylic Acid

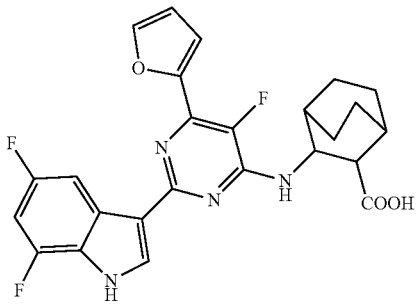 [SMILES: O=C(O)C1C2CCC(CC2)C1Nc1nc(-c2c[nH]c3c(F)cc(F)cc23)nc(-c2ccco2)c1F]

Step 1: (+/−)-trans-methyl 3-((2,6-chloro-5-fluoro-pyrimidin-4-yl)amino)bicyclo[2.2.2]octane-2-carboxylate To a reaction flask were added 2,4,6-trichloro-5-fluoropyrimidine (10.00 g, 49.65 mmol), potassium carbonate (21.00 g, 148.90 mmol), (+/−)-trans-methyl 3-aminobicyclo[2.2.2]octane-2-carboxylate (10.00 g, 54.61 mmol) and DMF (50 mL), and the mixture was stirred at rt for 5 h. To the reaction mixture was added water (100 mL), and the aqueous layer was extracted with ethyl acetate (100 mL×3). The combined organic layers were washed with saturated brine (200 mL) one time, dried over anhydrous sodium sulfate and filtered. The filtrate was concentrated in vacuo, and the residue was purified by silica gel column chromatography (PE/EtOAc (v/v)=20/1) to give the title compound as a light yellow solid (12.00 g, 69%).

MS (ESI, pos. ion) m/z: 348.10[M+H]$^+$.

Step 2: (+/−)-trans-methyl 3-((2-chloro-5-fluoro-6-(furan-2-yl)pyrimidin-4-yl)amino)bicyclo[2.2.2]octane-2-carboxylate To acetonitrile (100 mL) were added (+/−)-trans-methyl 3-((2,6-dichloro-5-fluoropyrimidin-4-yl)amino)bicyclo[2.2.2]octane-2-carboxylate (2.00 g, 5.74 mmol), 2-furanboronic acid (0.65 g, 5.74 mmol), potassium acetate (1.70 g, 17.2 mmol) and Pd(dppf)Cl$_2$ (0.50 g, 0.57 mmol), then to the mixture was added water (5 mL). The resulting mixture was stirred at 80° C. for 12 h under nitrogen protection. The mixture was filtered through a celite pad to remove the solid impurities, and the filtrate was concentrated to remove the solvent. The residue was purified by silica gel column chromatography (PE/EtOAc (v/v)=20/1) to give the title compound as a yellow solid (700 mg, 30%).

MS (ESI, pos. ion) m/z: 380.2[M+H]$^+$.

Step 3: (+/−)-trans-methyl 3-((2-(5,7-difluoro-1-tosyl-1H-indol-3-yl)-5-fluoro-6-(furan-2-yl)pyrimidin-4-yl) amino)bicyclo[2.2.2]octane-2-carboxylate To a mixed solvent of 1,4-dioxane (10 mL) and water (1 mL) were added 5,7-difluoro-3-(4,4,5,5-tetramethyl-1,3,2-dioxaborolan-2-yl)-1-tosyl-1H-indole (630 mg, 0.87 mmol, 60% w.t), potassium phosphate (503 mg, 2.37 mmol), Pd(dppf)Cl$_2$ (78 mg, 0.08 mmol) and (+/−)-trans-methyl 3-((2-chloro-5-fluoro-6-(furan-2-yl)pyrimidin-4-yl)amino)bicyclo[2.2.2]octane-2-carboxylate (300 mg, 0.79 mmol). The mixture was heated to 100° C. and stirred for 12 h. The mixture was filtered to remove the solid impurities, and the filtrate was concentrated to remove the solvent. The residue was purified by silica gel column chromatography (PE/EtOAc (v/v)=8/1) to give the title compound as a light yellow solid (300 mg, 58%).

MS (ESI, pos. ion) m/z: 651.3[M+H]$^+$.

Step 4: (+/−)-trans-3-((2-(5,7-difluoro-1H-indol-3-yl)-5-fluoro-6-(furan-2-yl)pyrimidin-4-yl)amino)bicyclo[2.2.2]octane-2-carboxylic Acid To a solution of (+/−)-trans-methyl 3-((2-(5,7-difluoro-1-tosyl-1H-indol-3-yl)-5-fluoro-6-(furan-2-yl) pyrimidin-4-yl)amino)bicyclo[2.2.2]octane-2-carboxylate (300 mg, 0.46 mmol) in THF/MeOH (v/v=2/1, 12 mL) was added a solution of NaOH (184 mg, 4.60 mmol) in water (2 mL). The mixture was stirred at rt overnight. To the reaction mixture was added water (10 mL), and the mixture was acidified with hydrochloric acid (1 M) to pH about 4. The resulting mixture was extracted with EtOAc (20 mL×3). The combined organic layers were washed with saturated brine (50 mL), dried over anhydrous sodium sulfate, and filtered. The filtrate was concentrated in vacuo to remove the solvent, and the residue was purified by silica gel column chromatography (DCM/MeOH (v/v)=10/1~5/1) to give the title compound as a white solid (130 mg, 58%).

MS (ESI, pos. ion) m/z: 483.1[M+H]$^+$;
HRMS (ESI, pos. ion) m/z: 483.1649[M+H]$^+$, ($C_{23}H_{22}ClFN_6O_3$) [M+H]$^+$ theoretical value: 483.1644;
$^1$H NMR (400 MHz, DMSO-d$_6$) δ(ppm): 12.22 (s, 1H), 8.19 (d, J=9.5 Hz, 2H), 8.00 (s, 1H), 7.63 (t, J=13.5 Hz, 1H), 7.27 (d, J=17.4 Hz, 1H), 7.05 (t, J=9.6 Hz, 1H), 6.81 (d, J=42.4 Hz, 1H), 4.72 (s, 1H), 2.89 (d, J=6.5 Hz, 1H), 2.18 (s, 1H), 2.03-1.97 (m, 2H), 1.90-1.72 (m, 3H), 1.66-1.39 (m, 5H), 1.25-1.09 (m, 1H);
$^{13}$C NMR (151 MHz, DMSO-d$_6$) δ(ppm): 176.01, 145.62, 139.72, 131.15, 125.35, 121.91, 112.64, 103.16, 97.23, 51.17, 48.21, 40.60, 40.39, 40.18, 39.97, 39.76, 39.55, 39.34, 28.82, 28.76, 25.78, 24.21, 21.58, 21.44, 19.48.

EXAMPLES OF BIOLOGICAL ASSAY

Using parts of the compounds of the invention as examples, the inventors have detected antiviral activities and cytotoxicity, pharmacokinetic properties, and stability in liver microsomes of the compounds of the invention in the following examples.

Antiviral and Cytotoxicity Assay

Example A: Cytopathic Effect Assay (CPE Assay)

Detection of the inhibitory effect of the compound of the invention against cytopathic effect (CPE) caused by virus H1N1 A/Weiss/43 on cellular level in vitro.

Experimental procedure: MDCK cells were seeded in a 384-well plate with 2000 cells per well and cultured at 37° C. under 5% CO$_2$ condition overnight. Next day, cell culture medium was replenished with fresh medium containing various concentrations of test compounds and virus H1N1 A/Weiss/43 at a multiplicity of infection to yield 80-95% CPE. The top final concentration of the test compounds was 100 nM and then diluted by 3-fold serially for a total of 8 concentrations at 100 nM, 33.33 nM, 11.11 nM, 3.70 nM, 1.23 nM, 0.41 nM, 0.14 nM, 0.05 nM. A cytotoxicity test group without influenza virus containing relevant concentrations of compound was set, while a virus control group without drug and a no virus infecting cell control group without drug were set at the same time. Each group was set in duplicate, and incubated at 37° C. under 5% $CO_2$ condition for 5 days. The cell activity was detected by using CCK-8 kits, and the data were used for calculating the antiviral effect and cytotoxicity against virus-infected cell of the compound. Data were analyzed by using GraphPad Prism software, and the CPE inhibition ratio was calculated. $EC_{50}$ was obtained according to the curve fitting.

CPE inhibition ratio=((absorbance of dosing well–absorbance of virus control well)/(absorbance of cell control well–absorbance of virus control well))×100%

TABLE 1

Inhibitory acitivities of compounds of the invention aganist influenza virus (A/Weiss/43(H1N1))

| Example No. | $EC_{50}$ (nM) |
|---|---|
| Example 1 | 5.503 |
| Example 6 | 6.010 |
| Example 9 | 2.24 |
| Example 10 | 27.90 |
| Example 24 | 11.01 |
| Example 31 | 17.10 |
| Example 34 | 2.19 |
| Example 35 | 4.04 |
| Example 52 | 1.21 |
| Example 56 | 1.05 |

JNJ-872, the structure as shown below) in SD rat, dog and monkey were evaluated. The compounds disclosed herein were administered in form of a saline solution containing 5% DMSO, 5% Kolliphor HS 15 and 90% Saline. For intravenous administration (iv), the animals were administered with a dose of 1 mg/kg, and blood samples (0.3 mL) were collected at the time points of 0.083, 0.25, 0.5, 1.0, 2.0, 5.0, 7.0 and 24 h after drug administration, then each blood sample was processed to separate plasma by centrifugation at 3000 rpm or 4000 rpm for 10 minutes. For oral administration (po), the animals were administered with a dose of 5 mg/kg, and blood samples (0.3 mL) were collected at the time points of 0.25, 0.5, 1.0, 2.0, 5.0, 7.0 and 24 h after drug administration, then each blood sample was processed to separate plasma by centrifugation at 3000 rpm or 4000 rpm for 10 minutes. Plasma samples were collected and stored at −20° C. or −70° C. until LC/MS/MS analysis. The pharmacokinetic data of the compounds of the invention in SD rat was showed in table 2.

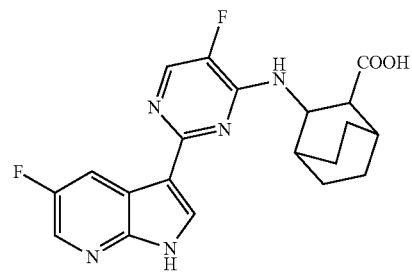

VX-787

TABLE 2

Pharmacokinetic data of the compounds of the invention in SD rat

| Test compound | Administration route | dosage mg/kg | $T_{max}$ h | $C_{max}$ ng/mL | $t_{1/2}$ h | $AUC_{last}$ hr * ng/mL | $AUC_{INF}$ hr * ng/mL | F % | CL L/h/Kg | Vss L/Kg |
|---|---|---|---|---|---|---|---|---|---|---|
| Control | iv | 1 | 0.083 | 2840 | 5.72 | 1180 | 1210 | N/A | 13.8 | 1.81 |
| VX-787 (racemization) | po | 5 | 0.333 | 1970 | 4.14 | 3510 | 3530 | 58.4 | N/A | N/A |
| Example 1 | iv | 1 | 0.083 | 4650 | 1.48 | 2890 | 2950 | N/A | 5.74 | 0.378 |
|  | po | 5 | 1.5 | 2910 | 1.37 | 10500 | 10600 | 72.1 | N/A | N/A |
| Example 34 | iv | 1 | 0.083 | 5400 | 1.35 | 3920 | 3940 | N/A | 4.23 | 0.515 |
|  | po | 5 | 0.5 | 8880 | 1.38 | 19600 | 19700 | 100.2 | N/A | N/A |
| Example 35 | iv | 1 | 0.083 | 6080 | 1.23 | 5050 | 5080 | N/A | 3.3 | 0.264 |
|  | po | 5 | 0.5 | 9920 | 1.21 | 24000 | 24000 | 94.6 | N/A | N/A |
| Example 52 | iv | 1 | 0.083 | 7420 | 1.38 | 5490 | 5570 | N/A | 3.02 | 0.229 |
|  | po | 5 | 1.17 | 6430 | 1.29 | 22600 | 22700 | 81.5 | N/A | N/A |

Notes:
Control compound - (+/−)-trans-3-((5-fluoro-2-(5-fluoro-1H-pyrrolo[2,3-b]pyridin-4-yl)pyrimidin-4-yl)amino)bicyclo[2.2.2]octane-2-carboxylic acid (The specific synthetic procedure can be seen in patent WO 2010148197);
$AUC_{last}$ - AUC of 0 to 24 h;
$AUC_{INF}$ - AUC of 0 to infinite time.

The assay shows that the compounds of the invention have good anti-influenza virus activities.

Pharmacokinetic Test

Example B: Pharmacokinetic Evaluation after Administering a Certain Amount of the Compound of the Invention by Intravenous or Oral to Rats Pharmacokinetic characteristics of the compound of the invention and the control compound VX-787 (also named Table 2 shows that $C_{max}$, $AUC_{last}$ and $AUC_{INF}$ of the compounds of the invention in SD rat are higher than these of the compound VX-787 in both intravenous administration and oral administration. It indicates that the compounds of the invention have high exposure level and good absorption, thus the pharmacokinetic properties of the compounds of the invention are significantly better than control compound VX-787.

Stability Test of the Compounds in Liver Microsomes

Example C: Stability Evaluation of the Compounds in Human Liver Microsomes

The stability of the compounds of the invention and control compound VX-787 (also named JNJ-872, the specific structure were shown in example B) in rat and human liver microsomes have been evaluated in the invention. The compounds of the invention and rat or human liver microsome were co-incubated under the condition of 37° C., pH=7.4. The compound concentration at different incubation time was determined, and the rate constant was obtained according to Log[drug concentration]–incubation time curve. The half life and clearance rate in vivo ($Cl_{in\ vivo}$) of the compound were calculated, and the stability of the compounds in liver microsomes were evaluated by half life and clearance rate in vivo. The specific experimental system was shown in table 3. The data of stability of the compounds of the invention in human liver microsomes was showed in table 4.

TABLE 3

| | |
|---|---|
| Reference substance | Verapamil |
| Test concentration | 1 µM |
| Test system | Mixed human liver microsome, test concentration 0.5 mg/ml |
| Test condition | 0, 15, 30, 60 min, pH 7.4, 37° C. |
| Number of duplicate sample | 2 |
| Analytical method | LC/MS/MS |

TABLE 4

The data of stability of the compounds of the invention in human liver microsomes

| | | | human liver microsome | | |
|---|---|---|---|---|---|
| Test compound | Concentration (µM) | $T_{1/2}$ (min) | $Cl_{Hep}$ (mL/min/kg) | $Cl_{in\ vivo}$ (mL/min/kg) | ER |
| Verapamil | 1 | 10.1 | 171.6 | 18.5 | 0.9 |
| VX-787 (racemization) | 1 | 213.8 | 8.1 | 5.8 | 0.3 |
| Example 1 | 1 | 766.9 | 2.3 | 2.0 | 0.1 |
| Example 34 | 1 | 465.2 | 3.7 | 3.2 | 0.2 |
| Example 35 | 1 | 399.6 | 4.4 | 3.6 | 0.2 |

Notes:
$T_{1/2}$—half-time; $Cl_{Hep}$—hepatic clearance; $Cl_{in\ vivo}$—clearance rate in vivo; ER—extraction ratio.

Table 4 shows that the compounds of the invention have good stability in human liver microsomes.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound having Formula (I) or a stereoisomer, a tautomer, an N-oxide, a solvate, a metabolite, or a pharmaceutically acceptable salt thereof,

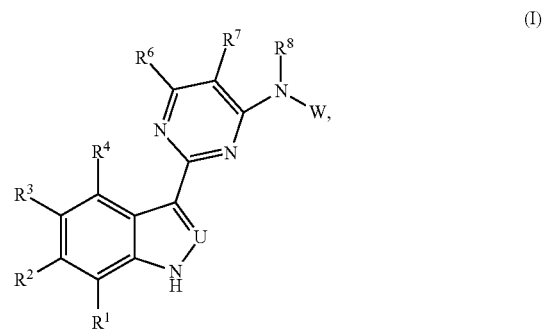

(I)

wherein,

U is N or $CR^5$;

each of $R^1$, $R^2$, $R^3$, $R^4$ and $R^5$ is independently H, D, F, Cl, Br, CN, $NO_2$, —C(=O)$R^a$, —C(=O)$OR^b$, —C(=O)$NR^cR^d$, $OR^b$, —$NR^cR^d$, $R^bO$—$C_{1-4}$ alkylene, $R^dR^cN$—$C_{1-4}$ alkylene, $C_{1-6}$ alkyl, $C_{2-6}$ alkenyl or $C_{2-6}$ alkynyl, and wherein each of the $C_{1-6}$ alkyl, $C_{2-6}$ alkenyl and $C_{2-6}$ alkynyl is independently unsubstituted or substituted with 1, 2, 3 or 4 substituents independently selected from D, F, Cl, Br, CN, $OR^b$, —$NR^cR^d$, $C_{1-6}$ alkyl, $C_{1-6}$ haloalkyl, $R^bO$—$C_{1-4}$ alkylene or $R^dR^cN$—$C_{1-4}$ alkylene;

$R^6$ is $OR^b$, $C_{2-6}$ alkyl, $C_{2-6}$ alkenyl, $C_{2-6}$ alkynyl, $C_{3-12}$ carbocyclyl, $C_{3-12}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 16-membered heteroaryl or (5- to 16-membered heteroaryl)-$C_{1-4}$ alkylene, and wherein each of the $C_{2-6}$ alkyl, $C_{2-6}$ alkenyl, $C_{2-6}$ alkynyl, $C_{3-12}$ carbocyclyl, $C_{3-12}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 16-membered heteroaryl and (5- to 16-membered heteroaryl)-$C_{1-4}$ alkylene is independently unsubstituted or substituted with 1, 2, 3, 4 or 5 R';

$R^7$ is H, D, F, Cl, Br, CN, $NO_2$, —C(=O)$R^a$, —C(=O)$OR^b$, —C(=O)$NR^cR^d$, $OR^b$, —$NR^cR^d$, $R^bO$—$C_{1-4}$ alkylene, $R^dR^cN$—$C_{1-4}$ alkylene, $C_{1-6}$ alkyl, $C_{2-6}$ alkenyl, $C_{2-6}$ alkynyl, $C_{3-12}$ cycloalkyl, $C_{3-12}$ cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene, and wherein each of the $C_{1-6}$ alkyl, $C_{2-6}$ alkenyl, $C_{2-6}$ alkynyl, $C_{3-12}$ cycloalkyl, $C_{3-12}$ cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl and (5- to 10-membered heteroaryl)-$C_{1-4}$ alkylene is independently unsubstituted or substituted with 1, 2, 3, 4 or 5 R';

or, $R^6$ and $R^7$, together with the carbon atoms to which they are attached, form a $C_{3-12}$ carbocyclic ring, 3- to 12-membered heterocyclic ring, $C_{6-10}$ aromatic ring or 5- to 10-membered heteroaromatic ring, and wherein each of the $C_{3-12}$ carbocyclic ring, 3- to 12-membered heterocyclic ring, $C_{6-10}$ aromatic ring and 5- to 10-membered heteroaromatic ring is independently unsubstituted or substituted with 1, 2, 3, 4 or 5 R';

each R' is independently D, F, Cl, Br, CN, $NO_2$, $OR^b$, $-NR^cR^d$, $R^bO-C_{1-4}$ alkylene, $R^dR^cN-C_{1-4}$ alkylene, $-C(=O)R^a$, $-C(=O)OR^b$, $-C(=O)NR^cR^d$, $C_{1-12}$ alkyl, $C_{1-6}$ haloalkyl, $C_{3-6}$ cycloalkyl, $C_{3-6}$ cycloalkyl-$C_{1-4}$ alkylene, 3- to 8-membered heterocyclyl, (3- to 8-membered heterocyclyl)-$C_{1-4}$ alkylene, $C_{6-10}$ aryl, $C_{6-10}$ aryl-$C_{1-4}$ alkylene, 5- to 8-membered heteroaryl or (5- to 8-membered heteroaryl)-$C_{1-4}$ alkylene, and wherein each of the $C_{1-12}$ alkyl, $C_{1-6}$ haloalkyl, $C_{3-6}$ cycloalkyl, $C_{3-6}$ cycloalkyl-$C_{1-4}$ alkylene, 3- to 8-membered heterocyclyl, (3- to 8-membered heterocyclyl)-$C_{1-4}$ alkylene, $C_{6-10}$ aryl, $C_{6-10}$ aryl-$C_{1-4}$ alkylene, 5- to 8-membered heteroaryl and (5- to 8-membered heteroaryl)-$C_{1-4}$ alkylene is independently unsubstituted or substituted with 1, 2, 3 or 4 substituents independently selected from D, F, Cl, Br, CN, $NO_2$, $OR^b$, $-NR^cR^d$, $C_{1-6}$ alkyl, $C_{1-6}$ haloalkyl, $R^bO-C_{1-4}$ alkylene or $R^dR^cN-C_{1-4}$ alkylene;

$R^8$ is H, D or $C_{1-6}$ alkyl, and wherein $C_{1-6}$ alkyl is optionally substituted with 1, 2, 3 or 4 substituents independently selected from D, F, Cl, Br, CN, $NO_2$ or $OR^b$;

W is one of the following sub-formulae:

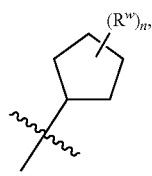
(W-1)

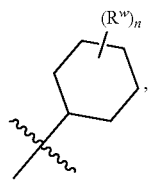
(W-2)

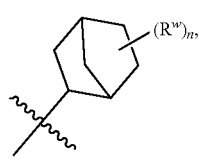
(W-3)

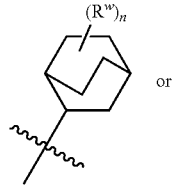
or
(W-4)

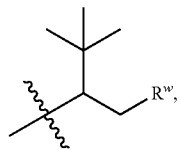
(W-5)

wherein n is 0, 1, 2, 3, or 4;

each $R^w$ is independently D, F, Cl, Br, CN, $NO_2$, oxo (=O), $-C(=O)R^a$, $-C(=O)OR^b$, $-NR^eC(=O)R^a$, $-NR^eC(=O)NR^cR^d$, $-S(=O)_2R^f$, $-S(=O)_2NR^eC(=O)R^a$, $-S(=O)_2NR^cR^d$, $(R^bO)_2P(=O)-C_{0-2}$ alkylene, $OR^b$, $R^bO-C_{1-2}$ alkylene, $C_{1-6}$ alkyl or 5- to 6-membered heteroaryl, and wherein each of the $C_{1-6}$ alkyl and 5- to 6-membered heteroaryl is independently unsubstituted or substituted with 1, 2, 3 or 4 substituents independently selected from D, F, Cl, Br, CN, $N_3$, oxo (=O), $NO_2$, $OR^b$, $C_{1-6}$ alkyl or $C_{1-6}$ haloalkyl;

each $R^a$, $R^b$, $R^c$, $R^d$, $R^e$ and $R^f$ is independently H, D, $C_{1-6}$ haloalkyl, $C_{1-6}$ alkyl, $C_{2-6}$ alkenyl, $C_{2-6}$ alkynyl, $C_{3-6}$ carbocyclyl, $C_{3-6}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl, (5- to 10-membered heteroaryl)-$C_{1-4}$ alkylene; or, $R^c$ and $R^d$, together with the nitrogen atom to which they are attached, form 3- to 8-membered heterocyclyl or 5- to 8-membered heteroaryl, and wherein each of the $C_{1-6}$ alkyl, $C_{2-6}$ alkenyl, $C_{2-6}$ alkynyl, $C_{3-6}$ carbocyclyl, $C_{3-6}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl, (5- to 10-membered heteroaryl)-$C_{1-4}$ alkylene, 3- to 8-membered heterocyclyl and 5- to 8-membered heteroaryl is independently unsubstituted or substituted with 1, 2, 3 or 4 substituents independently selected from D, F, Cl, CN, OH, $NH_2$, $C_{1-6}$ alkyl, $C_{1-6}$ haloalkyl, $C_{1-6}$ alkoxy or $C_{1-6}$ alkylamino.

2. The compound of claim 1 having Formula (II),

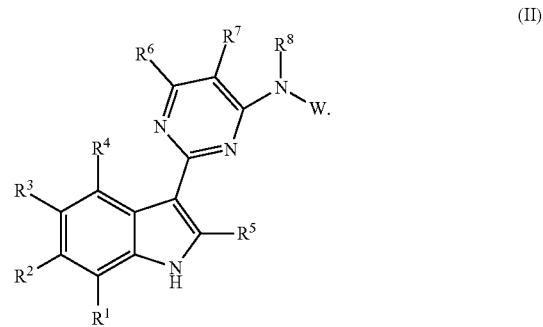
(II)

3. The compound of claim 1 having Formula (III),

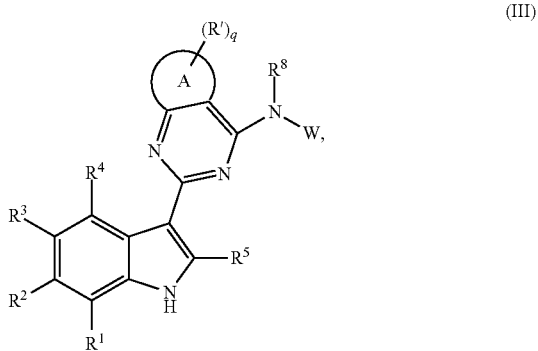

wherein, A is a $C_{3-12}$ carbocyclic ring, 3- to 12-membered heterocyclic ring, $C_{6-10}$ aromatic ring or 5- to 10-membered heteroaromatic ring; and
q is 0, 1, 2, 3, 4 or 5.

4. The compound of claim 1, wherein each of $R^1$, $R^2$, $R^3$, $R^4$ and $R^5$ is independently H, D, F, Cl, Br, CN, $NO_2$, —C(=O)$R^a$, —C(=O)$OR^b$, —C(=O)$NR^cR^d$, $OR^b$, —$NR^cR^d$, methyl, ethyl, n-propyl or i-propyl, and wherein each of methyl, ethyl, n-propyl and i-propyl is independently unsubstituted or substituted with 1, 2, 3 or 4 substituents independently selected from D, F, Cl, Br, CN, $OR^b$, —$NR^cR^d$ or $C_{1-3}$ haloalkyl.

5. The compound of claim 1, wherein $R^6$ is $OR^b$, $C_{2-3}$ alkyl, $C_{2-4}$ alkenyl, $C_{2-4}$ alkynyl, $C_{3-6}$ carbocyclyl, $C_{3-6}$ carbocyclyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 14-membered heteroaryl or (5- to 14-membered heteroaryl)-$C_{1-4}$ alkylene, and wherein each of the $C_{2-3}$ alkyl, $C_{2-4}$ alkenyl, $C_{2-4}$ alkynyl, $C_{3-6}$ carbocyclyl, $C_{3-6}$ carbocyclyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 14-membered heteroaryl and (5- to 14-membered heteroaryl)-$C_{1-4}$ alkylene is independently unsubstituted or substituted with 1, 2, 3, 4 or 5 R';
$R^7$ is H, D, F, Cl, Br, CN, $NO_2$, —C(=O)$R^a$, —C(=O)$OR^b$, —C(=O)$NR^cR^d$, $OR^b$, —$NR^cR^d$, $C_{1-3}$ alkyl, $C_{2-4}$ alkenyl, $C_{2-4}$ alkynyl, $C_{3-6}$ cycloalkyl, $C_{3-6}$ cycloalkyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 6-membered heteroaryl or (5- to 6-membered heteroaryl)-$C_{1-4}$ alkylene, and wherein each of the $C_{1-3}$ alkyl, $C_{2-4}$ alkenyl, $C_{2-4}$ alkynyl, $C_{3-6}$ cycloalkyl, $C_{3-6}$ cycloalkyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 6-membered heteroaryl and (5- to 6-membered heteroaryl)-$C_{1-4}$ alkylene is independently unsubstituted or substituted with 1, 2, 3, 4 or 5 R';
or, $R^6$ and $R^7$, together with the carbon atoms to which they are attached, form a $C_{3-6}$ carbocyclic ring, 3- to 6-membered heterocyclic ring, $C_{6-10}$ aromatic ring or 5- to 10-membered heteroaromatic ring, and wherein each of the $C_{3-6}$ carbocyclic ring, 3- to 6-membered heterocyclic ring, $C_{6-10}$ aromatic ring and 5- to 10-membered heteroaromatic ring is independently unsubstituted or substituted with 1, 2, 3, 4 or 5 R'.

6. The compound of claim 1, wherein each R' is independently D, F, Cl, Br, CN, $NO_2$, $OR^b$, —$NR^cR^d$, —C(=O)$R^a$, —C(=O)$NR^cR^d$, $C_{1-9}$ alkyl, $C_{1-3}$ haloalkyl, $C_{3-6}$ cycloalkyl, 5- to 6-membered heterocyclyl, phenyl, phenyl-$C_{1-2}$ alkylene or 5- to 6-membered heteroaryl, and wherein each of the $C_{1-9}$ alkyl, $C_{1-3}$ haloalkyl, $C_{3-6}$ cycloalkyl, 5- to 6-membered heterocyclyl, phenyl, phenyl-$C_{1-2}$ alkylene and 5- to 6-membered heteroaryl is independently unsubstituted or substituted with 1, 2, 3 or 4 substituents independently selected from D, F, Cl, Br, CN, $NO_2$, $OR^b$, —$NR^cR^d$, methyl, ethyl, n-propyl or i-propyl.

7. The compound of claim 1, wherein $R^8$ is H, D, $CF_3$, methyl, ethyl, n-propyl or i-propyl.

8. The compound of claim 1, wherein each $R^w$ is independently D, F, Cl, Br, CN, $NO_2$, oxo (=O), —C(=O)$OCH_3$, —C(=O)$OCH_2CH_3$, —C(=O)OH, —NHC(=O)$R^a$, —NHC(=O)$NR^cR^d$, —S(=O)$_2R^f$, —S(=O)$_2NHC(=O)R^a$, —S(=O)$_2NR^cR^d$, $(R^bO)_2P(=O)$—$C_{0-2}$ alkylene, $OR^b$, methyl, ethyl, n-propyl, i-propyl, furyl, pyrrolyl, pyridyl, pyrazolyl, imdazolyl, triazolyl, tetrazolyl, oxazolyl, oxadiazolyl, 1,3,5-triazinyl, thiazolyl, thienyl, pyrazinyl, pyridazinyl or primidinyl, and wherein each of methyl, ethyl, n-propyl, i-propyl, furyl, pyrrolyl, pyridyl, pyrazolyl, imdazolyl, triazolyl, tetrazolyl, oxazolyl, oxadiazolyl, 1,3,5-triazinyl, thiazolyl, thienyl, pyrazinyl, pyridazinyl and primidinyl independently unsubstituted or substituted with 1, 2, 3 or 4 substituents independently selected from D, F, Cl, Br, CN, $N_3$, oxo (=O), $NO_2$, —$OCH_3$, $C_{1-3}$ alkyl or $C_{1-3}$ haloalkyl.

9. The compound of claim 1, wherein each $R^a$, $R^b$, $R^c$, $R^d$, $R^e$ and $R^f$ is independently H, D, trifluoromethyl, methyl, ethyl, i-propyl, n-propyl, n-butyl, t-butyl, $C_{3-6}$ carbocyclyl, 5- to 6-membered heterocyclyl, phenyl, 5- to 6-membered heteroaryl, (5- to 6-membered heteroaryl)-$C_{1-4}$ alkylene; or, $R^c$ and $R^d$, together with the nitrogen atom to which they are attached, form a 5- to 6-membered heterocyclyl or 5- to 6-membered heteroaryl, and wherein each of methyl, ethyl, i-propyl, n-propyl, n-butyl, t-butyl, $C_{3-6}$ carbocyclyl, 5- to 6-membered heterocyclyl, phenyl, 5- to 6-membered heteroaryl and (5- to 6-membered heteroaryl)-$C_{1-4}$ alkylene is independently unsubstituted or substituted with 1, 2, 3 or 4 substituents independently selected from D, F, Cl, CN, OH, $NH_2$, $C_{1-3}$ alkyl, $C_{1-3}$ haloalkyl or methoxy.

10. The compound of claim 3, wherein A is a $C_{3-6}$ carbocyclic ring, 3- to 6-membered heterocyclic ring, $C_{6-10}$ aromatic ring or 5- to 10-membered heteroaryl.

11. The compound of claim 1, wherein $R^6$ is $OR^b$, $C_{2-4}$ alkynyl, $C_{3-6}$ carbocyclyl, 5- to 6-membered heterocyclyl, phenyl, naphthyl, furyl, benzofuryl, pyrrolyl, pyridyl, pyrazolyl, imdazolyl, benzimdazolyl, triazolyl, tetrazolyl, oxazolyl, oxadiazolyl, 1,3,5-triazinyl, thiazolyl, thienyl, benzothienyl, pyrazinyl, pyridazinyl, pyrimidinyl, indolyl, purinyl, quinolyl, isoquinolyl, phenoxathiinyl,

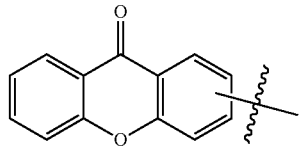,

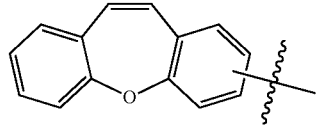 or

-continued

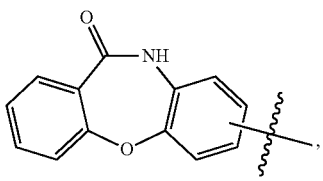

and wherein each of $C_{2-4}$ alkynyl, $C_{3-6}$ carbocyclyl, 5- to 6-membered heterocyclyl, phenyl, naphthyl, furyl, benzofuryl, pyrrolyl, pyridyl, pyrazolyl, imdazolyl, benzimdazolyl, triazolyl, tetrazolyl, oxazolyl, oxadiazolyl, 1,3,5-triazinyl, thiazolyl, thienyl, benzothienyl, pyrazinyl, pyridazinyl, pyrimidinyl, indolyl, purinyl, quinolyl, isoquinolyl, phenoxathiinyl,

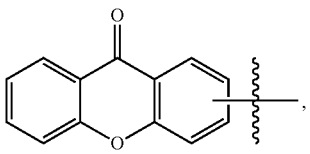

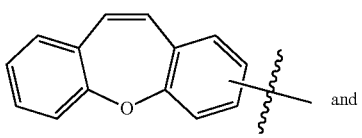
and

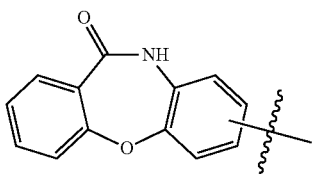

is independently unsubstituted or substituted with 1, 2, 3, 4 or 5 R'.

12. The compound of claim 3, wherein A is a $C_{3-6}$ carbocyclic ring, 3- to 6-membered heterocyclic ring, benzene, naphthalene, furan, benzofuran, pyrrole, pyridine, pyrazole, imidazole, benzoimidazole, triazole, tetrazole, oxazole, oxadiazole, 1,3,5-triazine, thiazole, thiophene, benzothiphene, pyrazine, pyridazine, pyrimidine, indole, purine, quinoline or isoquinoline.

13. The compound of claim 1 having Formula (IV), (V), (VI), (VII), (VIII), (IX), (X), (XI), (XII), (XIII), (XIV) or (XV),

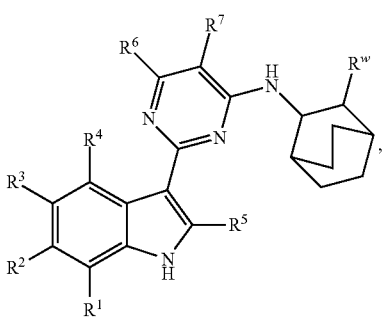
(IV)

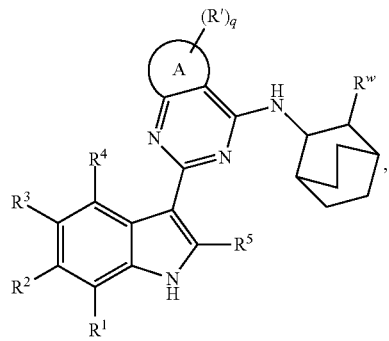
(V)

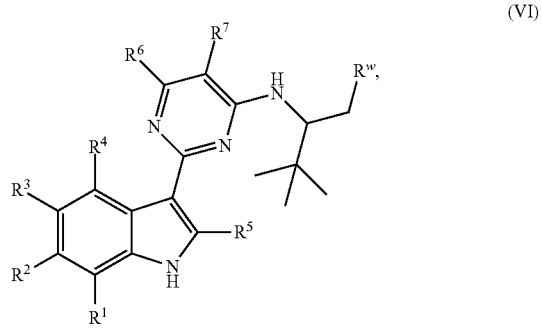
(VI)

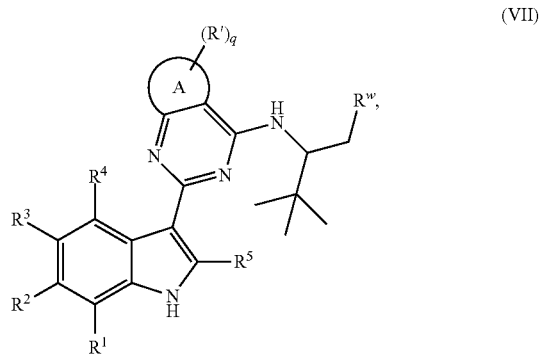
(VII)

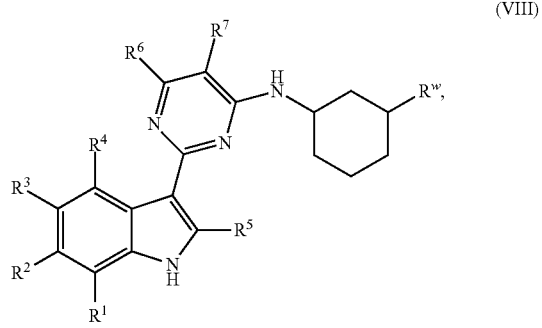
(VIII)

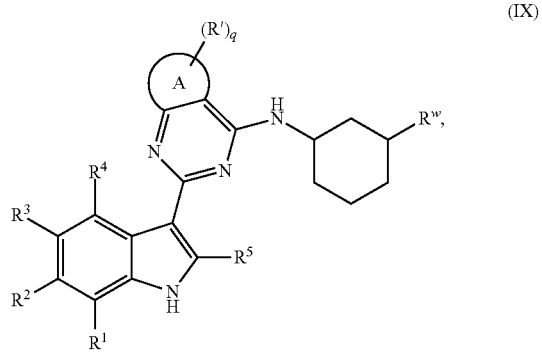
(IX)

-continued
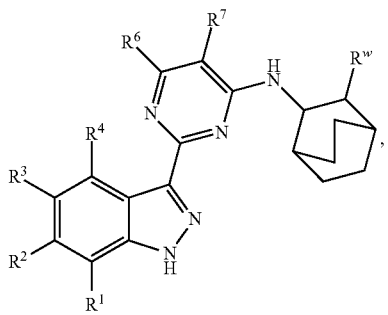
(X)
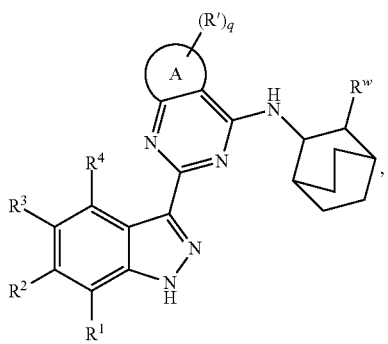
(XI)
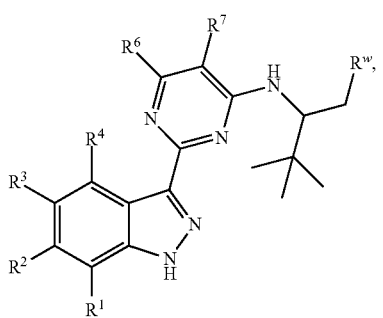
(XII)
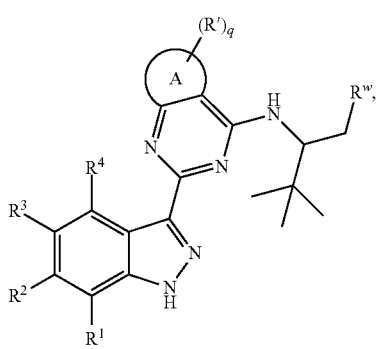
(XIII)
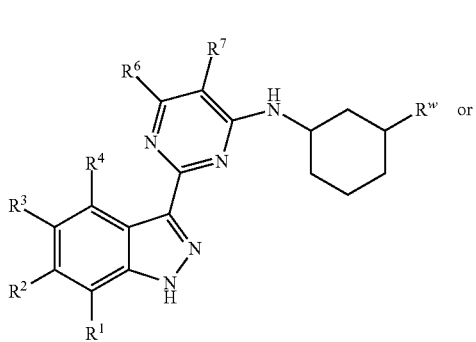
(XIV)
-continued
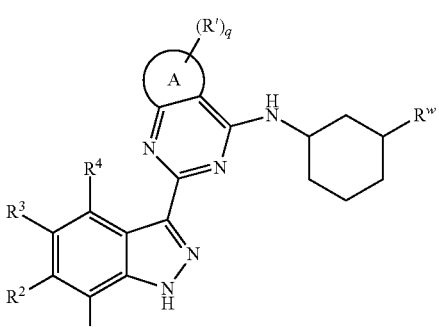
(XV)
wherein, A is a $C_{3-12}$ carbocyclic ring, 3- to 12-membered heterocyclic ring, $C_{6-10}$ aromatic ring or 5- to 10-membered heteroaromatic ring; and
q is 0, 1,2,3, 4 or 5.
14. A compound having one of the following structures,
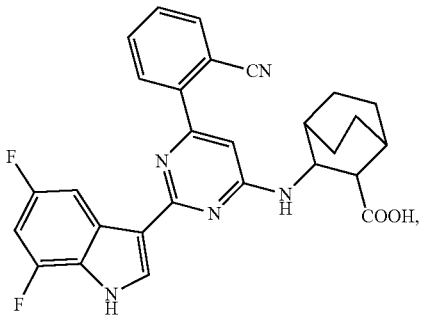
(1)
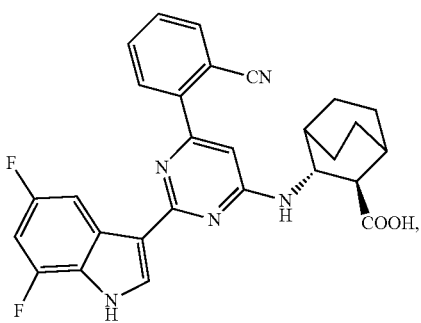
(2)
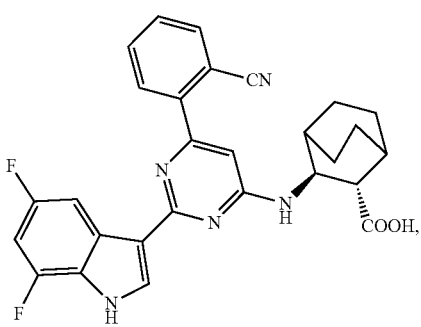
(3)

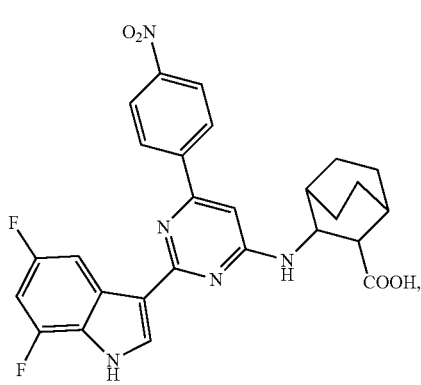
(4)
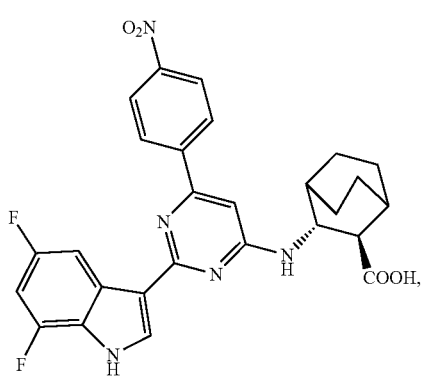
(5)
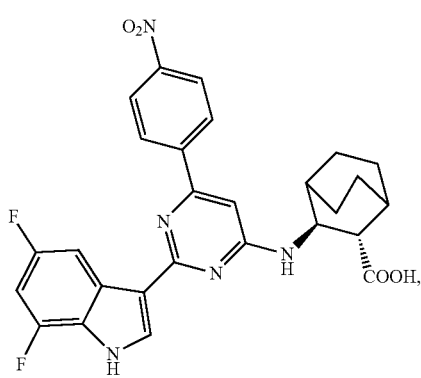
(6)
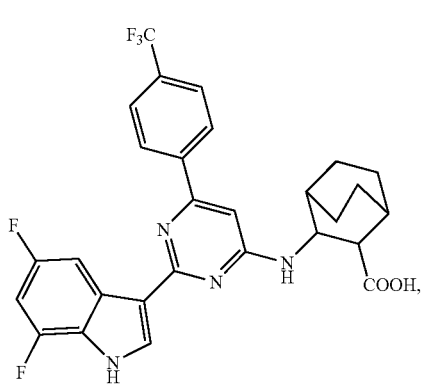
(7)
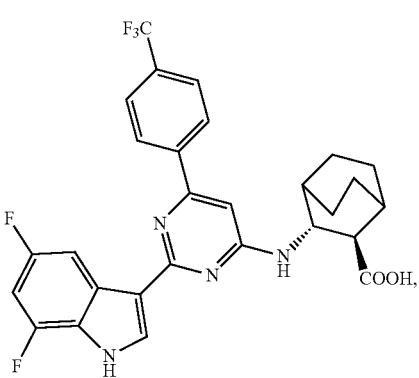
(8)
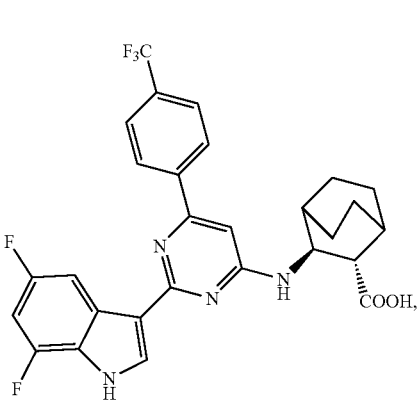
(9)
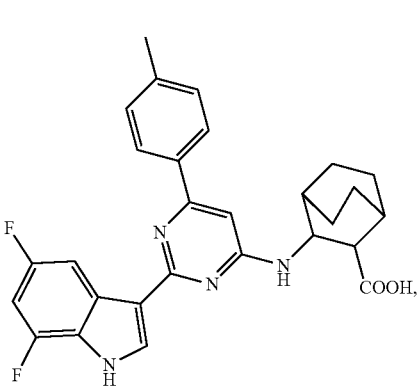
(10)
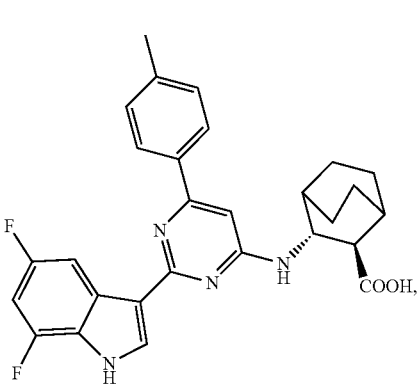
(11)

(12)
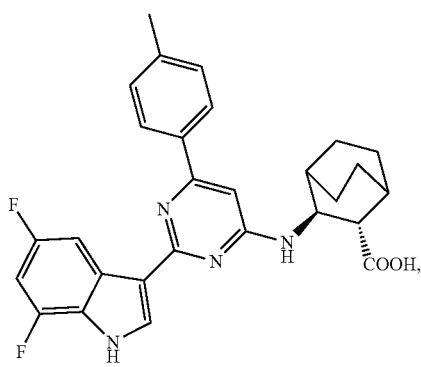
(13)
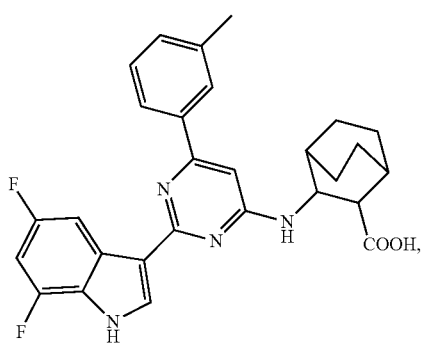
(14)
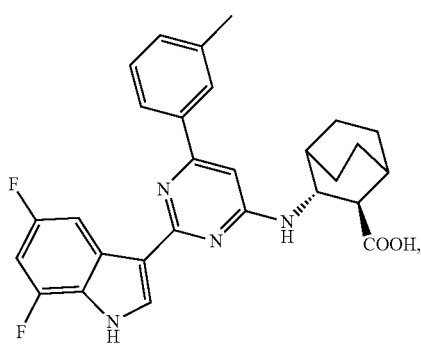
(15)
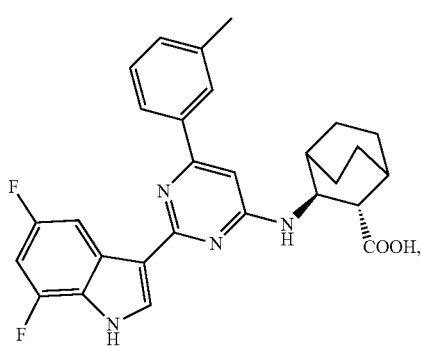
(16)
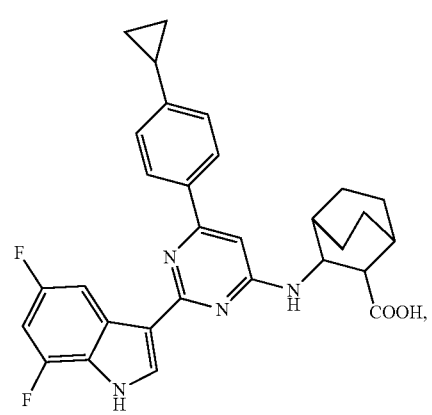
(17)
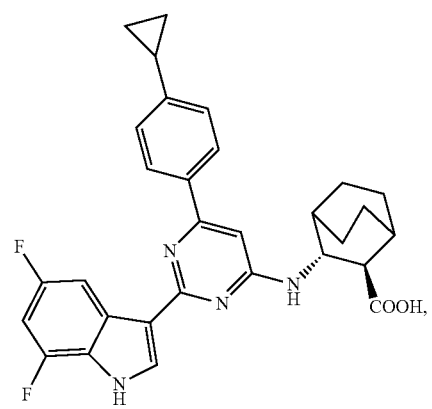
(18)
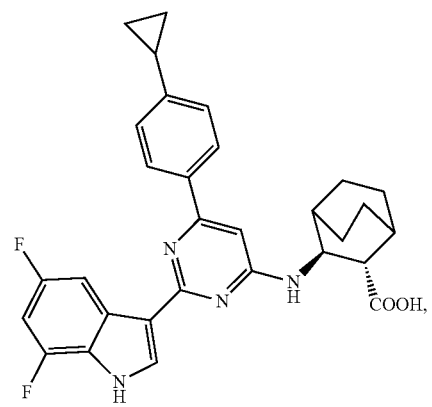
(19)
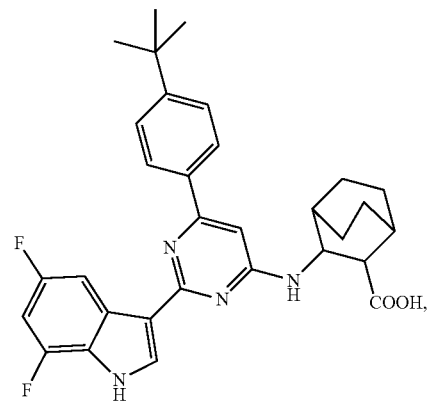

-continued
(20)
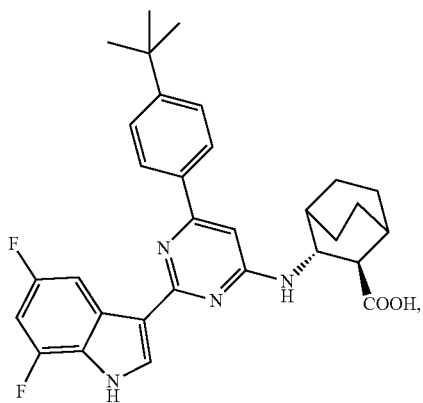
(21)
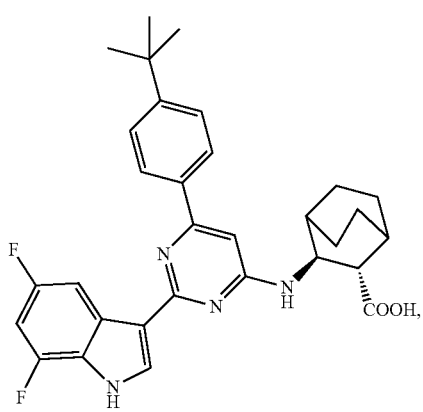
(22)
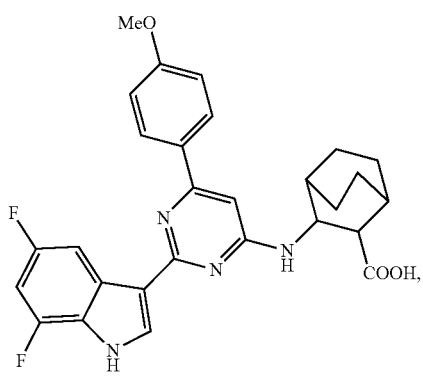
(23)
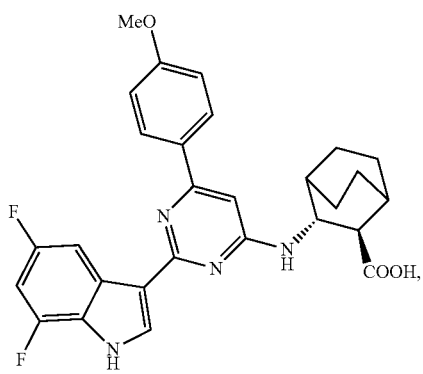
-continued
(24)
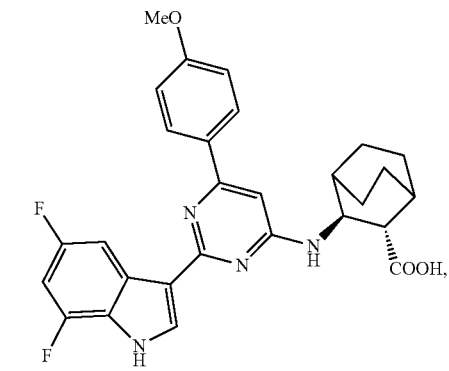
(25)
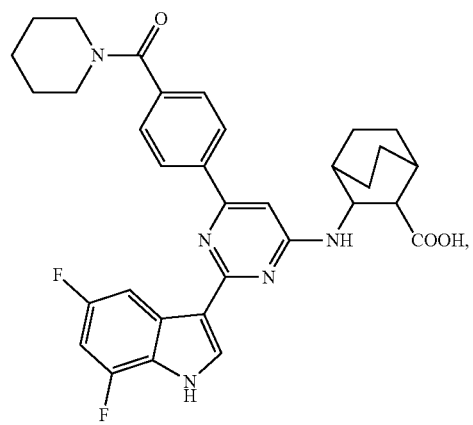
(26)
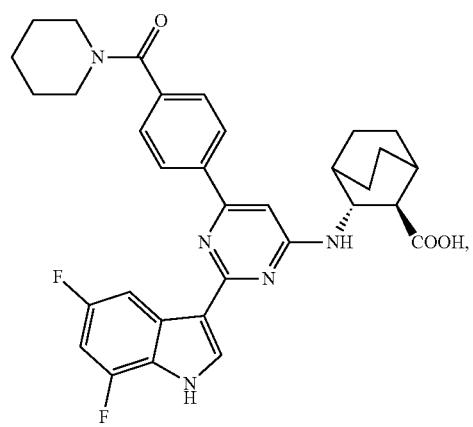
(27)
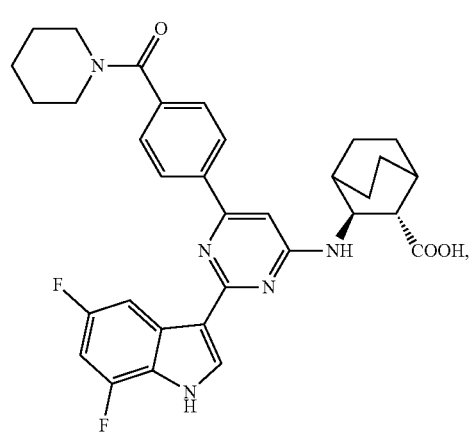

-continued
(28)
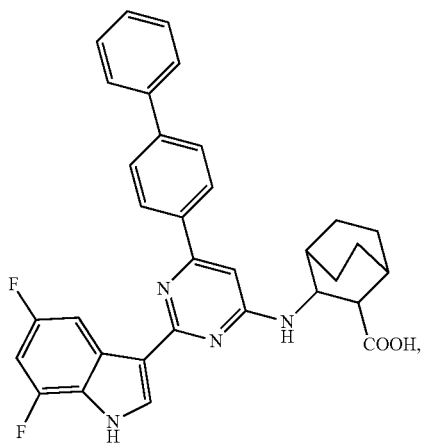
(29)
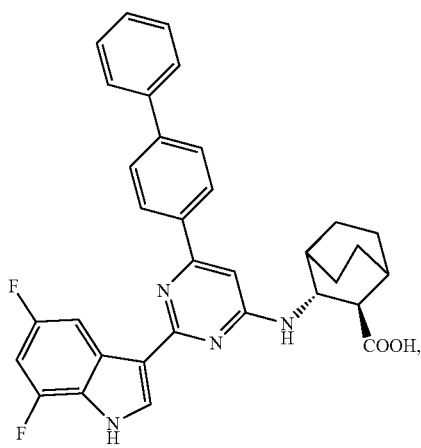
(30)
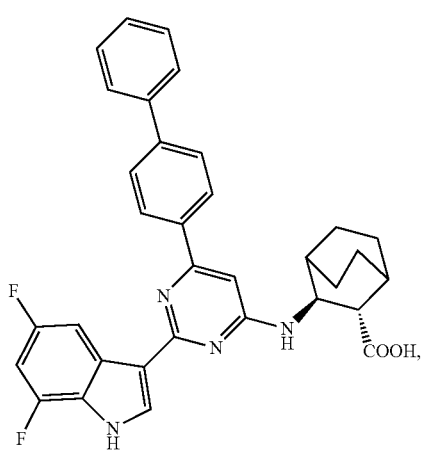
(31)
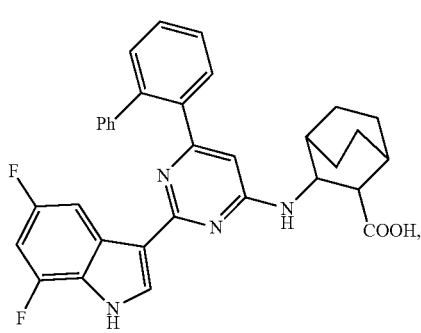
-continued
(32)
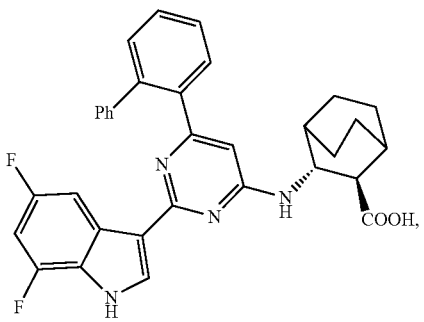
(33)
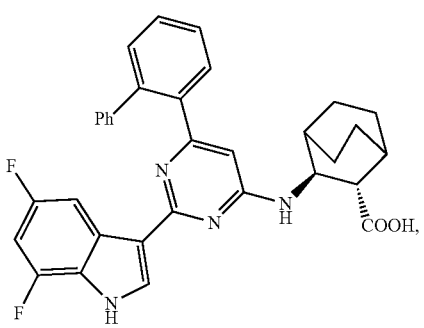
(34)
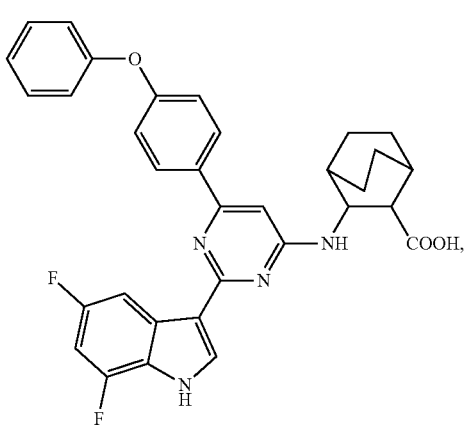
(35)
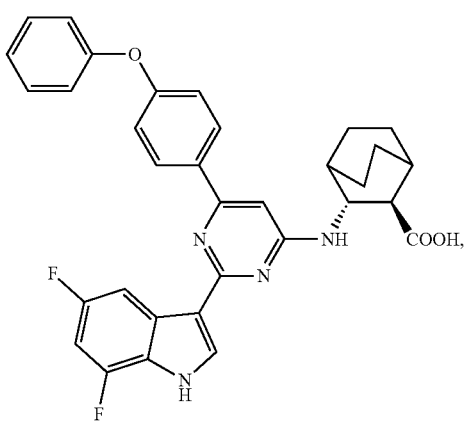

(36)
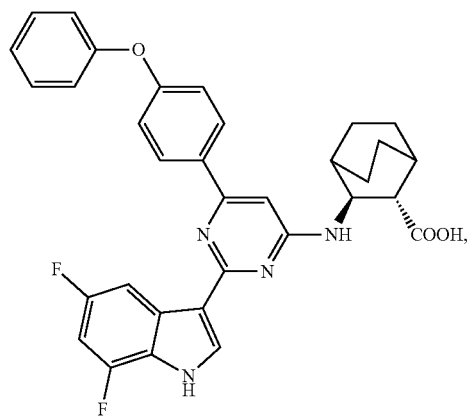
(37)
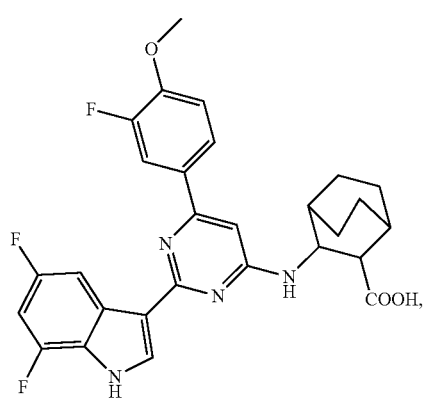
(38)
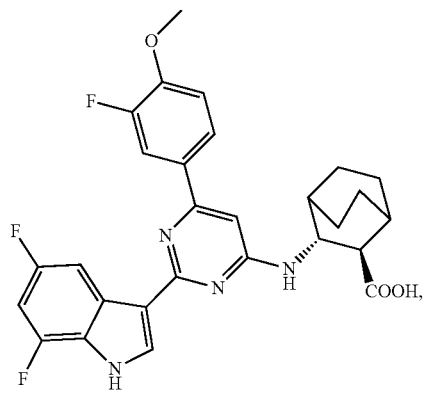
(39)
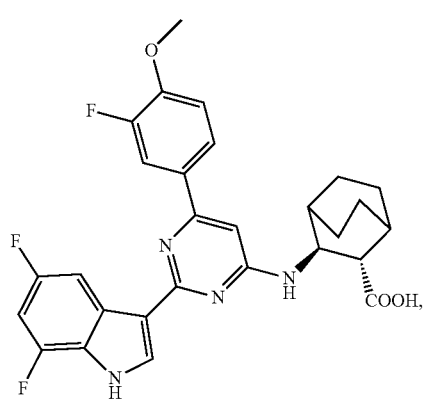
(40)
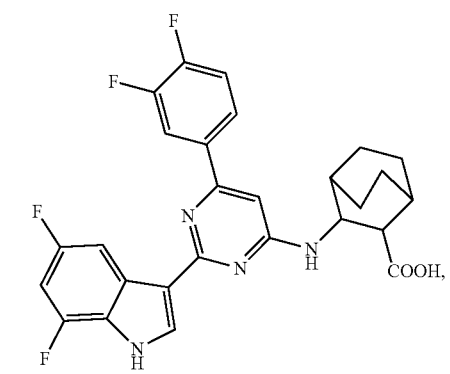
(41)
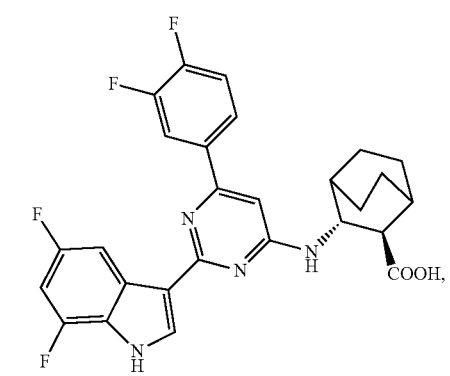
(42)
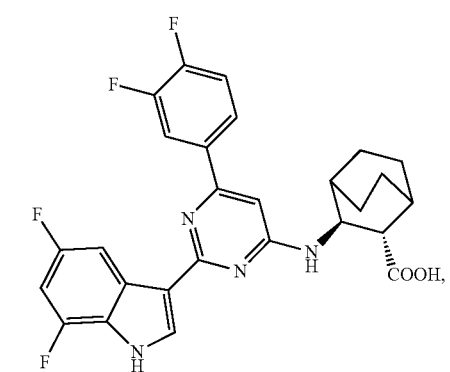
(43)
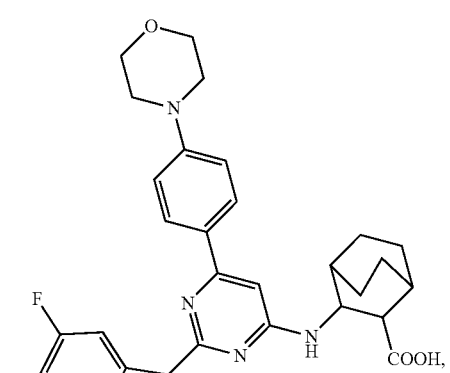

(44)
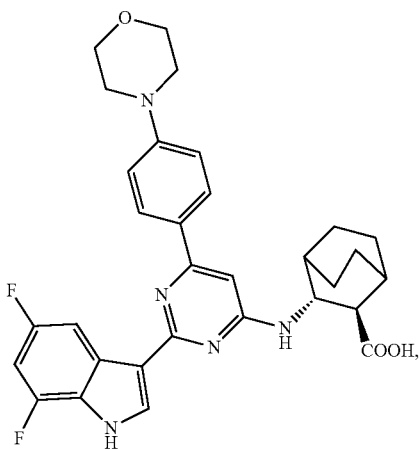
(45)
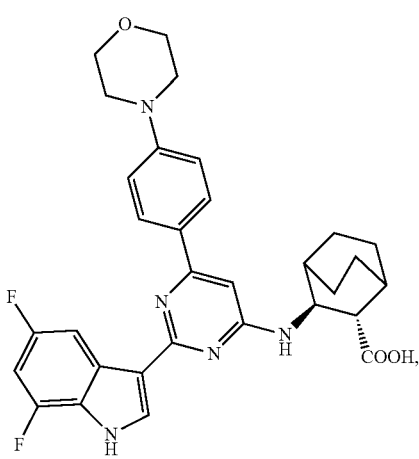
(46)
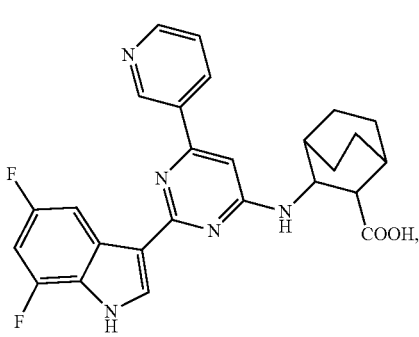
(47)
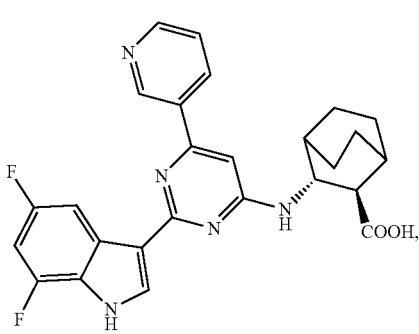
(48)
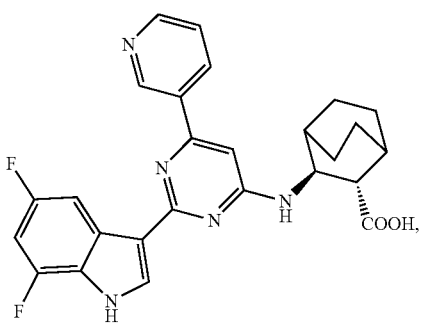
(49)
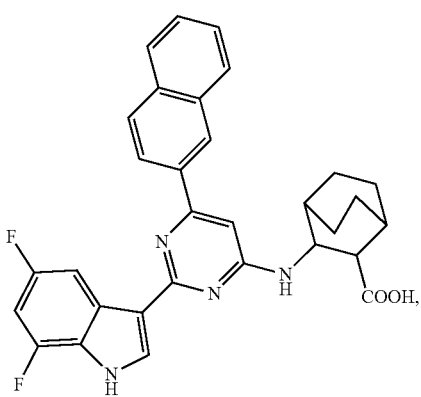
(50)
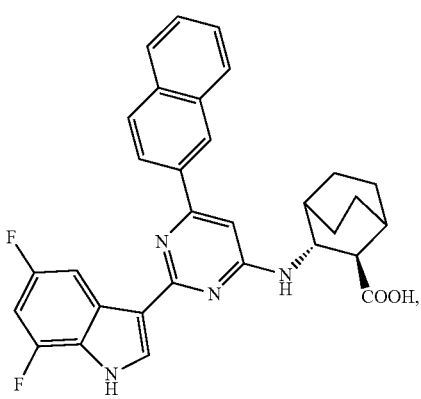
(51)
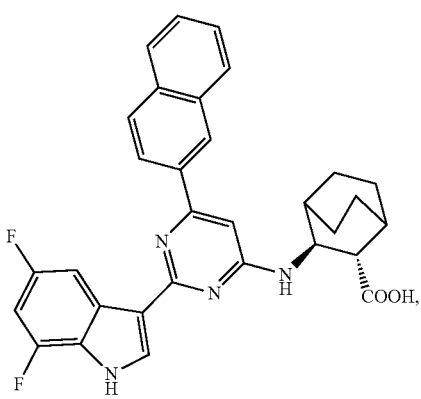

(52) 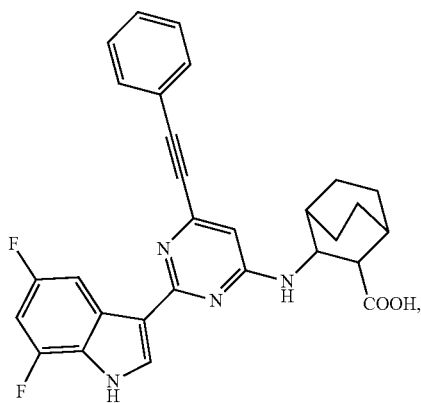
(53) 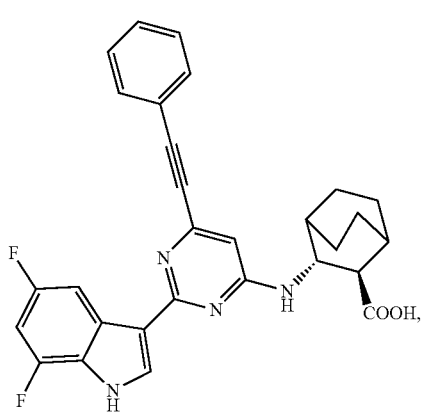
(54) 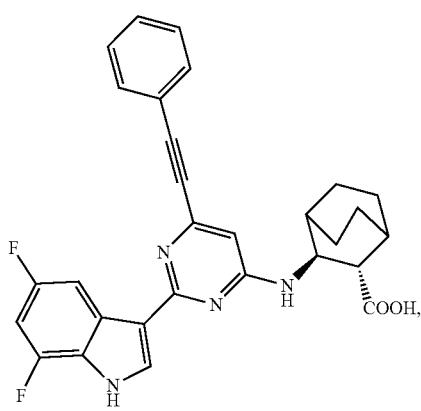
(55) 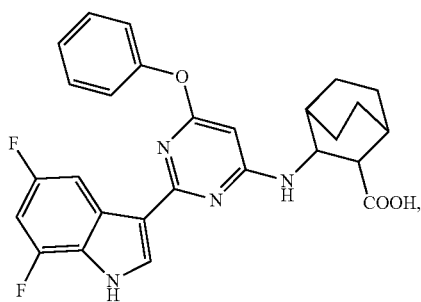
(56) 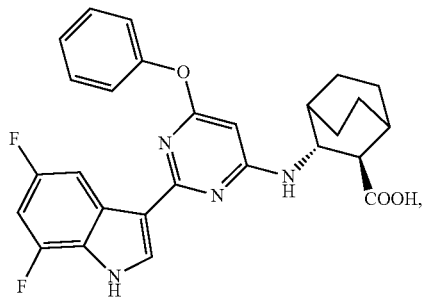
(57) 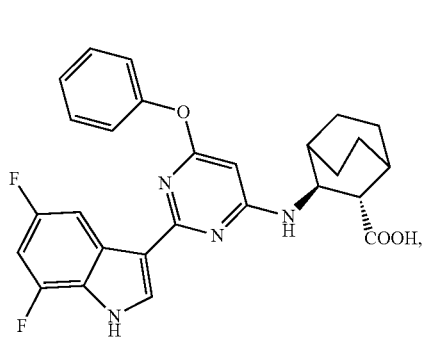
(58) 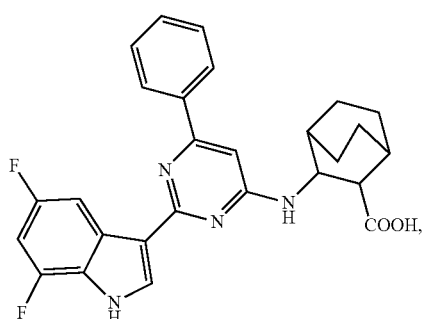
(59) 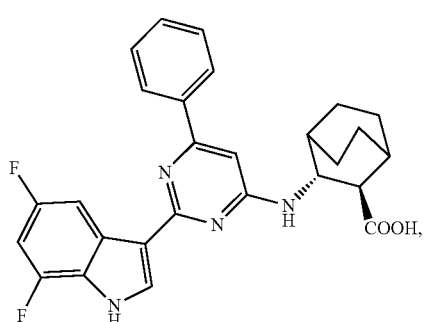
(60) 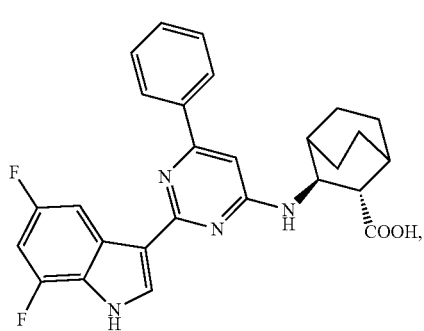

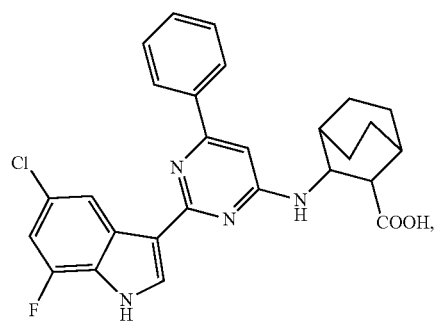
(61)
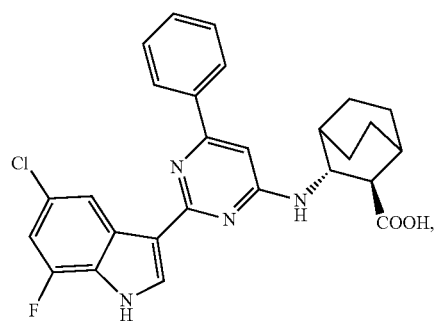
(62)
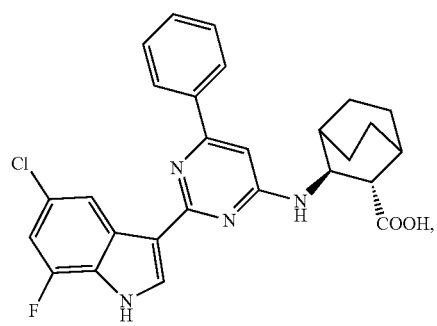
(63)
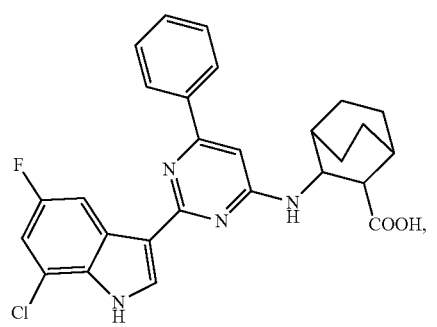
(64)
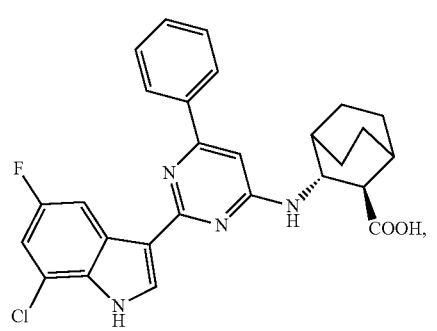
(65)
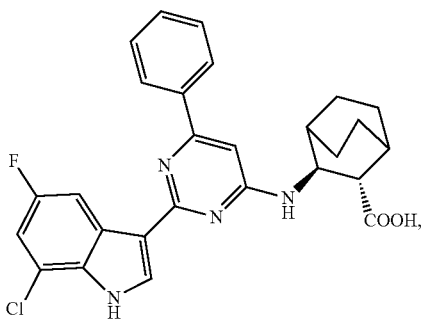
(66)
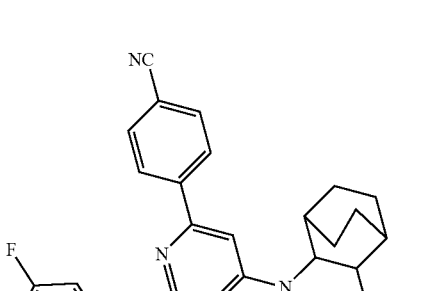
(67)
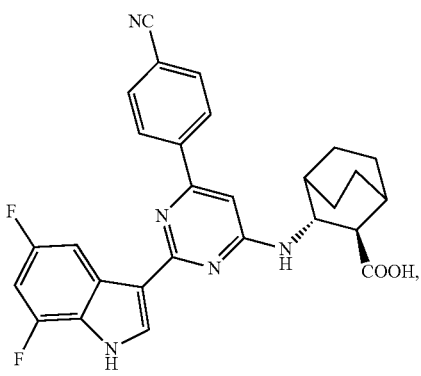
(68)
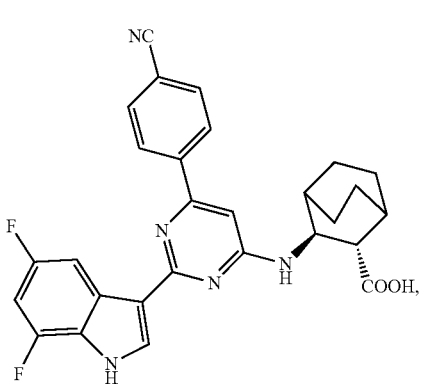
(69)

-continued
(70)
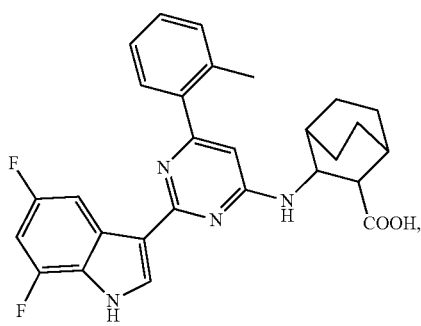
(71)
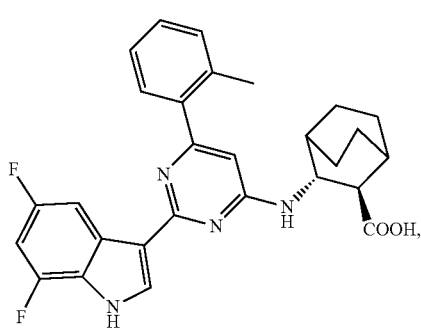
(72)
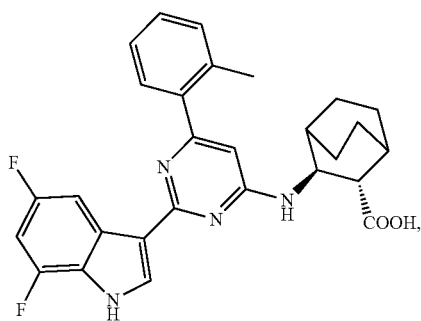
(73)
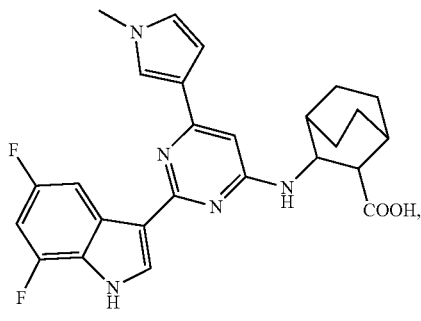
(74)
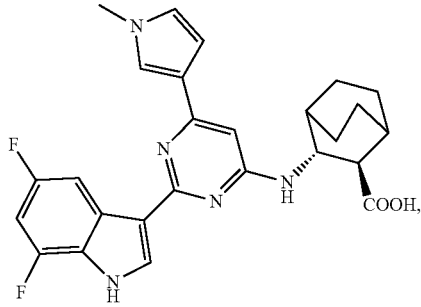
-continued
(75)
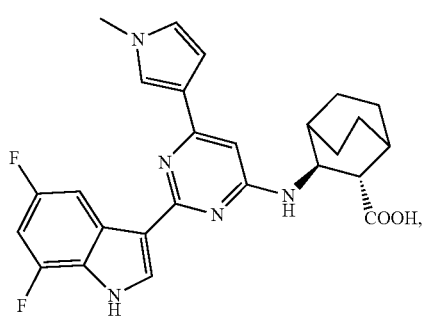
(76)
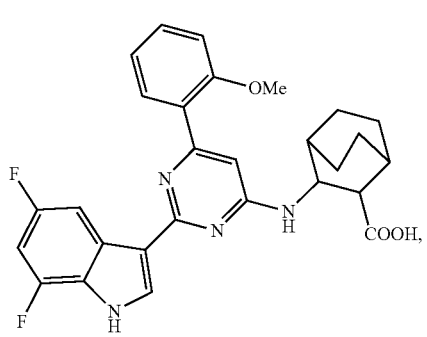
(77)
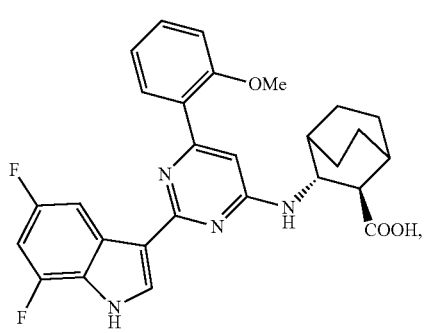
(78)
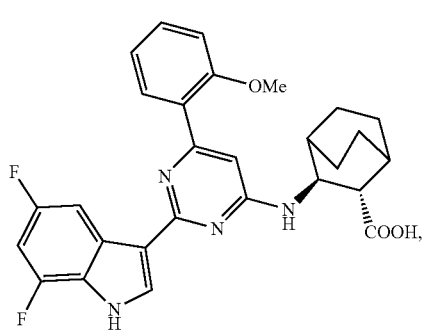
(79)
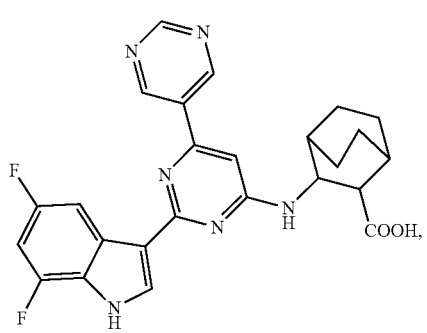

-continued
(80)
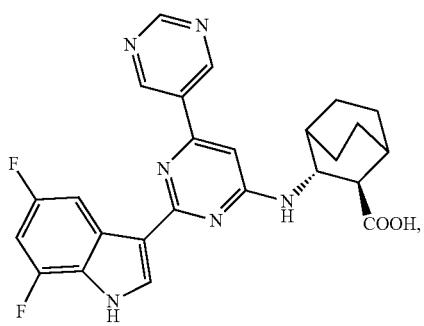
(81)
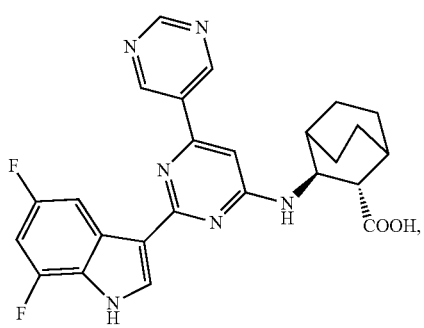
(82)
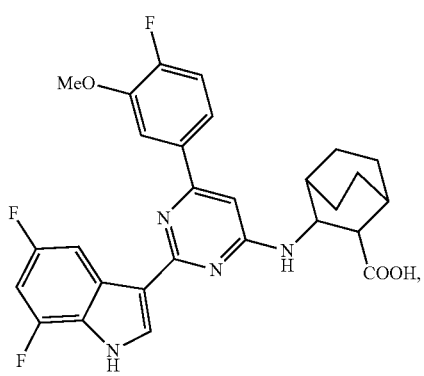
(83)
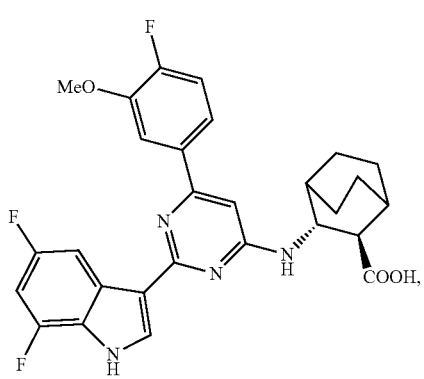
-continued
(84)
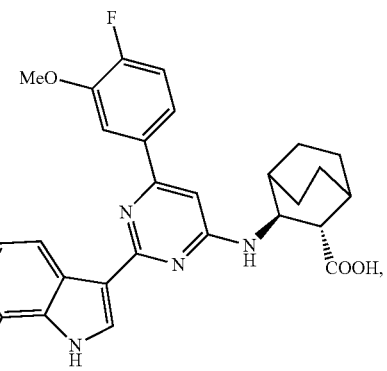
(85)
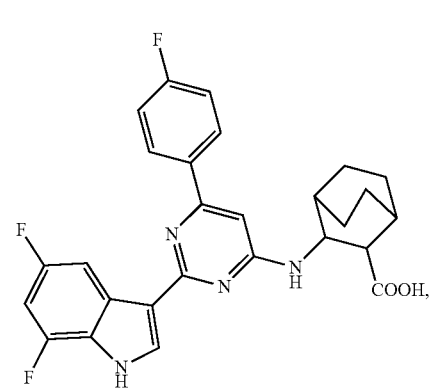
(86)
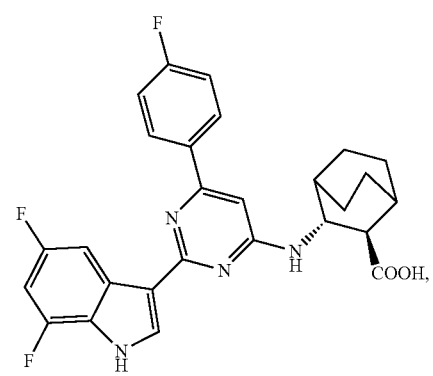
(87)
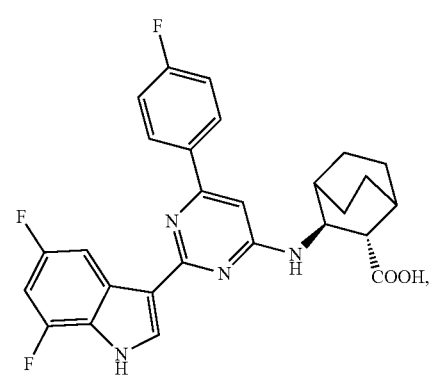

(88) 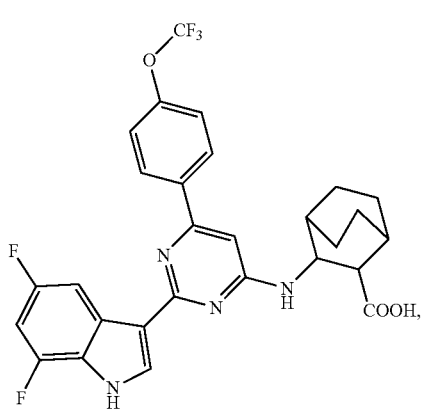
(92) 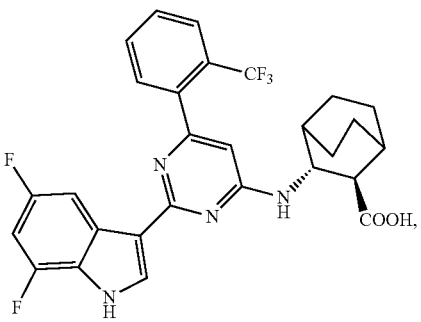
(89) 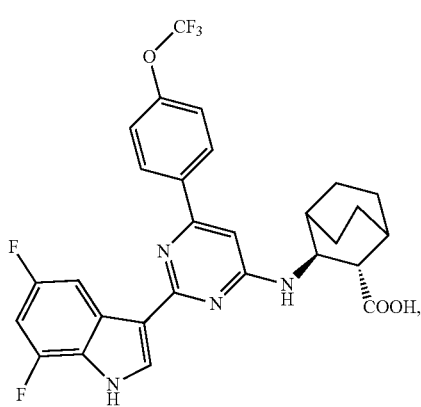
(93) 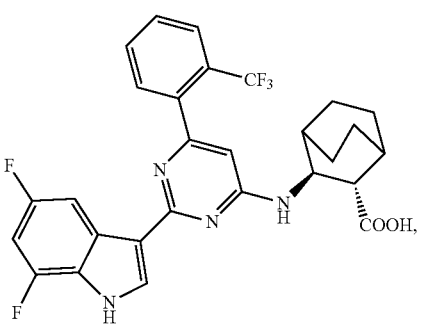
(90) 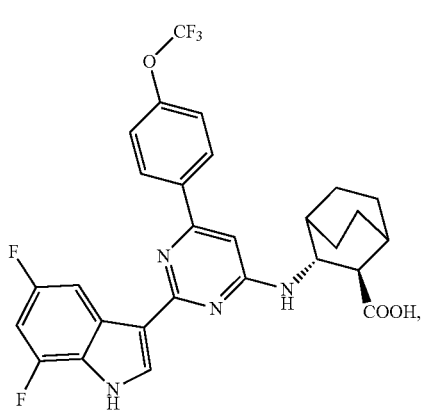
(94) 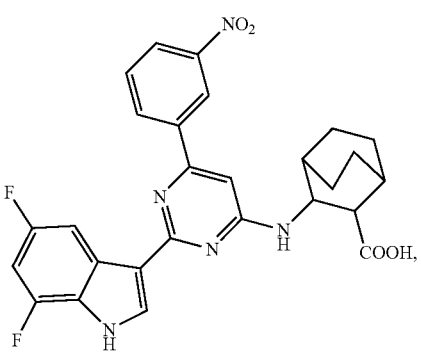
(91) 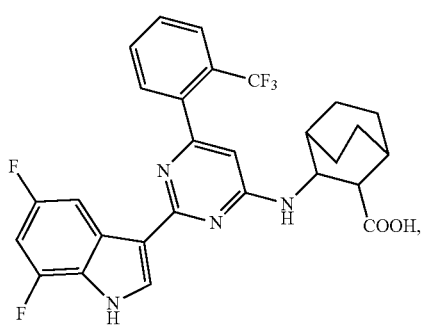
(95) 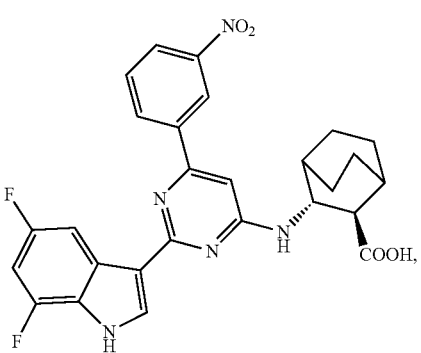

(96)
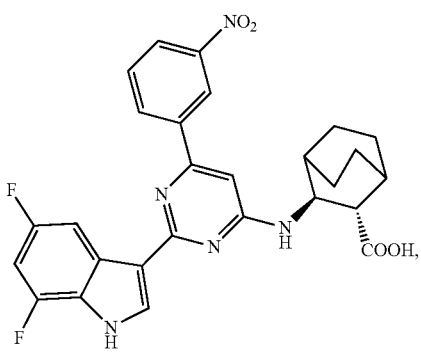
(97)
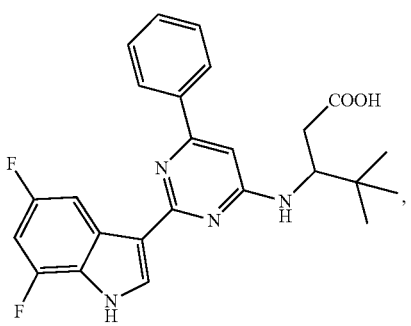
(98)
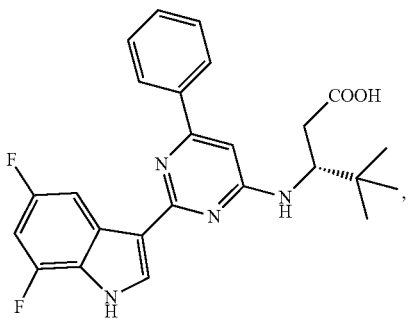
(99)
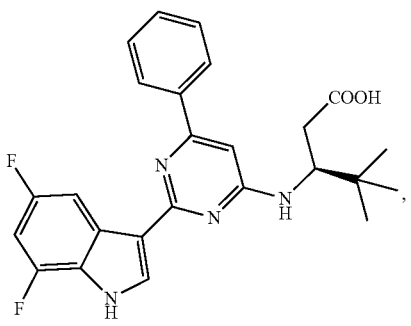
(100)
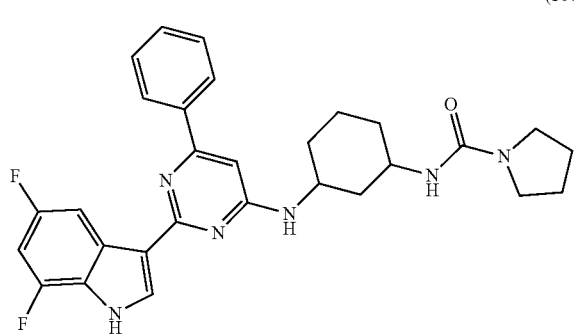
(101)
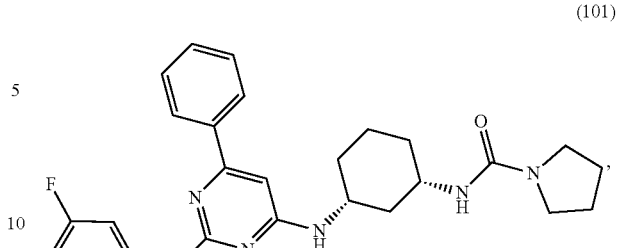
(102)
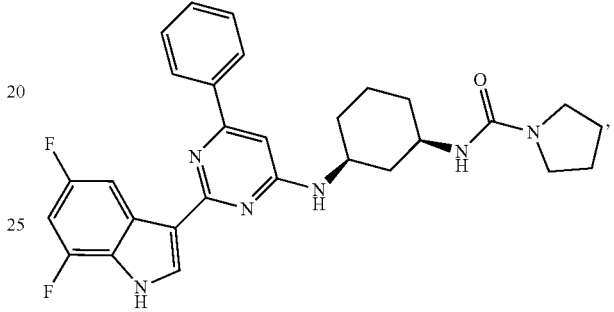
(103)
(104)
(105)
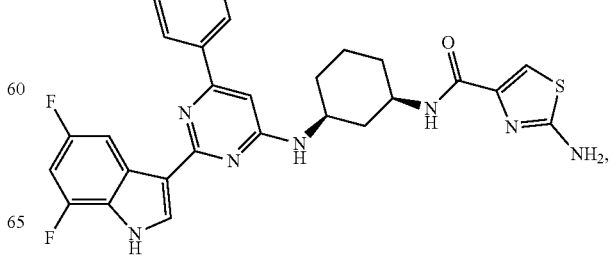

(106)
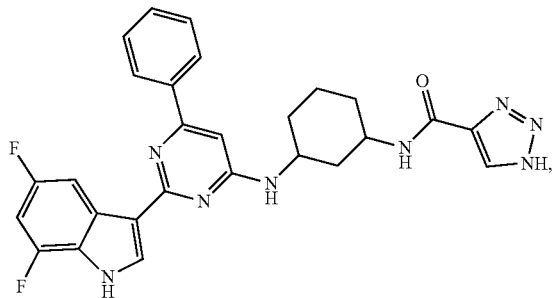
(107)
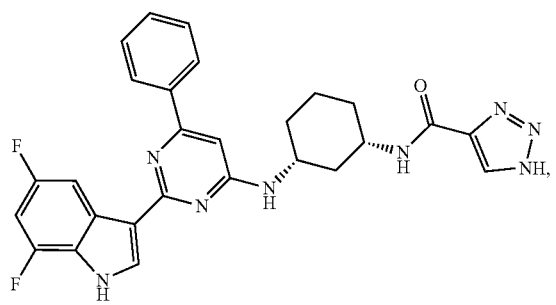
(108)
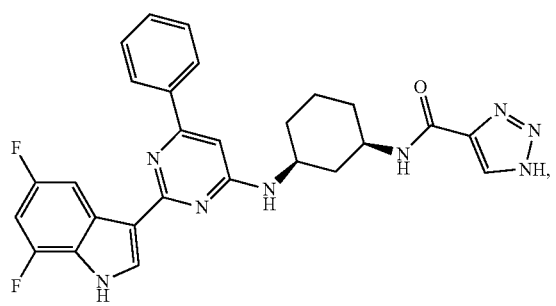
(109)
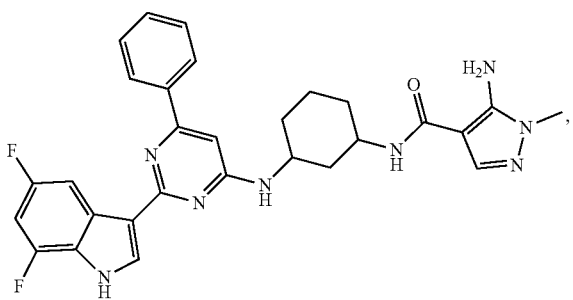
(110)
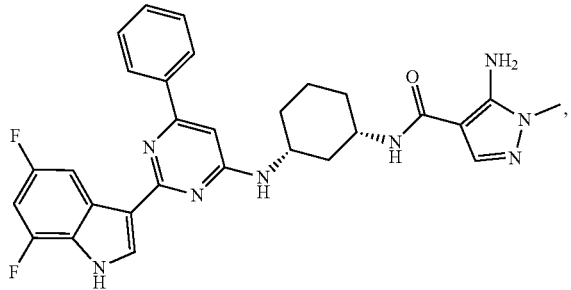
(111)
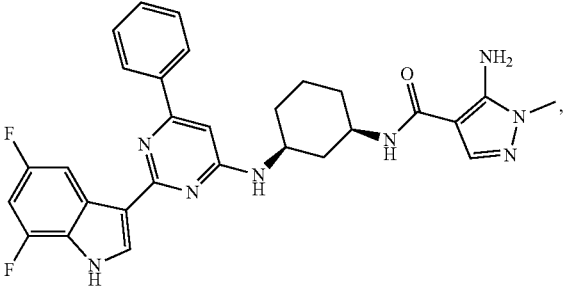
(112)
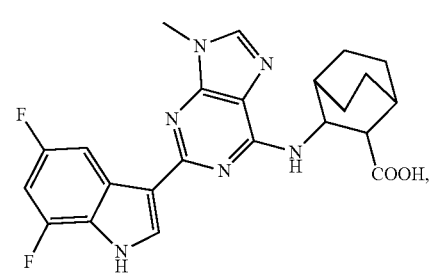
(113)
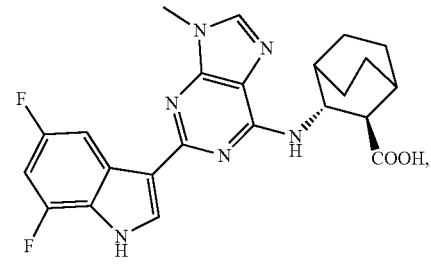
(114)
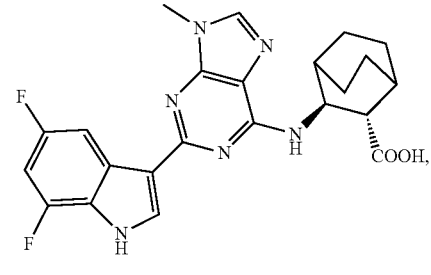
(115)
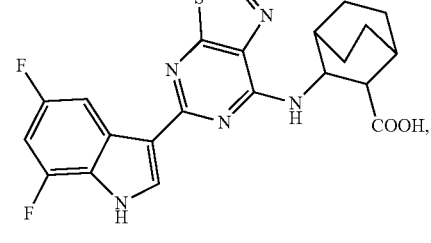
(116)
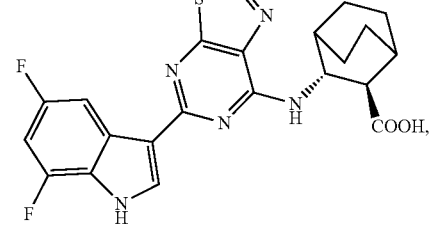

(117) 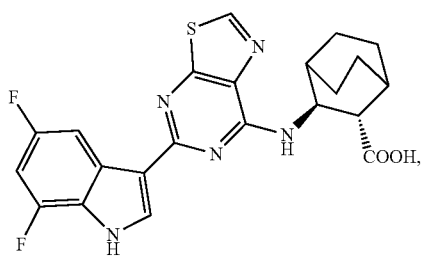
(118) 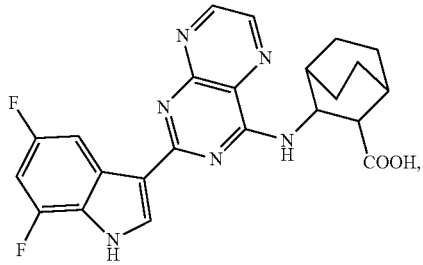
(119) 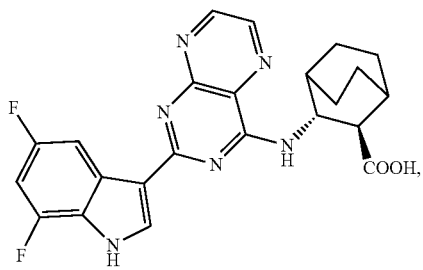
(120) 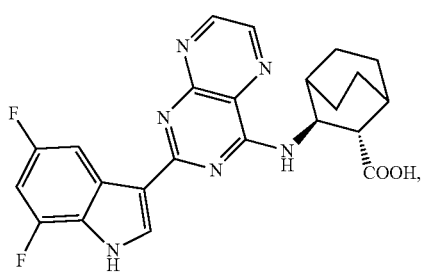
(121) 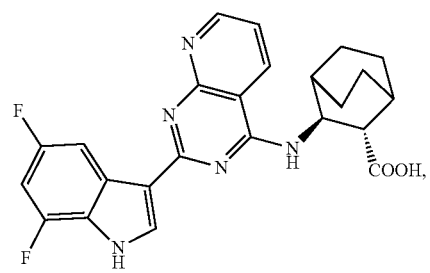
(122) 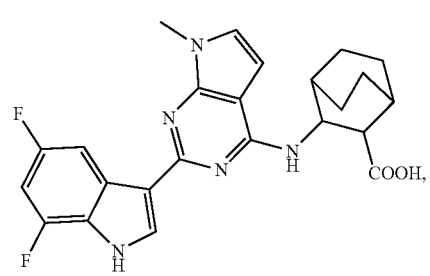
(123) 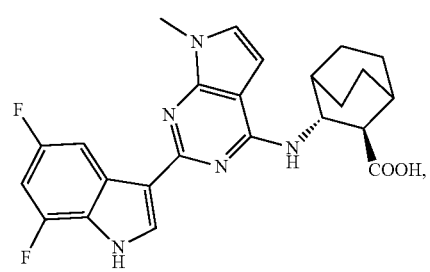
(124) 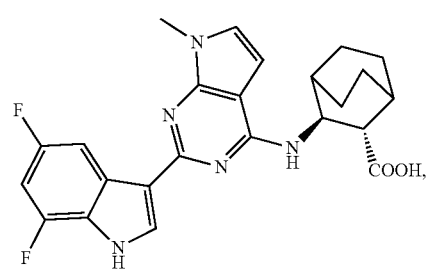
(125) 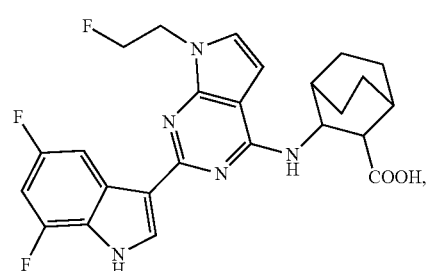
(126) 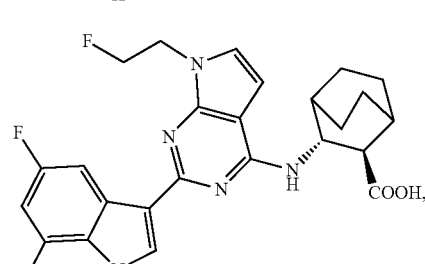
(127)
(128)

(129) 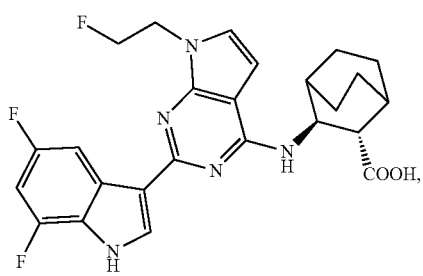
(130) 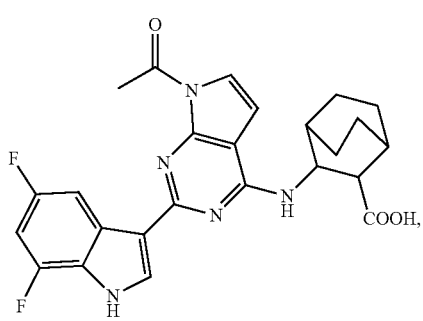
(131) 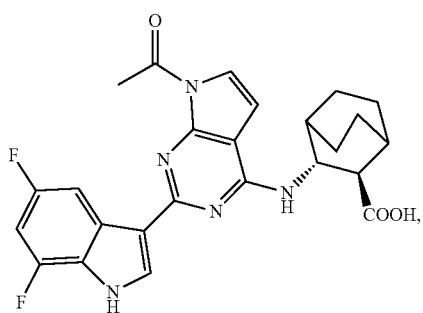
(132) 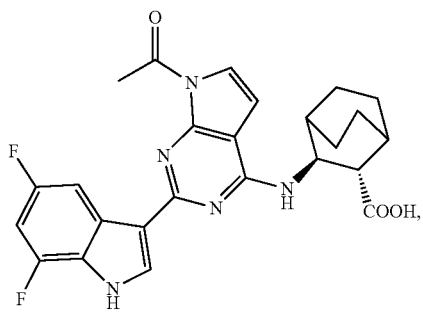
(133) 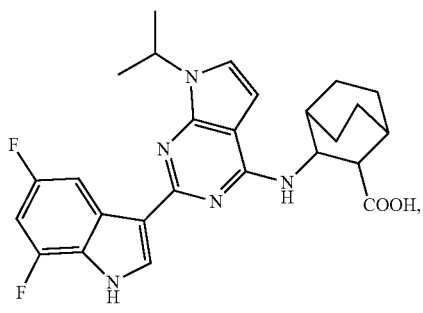
(134) 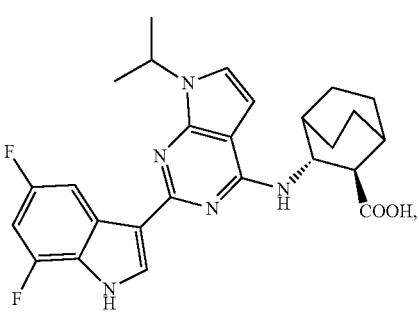
(135) 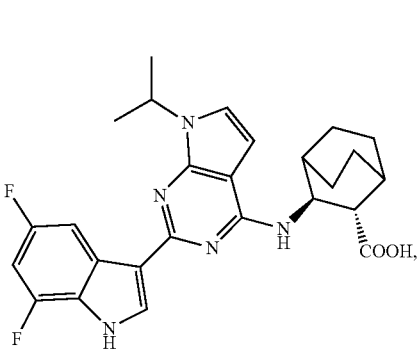
(136) 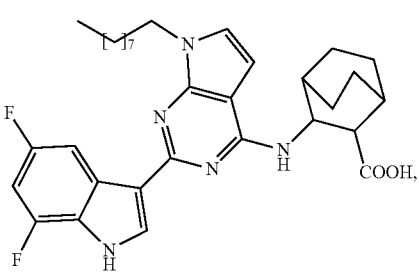
(137) 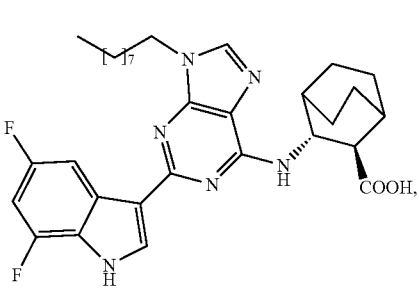
(138) 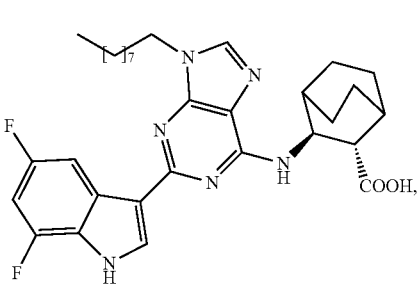

(139) 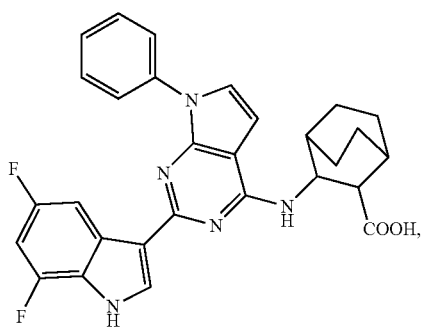
(140) 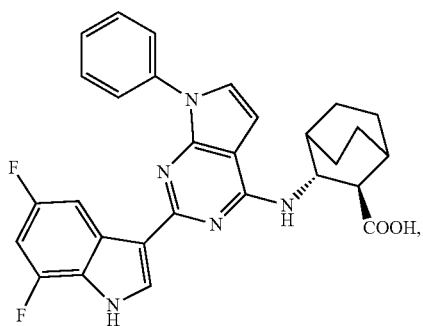
(141) 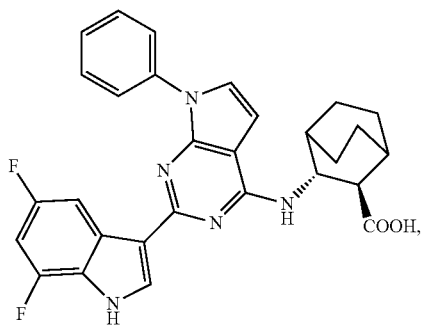
(142) 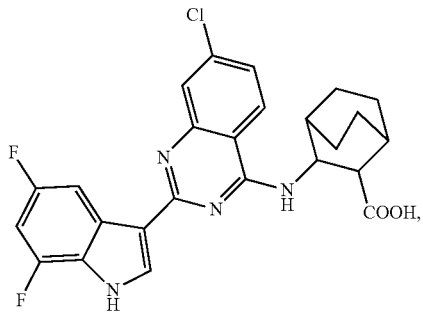
(143) 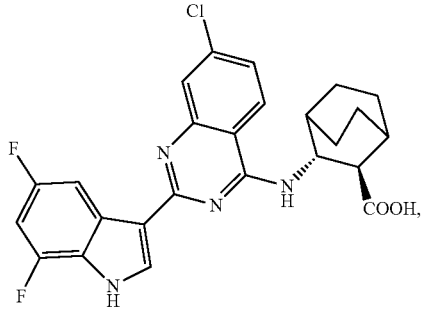
(144) 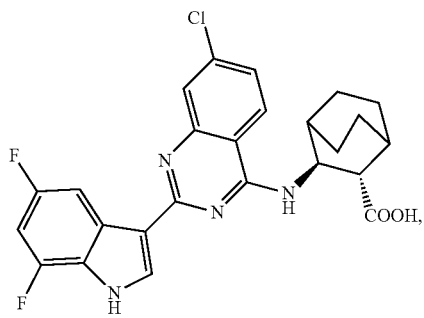
(145) 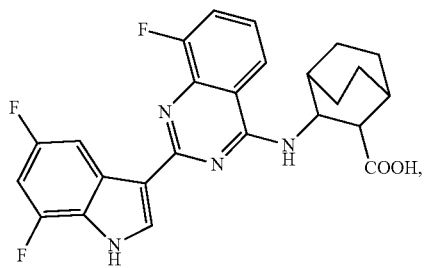
(146) 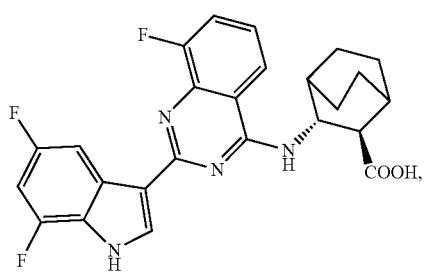
(147) 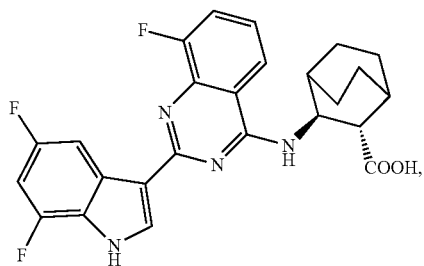
(148) 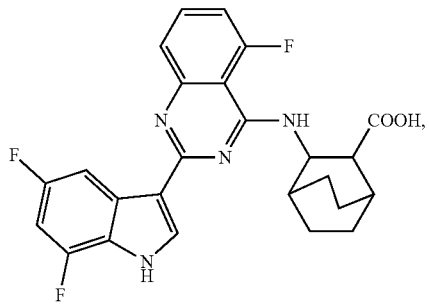

-continued
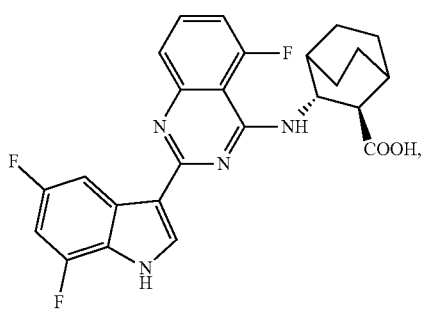
(149)
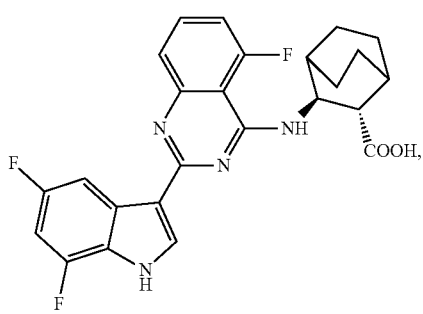
(150)
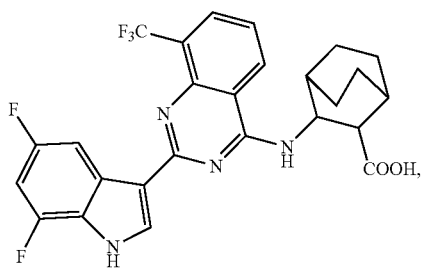
(151)
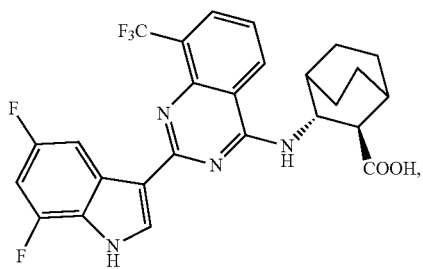
(152)
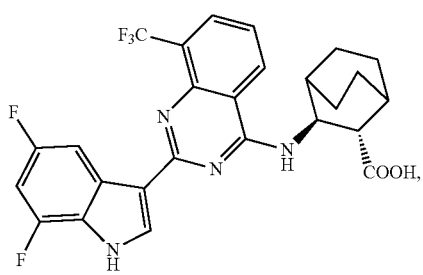
(153)
-continued
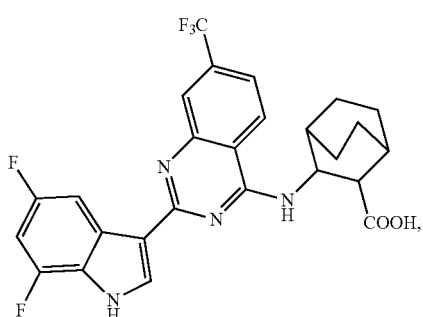
(154)
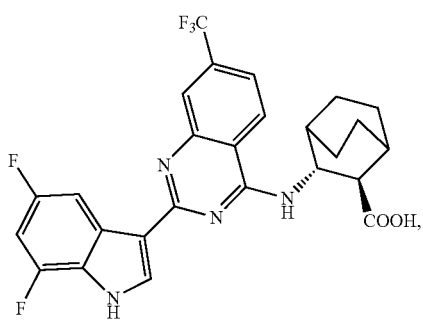
(155)
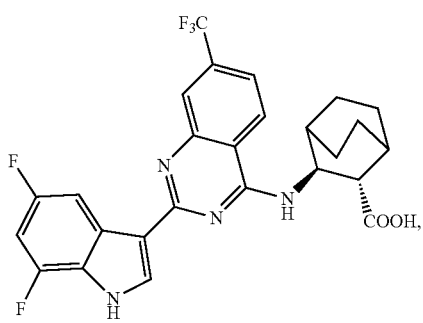
(156)
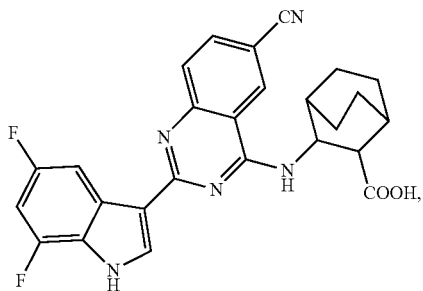
(157)
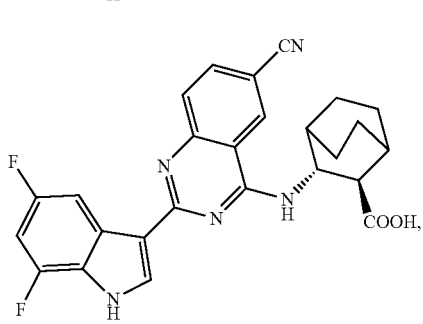
(158)

(159) 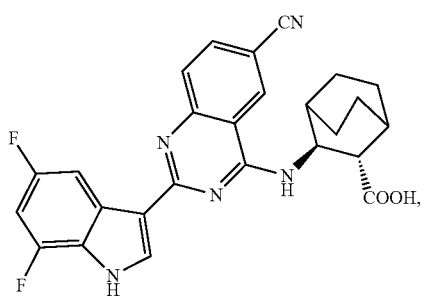
(160) 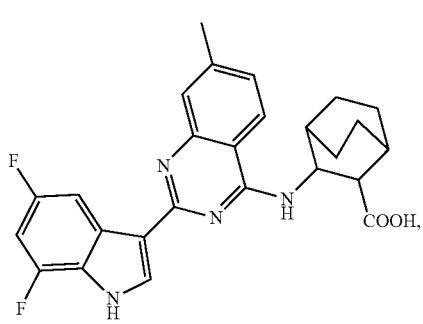
(161) 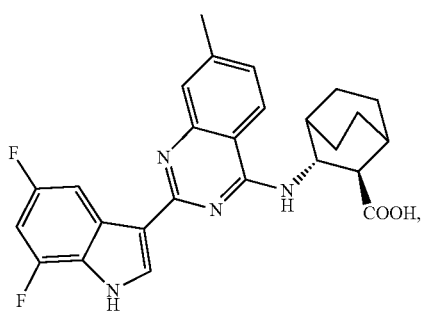
(162) 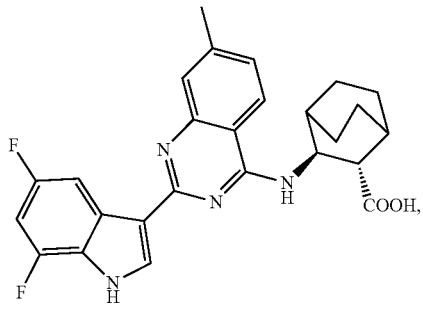
(163) 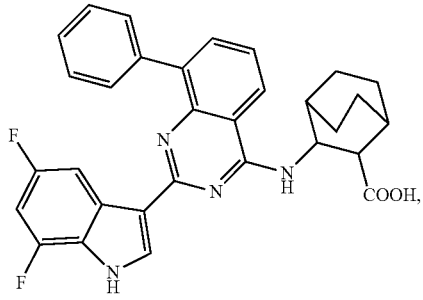
(164) 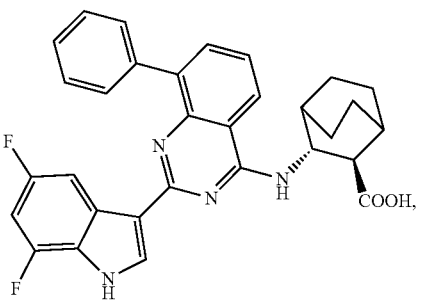
(165) 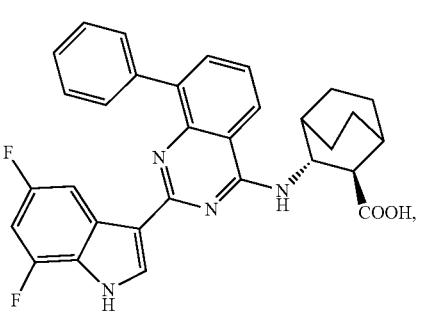
(166) 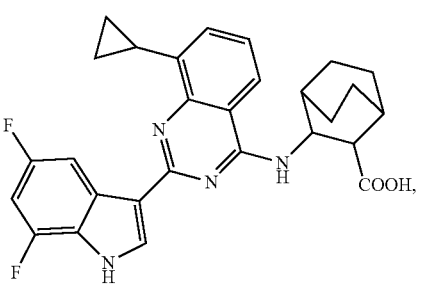
(167) 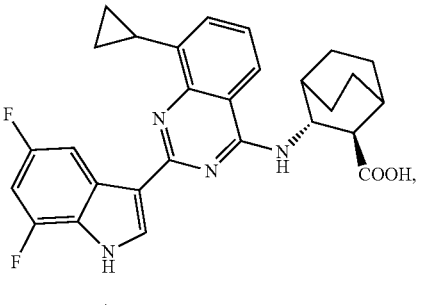
(168) 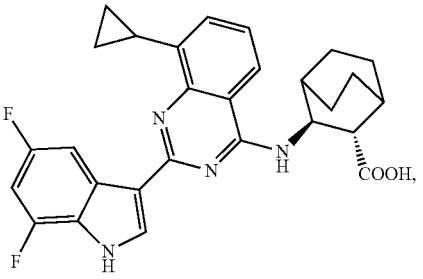

(169)
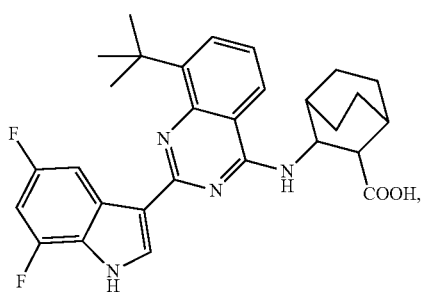
(170)
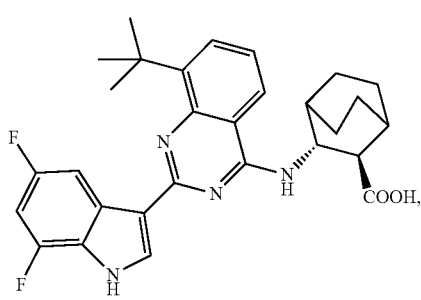
(171)
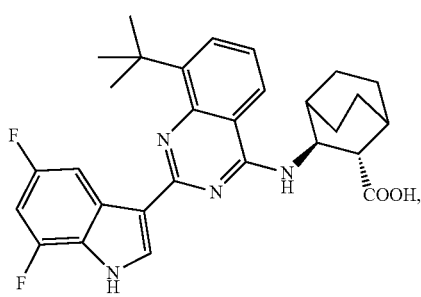
(172)
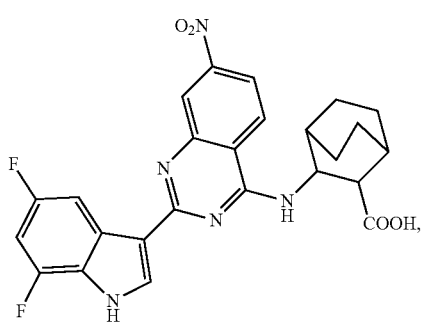
(173)
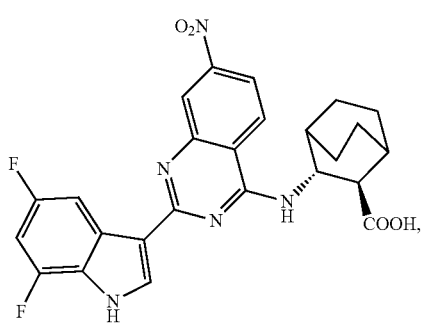
(174)
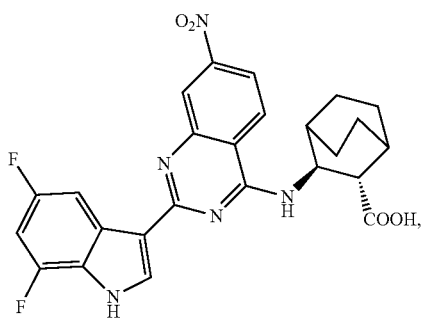
(175)
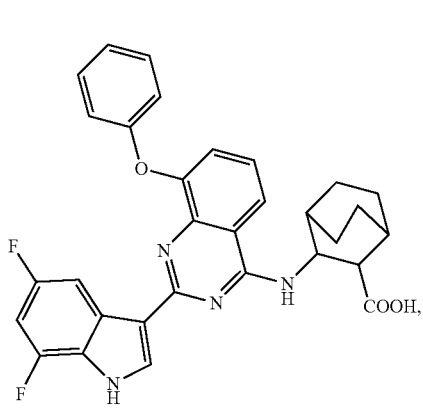
(176)
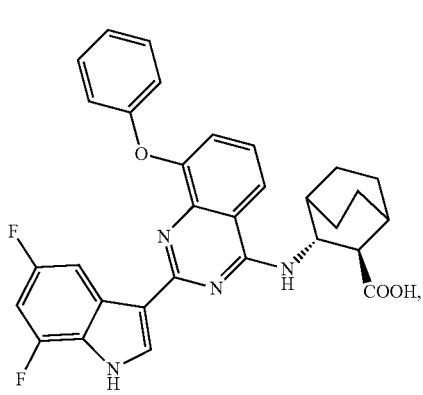
(177)
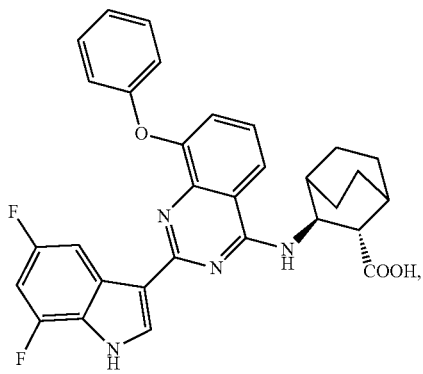

275
-continued
(178)
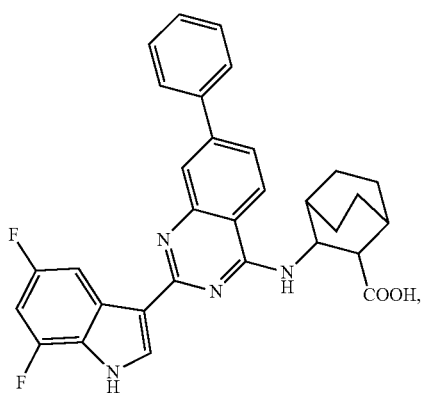
(179)
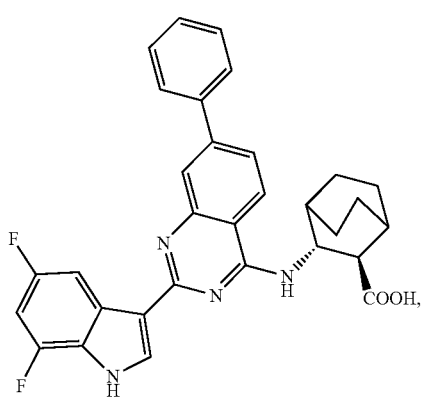
(180)
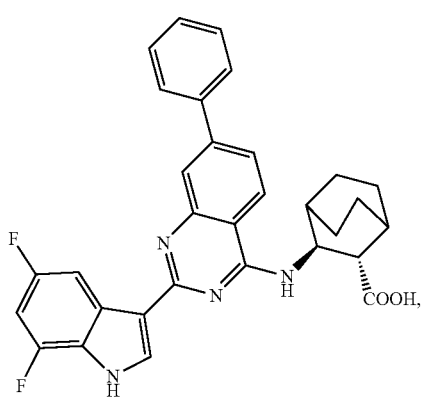
(181)
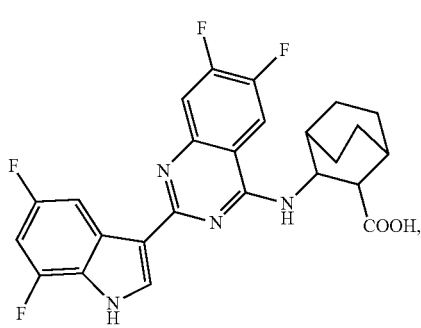
276
-continued
(182)
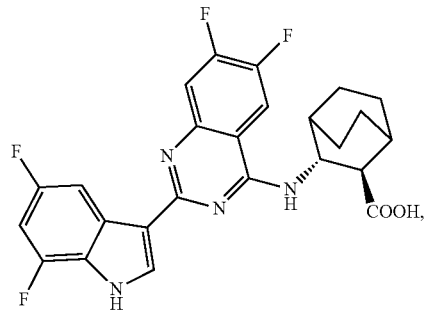
(183)
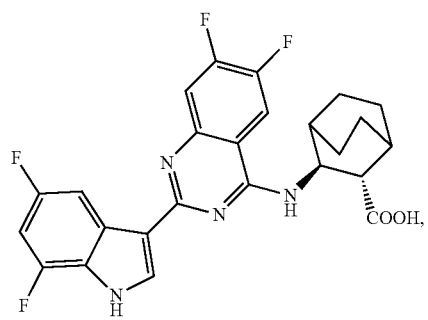
(184)
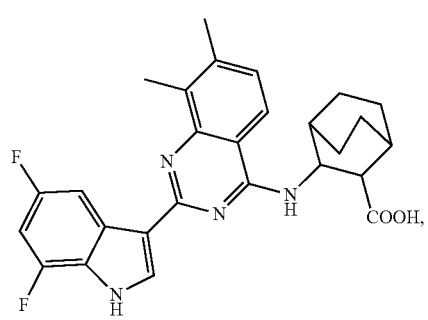
(185)
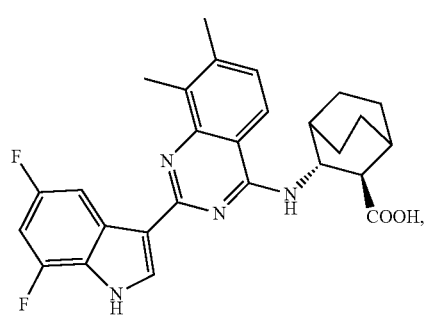
(186)
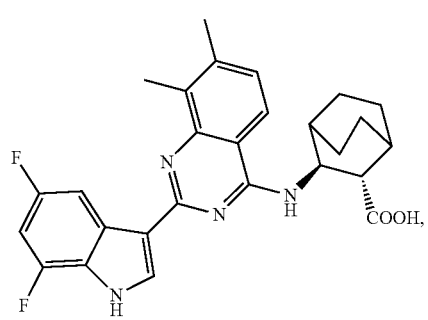

-continued
(187)
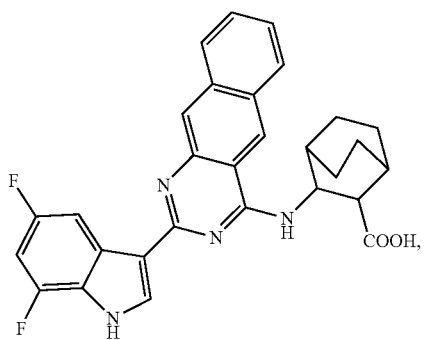
(188)
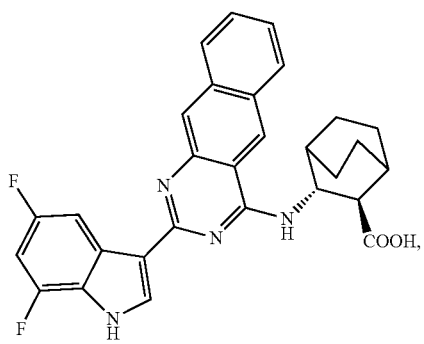
(189)
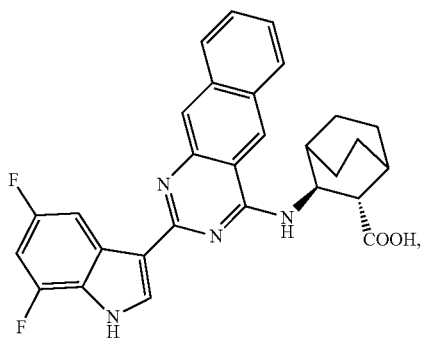
(190)
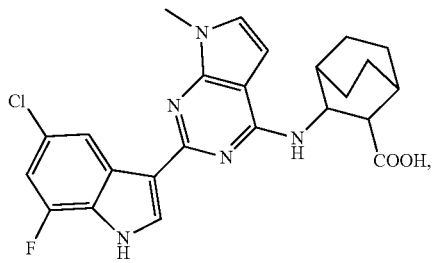
(191)
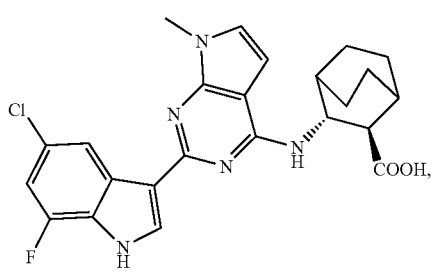
-continued
(192)
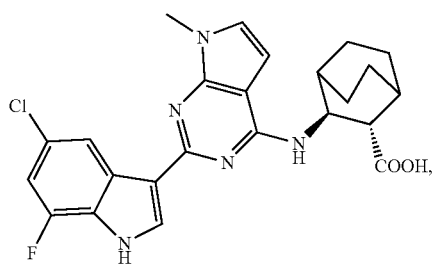
(193)
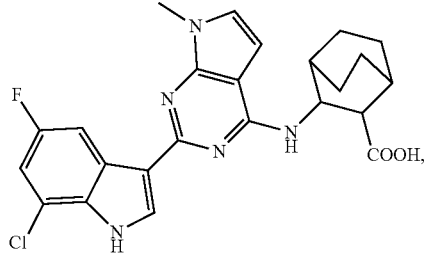
(194)
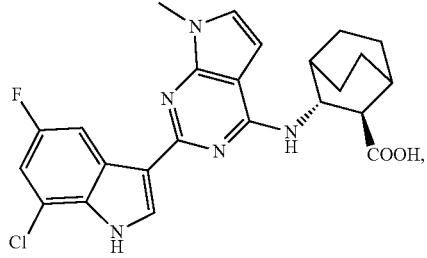
(195)
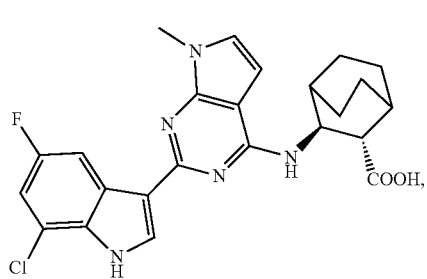
(196)
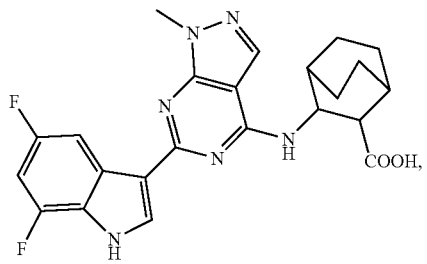
(197)
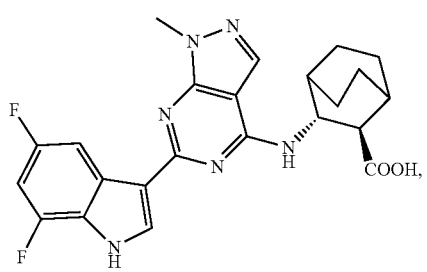

(198) 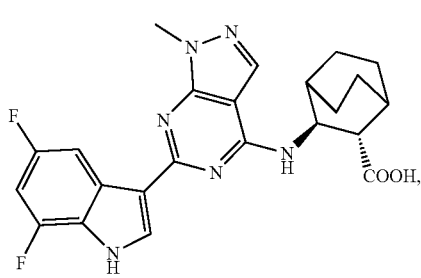
(199) 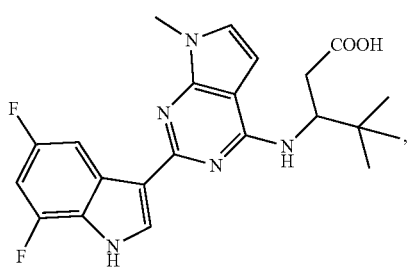
(200) 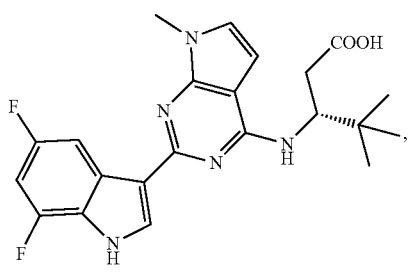
(201) 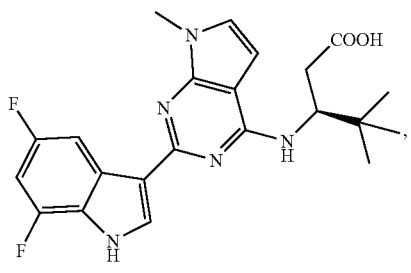
(202) 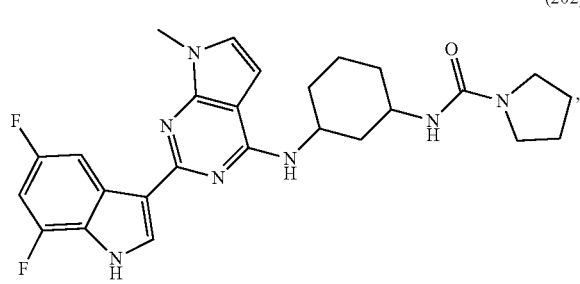
(203) 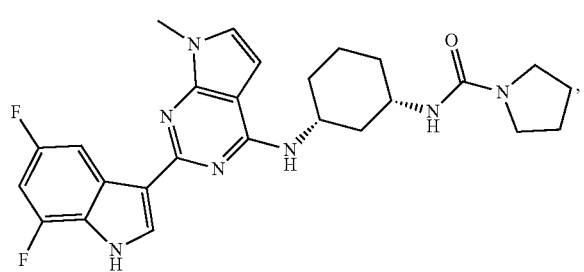
(204) 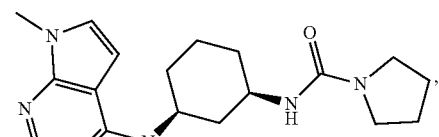
(205) 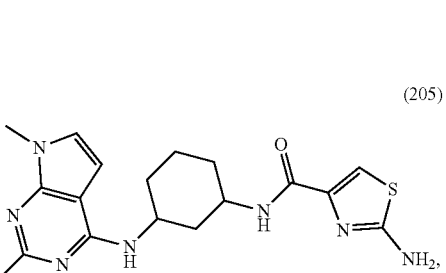
(206) 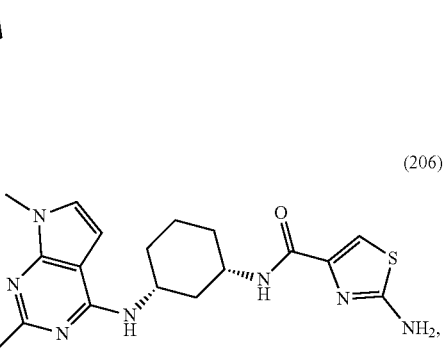
(207) 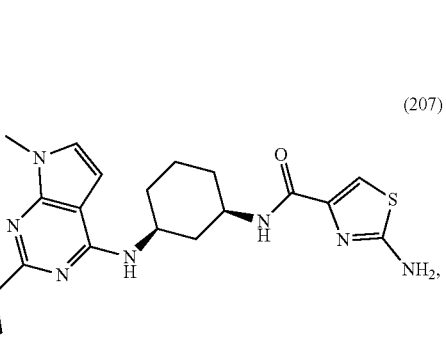
(208) 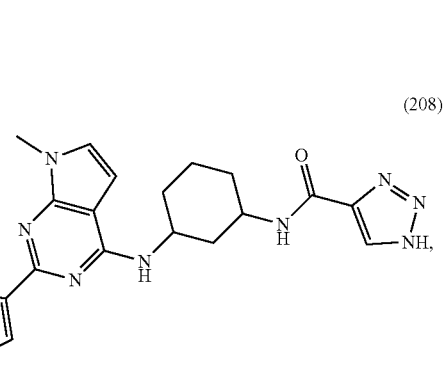

(209)
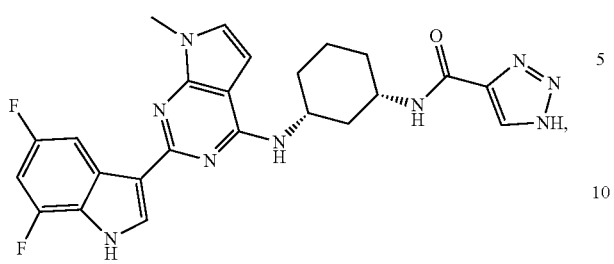
(210)
(211)
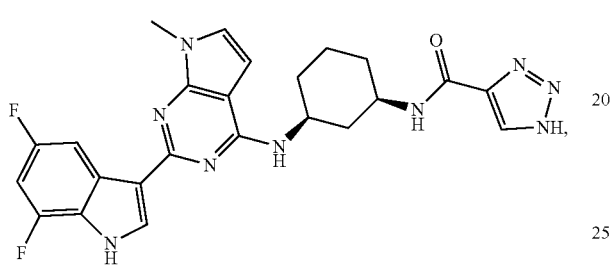
(212)
(213)
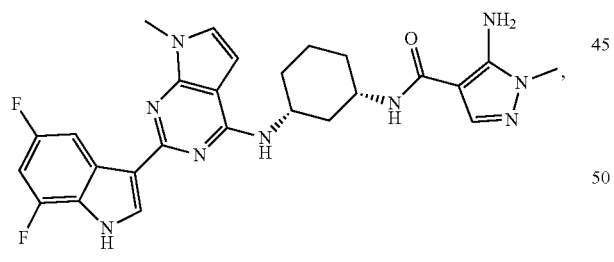
(214)
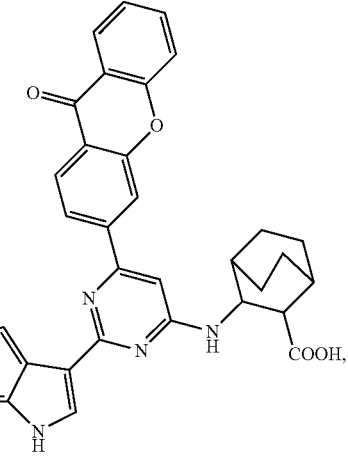
(215)
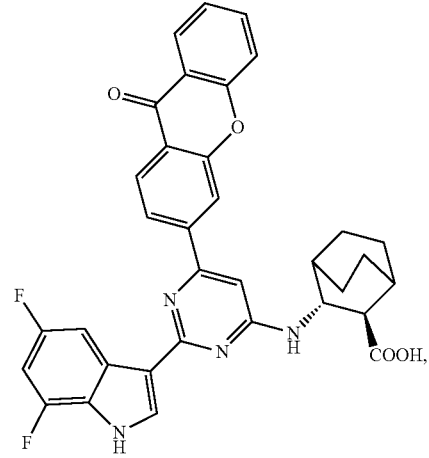
(216)
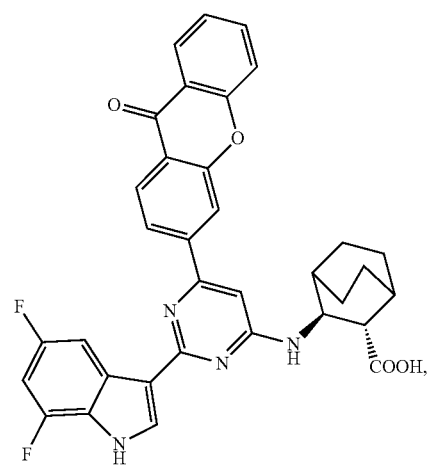

283
-continued
(217)
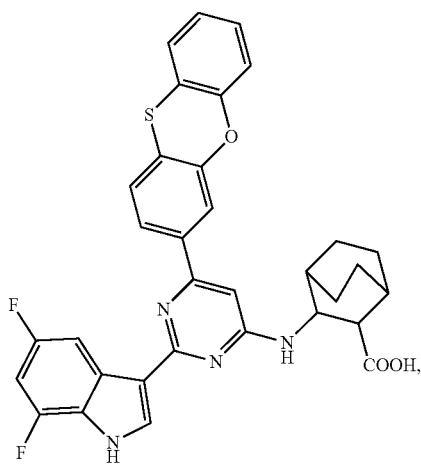
(218)
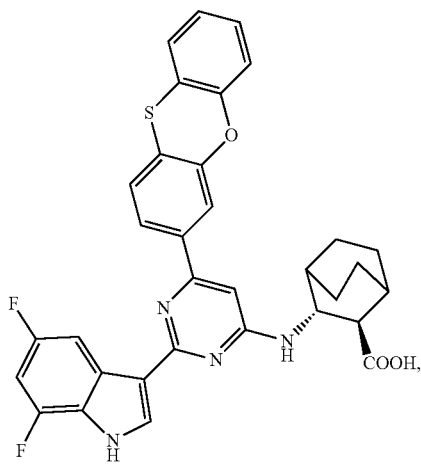
(219)
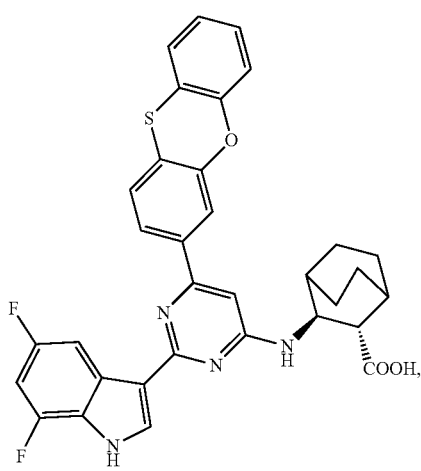
284
-continued
(220)
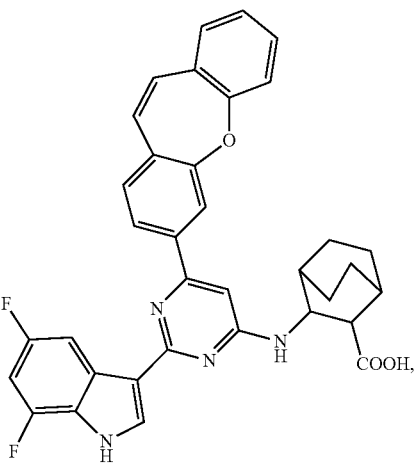
(221)
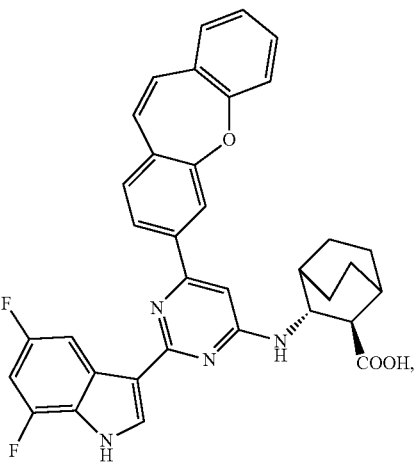
(222)
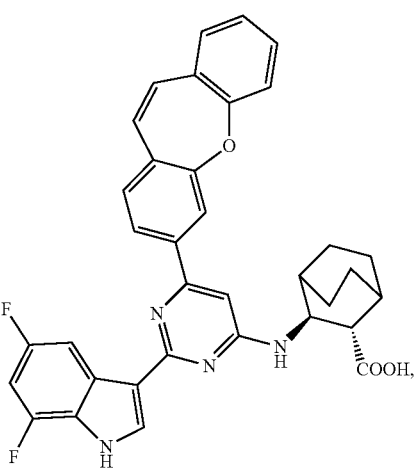

-continued
(223)
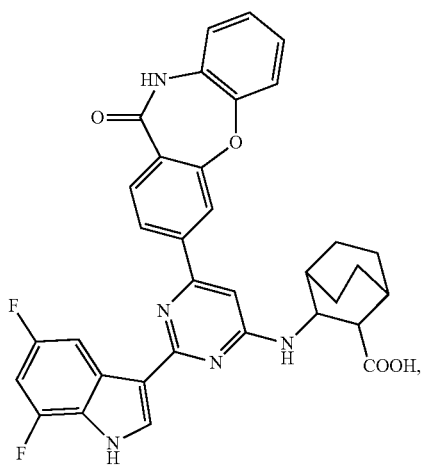
(224)
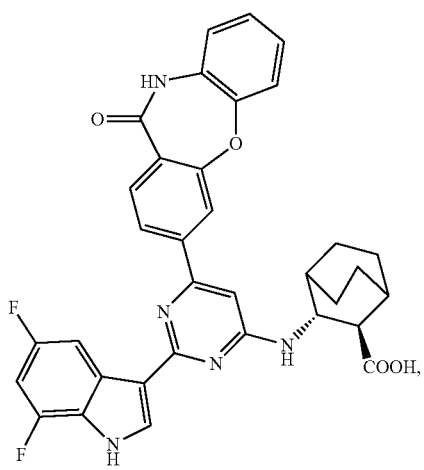
(225)
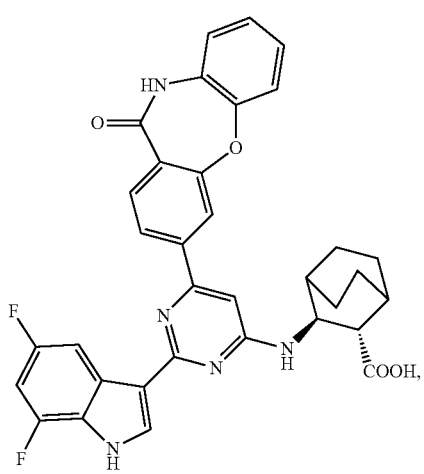
-continued
(226)
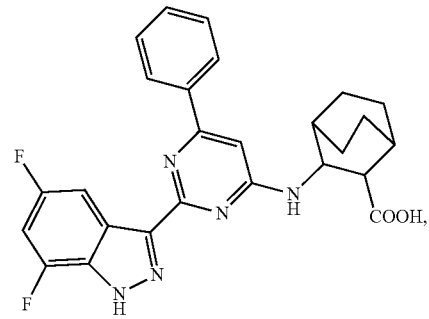
(227)
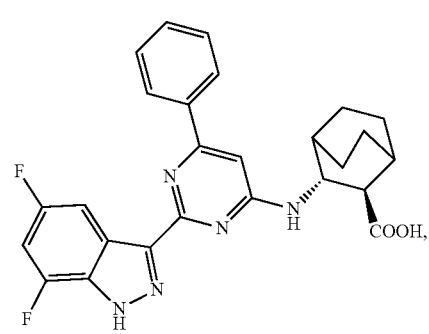
(228)
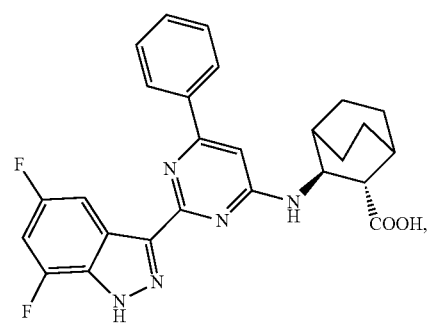
(229)
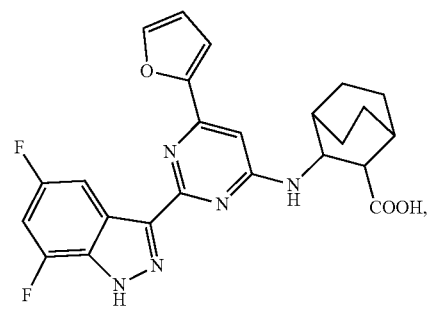
(230)
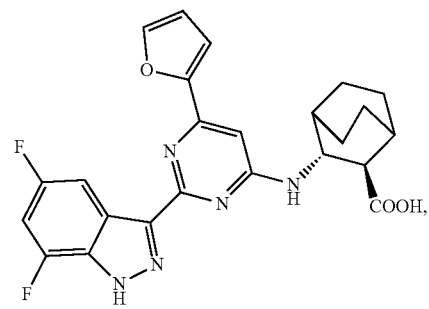

(231) 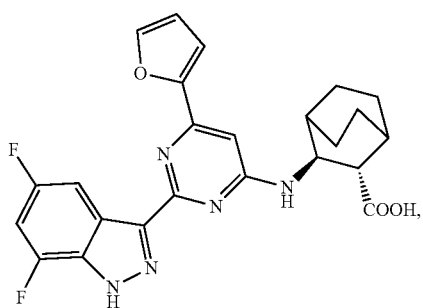
(232) 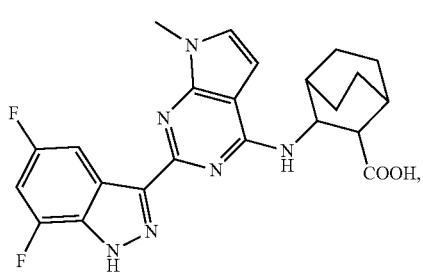
(233) 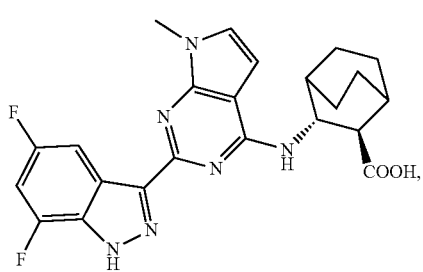
(234) 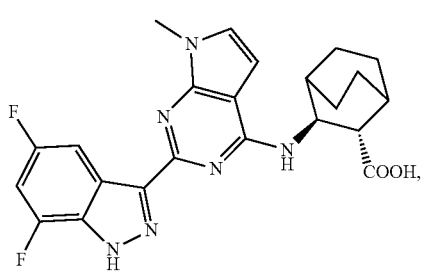
(235) 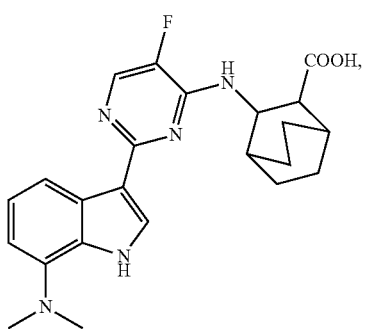
(236) 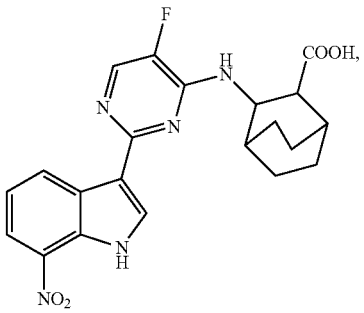
(237) 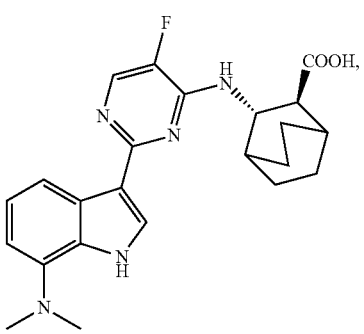
(238) 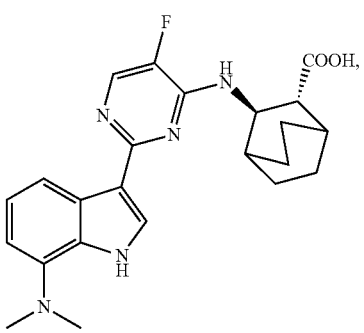
(239) 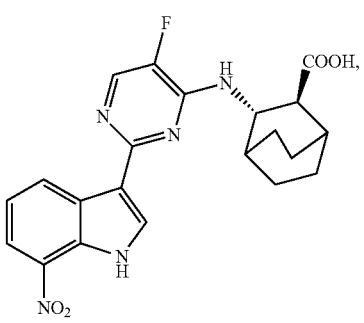
(240) 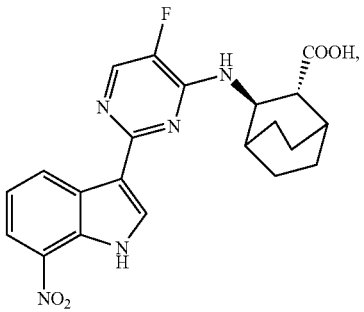

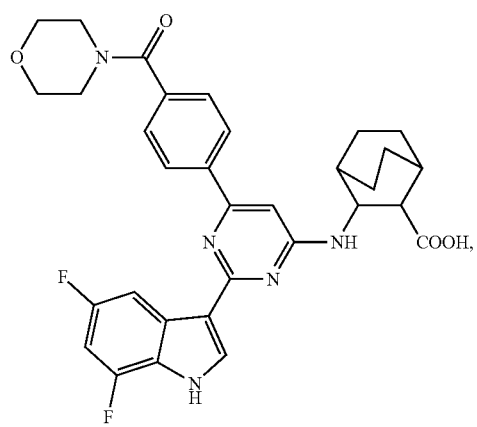
(241)
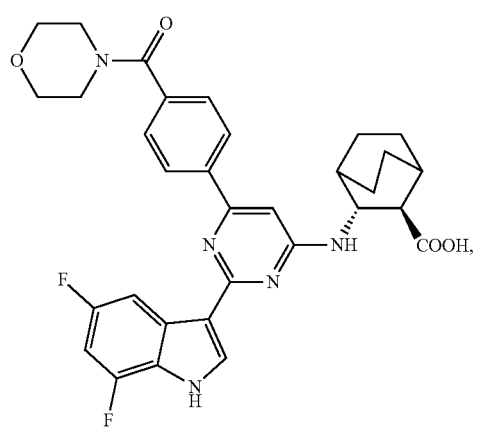
(242)
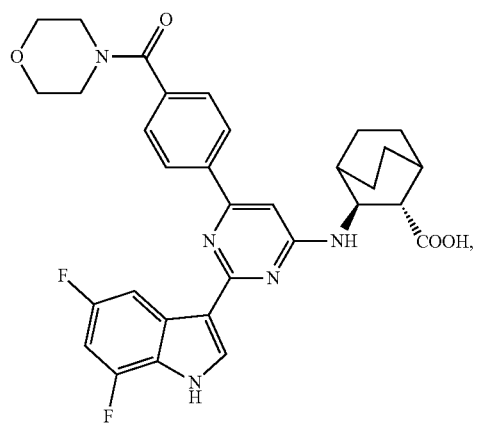
(243)
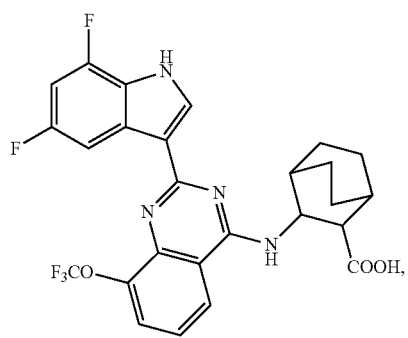
(244)
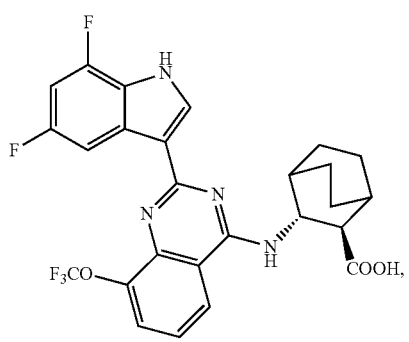
(245)
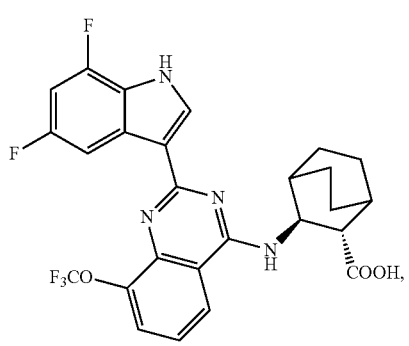
(246)
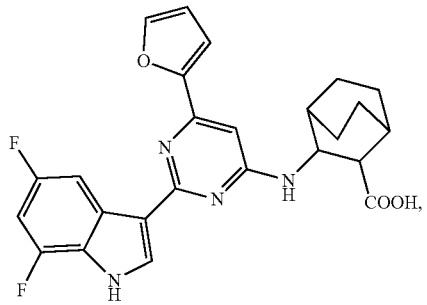
(247)
(248)
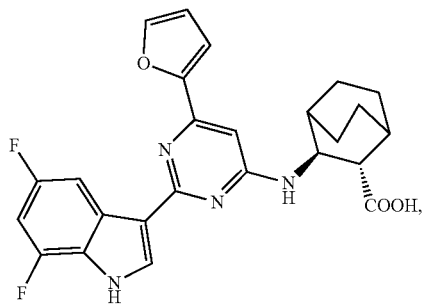
(249)

(250)
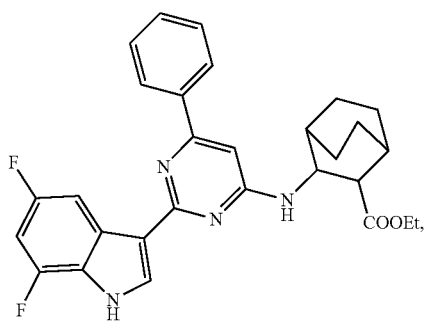
(251)
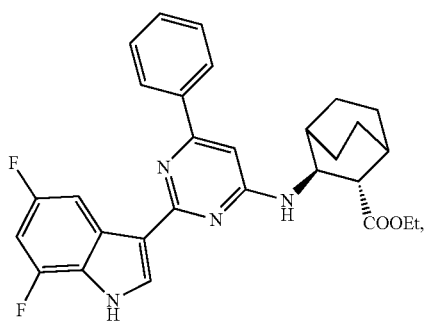
(252)
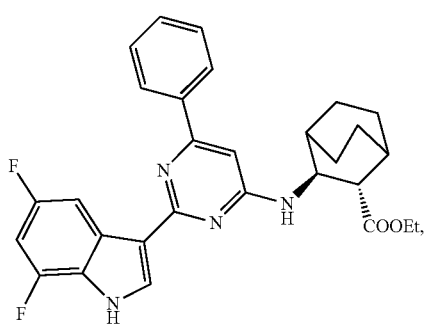
(253)
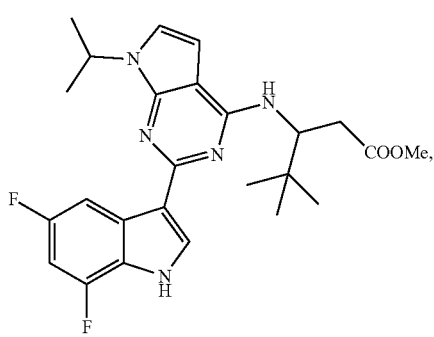
(254)
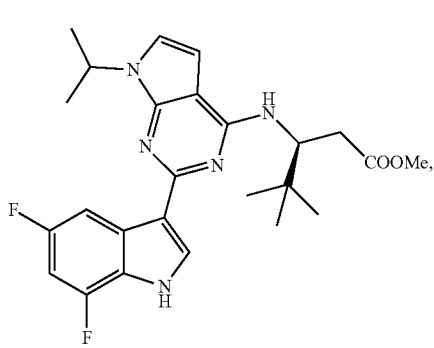
(255)
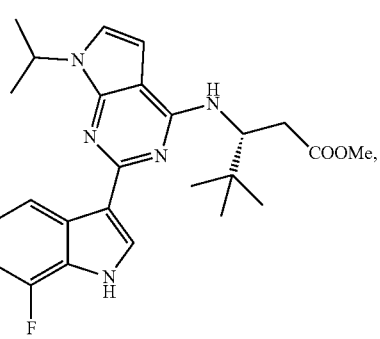
(256)
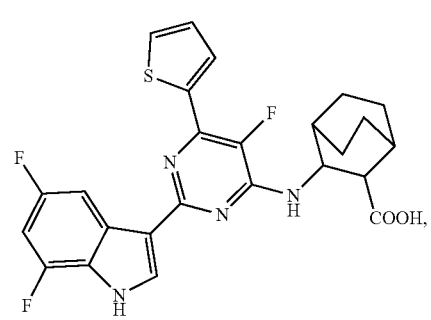
(257)
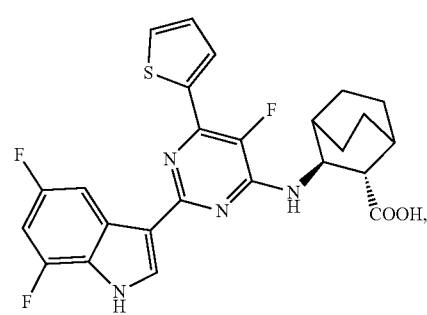
(258)
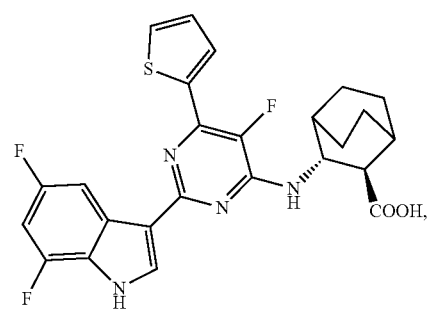
(259)
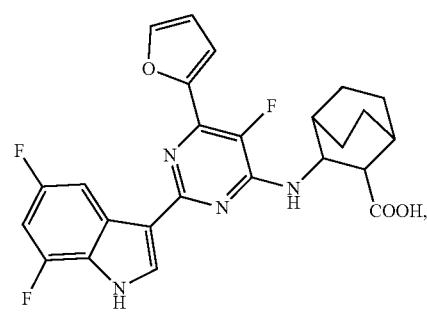

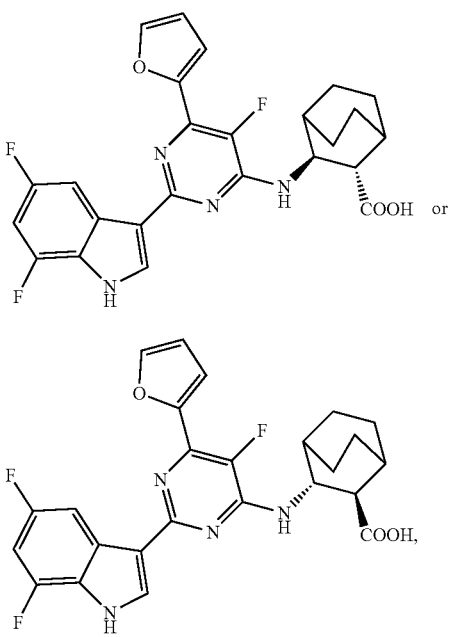

(260)

(261)

or a stereoisomer, a tautomer, an N-oxide, a solvate, a metabolite, or a pharmaceutically acceptable salt thereof.

15. A pharmaceutical composition comprising the compound of claim 1, optionally, the pharmaceutical composition further comprising a pharmaceutically acceptable carrier, adjuvant, vehicle or a combination thereof.

16. The pharmaceutical composition of claim 15 further comprising one or more other therapeutic agents, and wherein the other therapeutic agent is an anti-influenza virus agent or anti-influenza virus vaccine.

17. The pharmaceutical composition of claim 16, wherein the other therapeutic agent is amantadine, rimantadine, oseltamivir, zanamivir, peramivir, laninamivir, laninamivir octanoate hydrate, favipiravir, arbidol, ribavirin, stachyflin, ingavirin, fludase, CAS no. 1422050-75-6, JNJ-872, an influenza vaccine or a combination thereof.

18. A method of managing, treating or lessening a disorder or disease caused by a virus infection in a patient, comprising administering to the patient in need thereof a therapeutically effective amount of the compound of claim 1, wherein the virus infection is an influenza virus infection.

19. A method of inhibiting an influenza virus RNA polymerase in a patient, comprising administering to the patient in need thereof a therapeutically effective amount of the compound of claim 1.

20. A method of managing, treating or lessening a disorder or disease caused by a virus infection in a patient, comprising administering to the patient in need thereof a therapeutically effective amount of the pharmaceutical composition of claim 15, wherein the virus infection is an influenza virus infection.

21. A method of inhibiting an influenza virus RNA polymerase in a patient, comprising administering to the patient in need thereof a therapeutically effective amount of the pharmaceutical composition of claim 15.

* * * * *